(12) United States Patent
Romanczyk, Jr. et al.

(10) Patent No.: US 7,875,651 B2
(45) Date of Patent: *Jan. 25, 2011

(54) EPICATECHIN FOR HYPERTENSION TREATMENT

(75) Inventors: Leo J. Romanczyk, Jr., Hackettstown, NJ (US); Harold H. Schmitz, Bethesda, MD (US)

(73) Assignee: Mars, Inc., McLean, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/166,499

(22) Filed: Jun. 24, 2005

(65) Prior Publication Data

US 2005/0267052 A1   Dec. 1, 2005

Related U.S. Application Data

(60) Continuation of application No. 10/795,552, filed on Mar. 8, 2004, now Pat. No. 7,122,574, which is a continuation of application No. 10/770,969, filed on Feb. 2, 2004, now Pat. No. 6,900,241, which is a division of application No. 10/127,817, filed on Apr. 22, 2002, which is a continuation of application No. 09/717,893, filed on Nov. 21, 2000, now Pat. No. 6,670,390, which is a continuation of application No. 08/831,245, filed on Apr. 2, 1997, now Pat. No. 6,297,273, which is a continuation-in-part of application No. 08/631,661, filed on Apr. 2, 1996, now abandoned.

(51) Int. Cl.
*A61K 31/352* (2006.01)

(52) U.S. Cl. .................................... 514/456

(58) Field of Classification Search ............. 514/456; 549/200, 415
See application file for complete search history.

(56) References Cited

U.S. PATENT DOCUMENTS 4,840,966 A * 6/1989 Hara et al. ............... 514/456
5,554,645 A * 9/1996 Romanczyk et al. ...... 514/453

7,754,760 B2  7/2010  Romanczyk, Jr.

FOREIGN PATENT DOCUMENTS

| JP | 02295923 | * | 5/1989 |
| JP | 2295923 A | | 12/1990 |
| JP | 7-274894 | | 10/1995 |

OTHER PUBLICATIONS

Czochanska et al., J.C.S. Perkin I, (1980), pp. 2278-2286.*
"The tea plant—*Camellia sinesis* (L.)O. Kuntze," Scholz et al, Zeitschrift fur Phytotherapie, 1995 16(4) [Abstract in English; original article in German].
"Crategus as a herbal cardiac," Reuter et al, Zeitschrift fur Phytotherapie, 1994, 15(2) [Abstract in English; original article in German].
"Vasodilatory effects of flavonoids in rat aortic smooth muscle. Structure-activity relationships," Durarte et al, General Pharmacology, Jul. 1993, 24(2): 857-62.
"Enhancement of gap junctional intercellular communication in tumor promoter-treated cells by components of green tea," Sigler et al, Cancer Letters, Apr. 1993, 69: 15-19.
"Inhibitory effects of condensed tannins on angiotension converting enzyme (ACE)," Uchida et al, Japan J Pharmcol, 1987, 43(2): 242-46.
"Angiotension I converting enzyme inhibiting activity of tea components," Hara et al, Nippon Nogeikagaku Kaishi, 1987, 61(7): 803-08 [Abstract in English; original article in Japanese].
Villar, A., et al., Hypotensive Effect of *Rhamnus lycioides* Extracts, *Journal of Ethnopharmacology*, 16:269-273 (1986).
Clapperton, J. et al., 1992, Polyphenols and Cocoa Flavor, Presented at the XVIth International Conference of the Groupe Polyphenols, Lisbon, Portugal, Jul. 13-16.
Osawa T., 1995, Antioxidant Effect of Polyphenols in Chocolates and Cocoa, The 1$^{st}$ Symposium on Chocolate and Cocoa Nutrition, Chocolate and Cocoa Association of Japan, Tokyo, Japan, Sep. 27.
Ziegleder, G., and Sandmeier, D., 1983, Antioxidative Effects of Cocoa, Review for Chocolate, Confectionery and Bakery, 8:3-6.
Porter, L. J., et al., 1991, Cacao Procyanidins: Major Flavanoids and Indentification of Some Minor Metabolites, Phytochemistry, 30(5):1657-1663.
Duarte J. et al., Vasodilatory effects of flavonoids in rat aortic smooth muscle. Structure-activity relationships, 1993, *Gen. Pharmac.* vol. 24 (4):857-862.

* cited by examiner

*Primary Examiner*—Taofiq A Solola
(74) *Attorney, Agent, or Firm*—Nada Jain, P.C.

(57) ABSTRACT

Disclosed and claimed are flavanols, e.g. epicatechin, compositions such as pharmaceutical compositions containing an effective amount of flavanols, e.g. epicatechin, and methods of treatment or prevention of hypertension using the same.

33 Claims, 242 Drawing Sheets

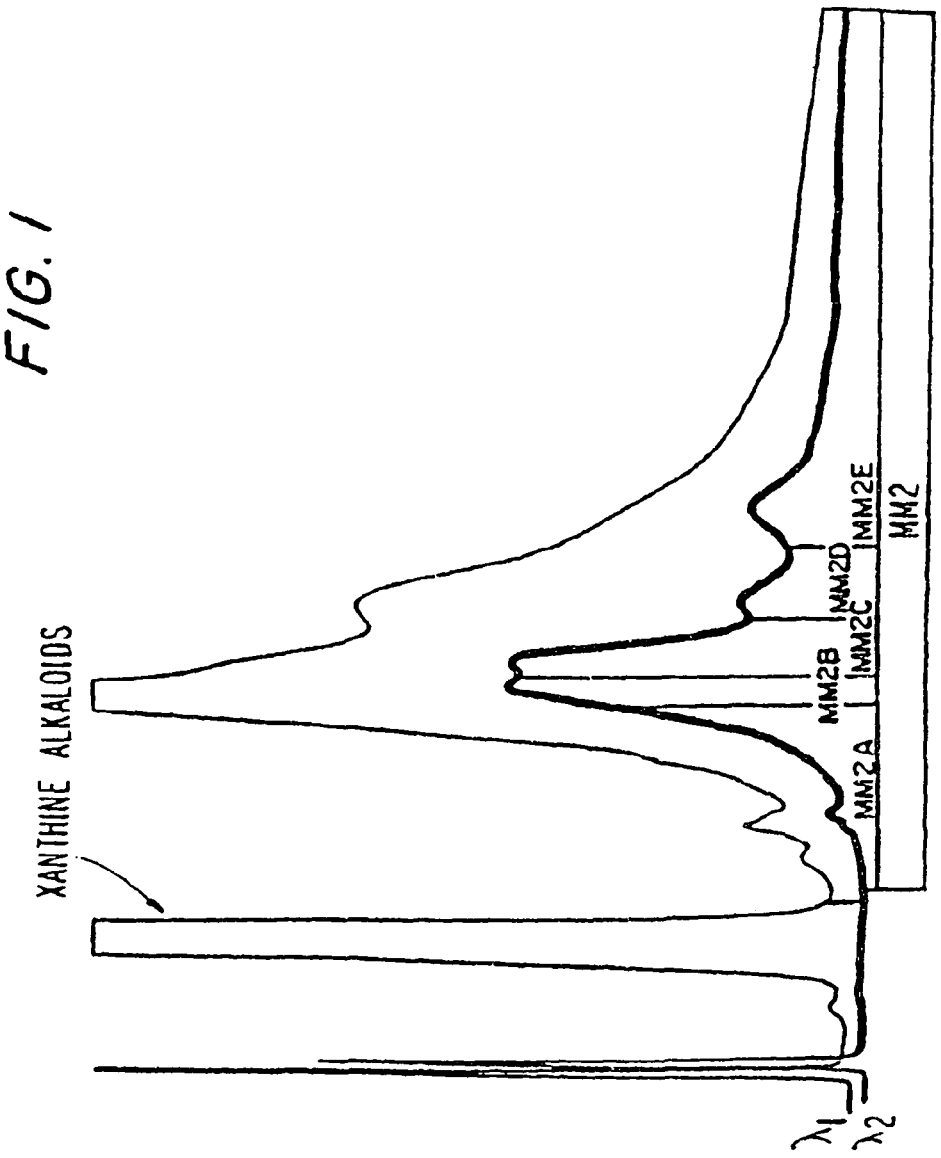

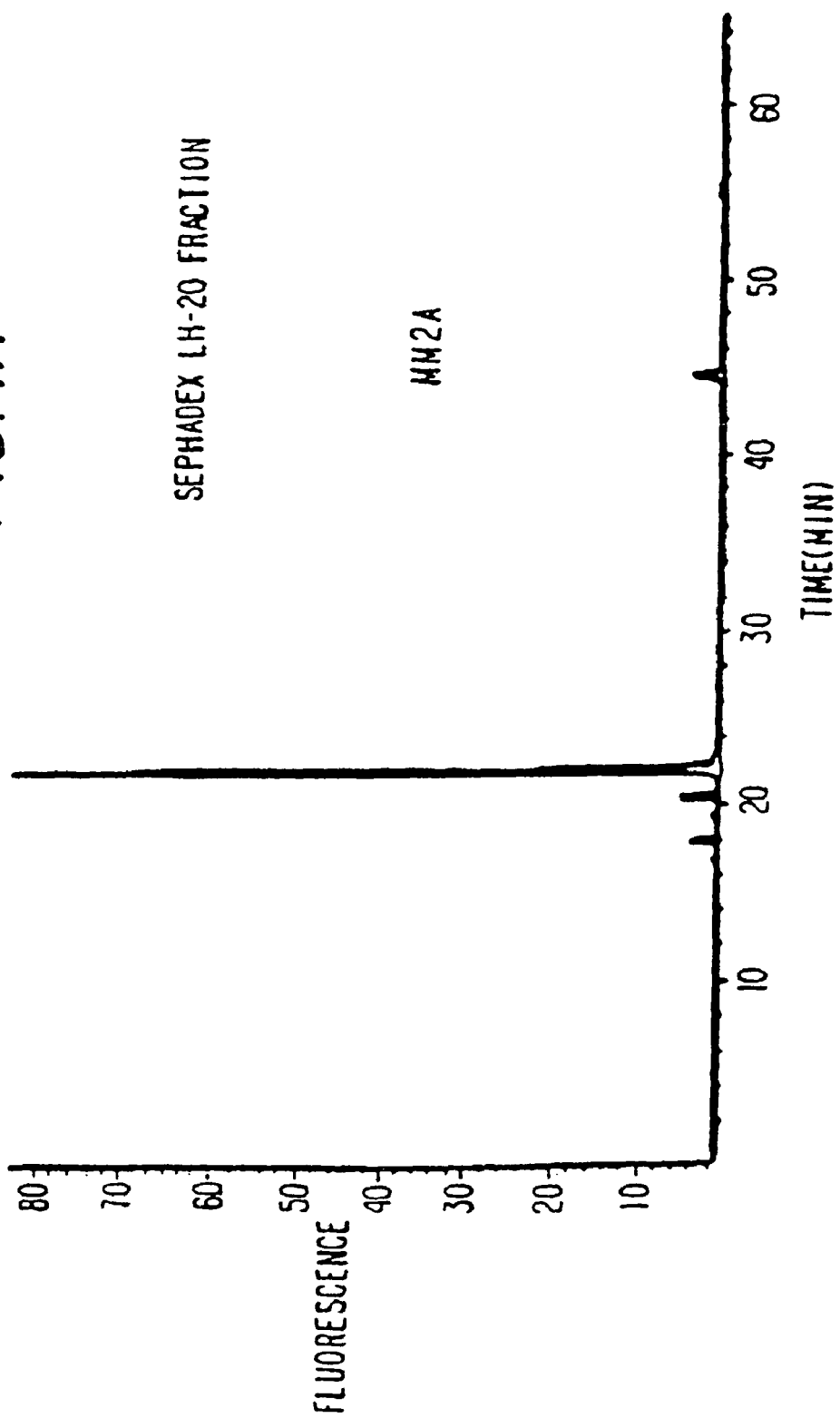

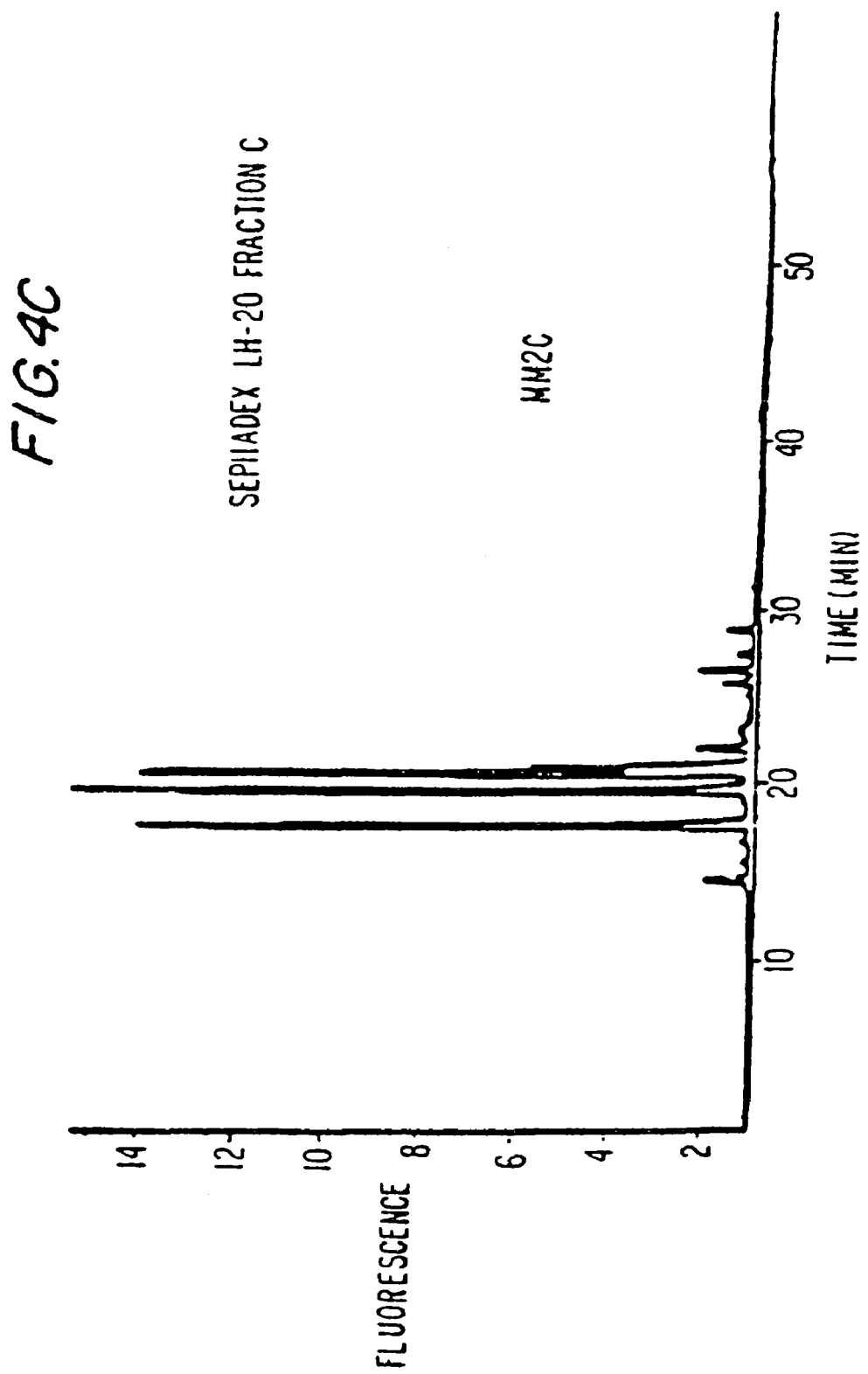

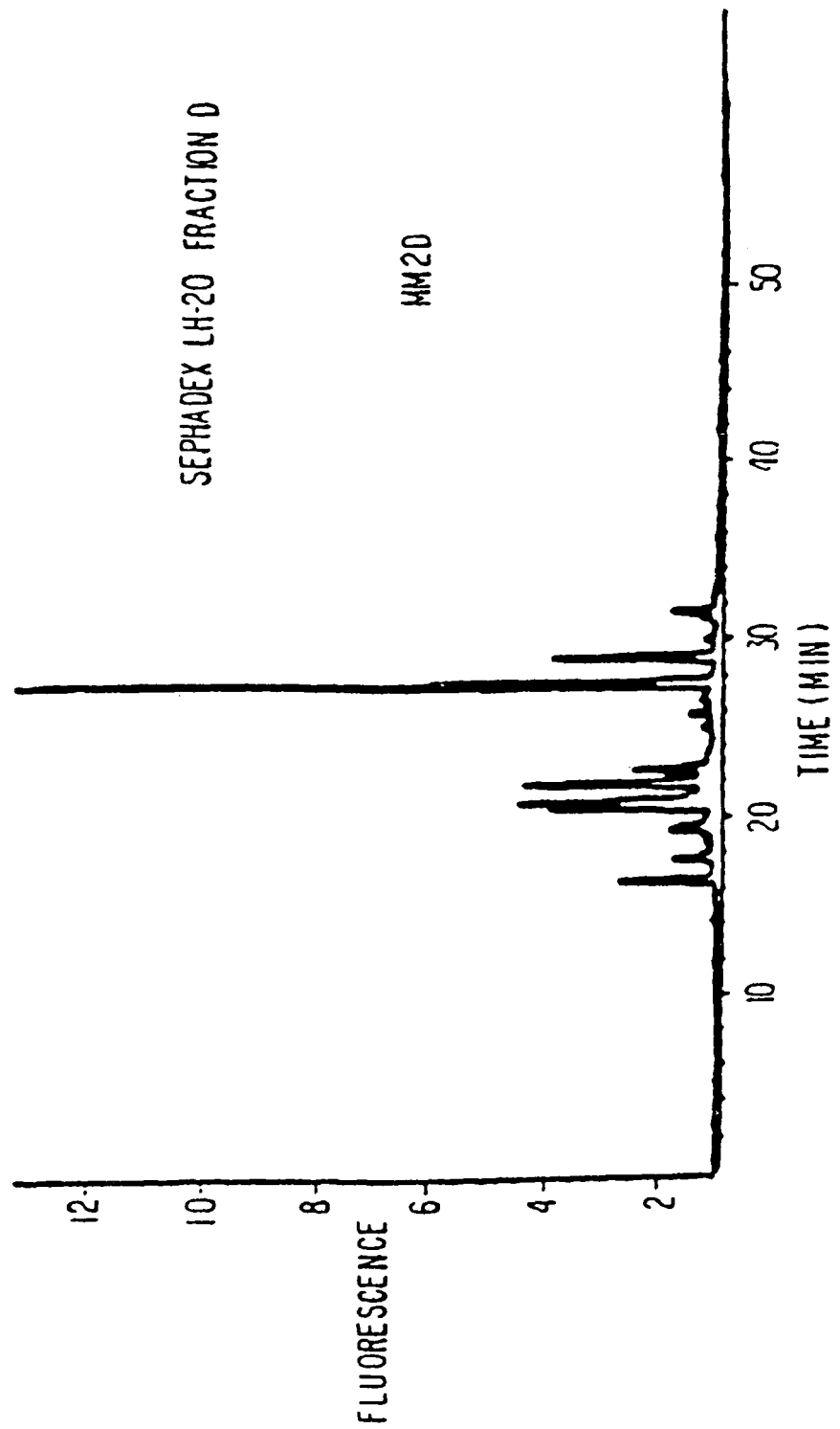

Comparison of XTT and Crystal Violet Cytotoxicity Assays on MCF-7 p168 cells Treated with Fraction D + E Dose Response for UIT-1 Crude Polyphenol Extract on MCF-7 p168 Cells

* NOTE: ABSORBANCE OF 2.0 INDICATES THE MAXIMUM ABSORBANCE OF THE PLATE READER. IT IS NOT REPRESENTATIVE OF CELL NUMBER.

Dose Response for UIT-1 Crude Polyphenol Extract on Hela Cells

* NOTE: ABSORBANCE OF 2.0 INDICATES THE MAXIMUM ABSORBANCE OF THE PLATE READER. IT IS NOT REPRESENTITVE OF CELL NUMBER.

Cytotoxicity of Cocoa Fractions at 100µL/mL on Hela Cells

* NOTE: ABSORBANCE OF 2.0 INDICATES THE MAXIMUM ABSORBANCE OF THE PLATE READER. IT IS NOT REPRESENTATIVE OF CELL NUMBER.

Cytoxicity Of Cocoa Fractions at 100μL/mL on SKBR - 3 Cells

Figure 15 H: Dose Response for Cocoa Fraction D + E on Hela Cells

Dose Response for Cocoa Fraction D + E on Hela Cells by Soft Agar Cloning Assay

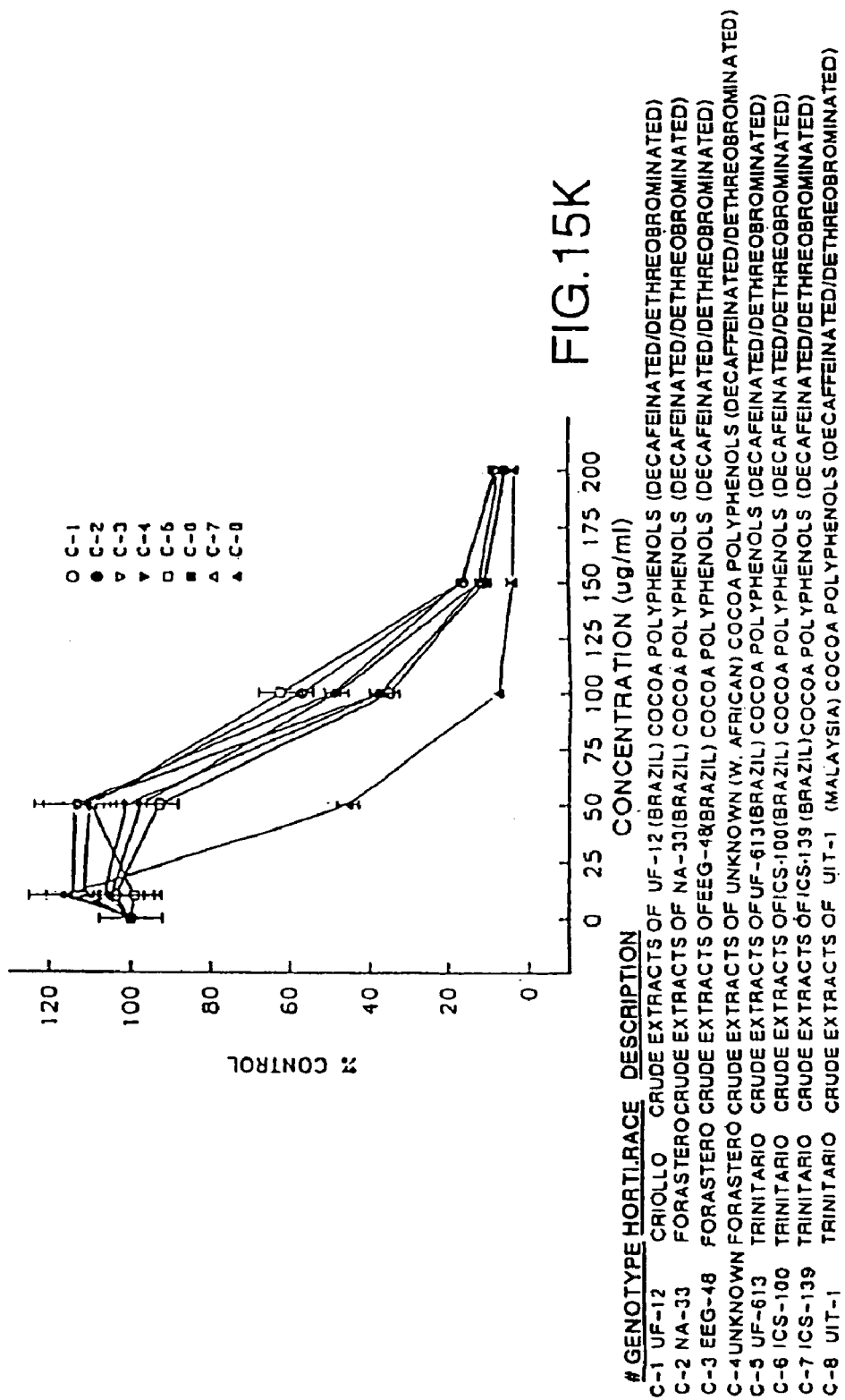

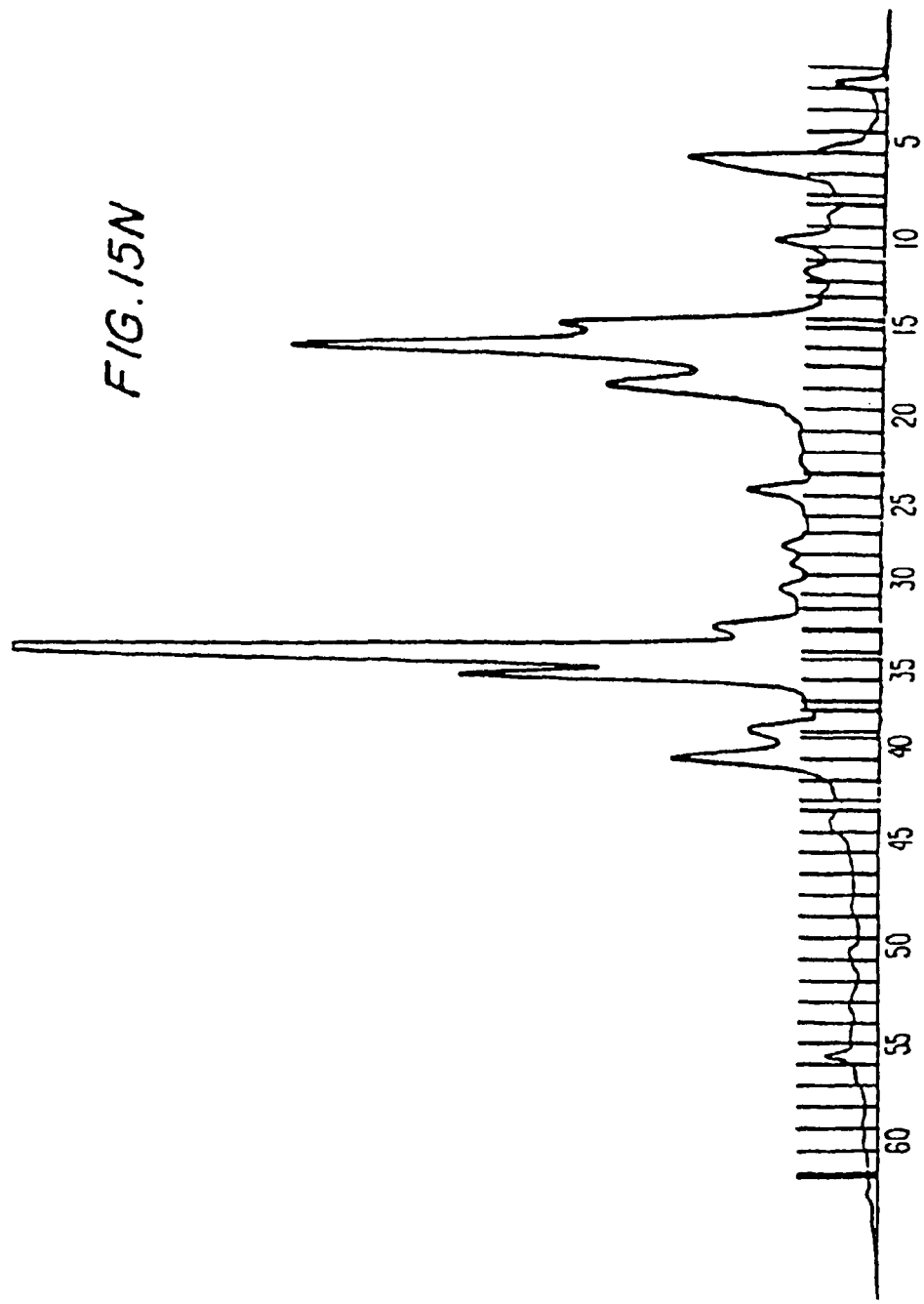

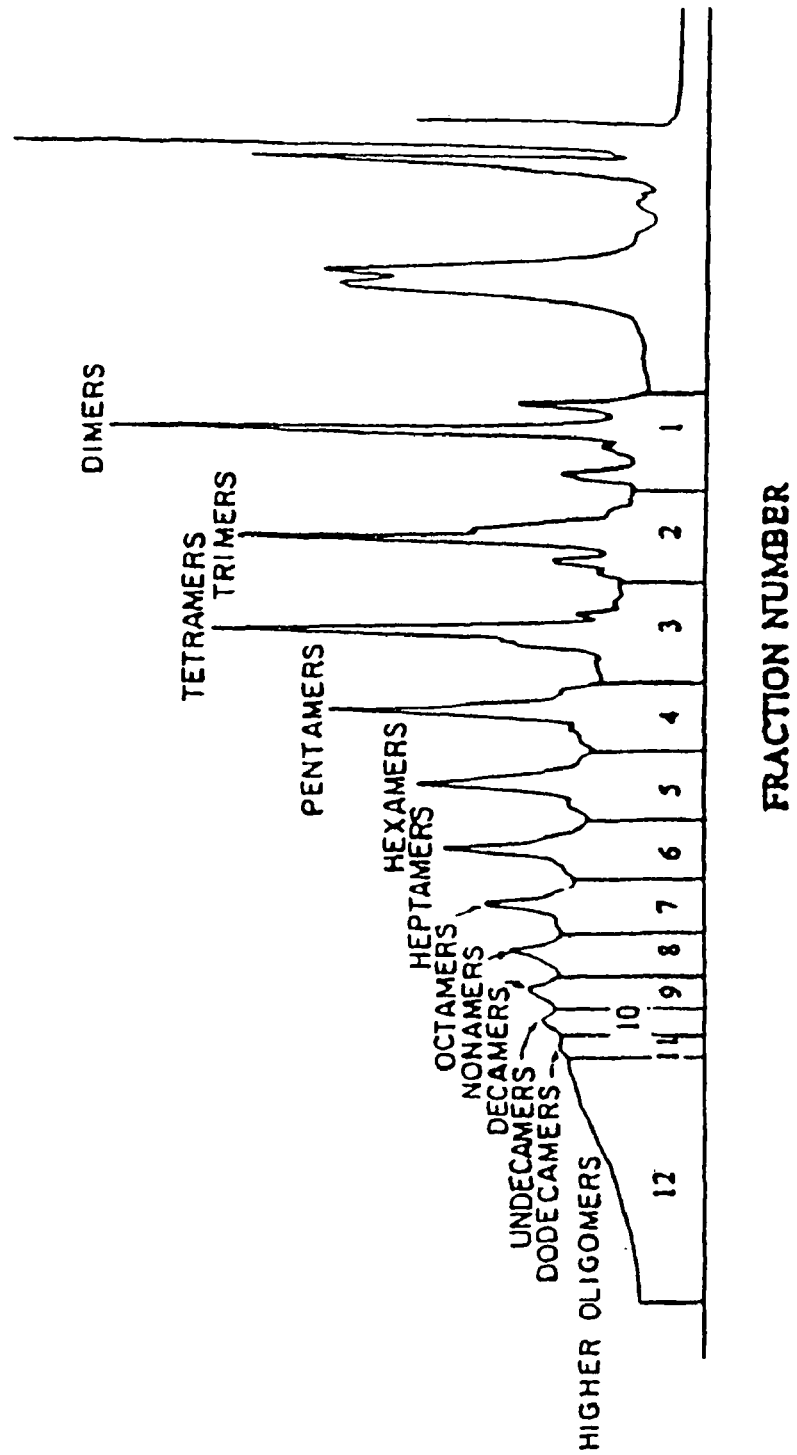

Rancimat Oxidation Curves for Cocoa Procyanidins and Synthetic Antioxidants
20 ppm Sample Set

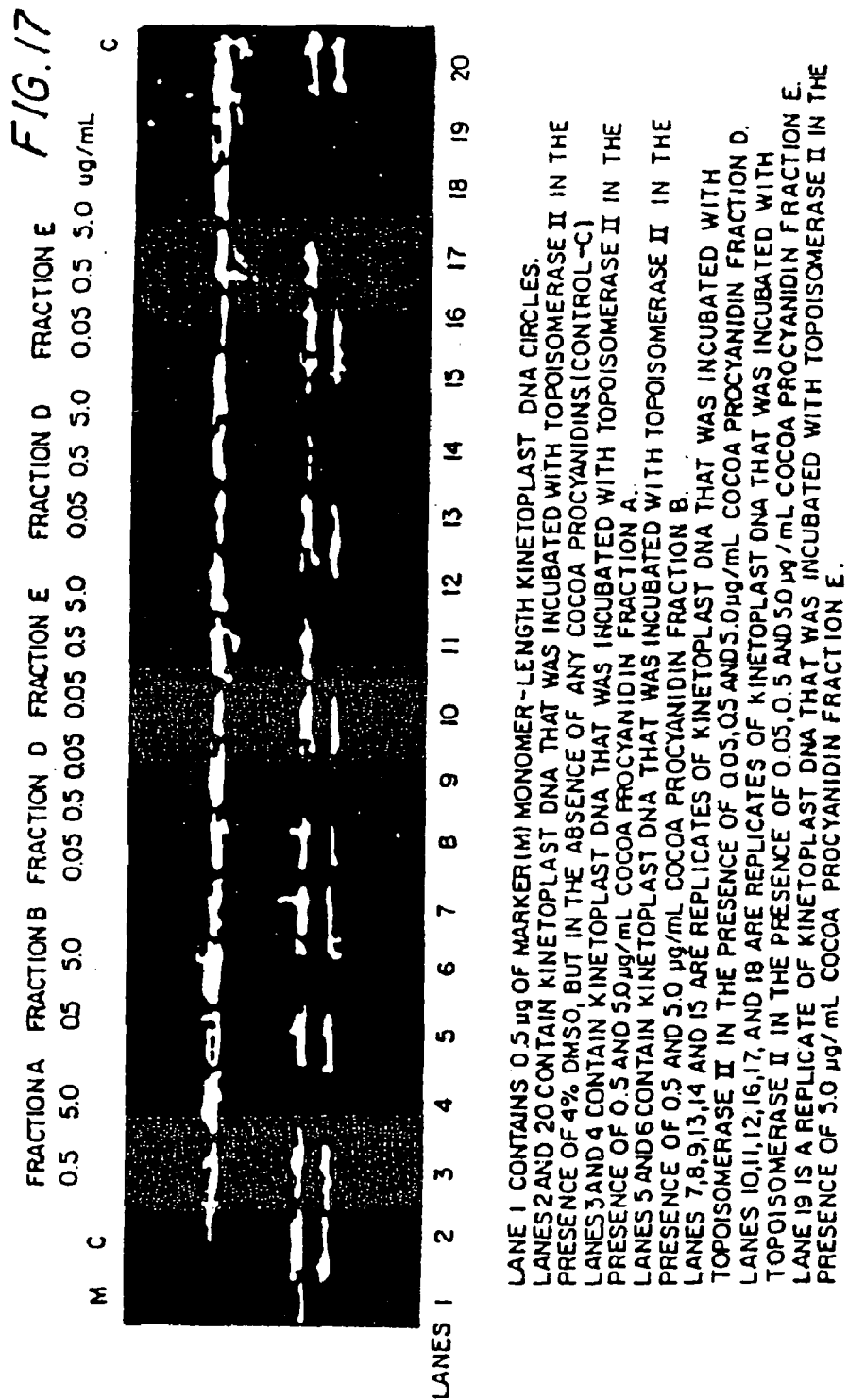

FIG. 17

LANE 1 CONTAINS 0.5 μg OF MARKER (M) MONOMER-LENGTH KINETOPLAST DNA CIRCLES.
LANES 2 AND 20 CONTAIN KINETOPLAST DNA THAT WAS INCUBATED WITH TOPOISOMERASE II IN THE PRESENCE OF 4% DMSO, BUT IN THE ABSENCE OF ANY COCOA PROCYANIDINS.(CONTROL-C)
LANES 3 AND 4 CONTAIN KINETOPLAST DNA THAT WAS INCUBATED WITH TOPOISOMERASE II IN THE PRESENCE OF 0.5 AND 5.0 μg/mL COCOA PROCYANIDIN FRACTION A.
LANES 5 AND 6 CONTAIN KINETOPLAST DNA THAT WAS INCUBATED WITH TOPOISOMERASE II IN THE PRESENCE OF 0.5 AND 5.0 μg/mL COCOA PROCYANIDIN FRACTION B.
LANES 7,8,9,13,14 AND 15 ARE REPLICATES OF KINETOPLAST DNA THAT WAS INCUBATED WITH TOPOISOMERASE II IN THE PRESENCE OF 0.05,0.5 AND 5.0 μg/mL COCOA PROCYANIDIN FRACTION D.
LANES 10,11,12,16,17, AND 18 ARE REPLICATES OF KINETOPLAST DNA THAT WAS INCUBATED WITH TOPOISOMERASE II IN THE PRESENCE OF 0.05, 0.5 AND 5.0 μg/mL COCOA PROCYANIDIN FRACTION E.
LANE 19 IS A REPLICATE OF KINETOPLAST DNA THAT WAS INCUBATED WITH TOPOISOMERASE II IN THE PRESENCE OF 5.0 μg/mL COCOA PROCYANIDIN FRACTION E.

Dose Response Curve for Adriamycin Resistant MCF-7 Cells in Comparison to
MCF-7 p168 Parental Cell Line with Cocoa Fraction D + E

| Fraction Number | Oligomeric Unit |
|---|---|
| #1 | dimers |
| #2 | trimers |
| #3 | tetramers |
| #4 | pentamers |
| #5 | hexamers |
| #6 | heptamers |
| #7 | octamers |
| #8 | nonamers |
| #9 | decamers |
| #10 | undecamers |
| #11 | dodemers |
| #12 | higher oligomers |
| #13 | unknon |

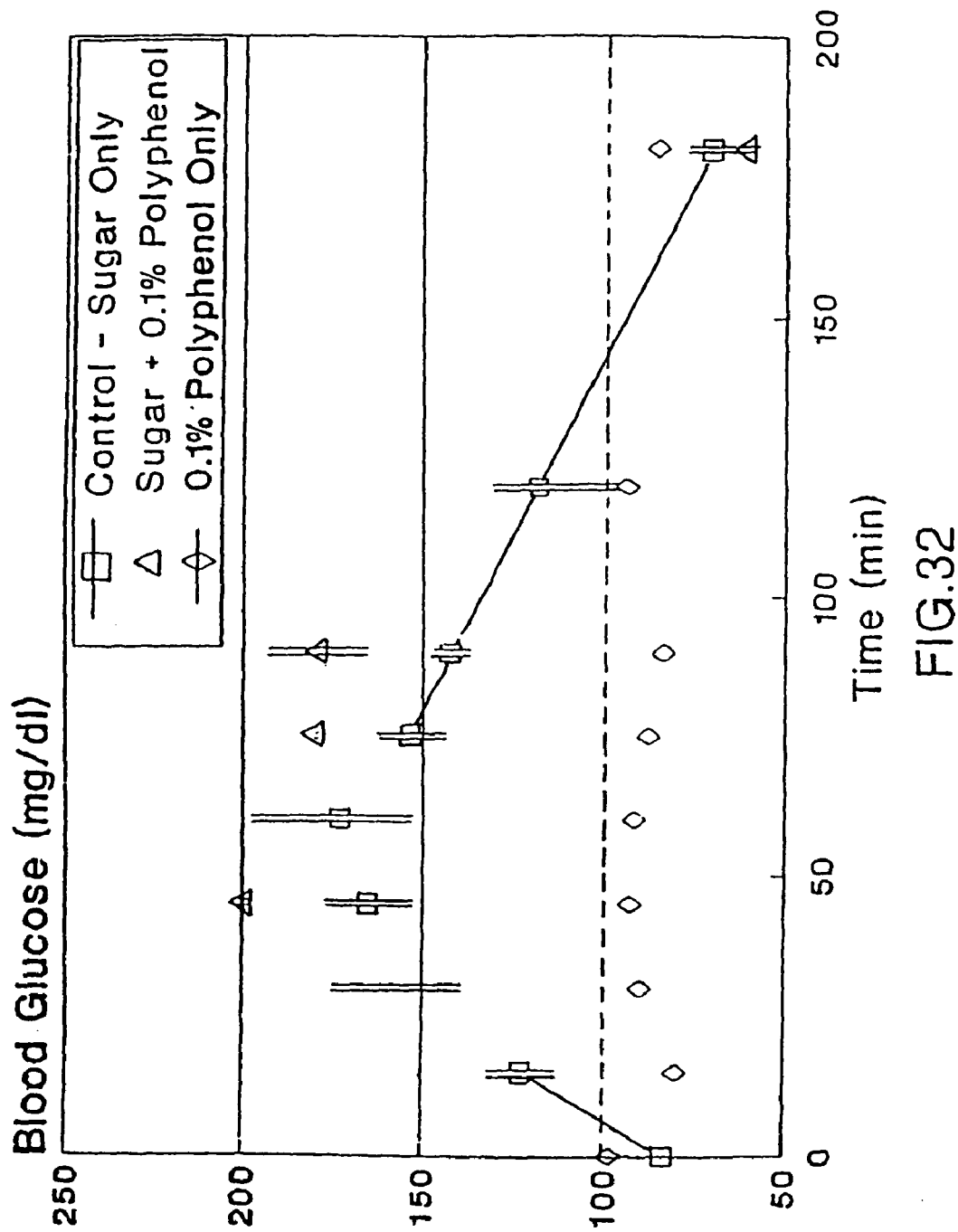

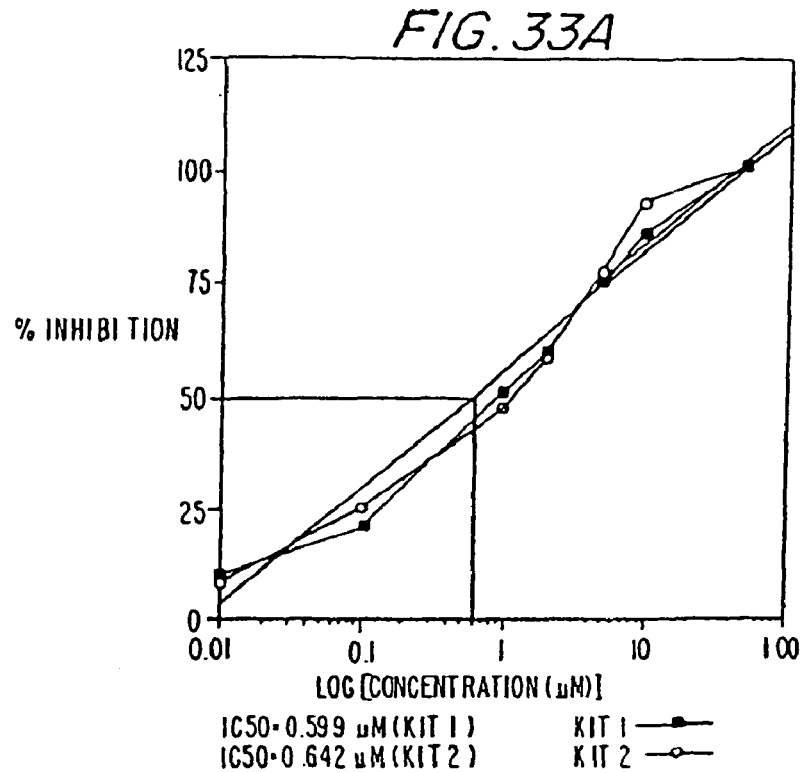
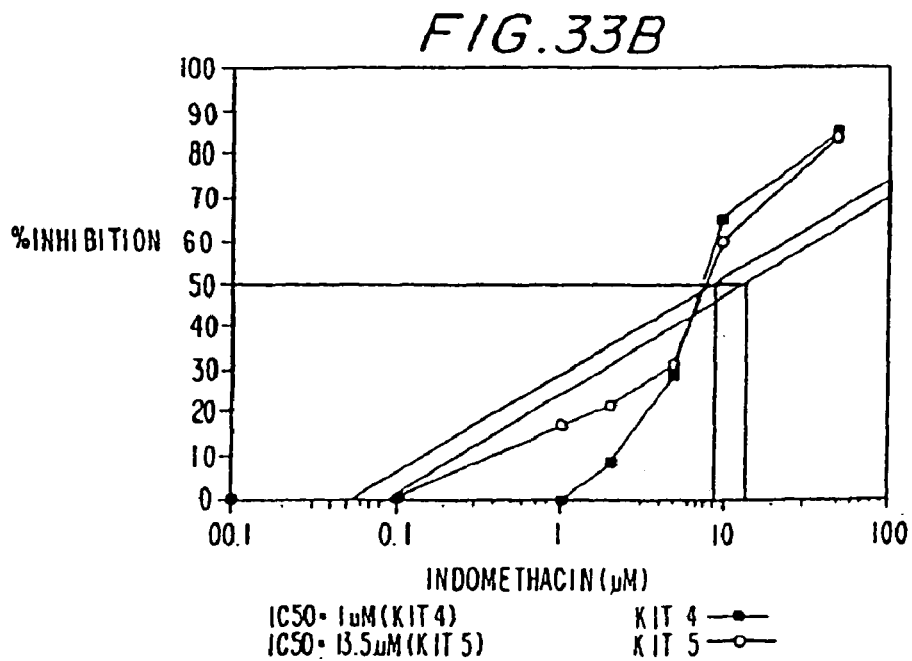

(*) With the exception of sample S11 expressed as mg/ml (*) With the exception of sample S11 expressed as mg/ml (*) with the exception of sample S11

EFFECT OF S4 SAMPLE ON COX-1 ACTIVITY

EFFECT OF S5 SAMPLE ON COX-1 ACTIVITY

EFFECT OF S10 SAMPLE ON COX-1 ACTIVITY

FIG. 37

Summary of the current purification protocol

Procyanidins are extracted from defatted freeze dried unfermented seeds from *Theobroma* or *Herrania* species with Acetone/H2O followed by MeOH/H2O

↓ 1

Extract Concentrated by Rotovap

↓ 2

Aqueous Extract is Freeze Dried

↓ 3

Alkaloids and some low MW oligomers are removed by GPC

↓ 4

Solvent is removed by rotovap and aqueous solution is freeze dried

↓ 5

Oligomers are separated/purified by Normal Phase HPLC

↓ 6

Additonal purification through a modified Normal Phase HPLC separation or Reverse Phase HPLC (4-8)(4-8)(4-8)(4-6) CENTAMER (4-8)(4-8)(4-8)(4-6) PENTAMER

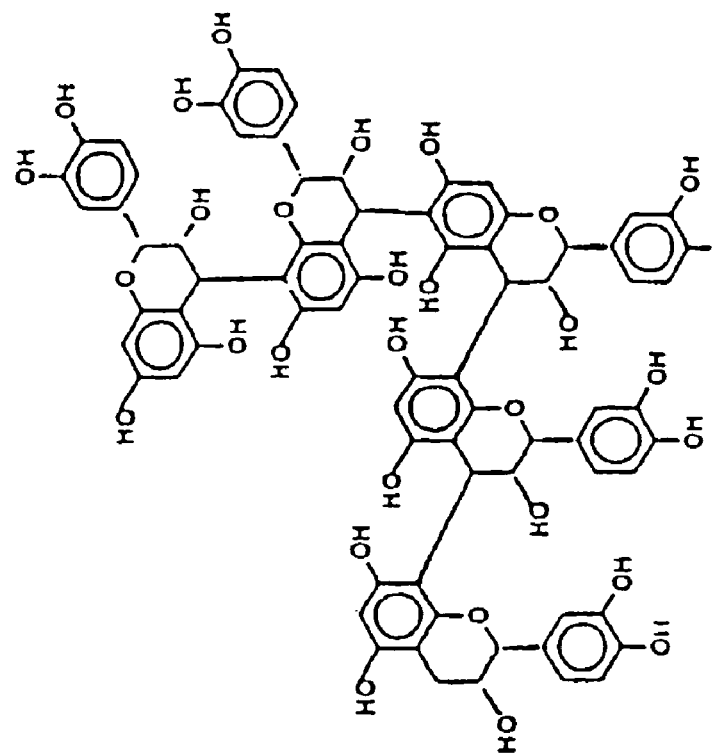
FIG. 38D (4-8)(4-6)(4-8)(4-8) PENTAMER
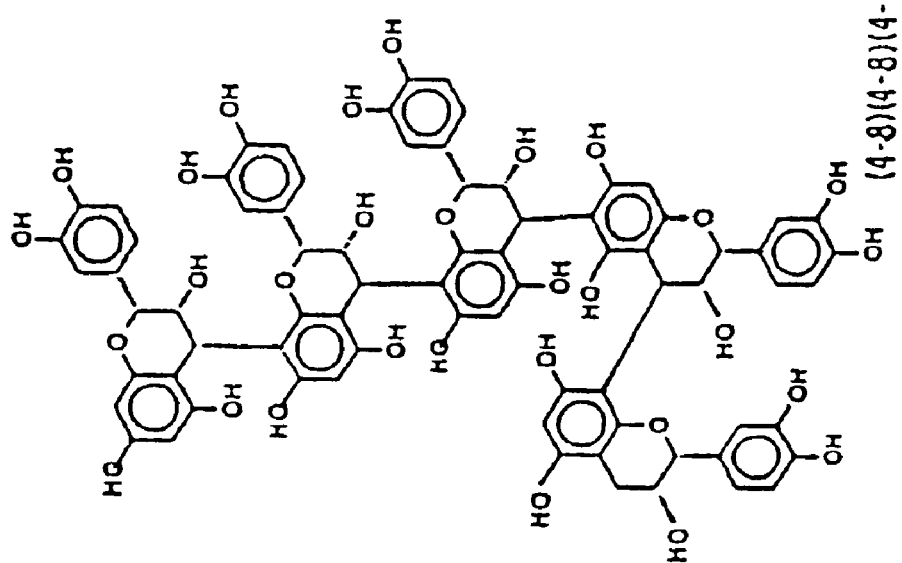
FIG. 38C (4-8)(4-8)(4-6)(4-6) PENTAMER (4-6)(4-8)(4-8)(4-8) PENTAMER (4-8)(4-6)(4-6)(4-8) PENTAMER

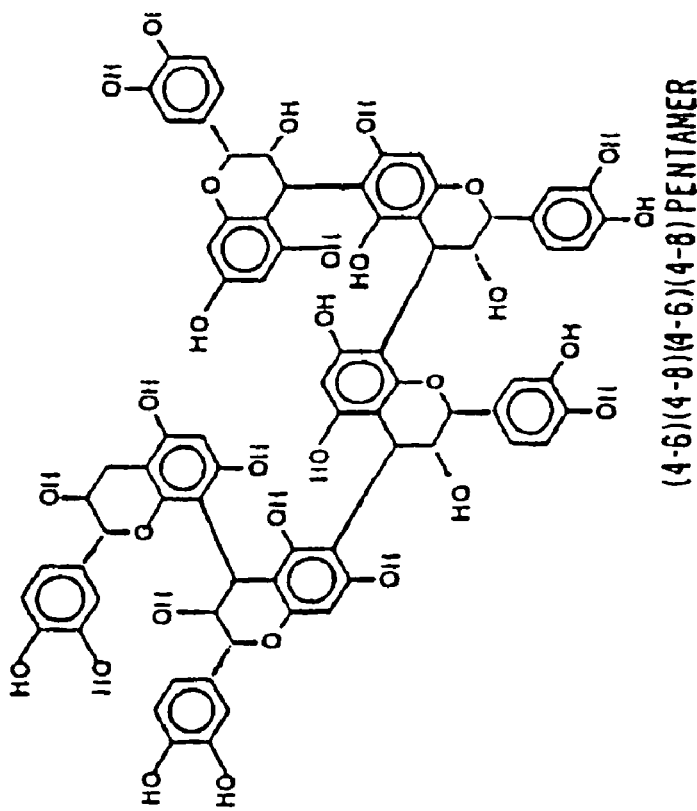
FIG. 38H (4-6)(4-8)(4-6)(4-8) PENTAMER
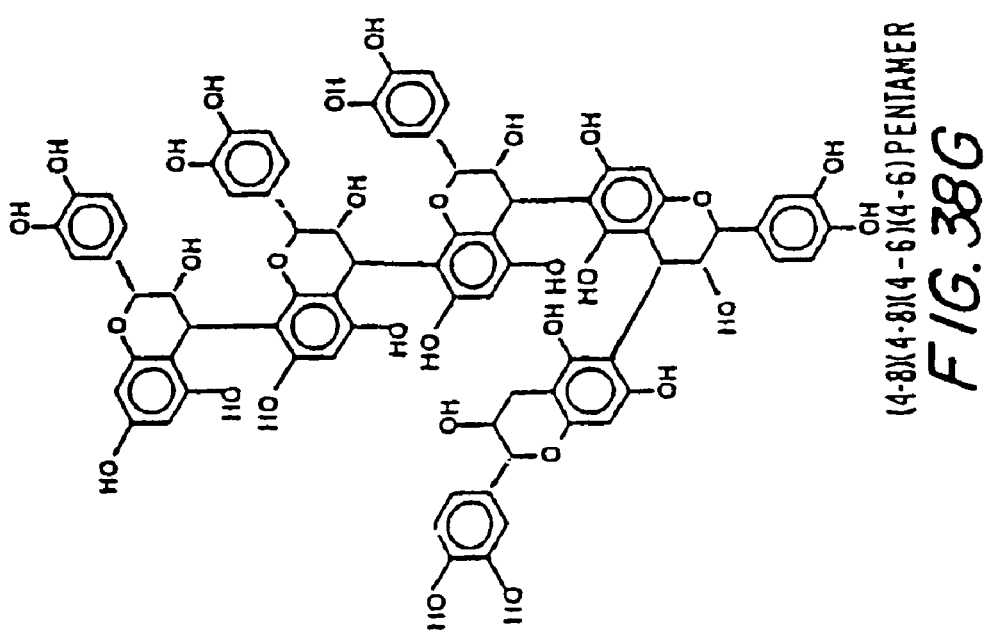
FIG. 38G (4-8)(4-8)(4-6)(4-6) PENTAMER (4-6)(4-6)(4-8)(4-8)PENTAMER

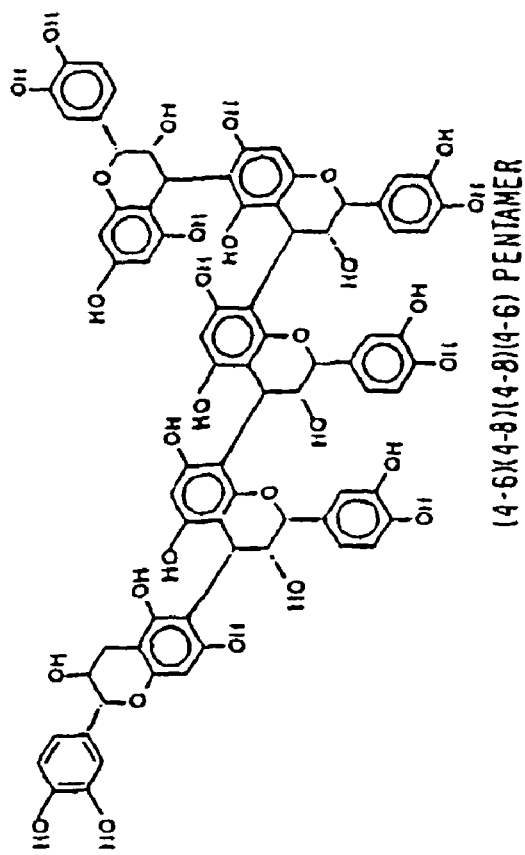
FIG. 38K (4-6)(4-8)(4-8)(4-6) PENTAMER
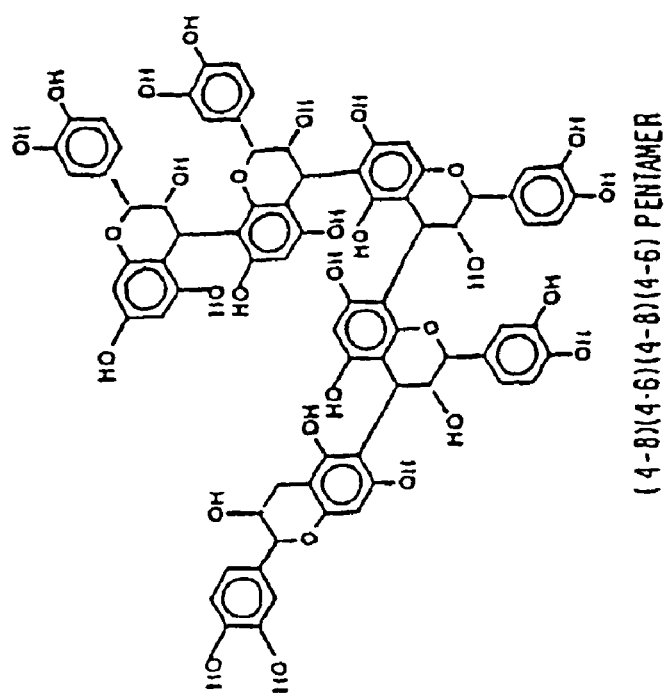
FIG. 38J (4-8)(4-6)(4-8)(4-6) PENTAMER

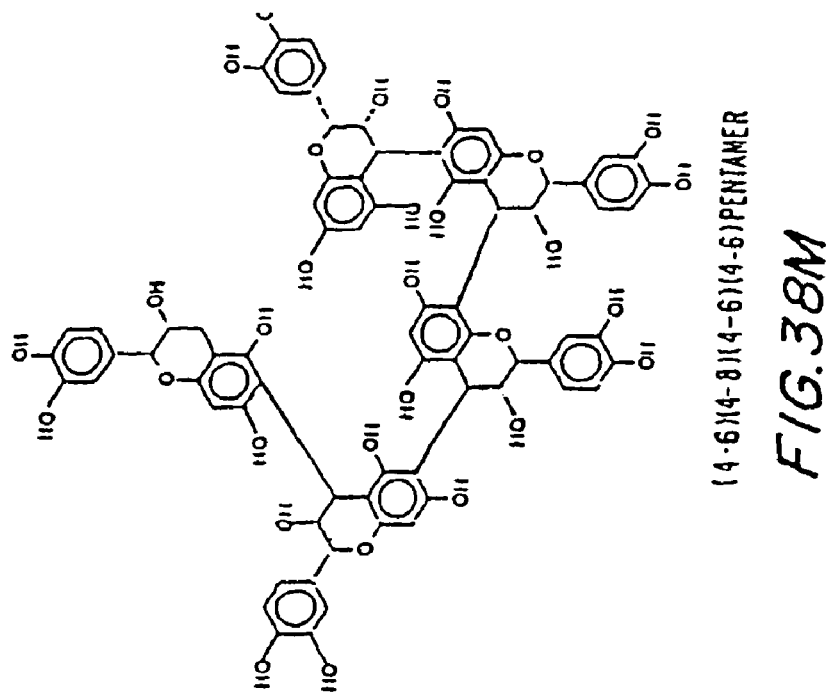
FIG.38M (4-6)(4-8)(4-6)(4-6)PENTAMER
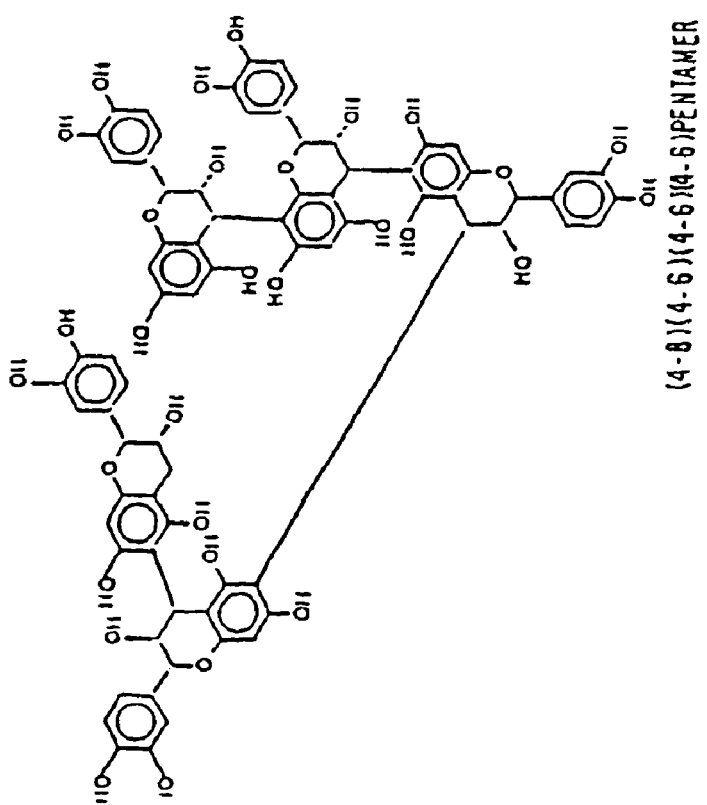
FIG.38L (4-8)(4-6)(4-6)PENTAMER (4-6)(4-6)(4-8)(4-6)PENTAMER (4-6)(4-6)(4-6)(4-6) PENTAMER (4-6)(4-6)(4-6)(4-8)PENTAMER

LEVEL 1

FIG. 39C (LEVEL 1)

X = CAT
O = EC

X: CAT
O: EC

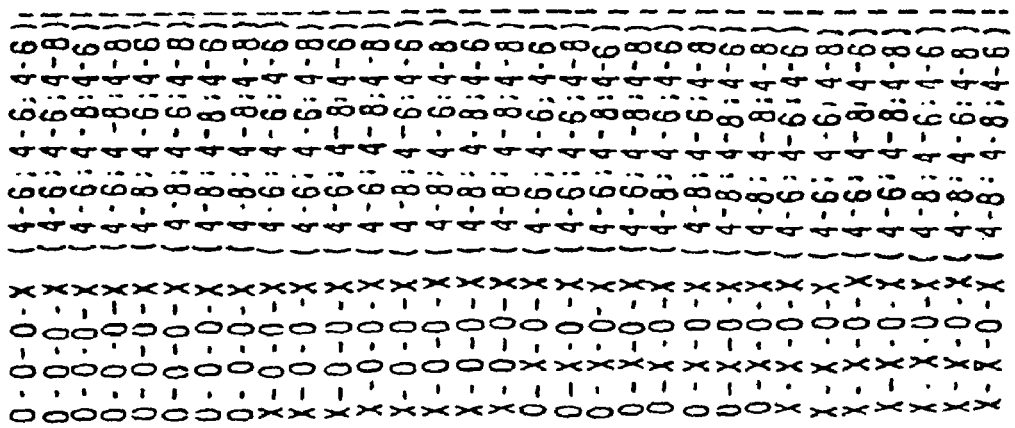

X・CAT
O・EG

FIG.39AA (CONTINUE LEVEL V)

X: CAT
O: EC

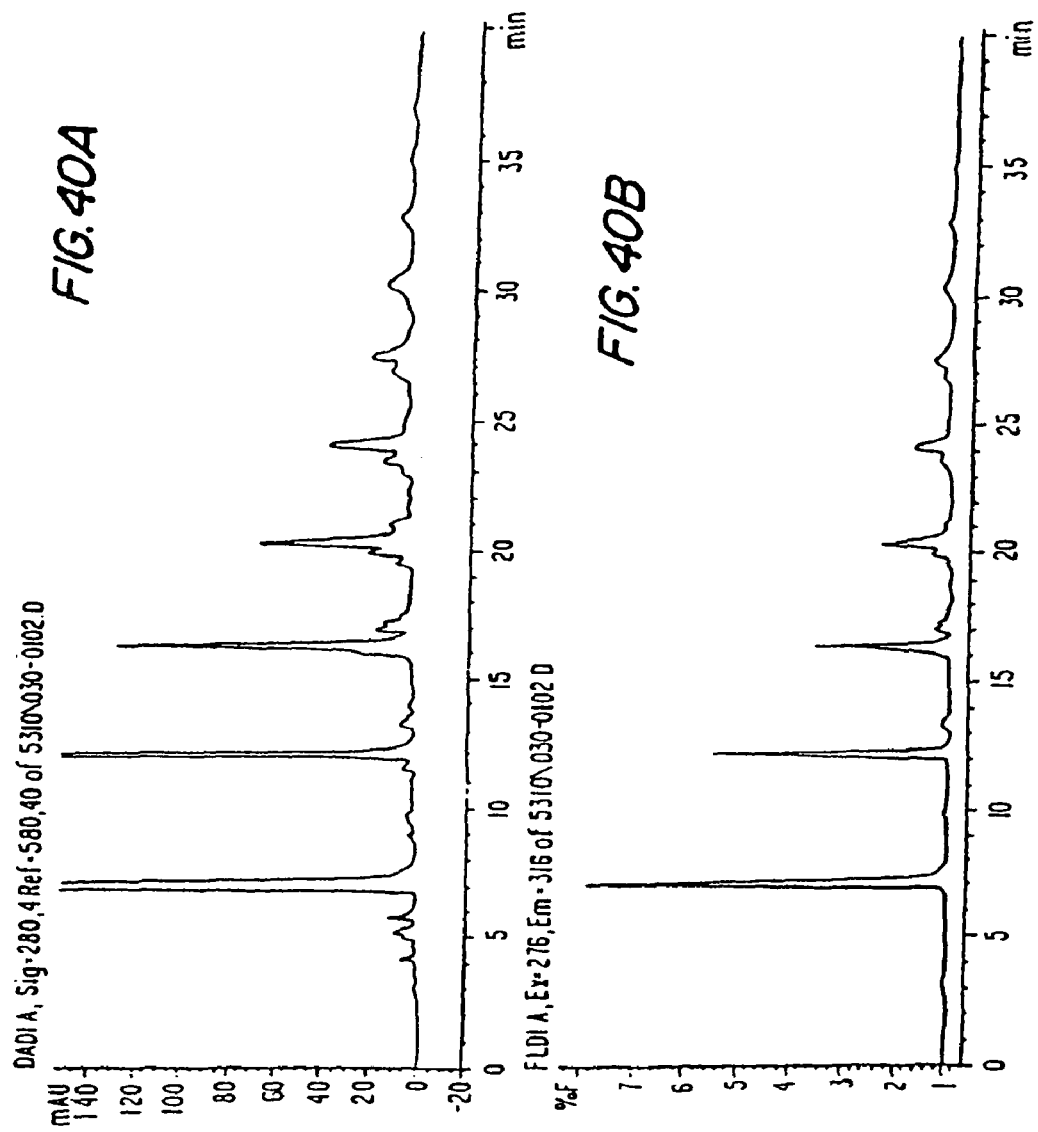

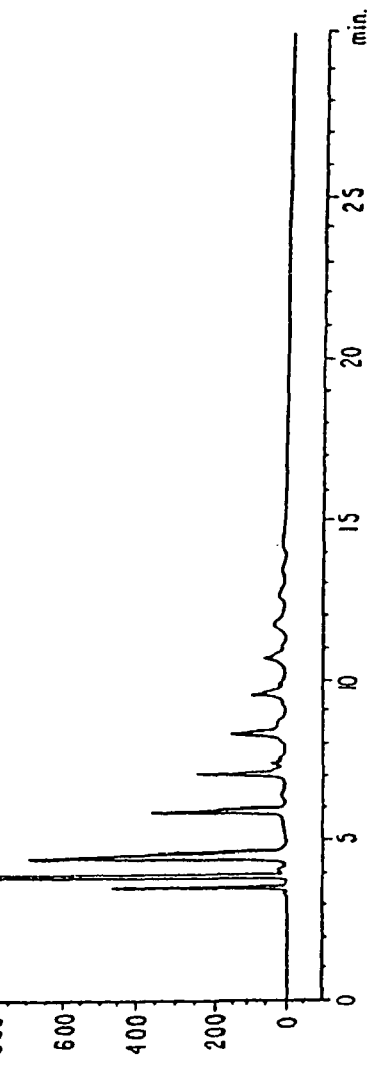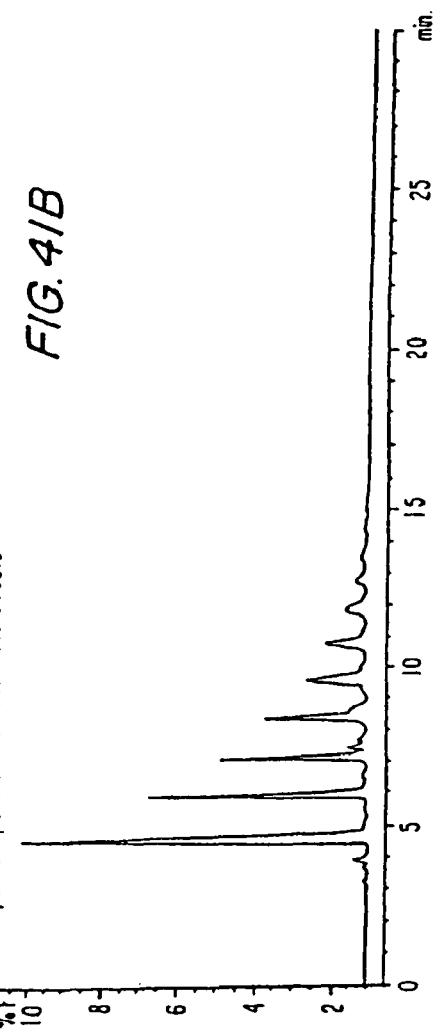

| EPICATECHIN | | | |
|---|---|---|---|
| $^1H$ | CHEMICAL SHIFT (ppm) | $^{13}C$ | CHEMICAL SHIFT (ppm) |
| 2 | 4.81 | 2 | 79.84 |
| 3 | 4.16 | 3 | 67.46 |
| 4α } 4β } | { 2.73 { 2.85 | 4 | 29.24 |
| | | 6 | 95.87 |
| 6 | 5.94 | 8 | 96.36 |
| 8 | 5.91 | 2' | 115.29 |
| 5' } 6' } | { 6.75 { 6.79 | 5' } 6' } | { 115.88 { 119.39 |
| 2' | 6.97 | | |

| CATECHIN | | | |
|---|---|---|---|
| $^1H$ | CHEMICAL SHIFT (ppm) | $^{13}C$ | CHEMICAL SHIFT (ppm) |
| 2 | 4.56 | 2 | 79.84 |
| 3 | 3.97 | 3 | 67.46 |
| 4α | 2.50 | 4 | 29.24 |
| 4β | 2.84 | 6 | 95.87 |
| 6 | 5.85 | 8 | 96.36 |
| 8 | 5.92 | 2' | 115.29 |
| 2' | 6.83 | 6' | 116.08 |
| 5' | 6.76 | 5' | 120.08 |
| 6' | 6.71 | | |

| B2 DIMER | | | |
|---|---|---|---|
| $^1H$ | CHEMICAL SHIFT (ppm) | $^{13}C$ | CHEMICAL SHIFT (ppm) |
| B4 | 2.69<br>2.83 | B4<br>T4 | 28.92<br>36.60 |
| T4 | 4.63 | B3 | 65.99 |
| B3 | 4.29 | T3 | 72.56 |
| T3 | 3.85 | T2 | 76.55 |
| T2 | 4.99 | B2 | 78.91 |
| B2 | 4.92 | T6 OR 8 | 95.48 |
| B6 | 5.92 | B6 | 96.03 |
| T6 OR 8 | 5.91 | T6 OR 8 | 96.81 |
| T6 OR 8 | 5.98 | | 100.22 |
| B2' | 7.12 | B2' | 114.77 |
| T2' | 6.92 | T2' | 115.05 |
| T5 | 6.68 | T5' | 115.35 |
| B5 | 6.70 | B5' | 115.48 |
| T6' | 6.87 | T6' | 118.95 |
| B6' | 6.58 | B6' | |
| | | T1' | 131.41<br>131.90 |

FIG. 46E

| B5 DIMER | | | |
|---|---|---|---|
| $^1H$ | CHEMICAL SHIFT (ppm) | $^{13}C$ | CHEMICAL SHIFT (ppm) |
| B4 | 2.565<br>2.745 | B4<br>T4 | 29.04<br>37.03 |
| T3 | 3.99 | B3 | 66.49 |
| B3 | 4.13 | T3 | 71.73 |
| T4 | 4.54 | T2 | 76.69 |
| B2 | 4.77 | B2 | 78.98 |
| T2 | 4.90 | B6-8 | 95.49 |
| T6+ | 6.02 | | 96.11 |
| T8 | 6.055 | T6-8 | 96.32 |
| B8 | 6.04 | | 100.18 |
| T6' | 6.64 | T2'+5' | 115.01 |
| T5' | 6.74 | B2'+5' | 115.38 |
| B5' | 6.75 | B6 | 118.90 |
| B6' | 6.78 | T6 | 118.98 |
| T2' | 6.95 | B1' | 131.62 |
| B2' | 6.99 | T1' | 131.72 |
| | | B & T | 145.00 |
| | | 3' + 4' | 145.04<br>145.04<br>145.12<br>145.20 |
| | | B + T<br>5, 7 + 8a | 154.73<br>155.50<br>157.44 |

EFFECT OF COCOA EXTRACTS ON MABP IN GUINEA PIGS

EPICATECHIN FOR HYPERTENSION TREATMENT

This application is a continuation application of U.S. application Ser. No. 10/795,552 filed Mar. 8, 2004, now U.S. Pat. No. 7,122,574, which is a continuation of U.S. application Ser. No. 10/770,969 filed Feb. 2, 2004, now U.S. Pat. No. 6,900,241, which is a divisional application of U.S. application Ser. No. 10/127,817 filed Apr. 22, 2002, which is a continuation of U.S. application Ser. No. 09/717,893 filed Nov. 21, 2000, now U.S. Pat. No. 6,670,390, which is a continuation of U.S. application Ser. No. 08/831,245 filed Apr. 2, 1997, now U.S. Pat. No. 6,297,273, which is a continuation-in-part of U.S. application Ser. No. 08/631,661 filed Apr. 2, 1996, now abandoned, each of which is hereby incorporated herein by reference.

REFERENCE TO RELATED APPLICATION

Reference is made to U.S. application Ser. No. 08/709,406, filed Sep. 6, 1996, Ser. No. 08/631,661, filed Apr. 2, 1996, and Ser. No. 08/317,226, filed Oct. 3, 1994 (now U.S. Pat. No. 5,554,645) and PCT/US96/04497, each of which is incorporated herein by reference.

FIELD OF THE INVENTION

This invention relates to cocoa extracts and compounds therefrom such as polyphenols preferably polyphenols enriched with procyanidins. This invention also relates to methods for preparing such extracts and compounds, as well as to uses for them; for instance, as antineoplastic agents, antioxidants, DNA topoisomerase II enzyme inhibitors, cyclo-oxygenase and/or lipoxygenase modulators, NO (Nitric Oxide) or NO-synthase modulators, as non-steroidal anti-inflammatory agents, apoptosis modulators, platelet aggregation modulators, blood or in vivo glucose modulators, antimicrobials, and inhibitors of oxidative DNA damage.

Documents are cited in this disclosure with a full citation for each appearing thereat or in a References section at the end of the specification, preceding the claims. These documents pertain to the field of this invention; and, each document cited herein is hereby incorporated herein by reference.

BACKGROUND OF THE INVENTION

Polyphenols are an incredibly diverse group of compounds (Ferreira et al., 1992) which widely occur in a variety of plants, some of which enter into the food chain. In some cases they represent an important class of compounds for the human diet. Although some of the polyphenols are considered to be nonnutrative, interest in these compounds has arisen because of their possible beneficial effects on health.

For instance, quercetin (a flavonoid) has been shown to possess anticarcinogenic activity in experimental animal studies (Deshner et al., 1991 and Kato et al., 1983). (+)-Catechin and (−)-epicatechin (flavan-3-ols) have been shown to inhibit Leukemia virus reverse transcriptase activity (Chu et al., 1992). Nobotanin (an oligomeric hydrolyzable tannin) has also been shown to possess anti-tumor activity (Okuda et al., 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al., 1992). Ellagic acid has also been shown to possess anticarcinogen activity in various animal tumor models (Bukharta et al., 1992). Lastly, proanthocyanidin oligomers have been patented by the Kikkoman Corporation for use as antimutagens. Indeed, the area of phenolic compounds in foods and their modulation of tumor development in experimental animal models has been recently presented at the $202^{nd}$ National Meeting of The American Chemical Society (Ho et al., 1992; Huang et al., 1992).

However, none of these reports teaches or suggests cocoa extracts or compounds therefrom, any methods for preparing such extracts or compounds therefrom, or, any uses for cocoa extracts or compounds therefrom, as antineoplastic agents, antioxidants, DNA topoisomerase II enzyme inhibitors, cyclo-oxygenase and/or lipoxygenase modulators, NO (Nitric Oxide) or NO-synthase modulators, as non-steroidal anti-inflammatory agents, apoptosis modulators, platelet aggregation modulators, blood or in vivo glucose modulators, antimicrobials, or inhibitors of oxidative DNA damage.

OBJECTS AND SUMMARY OF THE INVENTION

Since unfermented cocoa beans contain substantial levels of polyphenols, the present inventors considered it possible that similar activities of and uses for cocoa extracts, e.g., compounds within cocoa, could be revealed by extracting such compounds from cocoa and screening the extracts for activity. The National Cancer Institute has screened various *Theobroma* and *Herrania* species for anti-cancer activity as part of their massive natural product selection program. Low levels of activity were reported in some extracts of cocoa tissues, and the work was not pursued. Thus, in the antineoplastic or anti-cancer art, cocoa and its extracts were not deemed to be useful; i.e., the teachings in the antineoplastic or anti-cancer art lead the skilled artisan away from employing cocoa and its extracts as cancer therapy.

Since a number of analytical procedures were developed to study the contributions of cocoa polyphenols to flavor development (Clapperton et al., 1992), the present inventors decided to apply analogous methods to prepare samples for anti-cancer screening, contrary to the knowledge in the anti-neoplastic or anti-cancer art. Surprisingly, and contrary to the knowledge in the art, e.g., the National Cancer Institute screening, the present inventors discovered that cocoa polyphenol extracts which contain procyanidins, have significant utility as anti-cancer or antineoplastic agents.

Additionally, the inventors demonstrate that cocoa extracts containing procyanidins and compounds from cocoa extracts have utility as antineoplastic agents, antioxidants, DNA topoisomerase II enzyme inhibitors, cyclo-oxygenase and/or lipoxygenase modulators, NO (Nitric Oxide) or NO-synthase modulators, as non-steroidal antiinflammatory agents, apoptosis modulators, platelet aggregation modulators, blood or in vivo glucose modulators, antimicrobials, and inhibitors of oxidative DNA damage.

It is an object of the present invention to provide a method for producing cocoa extract and/or compounds therefrom.

It is another object of the invention to provide a cocoa extract and/or compounds therefrom.

It is still another object of the present invention to provide a polymeric compound of the formula $A_n$, wherein A is a monomer having the formula:

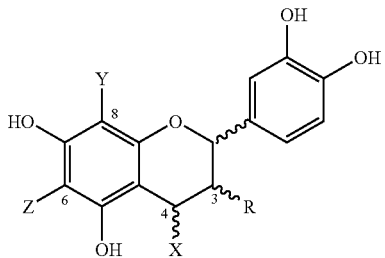

wherein n is an integer from 2 to 18, such that there is at least one terminal monomeric unit A, and a plurality of additional monomeric units;

R is 3-(α)-OH, 3-(β)-OH, 3-(α)-O-sugar, or 3-(β)-O-sugar; bonding between adjacent monomers takes place at positions 4, 6 or 8; a bond of an additional monomeric unit in position 4 has α or β stereochemistry;

X, Y and Z are selected from the group consisting of monomeric unit A, hydrogen, and a sugar, with the provisos that as to the at least one terminal monomeric unit, bonding of the additional monomeric unit thereto is at position 4 and Y=Z=hydrogen; the sugar is optionally substituted with a phenolic moiety at any position, for instance, via an ester bond, and pharmaceutically acceptable salts or derivatives thereof (including oxidation products).

It is still a further object of the present invention to provide a polymeric compound of the formula $A_n$, wherein A is a monomer having the formula:

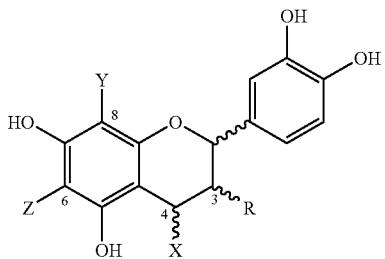

wherein n is an integer from 2 to 18, e.g., 3 to 18;

R is 3-(α)-OH, 3-(β)-OH, 3-(α)-O-sugar, or 3-(β)-O-sugar; adjacent monomers bind at position 4 by (4→6) or (4→8);

each of X, Y and Z is H, a sugar or an adjacent monomer, with the provisos that if X and Y are adjacent monomers, Z is H or sugar and if X and Z are adjacent monomers, Y is H or sugar, and that as to at least one of the two terminal monomers, bonding of the adjacent monomer is at position 4 and optionally, Y=Z=hydrogen;

a bond at position 4 has α or β stereochemistry;

the sugar is optionally substituted with a phenolic moiety at any position, for instance, via an ester bond, and pharmaceutically acceptable salts or derivatives thereof (including oxidation products).

It is another object of the invention to provide an antioxidant composition.

It is another object of the invention to demonstrate inhibition of DNA topoisomerase II enzyme activity.

It is yet another object of the present invention to provide a method for treating tumors or cancer.

It is still another object of the invention to provide an anti-cancer, anti-tumor or antineoplastic compositions.

It is still a further object of the invention to provide an antimicrobial composition.

It is yet another object of the invention to provide a cyclo-oxygenase and/or lipoxygenase modulating composition.

It is still another object of the invention to provide an NO or NO-synthase-modulating composition.

It is a further object of the invention to provide a non-steroidal antiinflammatory composition.

It is another object of the invention to provide a blood or in vivo glucose-modulating composition.

It is yet a further object of the invention to provide a method for treating a patient with an antineoplastic, antioxidant, antimicrobial, cyclo-oxygenase and/or lipoxygenase modulating or NO or NO-synthase modulating non-steroidal antiinflammatory modulating and/or blood or in vivo glucose-modulating composition.

It is an additional object of the invention to provide compositions and methods for inhibiting oxidative DNA damage.

It is yet an additional object of the invention to provide compositions and methods for platelet aggregation modulation.

It is still a further object of the invention to provide compositions and methods for apoptosis modulation.

It is a further object of the invention to provide a method for making any of the aforementioned compositions.

And, it is an object of the invention to provide a kit for use in the aforementioned methods or for preparing the aforementioned compositions.

It has been surprisingly discovered that cocoa extract, and compounds therefrom, have anti-tumor, anti-cancer or antineoplastic activity or, is an antioxidant composition or, inhibits DNA topoisomerase II enzyme activity or, is an antimicrobial or, is a cyclo-oxygenase and/or lipoxygenase modulator or, is a NO or NO-synthase modulator, is a non-steroidal antiinflammatory agent, apoptosis modulator, platelet aggregation modulator or, is a blood or in vivo glucose modulator, or is an inhibitor of oxidative DNA damage.

Accordingly, the present invention provides a substantially pure cocoa extract and compounds therefrom. The extract or compounds preferably comprises polyphenol(s) such as polyphenol(s) enriched with cocoa procyanidin(s), such as polyphenols of at least one cocoa procyanidin selected from (−) epicatechin, (+) catechin, procyanidin B-2, procyanidin oligomers 2 through 18, e.g., 3 through 18, such as 2 through 12 or 3 through 12, preferably 2 through 5 or 4 through 12, more preferably 3 through 12, and most preferably 5 through 12, procyanidin B-5, procyanidin A-2 and procyanidin C-1.

The present invention also provides an anti-tumor, anti-cancer or antineoplastic or antioxidant or DNA topoisomerase II inhibitor, or antimicrobial, or cyclo-oxygenase and/or lipoxygenase modulator, or an NO or NO-synthase modulator, nonsteroidal antiinflammatory agent, apoptosis modulator, platelet aggregation modulator, blood or in vivo glucose modulator, or oxidative DNA damage inhibitory composition comprising a substantially pure cocoa extract or compound therefrom or synthetic cocoa polyphenol(s) such as polyphenol(s) enriched with procyanidin(s) and a suitable carrier, e.g., a pharmaceutically, veterinary or food science acceptable carrier. The extract or compound therefrom preferably comprises cocoa procyanidin(s). The cocoa extract or compounds therefrom is preferably obtained by a process comprising reducing cocoa beans to powder, defatting the powder and, extracting and purifying active compound(s) from the powder.

The present invention further comprehends a method for treating a patient in need of treatment with an anti-tumor, anti-cancer, or antineoplastic agent or an antioxidant, or a DNA topoisomerase II inhibitor, or antimicrobial, or cyclo-oxygenase and/or lipoxygenase modulator, or an NO or NO-synthase modulator, non-steroidal antiinflammatory agent, apoptosis modulator, platelet aggregation modulator, blood or in vivo glucose modulator or inhibitor of oxidative DNA damage, comprising administering to the patient a composition comprising an effective quantity of a substantially pure cocoa extract or compound therefrom or synthetic cocoa polyphenol(s) or procyanidin(s) and a carrier, e.g., a pharmaceutically, veterinary or food science acceptable carrier. The cocoa extract or compound therefrom can be cocoa procyanidin(s); and, is preferably obtained by reducing cocoa beans to powder, defatting the powder and, extracting and purifying active compound(s) from the powder.

Additionally, the present invention provides a kit for treating a patient in need of treatment with an anti-tumor, anti-cancer, or antineoplastic agent or antioxidant or DNA topoisomerase II inhibitor, or antimicrobial, or cyclo-oxygenase and/or lipoxygenase modulator, or an NO or NO-synthase modulator, non-steroidal antiinflammatory agent, apoptosis modulator, platelet aggregation modulator inhibitor of oxidative DNA damage, or blood or in vivo glucose modulator comprising a substantially pure cocoa extract or compounds therefrom or synthetic cocoa polyphenol(s) or procyanidin(s) and a suitable carrier, e.g., a pharmaceutically, veterinary or food science acceptable carrier, for admixture with the extract or compound therefrom or synthetic polyphenol(s) or procyanidin(s).

The present invention provides compounds as illustrated in FIGS. 38A to 38P and 39A to 39AA; and linkages of 4→6 and 4→8 are presently preferred.

The invention even further encompasses food preservation or preparation compositions comprising an inventive compound, and methods for preparing or preserving food by adding the composition to food.

And, the invention still further encompasses a DNA topoisomerase II inhibitor comprising an inventive compound and a suitable carrier or diluent, and methods for treating a patient in need of such treatment by administration of the composition.

Considering broadly the aforementioned embodiments involving cocoa extracts, the invention also includes such embodiments wherein an inventive compound is used instead of or as the cocoa extracts. Thus, the invention comprehends kits, methods, and compositions analogous to those above-stated with regard to cocoa extracts and with an inventive compound.

These and other objects and embodiments are disclosed or will be obvious from the following Detailed Description.

BRIEF DESCRIPTION OF THE DRAWINGS

The following Detailed Description will be better understood by reference to the accompanying drawings wherein:

FIG. 1 shows a representative gel permeation chromatogram from the fractionation of crude cocoa procyanidins;

FIGS. 4A-4E show representative HPLC chromatograms of five fractions employed in screening for anti-cancer or antineoplastic activity;

FIG. 15K shows the growth inhibition of Hela cells when treated with crude polyphenol extracts obtained from eight different cocoa genotypes (% control vs. concentration, µg/mL; open circle is C-1, darkened circle is C-2, open inverted triangle is C-3, darkened inverted triangle is C4, open square is C-5, darkened circle is C-6, open triangle is C-7, darkened triangle is C-8; C-1=UF-12: horti race=Trinitario and description is crude extracts of UF-12 (Brazil) cocoa polyphenols (decaffeinated/detheobrominated); C-2=NA-33: horti race=Forastero and description is crude extracts of NA-33 (Brazil) cocoa polyphenols (decaffeinated/detheobrominated); C-3=EEG-48: horti race=Forastero and description is crude extracts of EEG48 (Brazil) cocoa polyphenols (decaffeinated/detheobrominated); C4=unknown: horti race=Forastero and description is crude extracts of unknown (W. African) cocoa polyphenols (decaffeinated/detheobrominated); C-5=UF-613: horti race=Trinitario and description is crude extracts of UF-613 (Brazil) cocoa polyphenols (decaffeinated/detheobrominated); C-6=ICS-100: horti race=Trinitario (to Nicaraguan Criollo ancestor) and description is crude extracts of ICS-100 (Brazil) cocoa polyphenols (decaffeinated/detheobrominated); C-7=ICS-139: horti race=Trinitario (Nicaraguan Criollo ancestor) and description is crude extracts of ICS-139 (Brazil) cocoa polyphenols (decaffeinated/detheobrominated); C-8=UIT-1: horti race=Trinitario and description is crude extracts of UIT-1 (Malaysia) cocoa polyphenols (decaffeinated/detheobrominated);

FIG. 15N shows a representative semi-preparative reverse phase HPLC separation for combined cocoa procyanidin fractions D and E;

FIG. 15O shows a representative normal phase semi-preparative HPLC separation of a crude cocoa polyphenol extract;

FIG. 17 shows a typical Agarose Gel indicating inhibition of topoisomerase II catalyzed decatenation of kinetoplast DNA by cocoa procyanidin fractions (Lane 1 contains 0.5 µg of marker (M) monomer-length kinetoplast DNA circles; Lanes 2 and 20 contain kinetoplast DNA that was incubated with Topoisomerase II in the presence of 4% DMSO, but in the absence of any cocoa procyanidins. (Control-C); Lanes 3 and 4 contain kinetoplast DNA that was incubated with Topoisomerase II in the presence of 0.5 and 5.0 µg/mL cocoa procyanidin fraction A; Lanes 5 and 6 contain kinetoplast DNA that was incubated with Topoisomerase II in the presence of 0.5 and 5.0 µg/mL cocoa procyanidin fraction B; Lanes 7, 8, 9, 13, 14 and 15 are replicates of kinetoplast DNA that was incubated with Topoisomerase II in the presence of 0.05, 0.5 and 5.0 µg/mL cocoa procyanidin fraction D; Lanes 10, 11, 12, 16, 17 and 18 are replicates of kinetoplast DNA that was incubated with Topoisomerase II in the presence of 0.05, 0.5, and 5.0 µg/mL cocoa procyanidin fraction E; Lane 19 is a replicate of kinetoplast DNA that was incubated with Topoisomerase II in the presence of 5.0 µg/mL cocoa procyanidin fraction E);

FIG. 32 shows the blood glucose tolerance profiles from various test mixtures;

FIGS. 33A-B show the effects of indomethacin on COX-1 and COX-2 activities;

FIG. 37 shows the purification scheme for the isolation of procyanidins from cocoa;

FIGS. 40A-B show 70 minute gradients for normal phase HPLC separation of procyanidins, detected by UV and fluorescence, respectively;

FIGS. 41A-B show 30 minute gradients for normal phase HPLC separation of procyanidins, detected by UV and fluorescence, respectively;

FIGS. 46B-G show the $^{13}C$, APT, $^1H$, HMQC, COSY and HOHAHA NMR spectra for the B2 dimer;

DETAILED DESCRIPTION

Compounds of the Invention

Figure 2A:
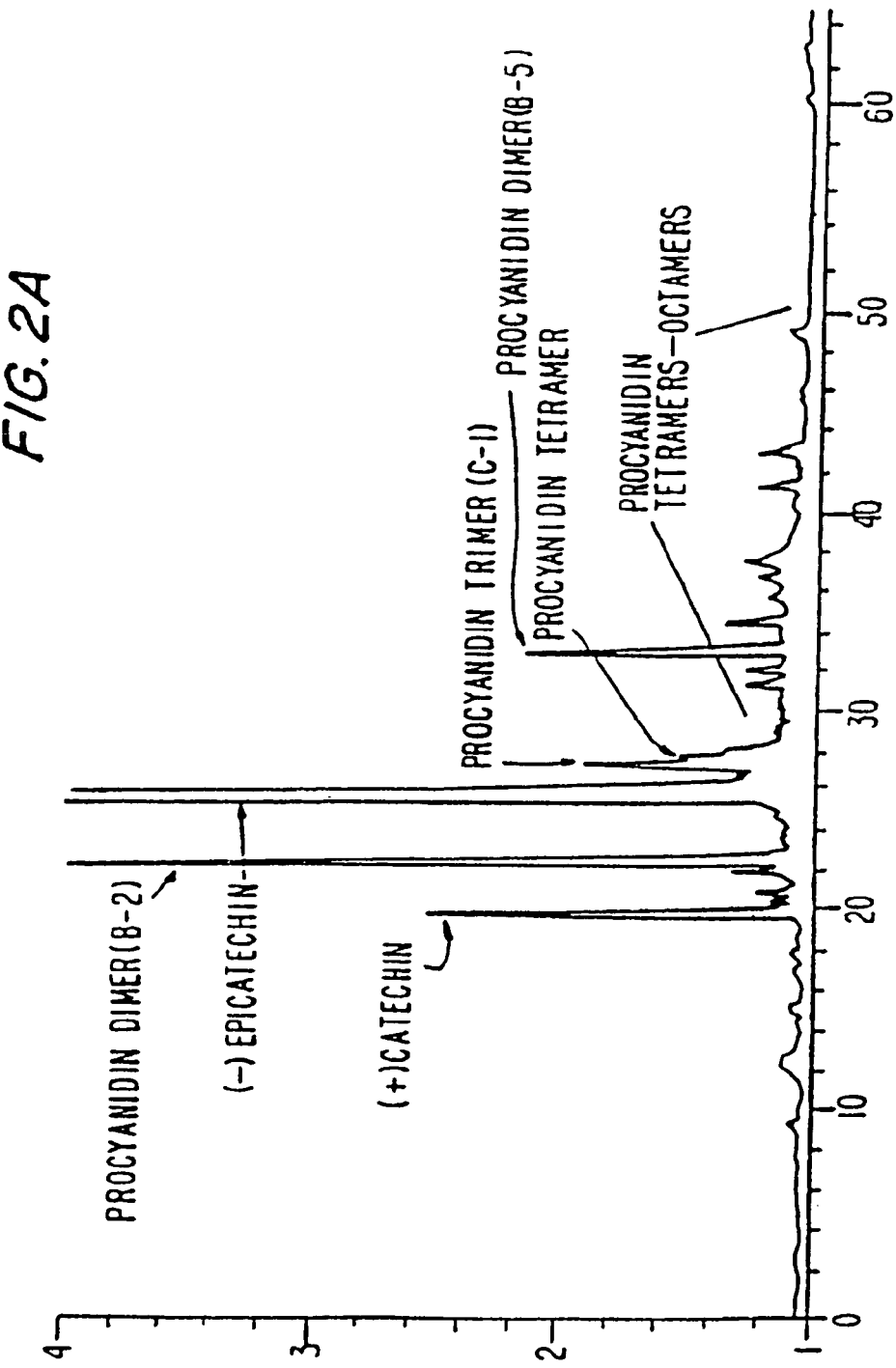
FIG. 2A shows a representative reverse-phase HPLC chromatogram showing the separation (elution profile) of cocoa procyanidins extracted from unfermented cocoa.

As discussed above, it has now been surprisingly found that cocoa extracts or compounds derived therefrom exhibit anti-cancer, anti-tumor or antineoplastic activity, antioxidant activity, inhibit DNA topoisomerase II enzyme and oxidative damage to DNA, and have antimicrobial, cyclo-oxygenase and/or lipoxygenase, NO or NO-synthase, apoptosis, platelet aggregation and blood or in vivo glucose-modulating activities, as well as efficacy as a non-steroidal antiinflammatory agent.

The extracts, compounds or combination of compounds derived therefrom are generally prepared by reducing cocoa beans to a powder, defatting the powder, and extracting and purifying the active compound(s) from the defatted powder. The powder can be prepared by freeze-drying the cocoa beans and pulp, depulping and dehulling the freeze-dried cocoa beans and grinding the dehulled beans. The extraction of active compound(s) can be by solvent extraction techniques. The extracts comprising the active compounds can be purified, e.g., to be substantially pure, for instance, by gel permeation chromatography or by preparative High Performance Liquid Chromatography (HPLC) techniques or by a combination of such techniques.

With reference to the isolation and purification of the compounds of the invention derived from cocoa, it will be understood that any species of *Theobroma, Herrania* or inter- and intra-species crosses thereof may be employed. In this regard, reference is made to Schultes, "Synopsis of *Herrania*," Journal of the Arnold Arboretum, Vol. XXXIX, pp. 217 to 278, plus plates I to XVII (1985), Cuatrecasas, "Cocoa and Its Allies, A Taxonomic Revision of the Genus *Theobroma*," Bulletin of the United States National Museum, Vol. 35, part 6, pp. 379 to 613, plus plates 1 to 11 (Smithsonian Institution, 1964), and Addison, et al., "Observations on the Species of the Genus *Theobroma* Which Occurs in the Amazon," Bol. Tech. Inst. Agronomico de Nortes, 25(3) (1951).

Additionally, Example 25 lists the heretofore never reported concentrations of the inventive compounds found in *Theobroma* and *Herrania* species and their inter- and intra-species crosses; and Example 25 also describes methods of modulating the amounts of the inventive compounds which may be obtained from cocoa by manipulating cocoa fermentation conditions.

An outline of the purification protocol utilized in the isolation of substantially pure procyanidins is shown in FIG. 37. Steps 1 and 2 of the purification scheme are described in Examples 1 and 2; steps 3 and 4 are described in Examples 3, 13 and 23; step 5 is described in Examples 4 and 14; and step 6 is described in Examples 4, 14 and 16. The skilled artisan would appreciate and envision modifications in the purification scheme outlined in FIG. 37 to obtain the active compounds without departing from the spirit or scope thereof and without undue experimentation.

The extracts, compounds and combinations of compounds derived therefrom having activity, without wishing to necessarily be bound by any particular theory, have been identified as cocoa polyphenol(s), such as procyanidins. These cocoa procyanidins have significant anti-cancer, anti-tumor or anti-neoplastic activity; antioxidant activity; inhibit DNA topoisomerase II enzyme and oxidative damage to DNA; possess antimicrobial activity; have the ability to modulate cyclo-oxygenase and/or lipoxygenase, NO or NO-synthase, apoptosis, platelet aggregation and blood or in vivo glucose, and have efficacy as non-steroidal antiinflammatory agents.

The present invention provides a compound of the formula:

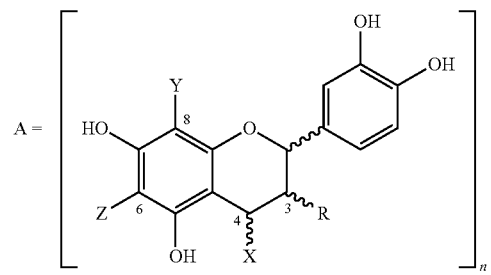

wherein: n is an integer from 2 to 18, e.g., 3 to 12, such that there is a first monomeric unit A, and a plurality of other monomeric units;

R is 3-(α)-OH, 3-(β)-OH, 3-(α)-O-sugar, or 3-(β)-O-sugar;

position 4 is alpha or beta stereochemistry;

X, Y and Z represent positions for bonding between monomeric units, with the provisos that as to the first monomeric unit, bonding of another monomeric unit thereto is at position 4 and Y=Z=hydrogen, and, that when not for bonding monomeric units, X, Y and Z are hydrogen, or Z, Y are sugar and X is hydrogen, or X is alpha or beta sugar and Z, Y are hydrogen, or combinations thereof. The compound can have n as 5 to 12, and certain preferred compounds have n as 5. The sugar can be selected from the group consisting of glucose, galactose, xylose, rhamnose, and arabinose. The sugar of any or all of R, X, Y and Z can optionally be substituted with a phenolic moiety via an ester bond.

Thus, the invention can provide a compound of the formula:

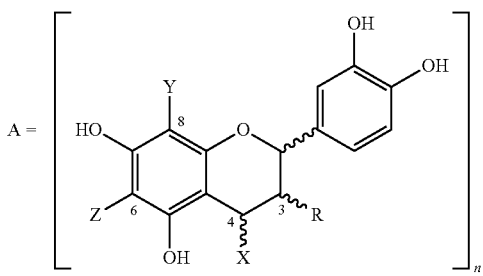

wherein: n is an integer from 2 to 18, e.g., 3 to 12, advantageously 5 to 12, and preferably n is 5, such that there is a first monomeric unit A,

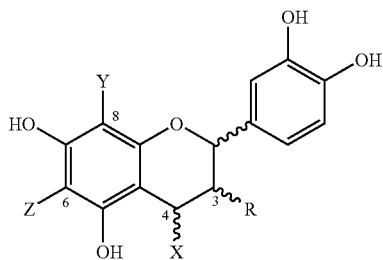

and a plurality of other monomeric units of A;

R is 3-(α)-OH, 3-(β)-OH, 3-(α)-O-sugar, or 3-(β)-O-sugar;

position 4 is alpha or beta stereochemistry;

X, Y and Z represent positions for bonding between monomeric units, with the provisos that as to the first monomeric unit, bonding of another monomeric unit thereto is at position 4 and Y=Z=hydrogen, and, that when not for bonding monomeric units, X, Y and Z are hydrogen or Z, Y are sugar and X is hydrogen, or X is alpha or beta sugar and Z and Y are hydrogen, or combinations thereof; and said sugar is optionally substituted with a phenolic moiety via an ester bond.

Accordingly, the present invention provides a polymeric compound of the formula $A_n$, wherein A is a monomer having the formula:

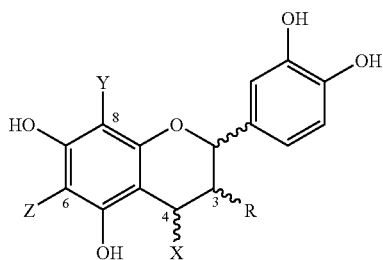

wherein n is an integer from 2 to 18, such that there is at least one terminal monomeric unit A, and at least one or a plurality of additional monomeric units;

R is 3-(α)-OH, 3-(β)-OH, 3-(α)-O-sugar, or 3-(β)-O-sugar;

bonding between adjacent monomers takes place at positions 4, 6 or 8;

a bond of an additional monomeric unit in position 4 has α or β stereochemistry;

X, Y and Z are selected from the group consisting of monomeric unit A, hydrogen, and a sugar, with the provisos that as to the at least one terminal monomeric unit, bonding of the additional monomeric unit thereto (i.e., the bonding of the monomeric unit adjacent the terminal monomeric unit) is at position 4 and optionally, Y=Z=hydrogen;

the sugar is optionally substituted with a phenolic moiety at any position, for instance via an ester bond, and pharmaceutically acceptable salts or derivatives thereof (including oxidation products).

In preferred embodiments, n can be 3 to 18, 2 to 18, 3 to 12, e.g., 5 to 12; and, advantageously, n is 5. The sugar is selected from the group consisting of glucose, galactose, xylose, rhamnose and arabinose. The sugar of any or all of R, X, Y and Z can optionally be substituted at any position with a phenolic moiety via an ester bond. The phenolic moiety is selected from the group consisting of caffeic, cinnamic, coumaric, ferulic, gallic, hydroxybenzoic and sinapic acids.

Additionally, the present invention provides a polymeric compound of the formula $A_n$, wherein A is a monomer having the formula:

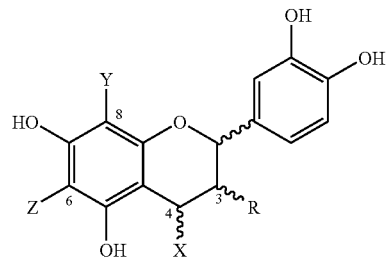

wherein n is an integer from 2 to 18, e.g., 3 to 18, advantageously 3 to 12, e.g., 5 to 12, preferably n is 5;

R is 3-(α)-OH, 3-(β)-OH, 3-(α)-O-sugar, or 3-(β)-O-sugar;

adjacent monomers bind at position 4 by (4→6) or (4→8);

each of X, Y and Z is H, a sugar or an adjacent monomer, with the provisos that if X and Y are adjacent monomers, Z is H or sugar and if X and Z are adjacent monomers, Y is H or sugar, and that as to at least one of the two terminal monomers, bonding of the adjacent monomer is at position 4 and optionally, Y=Z=hydrogen;

a bond at position 4 has α or β stereochemistry;

the sugar is optionally substituted with a phenolic moiety at any position, for instance, via an ester bond, and pharmaceutically acceptable salts or derivatives thereof (including oxidation products).

With regard to the recitation of "at least one terminal monomeric unit A", it will be understood that the inventive compounds have two terminal monomeric units, and that the two terminal monomeric unit A may be the same or different. Additionally, it will be understood that the recitation of "at least one terminal monomeric unit A" includes embodiments wherein the terminal monomeric unit A is referred to as a "first monomeric unit", with the recitation of "first monomeric unit" relating to that monomer to which other monomeric units are added, resulting in a polymeric compound of the formula $A_n$. Moreover, with regard to the at least one of the two terminal monomers, bonding of the adjacent monomer is at position 4 and optionally, Y=Z=hydrogen.

As to the recitation of the term "combinations thereof", it will be understood that one or more of the inventive compounds may be used simultaneously, e.g., administered to a subject in need of treatment in a formulation comprising one or more inventive compounds.

The inventive compounds or combinations thereof display the utilities noted above for cocoa extracts; and throughout the disclosure, the term "cocoa extract" may be substituted by compounds of the invention or combinations thereof, such that it will be understood that the inventive compounds or combinations thereof can be cocoa extracts.

The term "oligomer", as used herein, refers to any compounds or combinations thereof of the formula presented above, wherein n is 2 through 18. When n is 2, the oligomer is termed a "dimer"; when n is 3, the oligomer is termed a "trimer"; when n is 4, the oligomer is termed a "tetramer"; when n is 5; the oligomer is termed a "pentamer"; and similar recitations may be designated for oligomers having n up to and including 18, such that when n is 18, the oligomer is termed an "octadecamer".

The inventive compounds or combinations thereof can be isolated, e.g., from a natural source such as any species of *Theobroma, Herrania* or inter- or intra-species crosses thereof; or, the inventive compounds or combinations thereof can be purified, e.g., compounds or combinations thereof can be substantially pure; for instance, purified to apparent homogeneity. Purity is a relative concept, and the numerous Examples demonstrate isolation of inventive compounds or combinations thereof, as well as purification thereof, such that by methods exemplified a skilled artisan can obtain a substantially pure inventive compound or combination thereof, or purify them to apparent homogeneity (e.g., purity by separate, distinct chromatographic peak). Considering the Examples (e.g., Example 37), a substantially pure compound or combination of compounds is at least about 40% pure, e.g., at least about 50% pure, advantageously at least about 60% pure, e.g., at least about 70% pure, more advantageously at least about 75-80% pure, preferably, at least about 90% pure, more preferably greater than 90% pure, e.g., at least 90-95% pure, or even purer, such as greater than 95% pure, e.g., 95-98% pure.

Further, examples of the monomeric units comprising the oligomers used herein are (+)-catechin and (−)-epicatechin, abbreviated C and EC, respectively. The linkages between adjacent monomers are from position 4 to position 6 or position 4 to position 8; and this linkage between position 4 of a monomer and position 6 and 8 of the adjacent monomeric units is designated herein as (4→6) or (4→8). There are four possible stereochemical linkages between position 4 of a monomer and position 6 and 8 of the adjacent monomer; and the stereochemical linkages between monomeric units is designated herein as (4α→6) or (4β→46) or (4α→8) or (4β→8). When C is linked to another C or EC, the linkages are designated herein as (4α→6) or (4α→8). When EC is linked to another C or EC, the linkages are designated herein as (4β→6) or (4β→8).

Examples of compounds eliciting the activities cited above include dimers, EC-(4β→8)-EC and EC-(4β→6)-EC, wherein EC-(4β→8)-EC is preferred; trimers [EC-(4β→8)]$_2$-EC, [EC-(4β→8)]$_2$-C and [EC-(4β→6)]$_2$-EC, wherein [EC-(4β→8)]$_2$-EC is preferred; tetramers [EC-(4β→8)]$_3$-EC, [EC-(4β→8)]$_3$-C and [EC-(4β→8)]$_2$-EC-(4β→6)-C, wherein [EC-(4β→8)]$_3$-EC is preferred; and pentamers [EC-(4β→8)]$_4$-EC, [EC-(4β→8)]$_3$-EC-(4β→6)-EC, [EC-(4β→8)]$_3$-EC-(4β→8)-C and [EC-(4β→8)]$_3$-EC-(4β→6)-C, wherein the 3-position of the pentamer terminal monomeric unit is optionally derivatized with a gallate or β-D-glucose; [EC-(4β→8)]$_4$-EC is preferred.

Additionally, compounds which elicit the activities cited above also include hexamers to dodecamers, examples of which are listed below:

A hexamer, wherein one monomer (C or EC) having linkages to another monomer (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]$_5$-EC, [EC-(4β→8)]$_4$-EC-(4β→6)-EC, [EC-(4β→8)]$_4$-EC-(4β→8)-C, and [EC-(4β→8)]$_4$-EC-(4β→6)-C, wherein the 3-position of the hexamer terminal monomeric unit is optionally derivatized with a gallate or a β-D-glucose; in a preferred embodiment, the hexamer is [EC-(4β→8)]$_5$-EC;

A heptamer, wherein any combination of two monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]$_6$-EC, [EC-(4β→8)]$_5$-EC-4β→6)-EC, [EC-(4β→8)]$_5$-EC-(4β→8)-C, and [EC-(4β→8)]$_5$-EC-(4β→6)-C, wherein the 3-position of the heptamer terminal monomeric unit is optionally derivatized with a gallate or a β-D-glucose; in a preferred embodiment, the heptamer is [EC-(4β→8)]$_6$-EC;

An octamer, wherein any combination of three monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]$_7$-EC, [EC-(4β→8)]$_6$-EC-(4β→6)-EC, [EC-(4β→8)]$_6$-EC-(4β→8)-C, and [EC-(4β→8)]$_6$-EC-(4β→6)-C, wherein the 3-position of the octamer terminal monomeric unit is optionally derivatized with a gallate or a β-D-glucose; in a preferred embodiment, the octamer is [EC-(4β→8)]$_7$-EC;

A nonamer, wherein any combination of four monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]$_8$-EC, [EC-(4β→8)]$_7$-EC-(4β→6)-EC, [EC-(4β→8)]$_7$-EC-(4β→8)-C, and [EC-(4β→8)]$_7$-EC-(4β→6)-C, wherein the 3-position of the nonamer terminal monomeric unit is optionally derivatized with a gallate or a β-D-glucose; in a preferred embodiment, the nonamer is [EC-(4β→8)]$_8$-EC;

A decamer, wherein any combination of five monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]$_9$-EC, [EC-(4β→8)]$_8$-EC-(4β→6)-EC, [EC-(4β→8)]$_8$-EC-(4β→8)-C, and [EC-(4β→8)]$_8$-EC-(4β→6)-C, wherein the 3-position of the decamer terminal monomeric unit is optionally derivatized with a gallate or a β-D-glucose; in a preferred embodiment, the decamer is [EC-(4β→8)]$_9$-EC;

An undecamer, wherein any combination of six monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]10-EC, [EC-(4β→8)]$_9$-EC-(4β→6)-EC, [EC- (4β→8)]$_9$-EC-(4β→8)-C, and [EC-(4β→8)]$_9$-EC-(4β→6)-C, wherein the 3-position of the undecamer terminal monomeric unit is optionally derivatized with a gallate or a β-D-glucose; in a preferred embodiment, the undecamer is [EC-(4β→8)]$_{10}$-EC; and A dodecamer, wherein any combination of seven monomers (C and/or EC) having linkages to one another (4β→8) or (4β→6) for EC linked to another EC or C, and (4α→8) or (4α→6) for C linked to another C or EC; followed by a (4β→8) linkage to a pentamer compound listed above, e.g., [EC-(4β→8)]11-EC, [EC-(4β→8)]$_{10}$-EC-(4β→6)-EC, [EC-(4β→8)]$_{10}$-EC-(4β→8)—C, and [EC-(4β→8)]$_{10}$-EC-(4β→6)—C, wherein the 3-position of the dodecamer terminal monomeric unit is optionally derivatized with a gallate or a β-D-glucose; in a preferred embodiment, the dodecamer is [EC-(4β→8)]$_{11}$-EC.

It will be understood from the detailed description that the aforementioned list is exemplary and provided as an illustrative source of several non-limiting examples of compounds of the invention, which is by no means an exhaustive list of the inventive compounds encompassed by the present invention.

Figure 38B:
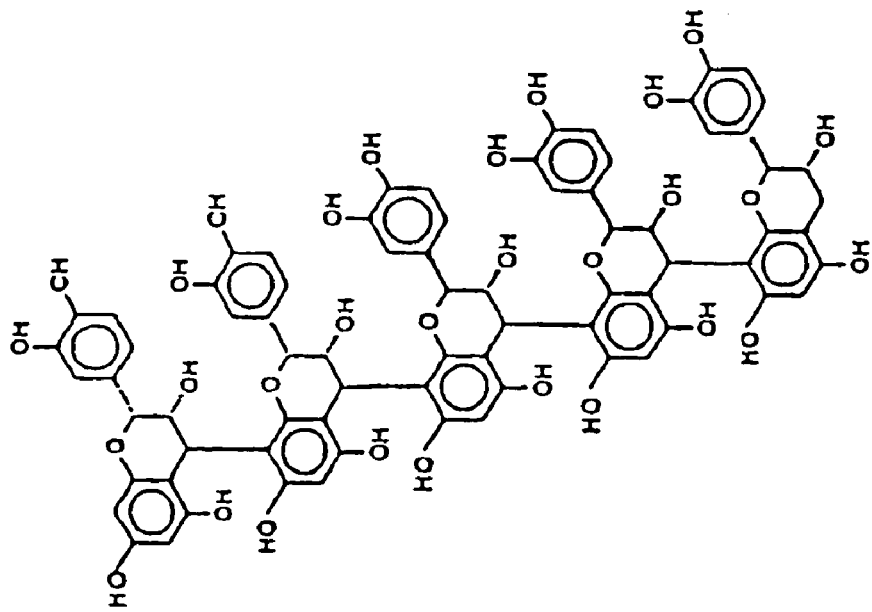
FIG. 38A to 38P shows the preferred structures of the pentamer.
Figure 38A:
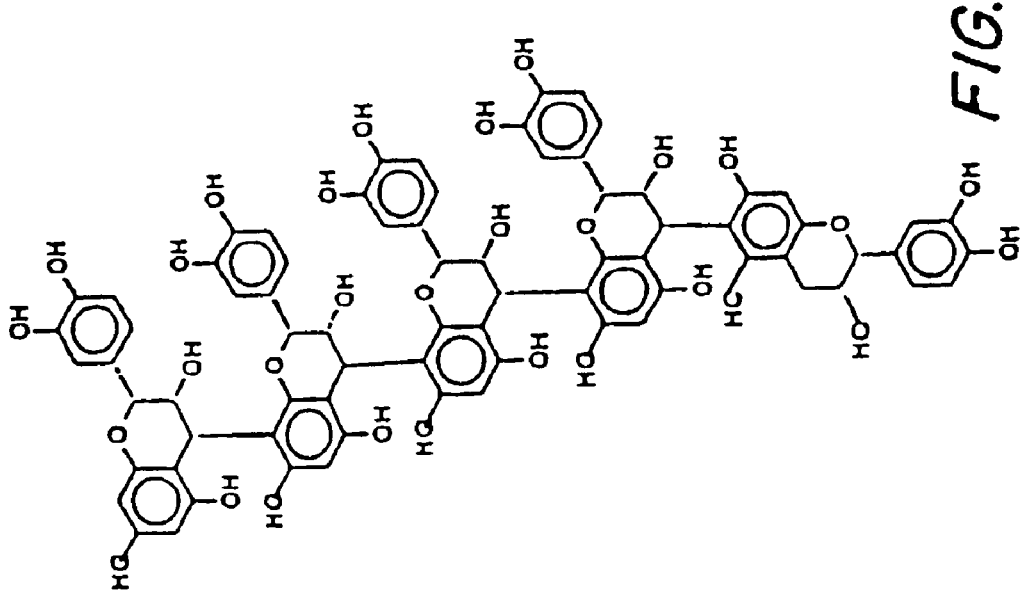
Figure 38E:
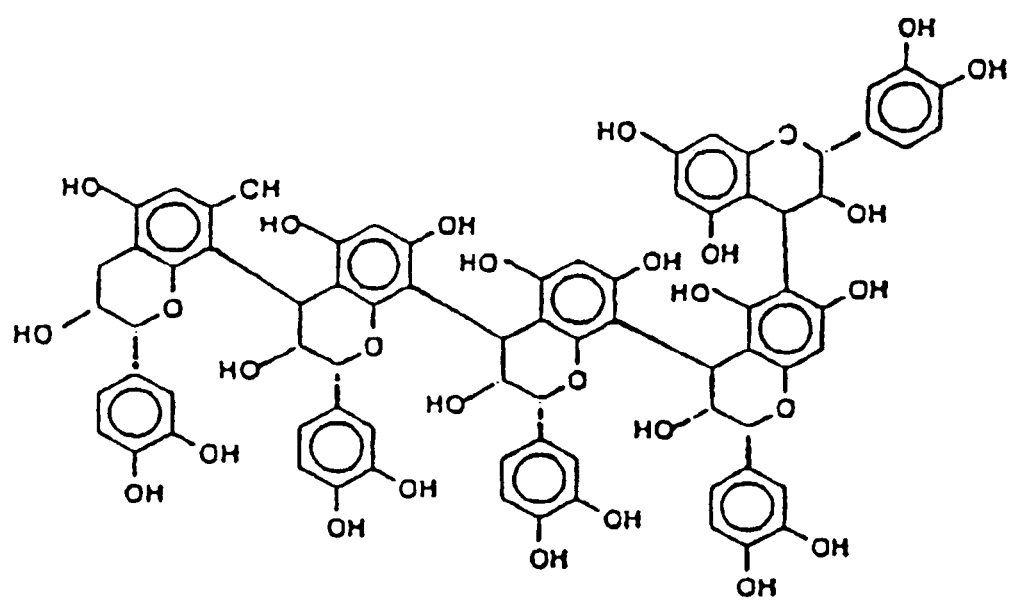
Figure 38F:
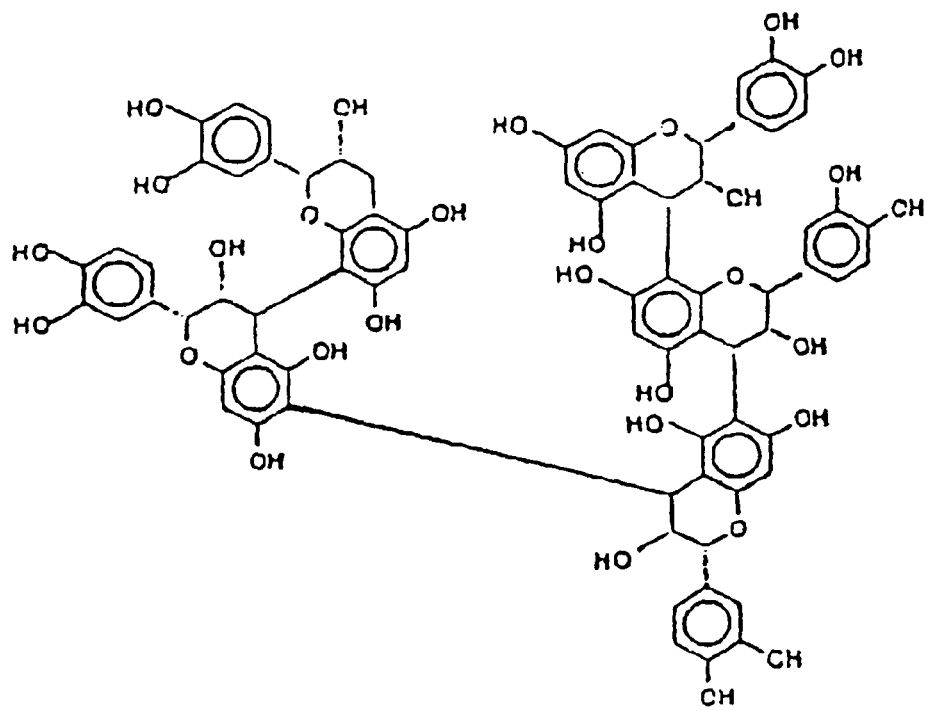
Figure 38I:
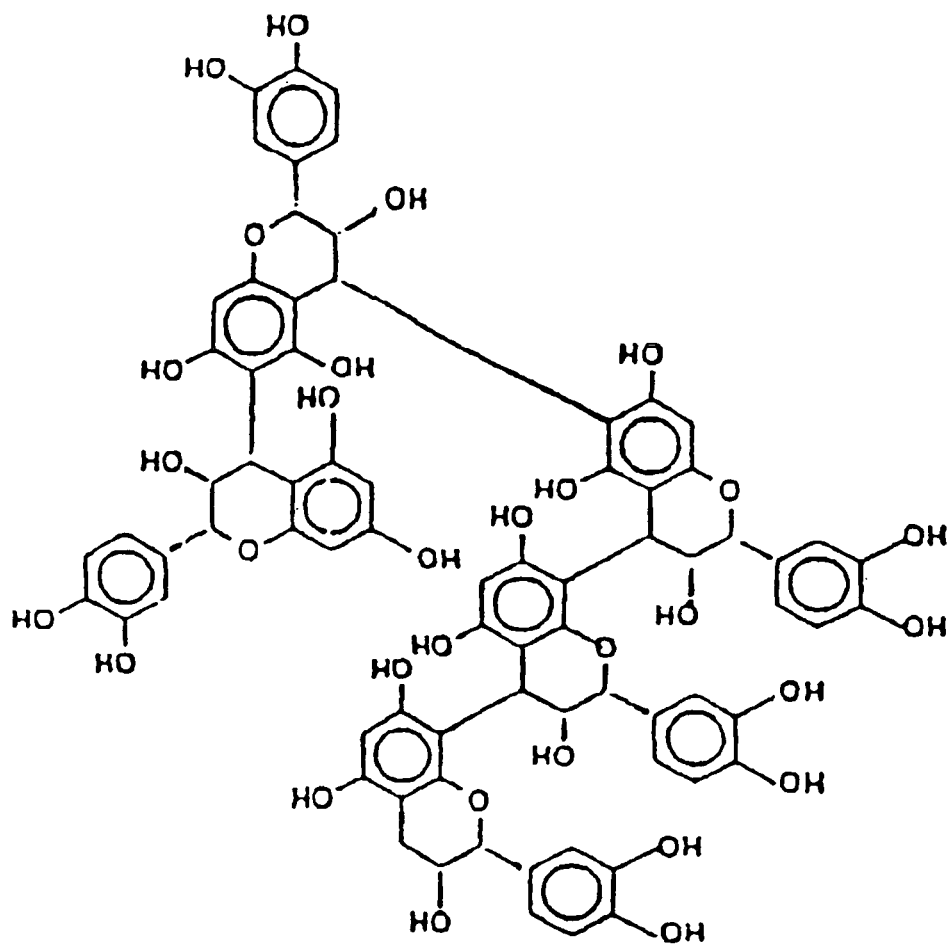
Figure 38N:
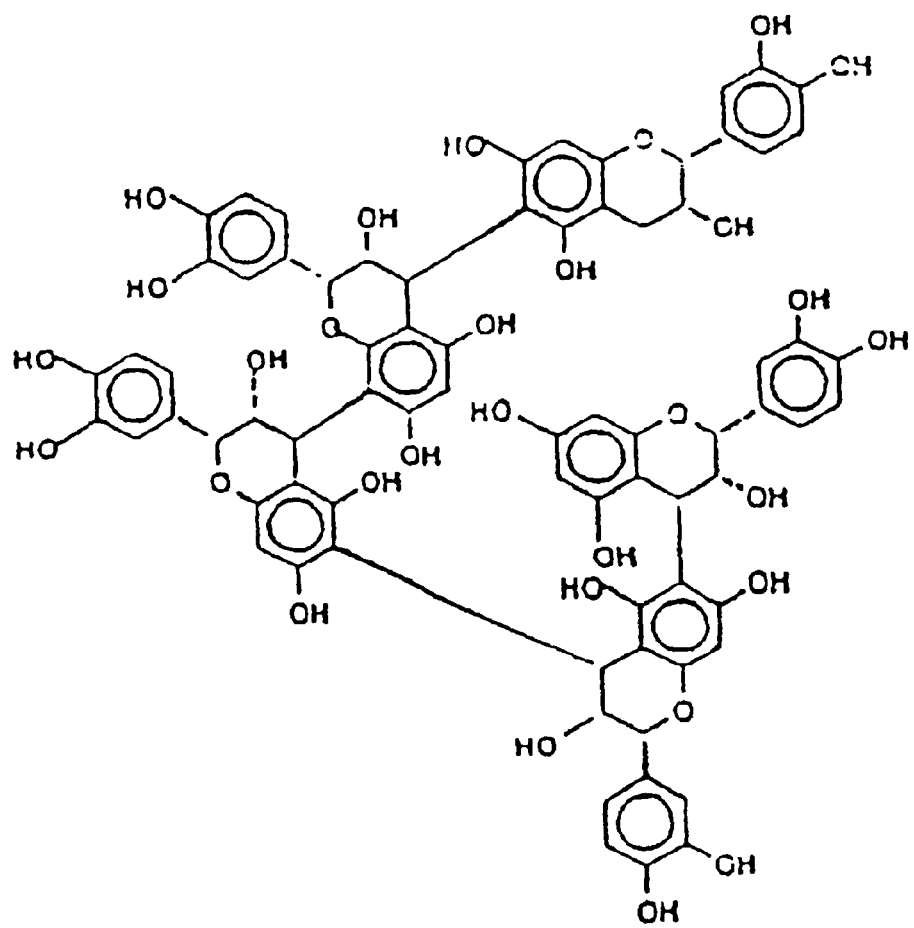
Figure 380:
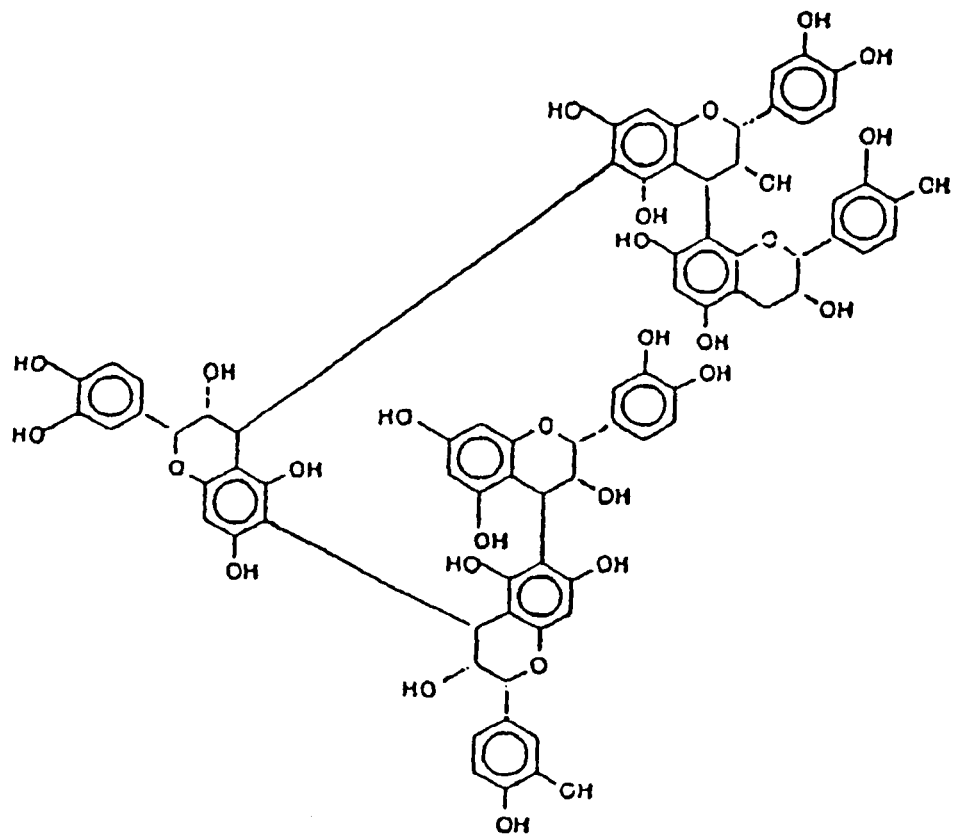
Figure 38P:
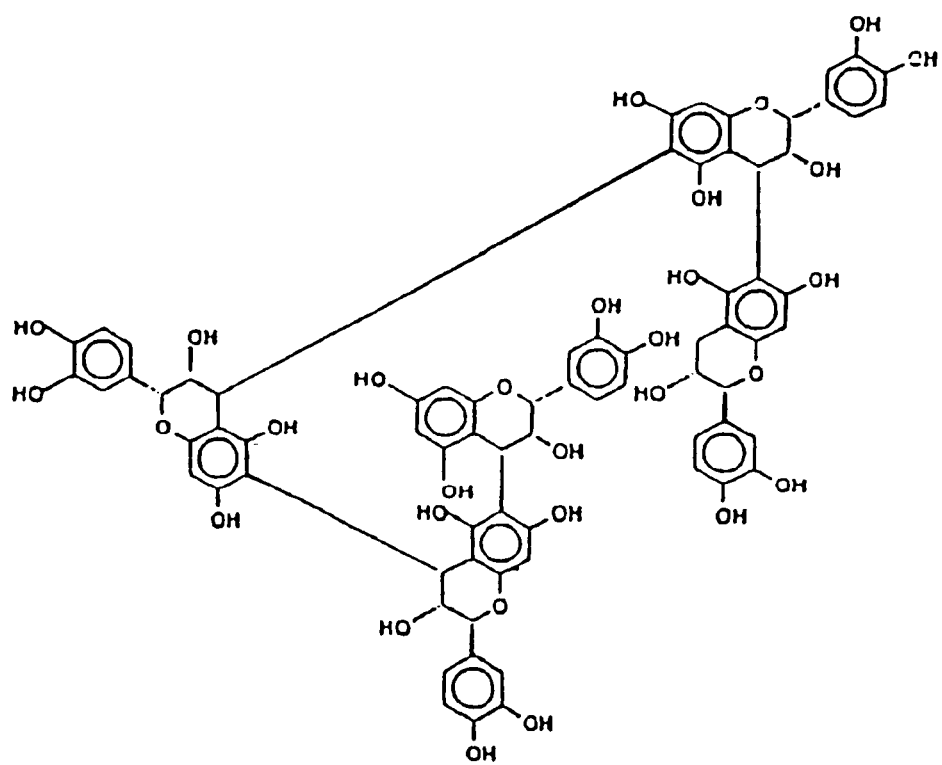
Figure 39A:
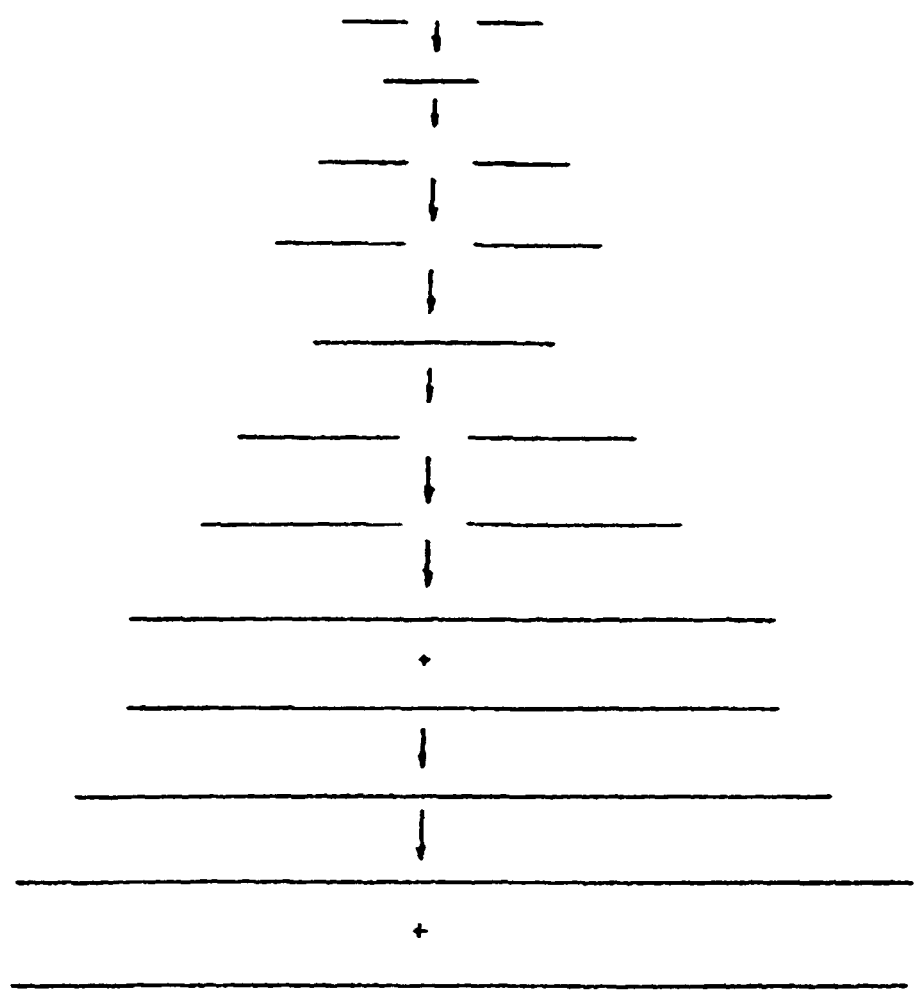
FIGS. 39A-AA show a library of stereoisomers of pentamers.
Figure 39B:
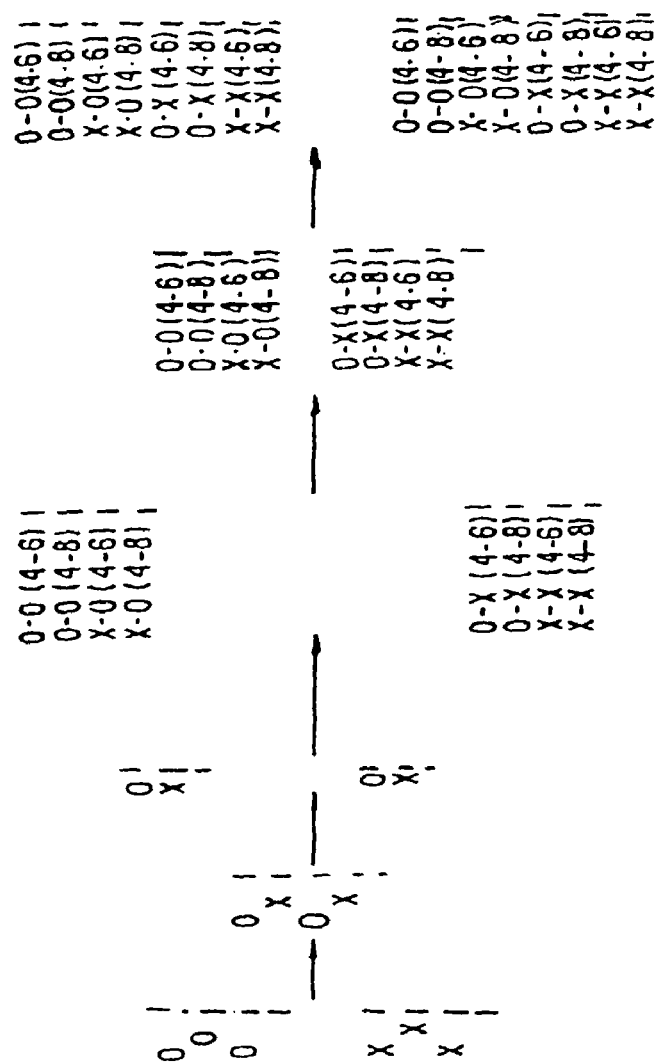
Figure 39C:
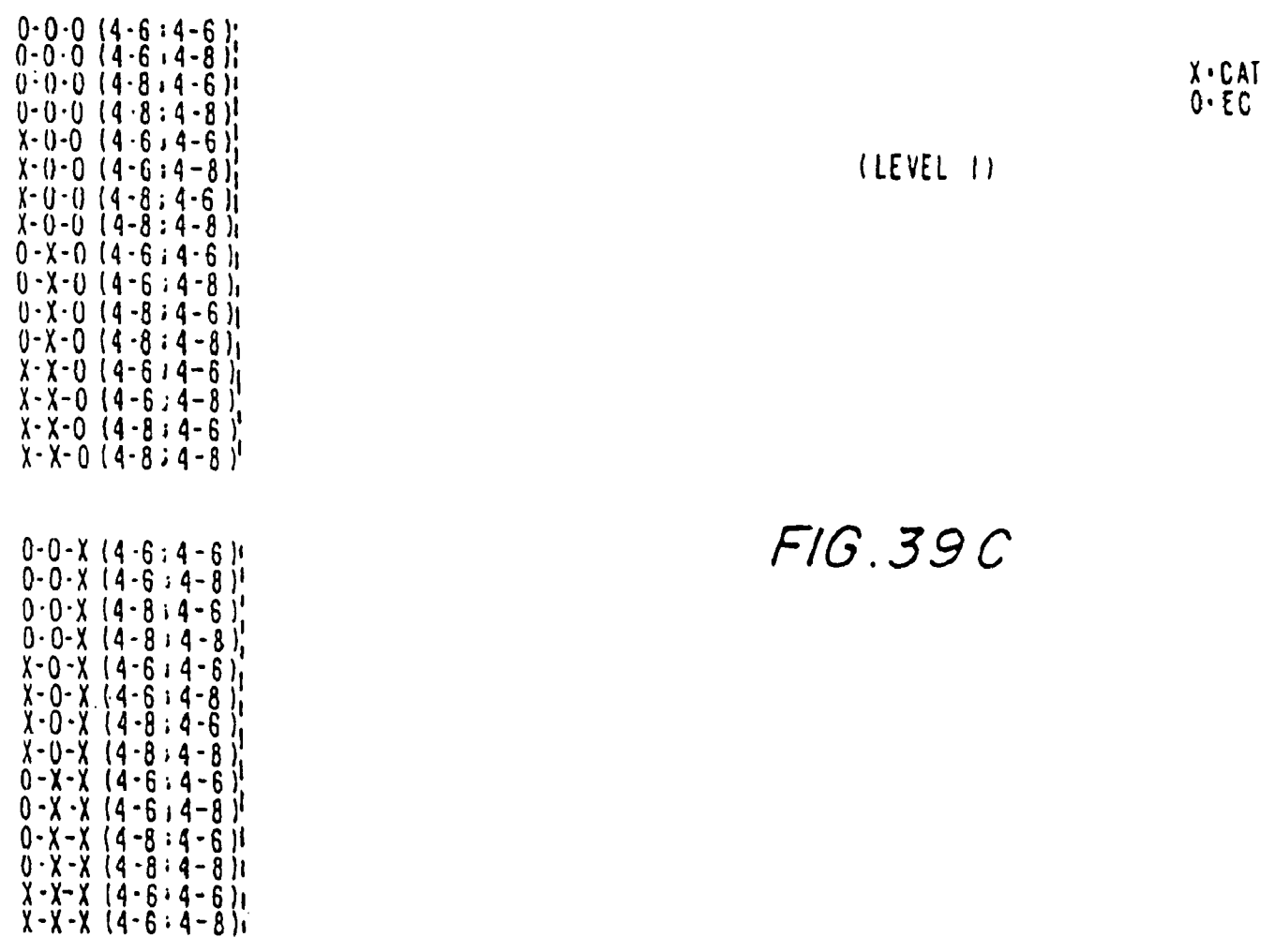
Figure 39E:
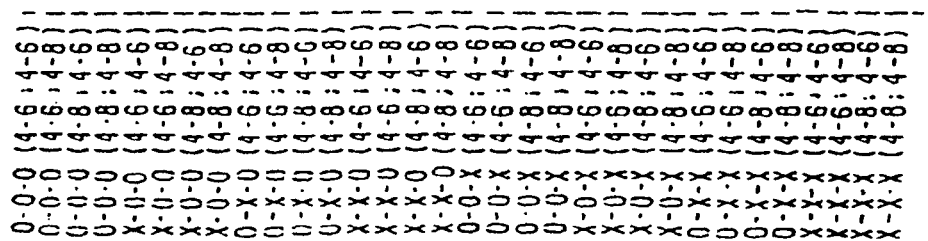
Figure 39F:
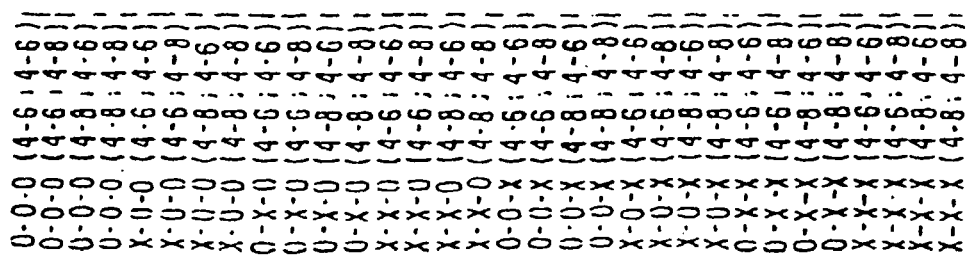
Figure 39G:
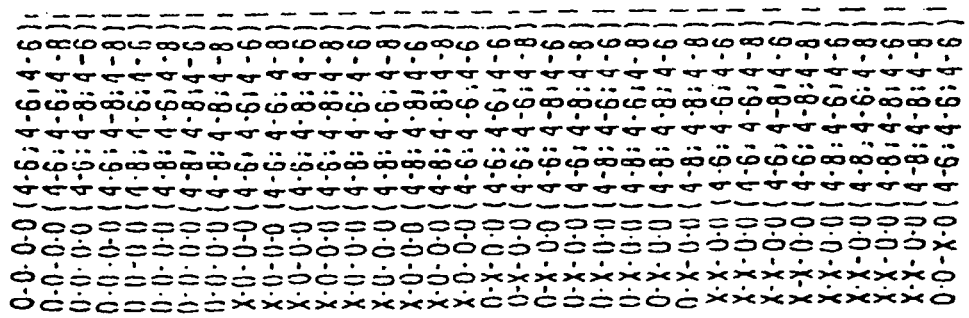
Figure 39H:
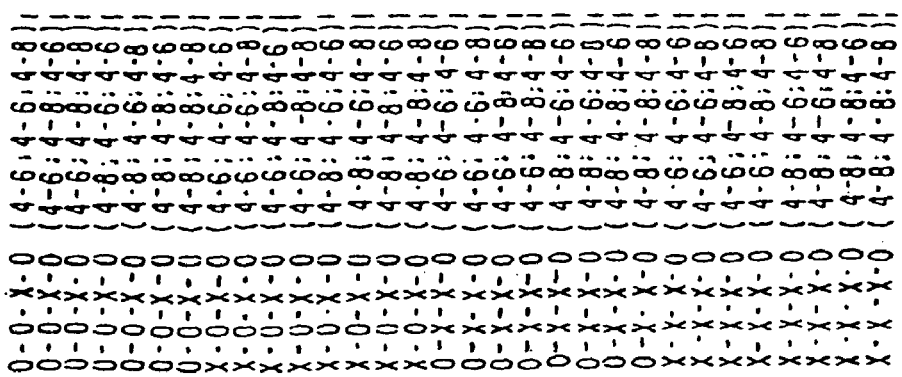
Figure 39:
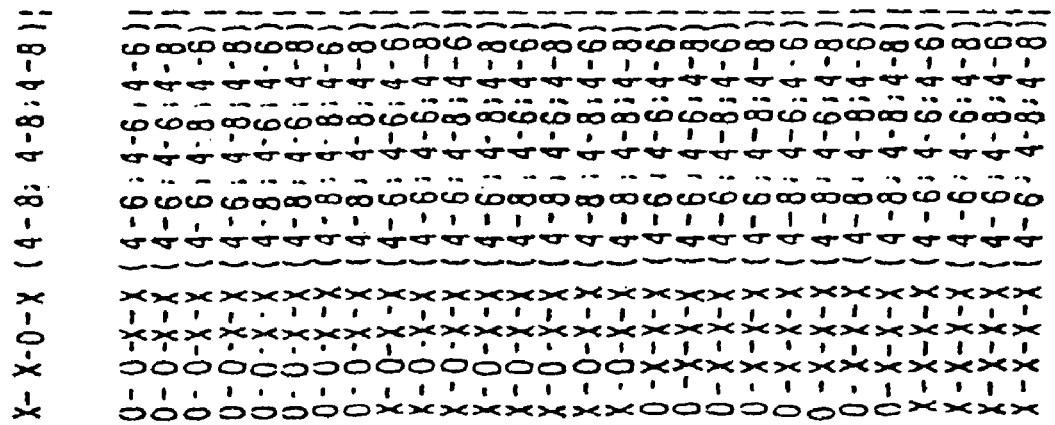
Figure 39L:
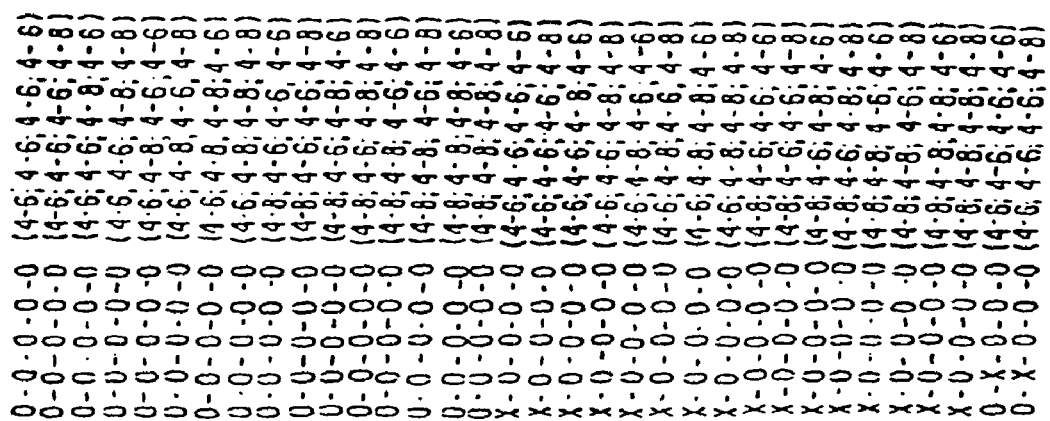
Figure 39M:
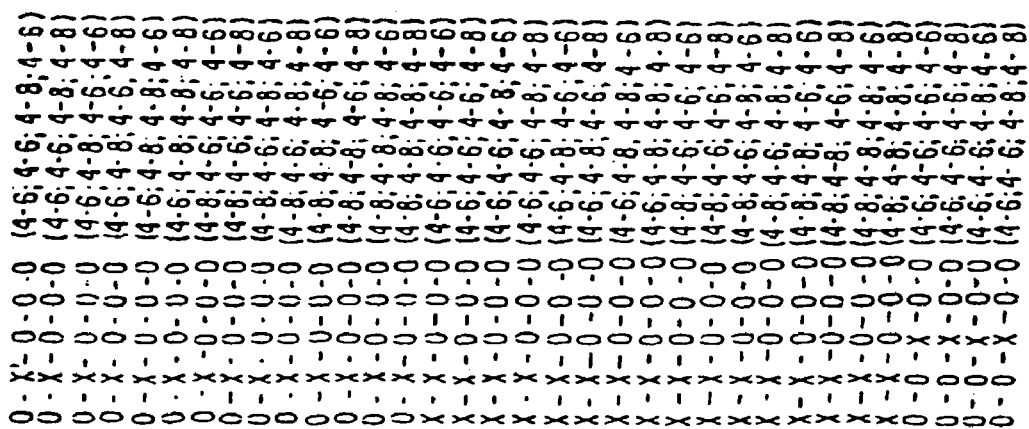
Figure 39N:
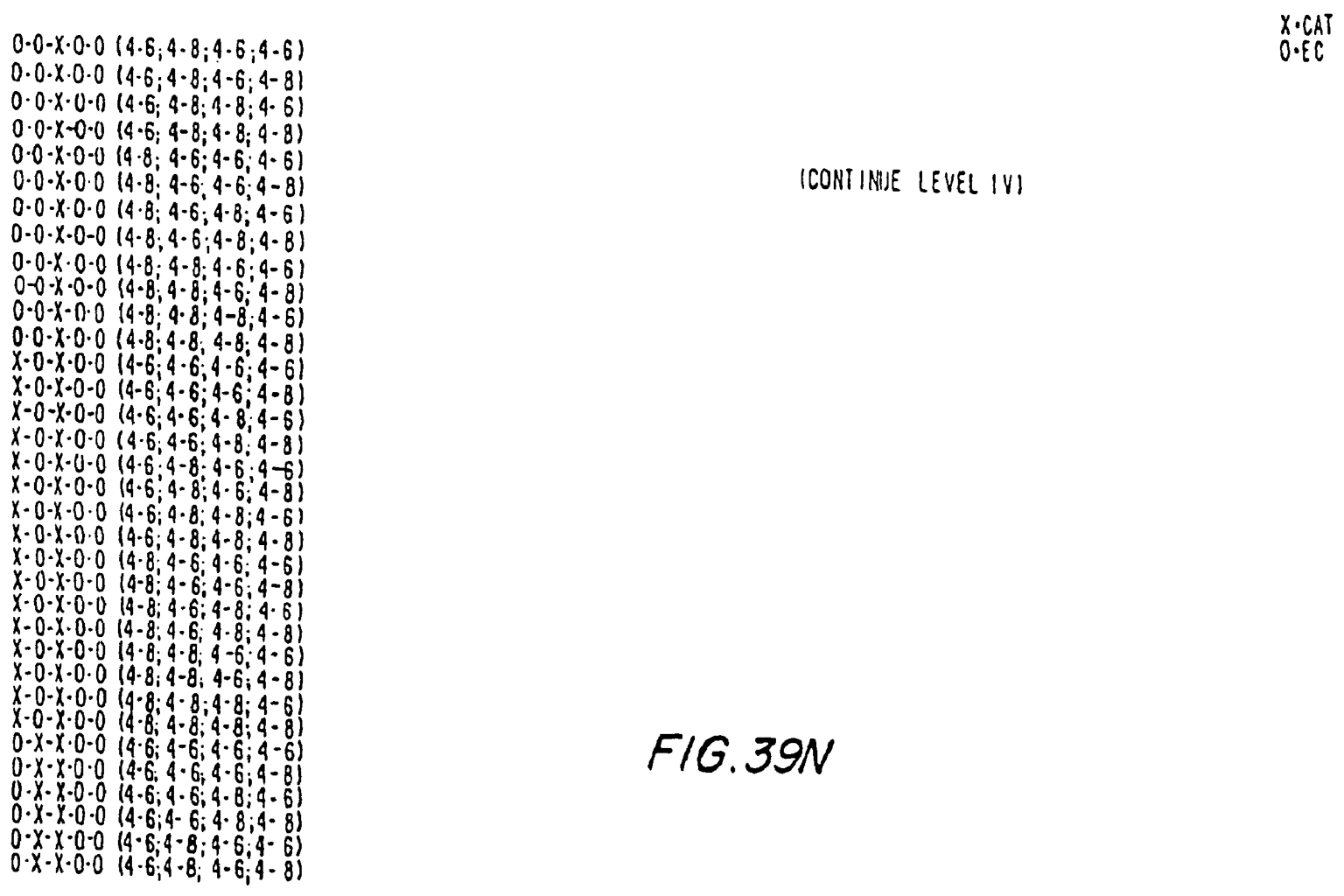
Figure 39:
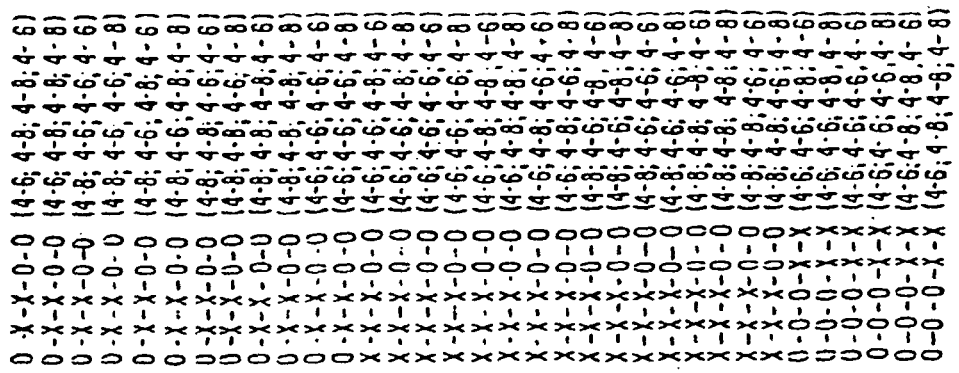

Examples 3A, 3B, 4, 14, 23, 24, 30 and 34 describe methods to separate the compounds of the invention. Examples 13, 14A-D and 16 describe methods to purify the compounds of the invention. Examples 5, 15, 18, 19, 20 and 29 describe methods to identify compounds of the invention. FIGS. 38A-P and 39A-AA illustrate a stereochemical library for representative pentamers of the invention. Example 17 describes a method to molecularly model the compounds of the invention. Example 36 provides evidence for higher oligomers in cocoa, wherein n is 13 to 18.

Furthermore, while the invention is described with respect to cocoa extracts preferably comprising cocoa procyanidins, from this disclosure the skilled organic chemist will appreciate and envision synthetic routes to obtain and/or prepare the active compounds (see e.g., Example 11). Accordingly, the invention comprehends synthetic cocoa polyphenols or procyanidins or their derivatives and/or their synthetic precursors which include, but are not limited to glycosides, gallates, esters, etc. and the like. That is, the inventive compounds can be prepared from isolation from cocoa or from any species within the *Theobroma* or *Herrania* genera, as well as from synthetic routes; and derivatives and synthetic precursors of the inventive compounds such as glycosides, gallates, esters, etc. are included in the inventive compounds. Derivatives can also include compounds of the above formulae wherein a sugar or gallate moiety is on the terminal monomer at positions Y or Z, or a substituted sugar or gallate moiety is on the terminal monomer at Y or Z.

For example, Example 8, Method C describes the use of cocoa enzymes to oxidatively modify the compounds of the invention or combinations thereof to elicit improved cytotoxicity (see FIG. 15M) against certain cancer cell lines. The invention includes the ability to enzymatically modify (e.g., cleavage or addition of a chemically significant moiety) the compounds of the invention, e.g., enzymatically with polyphenol oxidase, peroxidase, catalase combinations, and/or enzymes such as hydrolases, esterases, reductases, transferases, and the like and in any combination, taking into account kinetic and thermodynamic factors (see also Example 41 regarding hydrolysis).

With regard to the synthesis of the inventive compounds, the skilled artisan will be able to envision additional routes of synthesis, based on this disclosure and the knowledge in the art, without undue experimentation. For example, based upon a careful retrosynthetic analysis of the polymeric compounds, as well as the monomers. For instance, given the phenolic character of the inventive compounds, the skilled artisan can utilize various methods of selective protection/deprotection, coupled with organometallic additions, phenolic couplings and photochemical reactions, e.g., in a convergent, linear or biomimetic approach, or combinations thereof, together with standard reactions known to those well-versed in the art of synthetic organic chemistry, as additional synthetic methods for preparing the inventive compounds, without undue experimentation. In this regard, reference is made to W. Carruthers, *Some Modern Methods of Organic Synthesis*, 3$^{rd}$ ed., Cambridge University Press, 1986, and J. March, *Advanced Organic Chemistry*, 3$^{rd}$ ed., John Wiley & Sons, 1985, van Rensburg et al., Chem. Comm., 24: 2705-2706 (Dec. 21, 1996), Ballenegger et al., (Zyma S A) European Patent 0096 007 B1, and documents in the References section below, all of which are hereby incorporated herein by reference.

Utilities of Compounds of the Invention

With regard to the inventive compounds, it has been surprisingly found that the inventive compounds have discrete activities, and as such, the inventive compounds have broad applicability to the treatment of a variety of disease conditions, discussed hereinbelow.

COX/LOX-Associated Utilities

Atherosclerosis, the most prevalent of cardiovascular diseases, is the principle cause of heart attack, stroke and vascular circulation problems. Atherosclerosis is a complex disease which involves many cell types, biochemical events and molecular factors. There are several aspects of this disease, its disease states and disease progression which are distinguished by the interdependent consequences of Low Density Lipoprotein (LDL) oxidation, cyclo-oxygenase (COX)/lipoxygenase (LOX) biochemistry and Nitric Oxide (NO) biochemistry.

Clinical studies have firmly established that the elevated plasma concentrations of LDL are associated with accelerated atherogenesis. The cholesterol that accumulates in atherosclerotic lesions originate primarily in plasma lipoproteins, including LDL. The oxidation of LDL is a critical event in the initiation of atheroma formation and is associated with the enhanced production of superoxide anion radical ($O_2$.—). Oxidation of LDL by $O_2$.— or other reactive species (e.g., .OH, ONO.O—, lipid peroxy radical, copper ion, and iron based proteins) reduces the affinity of LDL for uptake in cells via receptor mediated endocytosis. Oxidatively modified LDLs are then rapidly taken up by macrophages which subsequently transform into cells closely resembling the "foam cells" observed in early atherosclerotic lesions.

Oxidized lipoproteins can also promote vascular injury through the formation of lipid hydroperoxides within the LDL particle. This event initiates radical chain oxidation reactions of unsaturated LDL lipids, thus producing more oxidized LDL for macrophage incorporation.

The collective accumulation of foam cells engorged with oxidized LDL from these processes results in early "fatty streak" lesions, which eventually progress to the more advanced complex lesions of atherosclerosis leading to coronary disease.

As discussed generally by Jean Marx at page 320 of Science, Vol. 265 (Jul. 15, 1994), each year about 330,000 patients in the United States undergo coronary and/or peripheral angioplasty, a procedure designed to open up blood vessels, e.g., coronary arteries, clogged by dangerous atherosclerotic plaques (atherosclerosis) and thereby restore normal blood flow. For a majority of these patients, the operation works as intended. Nearly 33% of these patients (and maybe more by some accounts), however, develop restenosis, wherein the treated arteries become quickly clogged again. These patients are no better off, and sometimes worse off, than they were before angioplasty. Excessive proliferation of smooth muscle cells (SMCs) in blood vessel walls contributes to restenosis. Increased accumulation of oxidized LDL within lesion SMCs might contribute to an atherogenic-related process like restenosis. Zhou et al., "Association Between Prior Cytomegalovirus Infection And The Risk Of Restenosis After Coronary Atherectomy," Aug. 29, 1996, New England Journal of Medicine, 335:624-630, and documents cited therein, all incorporated herein by reference. Accordingly, utility of the present invention with respect to atherosclerosis can apply to restenosis.

With regard to the inhibition by the inventive compounds of cyclooxygenases (COX; prostaglandin endoperoxide synthase), it is known that cyclooxygenases are central enzymes in the production of prostaglandins and other arachidonic acid metabolites (i.e., eicosanoids) involved in many physiological processes. COX-1 is a constitutive enzyme expressed in many tissues, including platelets, whereas COX-2, a second isoform of the enzyme, is inducible by various cytokines, hormones and tumor promoters. COX 1 produces thromboxane A2, which is involved in platelet aggregation, which in turn is involved in the progression of atherosclerosis. Its inhibition is the basis for the prophylactic effects on cardiovascular disease.

The activity of COX-1 and COX-2 is inhibited by aspirin and other nonsteroidal antiinflammatory drugs (NSAIDs), and the gastric side effects of NSAIDs are believed to be associated with the inhibition of COX-1. Moreover, it has been found that patients taking NSAIDs on a regular basis have a 40 to 50% lower risk of contracting colorectal cancer when compared to persons not being administered these type of medications; and COX-2 mRNA levels are markedly increased in 86% of human colorectal adenocarcinomas.

One significant property of COX-2 expressing cell lines is the enhanced expression of genes which participate in the modulation of apoptosis, i.e., programmed cell death. Several NSAIDs have been implicated in increased cell death and the induction of apoptosis in chicken embryo fibroblasts.

Cellular lipoxygenases are also involved in the oxidative modification of LDL through the peroxidation of unsaturated lipids. The generation of lipid peroxy radicals contributes to the further radical chain oxidation of unsaturated LDL lipids, producing more oxidized LDL for macrophage incorporation.

It has been surprisingly found that the inventive compounds have utility in the treatment of diseases associated with COX/LOX. In Example 28, COX was inhibited by individual inventive compounds at concentrations similar to a known NSAID, indomethacin.

For COX inhibition, the inventive compounds are oligomers, where n is 2 to 18. In a preferred embodiment, the inventive compounds are oligomers where n is 2 to 10, and more preferably, the inventive compounds are oligomers where n is 2 to 5.

Examples of compounds eliciting the inhibitory activity with respect to COX/LOX cited above include dimers, trimers, tetramers and pentamers, discussed above.

Hence, given the significant inhibitory potency of the inventive compounds on COX-2, coupled with the cytotoxic effects on a putative COX-2 expression colon cancer cell line, the inventive compounds possess apoptotic activity as inhibitors of the multistep progression leading to carcinomas, as well as activity as members of the NSAID family of medications possessing a broad spectrum of prophylactic activities (see, e.g., Example 8, FIGS. 9D to 9H).

Further, prostaglandins, the penultimate products of the COX catalyzed conversion of arachidonic acid to prostaglandin $H_2$, are involved in inflammation, pain, fever, fetal development, labor and platelet aggregation. Therefore, the inventive compounds are efficacious for the same conditions as NSAIDs, e.g., against cardiovascular disease, and stroke, etc. (indeed, the inhibition of platelet COX-1, which reduces thromboxane $A_2$ production, is the basis for the prophylactic effects of aspirin on cardiovascular disease).

Inflammation is the response of living tissues to injury. It involves a complex series of enzyme activation, mediator release, extravasation of fluid, cell migration, tissue breakdown and repair. Inflammation is activated by phospholipase $A_2$, which liberates arachidonic acid, the substrate for COX and LOX enzymes. COX converts arachidonic acid to the prostaglandin $PGE_2$, the major eicosanoid detected in inflammatory conditions ranging from acute edema to chronic arthritis. Its inhibition by NSAIDs is a mainstay for treatment.

Arthritis is one of the rheumatic diseases which encompass a wide range of diseases and pathological processes, most of which affect joint tissue. The basic structure affected by these diseases is the connective tissue which includes synovial membranes, cartilage, bone, tendons, ligaments, and interstitial tissues. Temporary connective tissue syndromes include sprains and strains, tendonitis, and tendon sheath abnormalities. The most serious forms of arthritis are rheumatoid arthritis, osteoarthritis, gout and systemic lupus erythematosus.

In addition to the rheumatic diseases, other diseases are characterized by inflammation. Gingivitis and periodontitis follows a pathological picture resembling rheumatoid arthritis. Inflammatory bowel disease refers to idiopathic chronic inflammatory conditions of the intestine, ulcerative colitis and Crohn's disease. Spondylitis refers to chronic inflammation of the joints of the spine. There is also a high incidence of osteoarthritis associated with obesity.

Thus, the inventive compounds have utility in the treatment of conditions involving inflammation, pain, fever, fetal development, labor and platelet aggregation.

The inhibition of COX by the inventive compounds would also inhibit the formation of postaglandins, e.g., $PGD_2$, $PGE_2$. Thus, the inventive compounds have utility in the treatment of conditions associated with prostaglandin $PGD_2$, $PGE_2$.

No-Associated Utilities

Nitric oxide (NO) is known to inhibit platelet aggregation, monocyte adhesion and chemotaxis, and proliferation of vascular smooth muscle tissue which are critically involved in the process of atherogenesis. Evidence supports the view that NO is reduced in atherosclerotic tissues due to its reaction with oxygen free radicals. The loss of NO due to these reactions leads to increased platelet and inflammatory cell adhesion to vessel walls to further impair NO mechanisms of relaxation. In this manner, the loss of NO promotes atherogenic processes, leading to progressive disease states.

Hypertension is a leading cause of cardiovascular diseases, including stroke, heart attack, heart failure, irregular heart beat and kidney failure. Hypertension is a condition where the pressure of blood within the blood vessels is higher than normal as it circulates through the body. When the systolic pressure exceeds 150 mm Hg or the diastolic pressure exceeds 90 mm Hg for a sustained period of time, damage is done to the body. For example, excessive systolic pressure can rupture blood vessels anywhere. When it occurs within the brain, a stroke results. It can also cause thickening and narrowing of the blood vessels which can lead to atherosclerosis. Elevated blood pressure can also force the heart muscle to enlarge as it works harder to overcome the elevated resting (diastolic) pressure when blood is expelled. This enlargement can eventually produce irregular heart beats or heart failure. Hypertension is called the "silent killer" because it causes no symptoms and can only be detected when blood pressure is checked.

The regulation of blood pressure is a complex event where one mechanism involves the expression of constitutive $Ca^{+2}$/calmodulin dependent form of nitric oxide synthase (NOS), abbreviated eNOS. NO produced by this enzyme produces muscle relaxation in the vessel (dilation), which lowers the blood pressure. When the normal level of NO produced by eNOS is not produced, either because production is blocked by an inhibitor or in pathological states, such as atherosclerosis, the vascular muscles do not relax to the appropriate degree. The resulting vasoconstriction increases blood pressure and may be responsible for some forms of hypertension.

Vascular endothelial cells contain eNOS. NO synthesized by eNOS diffuses in diverse directions, and when it reaches the underlying vascular smooth muscle, NO binds to the heme group of guanylyl cyclase, causing an increase in cGMP. Increased cGMP causes a decrease in intracellular free $Ca^{+2}$. Cyclic GMP may activate a protein kinase that phosphorylates $Ca^{+2}$ transporters, causing $Ca^{+2}$ to be sequestered in intracellular structures in the muscle cells. Since muscle contraction requires $Ca^{+2}$, the force of the contraction is reduced as the $Ca^{+2}$ concentration declines. Muscle relaxation allows the vessel to dilate, which lowers the blood pressure. Inhibition of eNOS therefore causes blood pressure to increase.

When the normal level of NO is not produced, either because production is blocked by administration of an NOS inhibitor or possibly, in pathological states, such as atherosclerosis, the vascular muscles do not relax to the appropriate degree. The resulting vasoconstriction increases blood pressure and may be responsible for some forms of hypertension. There is considerable interest in finding therapeutic ways to increase the activity of eNOS in hypertensive patients, but practical therapies have not been reported. Pharmacological agents capable of releasing NO, such as nitroglycerin or isosorbide dinitrate, remain mainstays of vasorelaxant therapy.

Although the inventive compounds inhibit the oxidation of LDL, the more comprehensive effects of these compounds is their multidimensional effects on atherosclerosis via NO. NO modulation by the inventive compounds brings about a collage of beneficial effects, including the modulation of hypertension, lowering NO affected hypercholesterolemia, inhibiting platelet aggregation and monocyte adhesion, all of which are involved with the progression of atherosclerosis.

The role of NO in the immune system is different from its function in blood vessels. Macrophages contain a form of NOS that is inducible, rather than constitutive, referred to as iNOS. Transcription of the iNOS gene is controlled both positively and negatively by a number of biological response modifiers called cytokines. The most important inducers are gamma-interferon, tumor necrosis factor, interleukin-1, interleukin-2 and lipopolysaccharide (LPS), which is a component of the cell walls of gram negative bacteria. Stimulated macrophages produce enough NO to inhibit ribonuclease reductase, the enzyme that converts ribonucleotides to the deoxyribonucleotides necessary for DNA synthesis. Inhibition of DNA synthesis may be an important way in which macrophages and other tissues possessing iNOS can inhibit the growth of rapidly dividing tumor cells or infectious bacteria.

With regard to the effects of NO and infectious bacteria, microorganisms play a significant role in infectious processes which reflect body contact and injury, habits, profession, environment of the individual, as well as food borne diseases brought about by improper storage, handling and contamination.

The inventive compounds, combinations thereof and compositions containing the same are useful in the treatment of conditions associated with modulating NO concentrations.

Example 9 described the antioxidant activity (as inhibitors of free radicals) of the inventive compounds. Given that NO is a free radical and that the inventive compounds are strong antioxidants, it was suspected that the administration of the inventive compounds to experimental in vitro and in vivo models would have caused a reduction in NO levels. Any reduction in NO would have resulted in a hypertensive, rather than a hypotensive effect. Contrary to expectations, the inventive compounds elicited increases in NO from in vitro experiments and produced a hypotensive effect from in vivo studies (Examples 31 and 32). These results were unanticipated and completely unexpected.

Example 27 describes an erythmia (facial flush) shortly after drinking a solution containing the inventive compounds and glucose, thus implying a vasodilation effect.

Example 31 describes the hypotensive effects elicited by the inventive compounds in an in vivo animal model, demonstrating the efficacy of the inventive compounds in the treatment of hypertension. In this example, the inventive compounds, combinations thereof and compositions comprising the same comprise oligomers wherein n is 2 to 18, and preferably, n is 2 to 10.

Example 32 describes the modulation of NO production by the inventive compounds in an in vitro model. In this example, the inventive compounds, combinations thereof and compositions comprising the same comprise oligomers wherein n is 2 to 18, and preferably n is 2 to 10.

Further, Example 35 provides evidence for the formation of $Cu^{+2}$—, $Fe^{+2}$— and $Fe^{+3}$— oligomer complexes detected by MALDI/TOF/MS. These results indicate that the inventive compounds can complex with copper and/or iron ions to minimize their effects on LDL oxidation.

Moreover, the inventive compounds have useful anti-microbial activities for the treatment of infections and for the prevention of food spoilage. Examples 22 and 30 describe the antimicrobial activity of the inventive compounds against several representative microbiota having clinical and food significance, as outlined below.

| MICROORGANISM | TYPE | CLINICAL/FOOD RELEVANCE |
| --- | --- | --- |
| Helicobacter pylori | gram negative | gastritis, ulcers, gastric cancer |
| Bacillus species | gram positive | food poisoning, wound infections, bovine mastitis, septicemia |
| Salmonella species | gram negative | food poisoning, diarrhea |
| Staphylococcus aureus | gram positive | boils, carbuncles, wound infection, septicemia, breast abscesses |
| Escherichia coli | gram negative | infant diarrhea, urinary tract infection |
| Pseudomonas species | gram negative | urinary tract infections, wound infections, "swimmer's ear" |
| Saccharomyces cervisea | yeast | food spoilage |
| Acetobacter pasteurianus | gram negative | food spoilage |

Example 33 describes the effects of the inventive compounds on macrophage NO production. In this example, the results demonstrate that the inventive compounds induce monocyte/macrophage NO production, both independent and dependent on stimulation by lipopolysaccharide (LPS) or cytokines. Macrophages producing NO can inhibit the growth of infectious bacteria.

Compounds of the invention eliciting antimicrobial activity are oligomers, where n is 2 to 18, and preferably, are oligomers where n is 2, 4, 5, 6, 8 and 10.

Examples of compounds eliciting the antimicrobial activity with respect to NO cited above include dimers, tetramers, pentamers, hexamers, octamers and decamers, discussed above.

Anti-Cancer Utilities

Cancers are classified into three groups: carcinomas, sarcomas and lymphomas. A carcinoma is a malignancy that arises in the skin, linings of various organs, glands and tissues. A sarcoma is a malignancy that arises in the bone, muscle or connective tissue. The third group comprises leukemias and lymphomas because both develop within the blood cell forming organs. The major types of cancer are prostate, breast, lung, colorectal, bladder, non-Hodgkin's lymphoma, uterine, melanoma of the skin, kidney, leukemia, ovarian and pancreatic.

The development of cancer results from alterations to the DNA of cells which is brought about by many factors such as inheritable genetic factors, ionizing radiation, pollutants, radon, and free radical damage to the DNA. Cells carrying mutations produce a defect in the ordered process of cell division. These cells fail to undergo apoptosis (programmed cell death) and continue to divide which either marks the beginnings of a malignant tumor or allows more mutations to occur over time to result in a malignancy.

There are three major features common to the many different cancers. These are (1) the ability to proliferate indefinitely; (2) invasion of the tumor into the surrounding tissue; and (3) the process of metastasis.

Certain types of cancer metastasize in characteristic ways. For example, cancers of the thyroid gland, lung, breast, kidney and prostate gland frequently metastasize to the bones. Lung cancer commonly spreads to the brain and adrenal glands and colorectal cancer often metastasizes to the liver. Leukemia is considered to be a generalized disease at the onset, where it is found in the bone marrow throughout the body.

It has been surprisingly found that the inventive compounds are useful in the treatment of a variety of cancers discussed above. Examples 6, 7, 8 and 15 describe the inventive compounds which elicit anti-cancer activity against human HeLa (cervical), prostate, breast, renal, T-cell leukemia and colon cancer cell lines. Example 12 (FIG. 20) illustrates the dose response effects on HeLa and SKBR-3 breast cancer cell lines treated with oligomeric (dimers-dodecamers) procyanidins, which were substantially purified by HPLC. Cytotoxicity against these cancer cell lines were dependent upon pentamer through dodecamer procyanidins, with the lower oligomers showing no effect.

While not wishing to be bound by any theory, there appeared to be a minimum structural motif that accounts for the effects described above. Example 37 also shows the same cytotoxic effects of the higher oligomers (pentamer-decamer) against a feline lymphoblastoid cancer cell line. Cytotoxicity was also observed with higher oligomers (FIGS. 58 to 61) against normal canine and feline cell lines.

In Example 8 (FIGS. 9D-H), the inventive compounds were shown to elicit cytotoxicity against a putative COX-2 expressing human colon cancer cell line (HCT 116).

Example 9 describes the antioxidant activity by the inventive compounds. The compounds of the invention inhibit DNA stand breaks, DNA-protein cross-links and free radical oxidation of nucleotides to reduce and/or prevent the occurrence of mutations.

Example 10 describes the inventive compounds as topoisomerase II inhibitors, which is a target for chemotherapeutic agents, such as doxorubicin.

Example 21 describes the in vivo effects of a substantially pure pentamer which elicited anti-tumor activity against a human breast cancer cell line (MDA-MB-231/LCC6) in a nude mouse model (average weight of a mouse is approximately 25 g). Repeat in vivo experiments with the pentamer at higher dosages (5 mg) have not entirely been successful, due to unexpected animal toxicity. It is currently believed that this toxicity may be related to the vasodilation effects of the inventive compounds.

Example 33 describes the effects of the inventive compounds on macrophage NO production. Macrophages which produce NO can inhibit the growth of rapidly dividing tumor cells.

Still further, the invention includes the use of the inventive compounds to induce the inhibition of cellular proliferation by apoptosis.

For anti-cancer activity, the inventive compounds are oligomers, where n is 2 to 18, e.g., 3 to 18, such as 3 to 12, and preferably, n is 5 to 12, and most preferably n is 5.

Compounds which elicit the inhibitory activity with respect to cancer cited above include pentamers to dodecamers, discussed above.

Formulations and Methods

Therefore, collectively, the inventive compounds, combinations thereof and compositions comprising the same have exhibited a wide array of activities against several aspects of atherosclerosis, cardiovascular disease, cancer, blood pressure modulation and/or hypertension, inflammatory disease, infectious agents and food spoilage.

Hence, the compounds of the invention, combinations thereof and compositions containing the same are COX inhibitors which affect platelet aggregation by inhibiting thromboxane $A_2$ formation, thus reducing the risk for thrombosis. Further, the inhibition of COX leads to decreased platelet and inflammatory cell adhesion to vessel walls to allow for improved NO mechanisms of relaxation. These results, coupled with the inhibition of COX at concentrations similar to a known NSAID, indomethacin, indicates antithrombotic efficacy.

Moreover, the compounds of the invention, combinations thereof and compositions containing the same are antioxidants which suppress the oxidation of LDL by reducing the levels of superoxide radical anion and lipoxygenase mediated lipid peroxy radicals. The inhibition of LDL oxidation at this stage slows macrophage activation and retards foam cell formation to interrupt further progression of atherosclerosis. The inhibition of LDL oxidation can also slow the progression of restenosis. Thus, compounds of the invention or combinations thereof or compositions containing compounds of the invention or combinations thereof can be used for prevention and/or treatment of atherosclerosis and/or restenosis. And thus, the inventive compounds can be administered before or after angioplasty or similar procedures to prevent or treat restenosis in patients susceptible thereto.

For treatment or prevention of restenosis and/or atherosclerosis, an inventive compound or compounds or a composition comprising an inventive compound or compounds, alone or with other treatment, may be administered as desired by the skilled medical practitioner, from this disclosure and knowledge in the art, e.g., at the first signs or symptoms of restenosis and/or atherosclerosis, immediately prior to, concomitant with or after angioplasty, or as soon thereafter as desired by the skilled medical practitioner, without any undue experimentation required; and the administration of the inventive compound or compounds or a composition thereof, alone or with other treatment, may be continued as a regimen, e.g., monthly, bimonthly, biannually, annually, or in some other regimen, by the skilled medical practitioner for such time as is necessary, without any undue experimentation required.

Further, the compounds of the invention, combinations thereof and compositions comprising the same have been shown to produce a hypotensive effect in vivo and induce NO in vitro. These results have practical application in the treatment of hypertension and in clinical situations involving hypercholesterolemia, where NO levels are markedly reduced.

Formulations of the inventive compounds, combinations thereof and compositions comprising the same can be prepared with standard techniques well known to those skilled in the pharmaceutical, food science, medical and veterinary arts, in the form of a liquid, suspension, tablet, capsule, injectable solution or suppository, for immediate or slow-release of the active compounds.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125-148.

A frequent choice of a carrier for pharmaceuticals and more recently for antigens is poly (d,l-lactide-co-glycolide) (PLGA). This is a biodegradable polyester that has a long history of medical use in erodible sutures, bone plates and other temporary prostheses where it has not exhibited any toxicity. A wide variety of pharmaceuticals have been formulated into PLGA microcapsules. A body of data has accumulated on the adaption of PLGA for controlled, for example, as reviewed by Eldridge, J. H., et al. *Current Topics in Microbiology and Immunology,* 1989, 146:59-66. The entrapment in PLGA microspheres of 1 to 10 microns in diameter can have an effect when administered orally. The PLGA microencapsulation process uses a phase separation of a water-in-oil emulsion. The inventive compound or compounds is or are prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, methyl cellulose) and the solvent removed by either drying in vacuo or solvent extraction.

Additionally, with regard to the preparation of slow-release formulations, reference is made to U.S. Pat. Nos. 5,024,843, 5,091,190, 5,082,668, 4,612,008 and 4,327,725, hereby incorporated herein by reference.

Additionally, selective processing coupled with the identification of cocoa genotypes of interest could be used to prepare Standard-of-Identity (SOI) and non-SOI chocolate products as vehicles to deliver the active compounds to a patient in need of treatment for the disease conditions described above, as well as a means for the delivery of conserved levels of the inventive compounds.

In this regard, reference is made to copending U.S. application Ser. No. 08/709,406, filed Sep. 6, 1996, hereby incorporated herein by reference. U.S. Ser. No. 08/709,406 relates to a method of producing cocoa butter and/or cocoa solids having conserved levels of polyphenols from cocoa beans using a unique combination of processing steps which does not require separate bean roasting or liquor milling equipment, allowing for the option of processing cocoa beans without exposure to severe thermal treatment for extended periods of time and/or the use of solvent extraction of fat. The benefit of this process lies in the enhanced conservation of polyphenols in contrast to that found in traditional cocoa processing, such that the ratio of the initial amount of polyphenol found in the unprocessed bean to that obtainable after processing is less than or equal to 2.

Compositions of the invention include one or more of the above noted compounds in a formulation having a pharmaceutically acceptable carrier or excipient, the inventive compounds having anti-cancer, anti-tumor or antineoplastic activities, antioxidant activity, inhibit DNA topoisomerase II enzyme, inhibit oxidative damage to DNA, induce monocyte/macrophage NO production, have antimicrobial, cyclo-oxygenase and/or lipoxygenase, NO or NO-synthase, apoptosis, platelet aggregation and blood or in vivo glucose modulating activities, and have efficacy as non-steroidal antiinflammatory agents.

Another embodiment of the invention includes compositions comprising the inventive compounds or combinations thereof, as well as at least one additional antineoplastic, blood pressure reducing, antiinflammatory, antimicrobial, antioxidant and hematopoiesis agents, in addition to a pharmaceutically acceptable carrier or excipient.

Such compositions can be administered to a subject or patient in need of such administration in dosages and by techniques well known to those skilled in the medical, nutritional or veterinary arts taking into consideration the data herein, and such factors as the age, sex, weight, genetics and condition of the particular subject or patient, and the route of administration, relative concentration of particular oligomers, and toxicity (e.g., $LD_{50}$).

The compositions can be co-administered or sequentially administered with other antineoplastic, anti-tumor or anti-cancer agents, antioxidants, DNA topoisomerase II enzyme inhibiting agents, inhibitors of oxidatively damaged DNA or cyclo-oxygenase and/or lipoxygenase, apoptosis, platelet aggregation, blood or in vivo glucose or NO or NO-synthase modulating agents, non-steroidal antiinflammatory agents and/or with agents which reduce or alleviate ill effects of antineoplastic, anti-tumor, anti-cancer agents, antioxidants, DNA topoisomerase II enzyme inhibiting agents, inhibitors of oxidatively damaged DNA, cyclo-oxygenase and/or lipoxygenase, apoptosis, platelet aggregation, blood or in vivo glucose or NO or NO-synthase modulating and/or non-steroidal antiinflammatory agents; again, taking into consideration such factors as the age, sex, weight, genetics and condition of the particular subject or patient, and, the route of administration.

Examples of compositions of the invention for human or veterinary use include edible compositions for oral administration, such solid or liquid formulations, for instance, capsules, tablets, pills and the like, as well as chewable solid or beverage formulations, to which the present invention may be well-suited since it is from an edible source (e.g., cocoa or chocolate flavored solid or liquid compositions); liquid preparations for orifice, e.g., oral, nasal, anal, vaginal etc., administration such as suspensions, syrups or elixirs (including cocoa or chocolate flavored compositions); and, preparations for parental, subcutaneous, intradermal, intramuscular or intravenous administration (e.g., injectable administration) such as sterile suspensions or emulsions. However, the active ingredient in the compositions may complex with proteins such that when administered into the bloodstream, clotting may occur due to precipitation of blood proteins; and, the skilled artisan should take this into account. In such compositions the active cocoa extract may be in admixture with a suitable carrier, diluent, or excipient such as sterile water, physiological saline, glucose, DMSO, ethanol, or the like. The active cocoa extract of the invention can be provided in lyophilized form for reconstituting, for instance, in isotonic aqueous, saline, glucose or DMSO buffer. In certain saline solutions, some precipitation has been observed; and, this observation may be employed as a means to isolate inventive compounds, e.g., by a "salting out" procedure.

Example 38 describes the preparation of the inventive compounds in a tablet formulation for application in the pharmaceutical, supplement and food areas. Further, Example 39 describes the preparation of the inventive compounds in capsule formulations for similar applications. Still further, Example 40 describes the formulation of Standard of Identity (SOI) and non-SOI chocolates containing the compounds of the invention or cocoa solids obtained from methods described in copending U.S. application Ser. No. 08/709,406, hereby incorporated herein by reference.

Kits

Further, the invention also comprehends a kit wherein the active cocoa extract is provided. The kit can include a separate container containing a suitable carrier, diluent or excipient. The kit can also include an additional anti-cancer, anti-tumor or antineoplastic agent, antioxidant, DNA topoisomerase II enzyme inhibitor or an inhibitor of oxidative DNA damage or antimicrobial, or cyclo-oxygenase and/or lipoxygenase, NO or NO-synthase non-steroidal antiinflammatory, apoptosis and platelet aggregation modulating or blood or in vivo glucose modulating agent and/or an agent which reduces or alleviates ill effects of antineoplastic, anti-tumor or anti-cancer agents, antioxidant, DNA topoisomerase II enzyme inhibitor or antimicrobial, or cyclo-oxygenase and/or lipoxygenase, NO or NO-synthase, apoptosis, platelet aggregation and blood or in vivo glucose modulating and/or non-steroidal antiinflammatory agents for co- or sequential-administration. The additional agent(s) can be provided in separate container(s) or in admixture with the active cocoa extract. Additionally, the kit can include instructions for mixing or combining ingredients and/or administration.

Identification of Genes

A further embodiment of the invention comprehends the modulation of genes expressed as a result of intimate cellular contact by the inventive compounds or a combination of compounds. As such, the present invention comprehends methods for the identification of genes induced or repressed by the inventive compounds or a combination of compounds which are associated with several diseases, including but not limited to atherosclerosis, hypertension, cancer, cardiovascular disease, and inflammation. Specifically, genes which are differentially expressed in these disease states, relative to their expression in "normal" nondisease states are identified and described before and after contact by the inventive compounds or a combination of compounds.

As mentioned in the previous discussion, these diseases and disease states are based in part on free radical interactions with a diversity of biomolecules. A central theme in these diseases is that many of the free radical reactions involve reactive oxygen species, which in turn induce physiological conditions involved in disease progression. For instance, reactive oxygen species have been implicated in the regulation of transcription factors such as nuclear factor (NF)-κB. The target genes for NF-κB comprise a list of genes linked to coordinated inflammatory response. These include genes encoding tumor necrosis factor (TNF)-α, interleukin (IL)-I, IL-6, IL-8, inducible NOS, Major Histocompatabilty Complex (MHC) class I antigens, and others. Also, genes that modulate the activity of transcription factors may in turn be induced by oxidative stress. Oxidative stress is the imbalance between radical scavenging and radical generating systems. Several known examples (Winyard and Blake, 1997) of these conditions include gadd153 (a gene induced by growth arrest and DNA damage), the product of which has been shown to bind NF-IL6 and form a heterodimer that cannot bind to DNA. NF-IL6 upregulates the expression of several genes, including those encoding interleukins 6 and 8. Another example of oxidative stress inducible genes are gadd45 which regulates the effects of the transcription factor p53 in growth arrest. p53 codes for the p53 protein which can halt cell division and induce abnormal cells (e.g. cancer) to undergo apoptosis.

Given the full panoply of unexpected, nonobvious and novel utilities for the inventive compounds or combination of compounds for utility in a diverse array of diseases based in part by free radical mechanisms, the invention further comprehends strategies to determine the temporal effects on gene(s) or gene product(s) expression by the inventive compounds in animal in vitro and/or in vivo models of specific disease or disease states using gene expression assays. These assays include, but are not limited to Differential Display, sequencing of cDNA libraries, Serial Analysis of Gene Expression (SAGE), expression monitoring by hybridization to high density oligonucleotide arrays and various reverse transcriptase-polymerization chain reaction (RT-PCR) based protocols or their combinations (Lockhart et al., 1996).

The comprehensive physiological effects of the inventive compounds or combination of compounds embodied in the invention, coupled to a genetic evaluation process permits the discovery of genes and gene products, whether known or novel, induced or repressed. For instance, the invention comprehends the in vitro and in vivo induction and/or repression of cytokines (e.g. IL-1, IL-2, IL-6, IL-8, IL-12, and TNF-α) in lymphocytes using RT-PCR. Similarly, the invention comprehends the application of Differential Display to ascertain the induction and/or repression of select genes; for the cardiovascular area (e.g. superoxide dismutase, heme oxidase, COX 1 and 2, and other oxidant defense genes) under stimulated and/or oxidant stimulated conditions (e.g. TNF-α or $H_2O_2$) conditions. For the cancer area, the invention comprehends the application of Differential Display to ascertain the induction and/or repression of genes or gene products such as CuZn-superoxide dismutase, Mn-superoxide dismutase, catalase, etc., in control and oxidant stressed cells.

The following non-limiting Examples are given by way of illustration only and are not to be considered a limitation of this invention, many apparent variations of which are possible without departing from the spirit or scope thereof.

EXAMPLES

Example 1

Cocoa Source and Method of Preparation

Several *Theobroma cacao* genotypes which represent the three recognized horticultural races of cocoa (Enriquez, 1967; Engels, 1981) were obtained from the three major cocoa producing origins of the world. A list of those genotypes used in this study are shown in Table 1. Harvested cocoa pods were opened and the beans with pulp were removed for freeze drying. The pulp was manually removed from the freeze dried mass and the beans were subjected to analysis as follows. The unfermented, freeze dried cocoa beans were first manually dehulled, and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

TABLE 1

Description of *Theobroma cacao* Source Material

| GENOTYPE | ORIGIN | HORTICULTURAL RACE |
| --- | --- | --- |
| UIT-1 | Malaysia | Trinitario |
| Unknown | West Africa | Forastero |
| ICS-100 | Brazil | Trinitario (Nicaraguan Criollo ancestor) |
| ICS-39 | Brazil | Trinitario (Nicaraguan Criollo ancestor) |
| UF-613 | Brazil | Trinitario |
| EEG-48 | Brazil | Forastero |
| UF-12 | Brazil | Trinitario |
| NA-33 | Brazil | Forastero |

Example 2

Procyanidin Extraction Procedures

A. Method 1

Procyanidins were extracted from the defatted, unfermented, freeze dried cocoa beans of Example 1 using a modification of the method described by Jalal and Collin (1977). Procyanidins were extracted from 50 gram batches of the defatted cocoa mass with 2×400 mL 70% acetone/deionized water followed by 400 mL 70% methanol/deionized water. The extracts were pooled and the solvents removed by evaporation at 45° C. with a rotary evaporator held under partial vacuum. The resultant aqueous phase was diluted to 1 L with deionized water and extracted 2× with 400 mL $CHCl_3$. The solvent phase was discarded. The aqueous phase was then extracted 4× with 500 mL ethyl acetate. Any resultant emulsions were broken by centrifugation on a Sorvall RC 28S centrifuge operated at 2,000×g for 30 min. at 10° C. To the combined ethyl acetate extracts, 100-200 mL deionized water was added. The solvent was removed by evaporation at 45° C. with a rotary evaporator held under partial vacuum. The resultant aqueous phase was frozen in liquid $N_2$ followed by freeze drying on a LABCONCO Freeze Dry System. The yields of crude procyanidins that were obtained from the different cocoa genotypes are listed in Table 2.

TABLE 2

Crude Procyanidin Yields

| GENOTYPE | ORIGIN | YIELDS (g) |
| --- | --- | --- |
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

B. Method 2

Alternatively, procyanidins are extracted from defatted, unfermented, freeze dried cocoa beans of Example 1 with 70% aqueous acetone. Ten grams of defatted material was slurried with 100 mL solvent for 5-10 min. The slurry was centrifuged for 15 min. at 4° C. at 3000×g and the supernatant passed through glass wool. The filtrate was subjected to distillation under partial vacuum and the resultant aqueous phase frozen in liquid $N_2$, followed by freeze drying on a LABCONCO Freeze Dry System. The yields of crude procyanidins ranged from 15-20%.

Without wishing to be bound by any particular theory, it is believed that the differences in crude yields reflected variations encountered with different genotypes, geographical origin, horticultural race, and method of preparation.

Example 3

Partial Purification of Cocoa Procyanidins

Procyanidins obtained from Example 2 were partially purified by liquid chromatography on Sephadex LH-20 (28×2.5 cm). Separations were aided by a step gradient from deionized water into methanol. The initial gradient composition started with 15% methanol in deionized water which was followed step wise every 30 min. with 25% methanol in deionized water, 35% methanol in deionized water, 70% methanol in deionized water, and finally 100% methanol. The effluent following the elution of the xanthine alkaloids (caffeine and theobromine) was collected as a single fraction. The fraction yielded a xanthine alkaloid free subtraction which was submitted to further subfractionation to yield five subfractions designated MM2A through MM2E. The solvent was removed from each subtraction by evaporation at 4°5C with a rotary evaporator held under partial vacuum. The resultant aqueous phase was frozen in liquid $N_2$ and freeze dried overnight on a LABCONCO Freeze Dry System. A representative gel permeation chromatogram showing the fractionation is shown in FIG. 1. Approximately, 100 mg of material was subfractionated in this manner.

Chromatographic Conditions: Column; 28×2.5 cm Sephadex LH-20, Mobile Phase: Methanol/Water Step Gradient, 15:85, 25:75, 35:65, 70:30, 100:0 Stepped at ½ Hour Intervals, Flow Rate; 1.5 mL/min, Detector; UV at $\lambda_1$=254 nm and $\lambda_2$=365 nm, Chart Speed: 0.5 mm/min, Column Load; 120 mg.

B. Semi-Preparative High Performance Liquid Chromatography (HPLC)

Method 1. Reverse Phase Separation

Procyanidins obtained from Example 2 and/or 3A were partially purified by semi-preparative HPLC. A Hewlett Packard 1050 HPLC System equipped with a variable wavelength detector, Rheodyne 7010 injection valve with 1 mL injection loop was assembled with a Pharmacia FRAC-100 Fraction Collector. Separations were effected on a Phenomenex Ultracarb™ 10µ ODS column (250×22.5 mm) connected with a Phenomenex 10µ ODS Ultracarb™ (60×10 mm) guard column. The mobile phase composition was A=water; B=methanol used under the following linear gradient conditions: [Time, % A]; (0, 85), (60, 50), (90, 0), and (110, 0) at a flow rate of 5 mL/min. Compounds were detected by UV at 254 nm.

A representative Semi-preparative HPLC trace is shown in FIG. 15N for the separation of procyanidins present in fraction D+E. Individual peaks or select chromatographic regions were collected on timed intervals or manually by fraction collection for further purification and subsequent evaluation. Injection loads ranged from 25-100 mg of material.

Method 2. Normal Phase Separation

Procyanidin extracts obtained from Examples 2 and/or 3A were partially purified by semi-preparative HPLC. A Hewlett Packard 1050 HPLC system, Millipore-Waters Model 480 LC detector set at 254 nm was assembled with a Pharmacia Frac-100 Fraction Collector set in peak mode. Separations were effected on a Supelco 5 µm Supelcosil LC-Si column (250×10 mm) connected with a Supelco 5 µm Supelguard LC-Si guard column (20×4.6 mm). Procyanidins were eluted by a linear gradient under the following conditions: (Time, % A, % B); (0, 82, 14), (30, 67.6, 28.4), (60, 46, 50), (65, 10, 86), (70, 10, 86) followed by a 10 min. re-equilibration. Mobile phase composition was A=dichloromethane; B=methanol; and C=acetic acid:water (1:1). A flow rate of 3 mL/min was used. Components were detected by UV at 254 nm, and recorded on a Kipp & Zonan BD41 recorder. Injection volumes ranged from 100-250 µL of 10 mg of procyanidin extracts dissolved in 0.25 mL 70% aqueous acetone. A representative semi-preparative HPLC trace is shown in FIG. 15O. Individual peaks or select chromatographic regions were collected on timed intervals or manually by fraction collection for further purification and subsequent evaluation.

HPLC Conditions: 250×10 mm Supelco Supelcosil LC-Si (5 µm) Semipreparative Column
    20×4.6 mm Supelco Supelcosil LC-Si (5 µm) Guard Column
    Detector: Waters LC
    Spectrophotometer Model 480@254 nm
    Flow rate: 3 mL/min,
    Column Temperature: ambient,
    Injection: 250 iL of 70% aqueous
    acetone extract.

| Gradient: Time (min) | $CH_2Cl_2$ | Methanol | Acetic Acid:$H_2O$ (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

The fractions obtained were as follows:

| FRACTION | TYPE |
|---|---|
| 1 | dimers |
| 2 | trimers |
| 3 | tetramers |
| 4 | pentamers |
| 5 | hexamers |
| 6 | heptamers |
| 7 | octamers |
| 8 | nonamers |
| 9 | decamers |
| 10 | undecamers |
| 11 | dodecamers |
| 12 | higher oligomers |

Example 4

Analytical HPLC Analysis of Procyanidin Extracts

Method 1. Reverse Phase Separation

Procyanidin extracts obtained from Example 3 were filtered through a 0.45µ filter and analyzed by a Hewlett Packard 1090 ternary HPLC system equipped with a Diode Array detector and a HP model 1046A Programmable Fluorescence Detector. Separations were effected at 45° C. on a Hewlett-Packard 51 Hypersil ODS column (200×2.1 mm). The flavanols and procyanidins were eluted with a linear gradient of 60% B into A followed by a column wash with B at a flow rate of 0.3 mL/min. The mobile phase composition was B=0.5% acetic acid in methanol and A=0.5% acetic acid in nanopure water. Acetic acid levels in A and levels in A and B mobile phases can be increased to 2%. Components were detected by fluorescence, where $\lambda_{ex}$=276 nm and $\lambda_{ex}$=316 nm and by UV at 280 nm. Concentrations of (+)-catechin and (−)-epicatechin were determined relative to reference standard solutions. Procyanidin levels were estimated by using the response factor for (−)-epicatechin. A representative HPLC chromatogram showing the separation of the various components is shown in FIG. 2A for one cocoa genotype. Similar HPLC profiles were obtained from the other cocoa genotypes.

HPLC Conditions: Column: 200×2.1 mm Hewlett Packard Hypersil ODS (5µ)
    Guard column: 20×2.1 mm Hewlett Packard Hypersil ODS (5µ)
    Detectors: Diode Array @ 280 nm
        Fluorescence λex=276 nm;
        λem=316 nm.
    Flow rate: 0.3 mL/min.
    Column Temperature: 45° C.

| Gradient: Time (min) | 0.5% Acetic Acid in nanopure water | 0.5% Acetic acid in methanol |
|---|---|---|
| 0 | 100 | 0 |
| 50 | 40 | 60 |
| 60 | 0 | 100 |

Method 2. Normal Phase Separation

Figure 2B:
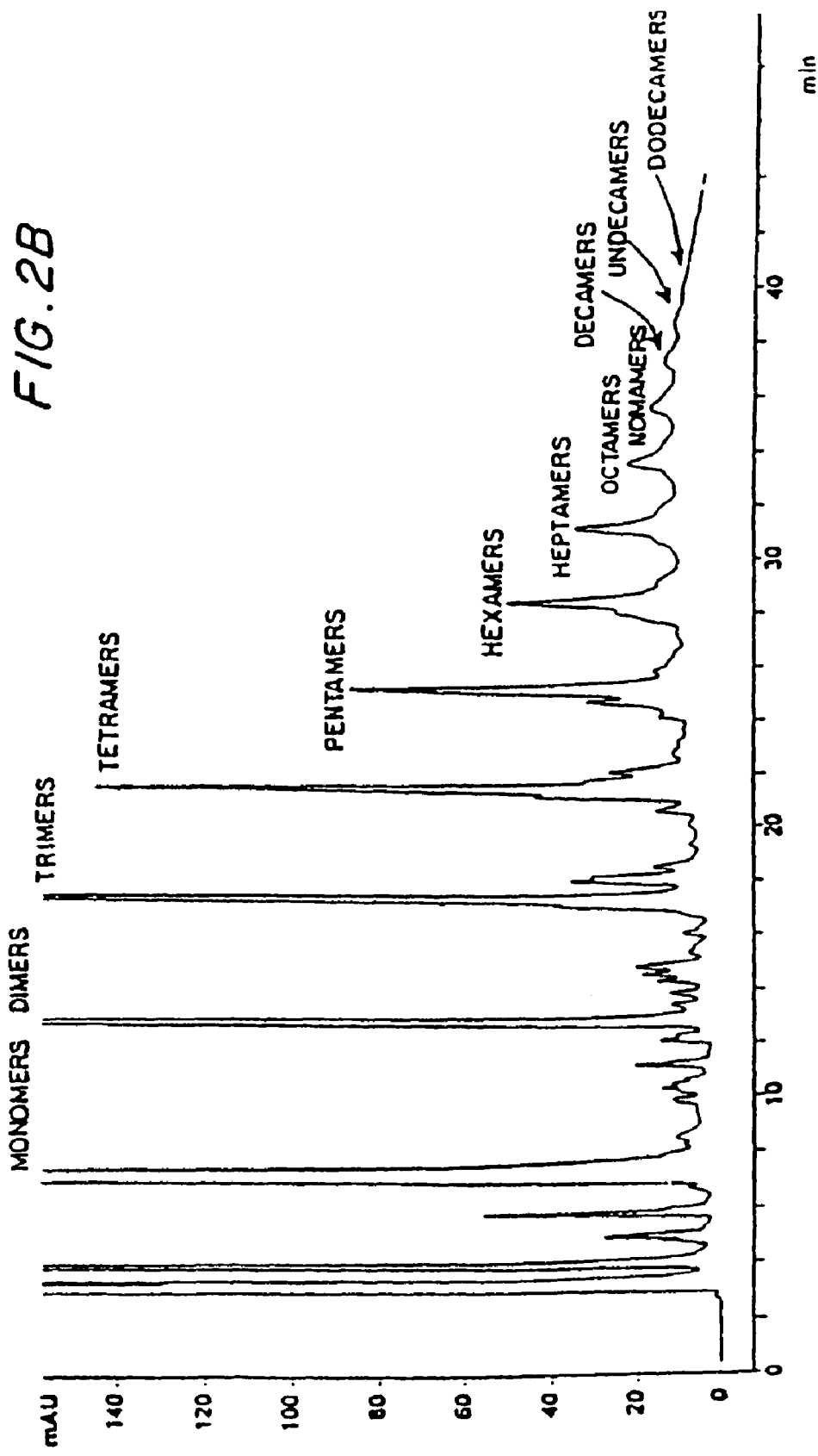
FIG. 2B shows a representative normal phase HPLC separation of cocoa procyanidins extracted from unfermented cocoa.

Procyanidin extracts obtained from Examples 2 and/or 3 were filtered through a 0.45µ filter and analyzed by a Hewlett Packard 1090 Series II HPLC system equipped with a HP model 1046A Programmable Fluorescence detector and Diode Array detector. Separations were effected at 37° C. on a 5µ Phenomenex Lichrosphere® Silica 100 column (250× 3.2 mm) connected to a Supelco Supelguard LC-Si 5µ guard column (20×4.6 mm). Procyanidins were eluted by linear gradient under the following conditions: (Time, % A, % B); (0, 82, 14), (30, 67.6, 28.4), (60, 46, 50), (65, 10, 86), (70, 10, 86) followed by an 8 min. re-equilibration. Mobile phase composition was A=dichloromethane, B=methanol, and C=acetic acid:water at a volume ratio of 1:1. A flow rate of 0.5 mL/min. was used. Components were detected by fluorescence, where $\lambda_{ex}$x=276 nm and $\lambda_{em}$=316 nm or by UV at 280 nm. A representative HPLC chromatogram showing the separation of the various procyanidins is shown in FIG. 2B for one genotype. Similar HPLC profiles were obtained from other cocoa genotypes.

HPLC Conditions: 250×3.2 mm Phenomenex Lichrosphere® Silica 100 column (5µ) 20×4.6 mm
 Supelco Supelguard LC-Si (5µ) guard column
 Detectors: Photodiode Array @ 280 nm
  Fluorescence $\lambda_{ex}$=276 nm;
  $\lambda_{em}$=316 nm.
 Flow rate: 0.5 mL/min.
 Column Temperature: 37° C.

| Gradient: Time (min.) | CH$_2$—Cl$_2$ | Methanol | Acetic Acid/Water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Example 5

Identification of Procyanidins

Procyanidins were purified by liquid chromatography on Sephadex LH-20 (28×2.5 cm) columns followed by semi-preparative HPLC using a 10µ Bondapak C18 (100×8 mm) column or by semi-preparative HPLC using a 5µ Supelcosil LC-Si (250×10 mm) column.

Partially purified isolates were analyzed by Fast Atom Bombardment—Mass Spectrometry (FAB-MS) on a VG ZAB-T high resolution MS system using a Liquid Secondary Ion Mass Spectrometry (LSIMS) technique in positive and negative ion modes. A cesium ion gun was used as the ionizing source at 30 kV and a "Magic Bullet Matrix" (1:1 dithiothreitol/dithioerythritol) was used as the proton donor.

Analytical investigations of these fractions by LSIMS revealed the presence of a number of flavan-3-ol oligomers as shown in Table 3.

TABLE 3

LSIMS (Positive Ion) Data from Cocoa Procyanidin Fractions

| Oligomer | (M + 1)$^+$ m/z | (M + Na)$^+$ m/z | Mol. Wt. |
|---|---|---|---|
| Monomers (catechins) | 291 | 313 | 290 |
| Dimer(s) | 577/579 | 599/601 | 576/578 |
| Trimer(s) | 865/867 | 887/889 | 864/866 |
| Tetramer(s) | 1155 | 1177 | 1154 |
| Pentamer(s) | 1443 | 1465 | 1442 |
| Hexamer(s) | 1731 | 1753 | 1730 |
| Heptamer(s) | — | 2041 | 2018 |
| Octamer(s) | — | 2329 | 2306 |
| Nonamer(s) | — | 2617 | 2594 |
| Decamer(s) | — | 2905 | 2882 |
| Undecamer(s) | — | — | 3170 |
| Dodecamer(s) | — | — | 3458 |

The major mass fragment ions were consistent with work previously reported for both positive and negative ion FAB-MS analysis of procyanidins (Self et al., 1986 and Porter et al., 1991). The ion corresponding to m/z 577 (M+H)$^+$ and its sodium adduct at m/z 599 (M+Na)$^+$ suggested the presence of doubly linked procyanidin dimers in the isolates. It was interesting to note that the higher oligomers were more likely to form sodium adducts (M+Na)$^+$ than their protonated molecular ions (M+H)$^+$. The procyanidin isomers B-2, B-5 and C-1 were tentatively identified based on the work reported by Revilla et al. (1991), Self et al. (1986) and Porter et al. (1991). Procyanidins up to both the octamer and decamer were verified by FAB-MS in the partially purified fractions. Additionally, evidence for procyanidins up to the dodecamer were observed from normal phase HPLC analysis (see FIG. 2B). Table 4 lists the relative concentrations of the procyanidins found in xanthine alkaloid free isolates based on reverse phase HPLC analysis. Table 5 lists the relative concentrations of the procyanidins based on normal phase HPLC analysis.

TABLE 4

Relative Concentrations of Procyanidins in the Xanthine Alkaloid Free Isolates

| Component | Amount |
|---|---|
| (+)-catechin | 1.6% |
| (−)-epicatechin | 38.2% |
| B-2 Dimer | 11.0% |
| B-5 Dimer | 5.3% |
| C-1 Trimer | 9.3% |
| Doubly linked dimers | 3.0% |
| Tetramer(s) | 4.5% |
| Pentamer-Octamer | 24.5% |
| Unknowns and higher oligomers | 2.6% |

TABLE 5

Relative Concentrations of Procyanidins in Aqueous Acetone Extracts

| Component | Amount |
|---|---|
| (+)-catechin and (−)-epicatechin | 41.9% |
| B-2 and B-5 Dimers | 13.9% |
| Trimers | 11.3% |
| Tetramers | 9.9% |
| Pentamers | 7.8% |
| Hexamers | 5.1% |
| Heptamers | 4.2% |
| Octamers | 2.8% |
| Nonamers | 1.6% |
| Decamers | 0.7% |
| Undecamers | 0.2% |
| Dodecamers | <0.1% |

Figure 3:
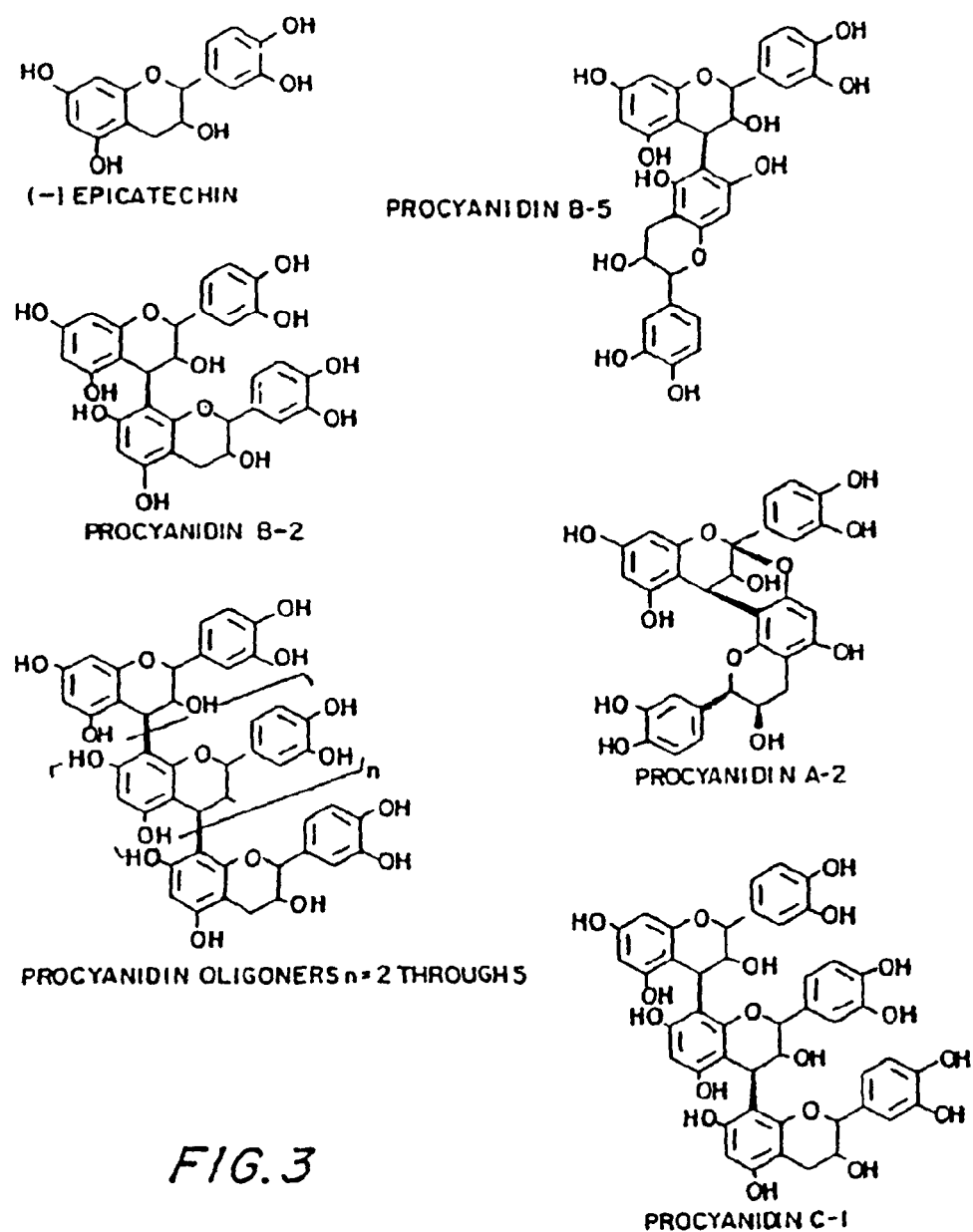
FIG. 3 shows several representative procyanidin structures.
Figure 4B:
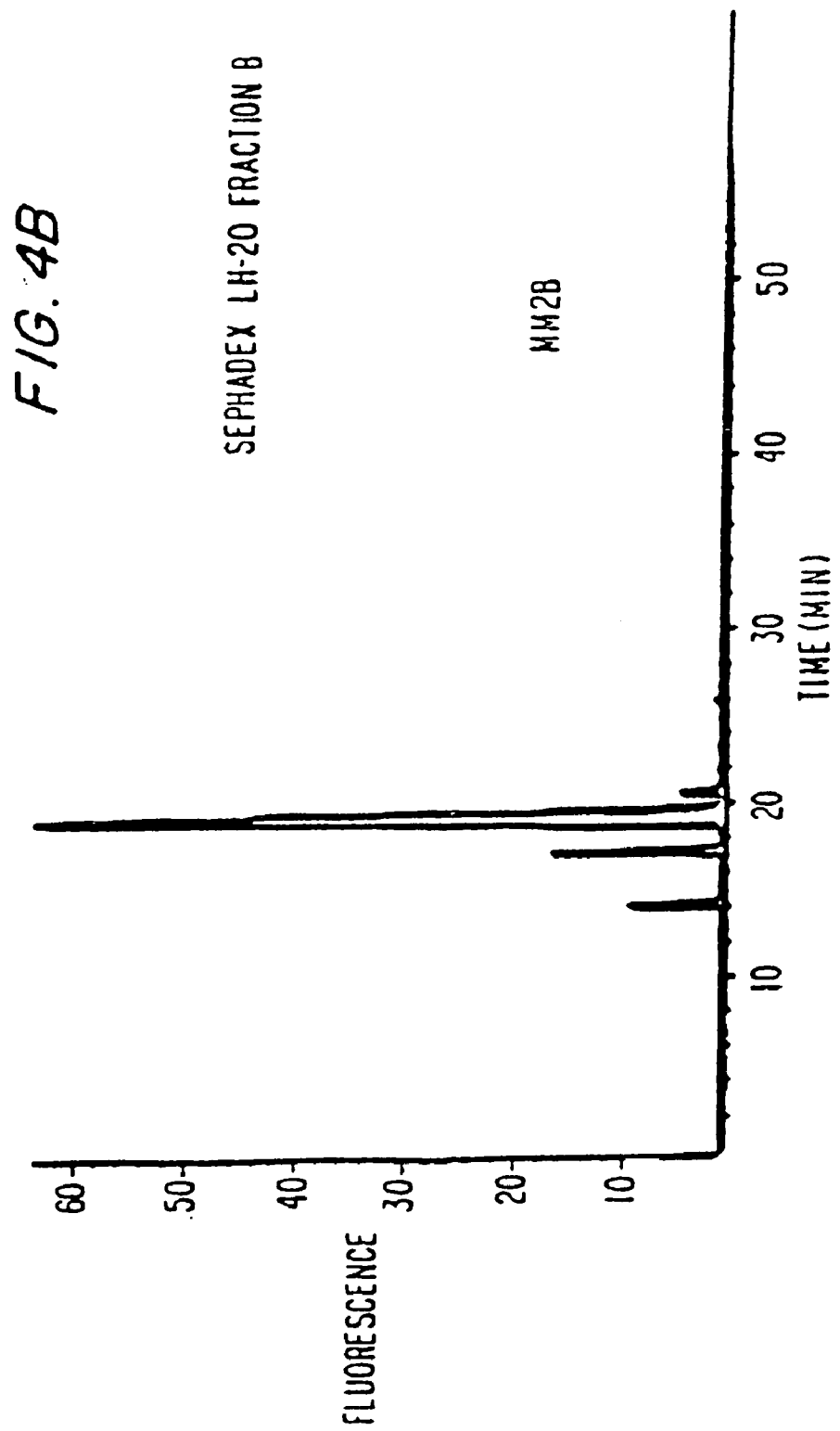
Figure 4E:
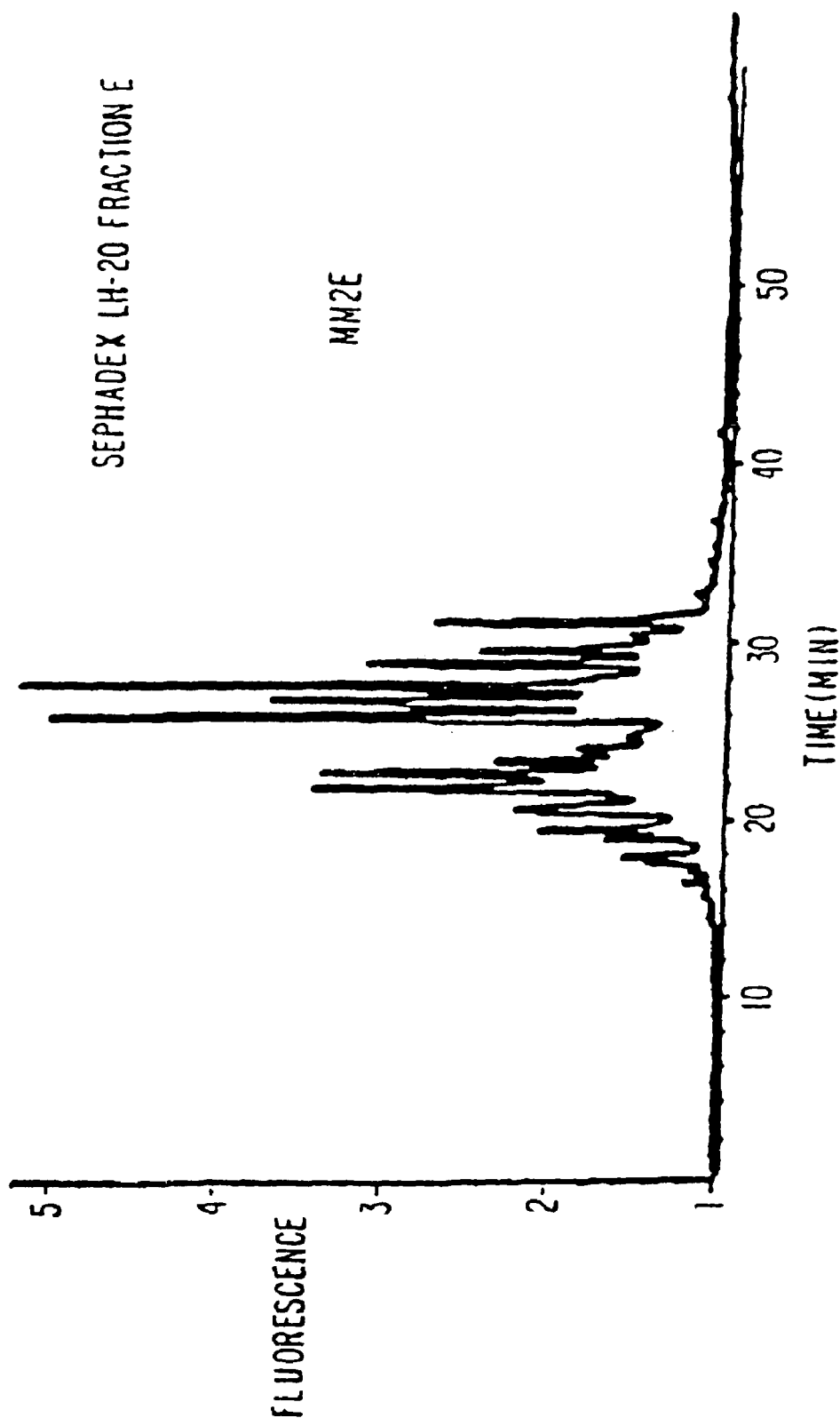

FIG. 3 shows several procyanidin structures and FIGS. 4A-4E show the representative HPLC chromatograms of the five fractions employed in the following screening for anti-cancer or antineoplastic activity. The HPLC conditions for FIGS. 4A-4E were as follows:

HPLC Conditions: Hewlett Packard 1090 ternary HPLC System equipped with HP Model 1046A Programmable Fluorescence Detector.
 Column: Hewlett Packard 5µ Hypersil ODS (200×2.1 mm) Linear Gradient of 60% B into A at a flow rate of 0.3 mL/min. B=0.5% acetic acid in methanol; A=0.5% acetic acid in deionized water. $\lambda_{ex}$=280 nm; $\lambda_{em}$=316 nm.

FIG. 15 O shows a representative semi-prep HPLC chromatogram of an additional 12 fractions employed in the screening for anticancer or antineoplastic activity (HPLC conditions stated above).

Example 6

Anti-Cancer, Anti-Tumor or Antineoplastic Activity of Cocoa Extracts (Procyanidins)

The MTT (3-[4,5-dimethyl thiazol-2yl]-2,5-diphenyltetrazolium bromide)—microtiter plate tetrazolium cytotoxicity assay originally developed by Mosmann (1983) was used to screen test samples from Example 5. Test samples, standards (cisplatin and chlorambucil) and MTT reagent were dissolved in 100% DMSO (dimethyl sulfoxide) at a 10 mg/mL concentration. Serial dilutions were prepared from the stock solutions. In the case of the test samples, dilutions ranging from 0.01 through 100 μg/mL were prepared in 0.5% DMSO.

All human tumor cell lines were obtained from the American Type Culture Collection. Cells were grown as mono layers in alpha-MEM containing 10% fetal bovine serum, 100 units/mL penicillin, 100 μg/mL streptomycin and 240 units/mL nystatin. The cells were maintained in a humidified, 5% $CO_2$ atmosphere at 37° C.

After trypsinization, the cells are counted and adjusted to a concentration of $50 \times 10^5$ cells/mL (varied according to cancer cell line). 200 μL of the cell suspension was plated into wells of 4 rows of a 96-well microtiter plate. After the cells were allowed to attach for four hours, 2 μL of DMSO containing test sample solutions were added to quadruplicate wells. Initial dose-response finding experiments, using order of magnitude test sample dilutions were used to determine the range of doses to be examined. Well absorbencies at 540 nm were then measured on a BIO RAD MP450 plate reader. The mean absorbance of quadruplicate test sample treated wells was compared to the control, and the results expressed as the percentage of control absorbance plus/minus the standard deviation. The reduction of MTT to a purple formazan product correlates in a linear manner with the number of living cells in the well. Thus, by measuring the absorbance of the reduction product, a quantitation of the percent of cell survival at a given dose of test sample can be obtained. Control wells contained a final concentration of 1% DMSO.

Figure 5:
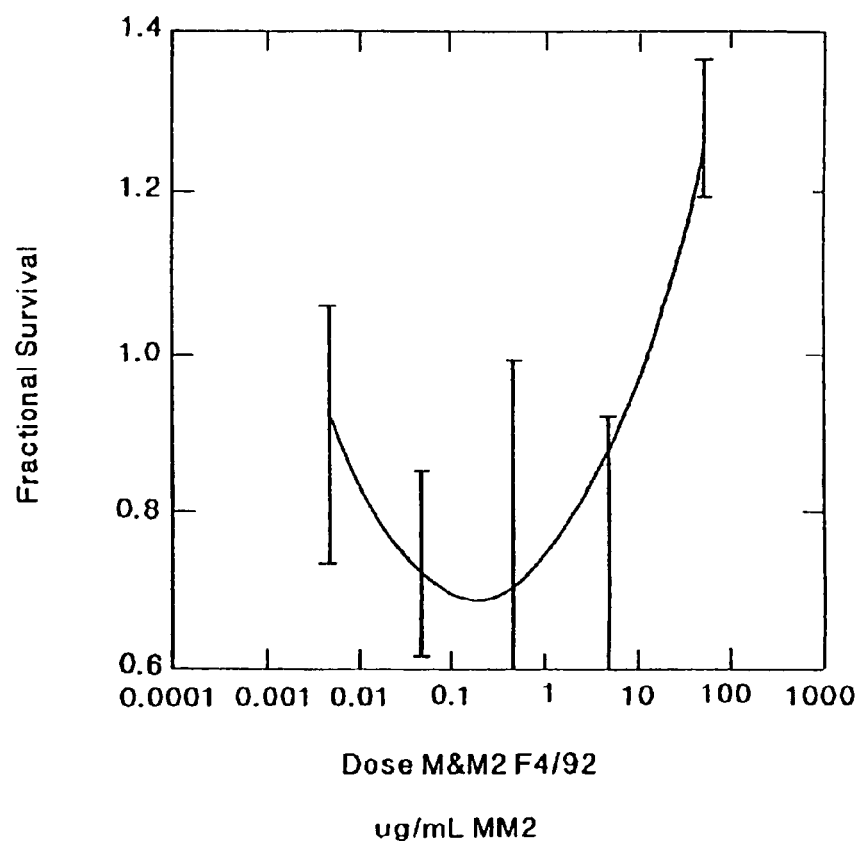
FIGS. 5 and 6A-6D show the dose-response relationship between cocoa extracts and cancer cells ACHN (FIG. 5) and PC-3 (FIGS. 6A-6D) (fractional survival vs. dose, 1 μg/mL); M&M2 F4/92, M&MA+E U12P1, M&MB+E Y192P1, M&MC+E U12P2, M&MD+E U12P2.
Figure 6A:
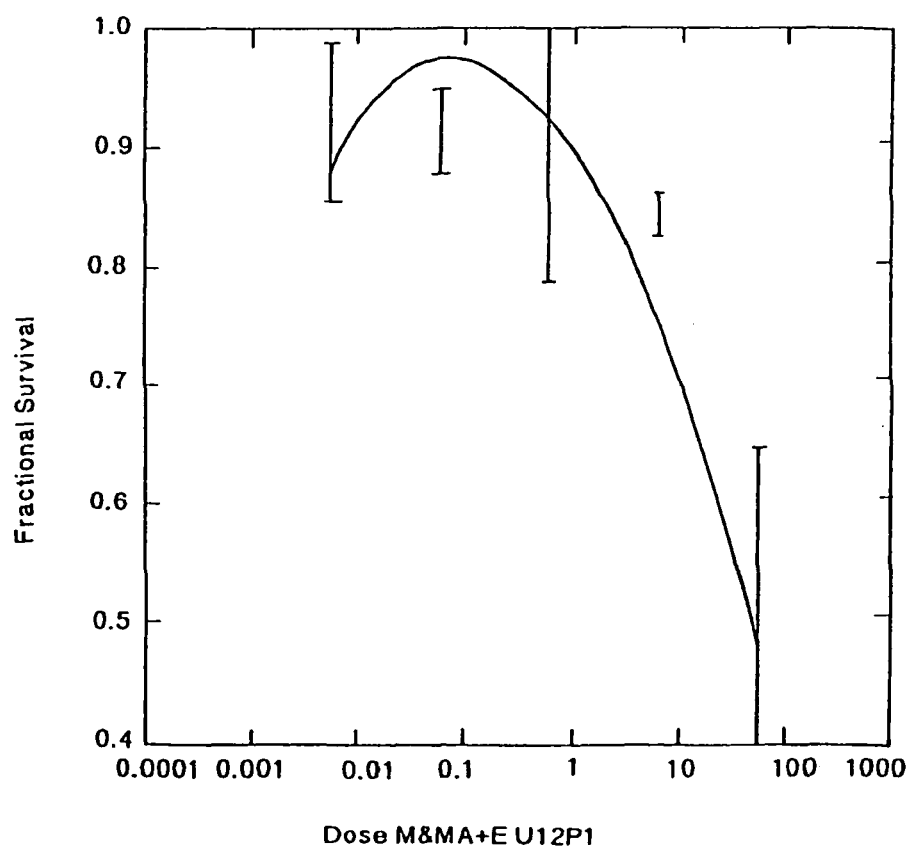
Figure 6:
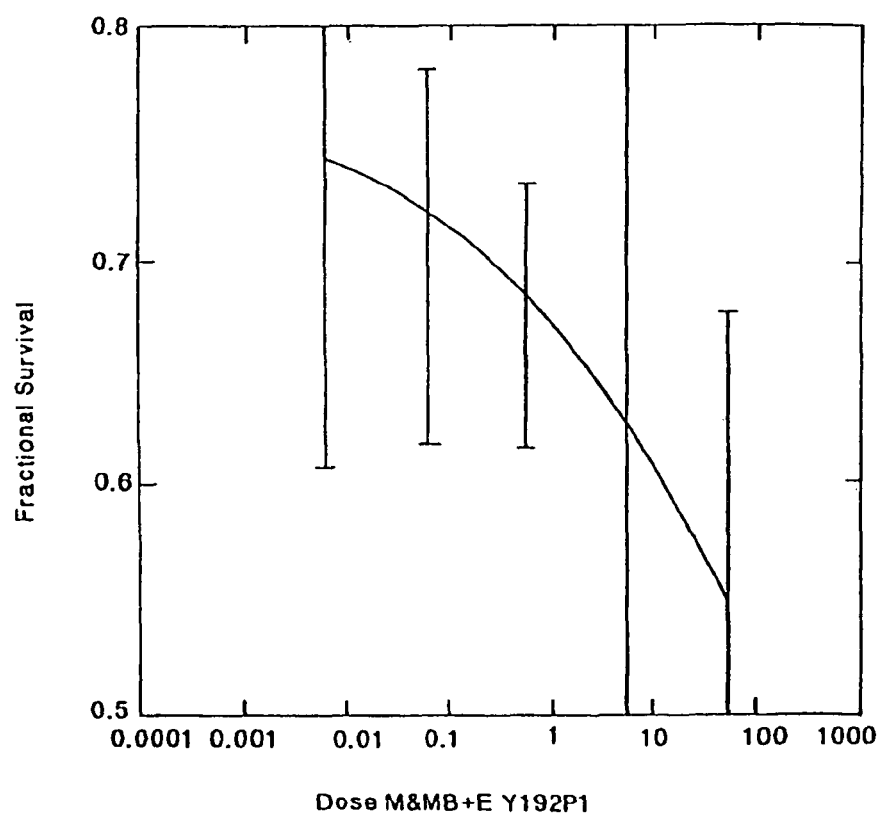
Figure 6C:
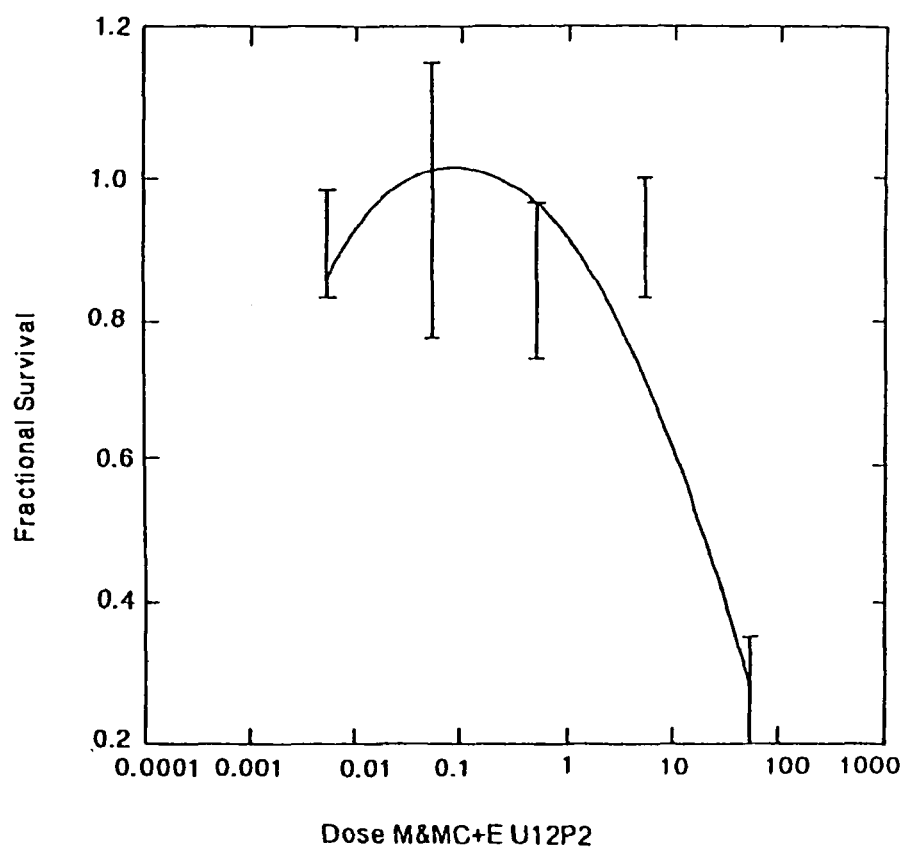
Figure 6D:
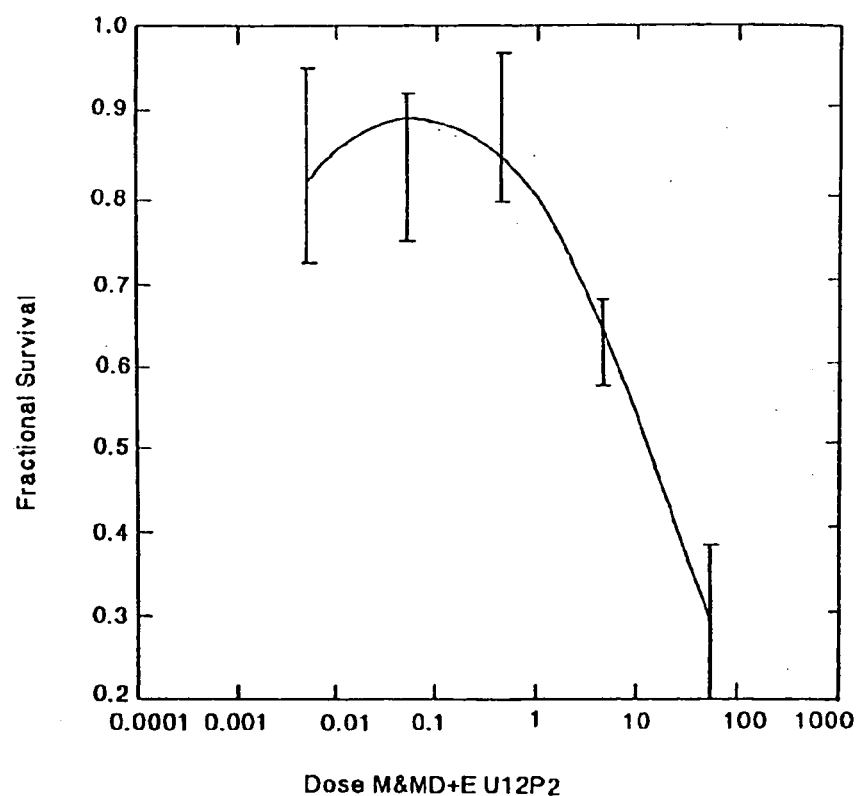

Two of the samples were first tested by this protocol. Sample MM1 represented a very crude isolate of cocoa procyanidins and contained appreciable quantities of caffeine and theobromine. Sample MM2 represented a cocoa procyanidin isolate partially purified by gel permeation chromatography. Caffeine and theobromine were absent in MM2. Both samples were screened for activity against the following cancer cell lines using the procedures previously described:

HCT 116 colon cancer
ACHN renal adenocarcinoma
SK-5 melanoma
A498 renal adenocarcinoma
MCF-7 breast cancer
PC-3 prostate cancer
CAPAN-2 pancreatic cancer Little or no activity was observed with MM1 on any of the cancer cell lines investigated. MM2 was found to have activity against HCT-116, PC-3 and ACHN cancer cell lines. However, both MM1 and MM2 were found to interfere with MTT such that it obscured the decrease in absorbance that would have reflected a decrease in viable cell number. This interference also contributed to large error bars, because the chemical reaction appeared to go more quickly in the wells along the perimeter of the plate. A typical example of these effects is shown in FIG. 5. At the high concentrations of test material, one would have expected to observe a large decrease in survivors rather than the high survivor levels shown. Nevertheless, microscopic examinations revealed that cytotoxic effects occurred, despite the MTT interference effects. For instance, an $IC_{50}$ value of 0.5 μg/mL for the effect of MM2 on the ACHN cell line was obtained in this manner.

These preliminary results, in the inventors' view, required amendment of the assay procedures to preclude the interference with MTT. This was accomplished as follows. After incubation of the plates at 37° C. in a humidified, 5% $CO_2$ atmosphere for 18 hours, the medium was carefully aspirated and replaced with fresh alpha-MEM media. This media was again aspirated from the wells on the third day of the assay and replaced with 100 μL of freshly prepared McCoy's medium. 11 μL of a 5 mg/mL stock solution of MTT in PBS (Phosphate Buffered Saline) were then added to the wells of each plate. After incubation for 4 hours in a humidified, 5% $CO_2$ atmosphere at 37° C., 100 μL of 0.04 N HCl in isopropanol was added to all wells of the plate, followed by thorough mixing to solubilize the formazan produced by any viable cells. Additionally, it was decided to subfractionate the procyanidins to determine the specific components responsible for activity.

The subfractionation procedures previously described were used to prepare samples for further screening. Five fractions representing the areas shown in FIG. 1 and component(s) distribution shown in FIGS. 4A-4E were prepared. The samples were coded MM2A through MM2E to reflect these analytical characterizations and to designate the absence of caffeine and theobromine.

Each fraction was individually screened against the HCT-116, PC-3 and ACHN cancer cell lines. The results indicated that the activity did not concentrate to any one specific fraction. This type of result was not considered unusual, since the components in "active" natural product isolates can behave synergistically. In the case of the cocoa procyanidin isolate (MM2), over twenty detectable components comprised the isolate. It was considered possible that the activity was related to a combination of components present in the different fractions, rather than the activity being related to an individual component(s).

On the basis of these results, it was decided to combine the fractions and repeat the assays against the same cancer cell lines. Several fraction combinations produced cytotoxic effects against the PC-3 cancer cell lines. Specifically, $IC_{50}$ values of 40 μg/mL each for MM2A and MM2E combination, and of 20 μg/mL each for MM2C and MM2E combination, were obtained. Activity was also reported against the HCT-116 and ACHN cell lines, but as before, interference with the MTT indicator precluded precise observations. Replicate experiments were repeatedly performed on the HCT-116 and ACHN lines to improve the data. However, these results were inconclusive due to bacterial contamination and exhaustion of the test sample material. FIGS. 6A-6D show the dose-response relationship between combinations of the cocoa extracts and PC-3 cancer cells.

Nonetheless, from this data, it is clear that cocoa extracts, especially cocoa polyphenols or procyanidins, have significant anti-tumor, anti-cancer or antineoplastic activity, especially with respect to human PC-3 (prostate), HCT-116 (colon) and ACHN (renal) cancer cell lines. In addition, those results suggest that specific procyanidin fractions may be responsible for the activity against the PC-3 cell line.

Example 7

Anti-Cancer, Anti-Tumor or Antineoplastic Activity of Cocoa Extracts (Procvanidins)

To confirm the above findings and further study fraction combinations, another comprehensive screening was performed.

All prepared materials and procedures were identical to those reported above, except that the standard 4-replicates per test dose was increased to 8 or 12-replicates per test dose. For this study, individual and combinations of five cocoa procyanidin fractions were screened against the following cancer cell lines.

PC-3 Prostate
KB Nasopharyngeal/HeLa
HCT-116 Colon
ACHN Renal
MCF-7 Breast
SK-5 Melanoma
A-549 Lung
CCRF-CEM T-cell leukemia Individual screenings consisted of assaying different dose levels (0.01-100 µg/mL) of fractions A, B, C, D, and E (See FIGS. 4A-4E and discussion thereof, supra) against each cell line. Combination screenings consisted of combining equal dose levels of fractions A+B, A+C, A+D, A+E, B+C, B+D, B+E, C+D, C+E, and D+E against each cell line. The results from these assays are individually discussed, followed by an overall summary.

A. PC-3 Prostate Cell Line

Figure 7A:
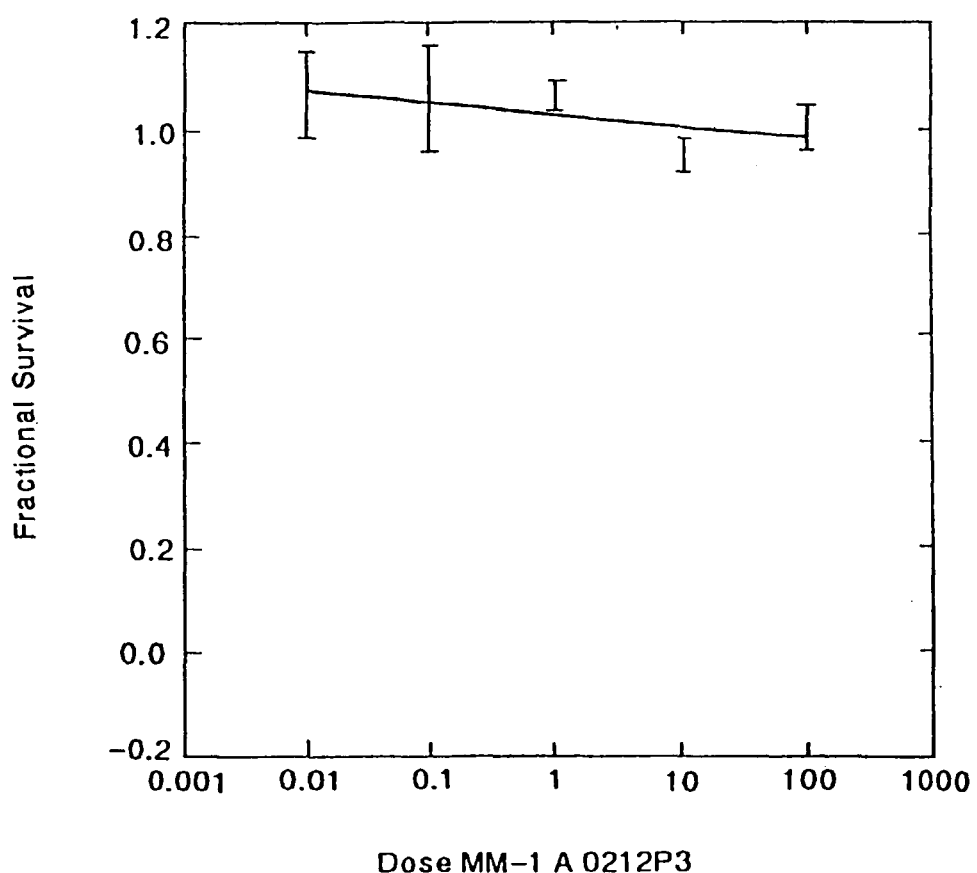
FIGS. 7A to 7H show the typical dose response relationships between cocoa procyanidin fractions A, B, C, D, E, A+B, A+E, and A+D, and the PC-3 cell line (fractional survival vs. dose, μg/mL); MM-1A 0212P3, MM-1B 0162P1, MM-1C 0122P3, MM-1D 0122P3, MM-1E 0292P8, MM-1 A/B 0292P6, MM-1 A/E 0292P6, MM-1 A/D 0292P6.
Figure 7B:
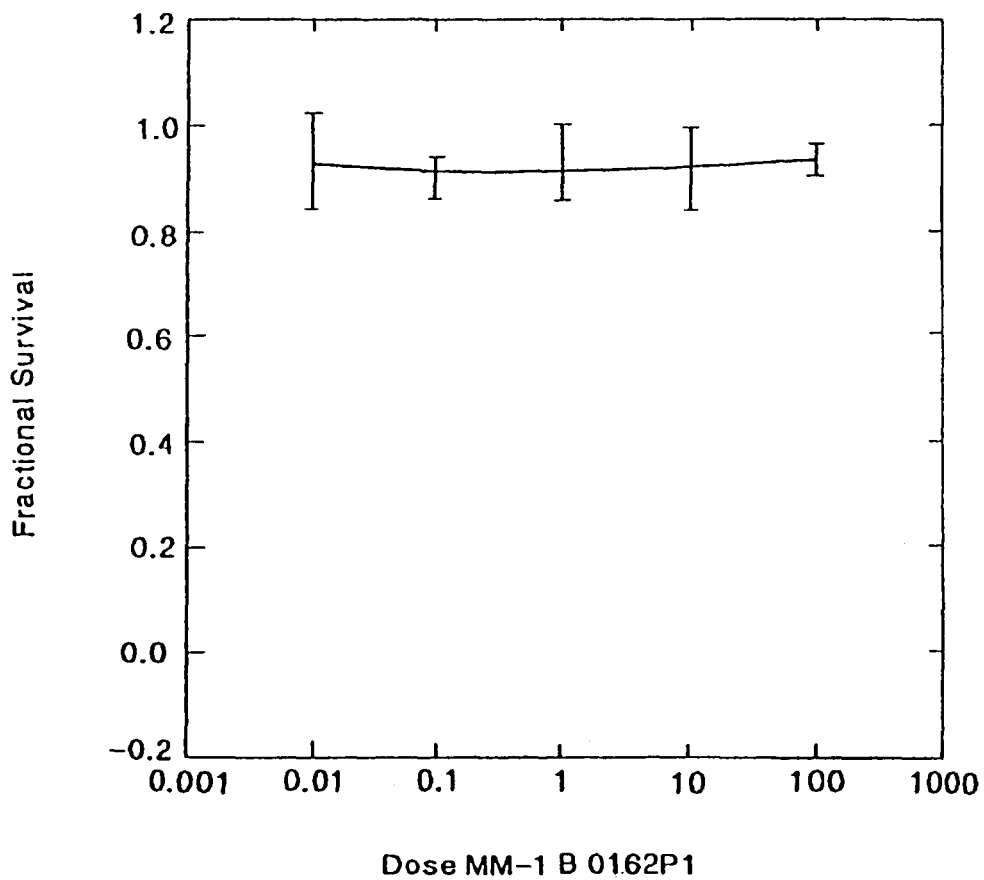
Figure 7C:
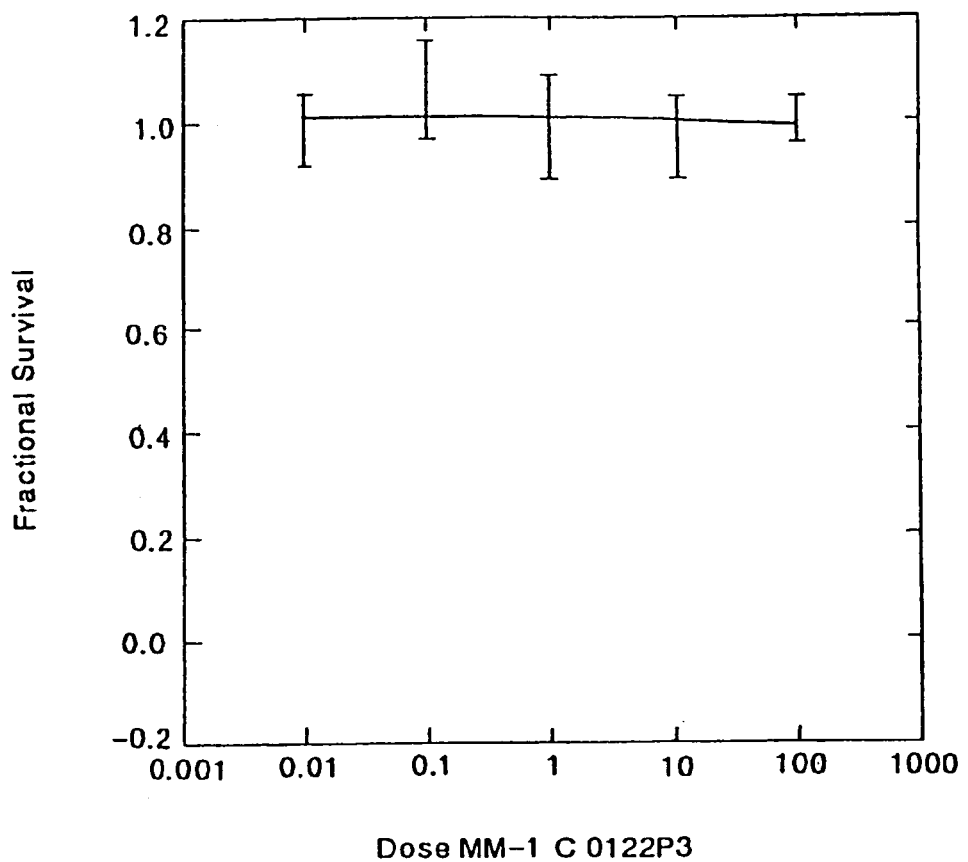
Figure 7D:
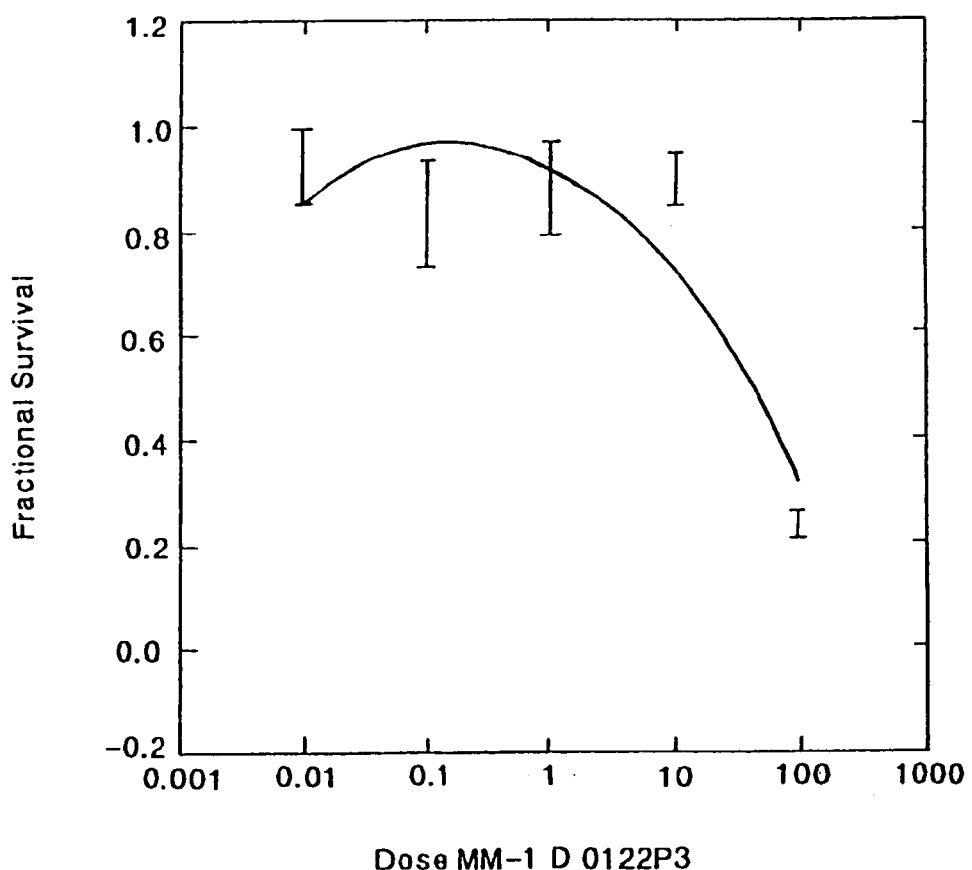
Figure 7E:
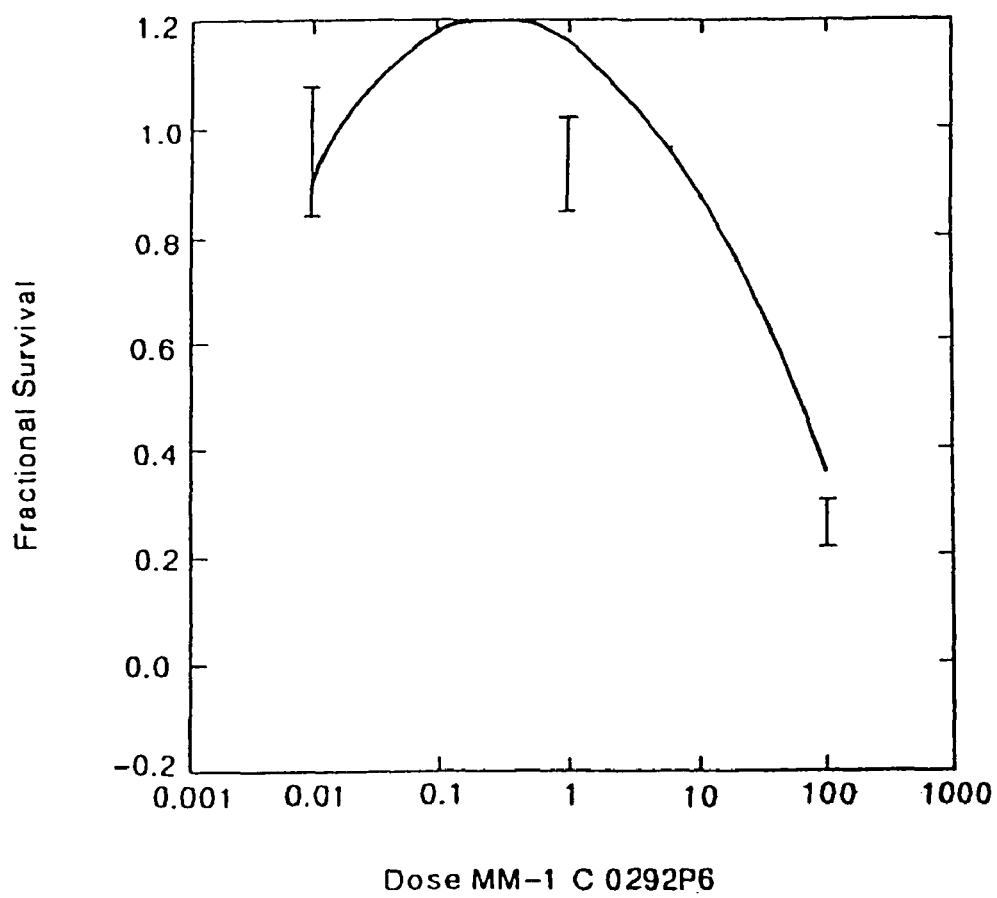
Figure 7F:
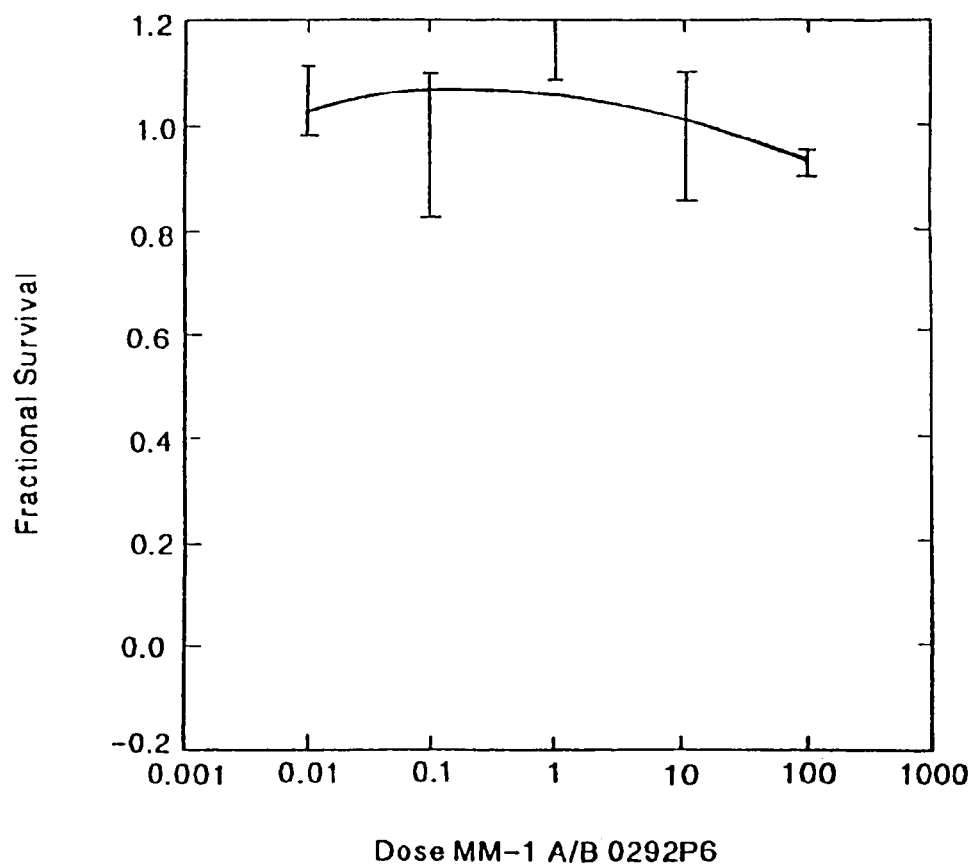
Figure 7G:
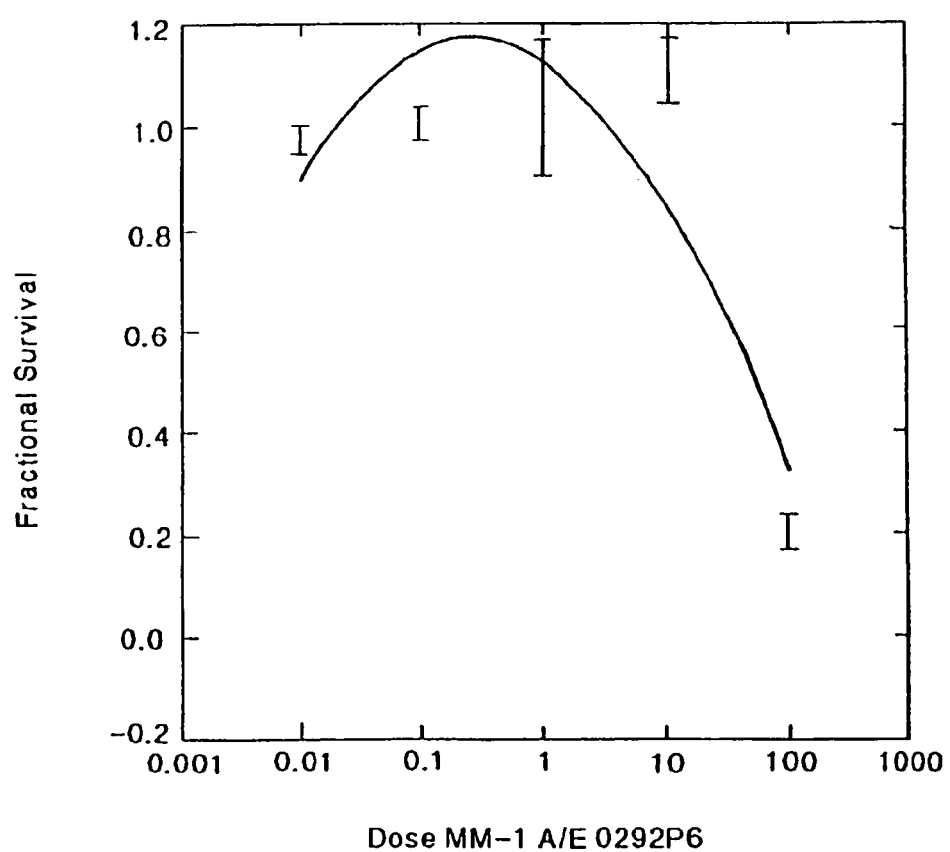
Figure 7H:
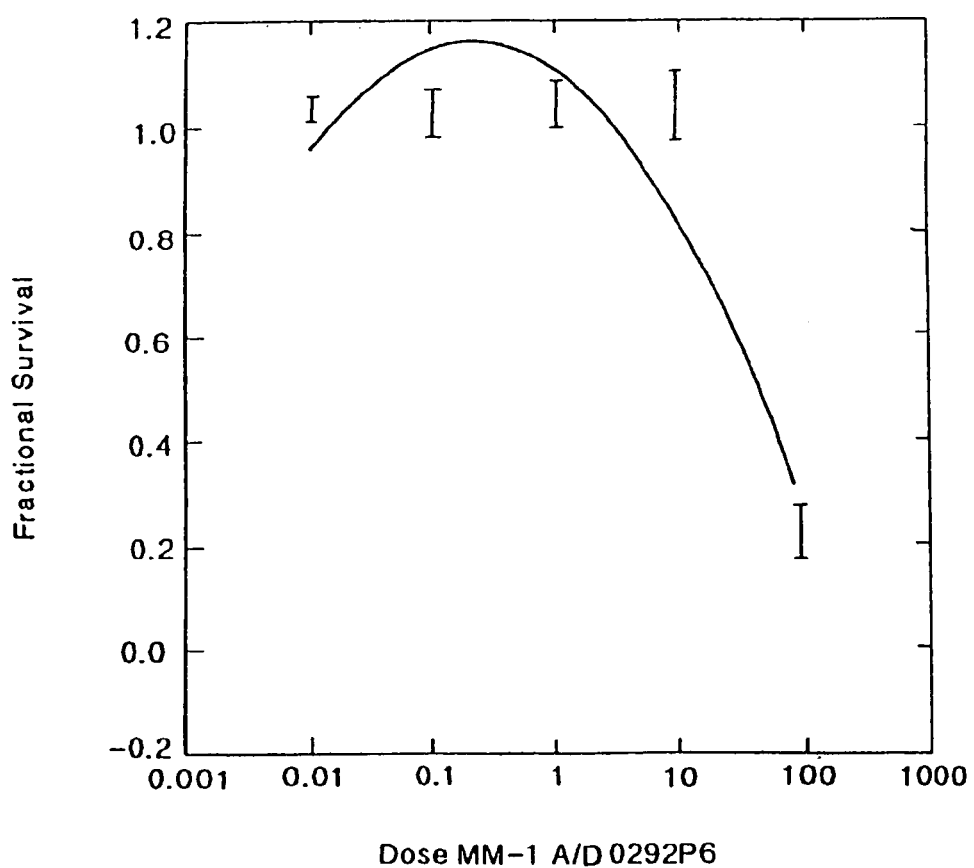

FIGS. 7A-7H show the typical dose response relationship between cocoa procyanidin fractions and the PC-3 cell line. FIGS. 7D and 7E demonstrate that fractions D and E were active at an $IC_{50}$ value of 75 µg/mL. The $IC_{50}$ values that were obtained from dose-response curves of the other procyanidin fraction combinations ranged between 60-80 µg/mL when fractions D or E were present. The individual $IC_{50}$ values are listed in Table 6.

B. KB Nasopharyngeal/HeLa Cell Line

Figure 8A:
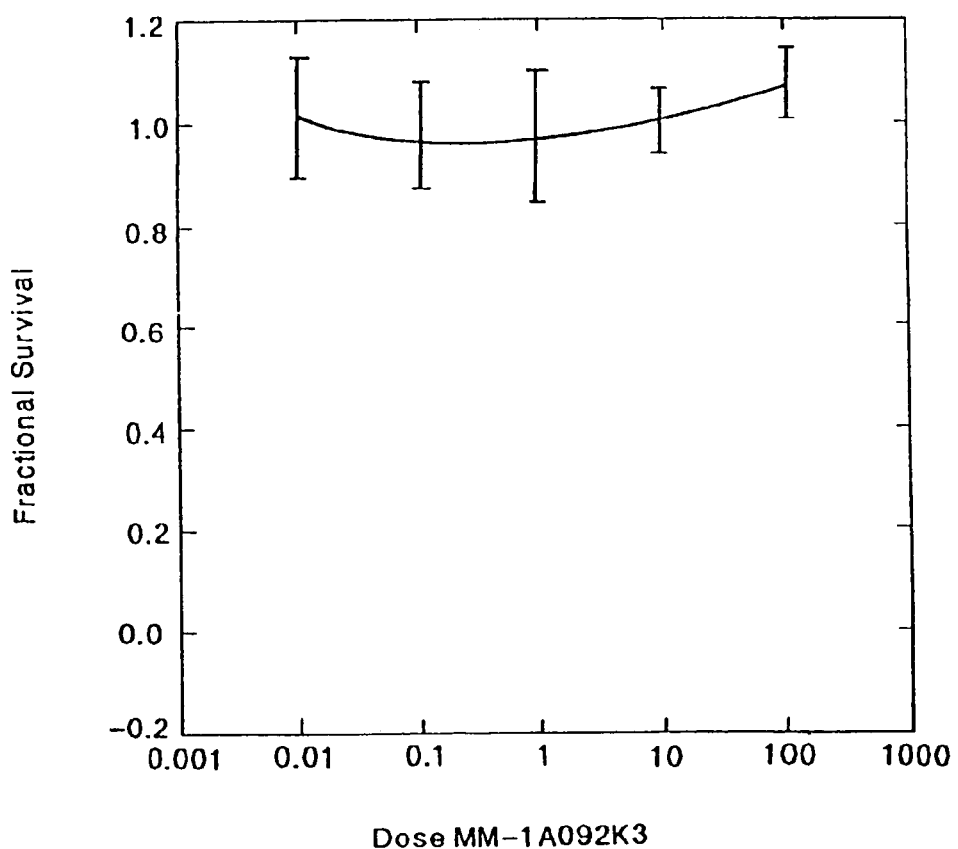
FIGS. 8A to 8H show the typical dose response relationships between cocoa procyanidin fractions A, B, C, D, E, A+B, B+E, and D+E and the KB Nasopharyngeal/HeLa cell line (fractional survival vs. dose, μg/mL); MM-1A092K3, MM-1B 0212K5, MM-1C 0162K3, MM-1D 0212K5, MM-1 E 0292K5, MM-1 A/B 0292K3, MM-1 B/E 0292K4, MM-1 D/E 0292K5.
Figure 8B:
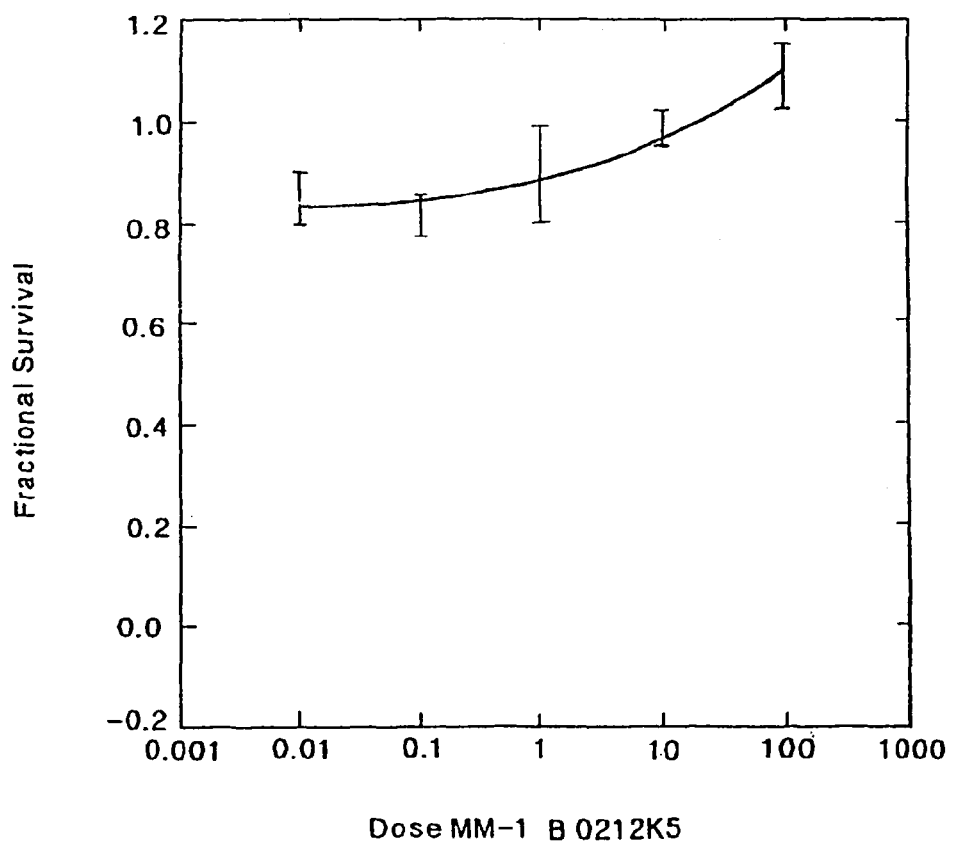
Figure 8C:
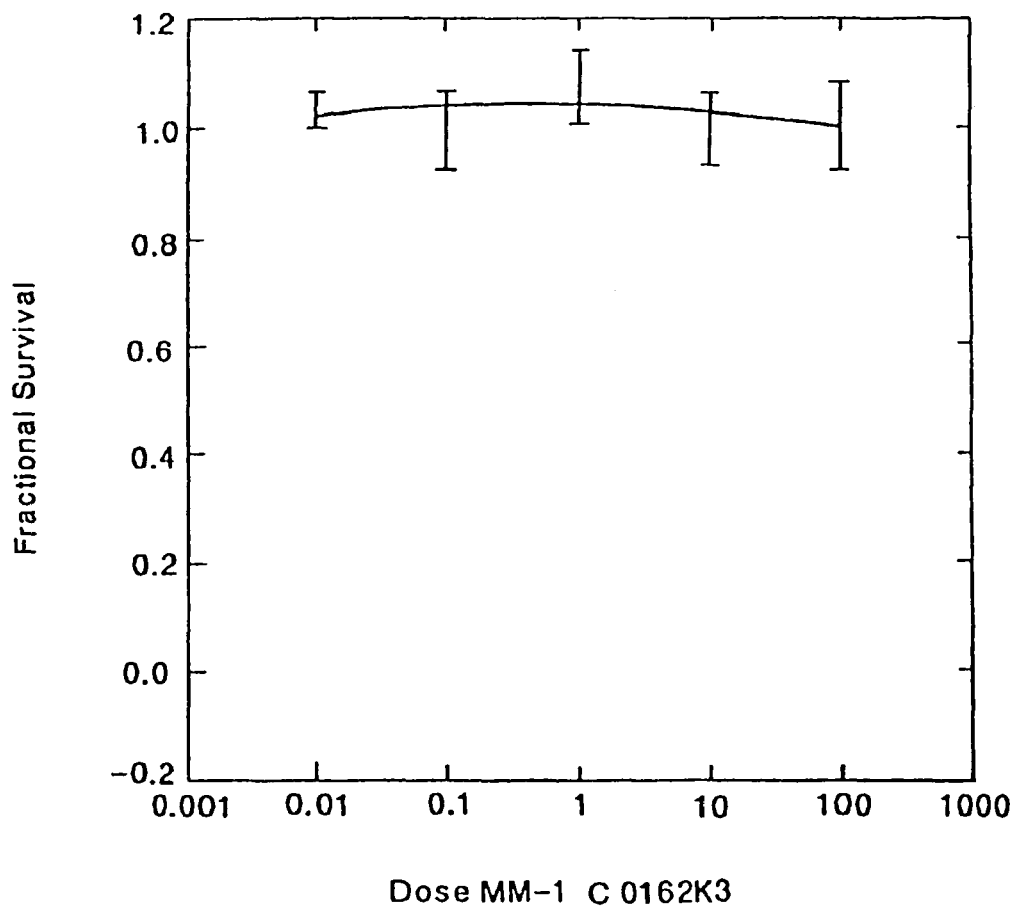
Figure 8D:
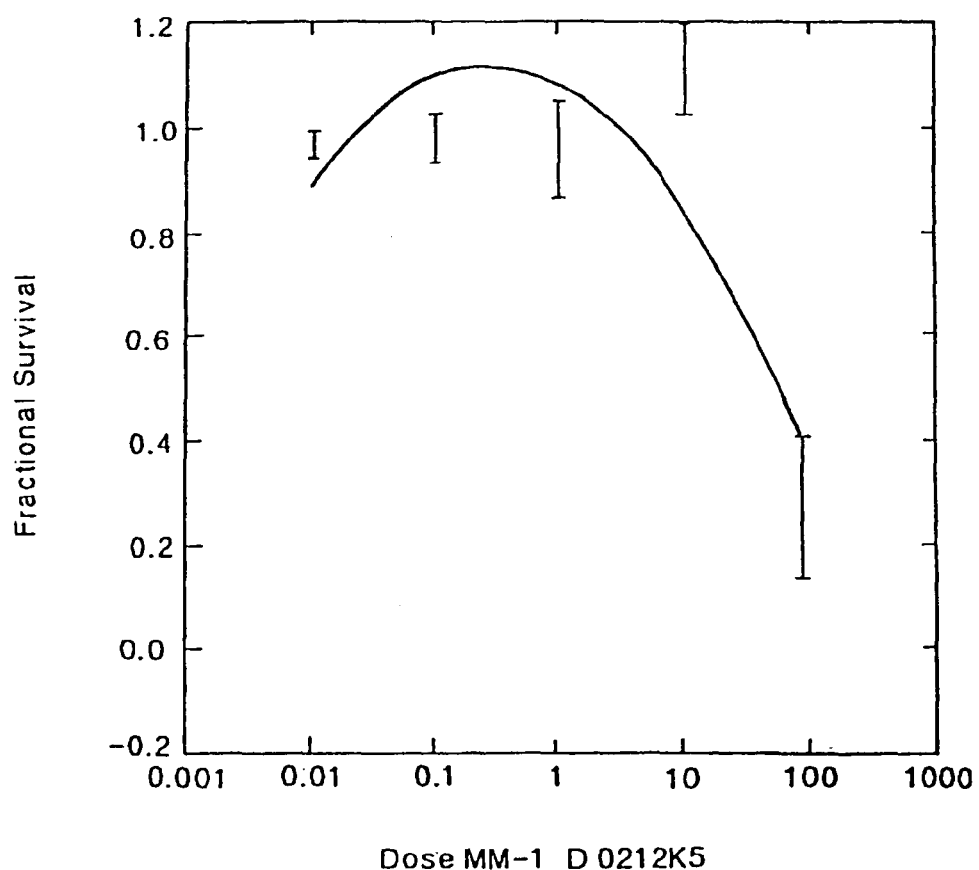
Figure 8E:
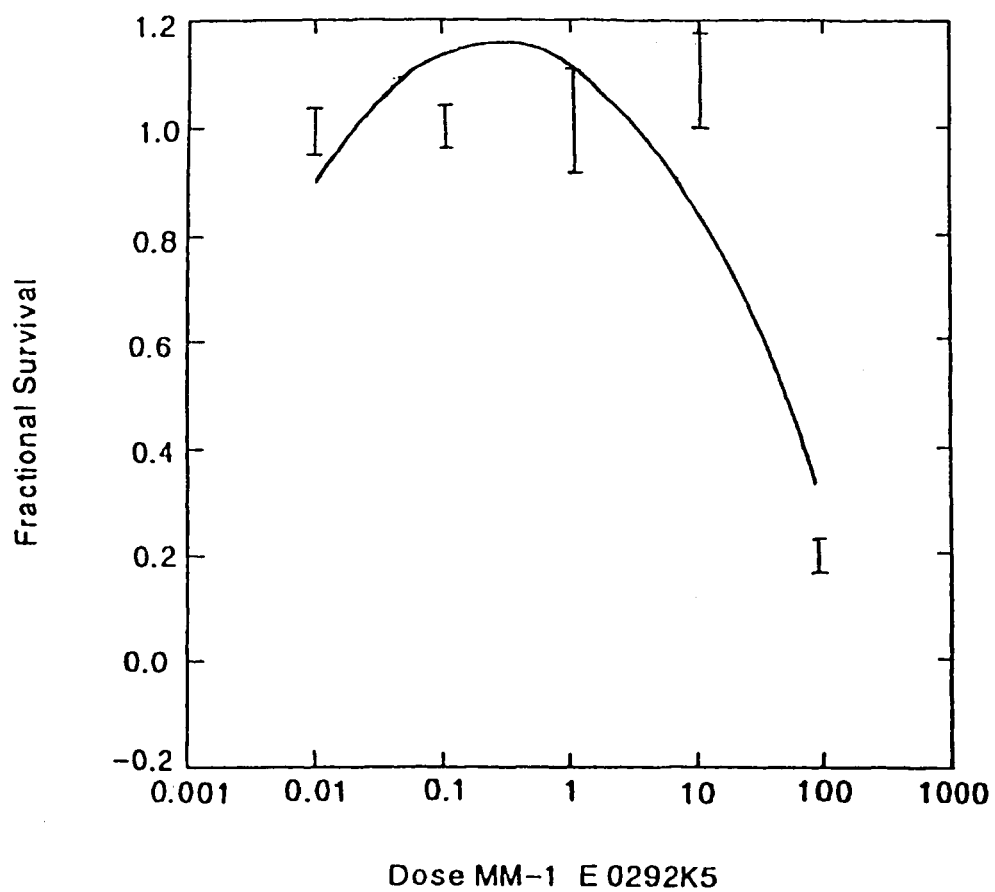
Figure 8F:
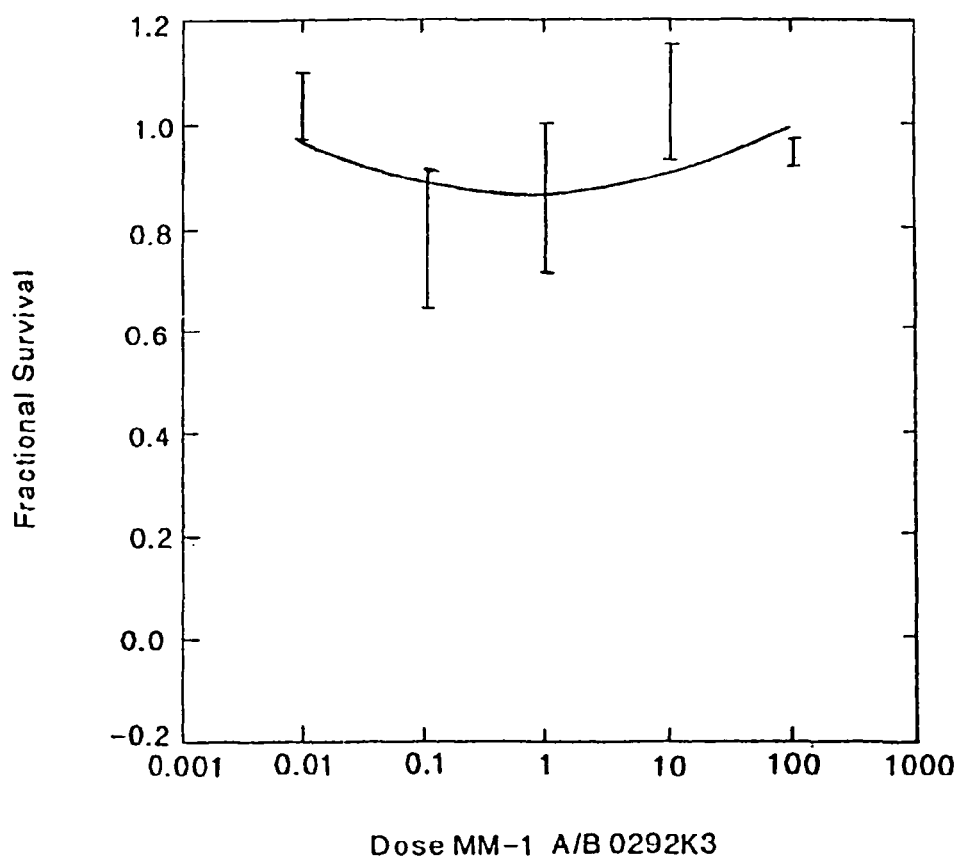
Figure 8G:
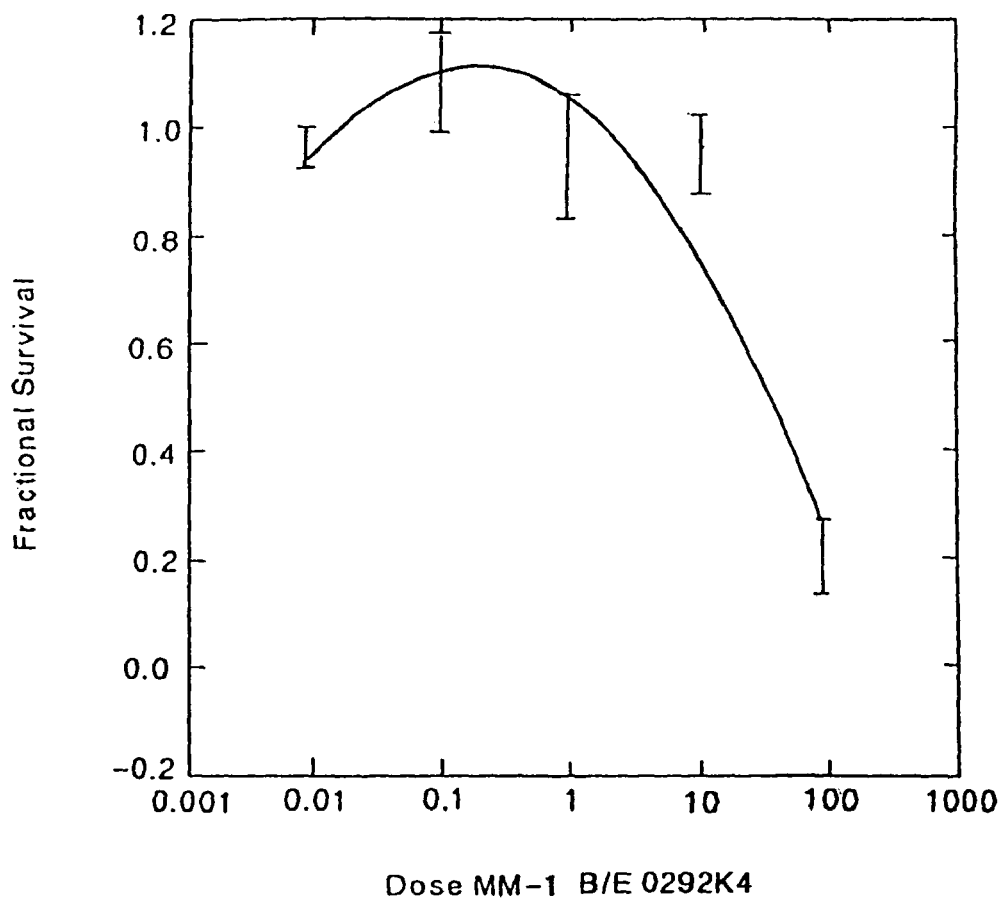
Figure 8H:
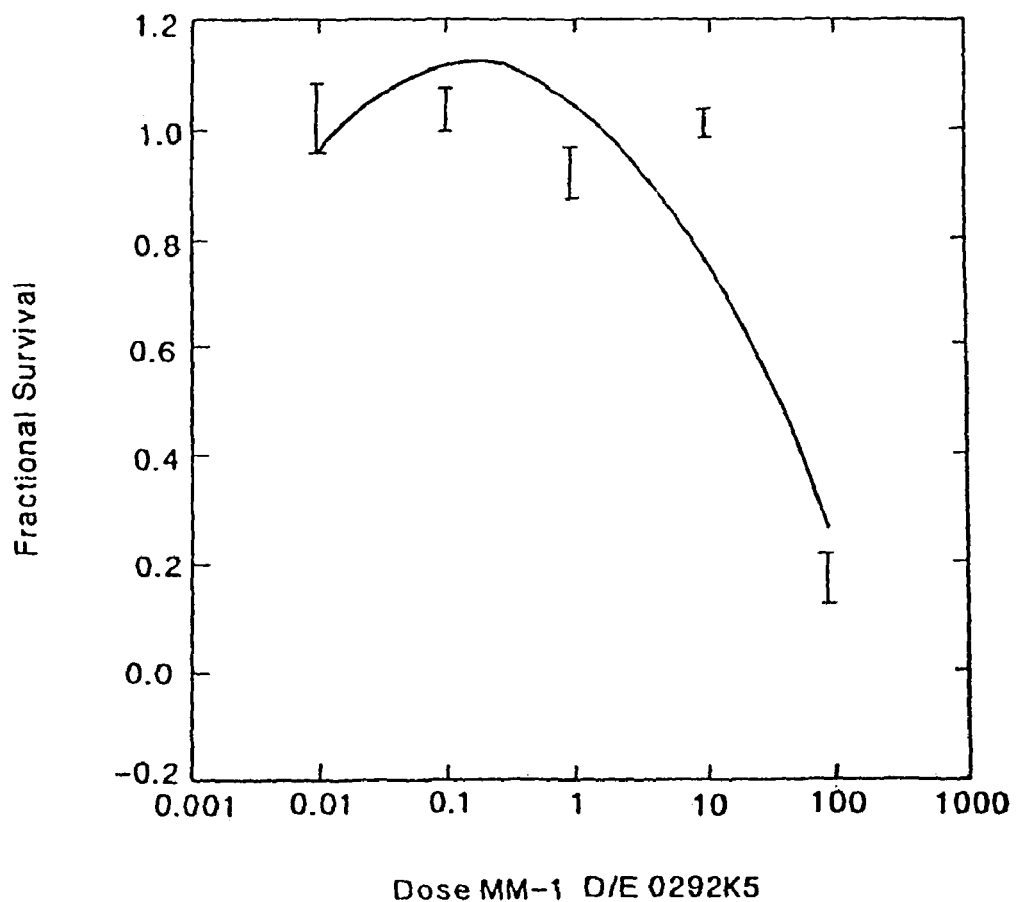

FIGS. 8A-8H show the typical dose response relationship between cocoa procyanidin fractions and the KB Nasopharyngeal/HeLa cell line. FIGS. 8D and 8E demonstrate that fractions D and E were active at an $IC_{50}$ value of 75 µg/mL. FIGS. 8F-8H depict representative results obtained from the fraction combination study. In this case, procyanidin fraction combination A+B had no effect, whereas fraction combinations B+E and D+E were active at an $IC_{50}$ value of 60 µg/mL. The $IC_{50}$ values that were obtained from other dose response curves from other fraction combinations ranged from 60-80 µg/mL when fractions D or E were present. The individual $IC_{50}$ values are listed in Table 6. These results were essentially the same as those obtained against the PC-3 cell line.

C. HCT-116 Colon Cell Line

Figure 9A:
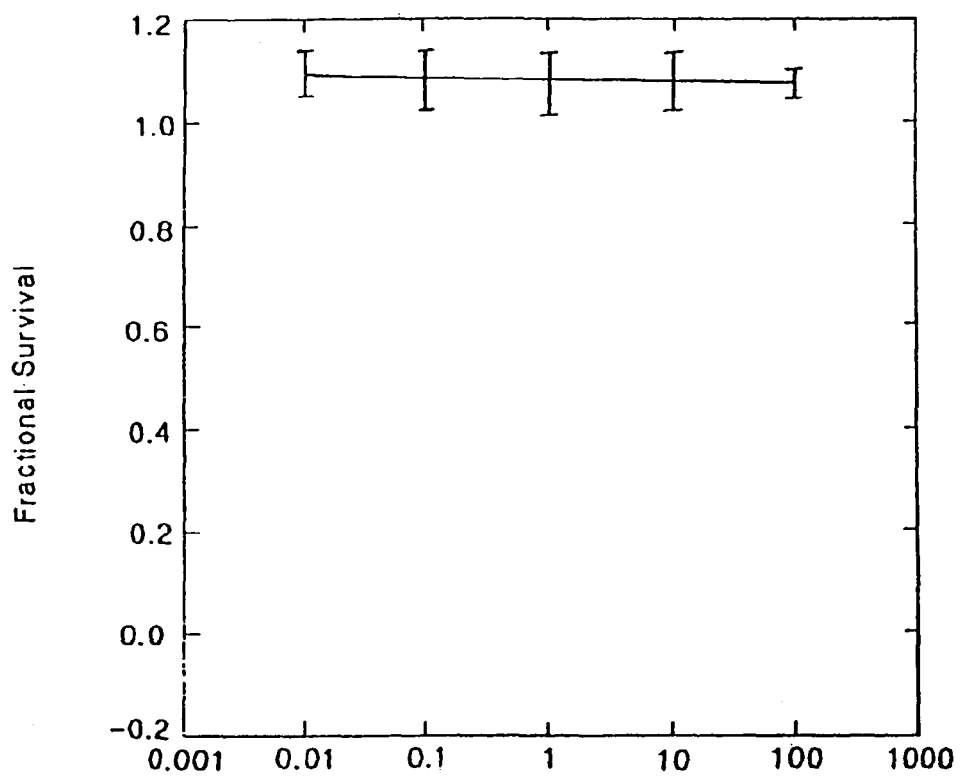
FIGS. 9A to 9H show the typical dose response relationship between cocoa procyanidin fractions A, B, C, D, E, B+D, A+E and D+E and the HCT-116 cell line (fractional survival vs. dose, μg/mL); MM-1 C 0192H5, D 0192H5, E 0192H5, MM-1 B&D 0262H2, A/E 0262H3, MM-1 D&E 0262H1.
Figure 9B:
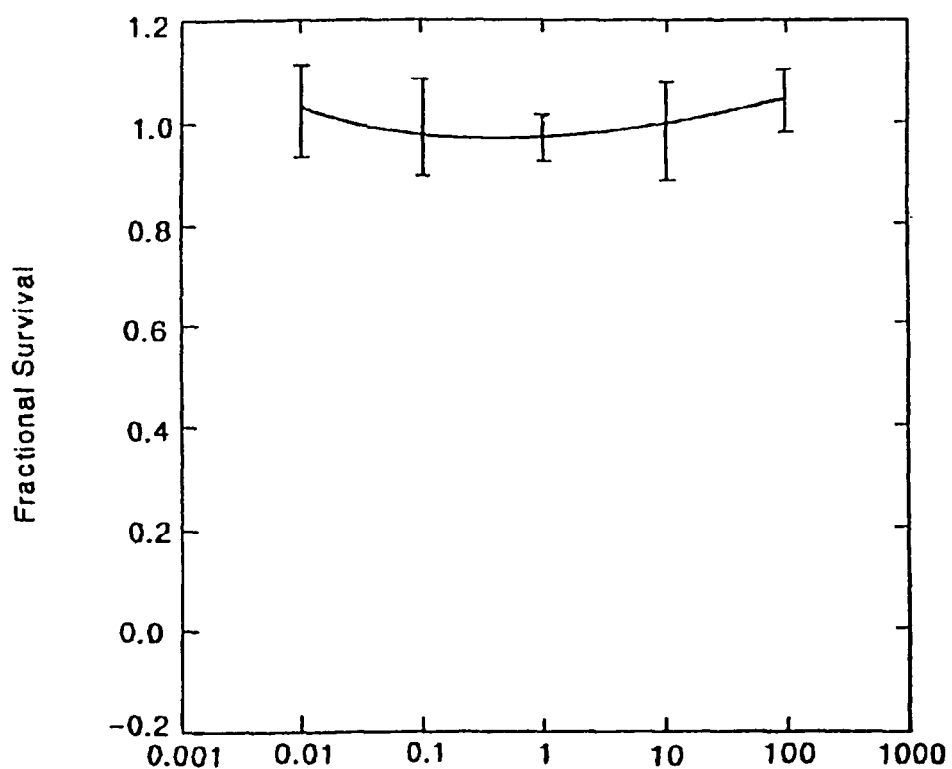
Figure 9C:
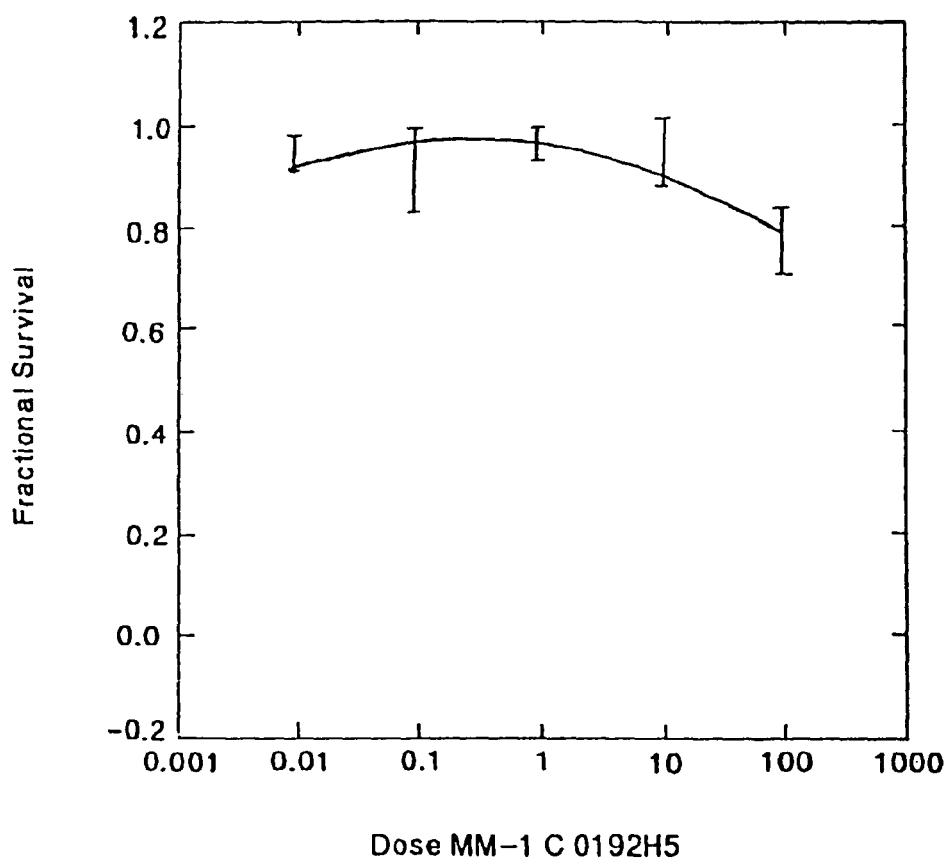
Figure 9D:
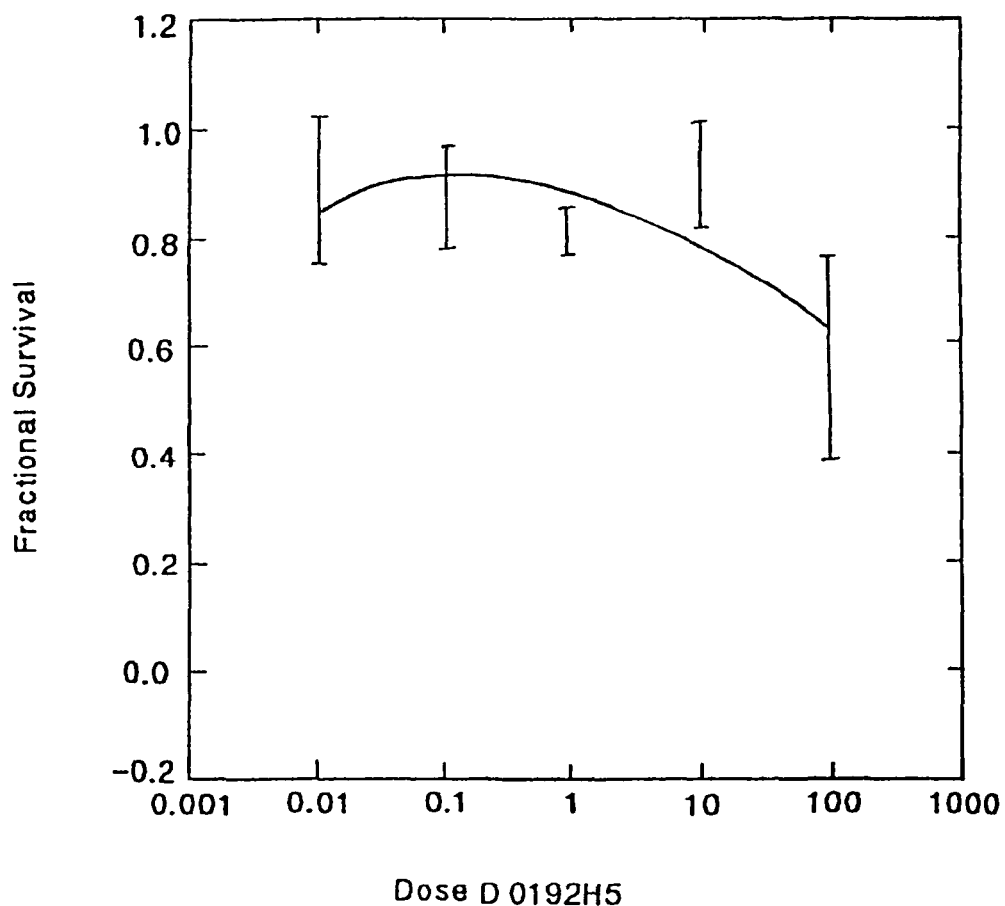
Figure 9E:
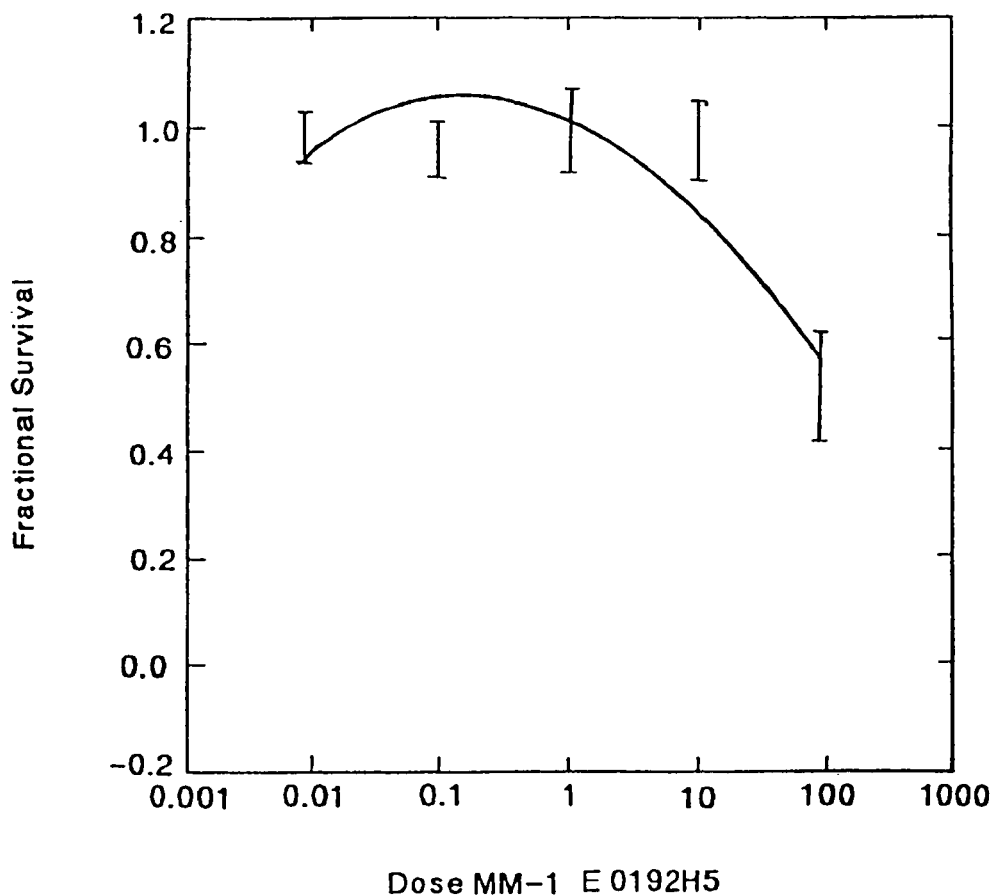
Figure 9F:
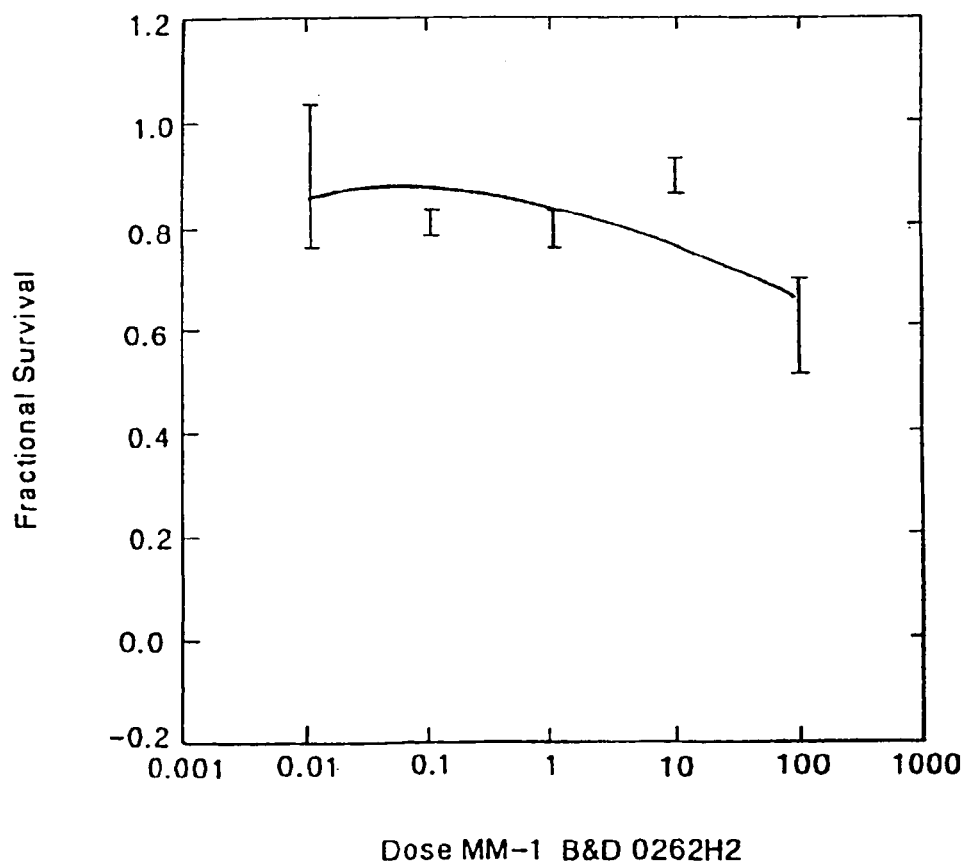
Figure 9G:
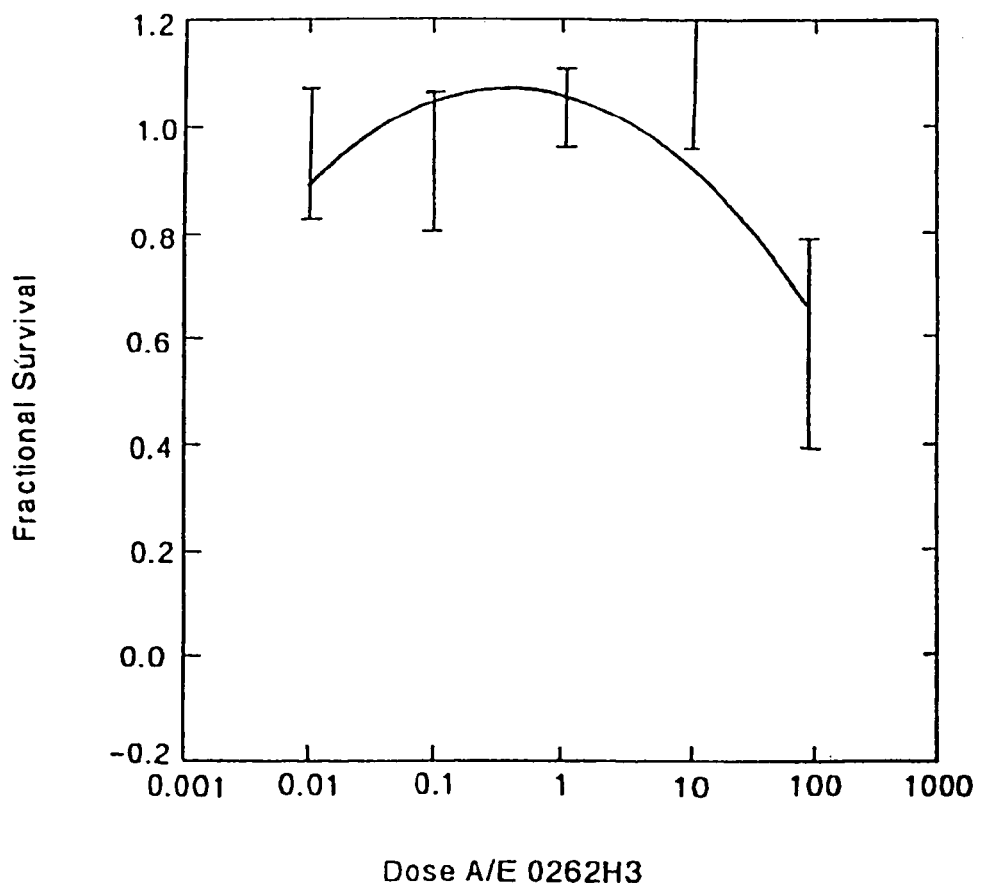
Figure 9H:
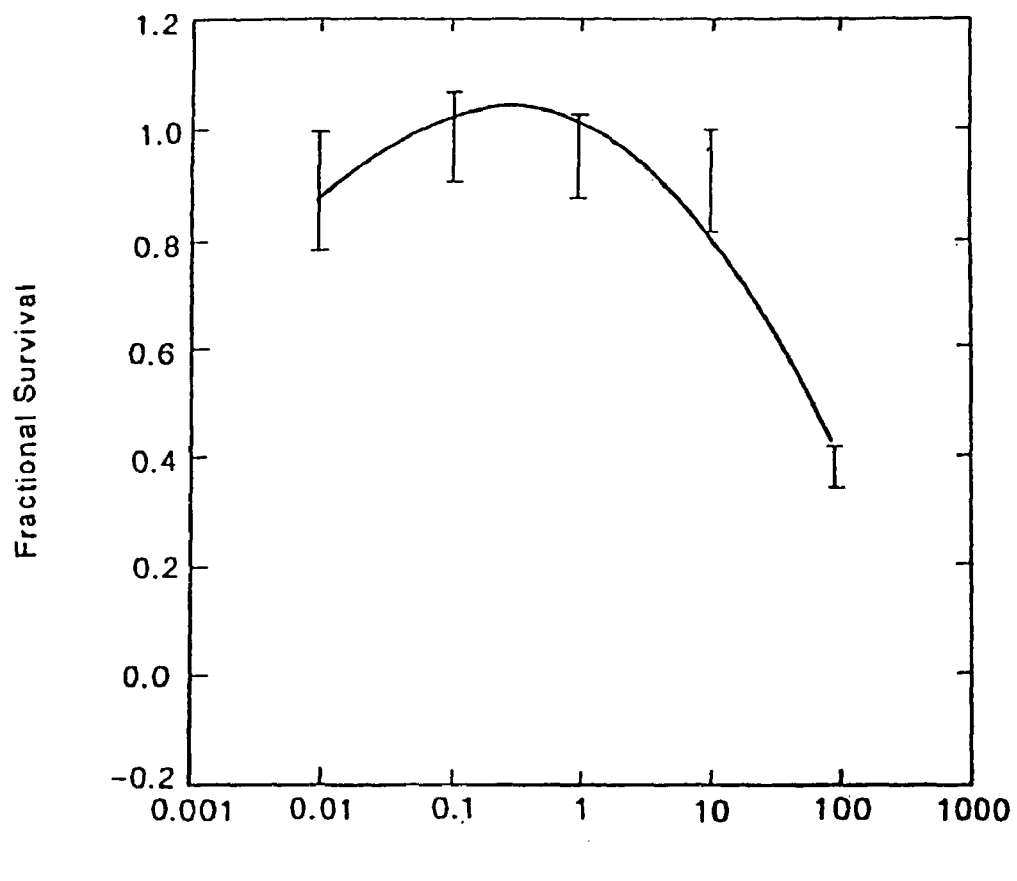

FIGS. 9A-9H show the typical dose response relationships between cocoa procyanidin fractions and the HCT-116 colon cell line. FIGS. 9D and 9E demonstrate that fraction E was active at an $IC_{50}$ value of approximately 400 µg/mL. This value was obtained by extrapolation of the existing curve. Note that the slope of the dose response curve for fraction D also indicated activity. However, no $IC_{50}$ value was determined from this plot, since the slope of the curve was too shallow to obtain a reliable value. FIGS. 9F-9H depict representative results obtained from the fraction combination study. In this case, procyanidin fraction combination B+D did not show appreciable activity, whereas fraction combinations A+E and D+E were active at $IC_{50}$ values of 500 µg/mL and 85 µg/mL, respectively. The $IC_{50}$ values that were obtained from dose response curves of other fraction combinations averaged about 250 µg/mL when fraction E was present. The extrapolated $IC_{50}$ values are listed in Table 6.

D. ACHN Renal Cell Line

Figure 10A:
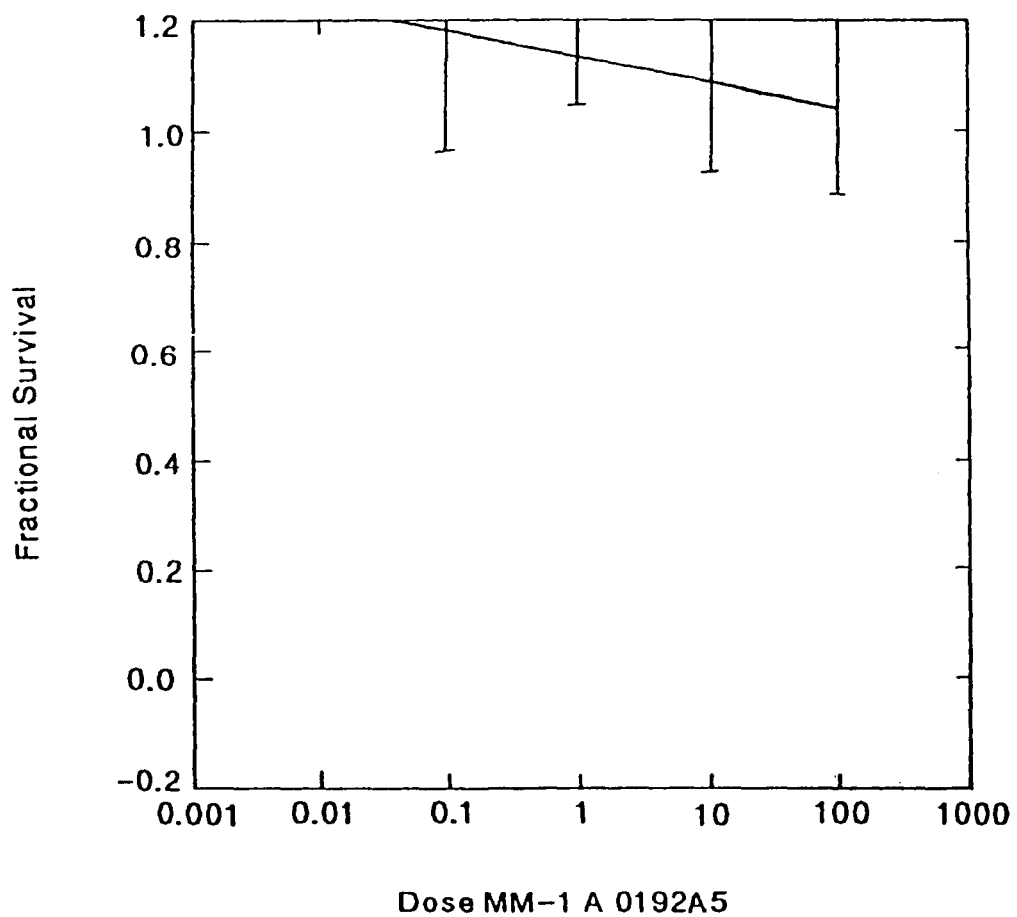
FIGS. 10A to 10H show typical dose response relationships between cocoa procyanidin fractions A, B, C, D, E, B+D, C+D and A+E and the ACHN renal cell line (fractional survival vs. dose, μg/mL); MM-1 A 092A5, MM-1 B 092A5, MM-1 C 0192A7, MM-1 D 0192A7, M&M1 E 0192A7, MM-1 B&D 0302A6, MM-1 C&D 0302A6, MM-1 A&E 0262A6.
Figure 10B:
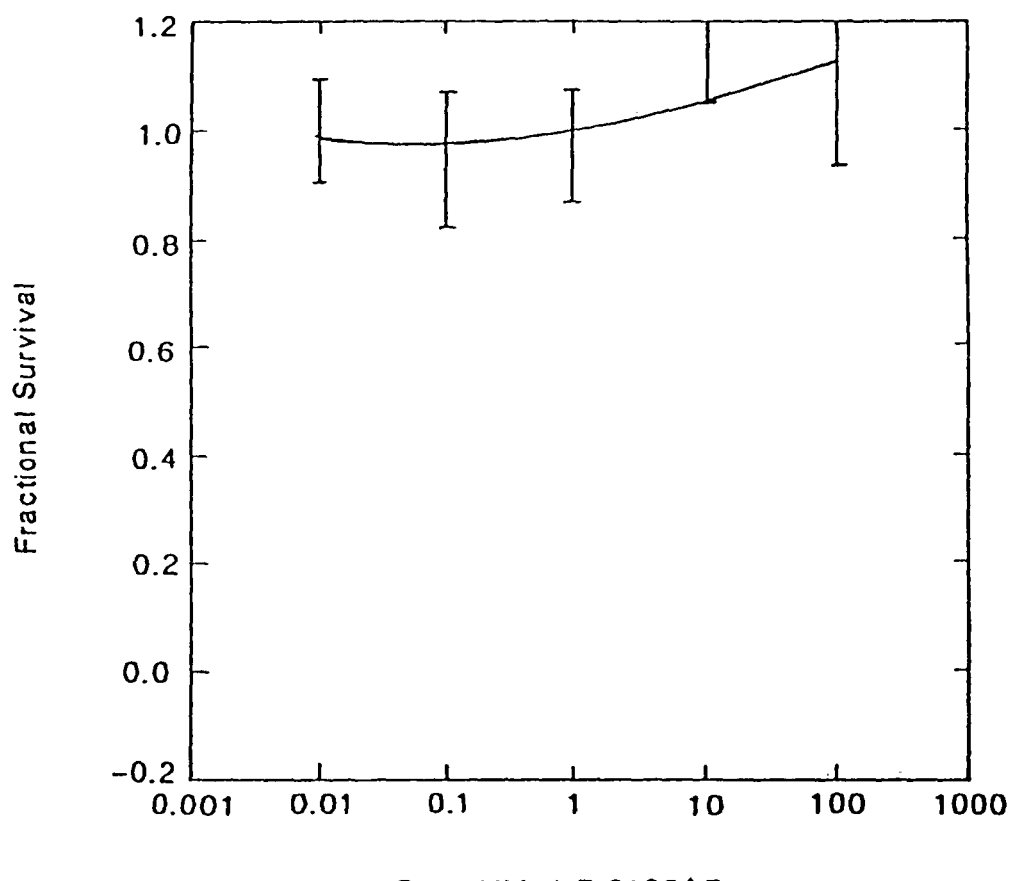
Figure 10C:
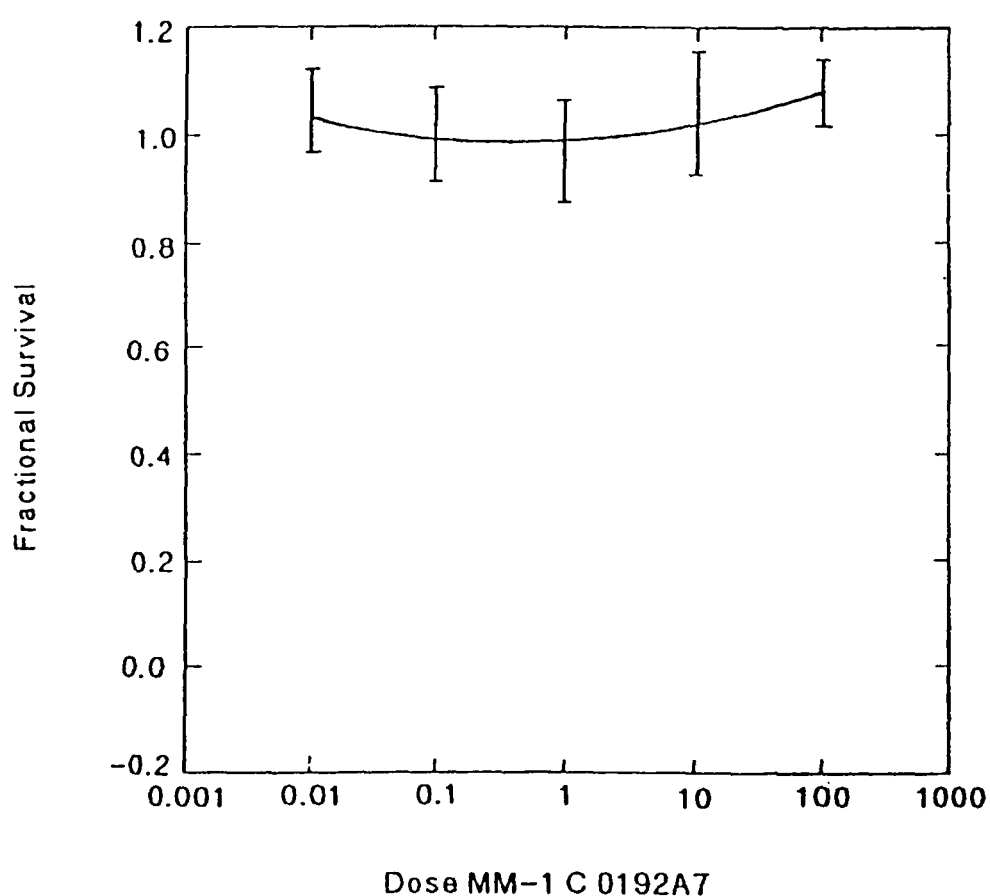
Figure 10D:
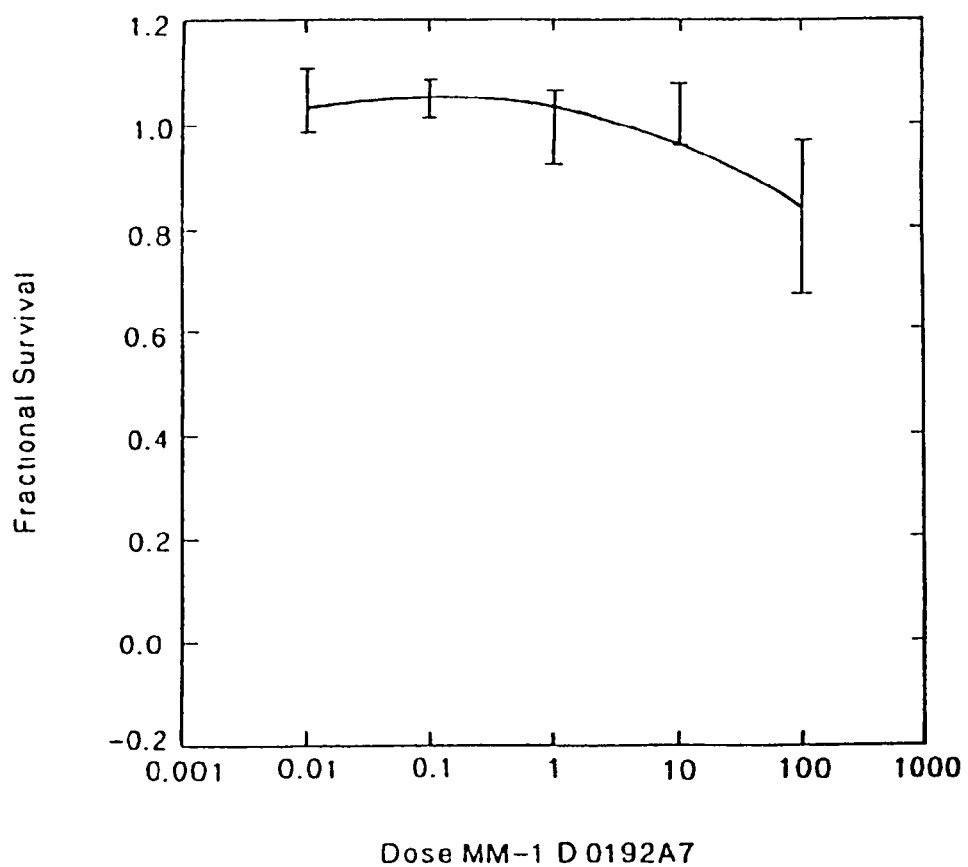
Figure 10E:
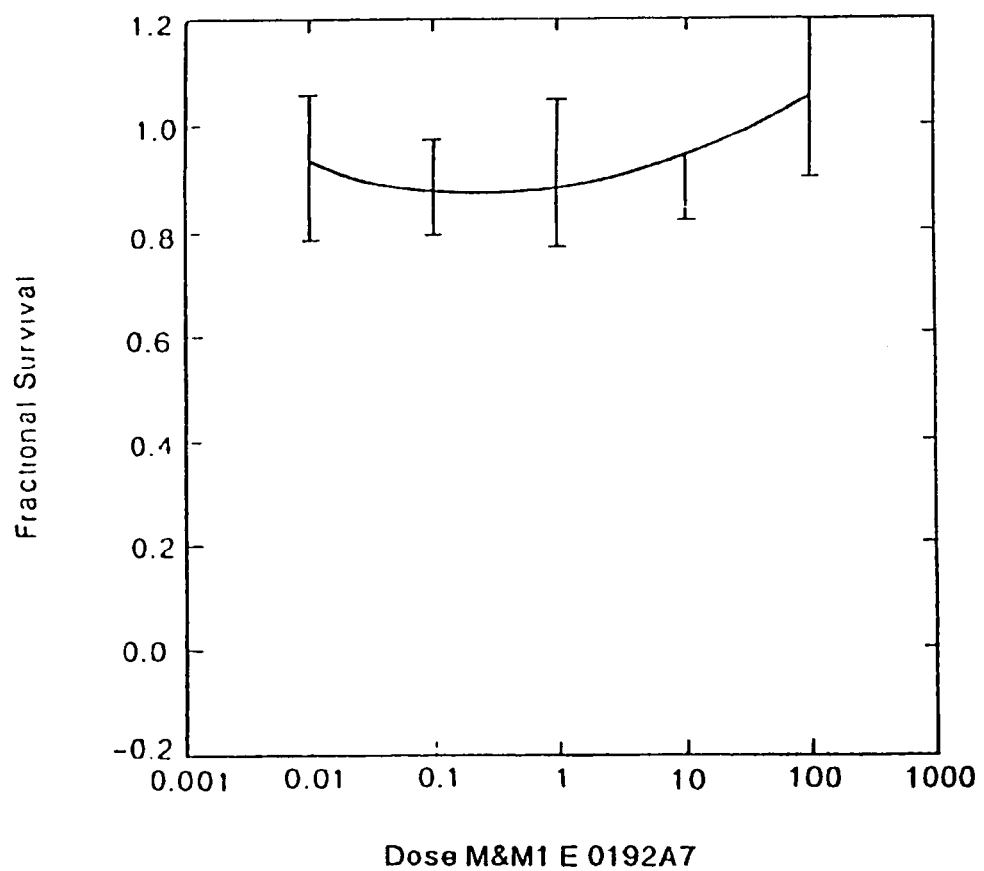
Figure 10F:
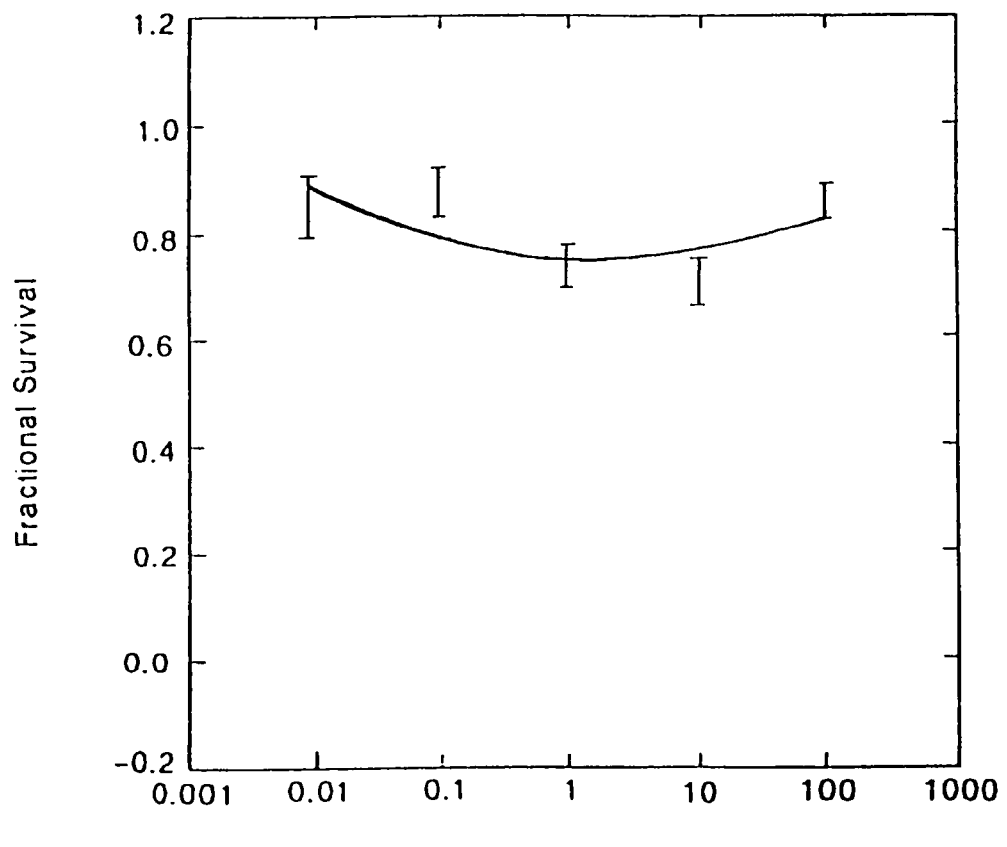
Figure 10G:
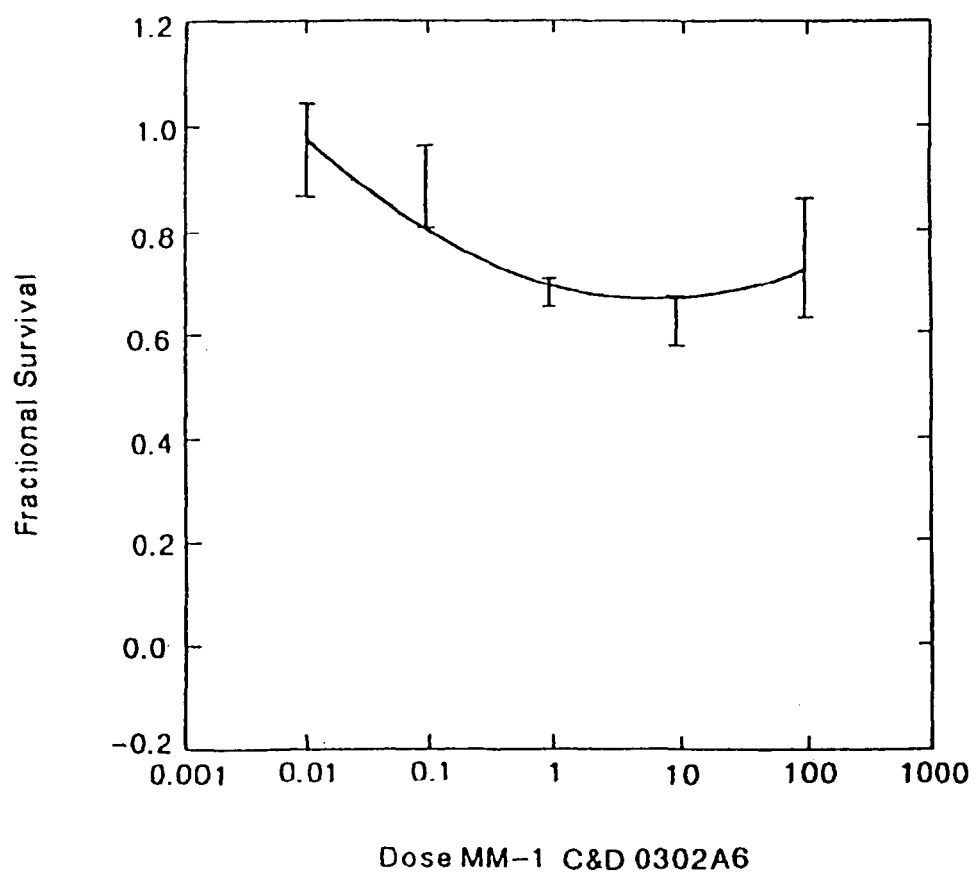
Figure 10H:
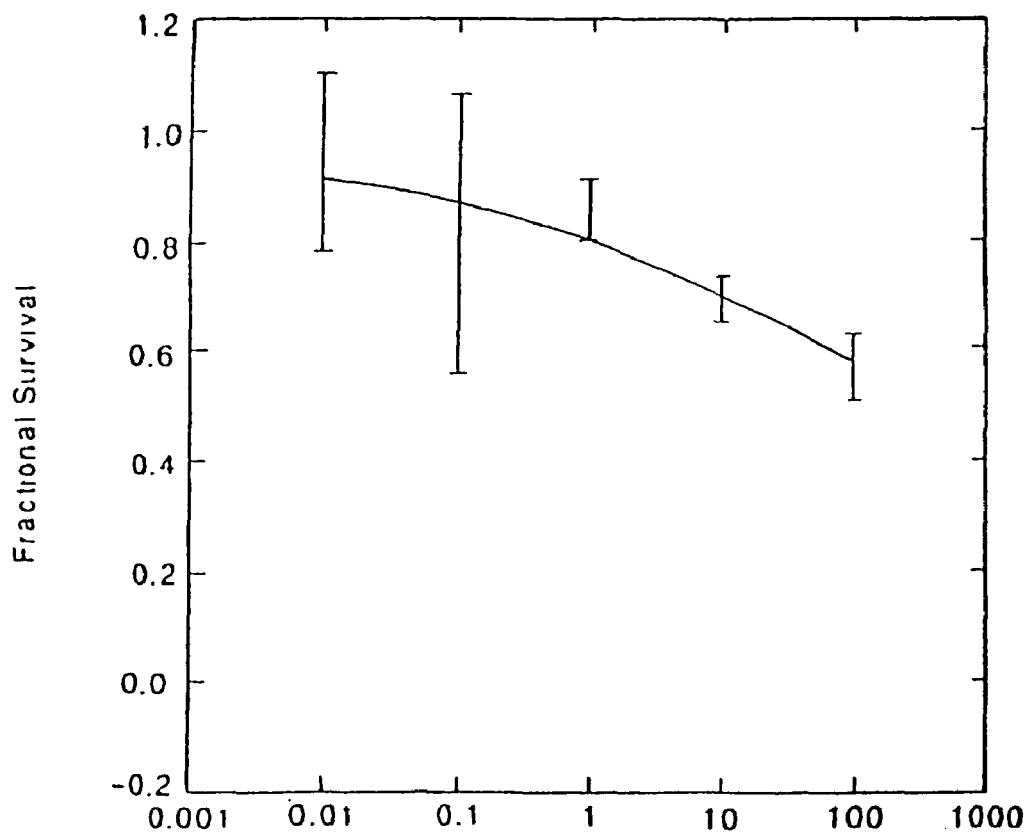
Figure 11A:
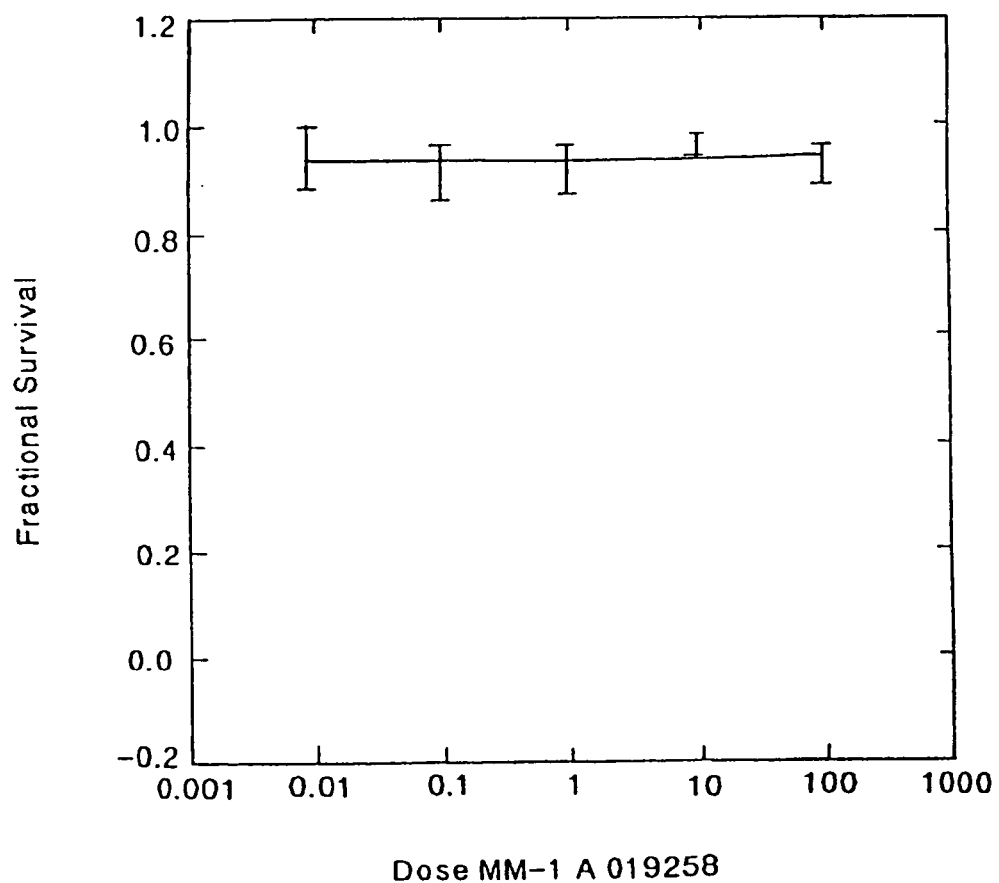
FIGS. 11A to 11H show typical dose response relationships between cocoa procyanidin fractions A, B, C, D, E, A+E, B+E and C+E and the A-549 lung cell line (fractional survival vs. dose, μg/mL); MM-1 A 019258, MM-1 B 09256, MM-1 C 019259, MM-1 D 019258, MM-1 E 019258, A/E 026254, MM-1 B&E 030255, MM-1 C&E N6255.
Figure 11B:
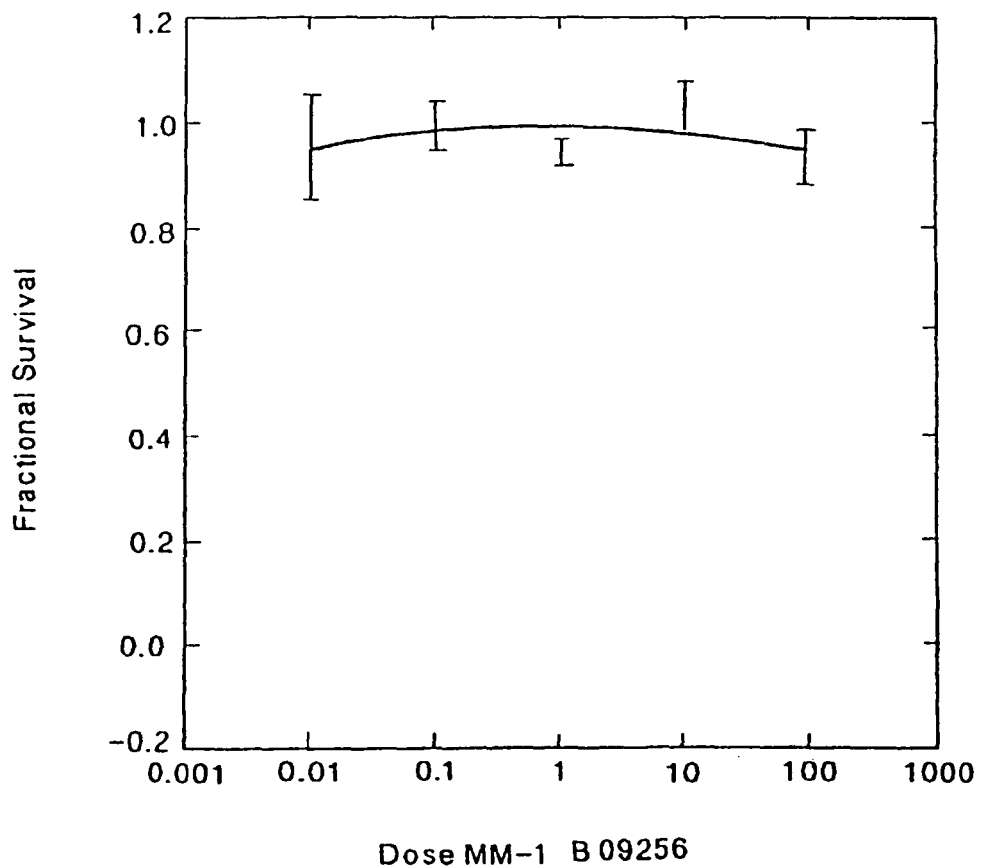
Figure 11C:
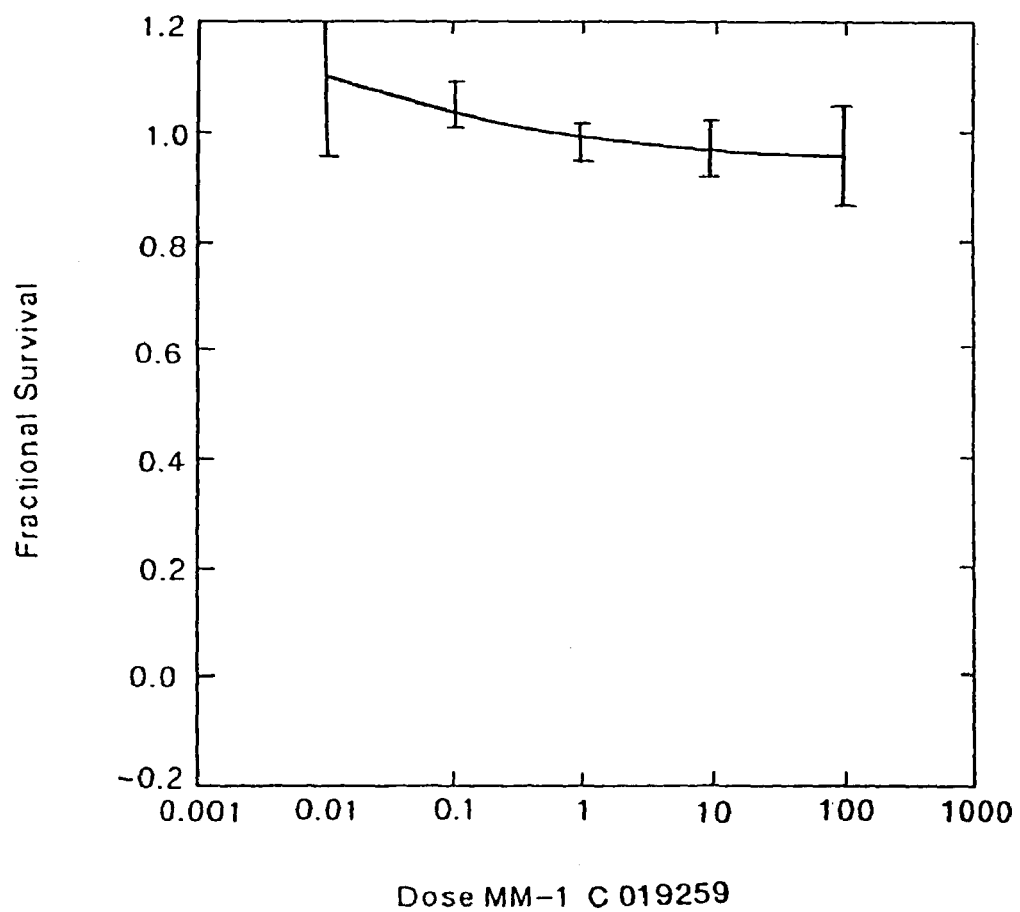
Figure 11D:
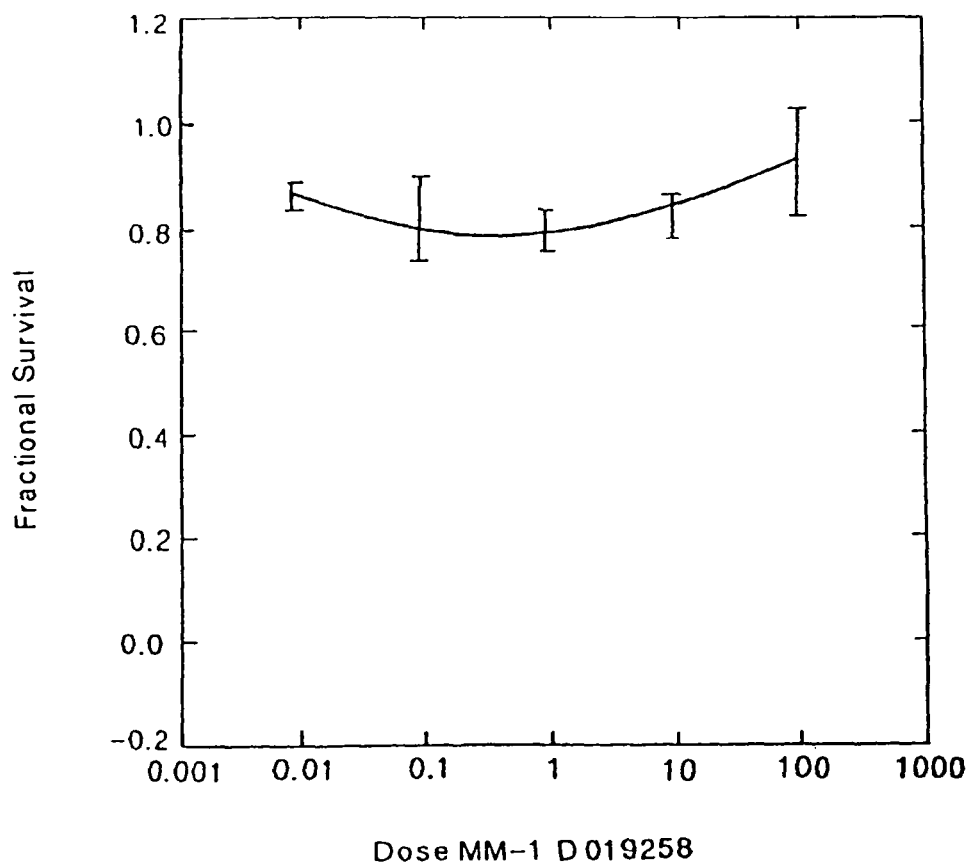
Figure 11E:
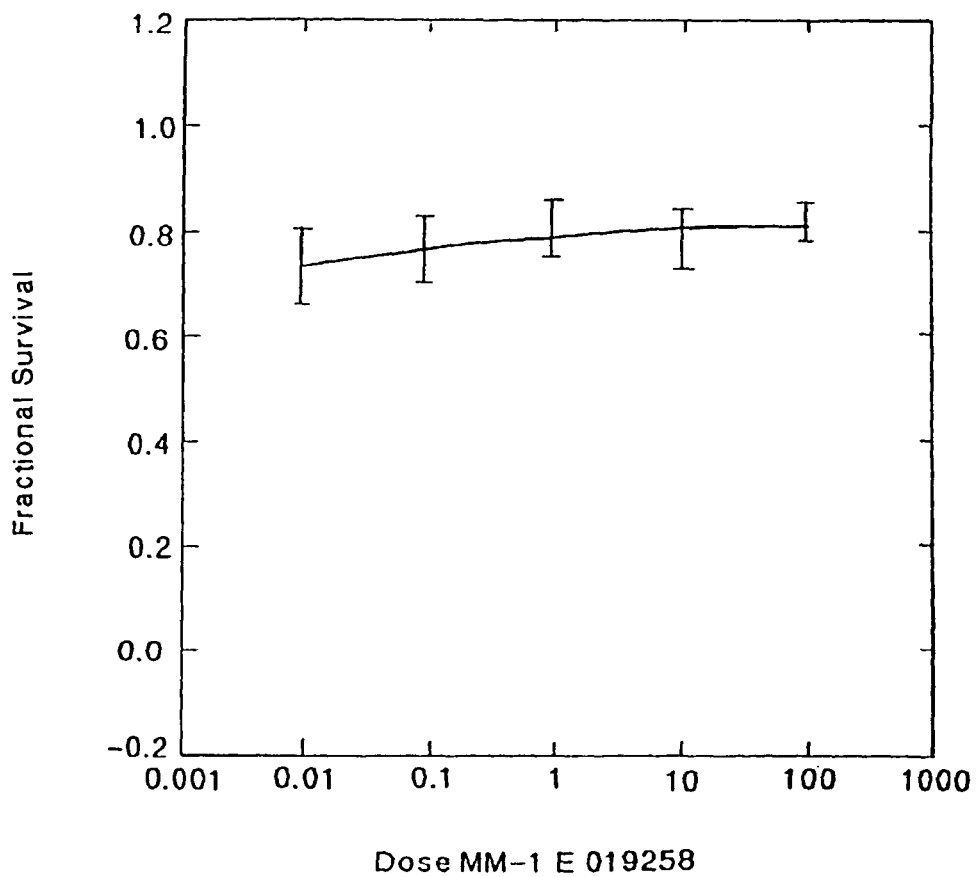
Figure 11F:
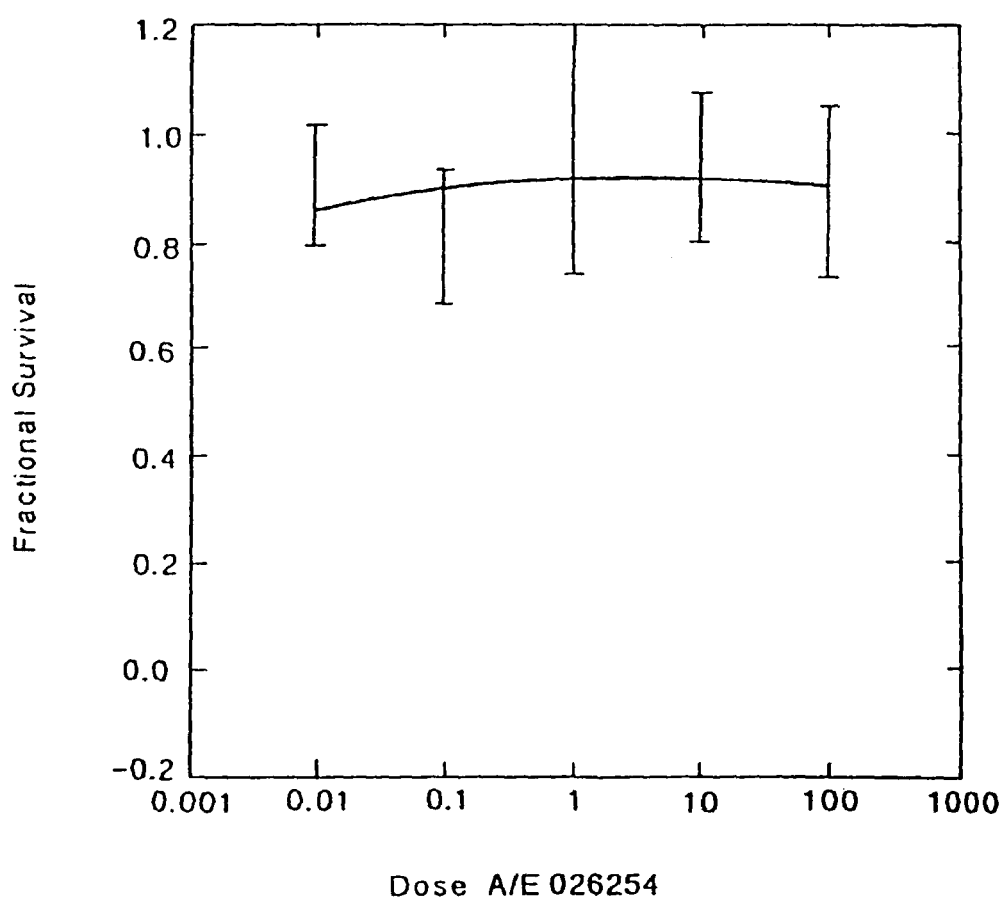
Figure 11G:
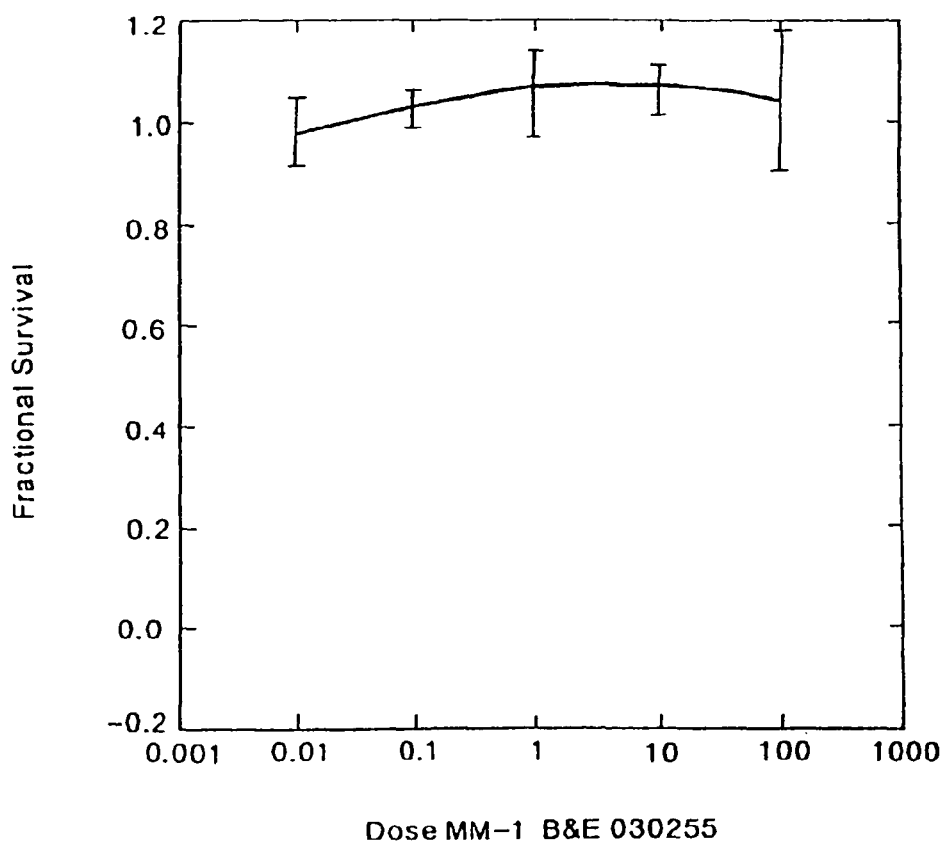
Figure 11H:
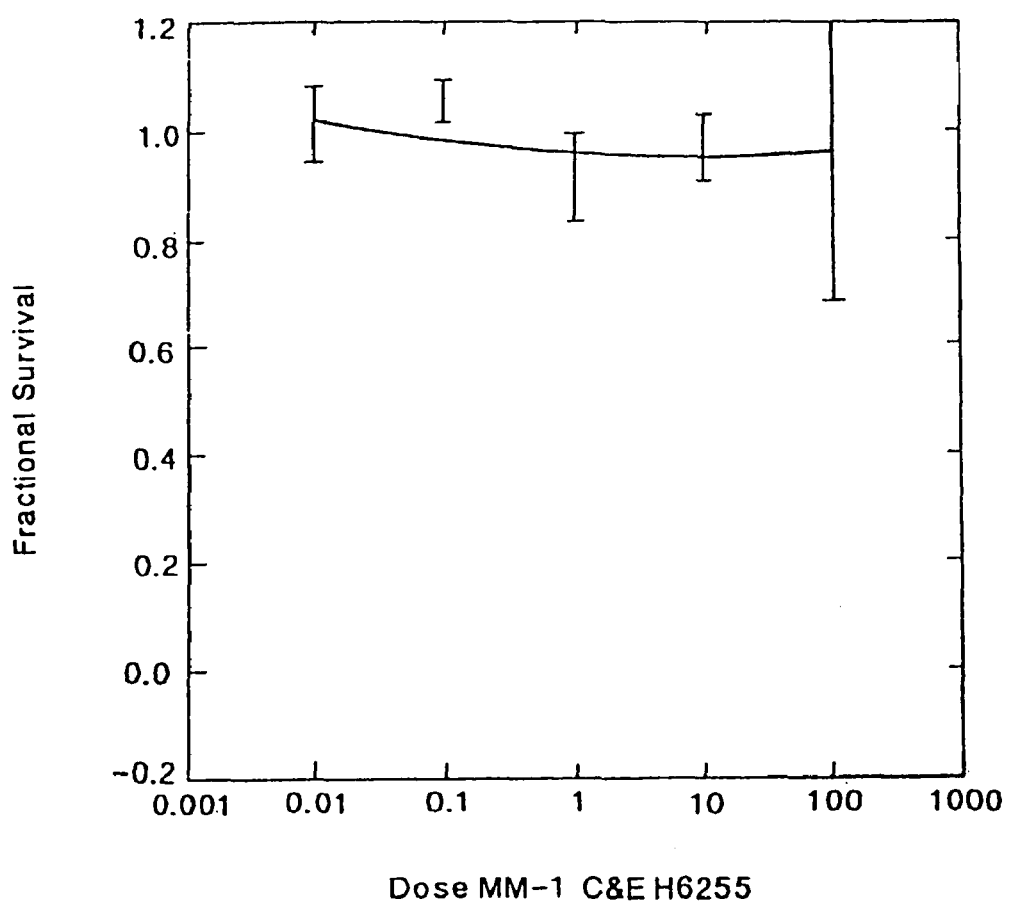
Figure 12A:
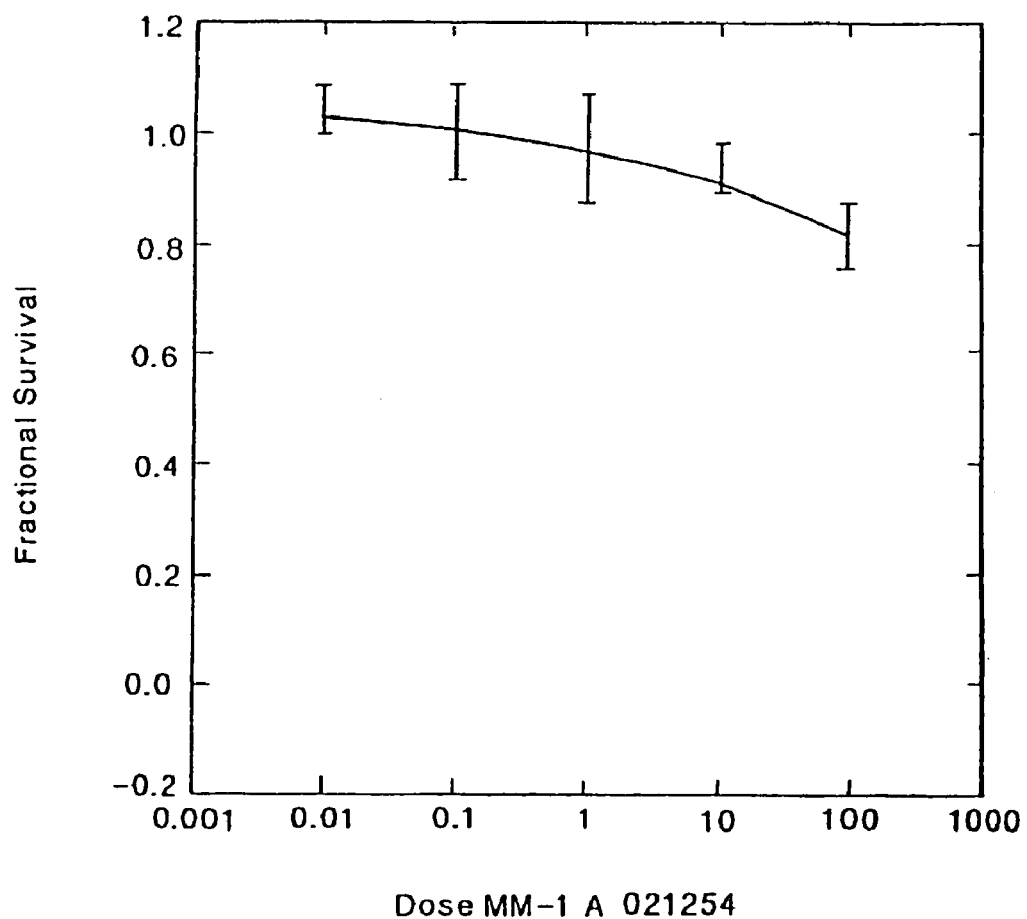
FIGS. 12A to 12H show typical dose response relationships between cocoa procyanidin fractions A, B, C, D, E, B+C, C+D and D+E and the SK-5 melanoma cell line (fractional survival vs. dose μg/mL); MM-1 A 0212S4, MM-1 B 0212S4, MM-1 C 0212S4, MM-1 D 0212S4, MM-1 E N32S1, MM-1 B&C N32S2, MM-1 C&D N32S3, MM-1 D&E N32S3.
Figure 12B:
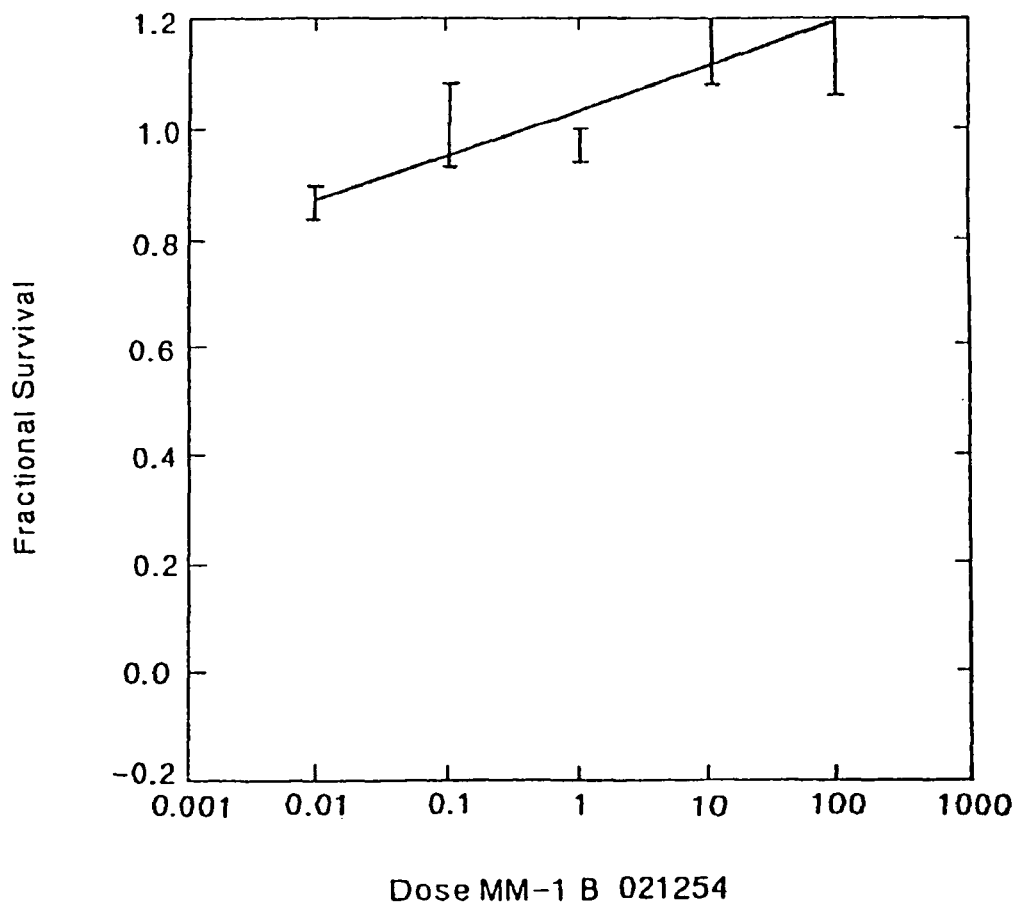
Figure 12C:
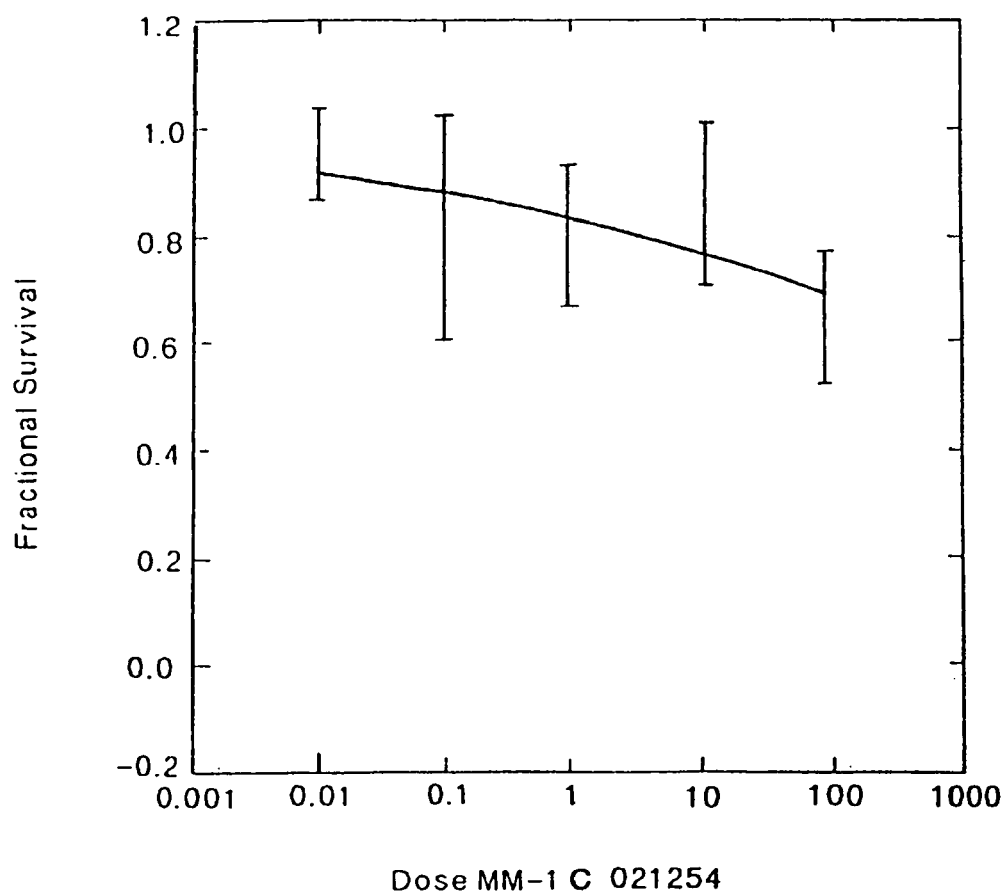
Figure 12D:
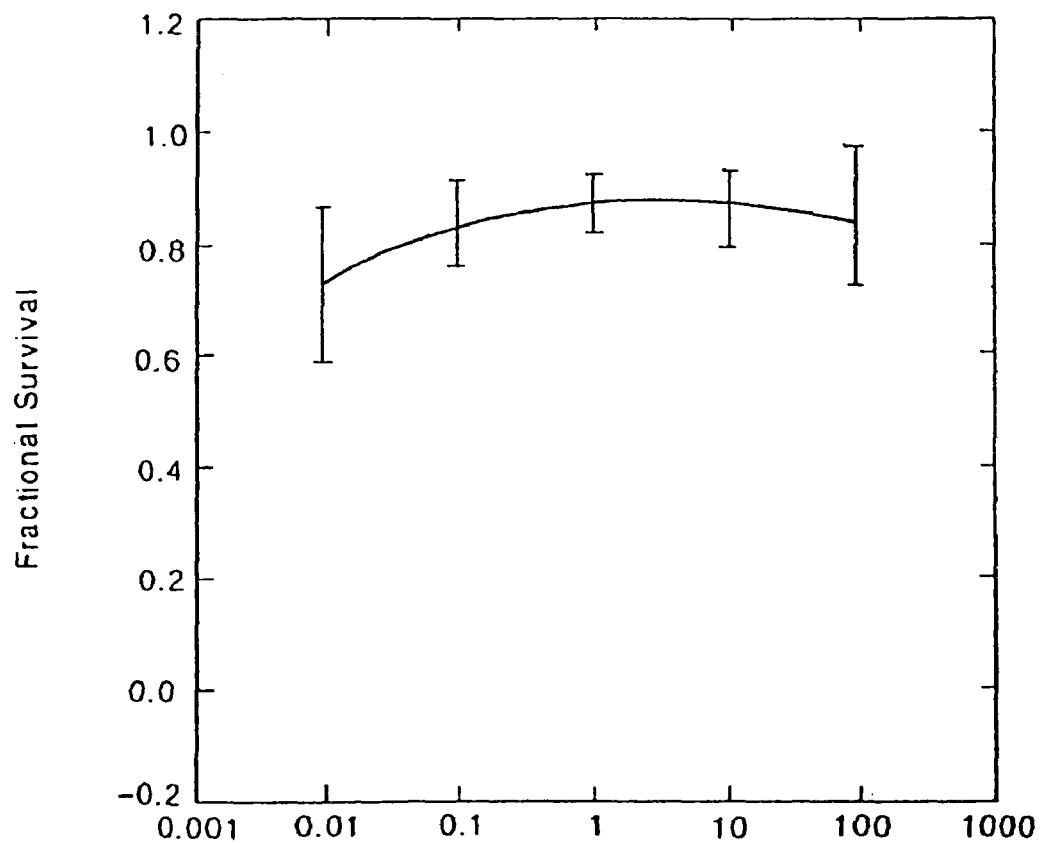
Figure 12E:
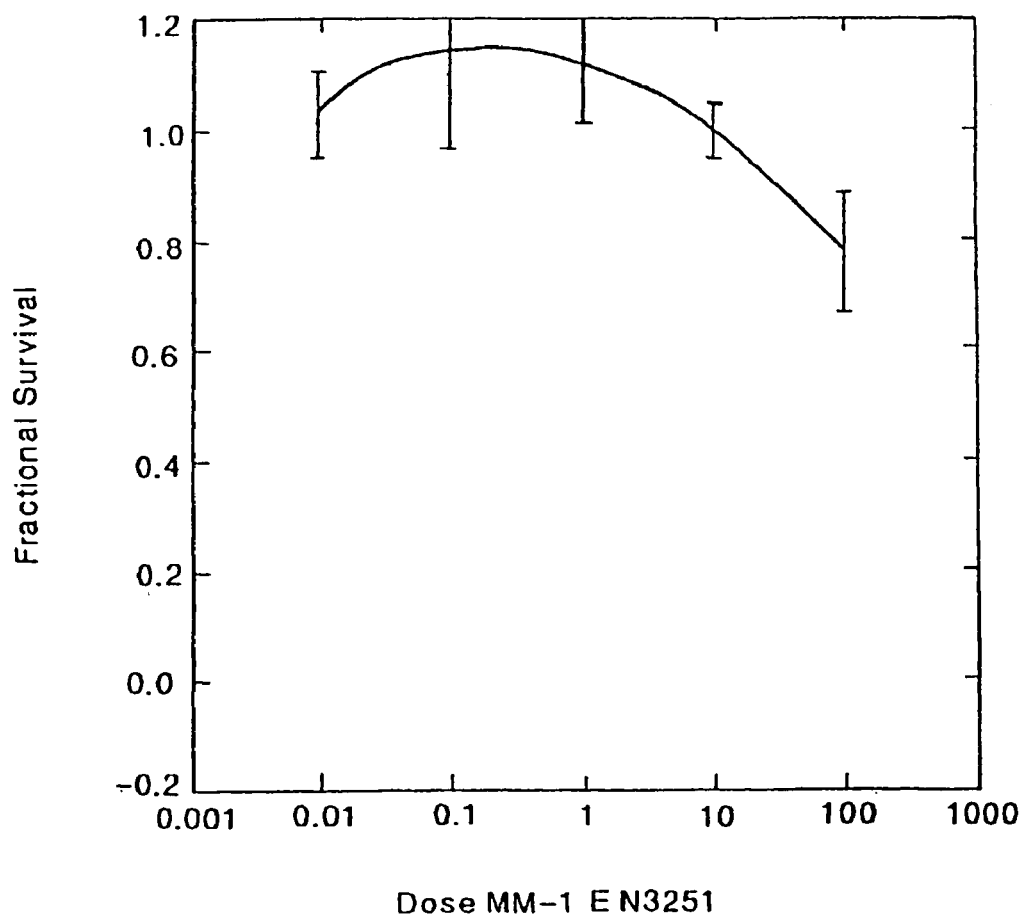
Figure 12F:
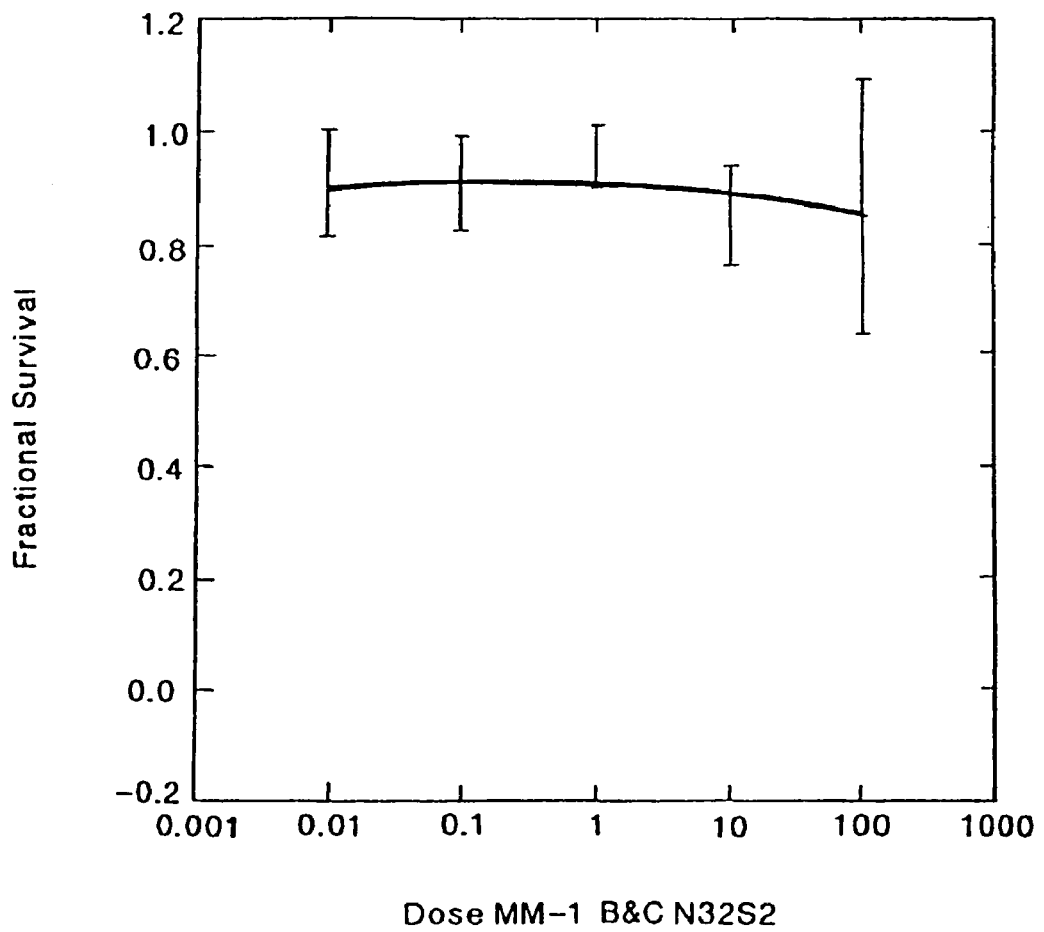
Figure 12G:
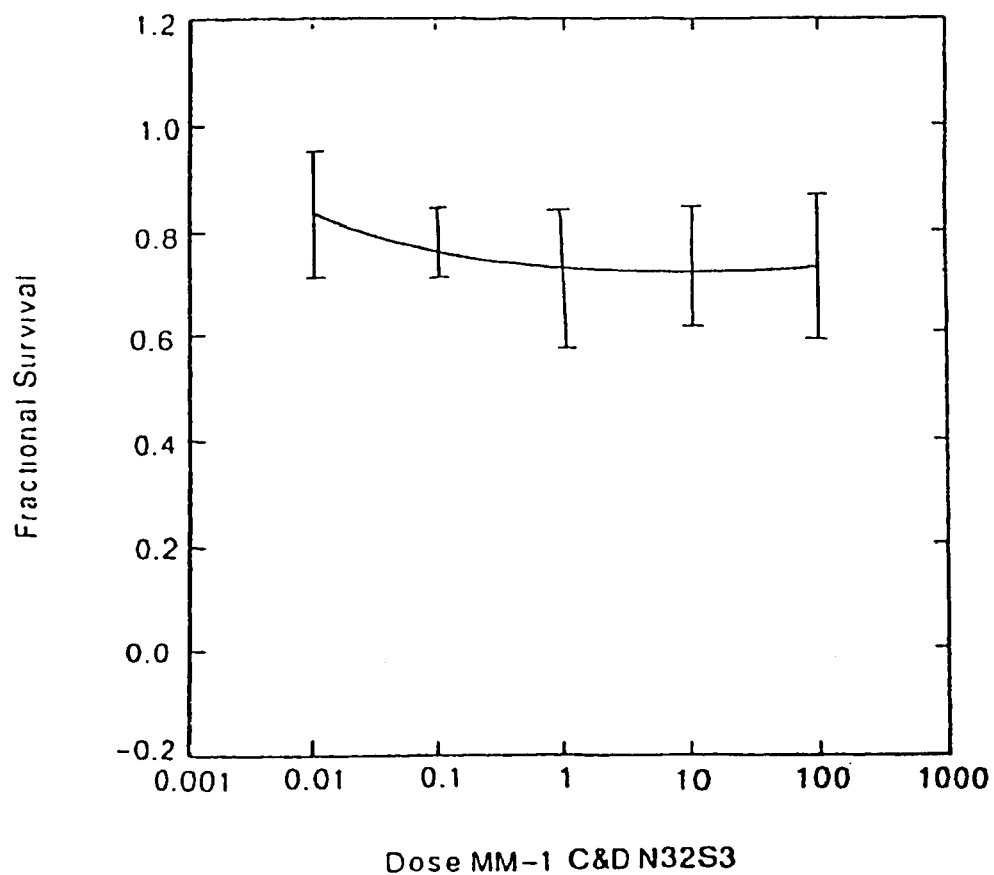
Figure 12H:
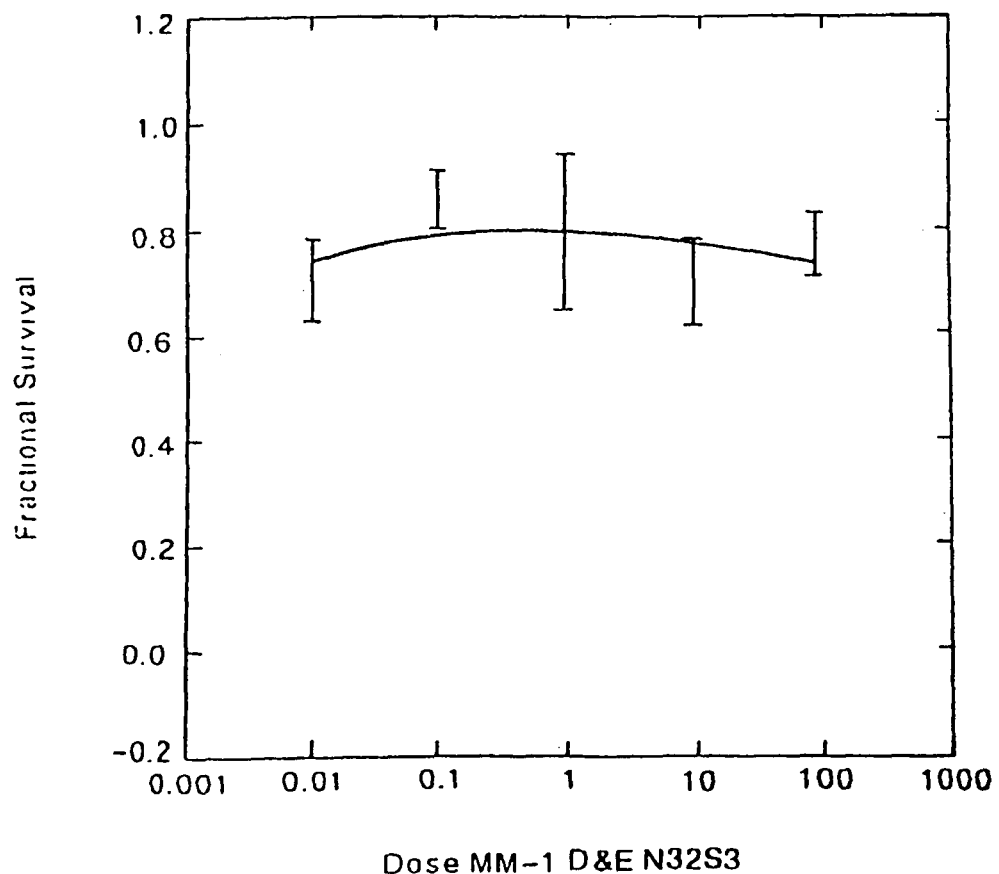
Figure 13A:
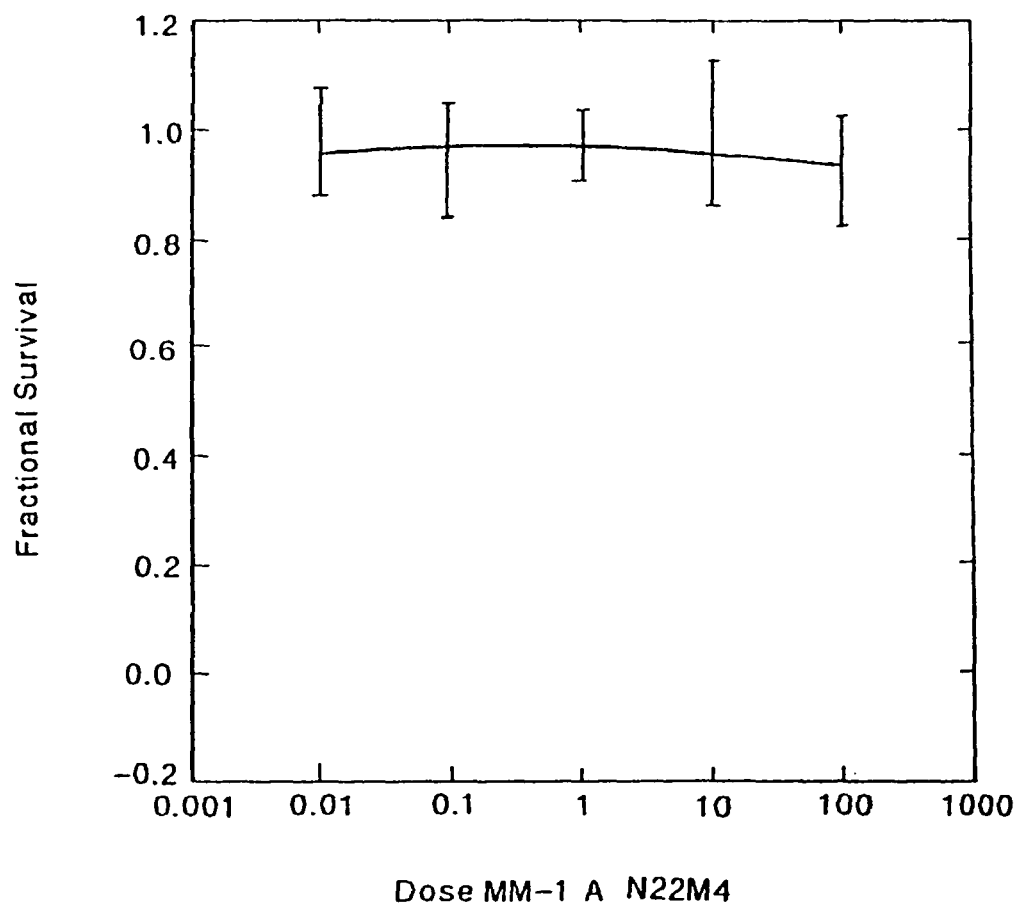
FIGS. 13A to 13H show typical dose response relationships between cocoa procyanidin fractions A, B, C, D, E, B+C, C+E, and D+E and the MCF-7 breast cell line (fractional survival vs. dose, μg/mL); MM-1 A N22M4, MM-1 B N22M4, MM-1 C N22M4, MM-1 D N22M3, MM-1 E 0302M2, MM-1 B/C 0302M4, MM-1 C&E N22M3, MM-1 D&E N22M3.
Figure 13B:
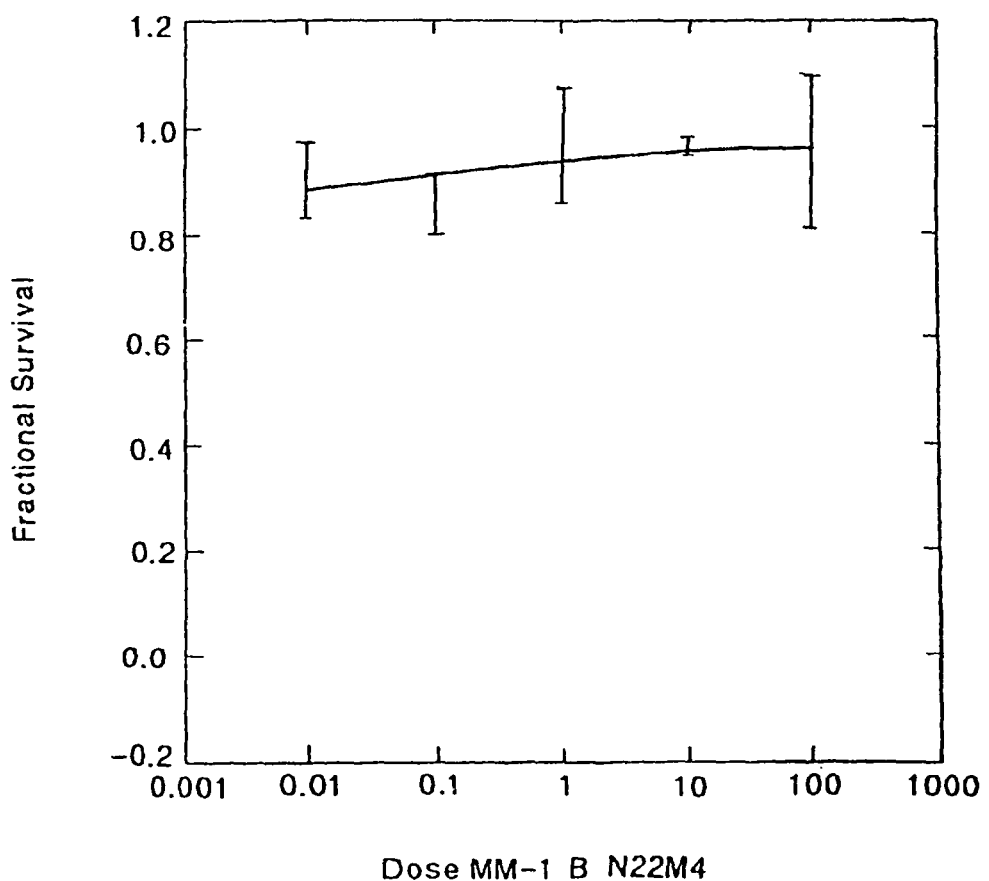
Figure 13C:
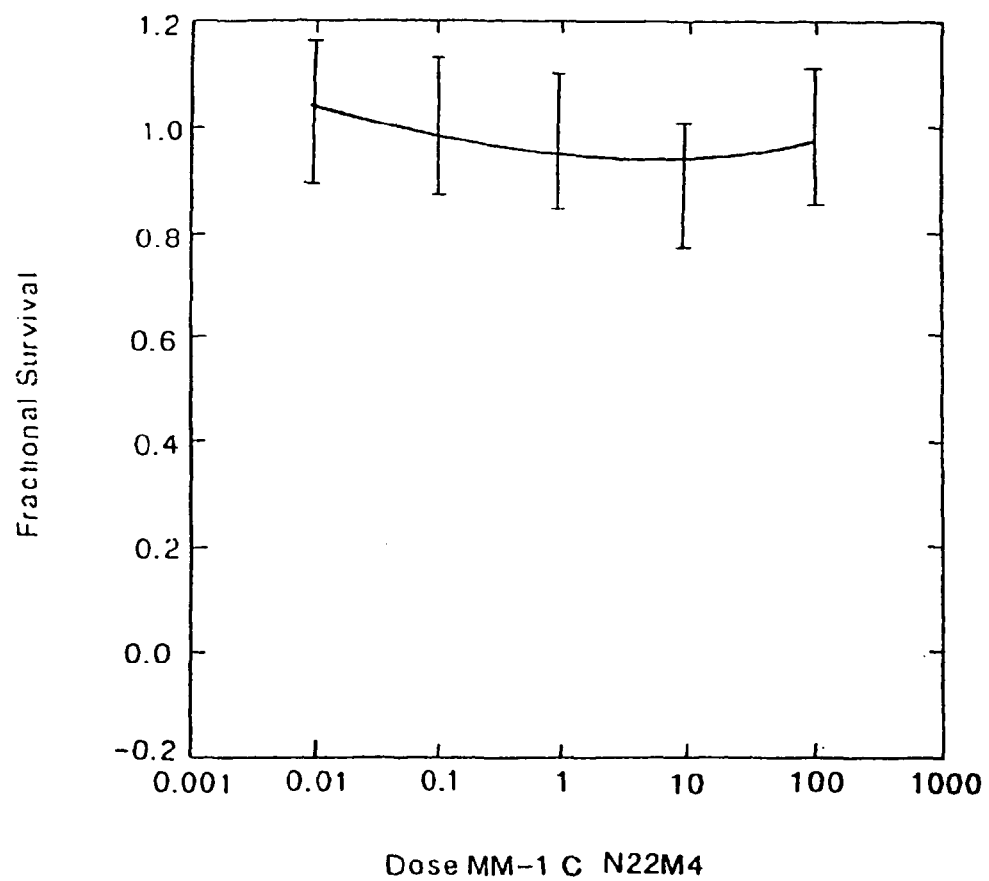
Figure 13D:
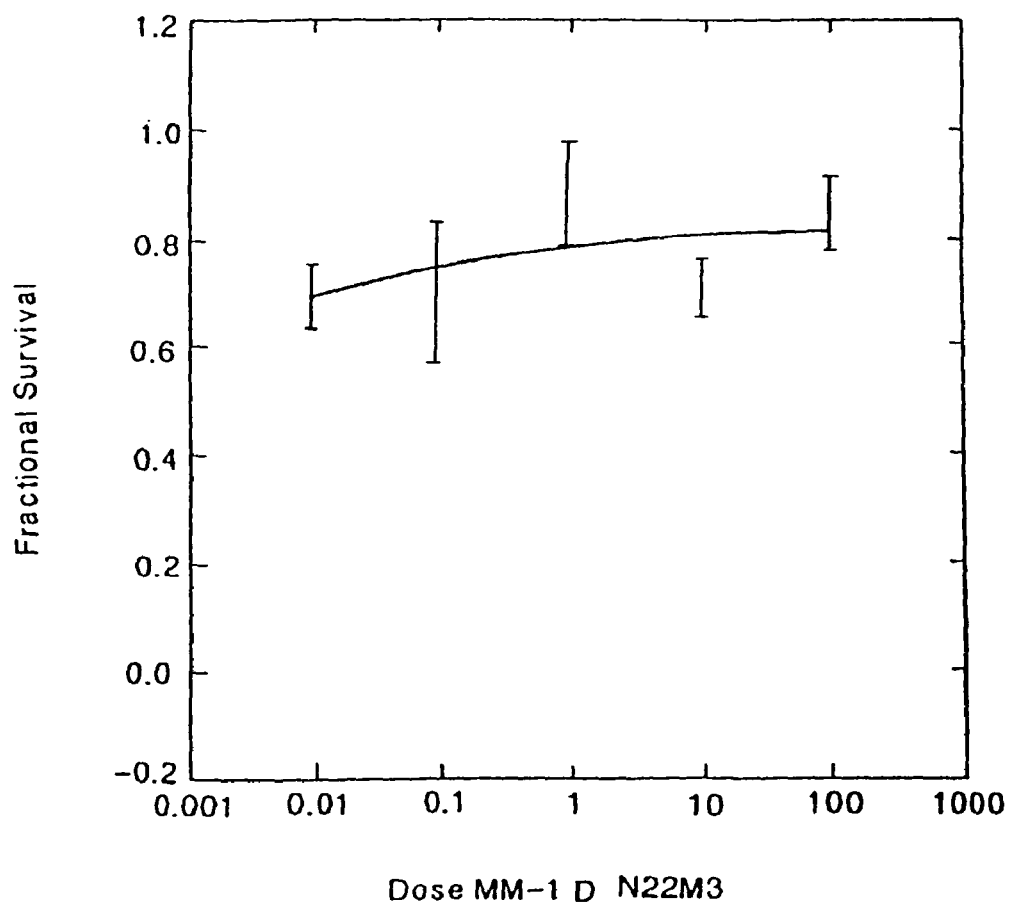
Figure 13E:
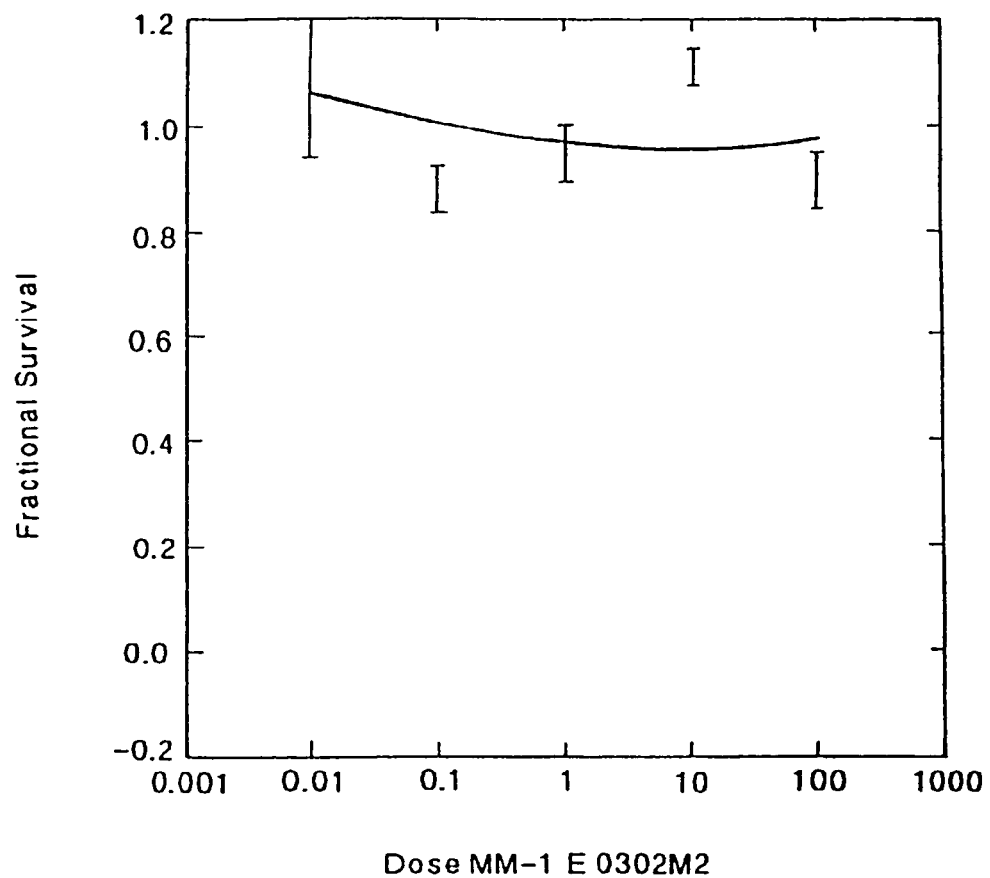
Figure 13F:
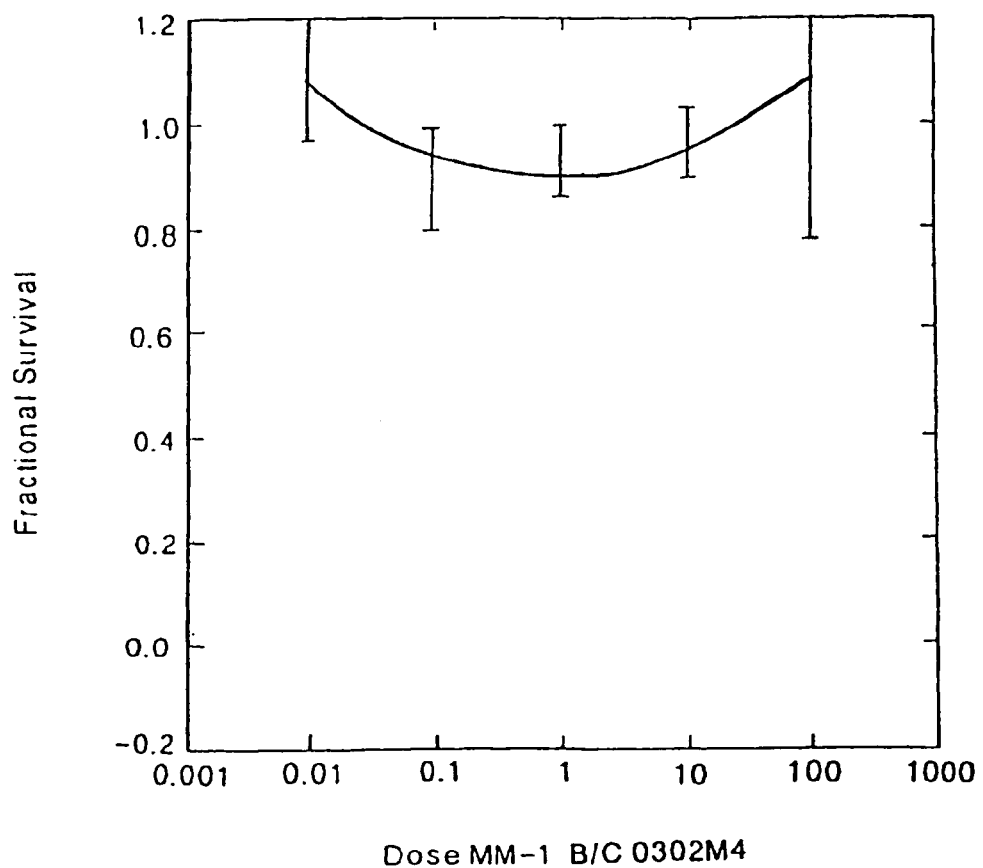
Figure 13G:
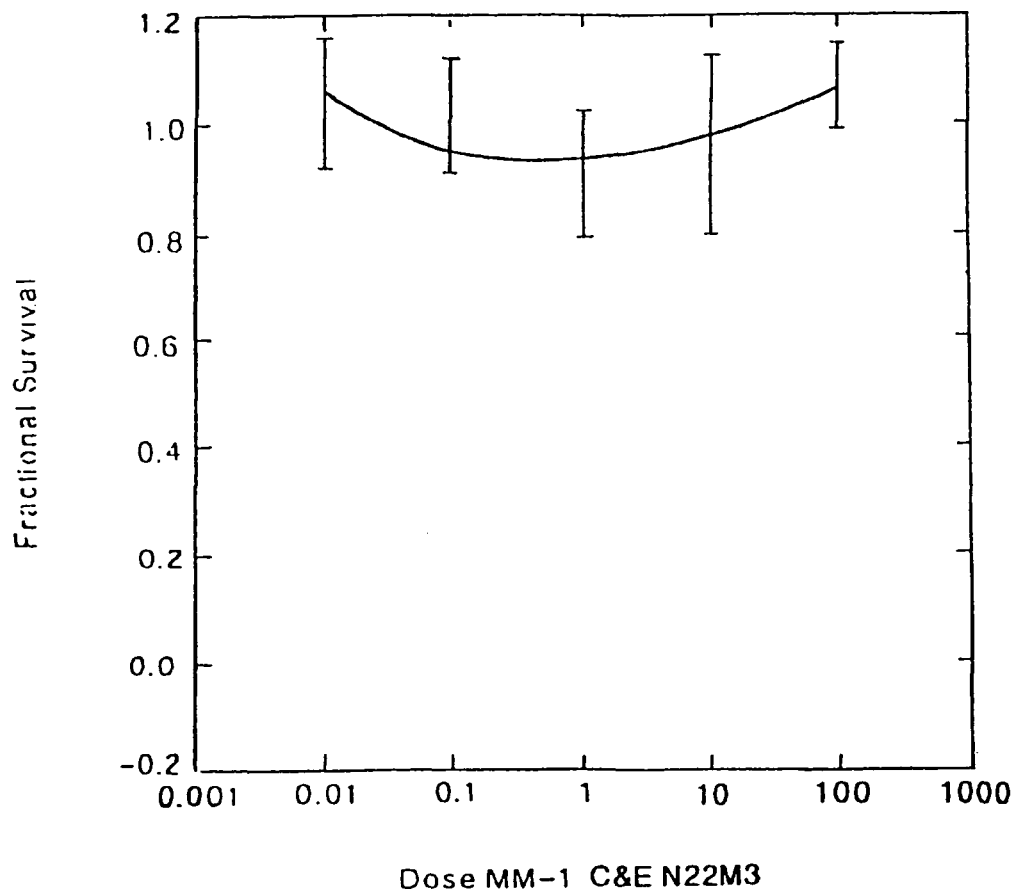
Figure 13H:
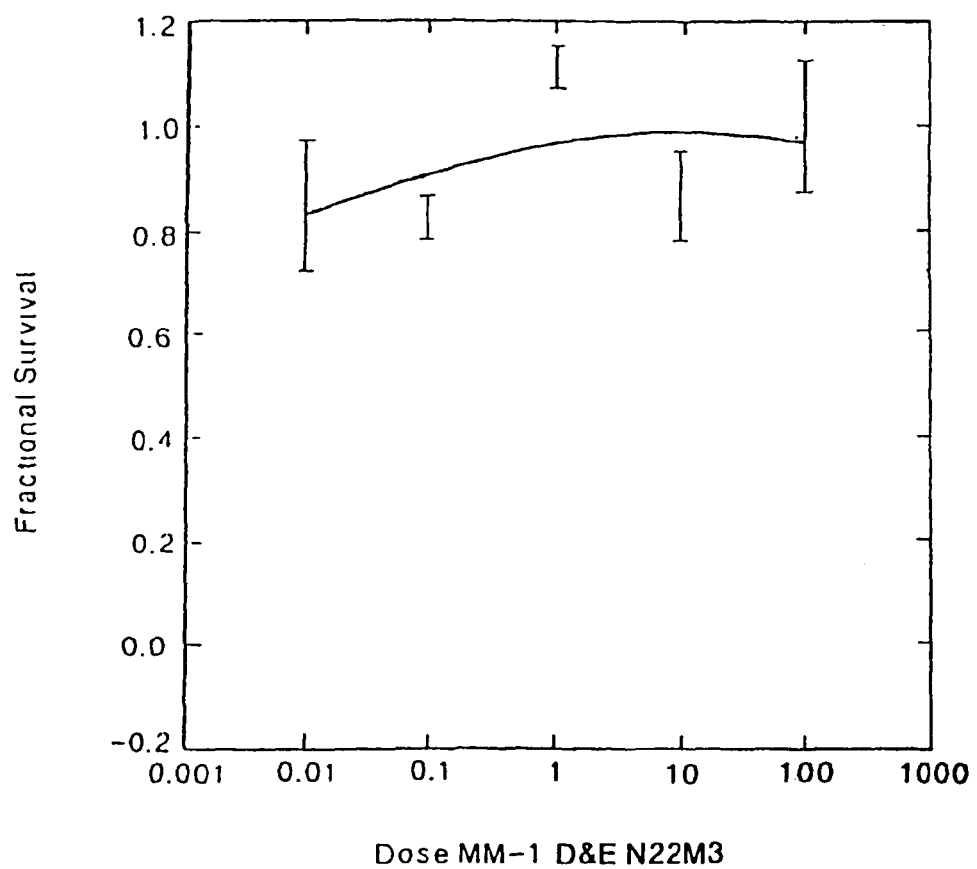

FIGS. 10A-10H show the typical dose response relationships between cocoa procyanidin fractions and the ACHN renal cell line. FIGS. 10A-10E indicated that no individual fraction was active against this cell line. FIGS. 10F-10H depict representative results obtained from the fraction combination study. In this case, procyanidin fraction combination B+C was inactive, whereas the fraction combination A+E resulted in an extrapolated $IC_{50}$ value of approximately 500 µg/mL. Dose response curves similar to the C+D combination were considered inactive, since their slopes were too shallow. Extrapolated $IC_{50}$ values for other fraction combinations are listed in Table 6.

E. A-549 Lung Cell Line

FIGS. 11A-11H show the typical dose response relationships between cocoa procyanidin fractions and the A-549 lung cell line. No activity could be detected from any individual fraction or combination of fractions at the doses used in the assay. However, procyanidin fractions may nonetheless have utility with respect to this cell line.

F. SK-5 Melanoma Cell Line

FIGS. 12A-12H show the typical dose response relationships between cocoa procyanidin fractions and the SK-5 melanoma cell line. No activity could be detected from any individual fraction or combination of fractions at the doses used in the assay. However, procyanidin fractions may nonetheless have utility with respect to this cell line.

G. MCF-7 Breast Cell Line

FIGS. 13A-13H show the typical dose response relationships between cocoa procyanidin fractions and the MCF-7 breast cell line. No activity could be detected from any individual fraction or combination of fractions at the doses used in the assay. However, procyanidin fractions may nonetheless have utility with respect to this cell line.

H. CCRF-CEM T-Cell Leukemia Line

Figure 14:
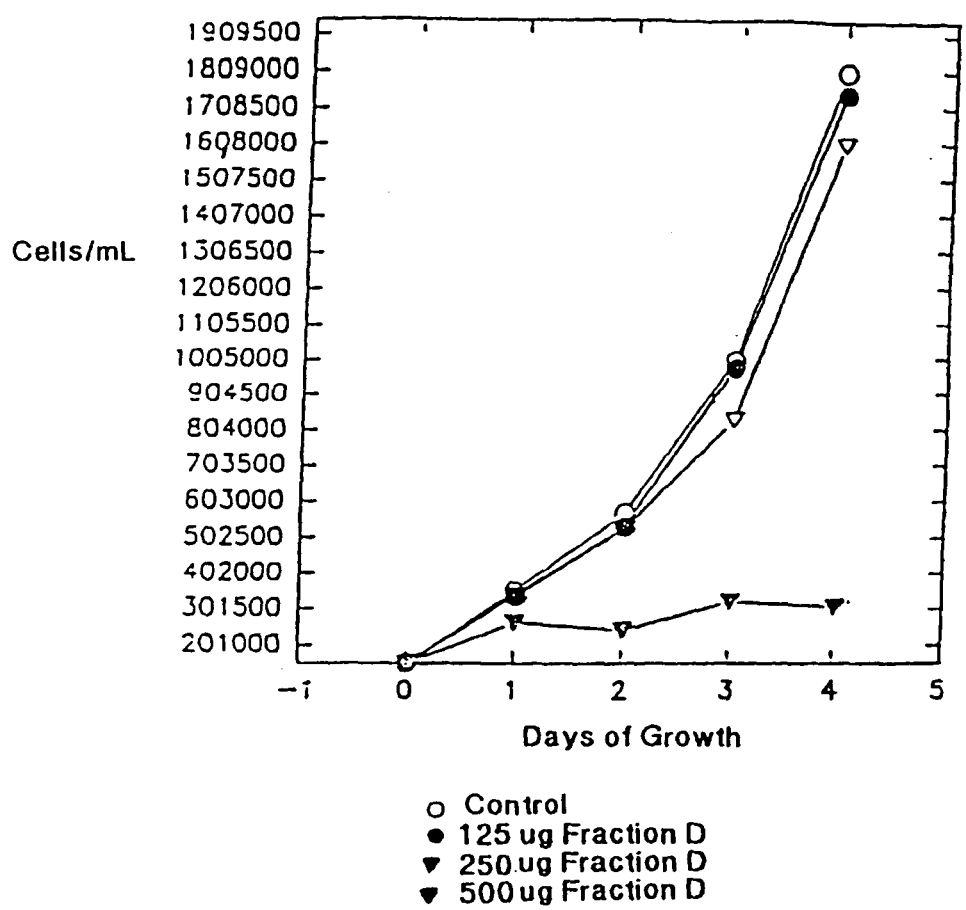
FIG. 14 shows typical dose response relationships for cocoa procyanidin (particularly fraction D) and the CCRF-CEM T-cell leukemia cell line (cells/mL vs. days of growth; open circle is control, darkened circle is 125 μg fraction D, open inverted triangle is 250 μg fraction D, darkened inverted triangle is 500 μg fraction D)

A typical dose response curves were originally obtained against the CCRF-CEM T-cell leukemia line. However, microscopic counts of cell number versus time at different fraction concentrations indicated that 500 µg of fractions A, B and D effected an 80% growth reduction over a four day period. A representative dose response relationship is shown in FIG. 14.

I. Summary

The $IC_{50}$ values obtained from these assays are collectively listed in Table 6 for all the cell lines except for CCRF-CEM T-cell leukemia. The T-cell leukemia data was intentionally omitted from the Table, since a different assay procedure was used. A general summary of these results indicated that the most activity was associated with fractions D and E. These fractions were most active against the PC-3 (prostate) and KB (nasopharyngeal/HeLa) cell lines. These fractions also evidenced activity against the HCT-116 (colon) and ACHN (renal) cell lines, albeit but only at much higher doses. No activity was detected against the MCF-7 (breast), SK-5 (melanoma) and A-549 (lung) cell lines. However, procyanidin fractions may nonetheless have utility with respect to these cell lines. Activity was also shown against the CCRF-CEM (T-cell leukemia) cell line. It should also be noted that fractions D and E are the most complex compositionally. Nonetheless, from this data it is clear that cocoa extracts, especially cocoa procyanidins, have significant anti-tumor, anti-cancer or antineoplastic activity.

TABLE 6

IC$_{50}$ Values for Cocoa Procyanidin Fractions Against Various Cell Lines
(IC$_{50}$ values in µg/mL)

| FRACTION | PC-3 | KB | HCT-116 | ACHN | MCF-7 | SK-5 | A-549 |
|---|---|---|---|---|---|---|---|
| A | | | | | | | |
| B | | | | | | | |
| C | | | | | | | |
| D | 90 | 80 | | | | | |
| E | 75 | 75 | 400 | | | | |
| A + B | | | | | | | |
| A + C | 125 | 100 | | | | | |
| A + D | 75 | 75 | | | | | |
| A + E | 80 | 75 | 500 | 500 | | | |
| B + C | | | | | | | |
| B + D | 75 | 80 | | | | | |
| B + E | 60 | 65 | 200 | | | | |
| C + D | 80 | 75 | | 1000 | | | |
| C + E | 80 | 70 | 250 | | | | |
| D + E | 80 | 60 | 85 | | | | |

Values above 100 µg/mL were extrapolated from dose response curves

Example 8

Anti-Cancer, Anti-Tumor or Antineoplastic Activity of Cocoa Extracts (Procyanidins)

Several additional in vitro assay procedures were used to complement and extend the results presented in Examples 6 and 7.

Method A. Crystal Violet Staining Assay

All human tumor cell lines were obtained from the American Type Culture Collection. Cells were grown as monolayers in IMEM containing 10% fetal bovine serum without antibiotics. The cells were maintained in a humidified, 5% CO$_2$ atmosphere at 37° C.

After trypsinization, the cells were counted and adjusted to a concentration of 1,000-2,000 cells per 100 mL. Cell proliferation was determined by plating the cells (1,000-2,000 cells/well) in a 96 well microtiter plate. After addition of 100 µL cells per well, the cells were allowed to attach for 24 hours. At the end of the 24 hour period, various cocoa fractions were added at different concentrations to obtain dose response results. The cocoa fractions were dissolved in media at a 2 fold concentration and 100 µL of each solution was added in triplicate wells. On consecutive days, the plates were stained with 50 µL crystal violet (2.5 g crystal violet dissolved in 125 mL methanol, 375 mL water), for 15 min. The stain was removed and the plate was gently immersed into cold water to remove excess stain. The washings were repeated two more times, and the plates allowed to dry. The remaining stain was solubilized by adding 100 µL of 0.1M sodium citrate/50% ethanol to each well. After solubilization, the number of cells were quantitated on an ELISA plate reader at 540 nm (reference filter at 410 nm). The results from the ELISA reader were graphed with absorbance on the y-axis and days growth on the x-axis.

Method B. Soft Agar Cloning Assay

Cells were cloned in soft agar according to the method described by Nawata et al. (1981). Single cell suspensions were made in media containing 0.8% agar with various concentrations of cocoa fractions. The suspensions were aliquoted into 35 mm dishes coated with media containing 1.0% agar. After 10 days incubation, the number of colonies greater than 60 µm in diameter were determined on an Ominicron 3600 Image Analysis System. The results were plotted with number of colonies on the y-axis and the concentrations of a cocoa fraction on the x-axis.

Method C. XTT-Microculture Tetrazolium Assay

The XTT assay procedure described by Scudiero et al. (1988) was used to screen various cocoa fractions. The XTT assay was essentially the same as that described using the MTT procedure (Example 6) except for the following modifications. XTT ((2,3-bis(2-methoxy-4-nitro-5-sulfophenyl)-5-((phenylamino)carbonyl)-2H-tetrazolium hydroxide) was prepared at 1 mg/mL medium without serum, prewarmed to 37° C. PMS was prepared at 5 mM PBS. XTT and PMS were mixed together; 10 µL of PMS per mL XTT and 50 µL PMS-XTT were added to each well. After an incubation at 37° C. for 4 hr, the plates were mixed 30 min. on a mechanical shaker and the absorbance measured at 450-600 nm. The results were plotted with the absorbance on the y-axis and days growth or concentration on the x-axis.

For methods A and C, the results were also plotted as the percent control as the y-axis and days growth or concentration on the x-axis.

Figure 15A:
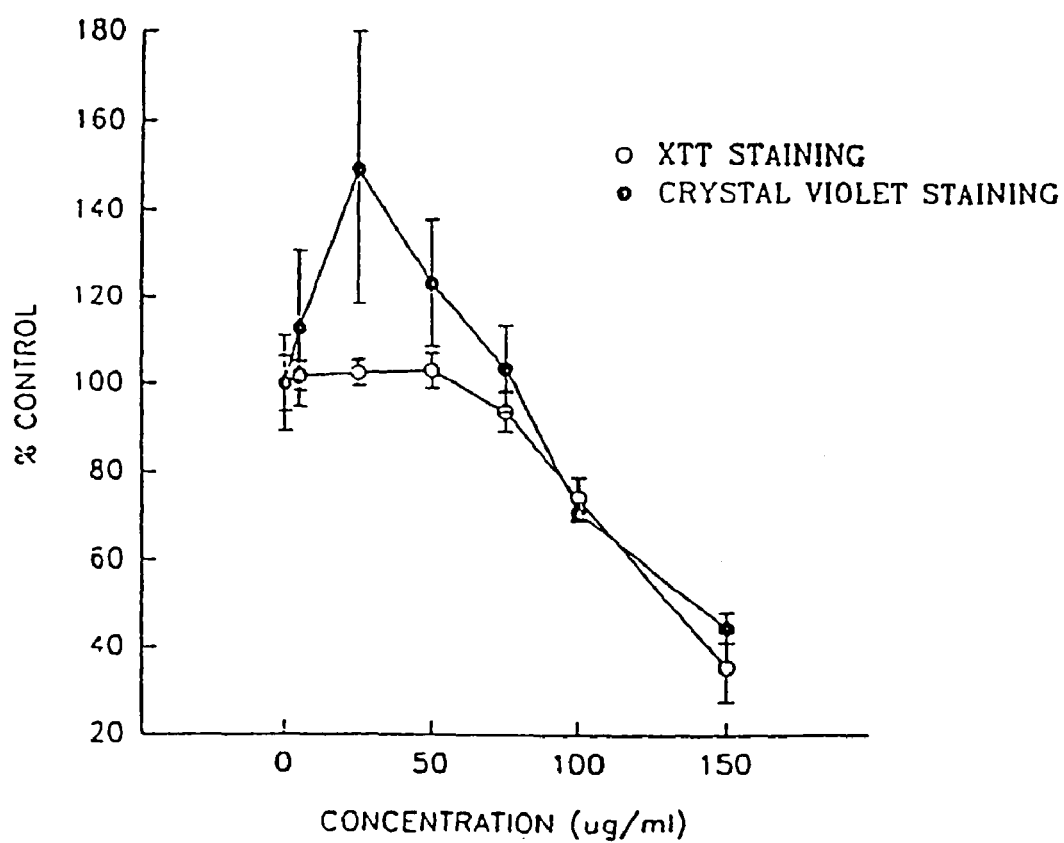
FIG. 15A shows a comparison of the XTT and Crystal Violet cytotoxicity assays against MCF-7 p 168 breast cancer cells treated with fraction D+E (open circle is XTT and darkened circle is Crystal Violet)
Figure 15B:
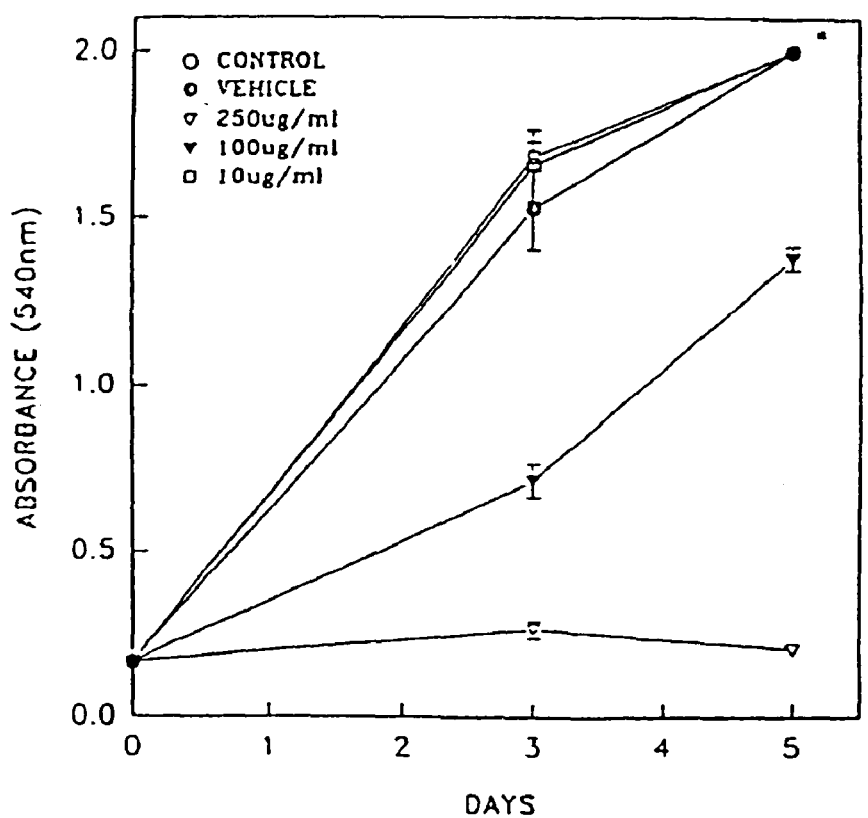
FIG. 15B shows a typical dose response curve obtained from MDA MB231 breast cell line treated with varying levels of crude polyphenols obtained from UIT-1 cocoa genotype (absorbance (540 nm) vs. Days; open circle is control, darkened circle is vehicle, open inverted triangle is 250 µg/mL, darkened inverted triangle is 100 µg/mL, open square is 10 µg/mL; absorbance of 2.0 is maximum of plate reader and may not be necessarily representative of cell number)
Figure 15C:
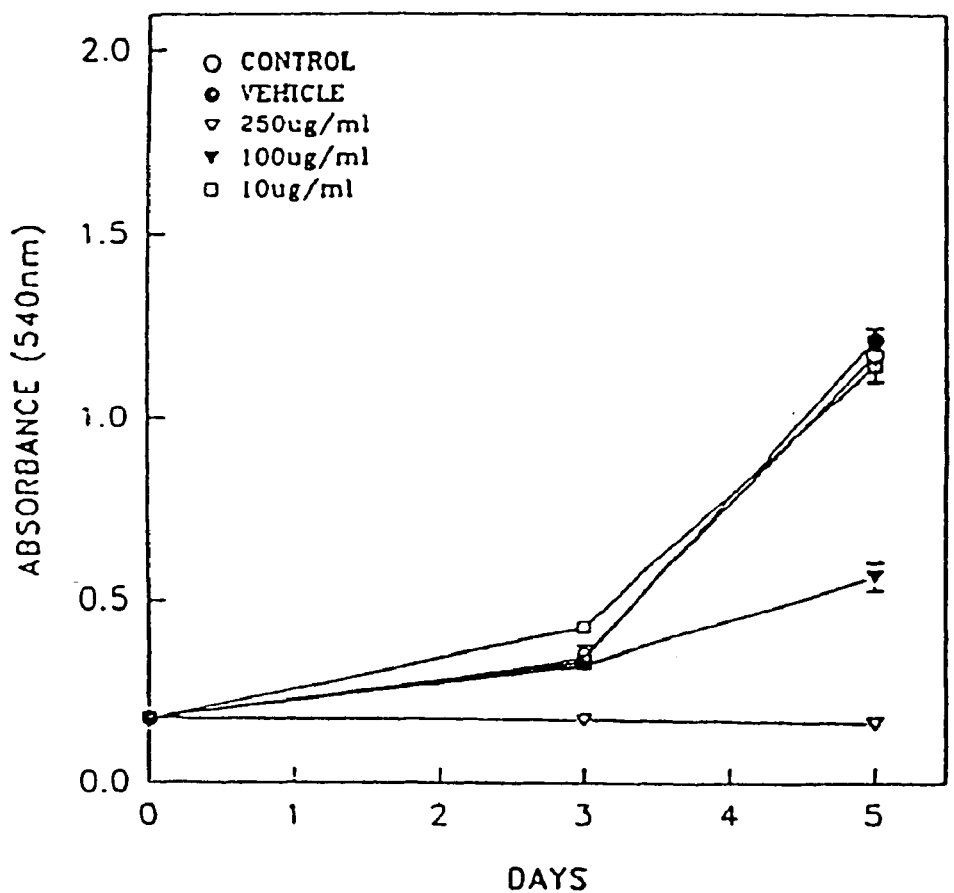
FIG. 15C shows a typical dose response curve obtained from PC-3 prostate cancer cell line treated with varying levels of crude polyphenols obtained from UIT-1 cocoa genotype (absorbance (540 nm) vs. Days; open circle is control, darkened circle is vehicle, open inverted triangle is 250 µg/mL, darkened inverted triangle is 100 µg/mL and open square is 10 µg/mL)
Figure 15D:
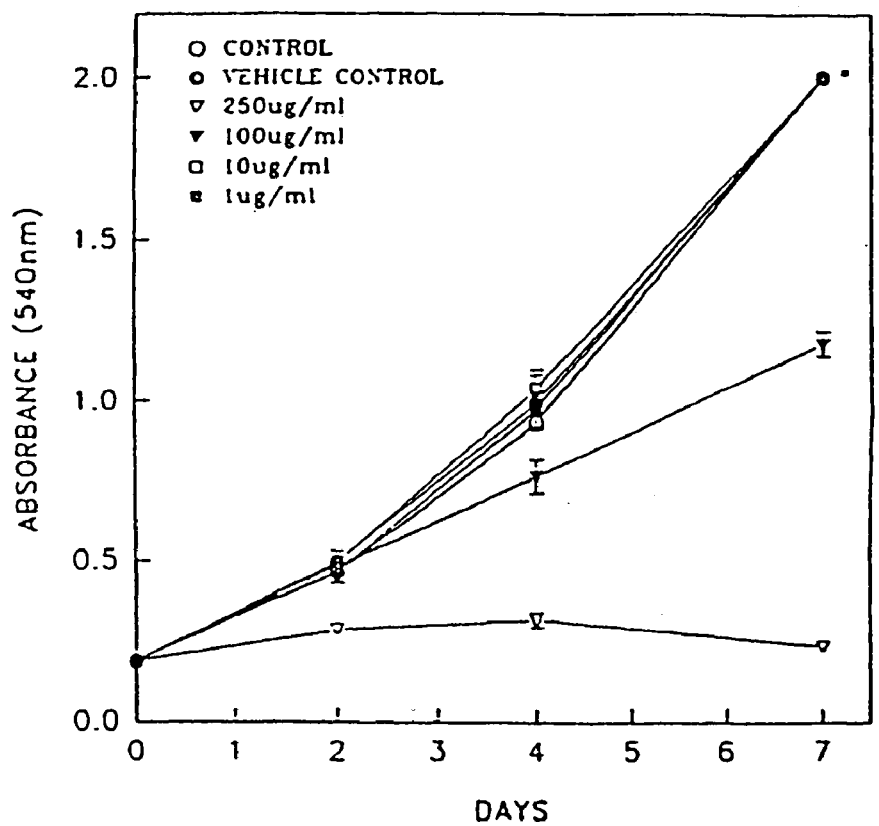
FIG. 15D shows a typical dose-response curve obtained from MCF-7 p168 breast cancer cell line treated with varying levels of crude polyphenols obtained from UIT-1 cocoa genotype (absorbance (540 nm) vs. Days; open circle is control, darkened circle is vehicle, open inverted triangle is 250 µg/mL, darkened inverted triangle is 100 µg/mL, open square is 10 µg/mL, darkened square is 1 µg/mL; absorbance of 2.0 is maximum of plate reader and may not be necessarily representative of cell number)
Figure 15E:
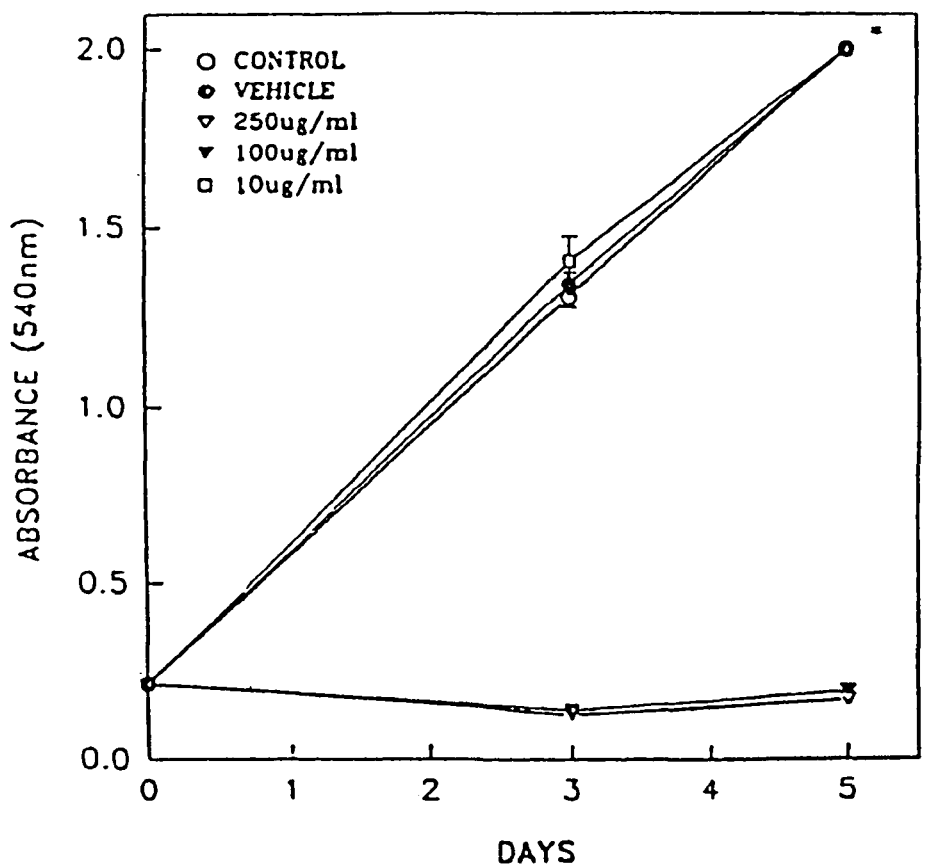
FIG. 15E shows a typical dose response curve obtained from Hela cervical cancer cell line treated with varying levels of crude polyphenols obtained from UIT-1 cocoa genotype (absorbance (540 nm) vs. Days; open circle is control, darkened circle is vehicle, open inverted triangle is 250 µg/mL, darkened inverted triangle is 100 µg/mL, open square is 10 µg/mL; absorbance of 2.0 is maximum of plate reader and may not be necessarily representative of cell number)
Figure 15F:
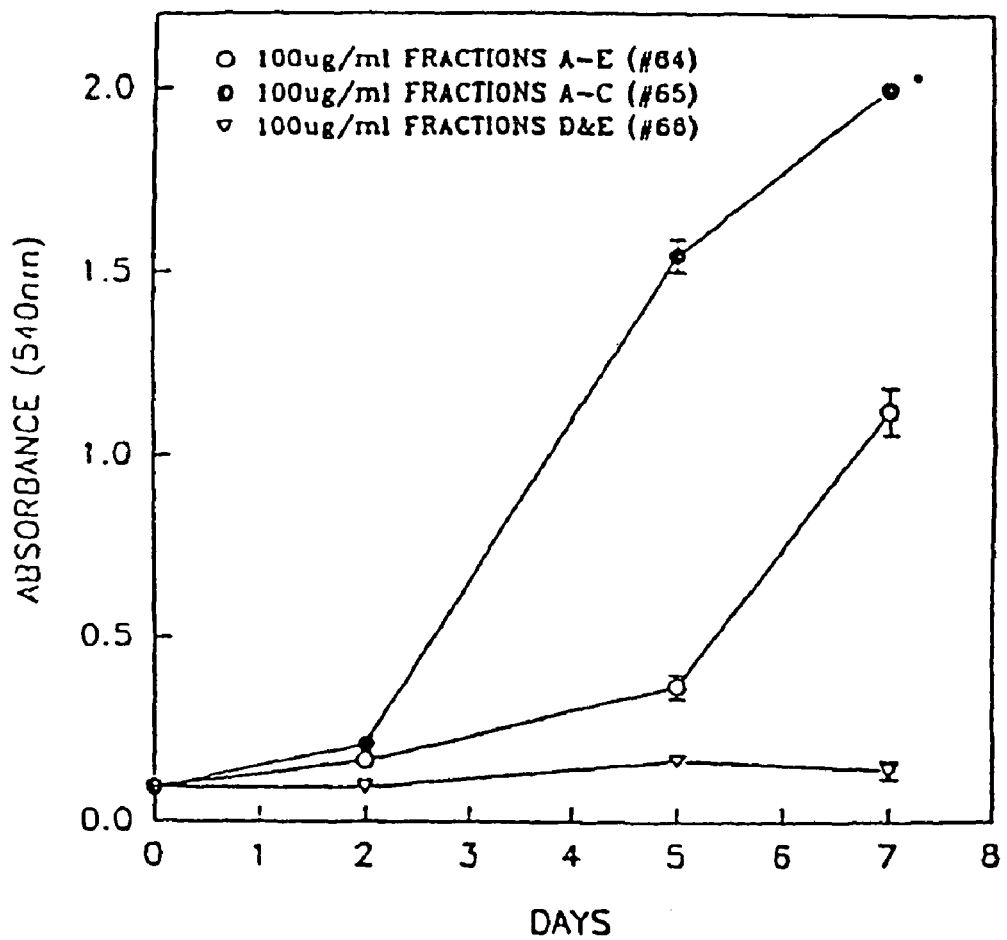
FIG. 15F shows cytotoxic effects against Hela cervical cancer cell line treated with different cocoa polyphenol fractions (absorbance (540 nm) vs. Days; open circle is 100 µg/mL fractions A-E, darkened circle is 100 µg/mL fractions A-C, open inverted triangle is 100 µg/mL fractions D&E; absorbance of 2.0 is maximum of plate reader and not representative of cell number)
Figure 15G:
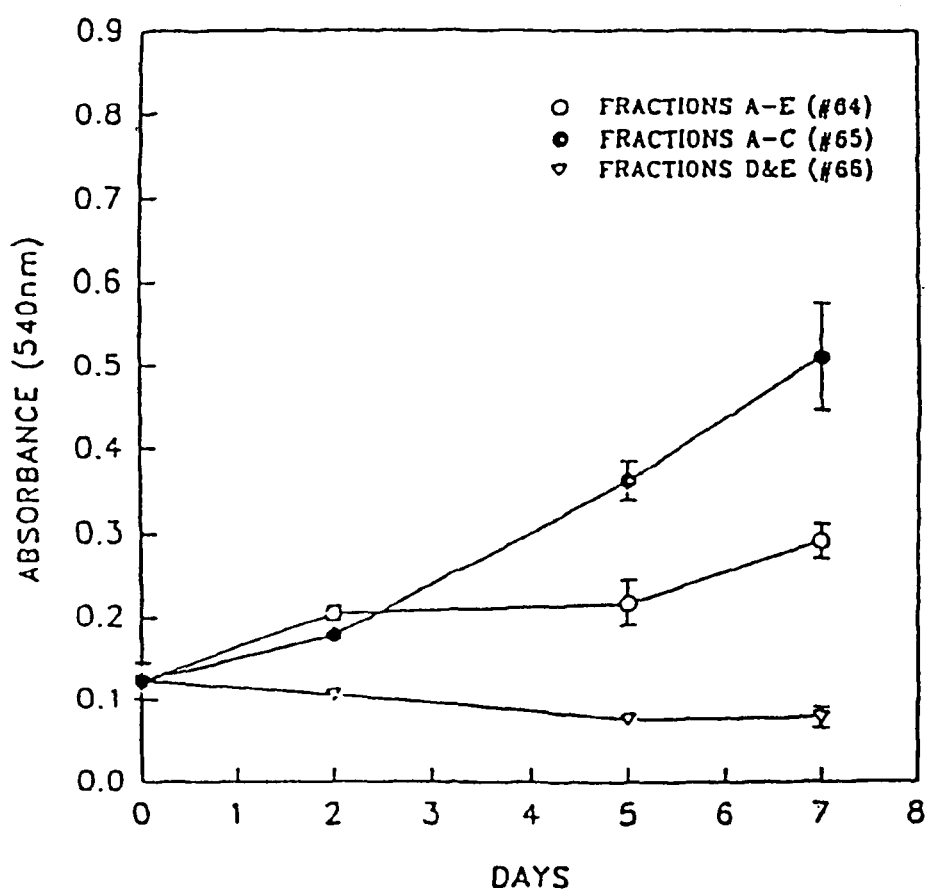
FIG. 15G shows cytotoxic effects at 100 ul/mL against SKBR-3 breast cancer cell line treated with different cocoa polyphenol fractions (absorbance (540 nm) vs. Days; open circle is fractions A-E, darkened circle is fractions A-C, open inverted triangle is fractions D&E)

A comparison of the XTT and Crystal Violet Assay procedures was made with cocoa fraction D & E (Example 3B) against the breast cancer cell line MCF-7 p 168 to determine which assay was most sensitive. As shown in FIG. 15A, both assays showed the same dose-response effects for concentrations >75 µg/mL. At concentrations below this value, the crystal violet assay showed higher standard deviations than the XTT assay results. However, since the crystal violet assay was easier to use, all subsequent assays, unless otherwise specified, were performed by this procedure.

Figure 15H:
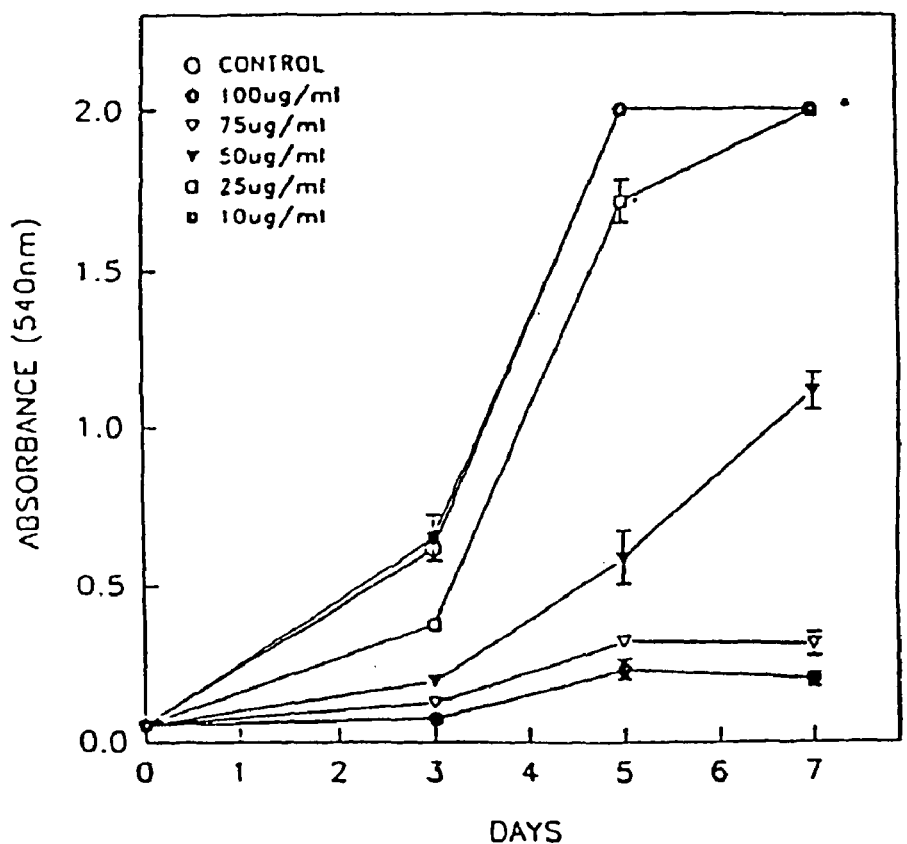
FIG. 15H shows typical dose-response relationships between cocoa procyanidin fraction D+E on Hela cells (absorbance (540 nm) vs. Days; open circle is control, darkened circle is 100 µg/mL, open inverted triangle is 75 µg/mL, darkened inverted triangle is 50 µg/mL, open square is 25 µg/ml, darkened square is 10 µg/mL; absorbance of 2.0 is maximum of plate reader and is not representative of cell number)
Figure 15I:
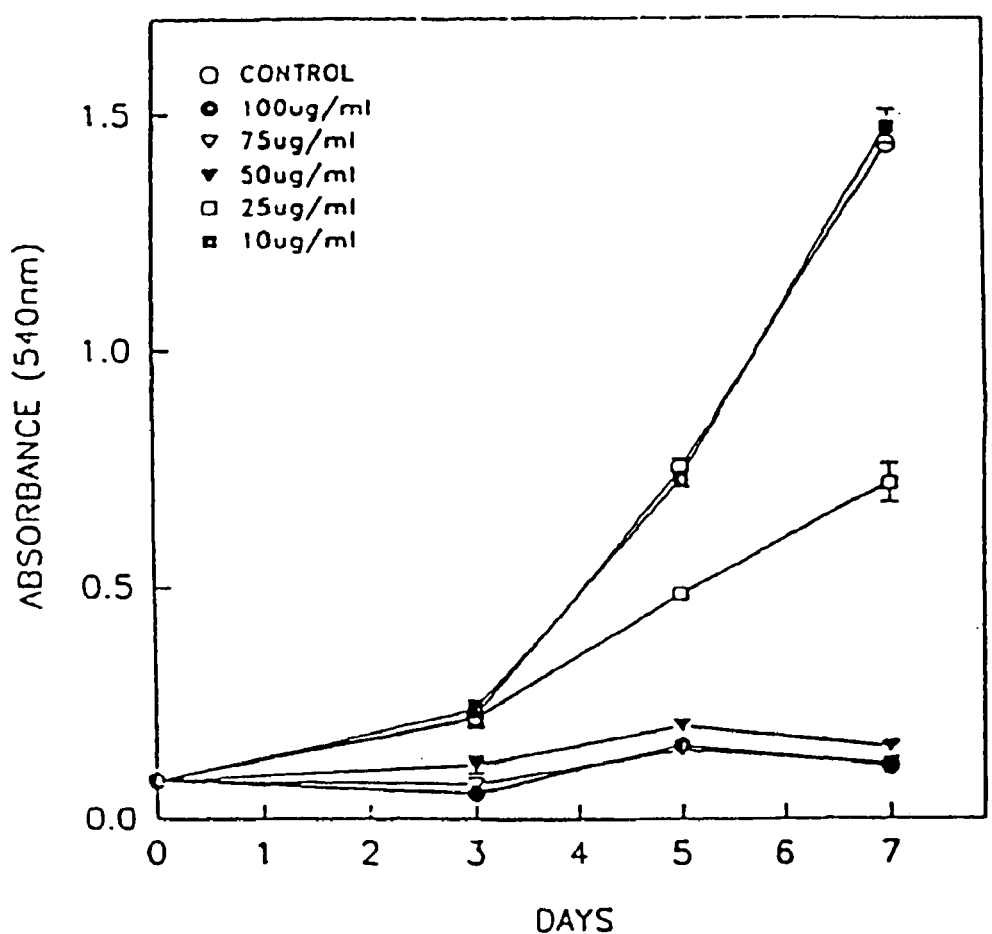
FIG. 15I shows typical dose-response relationship between cocoa procyanidin fraction D+E on SKBR-3 cells (absorbance (540 nm) vs. Days; open circle is control, darkened circle is 100 µg/mL, open inverted triangle is 75 µg/mL, darkened inverted triangle is 50 µg/mL, open square is 25 µg/mL, darkened square is 10 µg/mL)

Crystal violet assay results are presented (FIGS. 15B-15E) to demonstrate the effect of a crude polyphenol extract (Example 2) on the breast cancer cell line MDA MB231, prostate cancer cell line PC-3, breast cancer cell line MCF-7 p163, and cervical cancer cell line Hela, respectively. In all cases a dose of 250 µg/mL completely inhibited all cancer cell growth over a period of 5-7 days. The Hela cell line appeared to be more sensitive to the extract, since a 100 µg/mL dose also inhibited growth. Cocoa fractions from Example 3B were also assayed against Hela and another breast cancer cell line SKBR-3. The results (FIGS. 15F and 15G) showed that fraction D & E has the highest activity. As shown in FIGS. 15H and 15I, IC$_{50}$ values of about 40 µg/mL D & E were obtained from both cancer cell lines.

Figure 15J:
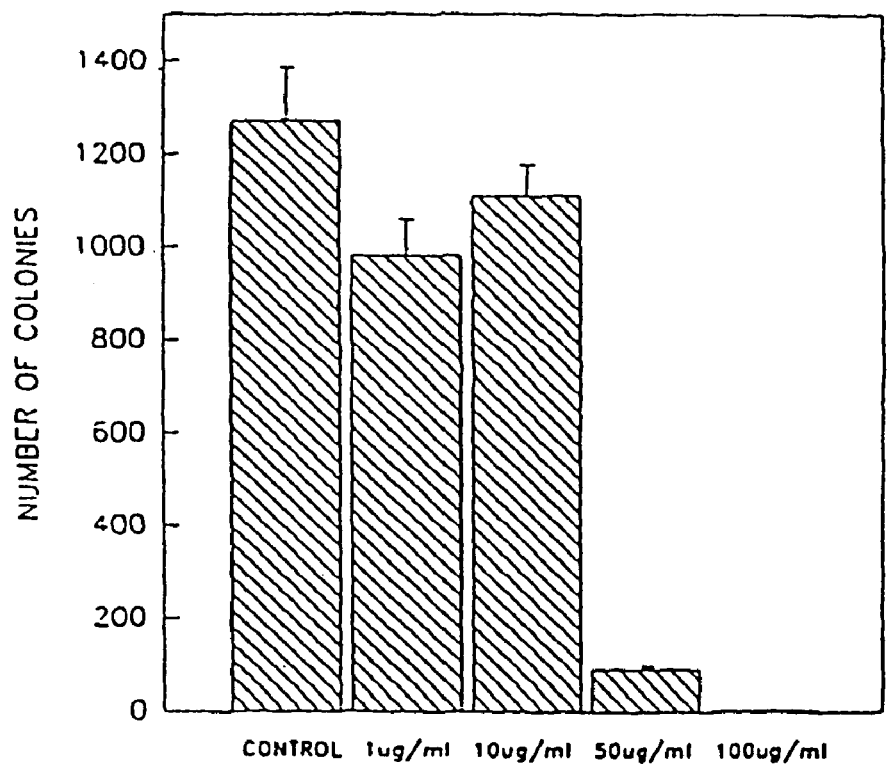
FIG. 15J shows typical dose-response relationships between cocoa procyanidin fraction D+E on Hela cells using the Soft Agar Cloning assay (bar chart; number of colonies vs. control, 1, 10, 50, and 100 µg/mL)

The cocoa fraction D & E was also tested in the soft agar cloning assay which determines the ability of a test compound(s) to inhibit anchorage independent growth. As shown in FIG. 15J, a concentration of 100 µg/1 mL completely inhibited colony formation of Hela cells.

Crude polyphenol extracts obtained from eight different cocoa genotypes representing the three horticultural races of cocoa were also assayed against the Hela cell line. As shown in FIG. 15K all cocoa varieties showed similar dose-response effects. The UIT-1 variety exhibited the most activity against the Hela cell line. These results demonstrated that all cocoa genotypes possess a polyphenol fraction that elicits activity against at least one human cancer cell line that is independent of geographical origin, horticultural race, and genotype.

Figure 15L:
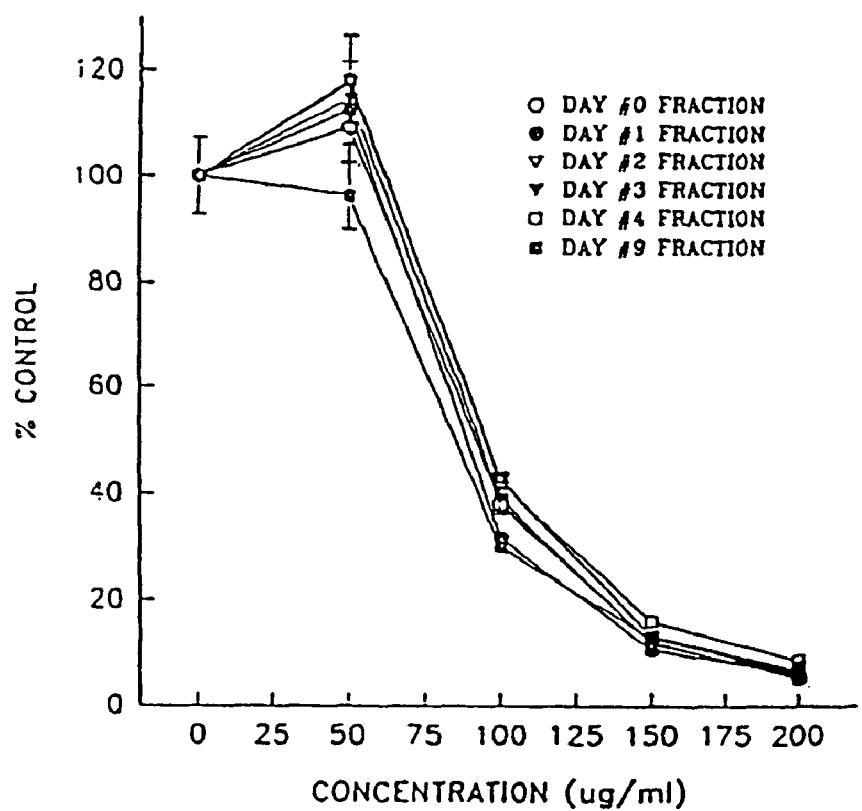
FIG. 15L shows the growth inhibition of Hela cells when treated with crude polyphenol extracts obtained from fermented cocoa beans and dried cocoa beans (stages throughout fermentation and sun drying; % control vs. concentration, µg/ml; open circle is day zero fraction, darkened circle is day 1 fraction, open inverted triangle is day 2 fraction, darkened inverted triangle is day 3 fraction, open square is day 4 fraction and darkened square is day 9 fraction)
Figure 15M:
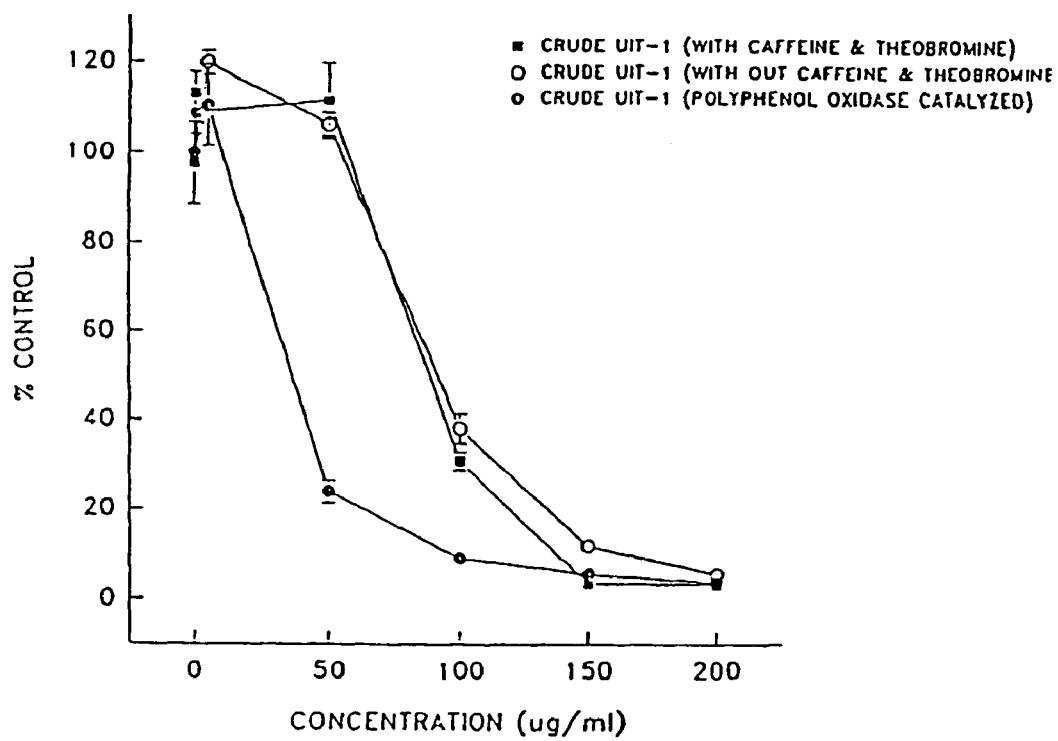
FIG. 15M shows the effect of enzymatically oxidized cocoa procyanidins against Hela cells (dose response for polyphenol oxidase treated crude cocoa polyphenol; % control vs. concentration, µg/mL; darkened square is crude UIT-1 (with caffeine and theobromine), open circle crude UIT-1 (without caffeine and theobromine) and darkened circle is crude UIT-1 (polyphenol oxidase catalyzed)

Another series of assays were performed on crude polyphenol extracts prepared on a daily basis from a one ton scale traditional 5-day fermentation of Brazilian cocoa beans, followed by a 4-day sun drying stage. The results shown in FIG. 15L showed no obvious effect of these early processing stages, suggesting little change in the composition of the polyphenols. However, it is known (Lehrian and Patterson, 1983) that polyphenol oxidase (PPO) will oxidize polyphenols during the fermentation stage. To determine what effect enzymatically oxidized polyphenols would have on activity, another experiment was performed. Crude PPO was prepared by extracting finely ground, unfermented, freeze dried, defatted Brazilian cocoa beans with acetone at a ratio of 1 gm powder to 10 mL acetone. The slurry was centrifuged at 3,000 rpm for 15 min. This was repeated three times, discarding the supernatant each time with the fourth extraction being poured through a Buchner filtering funnel. The acetone powder was allowed to air dry, followed by assay according to the procedures described by McLord and Kilara, (1983). To a solution of crude polyphenols (10 mg/10 mL Citrate-Phosphate buffer, 0.02M, pH 5.5) 100 mg of acetone powder (4,000 units activity/mg protein) was added and allowed to stir for 30 min. with a stream of air bubbled through the slurry. The sample was centrifuged at 5,000×g for 15 min. and the supernatant extracted 3× with 20 mL ethyl acetate. The ethyl acetate extracts were combined, taken to dryness by distillation under partial vacuum and 5 mL water added, followed by lyophilization. The material was then assayed against Hela cells and the dose-response compared to crude polyphenol extracts that were not enzymatically treated. The results (FIG. 15M) showed a significant shift in the dose-response curve for the enzymatically oxidized extract, showing that the oxidized products were more inhibitory than their native forms.

Example 9

Antioxidant Activity of Cocoa Extracts Containing Procyanidins

Evidence in the literature suggests a relationship between the consumption of naturally occurring antioxidants (Vitamins C, E and Beta-carotene) and a lowered incidence of disease, including cancer (Designing Foods, 1993; Caragay, 1992). It is generally thought that these antioxidants affect certain oxidative and free radical processes involved with some types of tumor promotion. Additionally, some plant polyphenolic compounds that have been shown to be anticarcinogenic, also possess substantial antioxidant activity (Ho et al., 1992; Huang et al., 1992).

To determine whether cocoa extracts containing procyanidins possessed antioxidant properties, a standard Rancimat method was employed. The procedures described in Examples 1, 2 and 3 were used to prepare cocoa extracts which were manipulated further to produce two fractions from gel permeation chromatography. These two fractions are actually combined fractions A through C, and D and E (See FIG. 1) whose antioxidant properties were compared against the synthetic antioxidants BHA and BHT.

Peanut Oil was pressed from unroasted peanuts after the skins were removed. Each test compound was spiked into the oil at two levels, ~100 ppm and ~20 ppm, with the actual levels given in Table 7. 50 μL of methanol solubilized antioxidant was added to each sample to aid in dispersion of the antioxidant. A control sample was prepared with 50 μL of methanol containing no antioxidant.

Figure 16:
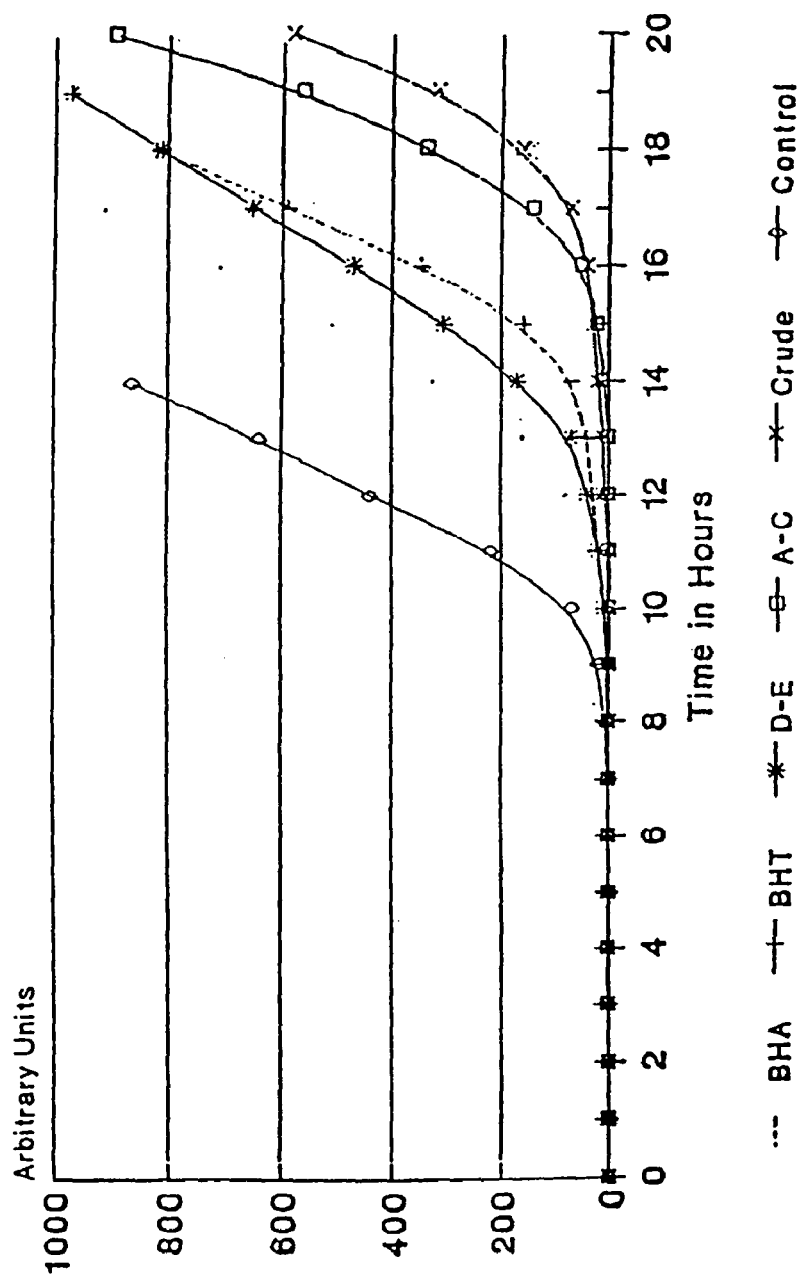
FIG. 16 shows typical Rancimat Oxidation curves for cocoa procyanidin extract and fractions in comparison to the synthetic antioxidants BHA and BHT (arbitrary units vs. time; dotted line and cross (+) is BHA and BHT; * is D-E; x is crude; open square is A-C; and open diamond is control)

The samples were evaluated in duplicate, for oxidative stability using the Rancimat stability test at 100° C. and 20 cc/min of air. Experimental parameters were chosen to match those used with the Active Oxygen Method (AOM) or Swift Stability Test (Van Oosten et al., 1981). A typical Rancimat trace is shown in FIG. 16. Results are reported in Table 8 as hours required to reach a peroxide level of 100 meq.

TABLE 7

Concentrations of Antioxidants

| SAMPLE | LEVEL 1 | LEVEL 2 |
|---|---|---|
| | ppm | |
| Butylated Hydroxytoluene (BHT) | 24 | 120 |
| Butylated Hydroxyanisole (BHA) | 24 | 120 |
| Crude Ethyl Acetate Fraction of Cocoa | 22 | 110 |
| Fraction A-C | 20 | 100 |
| Fraction D-E | 20 | 100 |

TABLE 8

Oxidative Stability of Peanut Oil with Various Antioxidants

| SAMPLE | 20 ppm | 100 ppm |
|---|---|---|
| | average | |
| Control | 10.5 ± 0.7 | |
| BHT | 16.5 ± 2.1 | 12.5 ± 2.1 |
| BHA | 13.5 ± 2.1 | 14.0 ± 1.4 |
| Crude Cocoa Fraction | 18.0 ± 0.0 | 19.0 ± 1.4 |
| Fraction A-C | 16.0 ± 6.4 | 17.5 ± 0.0 |
| Fraction D-E | 14.0 ± 1.4 | 12.5 ± 0.7 |

These results demonstrated increased oxidative stability of peanut oil with all of the additives tested. The highest increase in oxidative stability was realized by the sample spiked with the crude ethyl acetate extract of cocoa. These results demonstrated that cocoa extracts containing procyanidins have antioxidant potential equal to or greater than equal amounts of synthetic BHA and BHT. Accordingly, the invention may be employed in place of BHT or BHA in known utilities of BHA or BHT, for instance as an antioxidant and/or food additive. And, in this regard, it is noted too that the invention is from an edible source. Given these results, the skilled artisan can also readily determine a suitable amount of the invention to employ in such "BHA or BHT" utilities, e.g., the quantity to add to food, without undue experimentation.

Example 10

Topoisomerase II Inhibition Study

DNA topoisomerase I and II are enzymes that catalyze the breaking and rejoining of DNA strands, thereby controlling the topological states of DNA (Wang, 1985). In addition to the study of the intracellular function of topoisomerase, one of the most significant findings has been the identification of topoisomerase II as the primary cellular target for a number of clinically important antitumor compounds (Yamashita et al., 1990) which include intercalating agents (m-AMSA, Adriamycin® and ellipticine) as well as nonintercalating epipodophyllotoxins. Several lines of evidence indicate that some antitumor drugs have the common property of stabilizing the DNA—topoisomerase II complex ("cleavable complex") which upon exposure to denaturing agents results in the induction of DNA cleavage (Muller et al., 1989). It has been suggested that the cleavable complex formation by antitumor drugs produces bulky DNA adducts that can lead to cell death.

According to this attractive model, a specific new inducer of DNA topoisomerase II cleavable complex is useful as an anti-cancer, anti-tumor or antineoplastic agent. In an attempt to identify cytotoxic compounds with activities that target DNA, the cocoa procyanidins were screened for enhanced cytotoxic activity against several DNA—damage sensitive cell lines and enzyme assay with human topoisomerase II obtained from lymphoma.

A. Decatenation of Kinetoplast DNA by Topoisomerase II

The in vitro inhibition of topoisomerase II decatenation of kinetoplast DNA, as described by Muller et al. (1989), was performed as follows. Nuclear extracts containing topoisomerase II activity were prepared from human lymphoma by modifications of the methods of Miller et al. (1981) and Danks et al. (1988). One unit of purified enzyme was enough to decatenate 0.25 µg of kinetoplast DNA in 30 min. at 34° C. Kinetoplast DNA was obtained from the trypanosome *Crithidia fasciculata*. Each reaction was carried out in a 0.5 mL microcentrifuge tube containing 19.5 µL $H_2O$, 2.5 µL 10× buffer (1× buffer contains 50 mM tris-HCl, pH 8.0, 120 mM KCl, 10 mM $MgCl_2$, 0.5 mM ATP, 0.5 mM dithiothreitol and 30 µg BSA/mL), 1 µL kinetoplast DNA (0.2 µg), and 1 µL DMSO-containing cocoa procyanidin test fractions at various concentrations. This combination was mixed thoroughly and kept on ice. One unit of topoisomerase was added immediately before incubation in a waterbath at 34° C. for 30 min.

Following incubation, the decatenation assay was stopped by the addition of 5 µL stop buffer (5% sarkosyl, 0.0025% bromophenol blue, 25% glycerol) and placed on ice. DNA was electrophoresed on a 1% agarose gel in TAE buffer containing ethidium bromide (0.5 µg/mL). Ultraviolet illumination at 310 m wavelength allowed the visualization of DNA. The gels were photographed using a Polaroid Land camera.

FIG. 17 shows the results of these experiments. Fully catenated kinetoplast DNA does not migrate into a 1% agarose gel. Decatenation of kinetoplast DNA by topoisomerase II generates bands of monomeric DNA (monomer circle, forms I and II) which do migrate into the gel. Inhibition of the enzyme by addition of cocoa procyanidins is apparent by the progressive disappearance of the monomer bands as a function of increasing concentration. Based on these results, cocoa procyanidin fractions A, B, D, and E were shown to inhibit topoisomerase II at concentrations ranging from 0.5 to 5.0 µg/mL. These inhibitor concentrations were very similar to those obtained for mitoxanthrone and m-AMSA (4'-(9-acridinylamino)methanesulfon-m-anisidide).

B. Drug Sensitive Cell Lines

Cocoa procyanidins were screened for cytotoxicity against several DNA-damage sensitive cell lines. One of the cell lines was the xrs-6 DNA double strand break repair mutant developed by P. Jeggo (Kemp et al., 1984). The DNA repair deficiency of the xrs-6 cell line renders them particularly sensitive to x-irradiation, to compounds that produce DNA double strand breaks directly, such as bleomycin, and to compounds that inhibit topoisomerase II, and thus may indirectly induce double stand breaks as suggested by Warters et al. (1991). The cytotoxicity toward the repair deficient line was compared to the cytotoxicity against a DNA repair proficient CHO line, BR1. Enhanced cytotoxicity towards the repair deficient (xrs-6) line was interpreted as evidence for DNA cleavable double strand break formation.

The DNA repair competent CHO line, BR1, was developed by Barrows et al. (1987) and expresses $O^6$-alkylguanine-DNA-alkyltransferase in addition to normal CHO DNA repair enzymes. The CHO double strand break repair deficient line (xrs-6) was a generous gift from Dr. P. Jeggo and co-workers (Jeggo et al., 1989). Both of these lines were grown as monolayers in alpha-MEM containing serum and antibiotics as described in Example 6. Cells were maintained at 3°7C in a humidified 5% $CO_2$ atmosphere. Before treatment with cocoa procyanidins, cells grown as monolayers were detached with trypsin treatment. Assays were performed using the MTT assay procedure described in Example 6.

Figure 18:
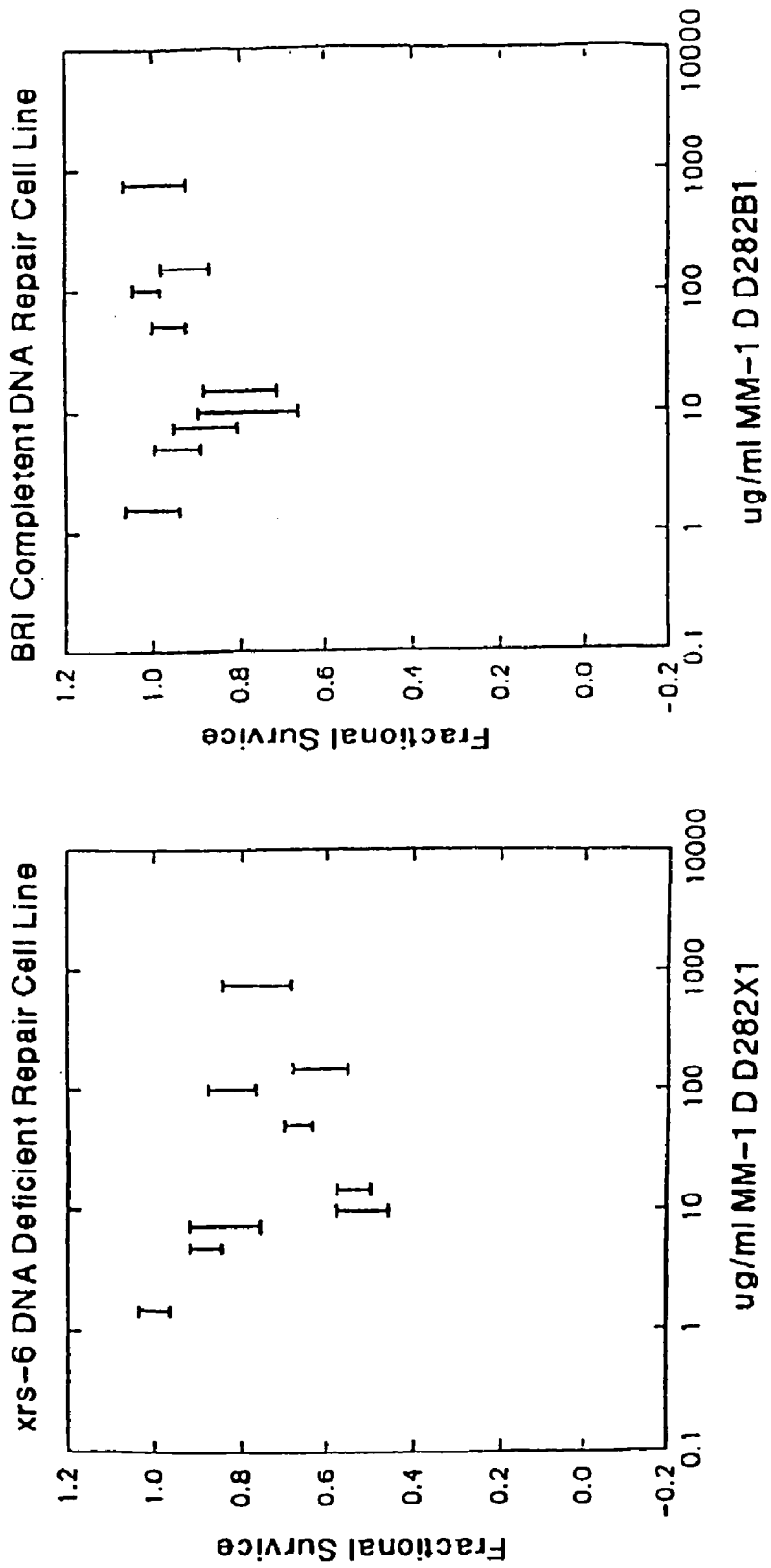
FIG. 18 shows dose response relationships of cocoa procyanidin fraction D against DNA repair competent and deficient cell lines (fractional survival vs. μg/mL; left side xrs-6 DNA Deficient Repair Cell Line, MM-1 D D282X1; right side BR1 Competent DNA Repair Cell Line, MM-1 D D282B1)

The results (FIG. 18) indicated no enhanced cytotoxicity towards the xrs-6 cells suggesting that the cocoa procyanidins inhibited topoisomerase II in a manner different from cleavable double strand break formation. That is, the cocoa procyanidins interact with topoisomerase II before it has interacted with the DNA to form a noncleavable complex.

Noncleavable complex forming compounds are relatively new discoveries. Members of the anthracyclines, podophyllin alkaloids, anthracenediones, acridines, and ellipticines are all approved for clinical anti-cancer, anti-tumor or antineoplastic use, and they produce cleavable complexes (Liu, 1989). Several new classes of topoisomerase II inhibitors have recently been identified which do not appear to produce cleavable complexes. These include amonafide (Hsiang et al., 1989), distamycin (Fesen et al., 1989), flavanoids (Yamashita et al., 1990), saintopin (Yamashita et al., 1991), membranone (Drake et al., 1989), terpenoids (Kawada et al., 1991), anthrapyrazoles (Fry et al., 1985), dioxopiperazines (Tanabe et al., 1991), and the marine acridine-dercitin (Burres et al., 1989).

Since the cocoa procyanidins inactivate topoisomerase II before cleavable complexes are formed, they have chemotherapy value either alone or in combination with other known and mechanistically defined topoisomerase II inhibitors. Additionally, cocoa procyanidins also appear to be a novel class of topoisomerase II inhibitors, (Kashiwada et al., 1993) and may thus be less toxic to cells than other known inhibitors, thereby enhancing their utility in chemotherapy.

Figure 19:
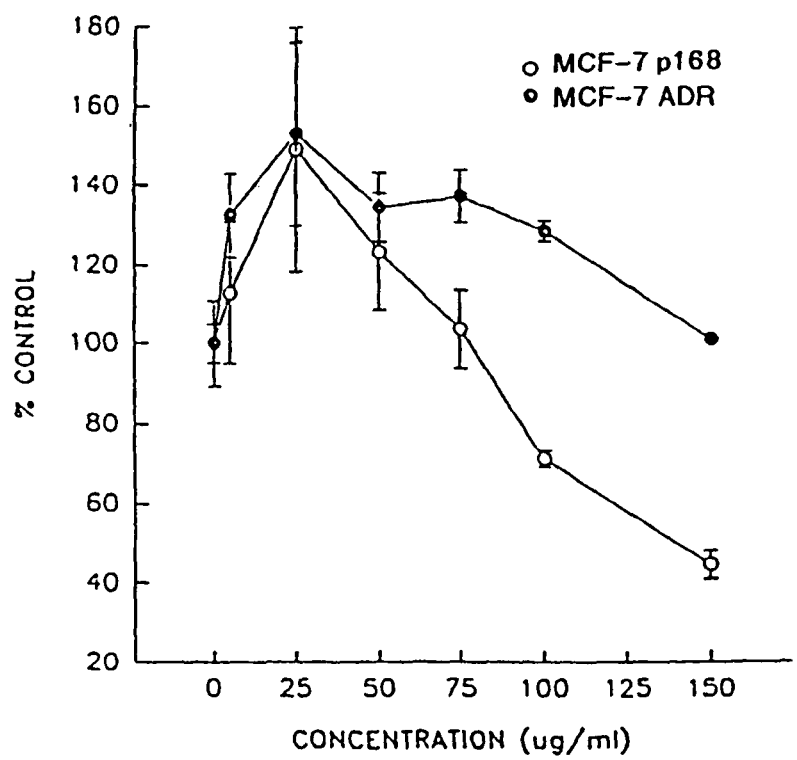
FIG. 19 shows the dose-response curves for Adriamycin resistant MCF-7 cells in comparison to a MCF-7 p 168 parental cell line when treated with cocoa fraction D+E (% control vs. concentration, μg/mL; open circle is MCF-7 p168; darkened circle is MCF-7 ADR)

The human breast cancer cell line MCF-7 (ADR) which expresses a membrane bound glycoprotein (gp170) to confer multi-drug resistance (Leonessa et al., 1994) and its parental line MCF-7 p168 were used to assay the effects of cocoa fraction D & E. As shown in FIG. 19, the parental line was inhibited at increasing dose levels of fraction D & E, whereas the Adriamycin (ADR) resistant line was less effected at the higher doses. These results show that cocoa fraction D & E has an effect on multi-drug resistant cell lines.

Example 11

Synthesis of Procyanidins

The synthesis of procyanidins was performed according to the procedures developed by Delcour et al. (1983), with modification. In addition to condensing (+)-catechin with dihydroquercetin under reducing conditions, (−)-epicatechin was also used to reflect the high concentrations of (−)-epicatechin that naturally occur in unfermented cocoa beans. The synthesis products were isolated, purified, analyzed, and identified by the procedures described in Examples 3, 4 and 5. In this manner, the biflavanoids, triflavanoids and tetraflavanoids are prepared and used as analytical standards and, in the manner described above with respect to cocoa extracts.

Example 12

Assay of Normal Phase Semi-Preparative Fractions

Figure 20A:
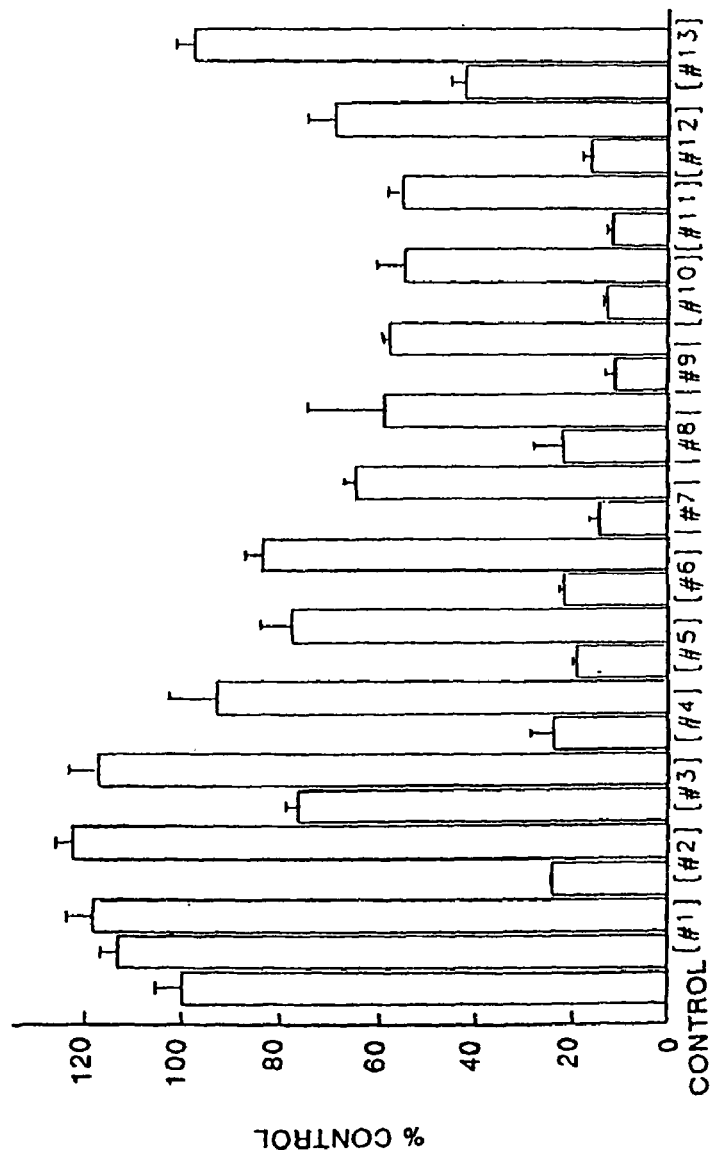
FIGS. 20A and B show the dose-response effects on Hela and SKBR-3 cells when treated at 100 μg/mL and 25 g/mL levels of twelve fractions prepared by Normal phase semi-preparative HPLC (bar chart, % control vs. control and fractions 1-12)
Figure 20B:
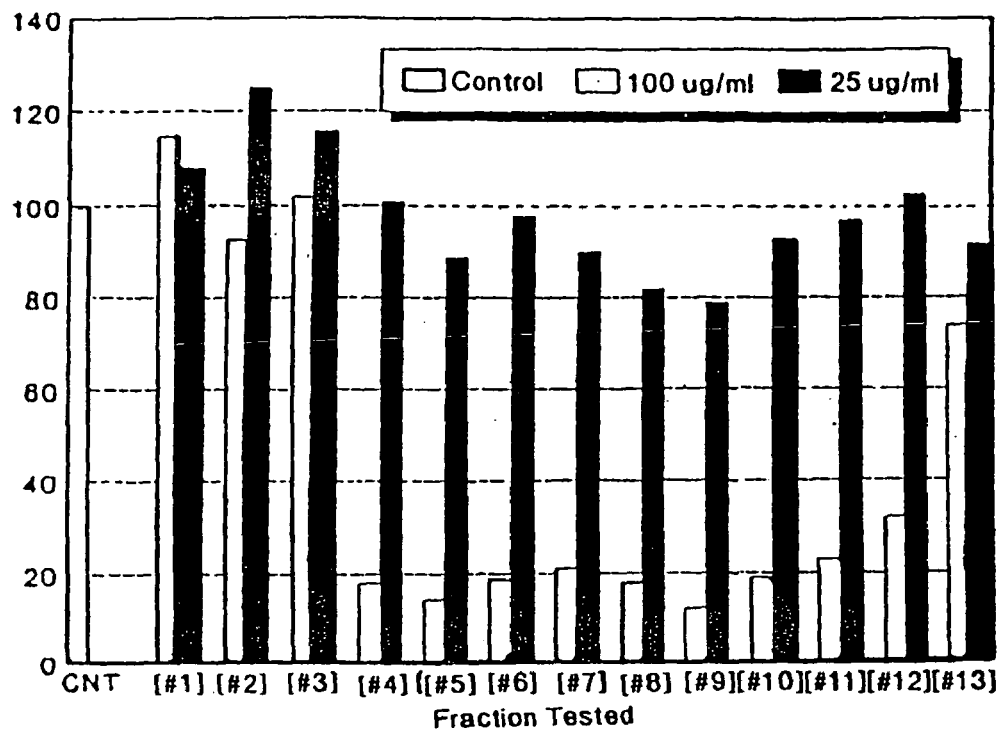
Figure 21A:
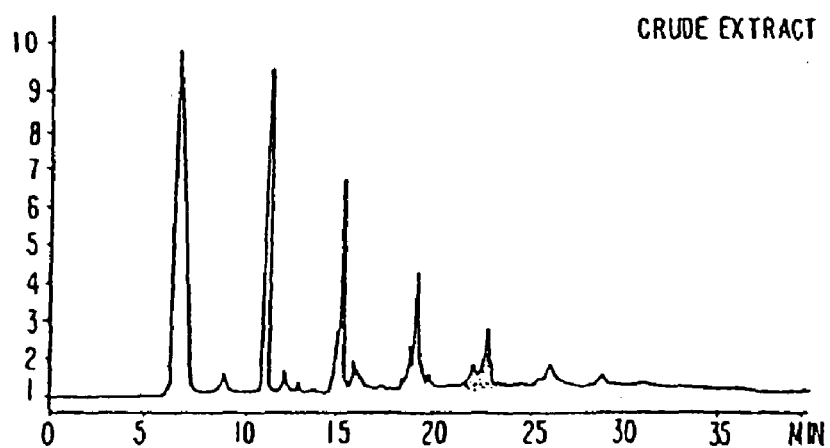
FIGS. 21A, 21B, and 21C show a normal phase HPLC separation of crude, enriched and purified pentamers from cocoa extract.
Figure 21B:
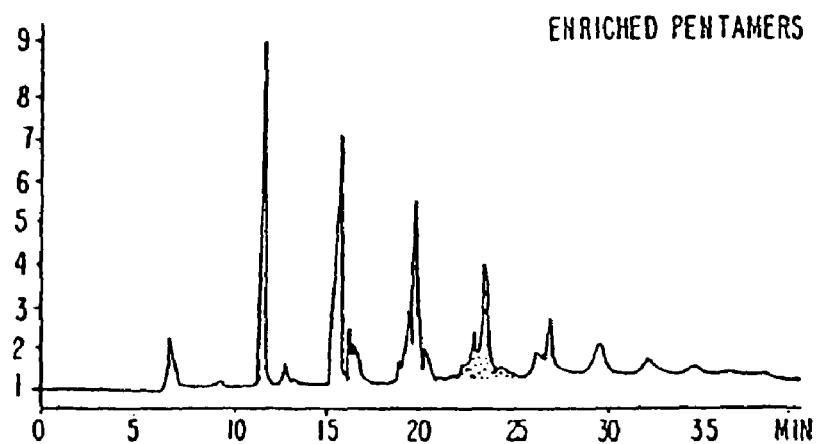
Figure 21C:
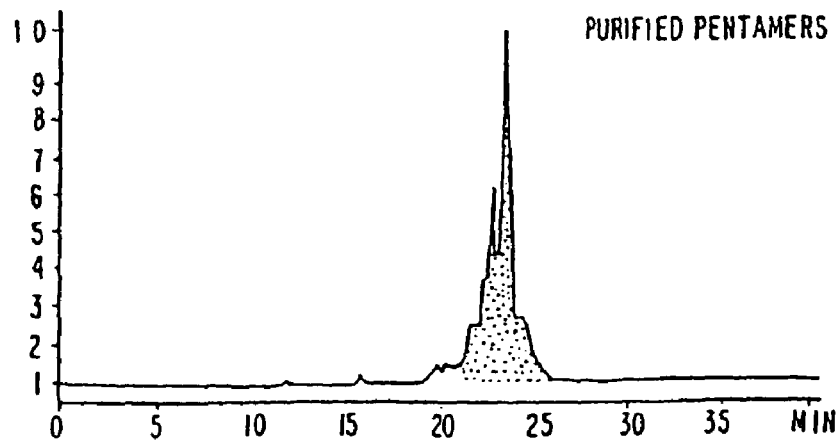

Since the polyphenol extracts are compositionally complex, it was necessary to determine which components were active against cancer cell lines for further purification, dose-response assays and comprehensive structural identification. A normal phase semi preparative HPLC separation (Example 3B) was used to separate cocoa procyanidins on the basis of oligomeric size. In addition to the original extract, twelve fractions were prepared (FIGS. 2B and 15 O) and assayed at 100 µg/mL and 25 µg/mL doses against Hela and SKBR-3 cancer cell lines to determine which oligomer possessed the greatest activity. As shown in FIGS. 20A and B, fractions 4-11 (pentamer-dodecamer) significantly inhibited HeLa and SKBr-3 cancer cell lines at the 100 µg/mL level. These results indicated that these specific oligomers had the greatest activity against Hela and SKBR-3 cells. Additionally, normal phase HPLC analysis of cocoa fraction D & E indicated that this fraction, used in previous investigations, e.g., Example 7, was enriched with these oligomers.

Example 13

HPLC Purification Methods

Method A. GPC Purification

Procyanidins obtained as in Example 2 were partially purified by liquid chromatography on Sephadex LH 20 (72.5×2.5 cm), using 100% methanol as the eluting solvent, at a flow rate of 3.5 mL/min. Fractions of the eluent were collected after the first 1.5 hours, and the fractions were concentrated by a rotary evaporator, redissolved in water and freeze dried. These fractions were referred to as pentamer enriched fractions. Approximately 2.00 g of the extract obtained from Example 2 was subfractionated in this manner. Results are shown in Table 9.

Method C. Reverse-Phase Separation

Procyanidins obtained as in Example 2 were separated purified by reverse phase chromatography on Hewlett Packard Hypersil ODS 5 µm. (200×2.1 mm), and a Hewlett Packard Hypersil ODS 5 µm guard column (20×2.1 mm). The procyanidins were eluted with a linear gradient of 20% B into A in 20 minutes, followed by a column wash with 100% B at a flow rate of 0.3 mL/min. The mobile phase composition was a degassed mixture of B=1.0% acetic acid in methanol and A=2.0% acetic acid in nanopure water. Components were detected by UV at 280 nm, and fluorescence where $\lambda_{ex}$=276 nm and $\lambda_{em}$=16 nm; and the injection volume was 2.0 µL (20 mg/mL).

Example 14

HPLC Separation of Pentamer Enriched Fractions

Method A. Semi-Preparative Normal Phase HPLC

The pentamer enriched fractions were further purified by semi-preparative normal phase HPLC by a Hewlett Packard 1050 HPLC system equipped with a Millipore—Waters model 480 LC detector set at 254 nm, which was assembled with a Pharmacia Frac-100 Fraction Collector set to peak mode. Separations were effected on a Supelco 5 µm Supelcosel LC-Si, 100 Å column (250×10 mm) connected with a Supelco 5µ Supelguard LC-Si guard column (20×4.6 mm). Procyanidins were eluted by a linear gradient under the fol-

TABLE 9

Composition of Fractions Obtained:

| Fraction (Time) | Mmonomer (% Area) | DDimer (% Area) | TTrimer (% Area) | Tetramer (% Area) | Pentamer (% Area) | Hexamer (% Area) | Heptamer (% Area) | Octamer (% Area) | Nonamer (% Area) | Decamer (% Area) | Undecamer (% Area) | Others (% Area) |
|---|---|---|---|---|---|---|---|---|---|---|---|---|
| 1:15 | 73 | 8 | 16 | 3 | ND | ND | ND | ND | ND | ND | ND | ND |
| 1:44 | 67 | 19 | 10 | 3 | 1 | tr | tr | tr | tr | tr | tr | tr |
| 2:13 | 30 | 29 | 24 | 11 | 4 | 1 | tr | tr | tr | tr | tr | tr |
| 2:42 | 2 | 16 | 31 | 28 | 15 | 6 | 2 | tr | tr | tr | tr | tr |
| 3:11 | 1 | 12 | 17 | 25 | 22 | 13 | 7 | 2 | 1 | tr | tr | tr |
| 3:40 | tr | 18 | 13 | 18 | 20 | 15 | 10 | 5 | 2 | tr | tr | tr |
| 4:09 | tr | 6 | 8 | 17 | 21 | 19 | 14 | 8 | 4 | 2 | tr | tr |

ND = not detected
tr = trace amount

Method B. Normal Phase Separation

Procyanidins obtained as Example 2 were separated purified by normal phase chromatography on Supelcosil LC-Si, 100 Å, 5 µm (250×4.6 mm), at a flow rate of 1.0 mL/min, or, in the alternative, Lichrosphere® Silica 100, 100 Å, 5 µm (235×3.2 mm), at a flow rate of 0.5 mL/min. Separations were aided by a step gradient under the following conditions: (Time, % A, % B); (0, 82, 14), (30, 67.6, 28.4), (60, 46, 50), (65, 10, 86), (70, 10, 86). Mobile phase composition was A=dichloromethane; B=methanol; and C=acetic acid:water (1:1). Components were detected by fluorescence where $\lambda_{ex}$=276 nm and $\lambda_{em}$=316 nm, and by UV at 280 nm. The injection volume was 5.0 µL (20 mg/mL) of the procyanidins obtained from Example 2. These results are shown in FIGS. 40A and 40B.

In the alternative, separations were aided by a step gradient under the following conditions: (Time, % A, % B); (0, 76, 20); (25, 46, 50); (30, 10, 86). Mobile phase composition was A=dichloromethane; B=methanol; and C=acetic acid:water (1:1). The results are shown in FIGS. 41A and 41B.

lowing conditions: (Time, % A, % B); (0, 82, 14), (30, 67.6, 28.4), (60, 46, 50), (65, 10, 86), (70, 10, 86) followed by a 10 minute re-equilibration. Mobile phase composition was A=dichloromethane; B=methanol; and C=acetic acid:water (1:1). A flow rate of 3 mL/min was used. Components were detected by UV at 254 nm; and recorded on a Kipp & Zonan BD41 recorder. Injection volumes ranged from 100-250 µl of 10 mg of procyanidin extracts dissolved in 0.25 mL 70% aqueous acetone. Individual peaks or select chromatographic regions were collected on timed intervals or manually by fraction collection for further purification and subsequent evaluation.

HPLC conditions: 250×100 mm Supelco Supelcosil LC-Si (5 µm) Semipreparative Column
20×4.6 mm Supelco Supelcosil LC-Si (5 µm) Guard Column
Detector: Waters LC
Spectrophotometer Model
480 @ 254 nm
Flow rate: 3 mL/min.,
Column Temperature: ambient,
Injection: 250 µL of pentamer enriched extract

| Gradient: | $CH_2Cl_2$ | methanol | acetic acid:water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Method B. Reverse Phase Separation

Procyanidin extracts obtained as in Example 13 were filtered through a 0.45μ nylon filter and analyzed by a Hewlett Packard 1090 ternary phase HPLC system equipped with a Diode Array detector and a HP model 1046A Programmable Fluorescence Detector. Separations were effected at 45° C. on a Hewlett Packard 5μ Hypersil ODS column (200×2.1 mm). The procyanidins were eluted with a linear gradient of 60% B into A followed by a column wash with B at a flow rate of 0.3 mL/min. The mobile phase composition was a de-gassed mixture of B=0.5% acetic acid in methanol and A=0.5% acetic acid in nanopure water. Acetic acid levels in A and B mobile phases can be increased to 2%. Components were detected by fluorescence, where $\lambda_{ex}$=276 nm and $\lambda_{em}$=316 nm, and by UV at 280 nm. Concentrations of (+)-catechin and (−)-epicatechin were determined relative to reference standard solutions. Procyanidin levels were estimated by using the response factor for (−)-epicatechin.

Method C. Normal Phase Separation

Pentamer enriched procyanidin extracts obtained as in Example 13 were filtered through a 0.45μ nylon filter and analyzed by a Hewlett Packard 1090 Series II HPLC system equipped with a HP Model 1046A Programmable Fluorescence detector and Diode Array detector. Separations were effected at 37° C. on a 5μ Phenomenex Lichrosphere® Silica 100 column (250×3.2 mm) connected to a Supelco Spuelguard LC-Si 5μ guard column (20×4.6 mm). Procyanidins were eluted by linear gradient under the following conditions: (time, % A, % B); (0, 82, 14), (30, 67.6, 28.4), (60, 46, 50), (65, 10, 86), (70, 10, 86), followed by an 8 minute re-equilibration. Mobile phase composition was A=dichloromethane, B=methanol, and C=acetic acid:water at a volume ratio of 1:1. A flow rate of 0.5 mL/min was used. Components were detected by fluorescence, where $\lambda_{ex}$=276 nm and $\lambda_{em}$=316 nm or by UV at 280 nm. A representative HPLC chromatogram showing the separation of the various procyanidins is shown in FIG. 2 for one genotype. Similar HPLC profiles were obtained from other *Theobroma, Herrania* and/or their inter or intra specific crosses.

HPLC conditions:
250×3.2 mm Phenomenex Lichrosphere® Silica 100 column (5μ) 20×4.6 mm Supelco Supelguard LC-Si (5μ) guard column
Detectors: Photodiode Array @ 280 nm
Fluorescence $\lambda_{ex}$=276 nm; $\lambda_{em}$=316 nm
Flow rate: 0.5 mL/min.
Column temperature: 37° C.
acetic acid:

| Gradient: | $CH_2Cl_2$ | methanol | water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Method D. Preparative Normal Phase Separation

The pentamer enriched fractions obtained as in Example 13 were further purified by preparative normal phase chromatography by modifying the method of Rigaud et al., (1993) J. Chrom. 654, 255-260.

Separations were affected at ambient temperature on a 5μ Supelcosil LC-Si 100 Å column (50×2 cm), with an appropriate guard column. Procyanidins were eluted by a linear gradient under the following conditions: (time, % A, % B, flow rate); (0, 92.5, 7.5, 10); (10, 92.5, 7.5, 40); (30, 91.5, 18.5, 40); (145, 88, 22, 40); (150, 24, 86, 40); (155, 24, 86, 50); (180, 0, 100, 50). Prior to use, the mobile phase components were mixed by the following protocol:

Solvent A preparation (82% $CH_2Cl_2$, 14% methanol, 2% acetic acid, 2% water):

1. Measure 80 mL of water and dispense into a 4 L bottle.
2. Measure 80 mL of acetic acid and dispense into the same 4 L bottle.
3. Measure 560 mL of methanol and dispense into the same 4 L bottle.
4. Measure 3280 mL of methylene chloride and dispense into the 4 L bottle.
5. Cap the bottle and mix well.
6. Purge the mixture with high purity Helium for 5-10 minutes to degas.

Repeat steps 1-6 two times to yield 8 volumes of solvent A.

Solvent B preparation (96% methanol, 2% acetic acid, 2% water):

1. Measure 80 mL of water and dispense into a 4 L bottle.
2. Measure 80 mL of acetic acid and dispense into the same 4 L bottle.
3. Measure 3840 mL of methanol and dispense 3840 mL of methanol and dispense into the same 4 L bottle.
4. Cap the bottle and mix well.
5. Purge the mixture with high purity Helium for 5-10 minutes to degas.

Figure 42:
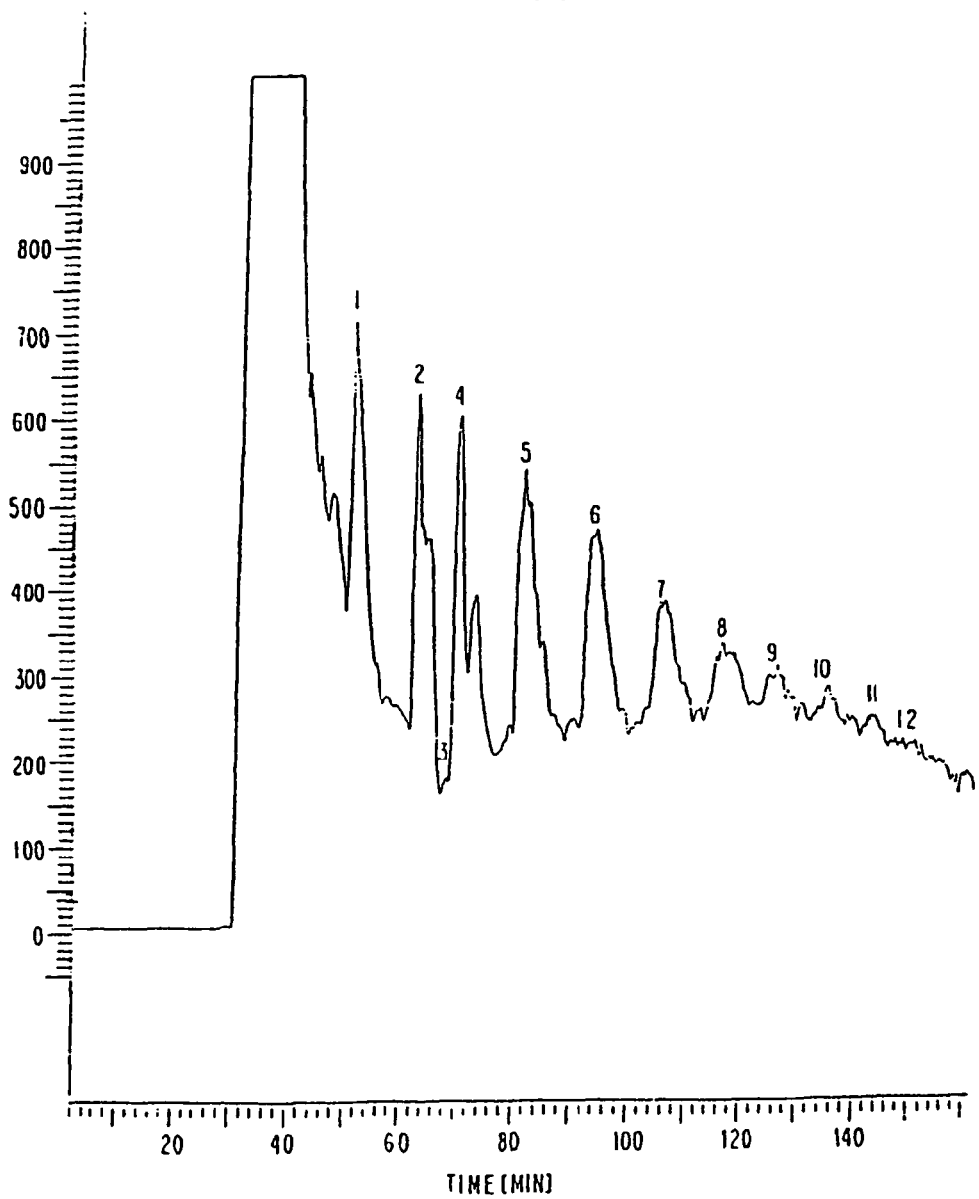
FIG. 42 shows a preparation normal phase HPLC separation of procyanidins.
Figure 43A:
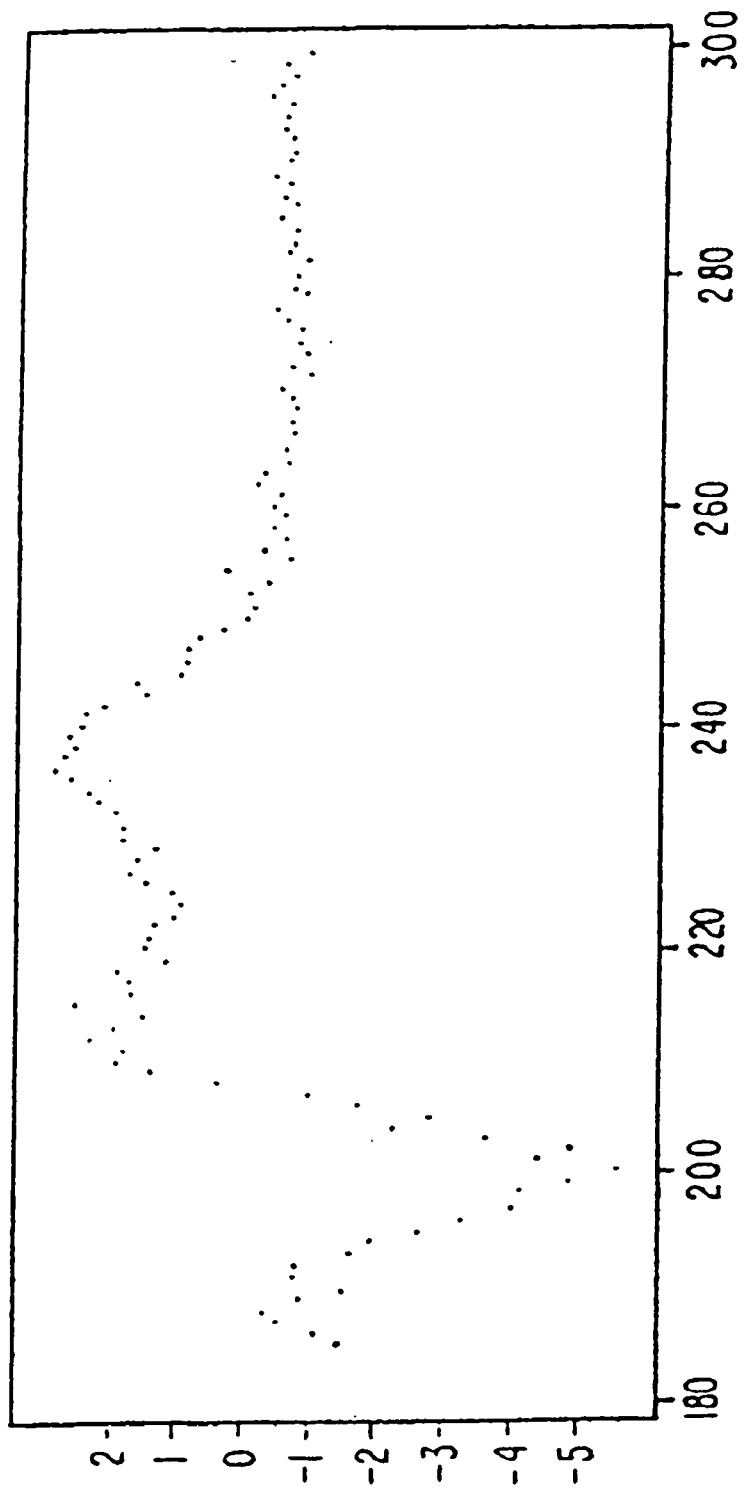
FIGS. 43A-G show CD (circular dichroism) spectra of procyanidin dimers, trimers, tetramers, pentamers, hexamers, heptamers and octamers, respectively.
Figure 43B:
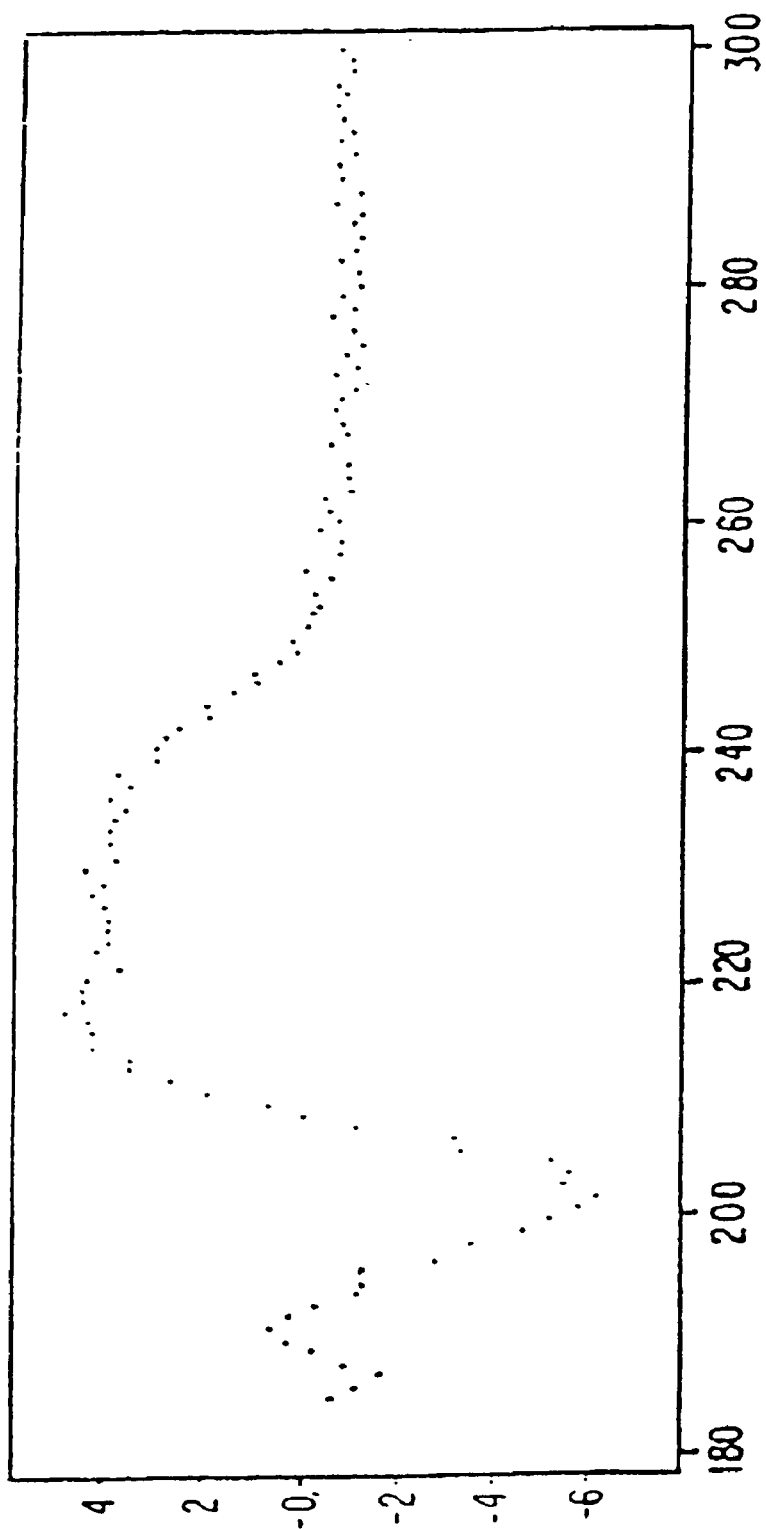
Figure 43C:
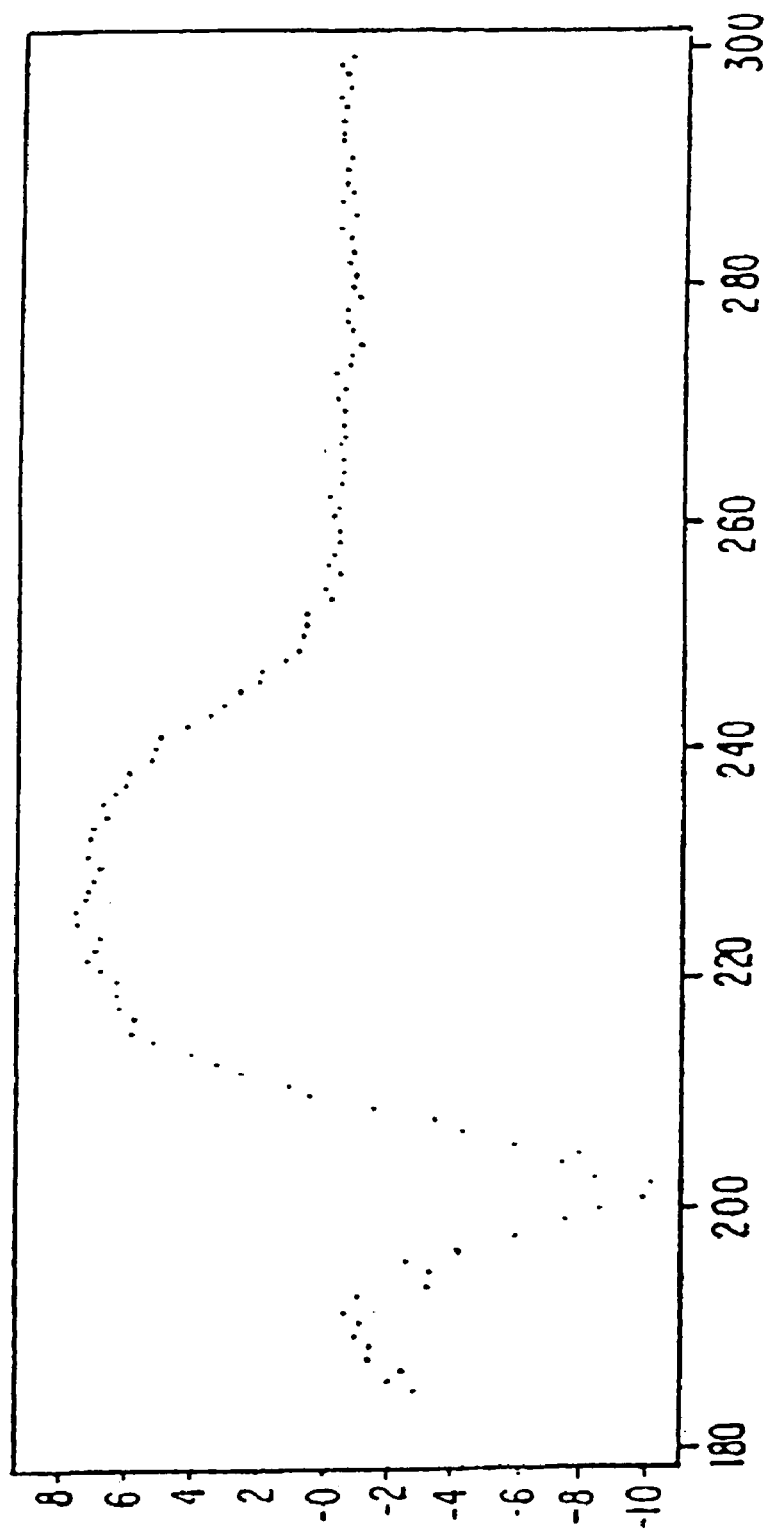
Figure 43D:
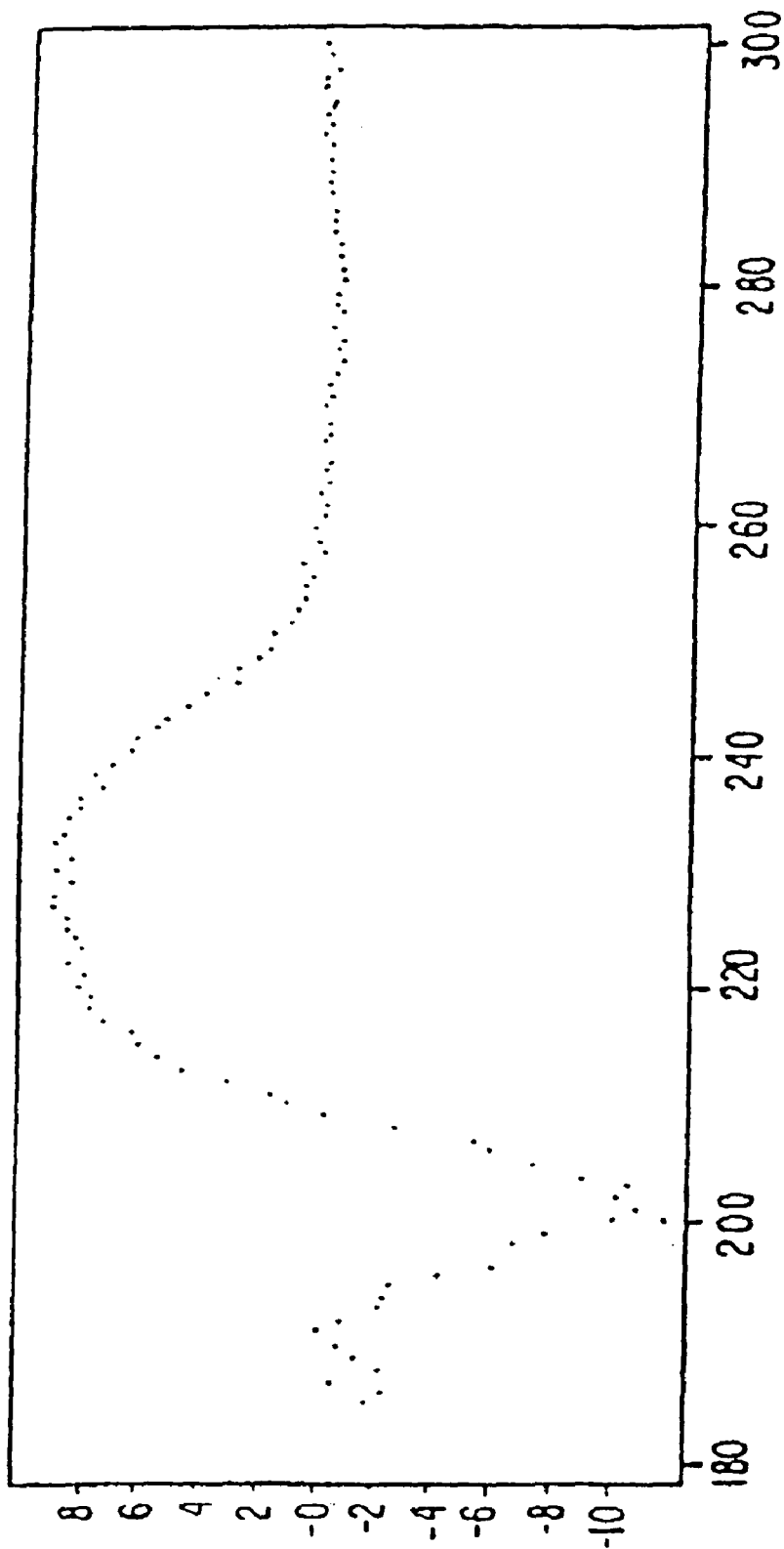
Figure 43E:
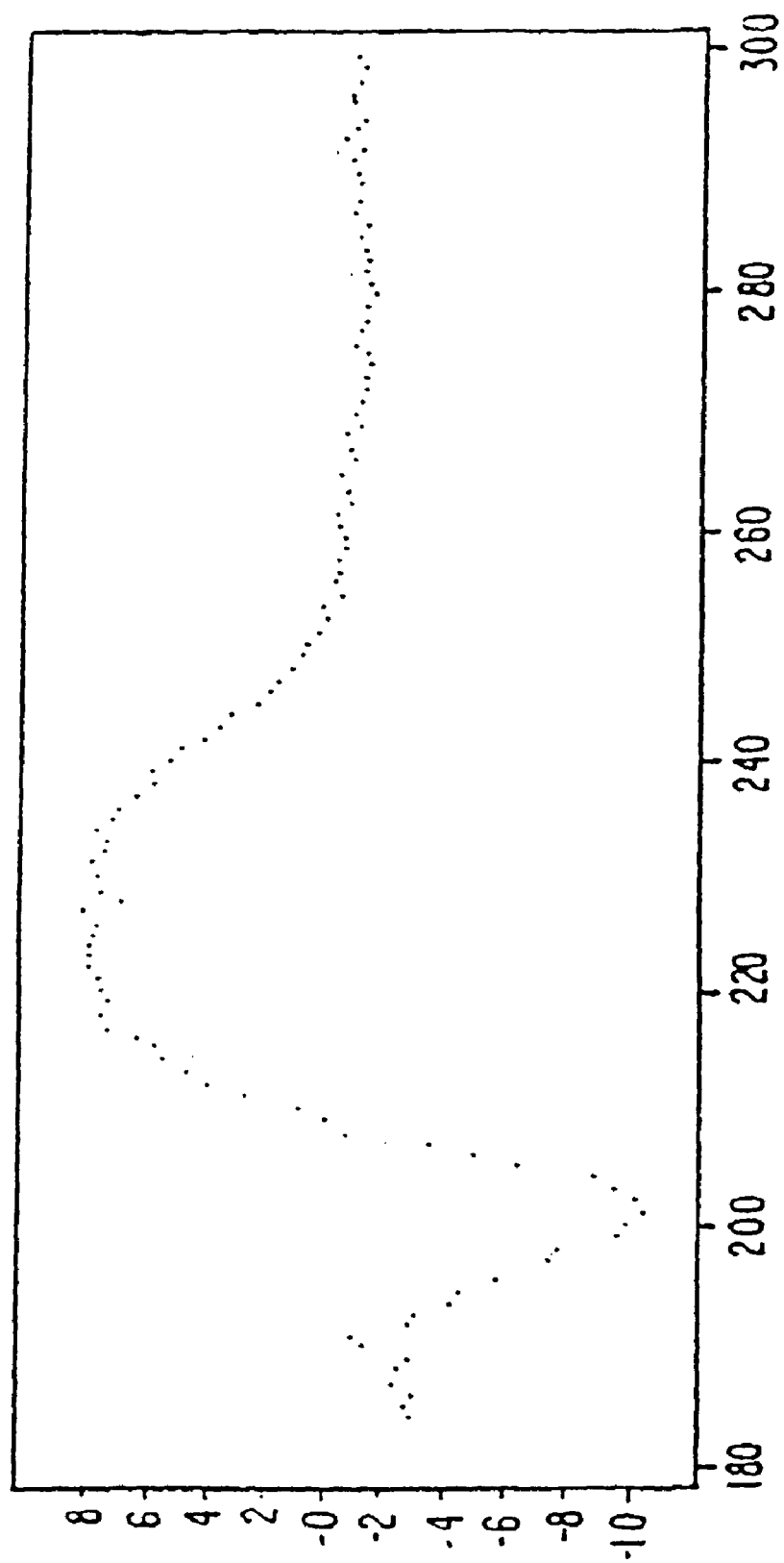
Figure 43F:
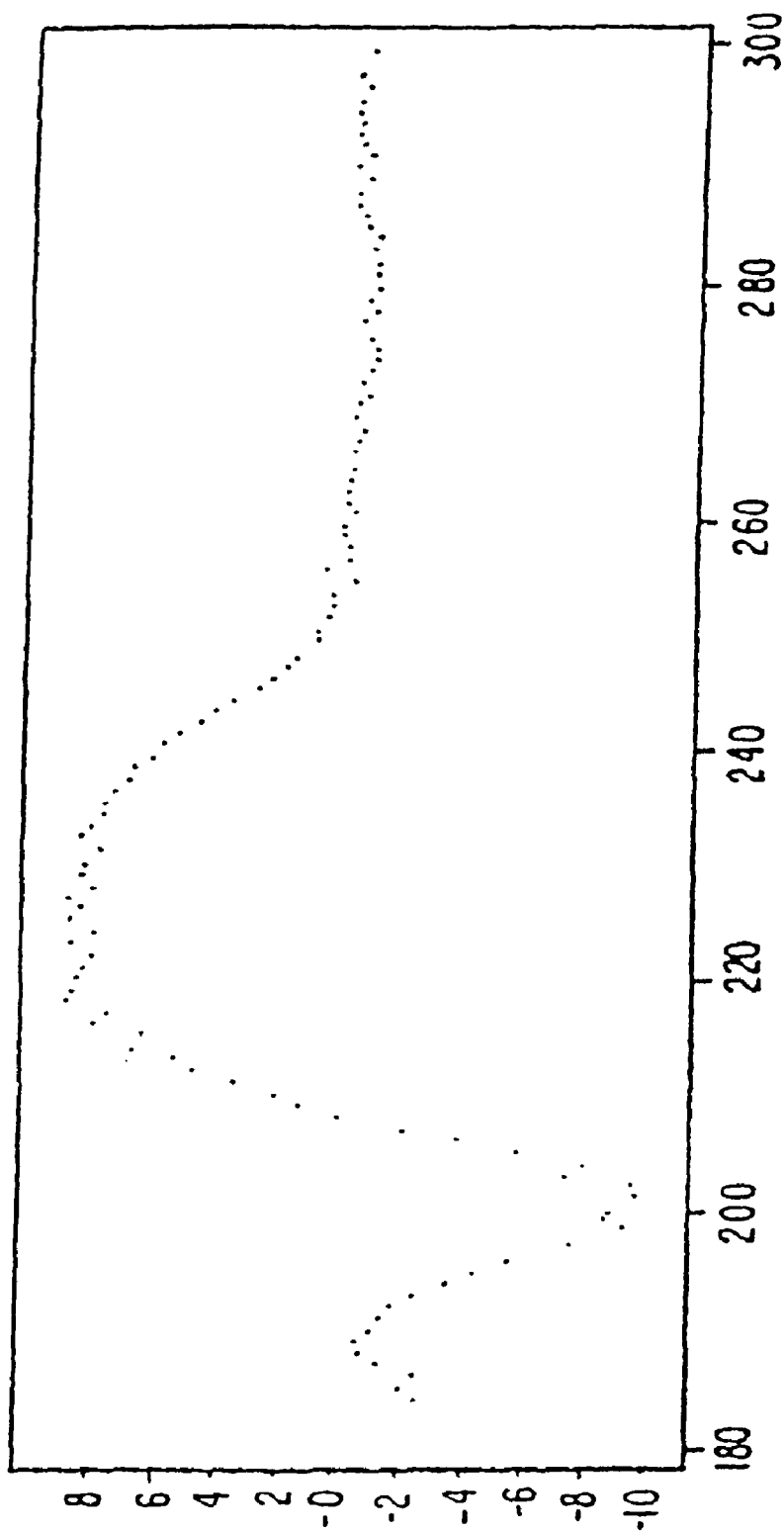
Figure 43G:
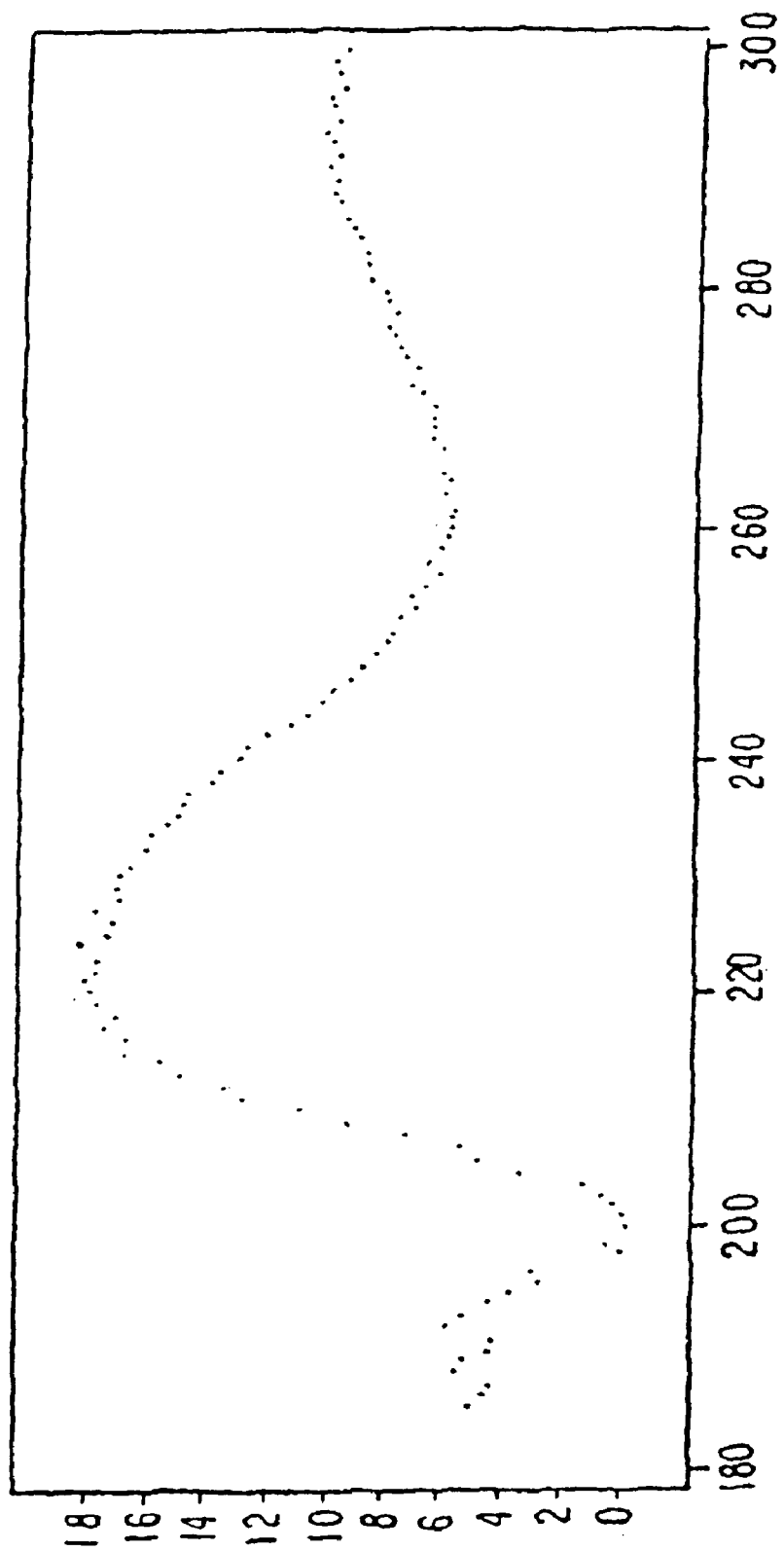

Repeat steps 1-5 to yield 4 volumes of solvent B. Mobile phase composition was A=methylene chloride with 2% acetic acid and 2% water; B=methanol with 2% acetic acid and 2% water. The column load was 0.7 g in 7 mL. components were detected by UV at 254 nm. A typical preparative normal phase HPLC separation of cocoa procyanidins is shown in FIG. 42.

HPLC Conditions:

Column: 50×2 cm 5μ Supelcosil LC-Si run @ ambient temperature.

Mobile Phase: A=Methylene Chloride with 2%
Acetic Acid and 2% Water.
B=Methanol with 2% Acetic Acid and 2% Water.

Gradient/Flow Profile:

| TIME (MIN) | % A | % B | FLOW RATE (mL/min) |
|---|---|---|---|
| 0 | 92.5 | 7.5 | 10 |
| 10 | 92.5 | 7.5 | 40 |
| 30 | 91.5 | 8.5 | 40 |
| 145 | 88.0 | 22.0 | 40 |
| 150 | 24.0 | 86.0 | 40 |
| 155 | 24.0 | 86.0 | 50 |
| 180 | 0.0 | 100.0 | 50 |

Example 15

Identification of Procyanidins

Figure 22A:
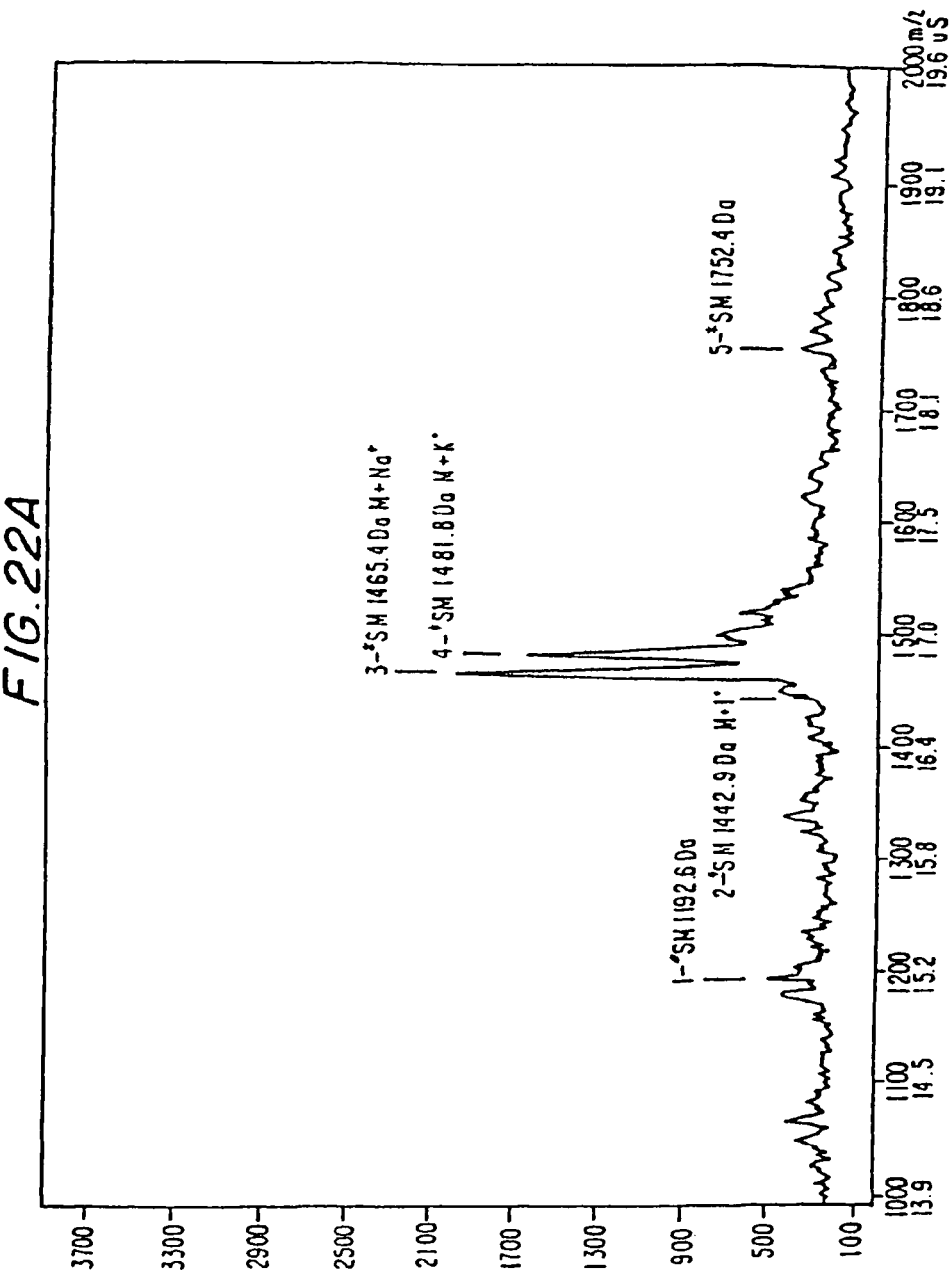
FIGS. 22A, B and C show MALDI-TOF/MS of pentamer enriched procyanidins, and of Fractions A-C and of Fractions D-E, respectively.

Procyanidins obtained as in Example 14, method D were analyzed by Matrix Assisted Laser Desorption Ionization-Time of Flight/Mass Spectrometry (MALDI-TOF/MS) using a HP G2025A MALDI-TOF/MS system equipped with a Lecroy 9350 500 MHz Oscilloscope. The instrument was calibrated in accordance with the manufacturer's instructions with a low molecular weight peptide standard (HP Part No. G2051A) or peptide standard (HP Part No. G2052A) with 2,5-dihydroxybenzoic acid (DHB)(HP Part No. G2056A) as the sample matrix. One (1.0) mg of sample was dissolved in 500 μL of 70/30 methanol/water, and the sample was then mixed with DHB matrix, at a ratio of 1:1, 1:10 or 1:50 (sample:matrix) and dried on a mesa under vacuum. The samples were analyzed in the positive ion mode with the detector voltage set at 4.75 kV and the laser power set between 1.5 and 8 μJ. Data was collected as the sum of a number of single shots and displayed as units of molecular weight and time of flight. A representative MALDI-TOF/MS is shown in FIG. 22A.

Figure 22B:
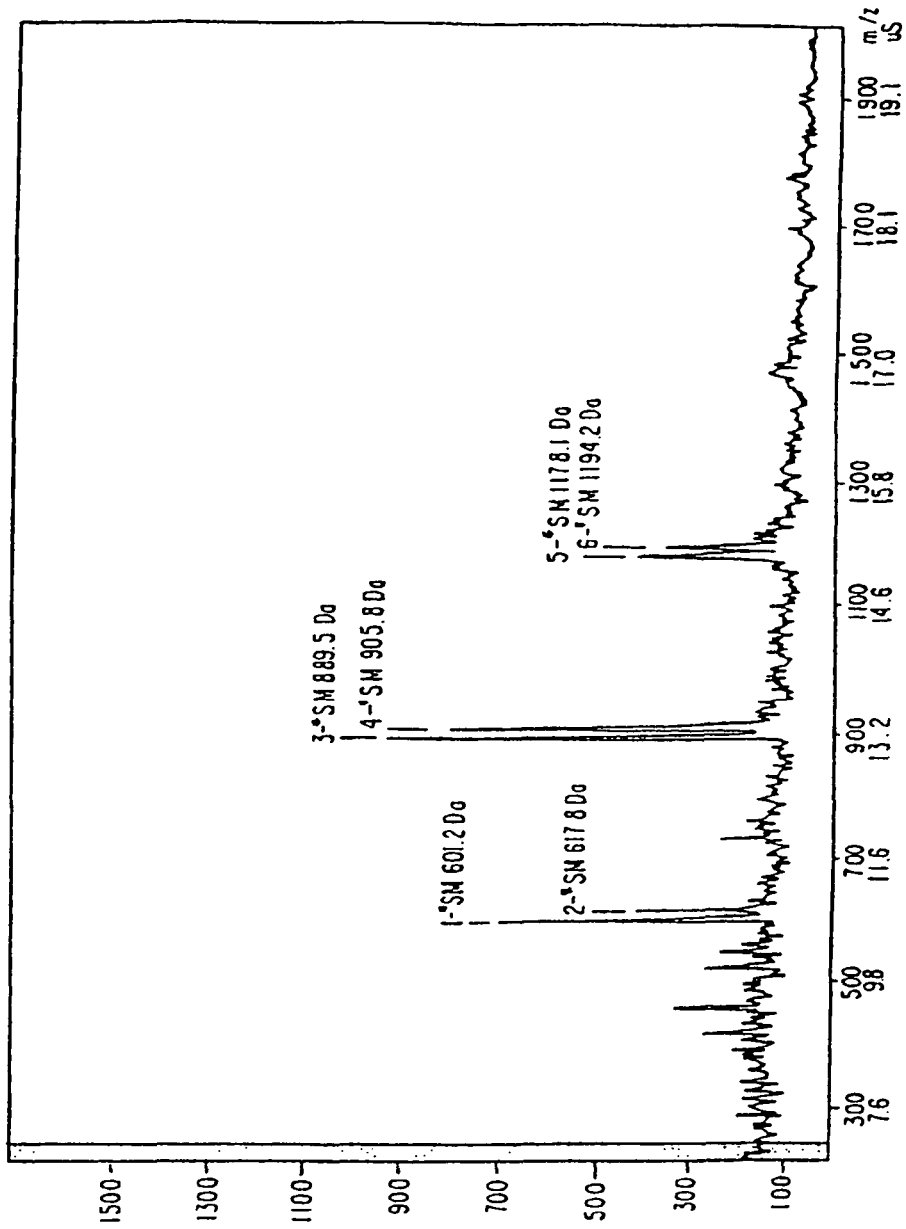
Figure 22C:
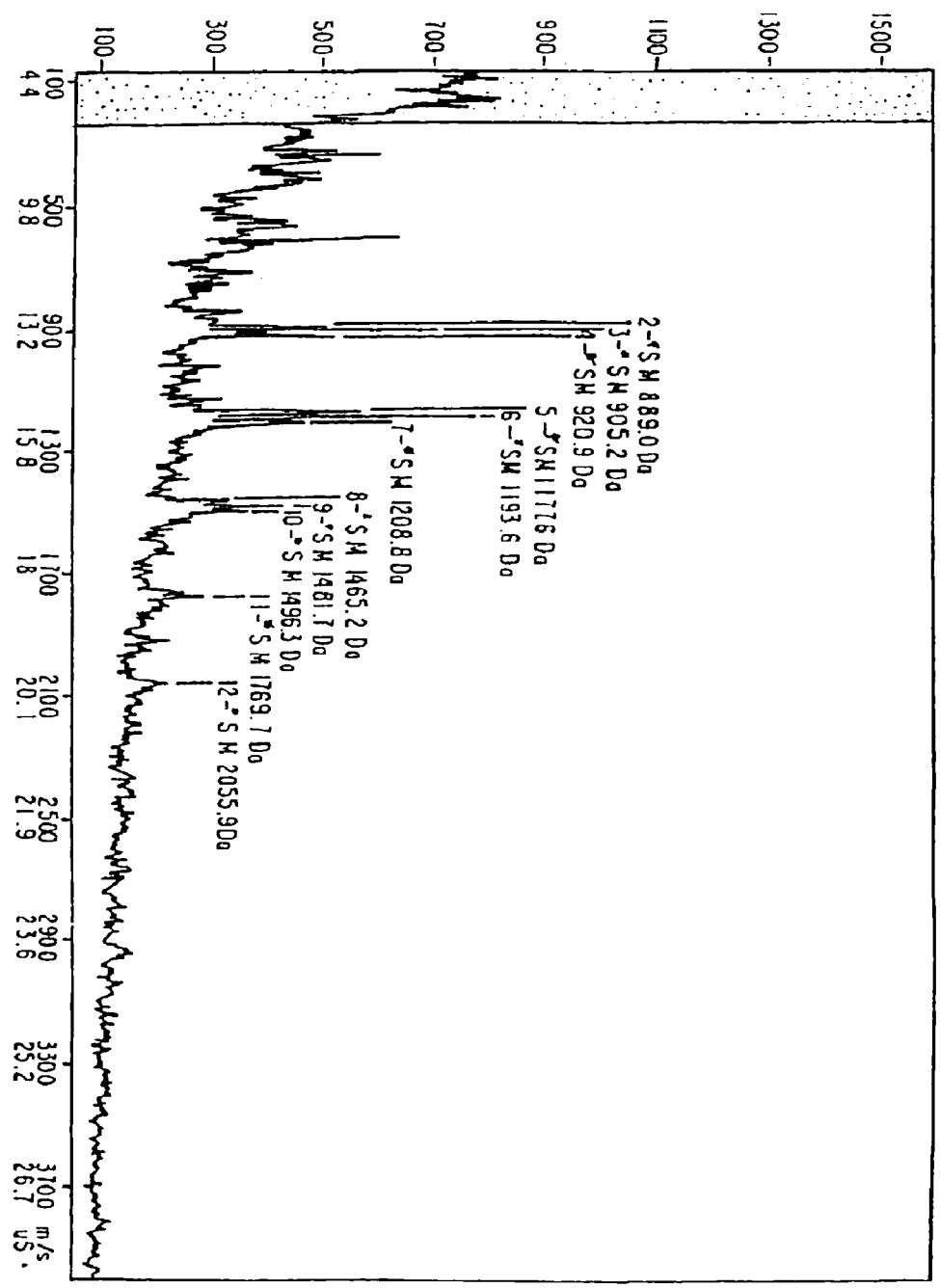

FIG. 22 and C show MALDI-TOF/MS spectra obtained from partially purified procyanidins prepared as described in Example 3, Method A and used for in vitro assessment as described in Examples 6 and 7, and whose results are summarized in Table 6. This data illustrates that the inventive compounds described herein were predominantly found in fractions D-E, but not A-C.

The spectra were obtained as follows:

The purified D-E fraction was subjected to MALDI-TOF/MS as described above, with the exception that the fraction was initially purified by SEP-PACK® C-18 cartridge. Five (5) mg of fraction D-E in 1 mL nanopure water was loaded onto a pre-equilibrated SEP-PACK® cartridge. The column was washed with 5 mL nanopure water to eliminate contaminants, and procyanidins were eluted with 1 mL 20% methanol. Fractions A-C were used directly, as they were isolated in Example 3, Method A, without further purification.

These results confirmed and extended earlier results (see Example 5, Table 3, FIGS. 20A and B) and indicate that the inventive compounds have utility as sequestrants of cations. In particular, MALDI-TOF/MS results conclusively indicated that procyanidin oligomers of n=5 and higher (see FIGS. 20A and B; and formula under Objects and Summary of the Invention) were strongly associated with anti-cancer activity with the HeLa and SKBR-3 cancer cell line model. Oligomers of n=4 or less were ineffective with these models. The pentamer structure apparently has a structural motif which is present in it and in higher oligomers which provides the activity. Additionally, it was observed that the MALDI-TOF/MS data showed strong $M^+$ ions of $Na^+$, $2 Na^+$, $K^+$, $2 K^+$, $Ca^{++}$, demonstrating the utility as cation sequestrants.

Example 16

Purification of Oligomeric Fractions

Method A. Purification by Semi-Preparative Reverse Phase HPLC

Figure 23A:
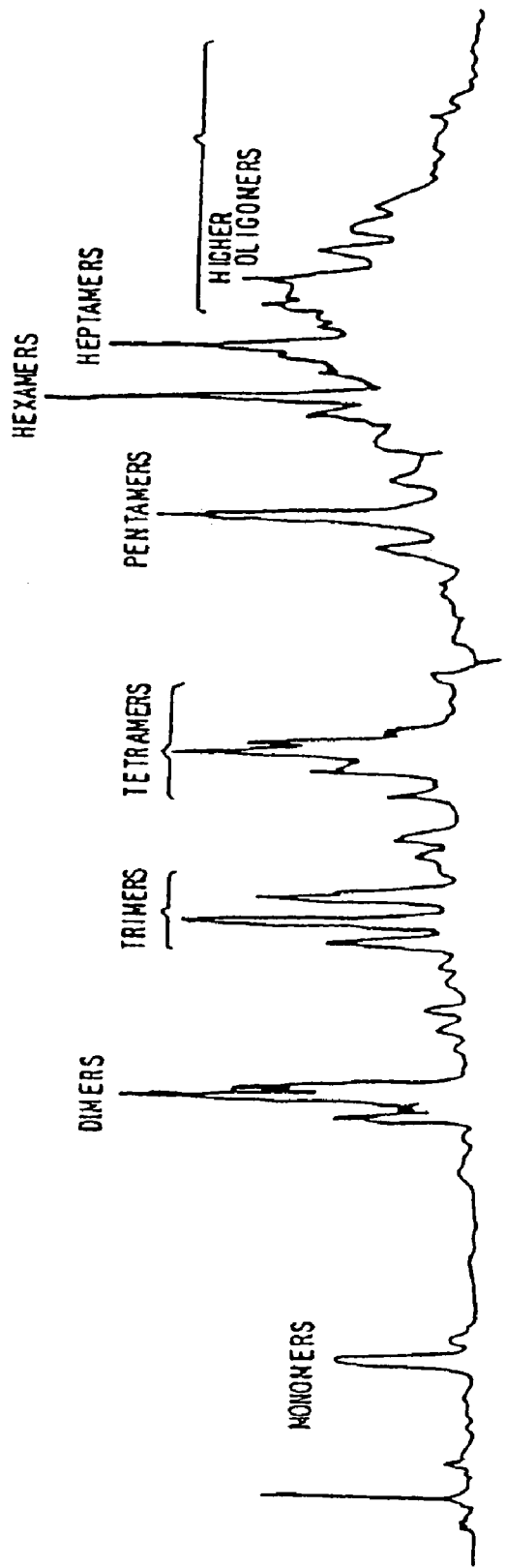
FIG. 23A shows an elution profile of oligomeric procyanidins purified by modified semi-preparative HPLC.
Figure 23B:
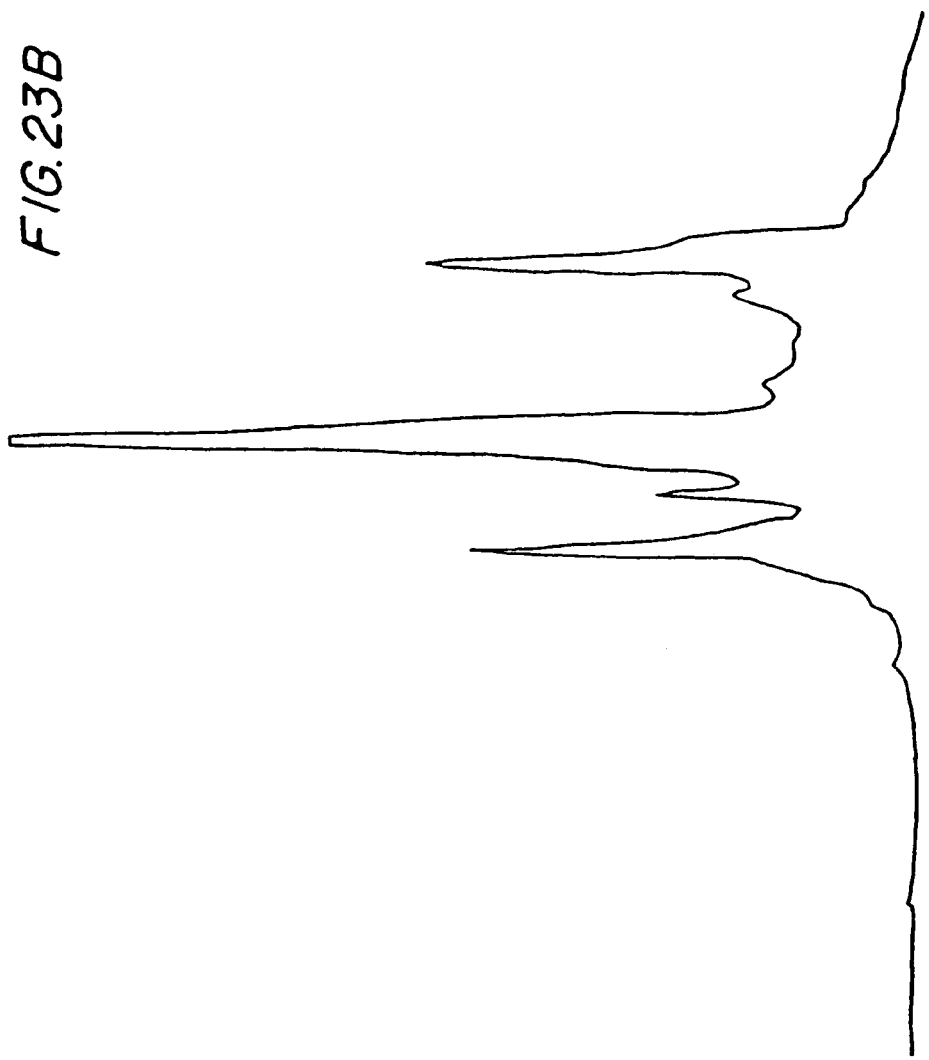
FIG. 23B shows an elution profile of a trimer procyanidin by modified semi-preparative HPLC.
Figure 24A:
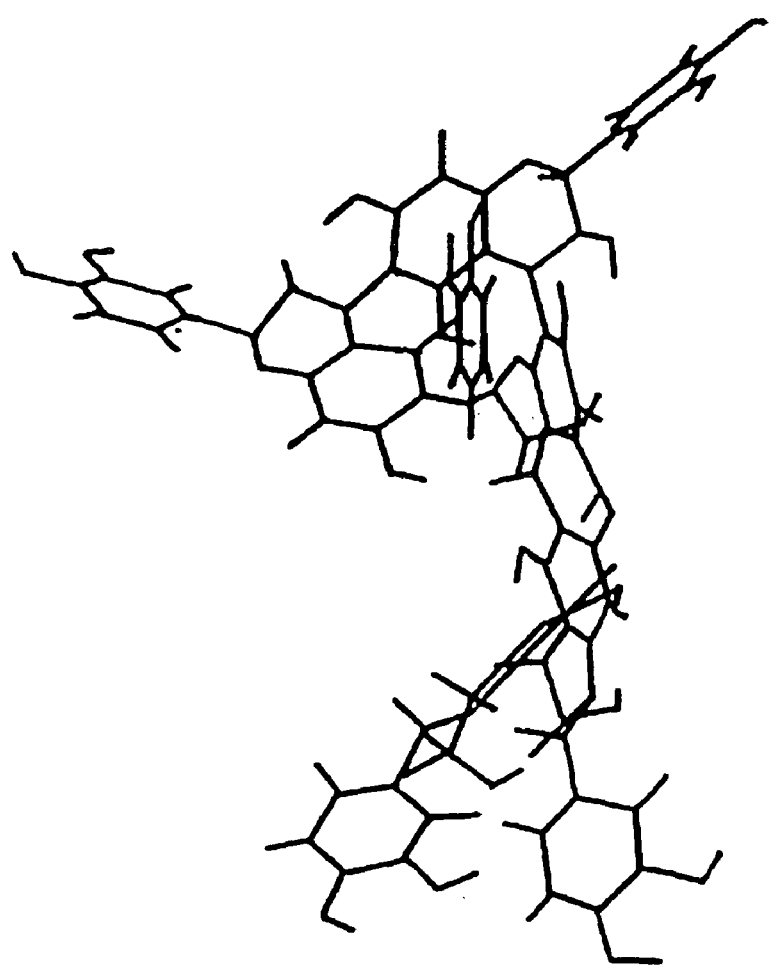
FIGS. 24A-D each show energy minimized structures of all (4-8) linked pentamers based on the structure of epicatechin.
Figure 24B:
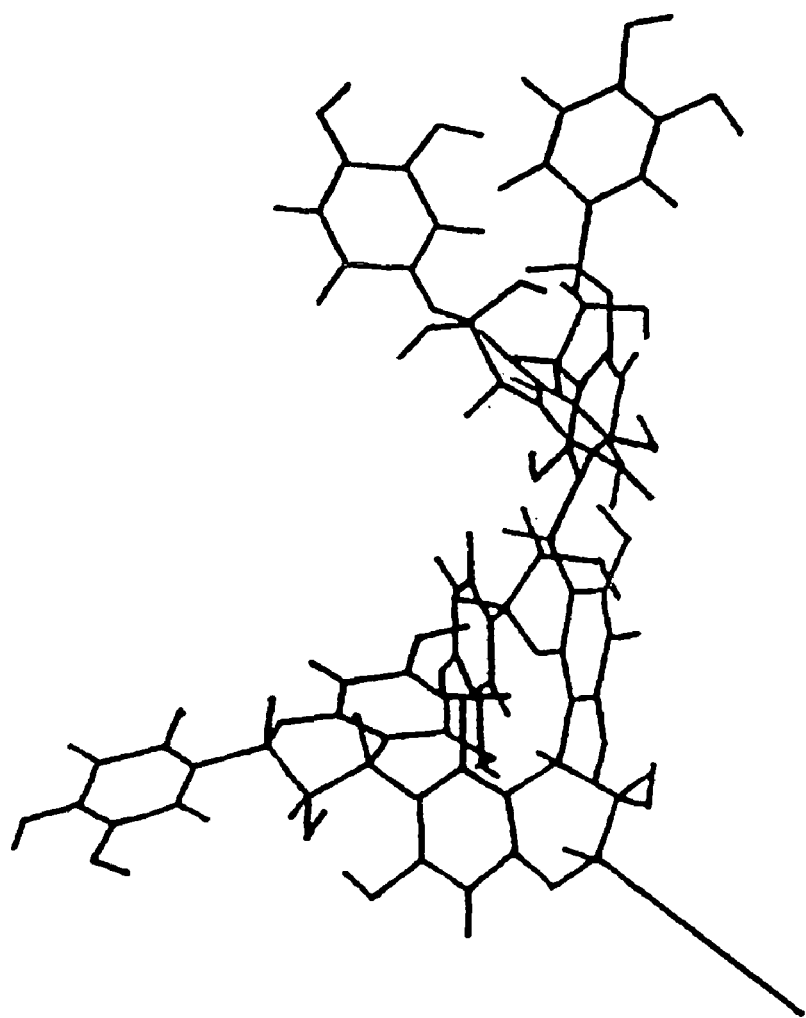
Figure 24C:
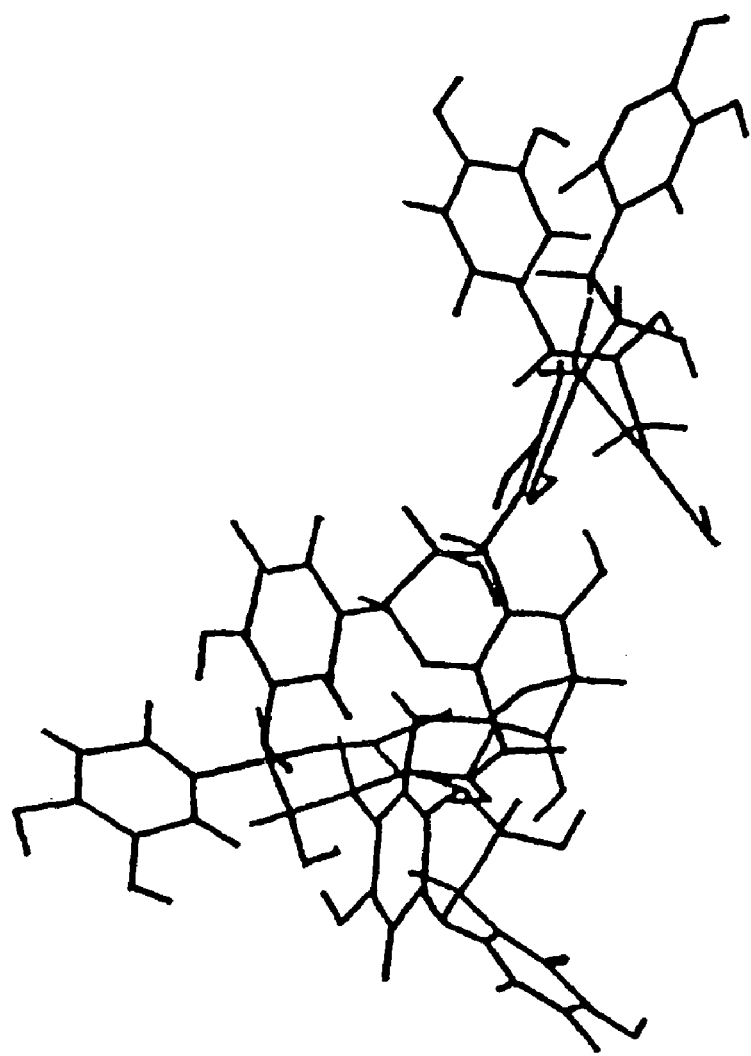
Figure 24D:
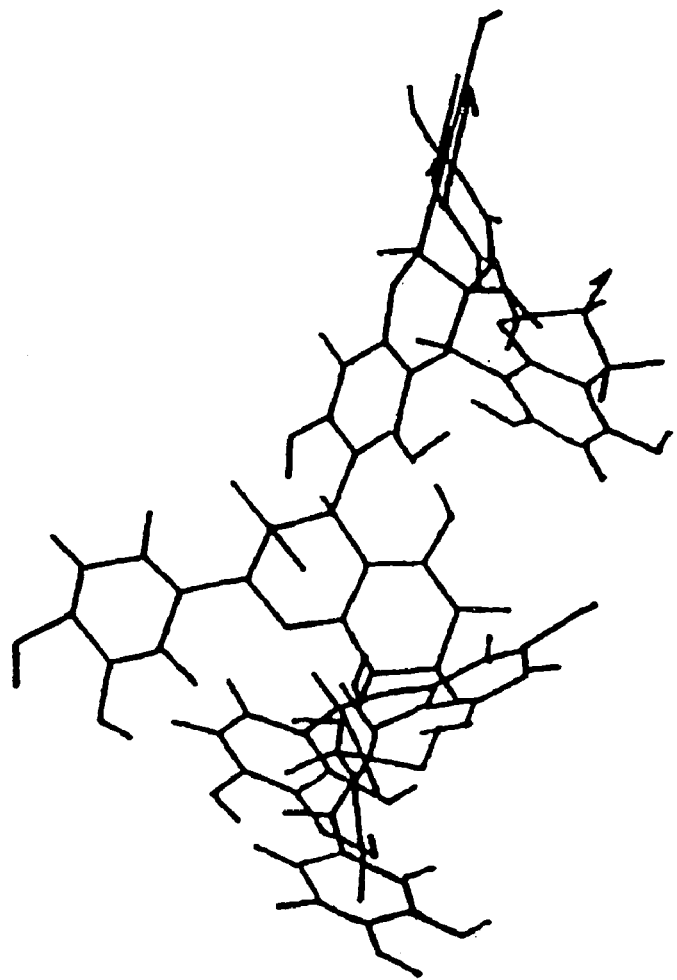

Procyanidins obtained from Example 14, Method A and B and D were further separated to obtain experimental quantities of like oligomers for further structural identification and elucidation (e.g., Example 15, 18, 19, and 20). A Hewlett Packard 1050 HPLC system equipped with a variable wavelength detector, Rheodyne 7010 injection valve with 1 mL injection loop was assembled with a Pharmacia FRAC-100 Fraction Collector. Separations were effected on a Phenomenex Ultracarb® 10μ ODS column (250×22.5 mm) connected with a Phenomenex 10μ ODS Ultracarb® (60×10 mm) guard column. The mobile phase composition was A=water; B=methanol used under the following linear gradient conditions: (time, % A); (0, 85), (60, 50), (90, 0 and (110, 0) at a flow rate of 5 mL/min. Individual peaks or select chromatographic regions were collected on timed intervals or manually by fraction collection for further evaluation by MALDI-TOF/MS and NMR. Injection loads ranged from 25-100 mg of material. A representative elution profile is shown in FIG. 23b.

Method B. Modified Semi-Preparative HPLC

Procyanidins obtained from Example 14, Method A and B and D were further separated to obtain experimental quantities of like oligomers for further structural identification and elucidation (e.g., Example 15, 18, 19, and 20). Supelcosil LC-Si 5μ column (250×10 mm) with a Supelcosil LC-Si 5μ (20×2 mm) guard column. The separations were effected at a flow rate of 3.0 mL/min, at ambient temperature. The mobile phase composition was A=dichloromethane; B=methanol; and C=acetic acid:water (1:1); used under the following linear gradient conditions: (time, %A, %B); (0, 82, 14); (22, 74, 21); (32, 74, 21); (60, 74, 50, 4); (61, 82, 14), followed by column re-equilibration for 7 minutes. Injection volumes were 60 μL containing 12 mg of enriched pentamer. Components were detected by UV at 280 nm. A representative elution profile is shown in FIG. 23A.

Example 17

Molecular Modeling of Pentamers

Figure 39P:
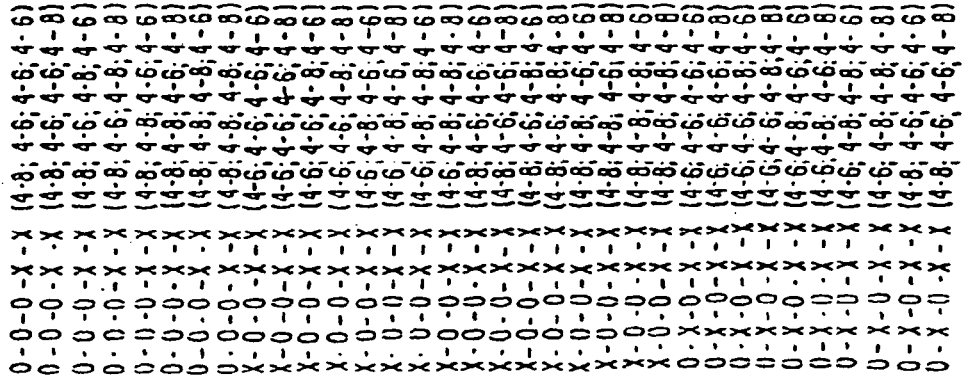
Figure 39Q:
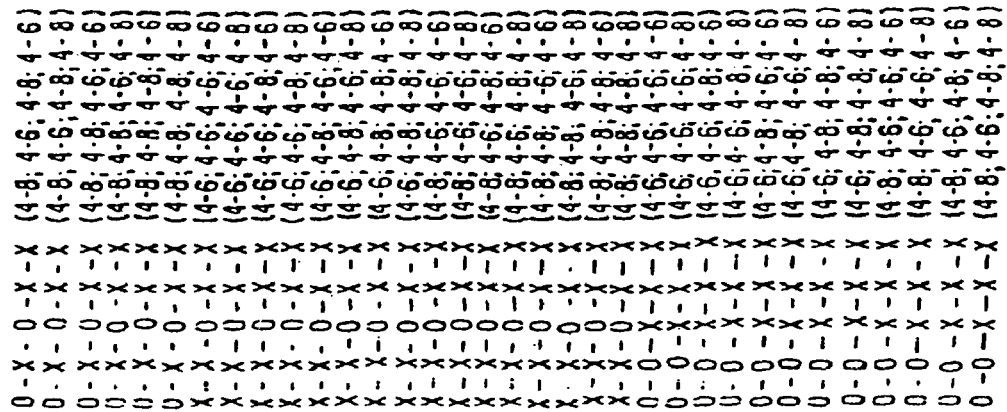
Figure 39R:
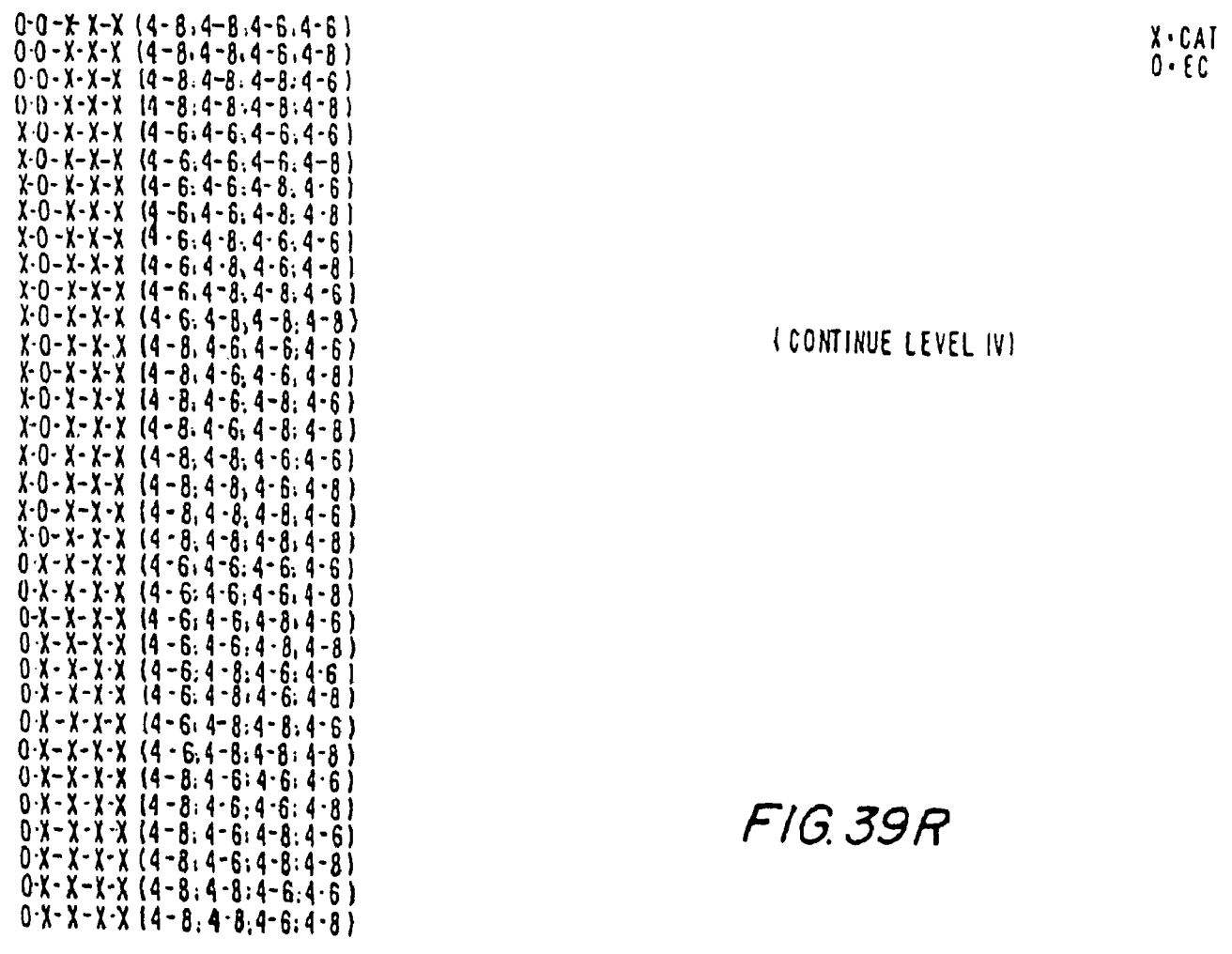
Figure 39S:
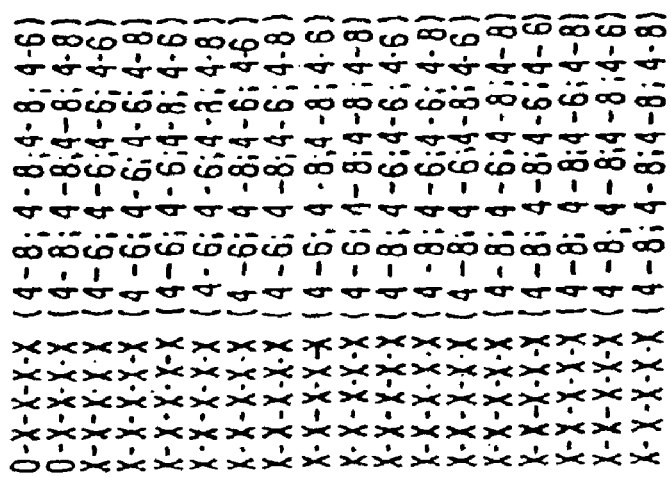
Figure 39T:
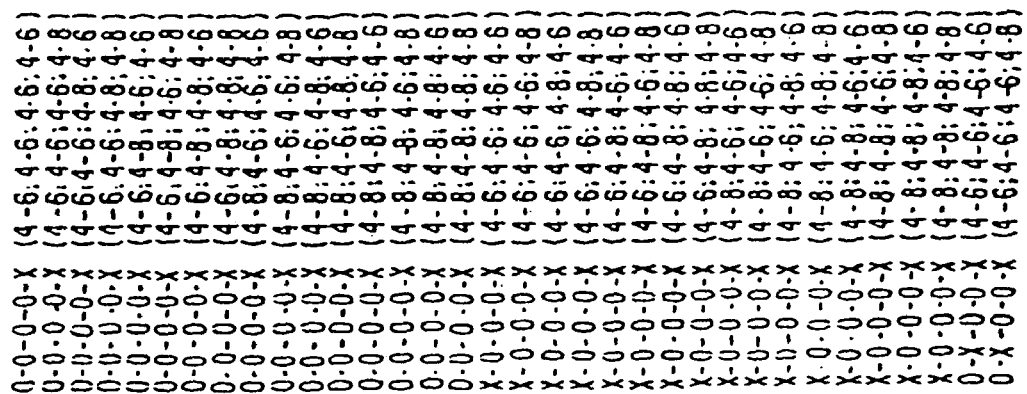
Figure 39U:
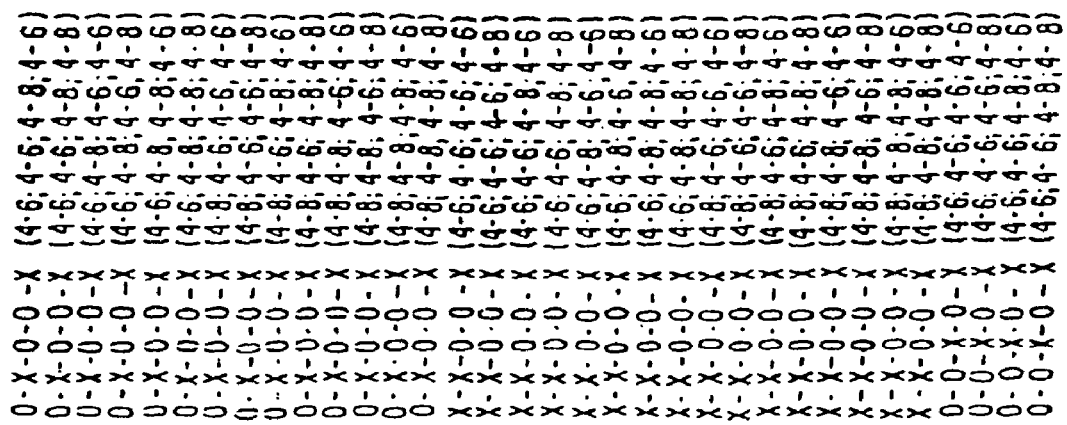
Figure 39V:
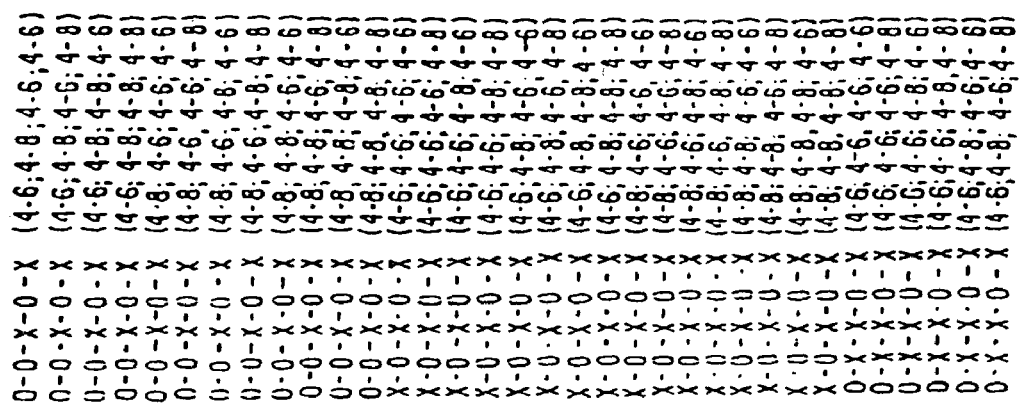
Figure 39W:
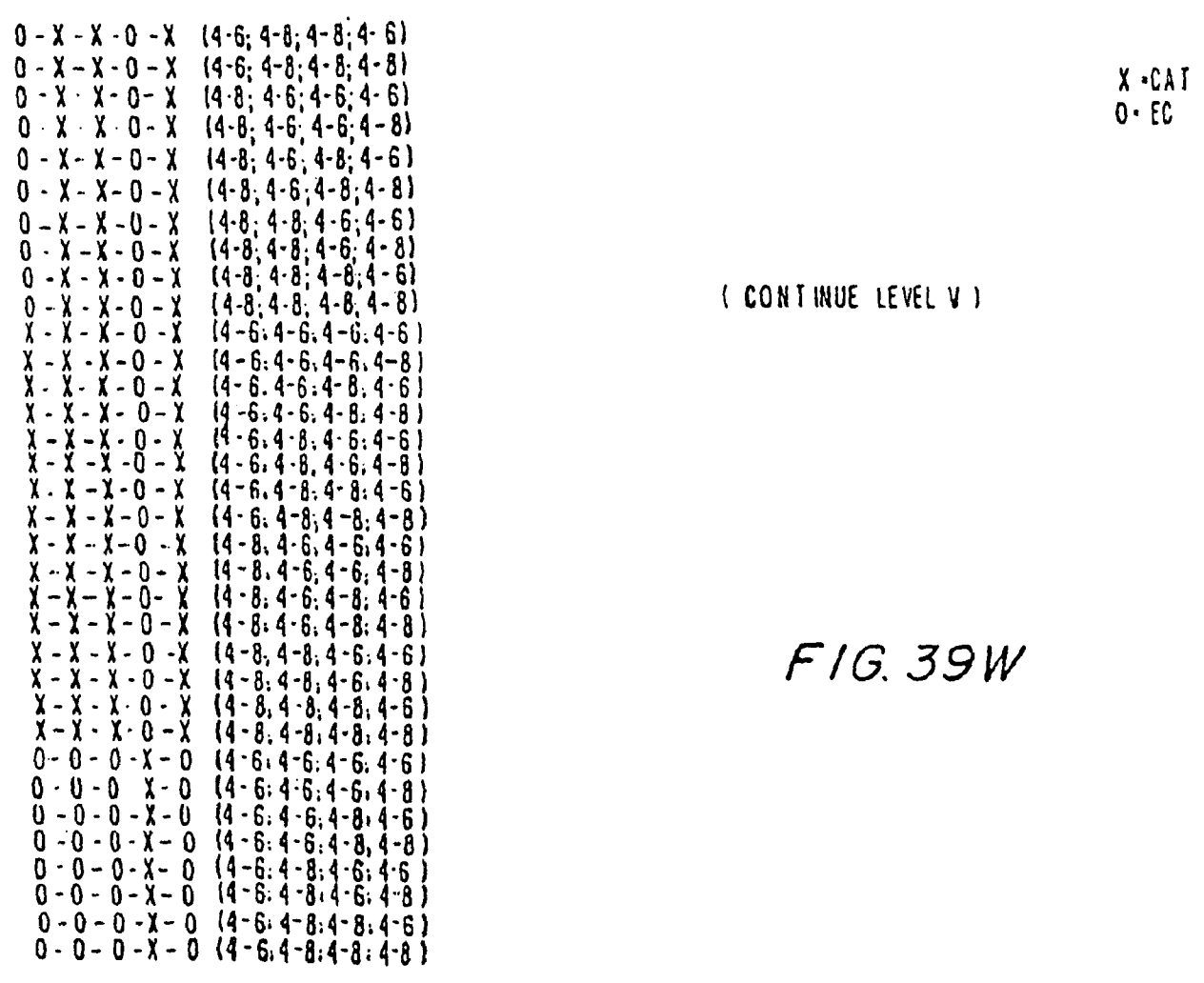
Figure 39X:
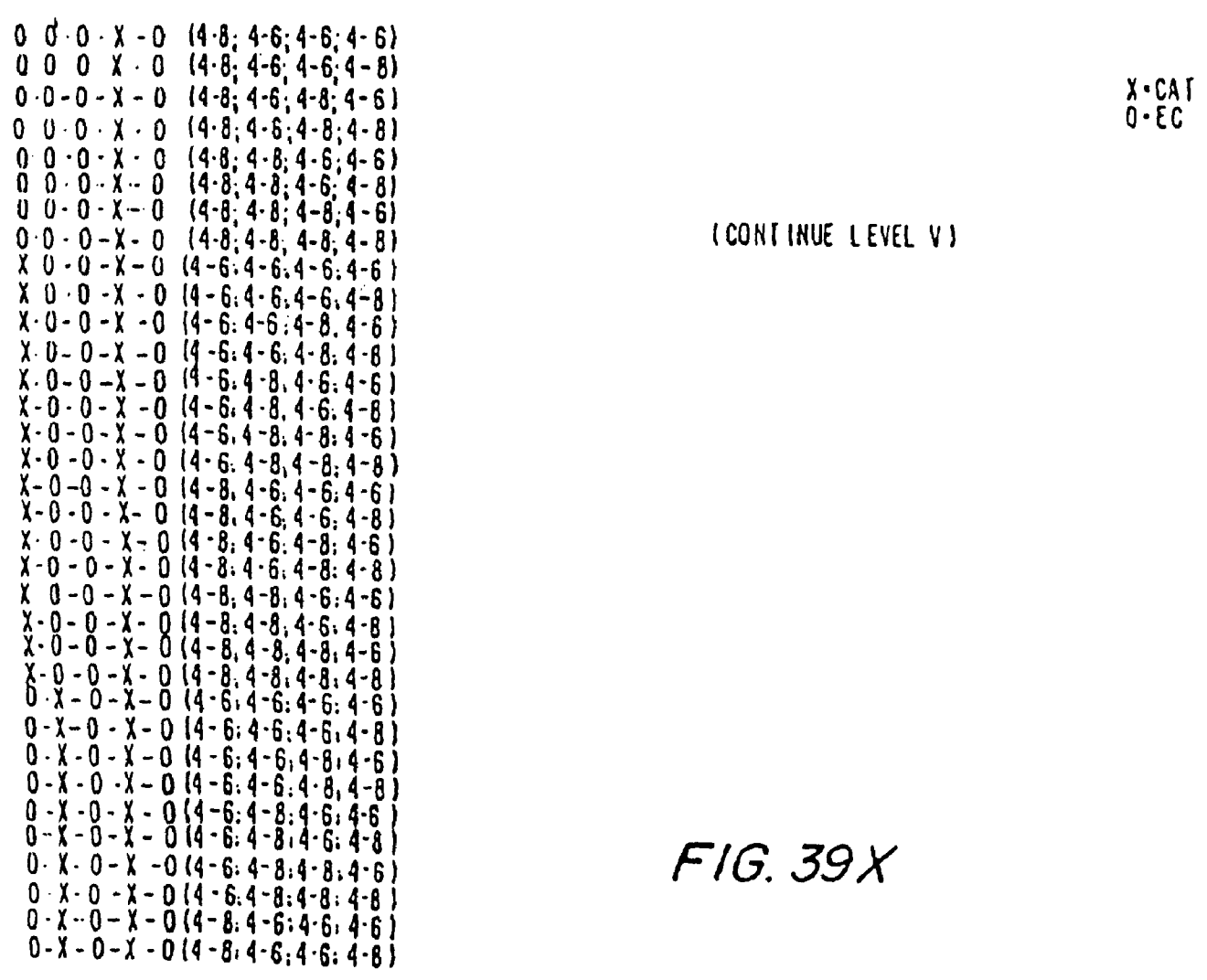
Figure 39Y:
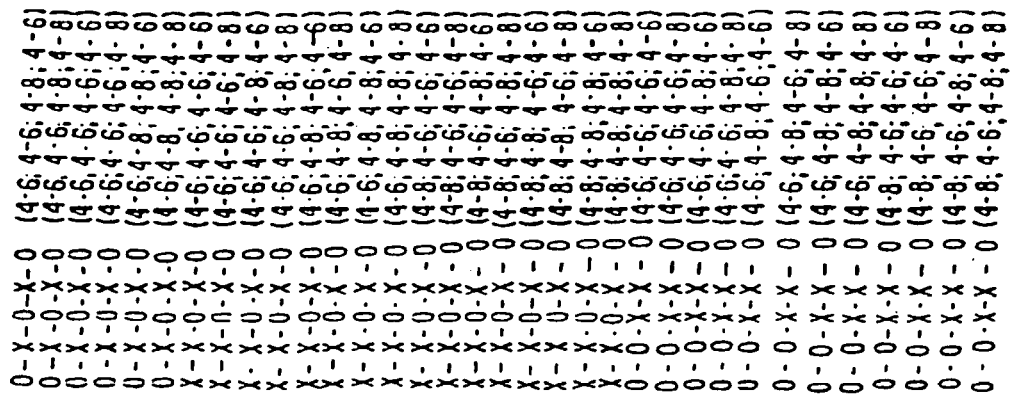
Figure 39Z:
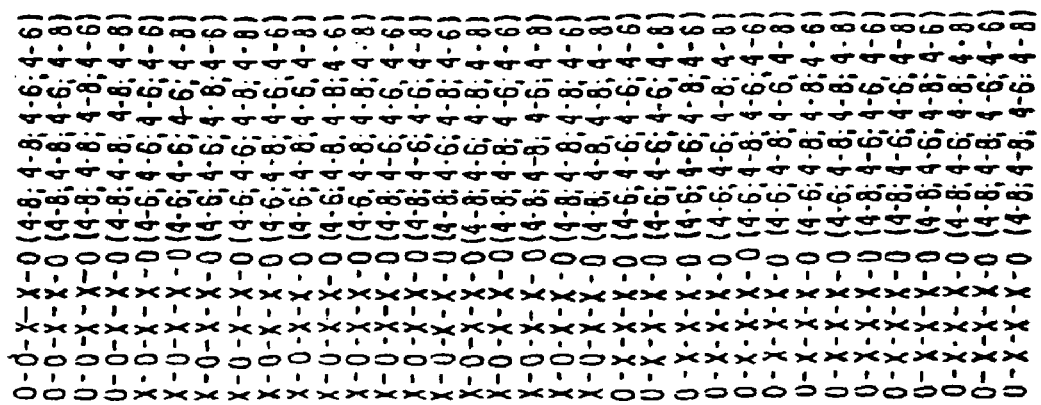

Energy minimized structures were determined by molecular modeling using Desktop Molecular Modeller, version 3.0, Oxford University Press, 1994. Four representative views of $[EC(4\rightarrow8)]_4$-EC (EC=epicatechin) pentamers based on the structure of epicatechin are shown in FIGS. 24A-D. A helical structure is suggested. In general when epicatechin is the first monomer and the bonding is 4→8, a beta configuration results, when the first monomer is catechin and the bonding is 4→8, an alpha configuration results; and, these results are obtained regardless of whether the second monomer is epicatechin or catechin (an exception is ent-EC(4→8)ent-EC). FIGS. 38A-38P show preferred pentamers, and, FIGS. 39A to 39P show a library of stereoisomers up to and including the pentamer, from which other compounds within the scope of the invention can be prepared, without undue experimentation.

Example 18

NMR Evaluation of Pyrocyanidins $^{13}C$ NMR spectroscopy was deemed a generally useful technique for the study of procyanidins, especially as the phenols usually provide good quality spectra, whereas proton NMR spectra are considerably broadened. The $^{13}C$ NMR spectra of oligomers yielded useful information for A or B ring substitution patterns, the relative stereochemistry of the C ring and in certain cases, the position of the interflavanoid linkages. Nonetheless, $^1H$ NMR spectra yielded useful information.

Further, HOHAHA, makes use of the pulse technique to transfer magnetization of a first hydrogen to a second in a sequence to obtain cross peaks corresponding to alpha, beta, gamma or delta protons. COSY is a 2D-Fourier transform NMR technique wherein vertical and horizontal axes provide $^1$H chemical shift and 1D spectra; and a point of intersection provides a correlation between protons, whereby spin-spin couplings can be determined. HMQC spectra enhances the sensitivity of NMR spectra of nuclei; other than protons and can reveal cross peaks from secondary and tertiary carbons to the respective protons. APT is a $^{13}$C technique used in determining the number of hydrogens present at a carbon. An even number of protons at a carbon will result in a positive signal, while an odd number of protons at a carbon will result in a negative signal.

Thus $^{13}$C NMR, $^1$H NMR, HOHAHA (homonuclear Hartmann-Hahn), HMQC (heteronuclear multiple quantum coherence), COSY (Homonuclear correlation spectroscopy), APT (attached proton test), and XHCORR (a variation on HMQC) spectroscopy were used to elucidate the structures of the inventive compounds.

Method A. Monomer

All spectra were taken in deuterated methanol, at room temperature, at an approximate sample concentration of 10 mg/mL. Spectra were taken on a Bruker 500 MHZ NMR, using methanol as an internal standard.

Figure 44A:
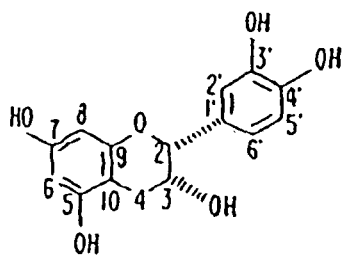
FIG. 44A shows the structure and $^1H/^{13}C$ NMR data for epicatechin.
Figure 44B:
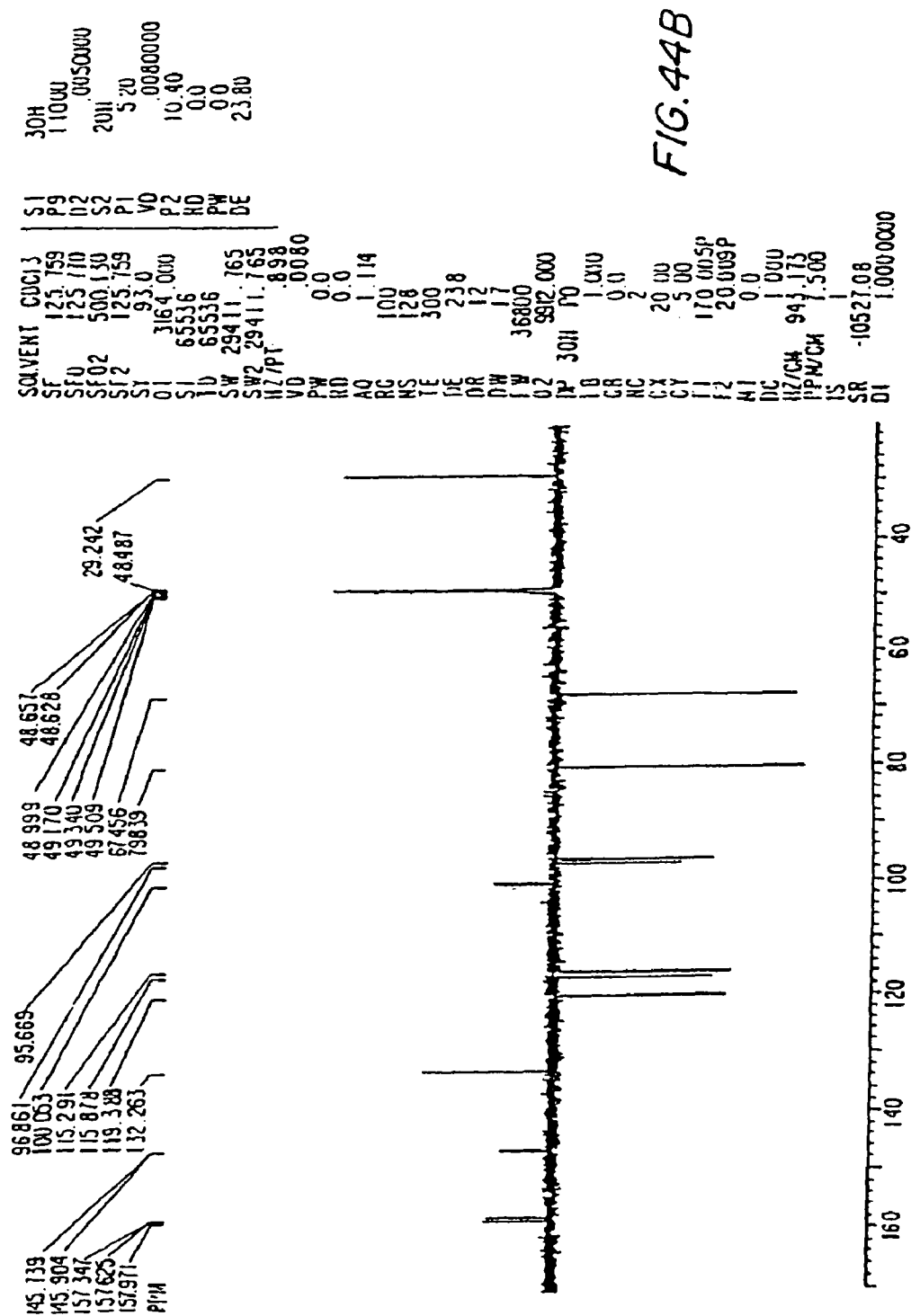
FIGS. 44B-F show the APT, COSY, XHCORR, $^1H$ and $^{13}C$ NMR spectra for epicatechin.
Figure 44C:
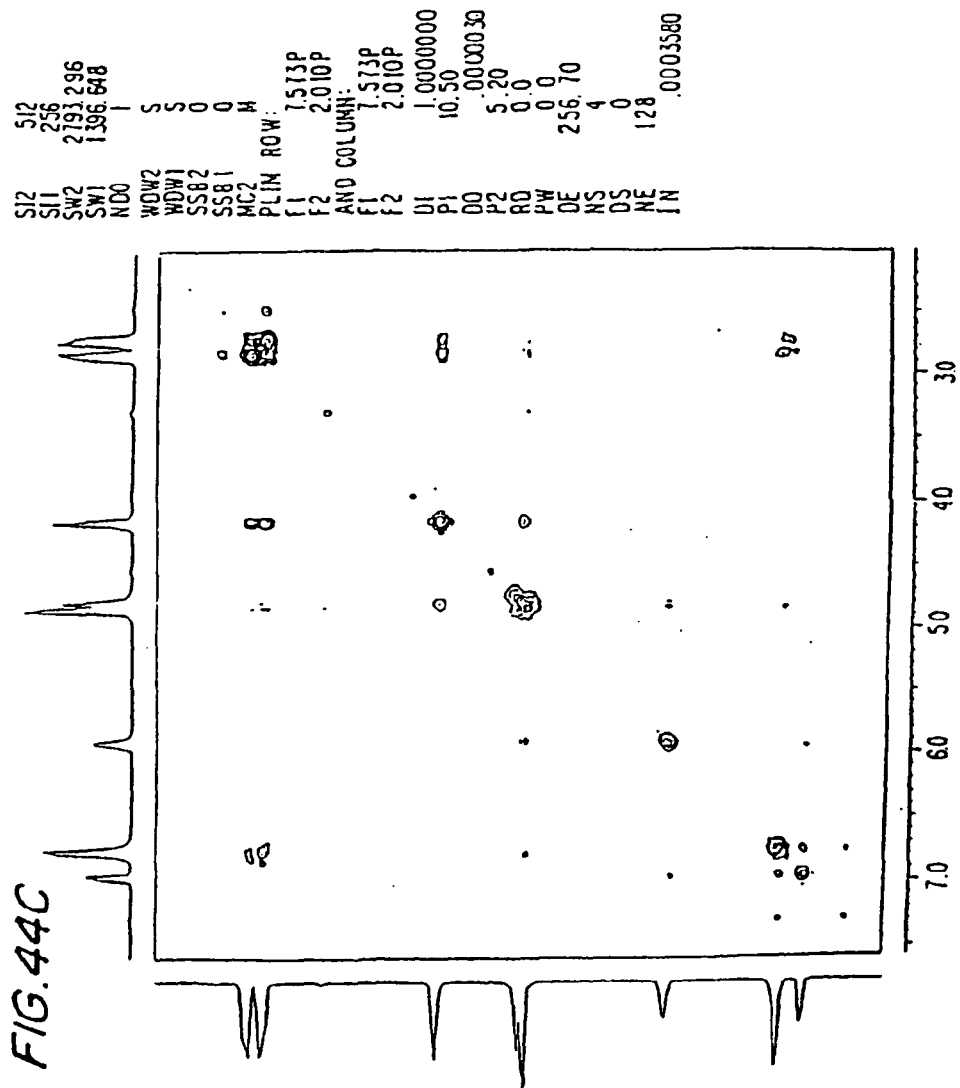
Figure 44D:
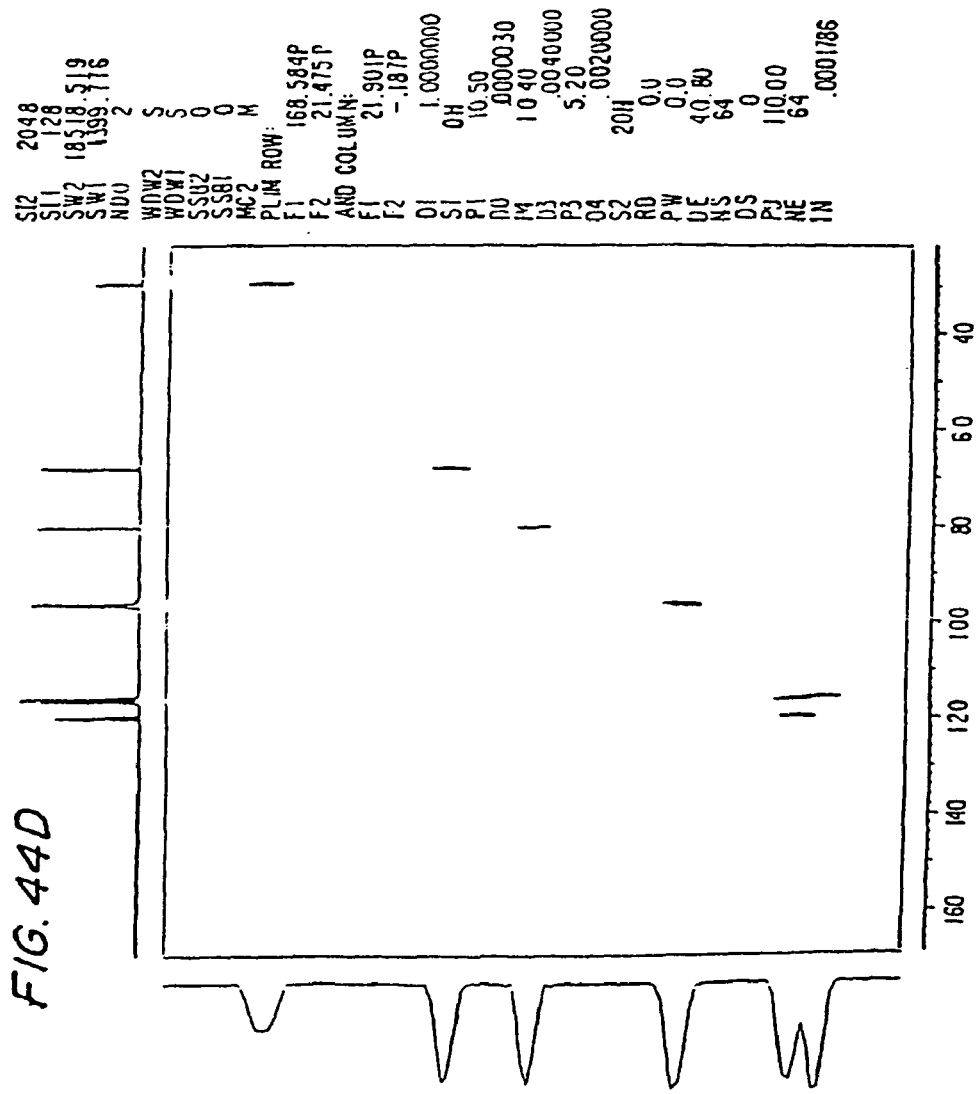
Figure 44E:
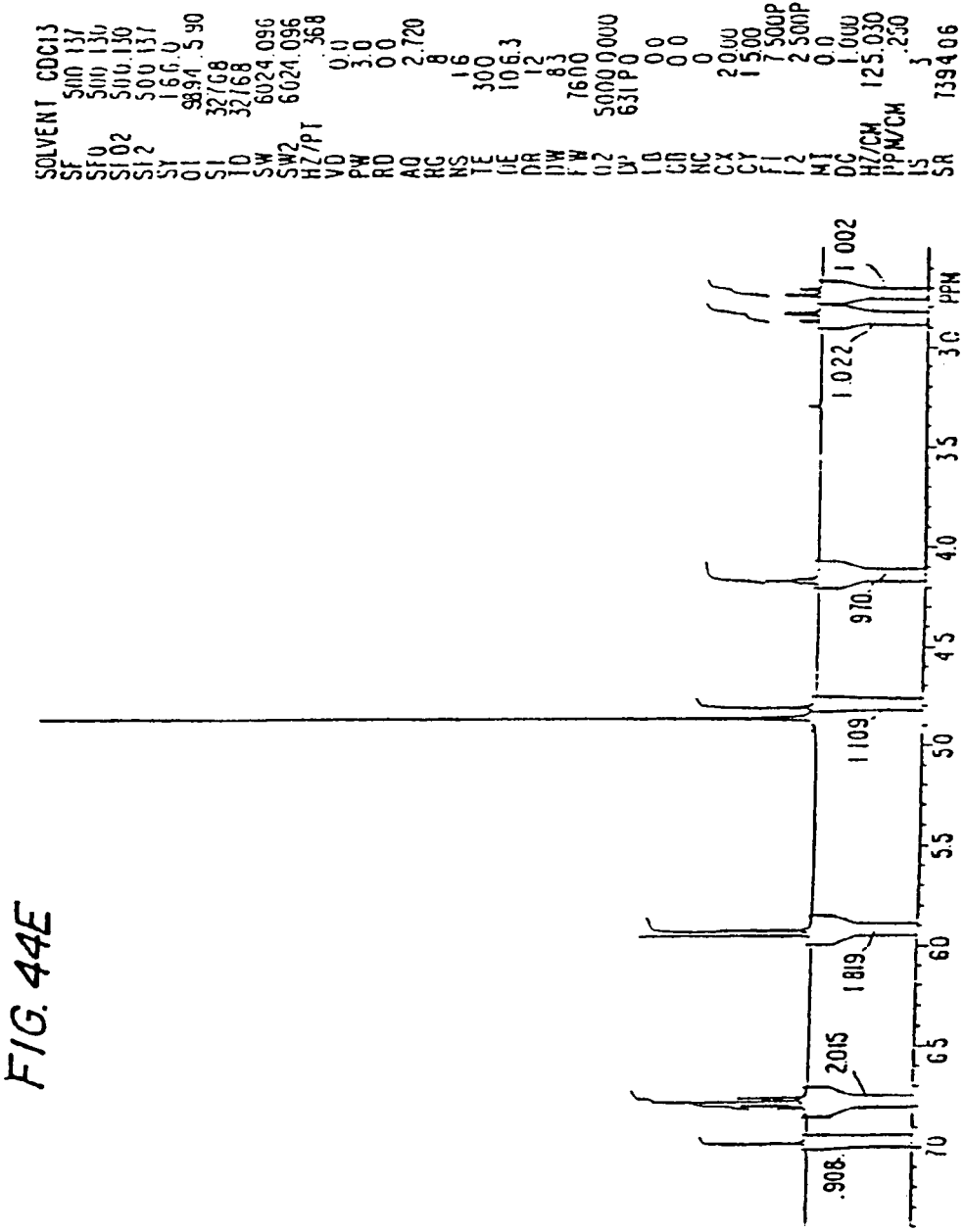
Figure 44F:
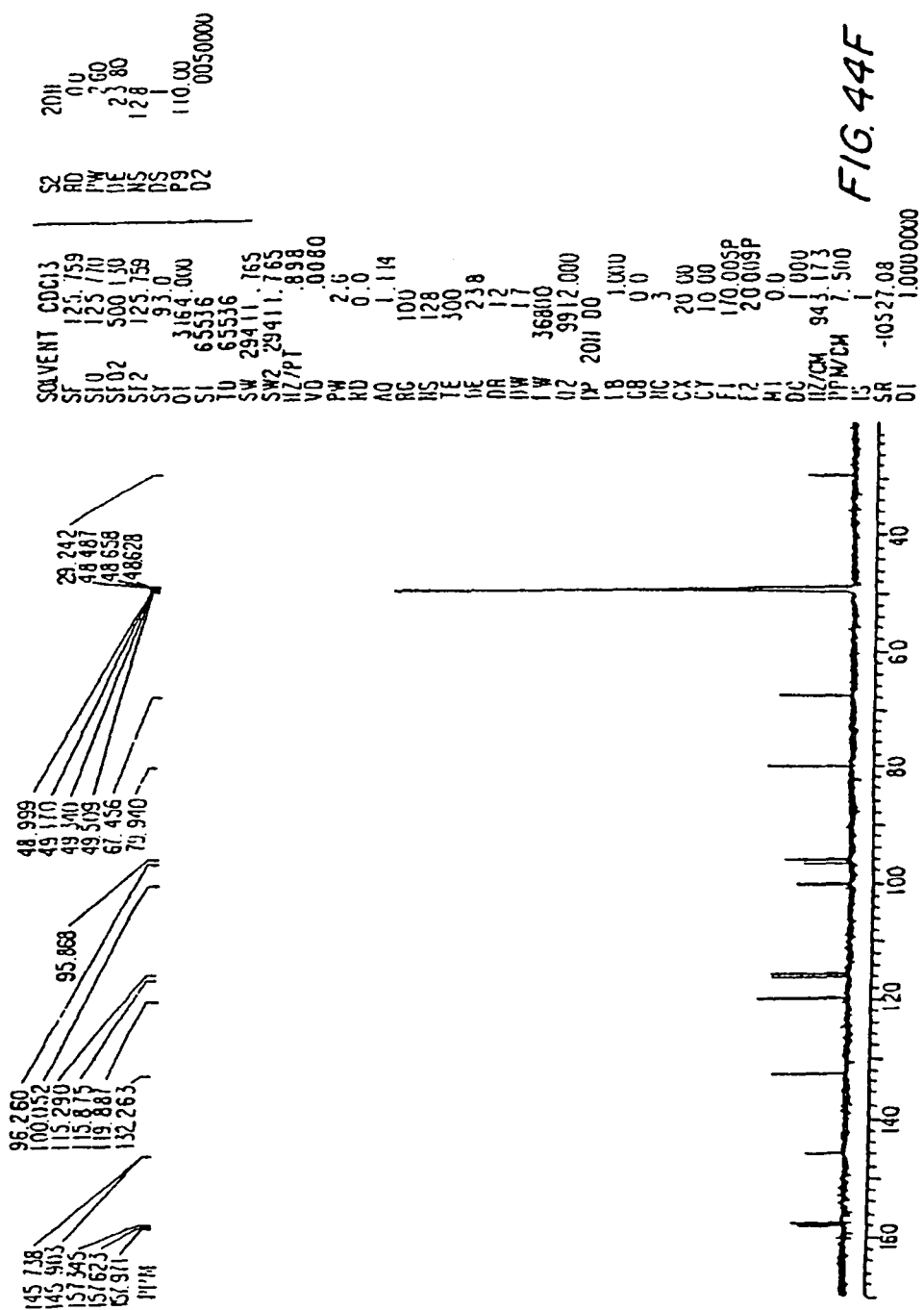

FIGS. 44A-E represent the NMR spectra which were used to characterize the structure of the epicatechin monomer. FIG. 44A shows the $^1$H and $^{13}$C chemical shifts, in tabular form. FIGS. 44 B-E show $^1$H, APT, XHCORR and COSY spectra for epicatechin.

Figure 45A:
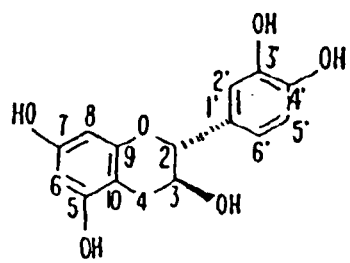
FIG. 45A shows the structure and $^1H/^{13}C$ NMR data for catechin.
Figure 45B:
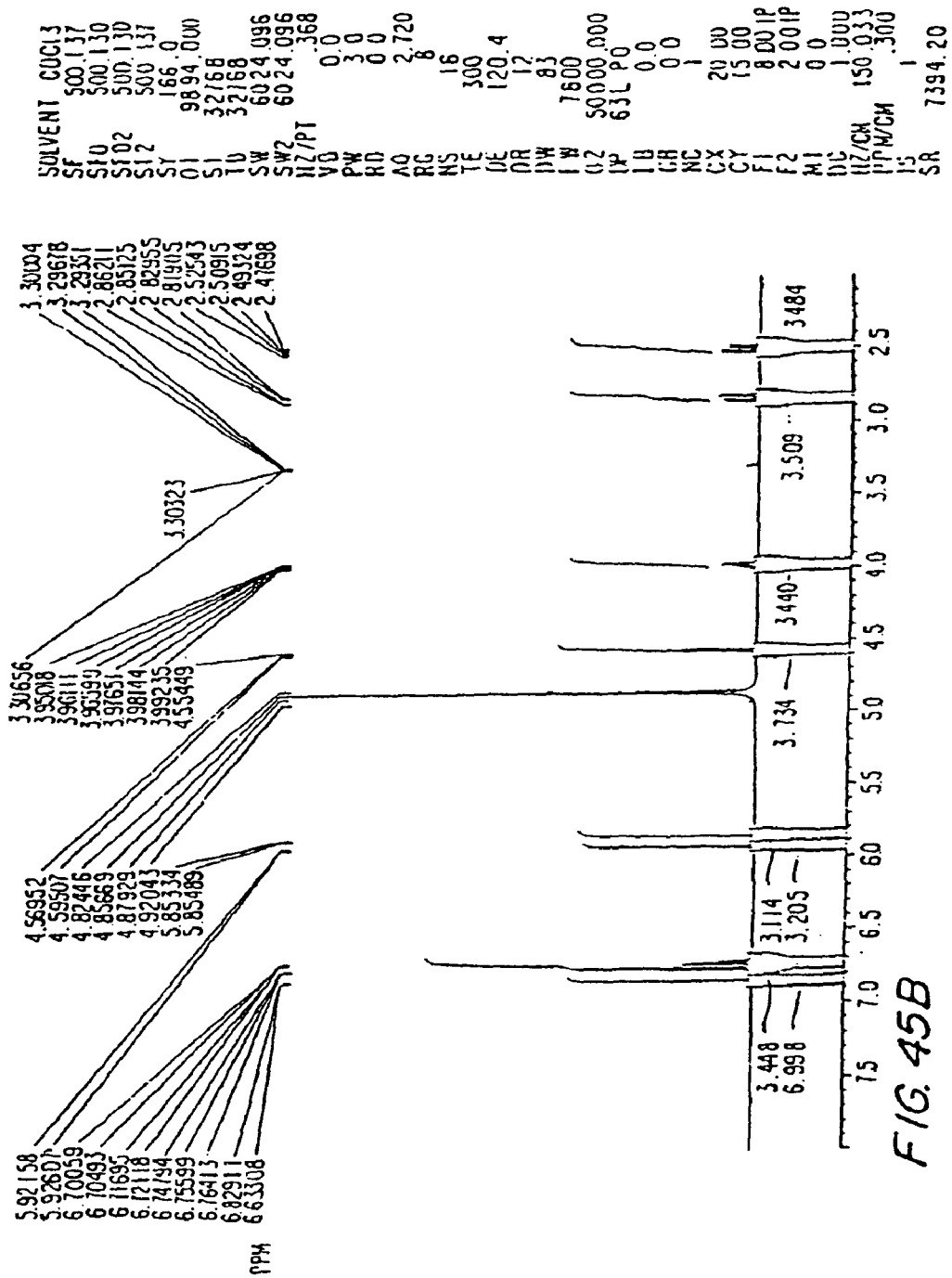
FIGS. 45B-E show the $^1H$, APT, XHCORR and COSY NMR spectra for catechin.
Figure 45C:
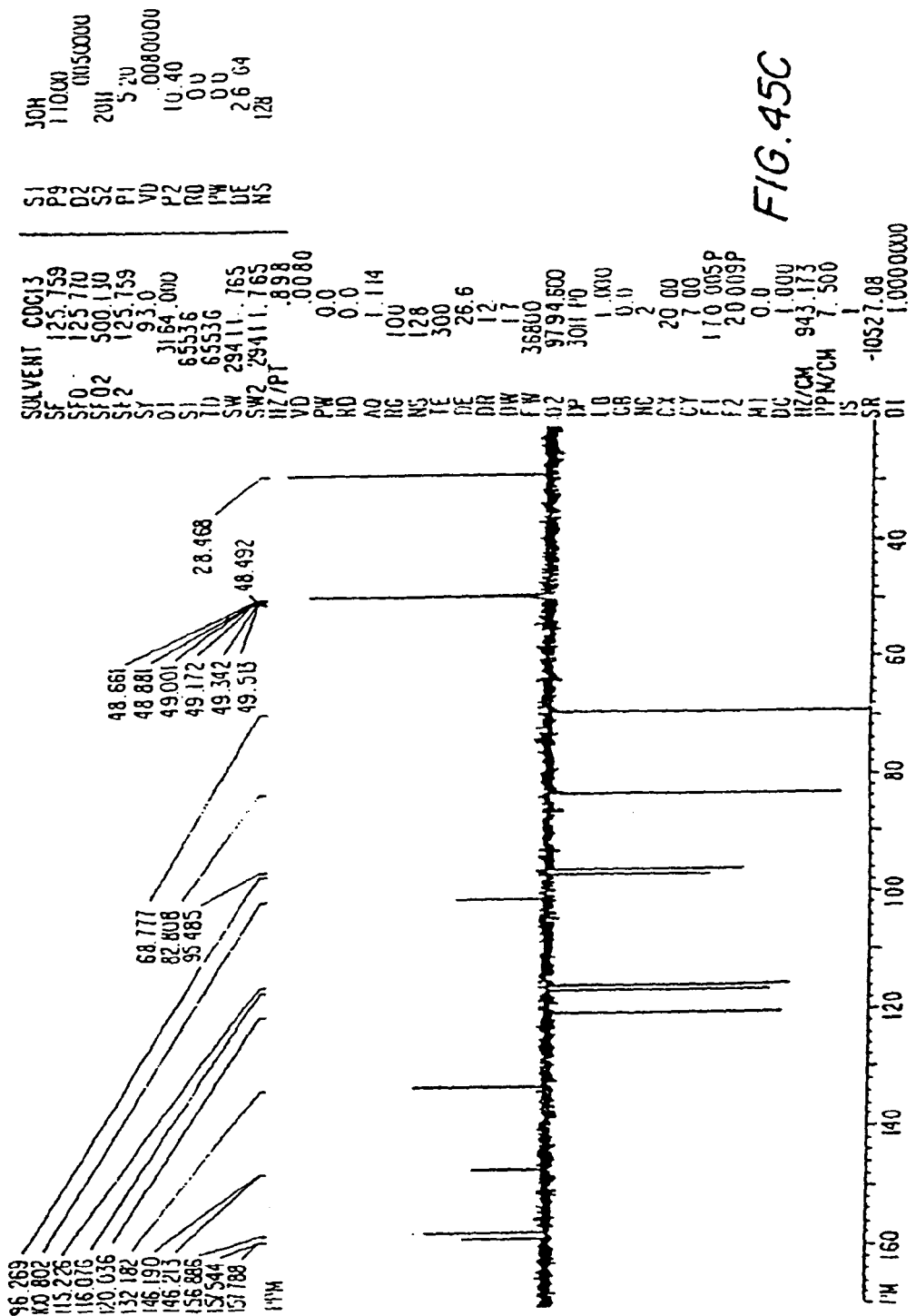
Figure 45D:
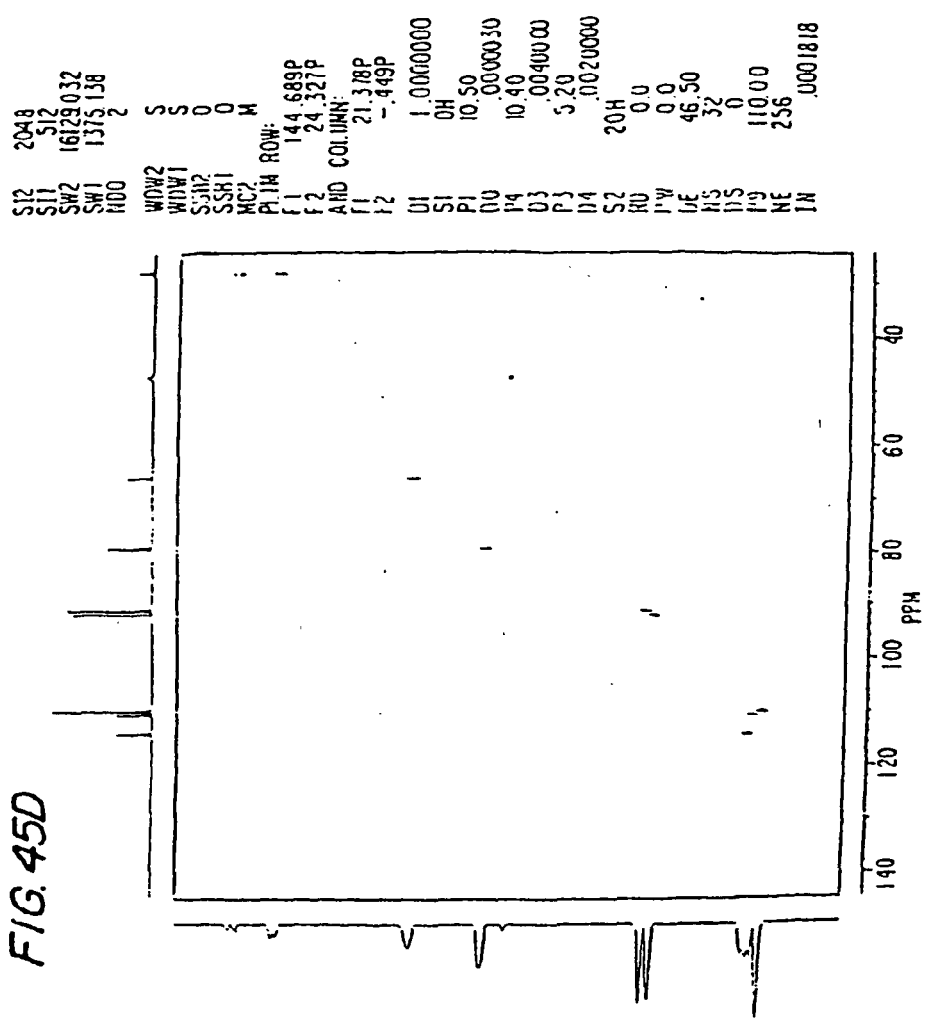
Figure 45E:
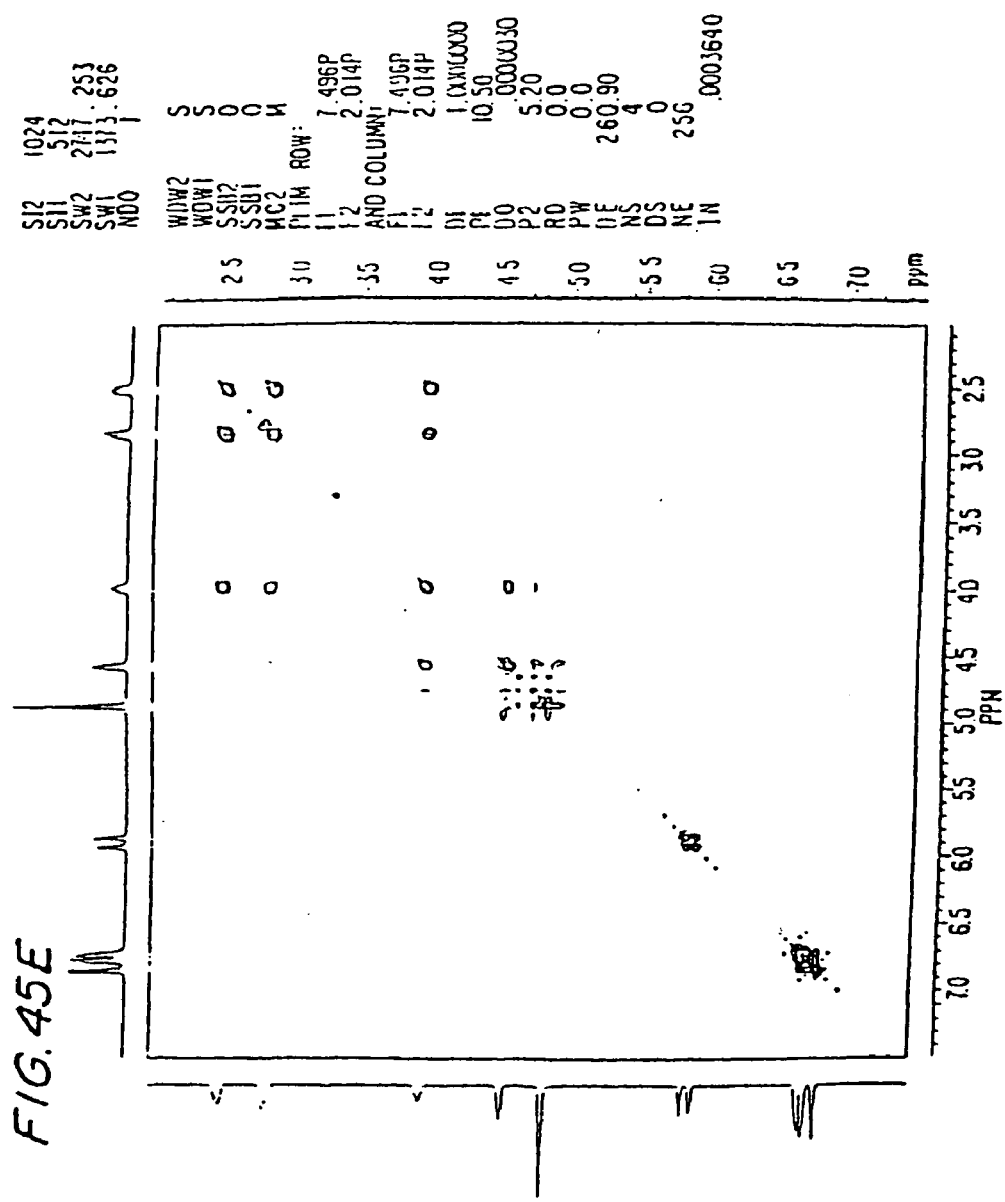

Similarly, FIGS. 45A-F represent the NMR spectra which were used to characterize the structure of the catechin monomer. FIG. 45A shows the $^1$H and $^{13}$C chemical shifts, in tabular form. FIGS. 44 B-F show $^1$H, $^{13}$C, APT, XHCORR and COSY spectra for catechin.

Method B. Dimers

All spectra were taken in 75% deuterated acetone in D$_2$O, using acetone as an internal standard, and an approximate sample concentration of 10 mg/mL.

Figure 46A:
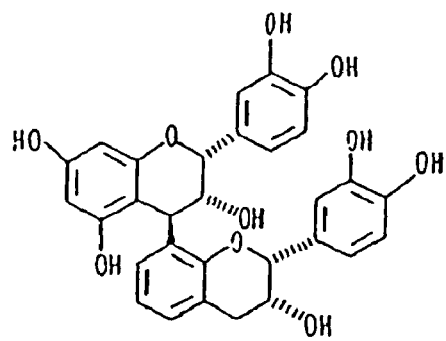
FIG. 46A shows the structure and $^1H/^{13}C$ NMR data for B2 dimer.

FIGS. 46A-G represent the spectra which were used to characterize the structure of the B2 dimer. FIG. 46A shows $^1$H and $^{13}$C chemical shifts, in tabular form. The terms T and B indicate the top half of the dimer and the bottom half of the dimer.

Figure 46B:
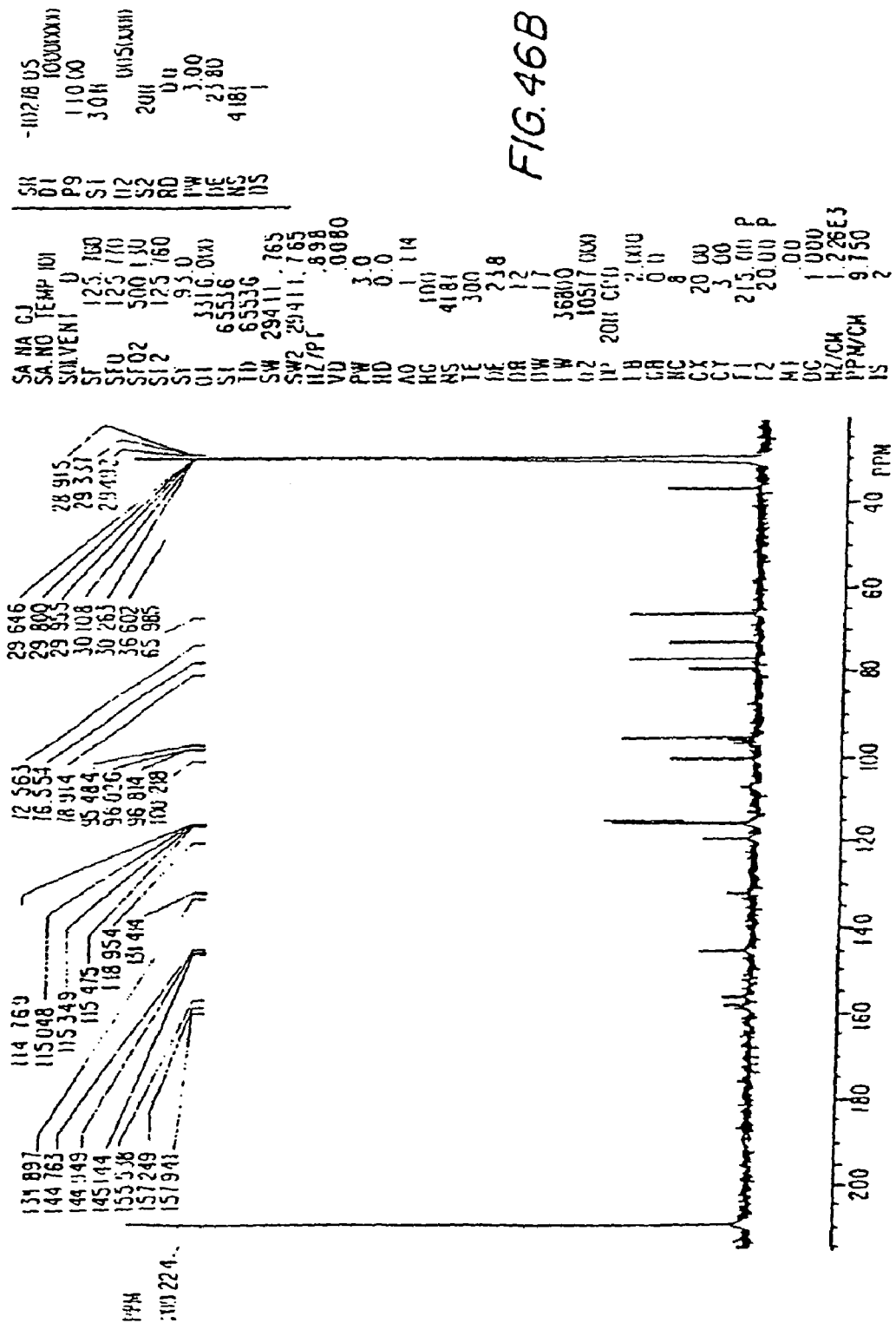
Figure 46C:
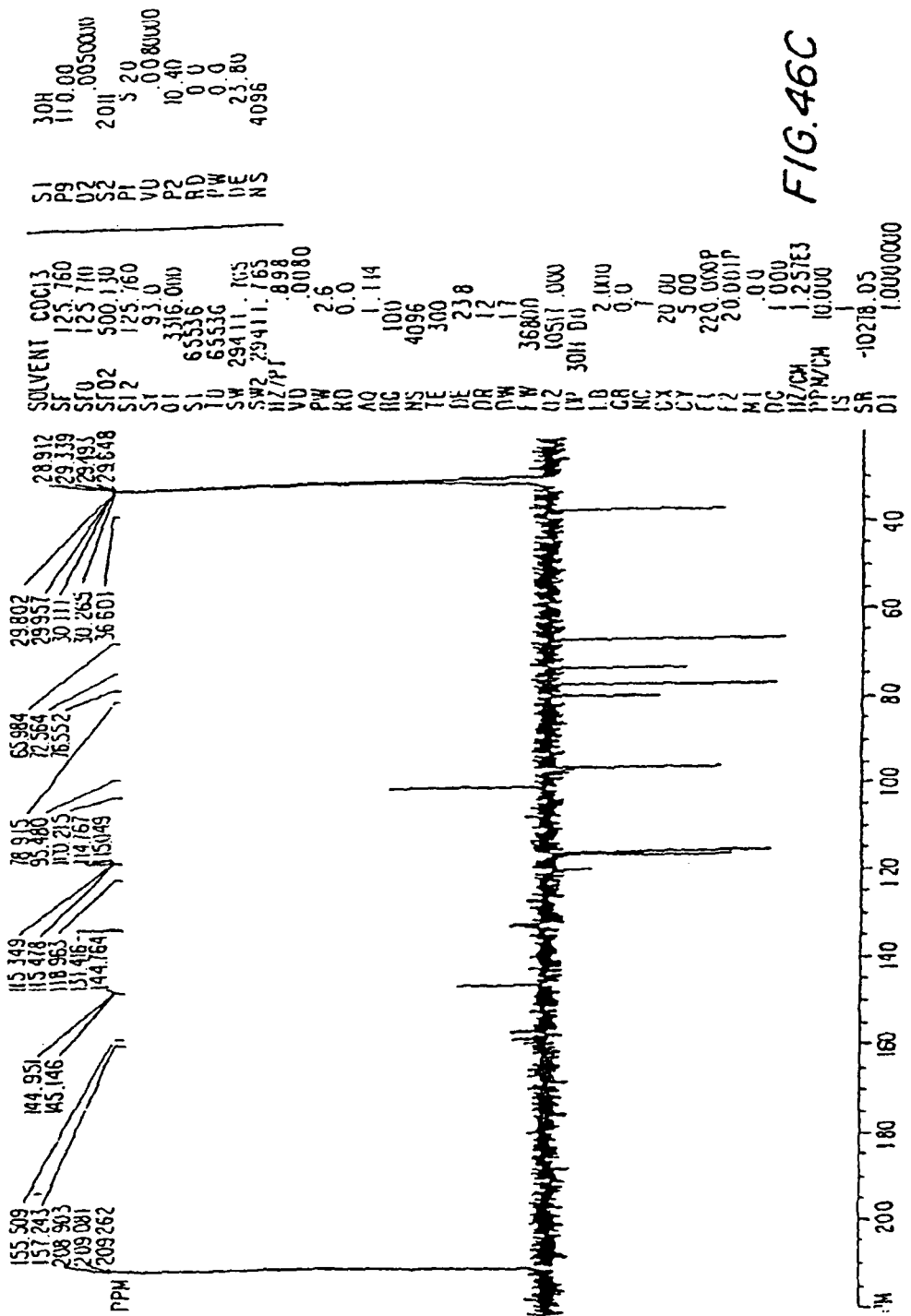
Figure 46D:
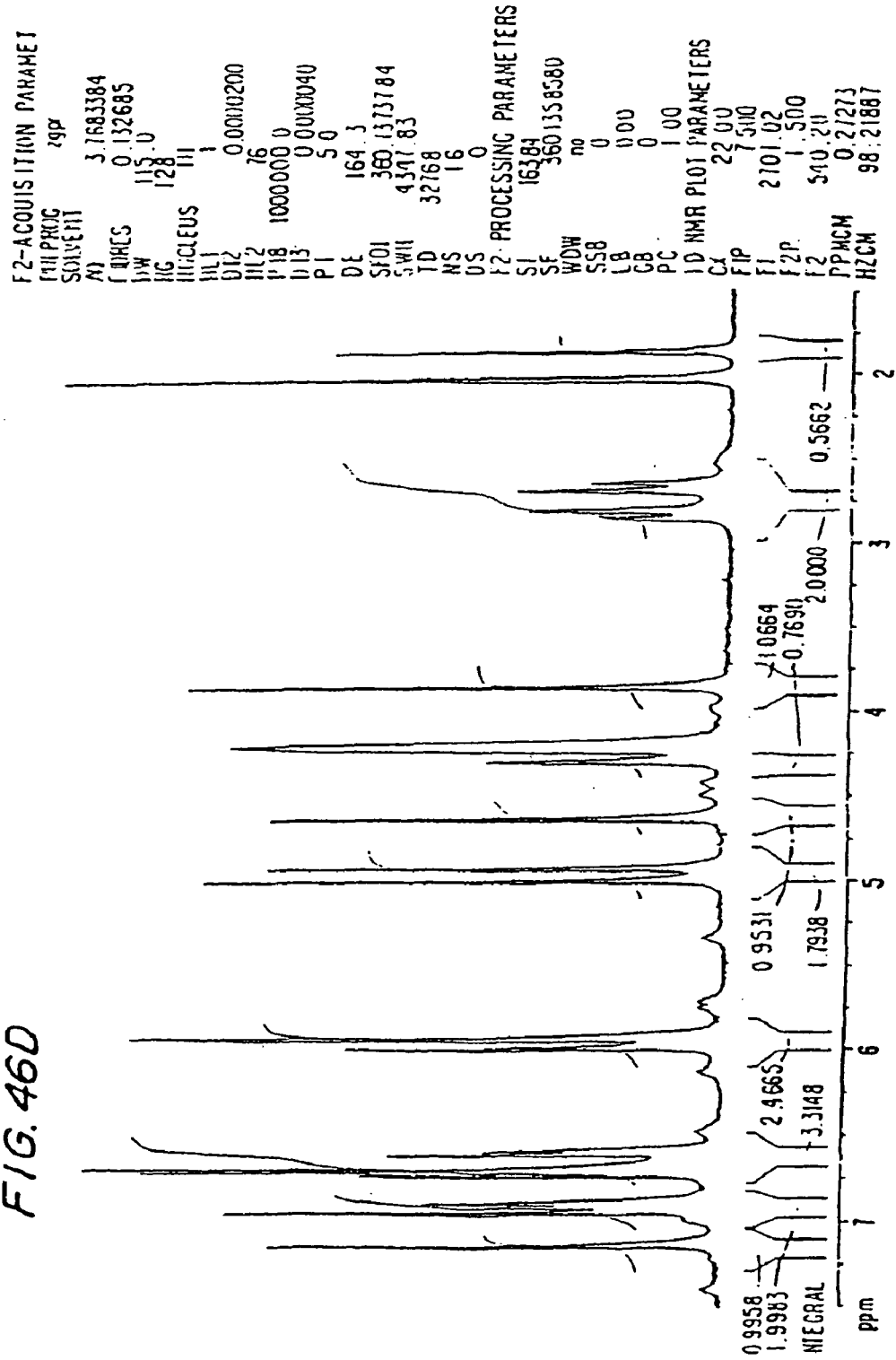
Figure 46E:
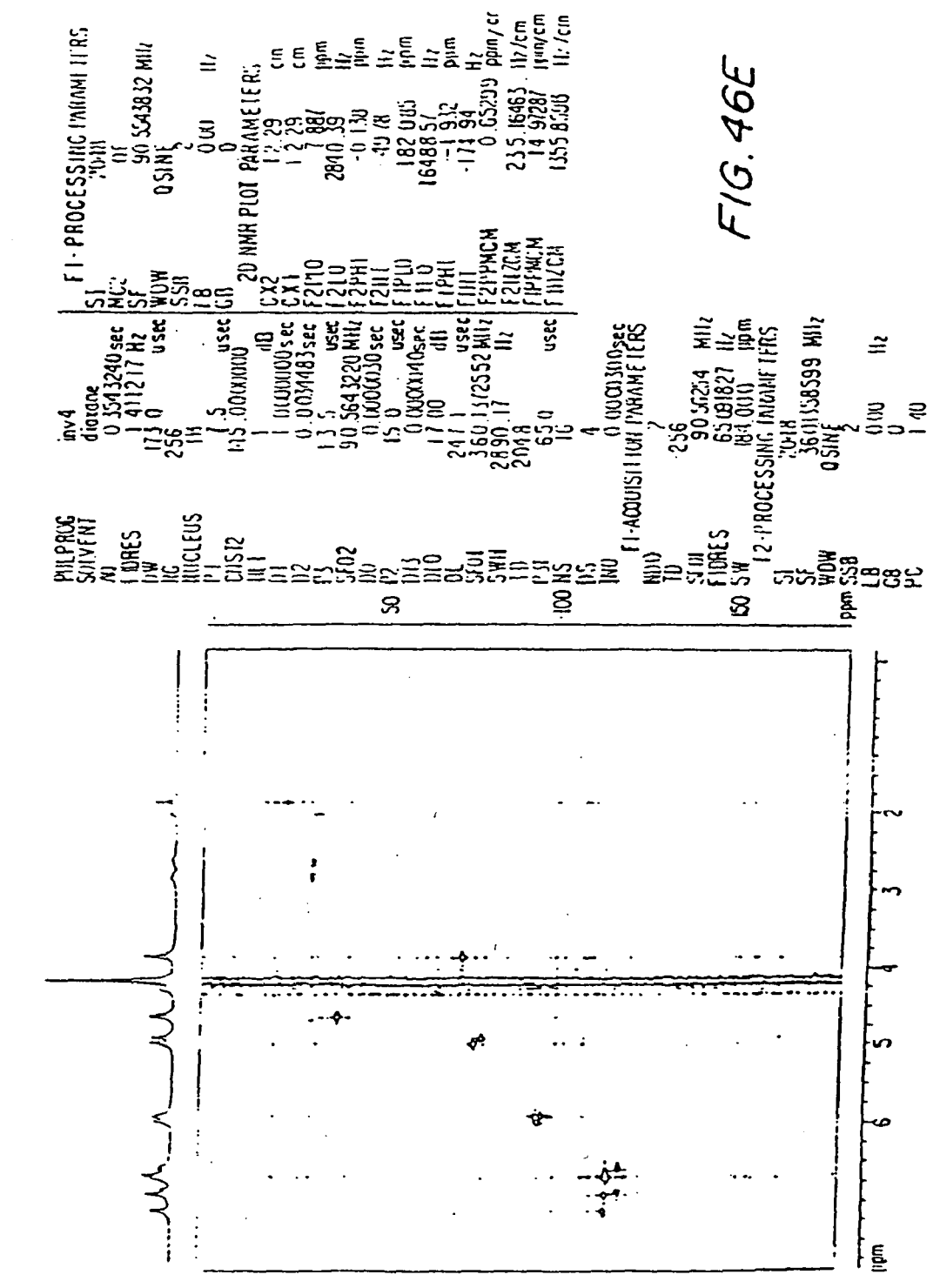
Figure 46F:
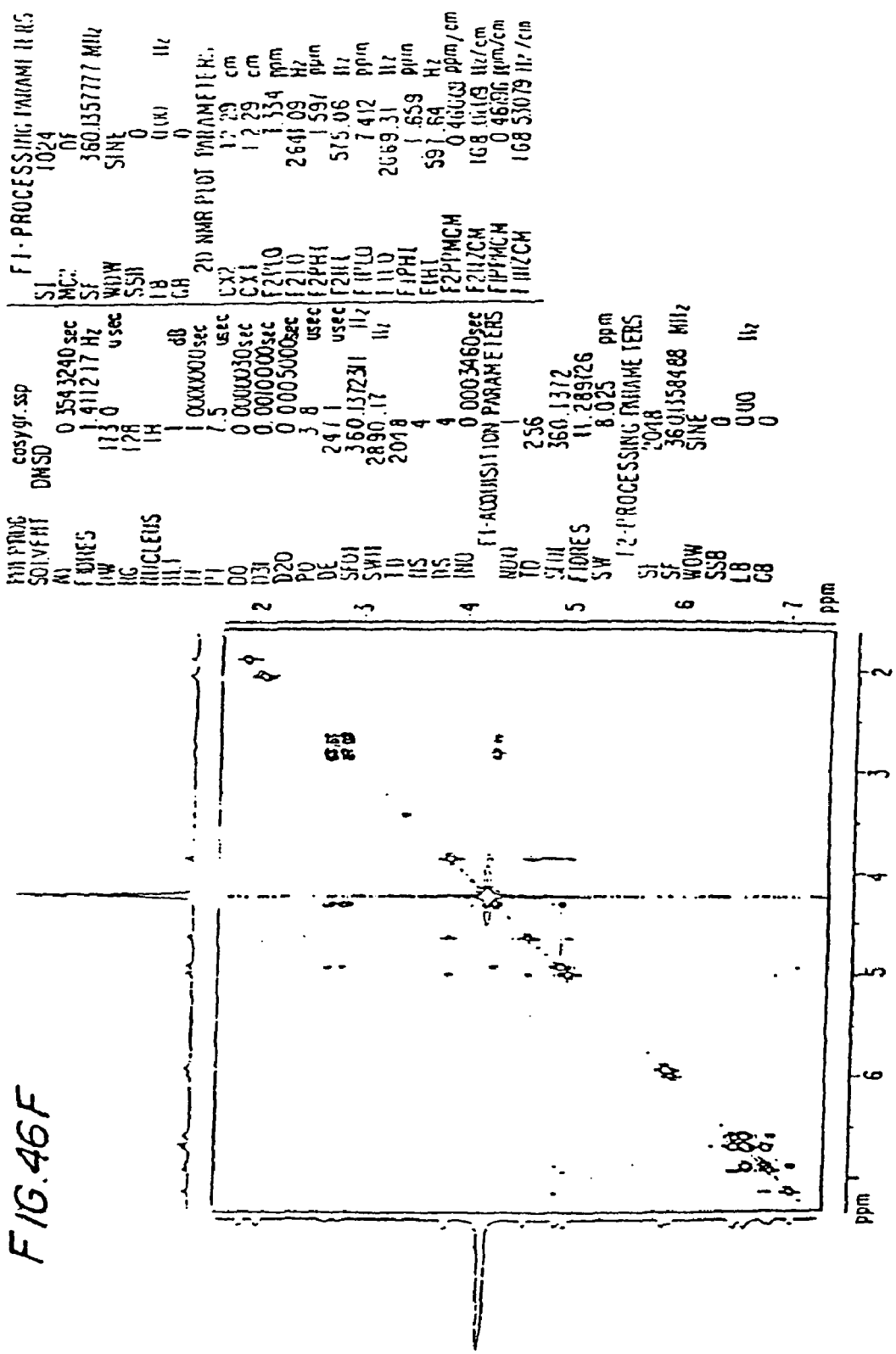
Figure 46G:
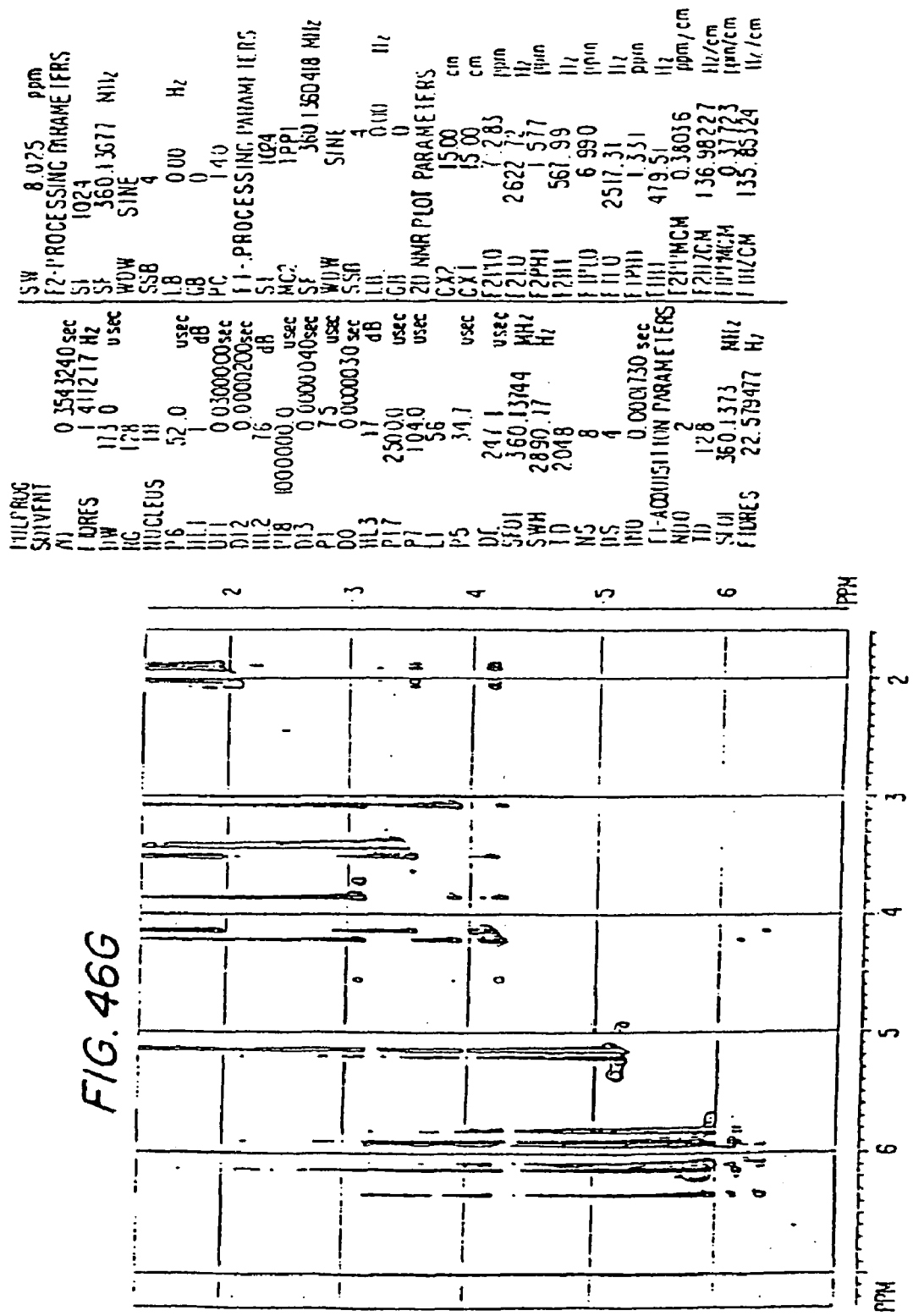

FIGS. 46B and C show the $^{13}$C and APT spectra, respectively, taken on a Bruker 500 MHZ NMR, at room temperature.

FIGS. 46D-G show the $^1$H, HMQC, COSY and HOHAHA, respectively, which were taken on AMZ-360 MHZ NMR at a $-7°$ C. The COSY spectrum was taken using a gradient pulse.

Figure 47A:
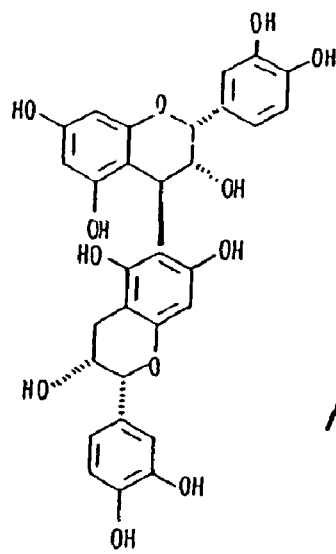
FIG. 47A shows the structure and $^1H/^{13}C$ NMR data for B5 dimer.

FIGS. 47A-G represent the spectra which were used to characterize the structure of the B5 dimer. FIG. 47A shows the $^{13}$C and $^1$H chemical shifts, in tabular form.

Figure 47B:
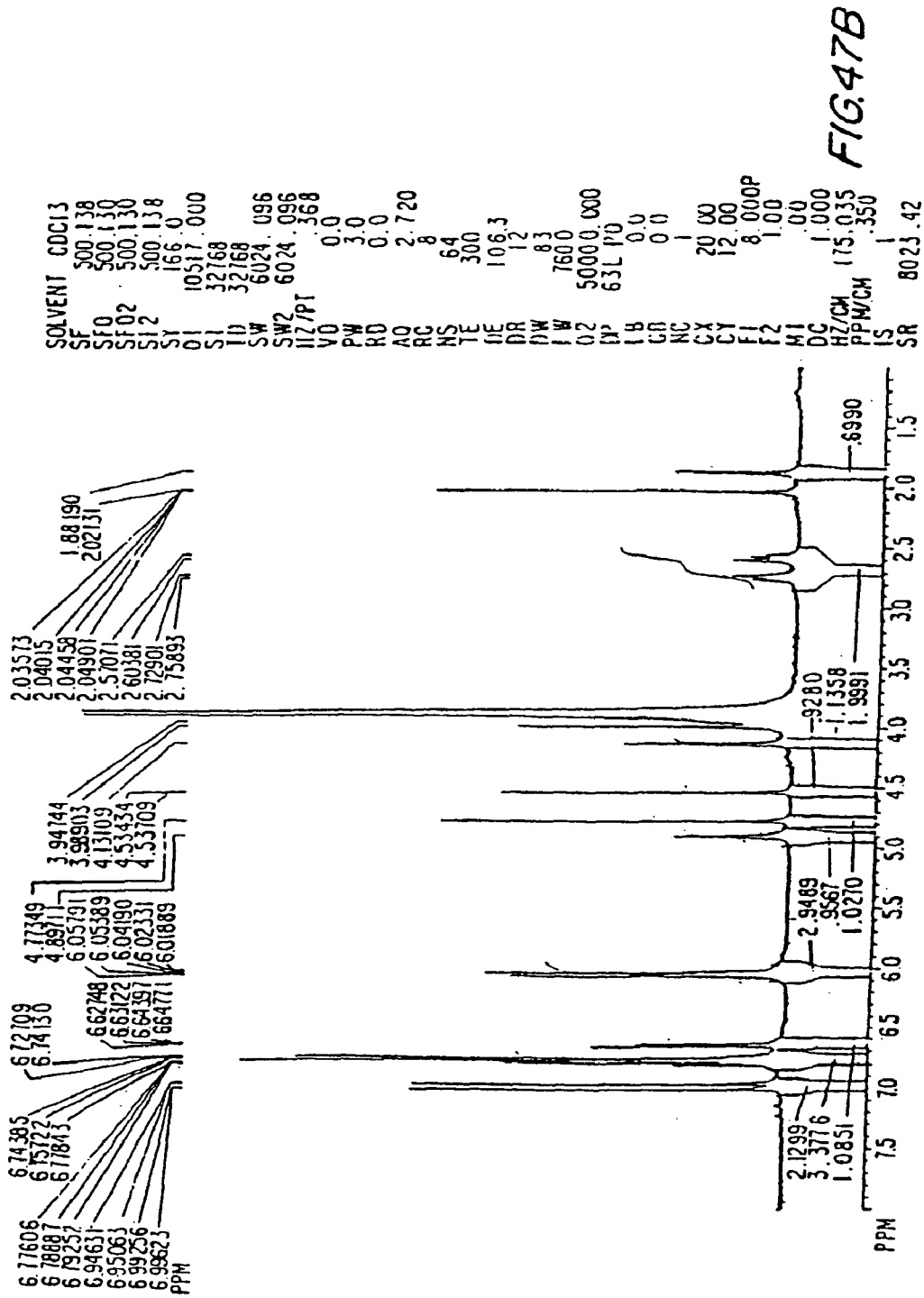
FIGS. 47B-G show the $^1H$, $^{13}C$, APT, COSY, HMQC and HOHAHA NMR spectra for B5 dimer.
Figure 47C:
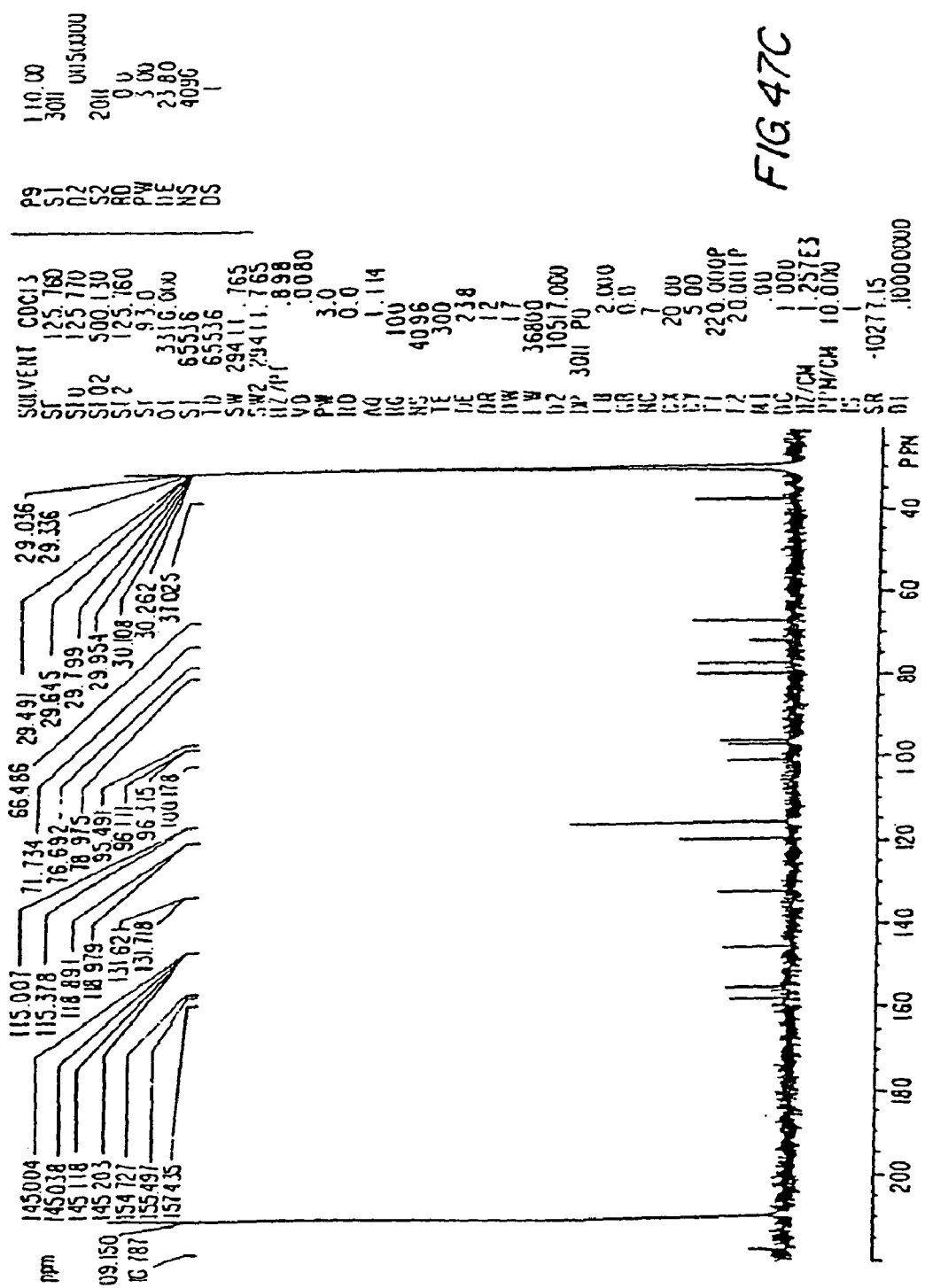
Figure 47D:
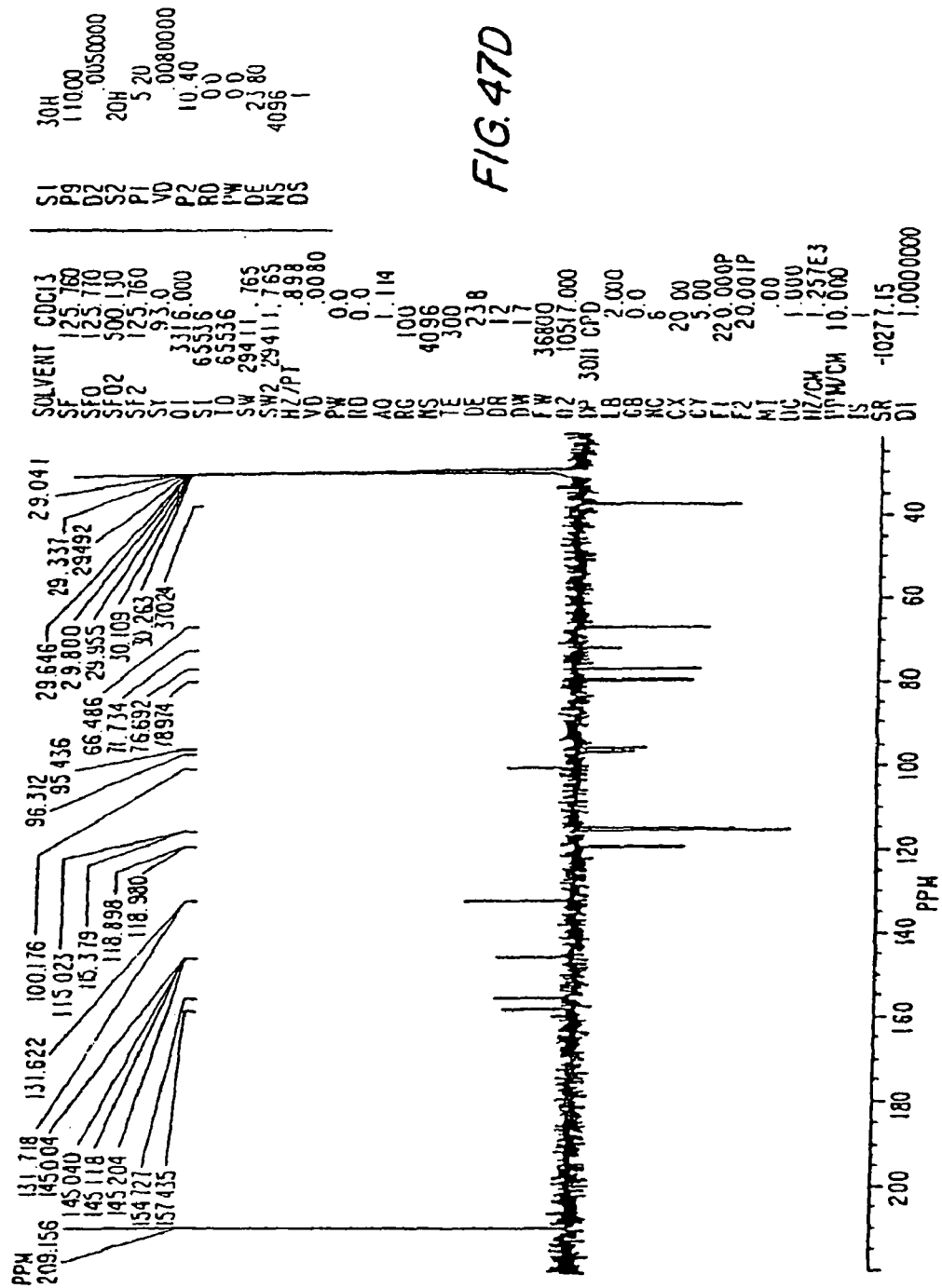

FIGS. 47B-D show the $^1$H, $^{13}$C and APT, respectively, which were taken on a Bruker 500 MHZ NMR, at room temperature.

Figure 47E:
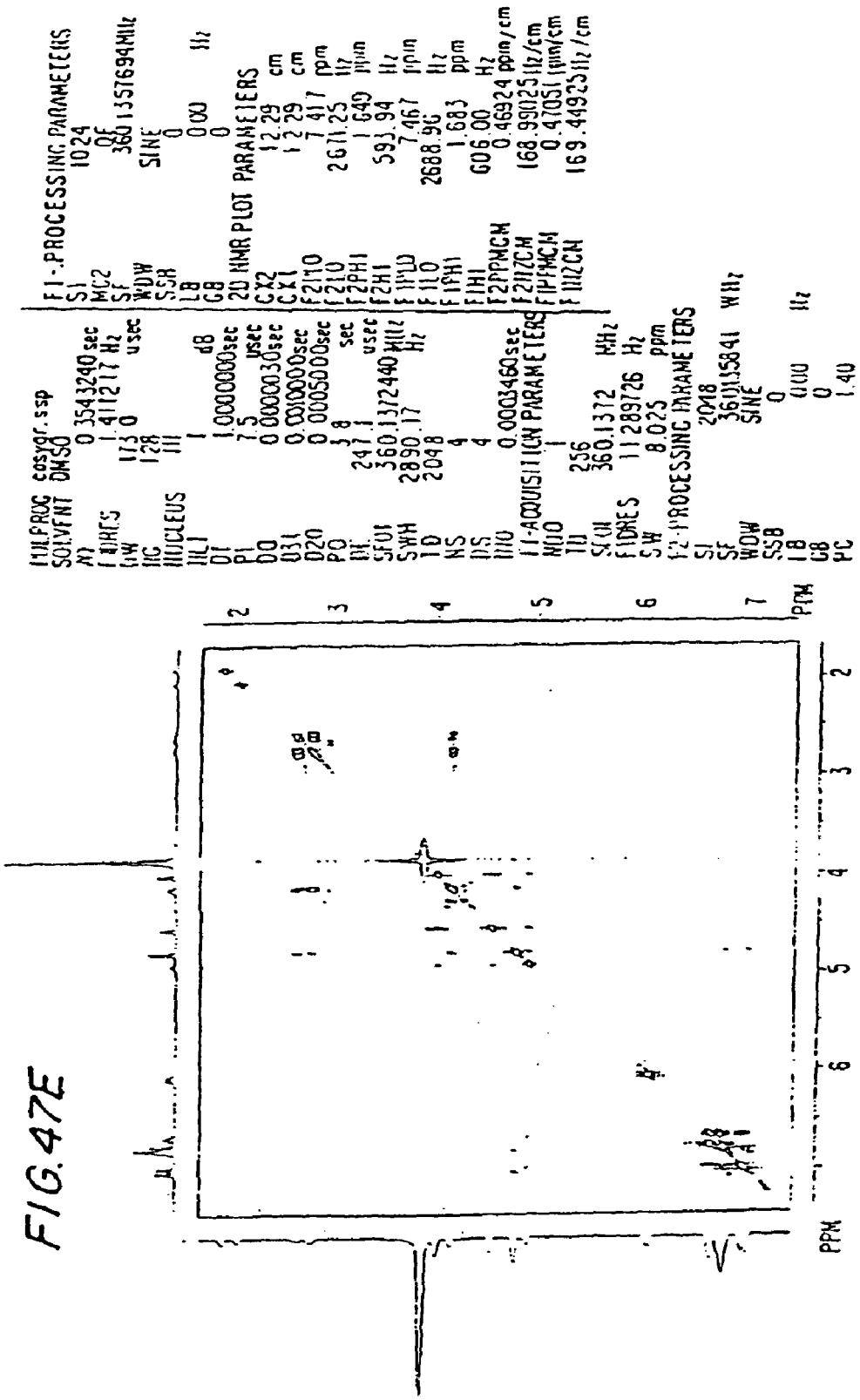

FIG. 47E shows the COSY spectrum, taken on an AMX-360, at room temperature, using a gradient pulse.

Figure 47F:
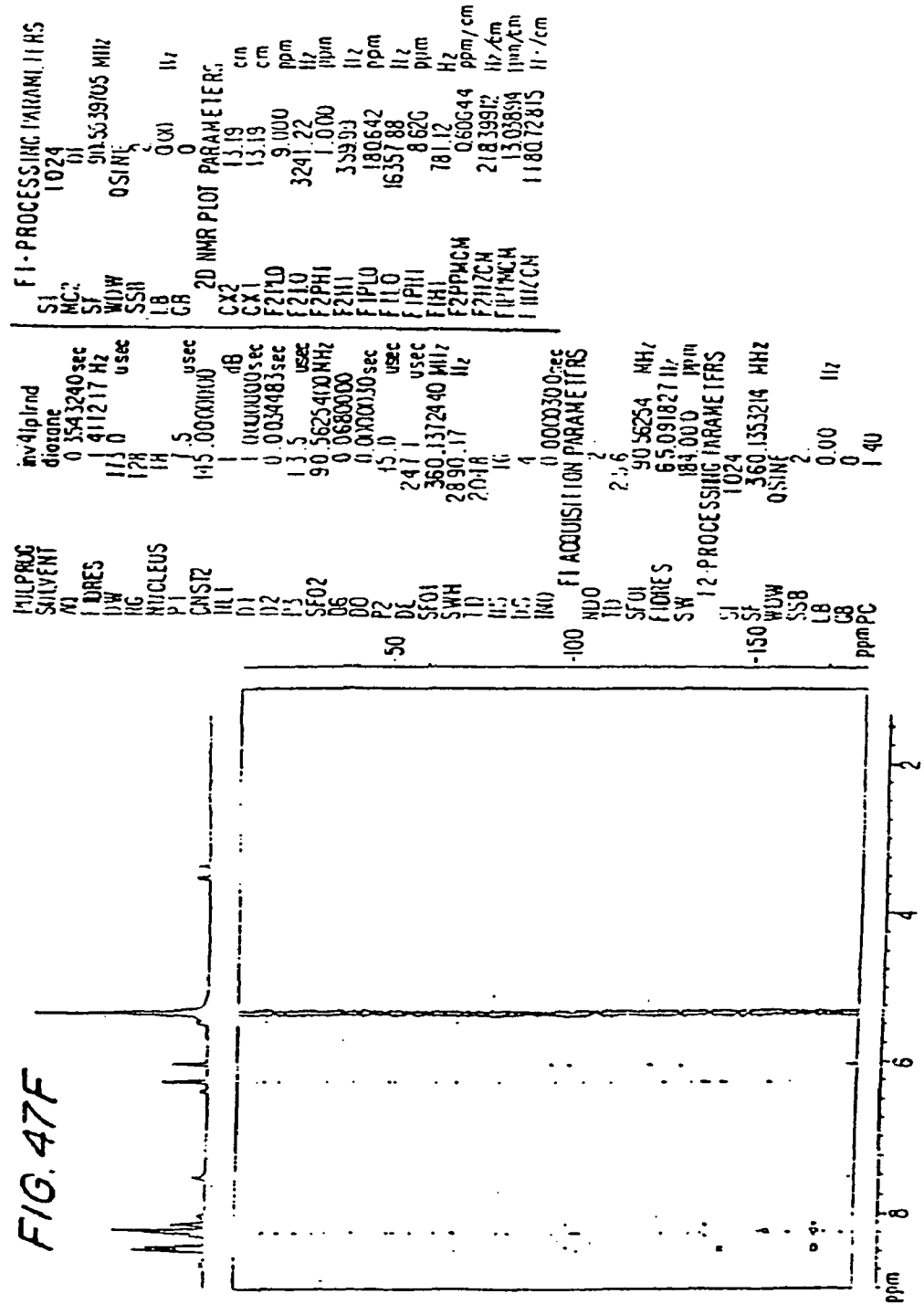
Figure 47G:
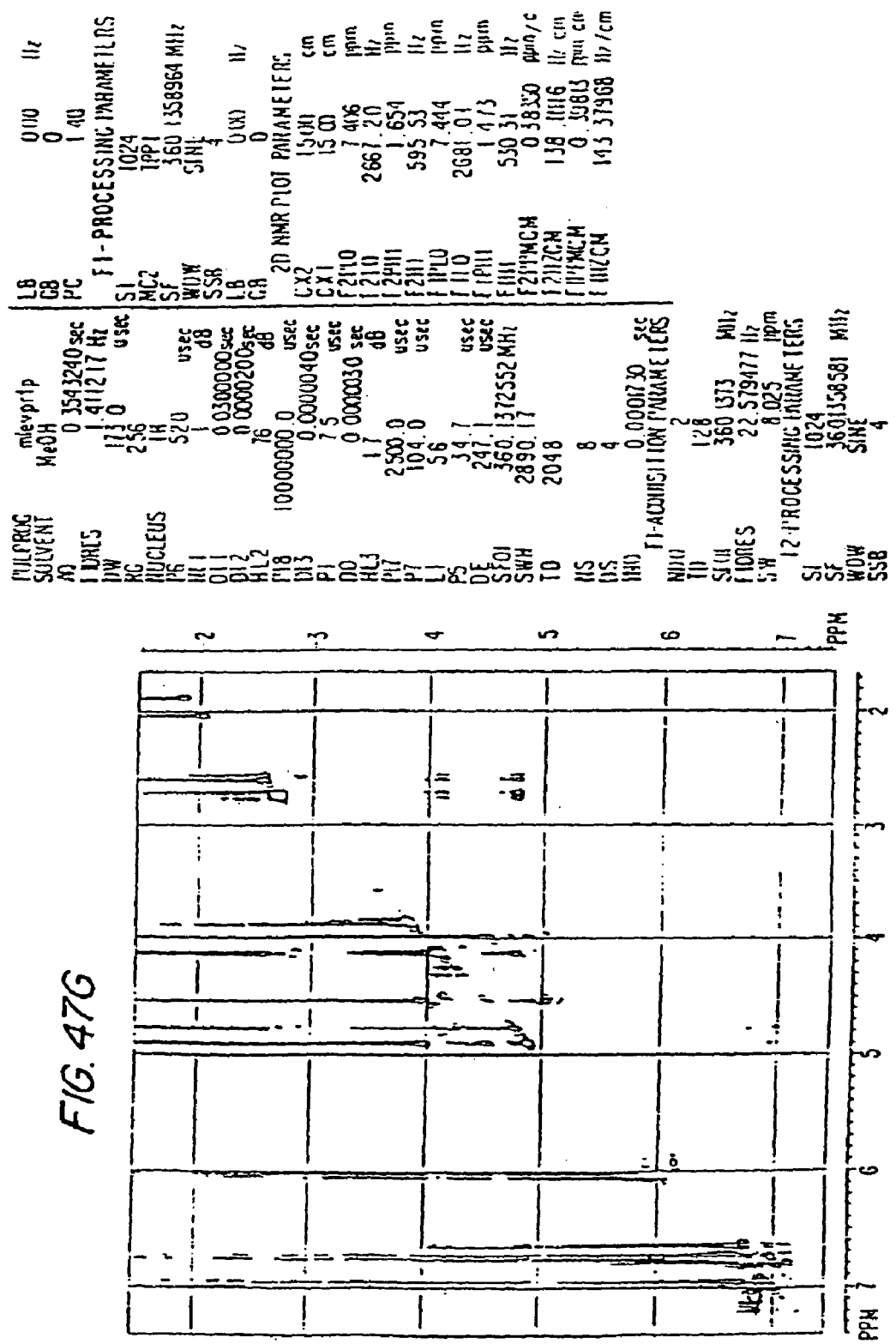
Figure 48A:
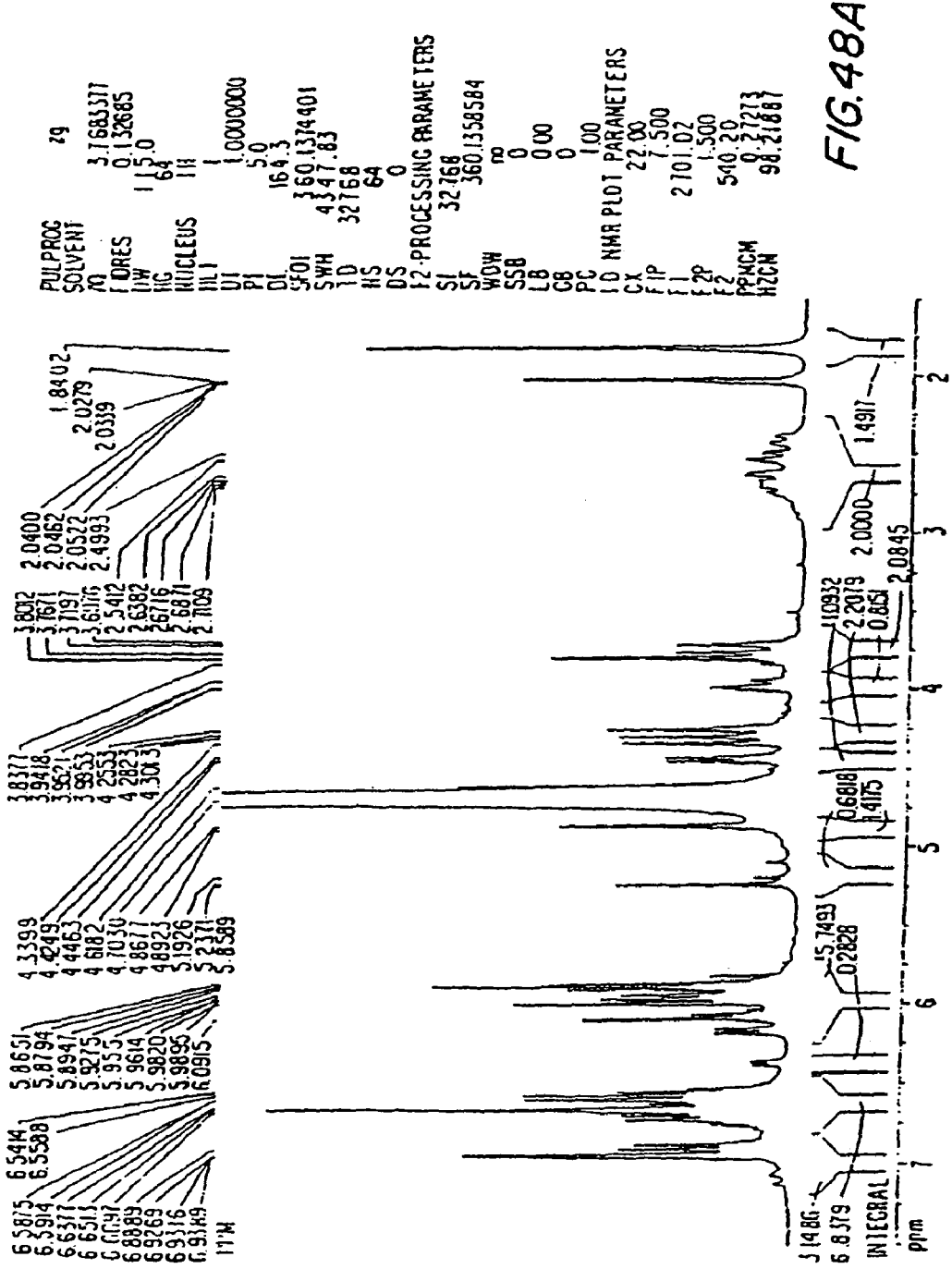
FIGS. 48A-D show the $^1H$, COSY, HMQC and HOHAHA NMR spectra for epicatechin/catechin trimer.
Figure 48B:
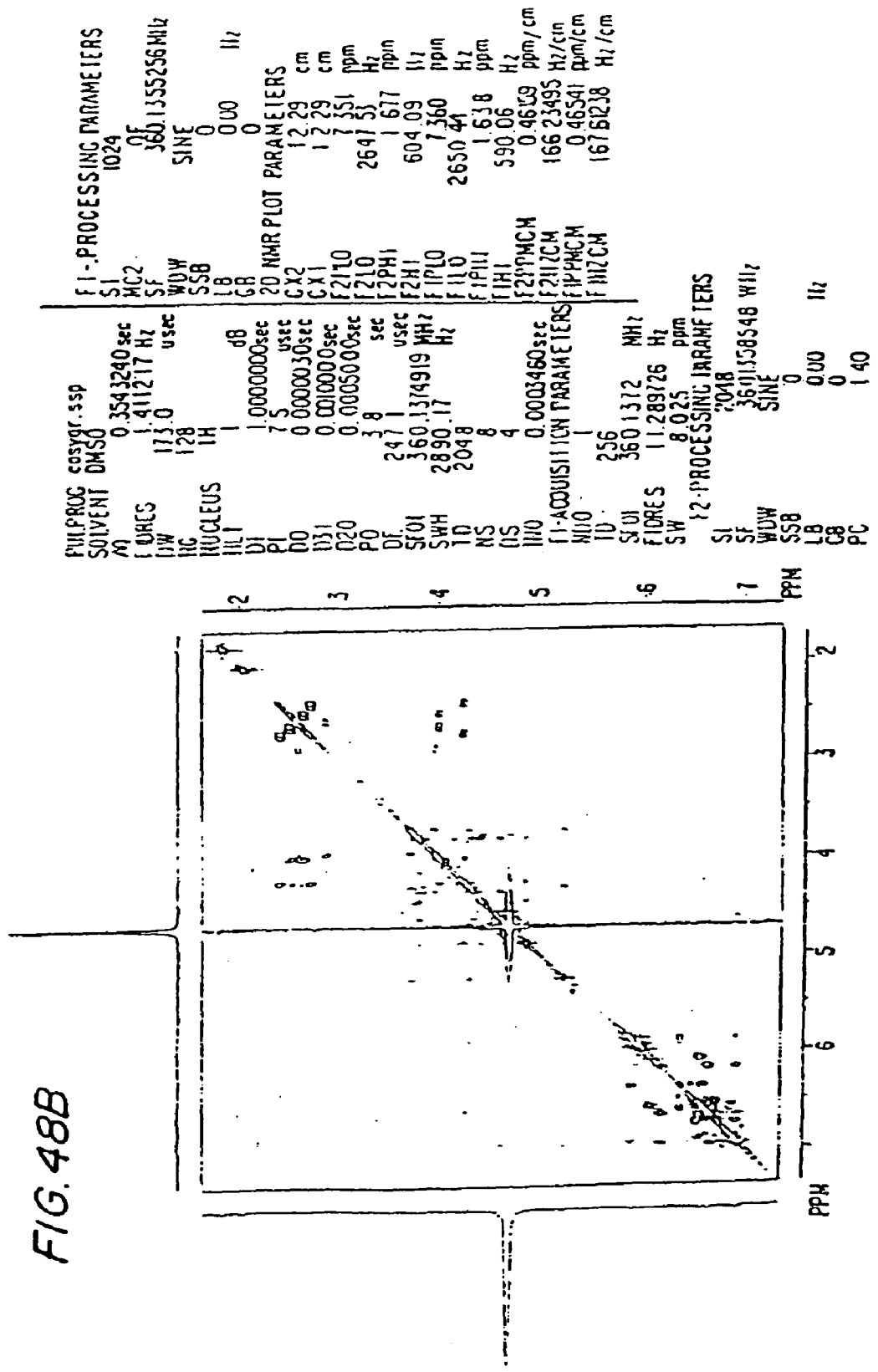
Figure 48C:
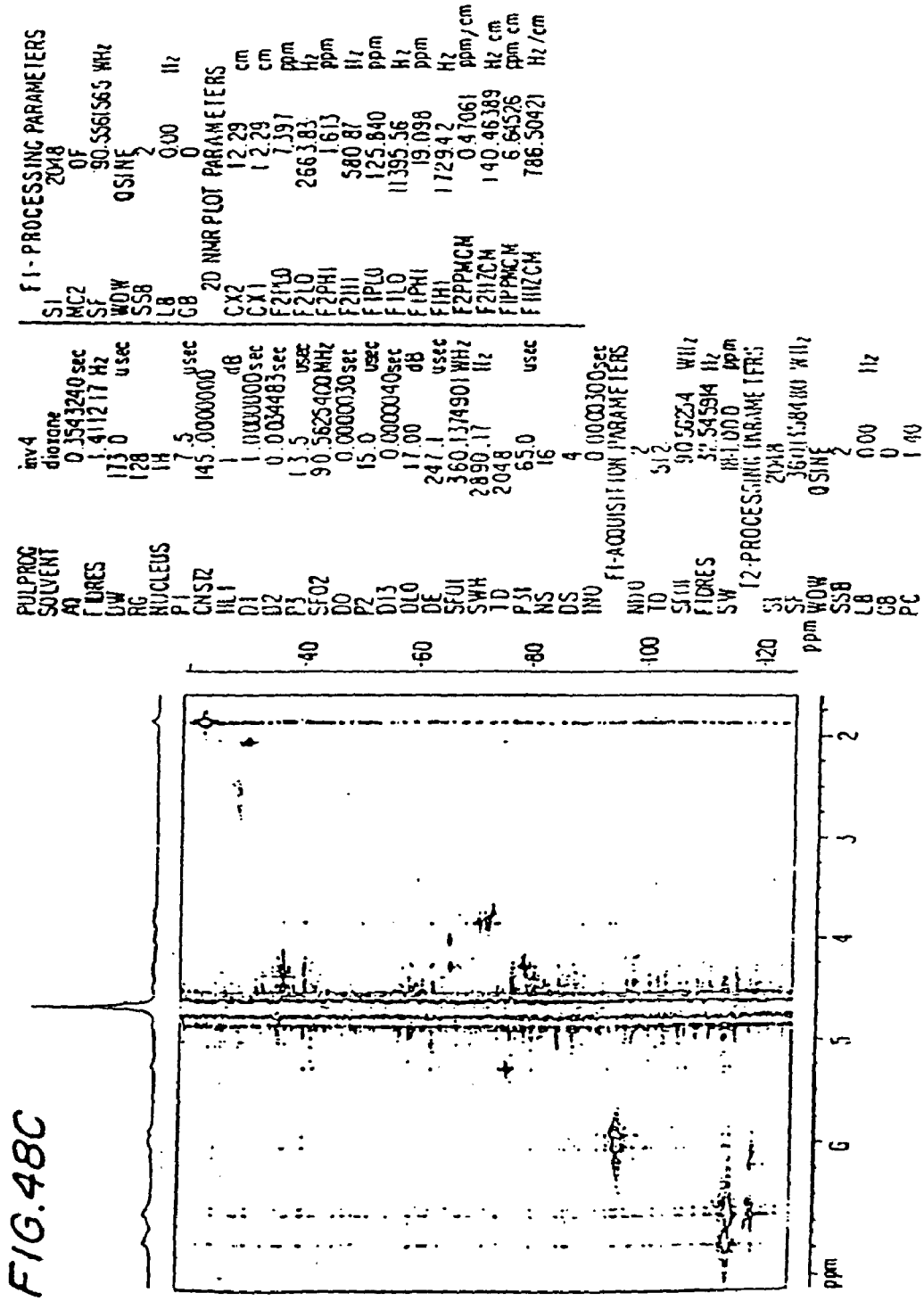
Figure 48D:
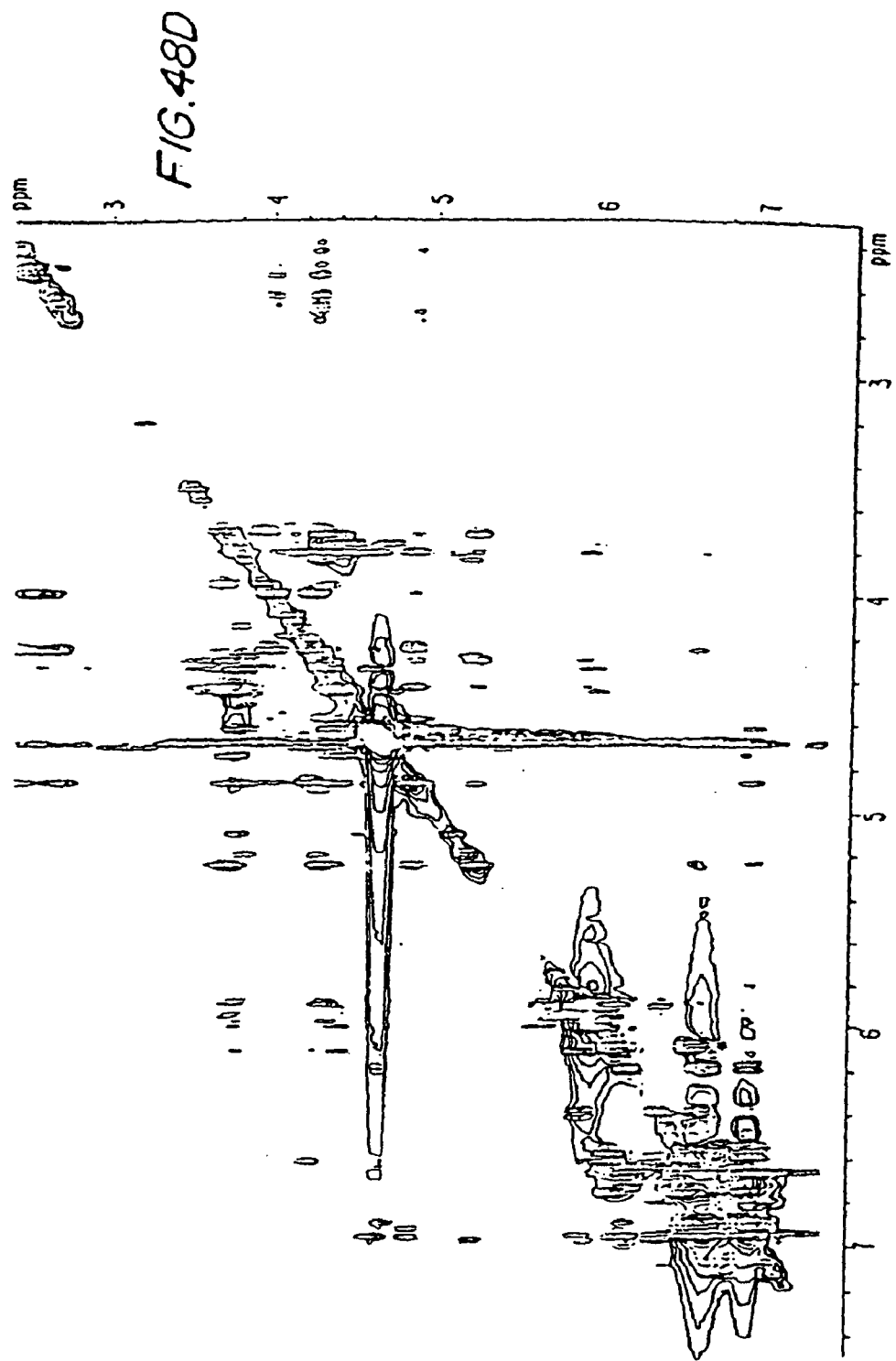
Figure 49A:
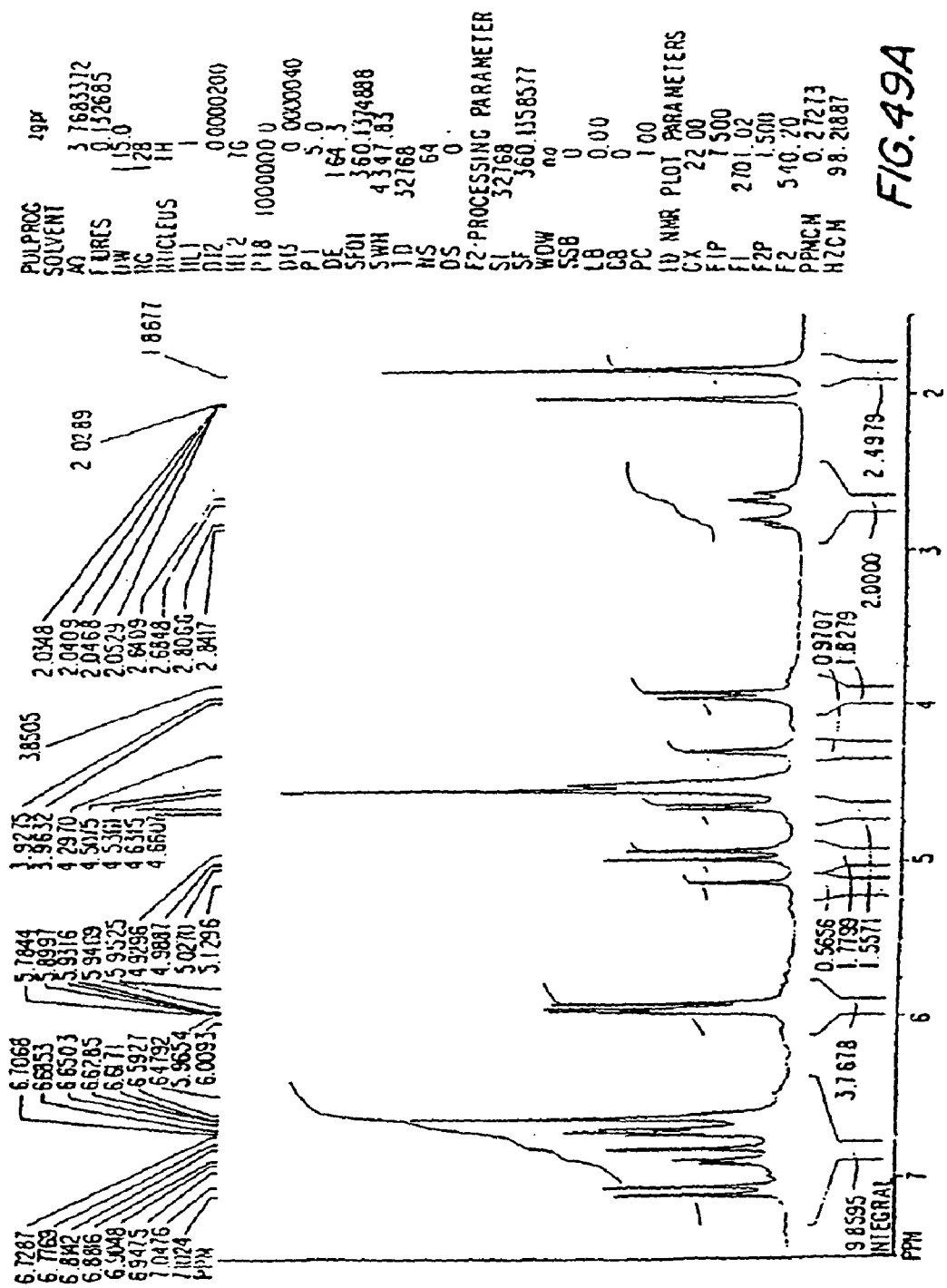
FIGS. 49A-D show the $^1H$, COSY, HMQC and HOHAHA NMR spectra for epicatechin trimer.
Figure 49B:
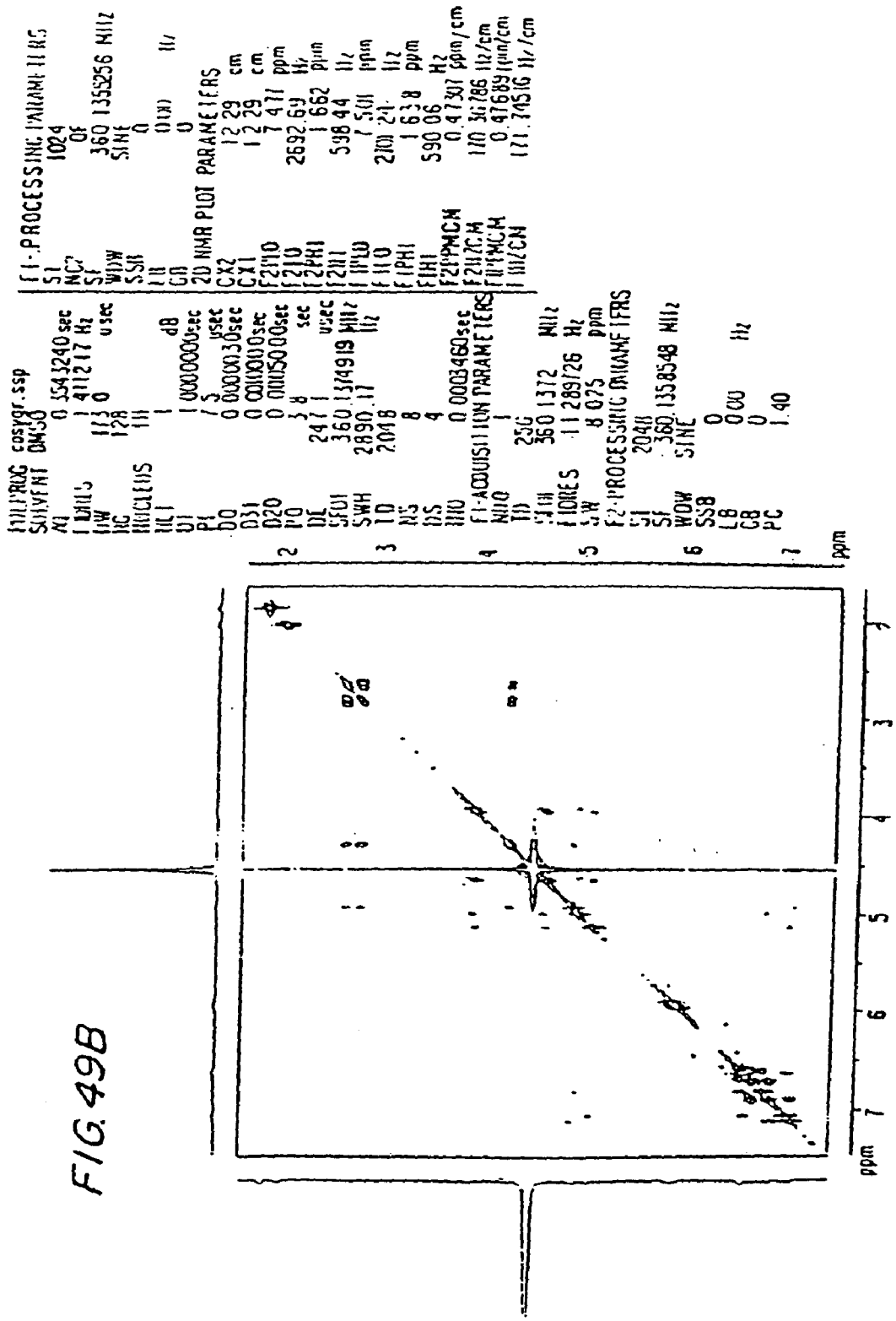
Figure 49C:
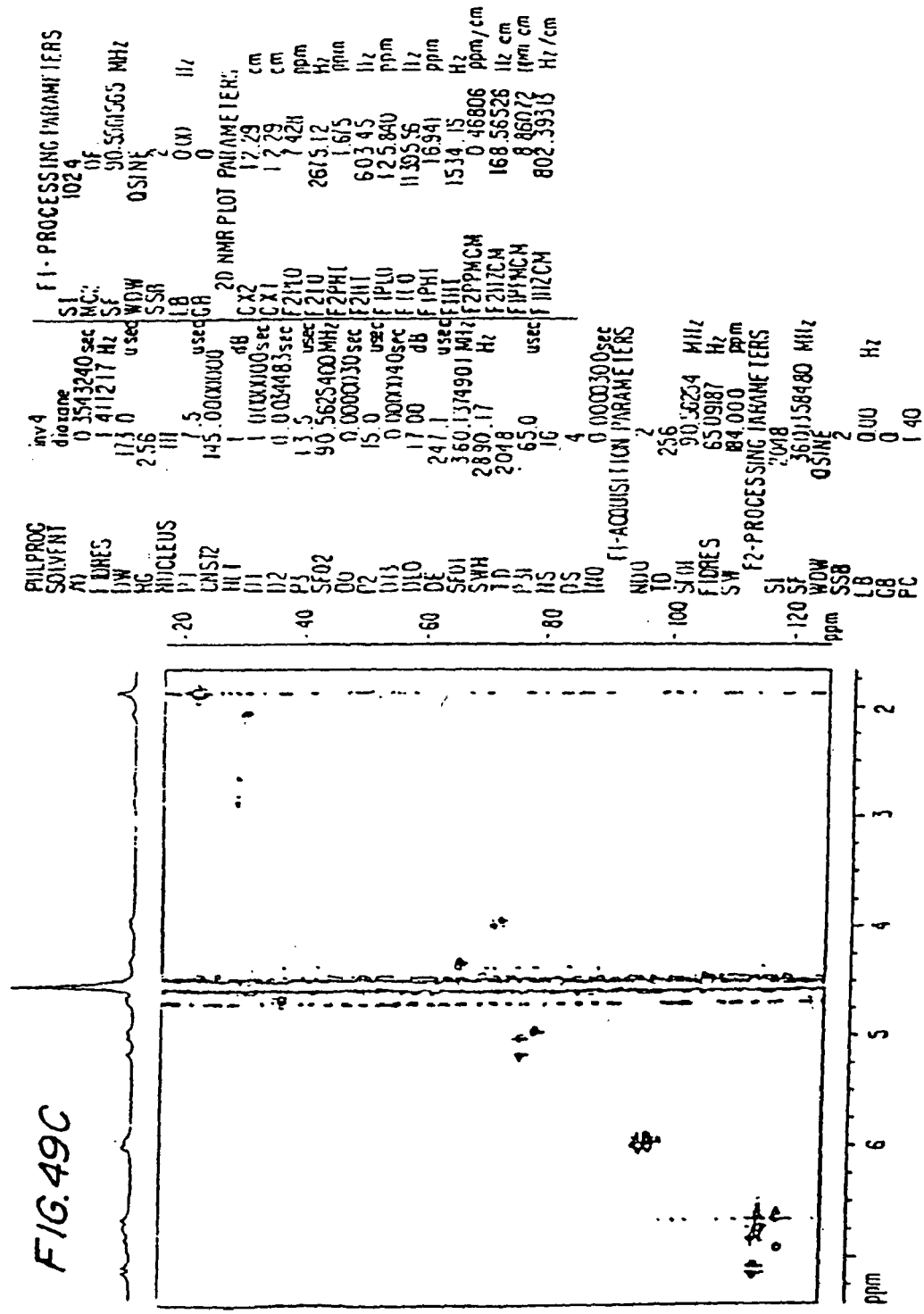
Figure 49D:
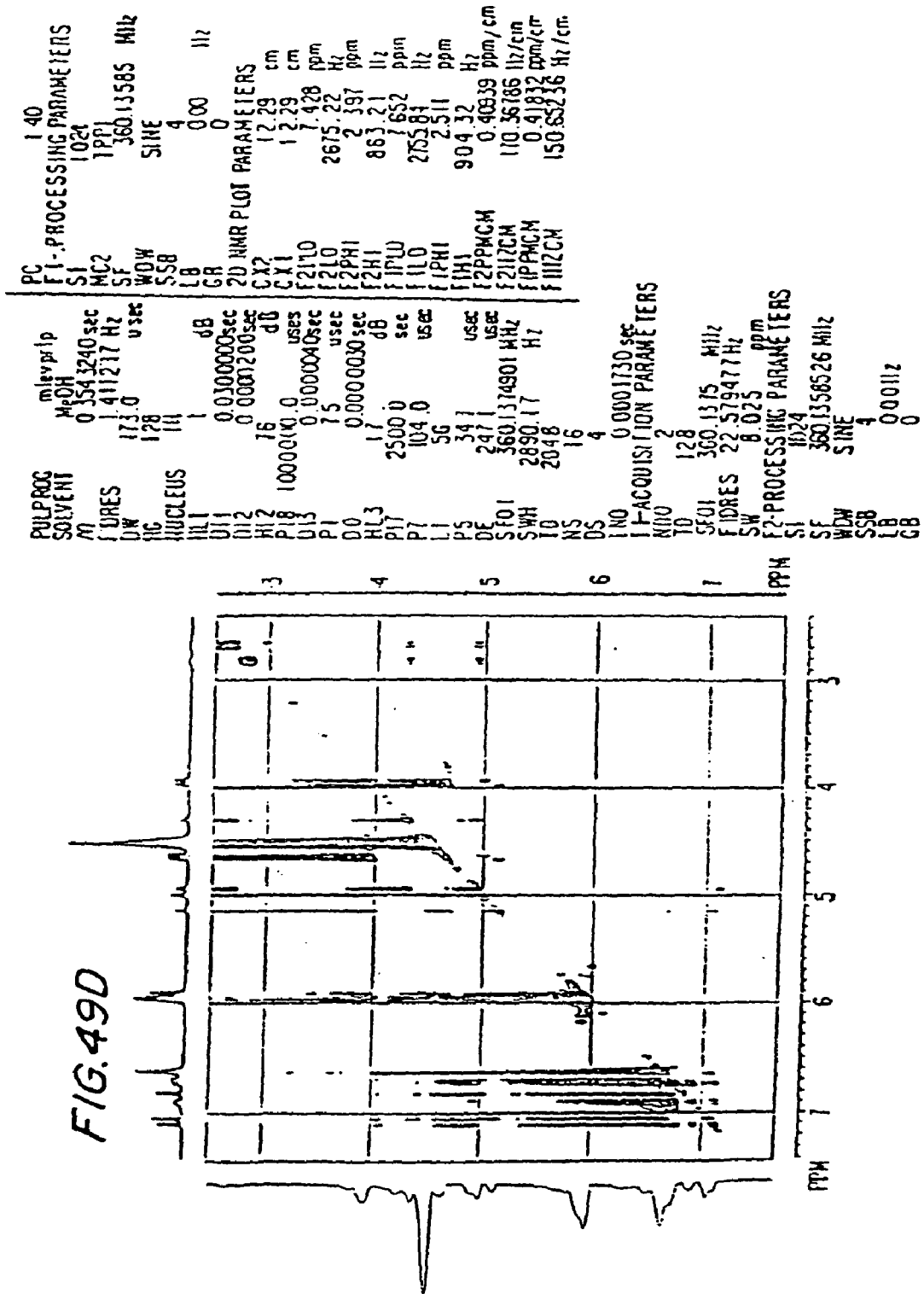

FIGS. 47F and G show the HMQC and HOHAHA, respectively, taken on an AMX-360 MHZ NMR, at room temperature.

Method C. Trimer-Epicatechin/Catechin

All spectra were taken in 75% deuterated acetone in D$_2$O, at $-3°$ C. using acetone as an internal standard, on an AMX-360 MHZ NMR, and an appropriate sample concentration of 10 mg/mL.

FIGS. 48A-D represent the spectra which were used to characterize the structure of the epicatechin/catechin trimer. These figures show $^1$H, COSY, HMQC and HOHAHA, respectively. The COSY spectrum was taken using a gradient pulse.

Method D. Trimer-All Epicatechin

All spectra were taken in 70% deuterated acetone in D$_2$O, at $-1.8°$ C., using acetone as an internal standard, on an AMX-360 MHZ NMR, and an appropriate sample concentration of 10 mg/mL.

FIGS. 49A-D represent the spectra which were used to characterize the structure of all epicatechin trimer. These figures show $^1$H, COSY, HMQC and HOHAHA, respectively. The COSY spectrum was taken using a gradient pulse.

Example 19

Thiolysis of Procyanidins

Figure 25A:
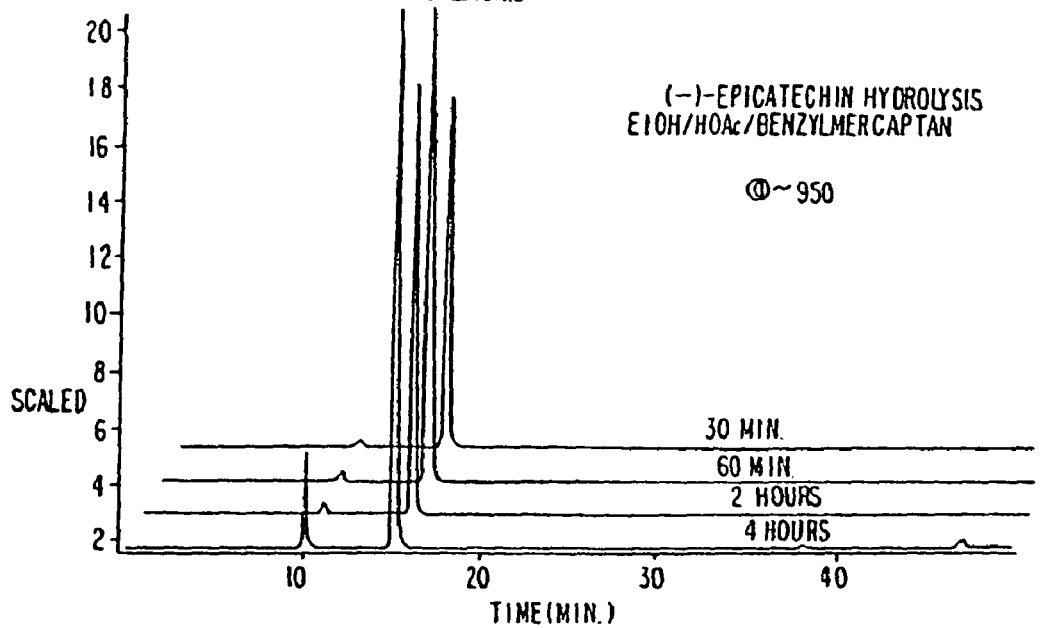
FIG. 25A shows relative fluorescence of epicatechin upon thiolysis with benzylmercapten.
Figure 25B:
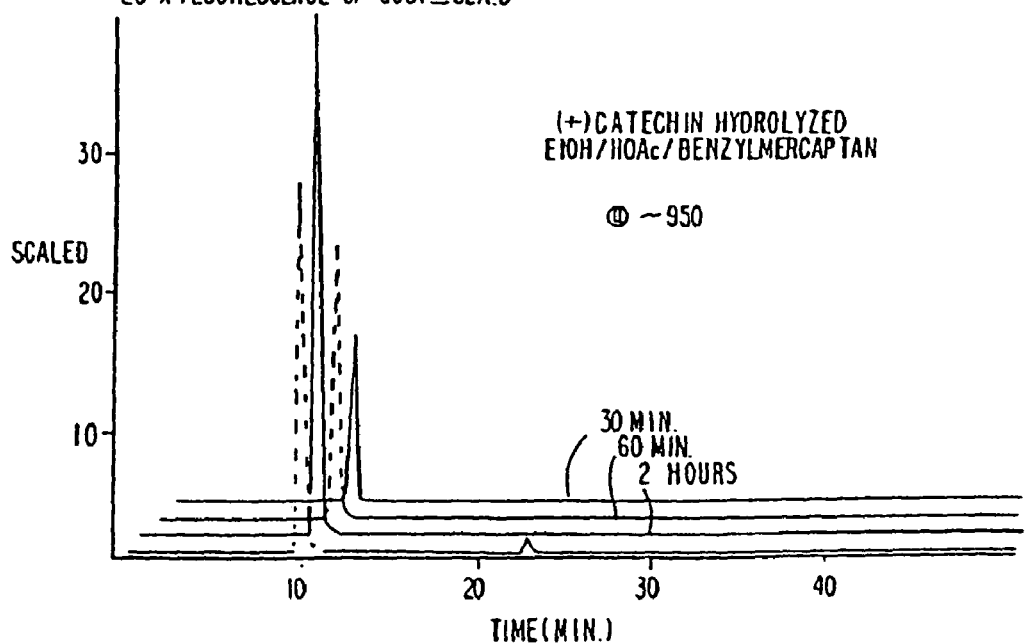
FIG. 25B shows relative fluorescence of catechin upon thiolysis with benzylmercapten.
Figure 25C:
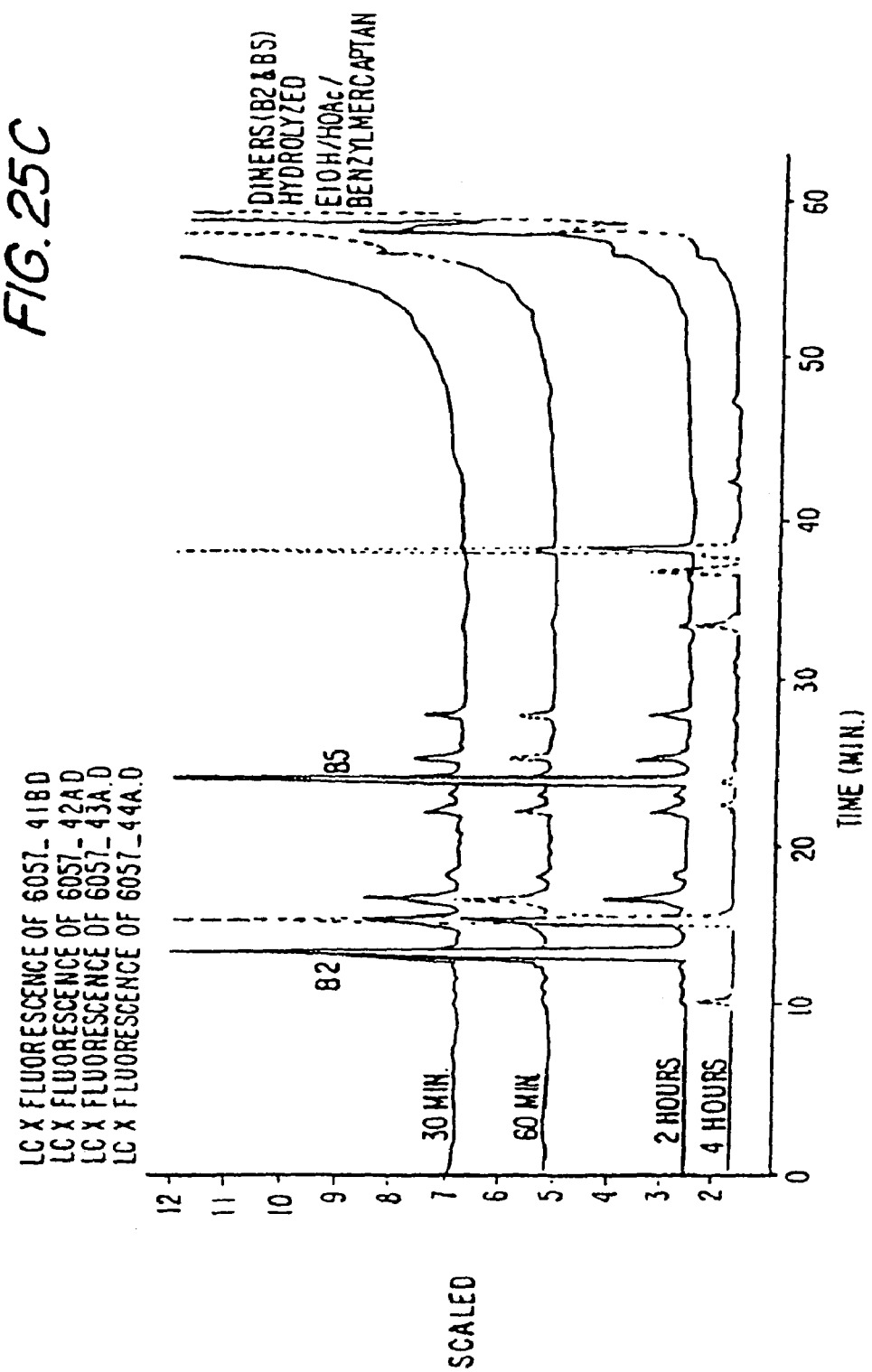
FIG. 25C shows relative fluorescence of dimers (B2 and B5) upon thiolysis with benzylmercapten.

In an effort to characterize the structure of procyanidins, benzyl mercaptan (BM) was reacted with catechin, epicatechin or dimers B2 and B5. Benzyl mercaptan, as well as phloroglucinol and thiophenol, can be utilized in the hydrolysis (thiolysis) of procyanidins in an alcohol/acetic acid environment. Catechin, epicatechin or dimer (1:1 mixture of B2 and B5 dimers)(2.5 mg) was dissolved in 1.5 mL ethanol, 100 µL BM and 50 µL acetic acid, and the vessel (Beckman amino acid analysis vessel) was evacuated and purged with nitrogen repeatedly until a final purge with nitrogen was followed by sealing the reaction vessel. The reaction vessel was placed in a heat block at 95° C., and aliquots of the reaction were taken at 30, 60, 120 and 240 minutes. The relative fluorescence of each aliquot is shown in FIGS. 25A-C, representing epicatechin, catechin and dimers, respectively. Higher oligomers are similarly thiolyzed.

Example 20

Thiolysis and Desulfurization of Dimers

Figure 26A:
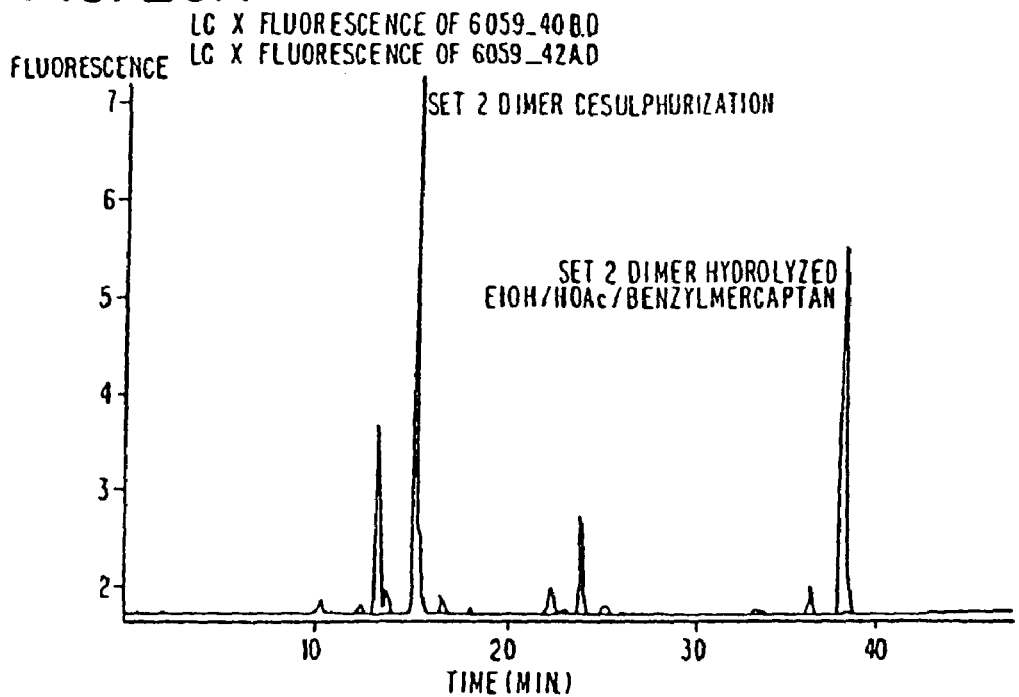
FIG. 26A shows relative fluorescence of dimer upon thiolysis.
Figure 26B:
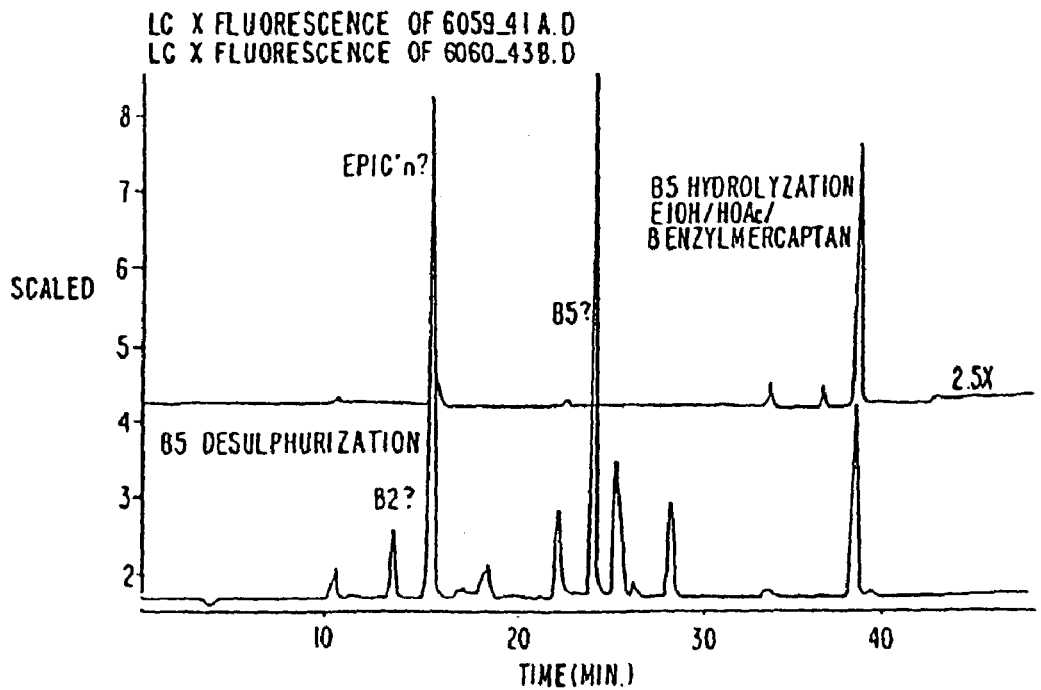
FIG. 26B shows relative fluorescence of B5 dimer upon thiolysis of dimer and subsequent desulphurization.

Dimers B2 and B5 were hydrolyzed with benzylmercaptan by dissolving dimer (B2 or B5; 1.0 mg) in 600 µl ethanol, 40 µL BM and 20 µL acetic acid. The mixture was heated at 95° C. for 4 hours under nitrogen in a Beckman Amino Acid Analysis vessel. Aliquots were removed for analysis by reverse-phase HPLC, and 75 µL of each of ethanol Raney Nickel and gallic acid (10 mg/mL) were added to the remaining reaction medium in a 2 mL hypovial. The vessel was purged under hydrogen, and occasionally shaken for 1 hour. The product was filtered through a 0.45µ filter and analyzed by reverse-phase HPLC. Representative elution profiles are shown in FIGS. 26 A and B. Higher oligomers are similarly desulfurized. This data suggests polymerization of epicatechan or catechin and therefore represents a synthetic route for preparation of inventive compounds.

Example 21

In Vivo Activity of Pentamer in MDA MB 231 Nude Mouse Model

MDA-MB-231/LCC6 cell line. The cell line was grown in improved minimal essential medium (IMEM) containing 10% fetal bovine serum and maintained in a humidified, 5% CO$_2$ atmosphere at 37° C.

Mice. Female six to eight week old NCr nu/nu (athymic) mice were purchased through NCI and housed in an animal facility and maintained according to the regulations set forth by the United States Department of Agriculture, and the American Association for the Accreditation of Laboratory Animal Care. Mice with tumors were weighed every other day, as well as weekly to determine appropriate drug dosing.

Tumor implantation. MDA-MD-231 prepared by tissue culture was diluted with IMEM to $3.3 \times 10^6$ cells/mL and 0.15 mL (i.e. $0.5 \times 10^6$ cells) were injected subcutaneously between nipples 2 and 3 on each side of the mouse. Tumor volume was calculated by multiplying: length×width×height×0.5. Tumor volumes over a treatment group were averaged and Student's t test was used to calculate p value.

Sample preparation. Plasma samples were obtained by cardiac puncture and stored at $-70°$ C. with 15-20 mM EDTA for the purposes of blood chemistry determinations. No differences were noted between the control group and experimental groups.

Fifteen nude mice previously infected with 500,000 cells subcutaneously with tumor cell line MDA-MB-231, were randomly separated into three groups of 5 animals each and treated by intraperitoneal injection with one of: (i) placebo containing vehicle alone (DMSO); (ii) 2 mg/mouse of purified pentameric procyanidin extract as isolated in Example 14 method D in vehicle (DMSO); and (iii) 10 mg/mouse purified pentameric procyanidin extract as isolated in Example 14, method D in vehicle (DMSO).

The group (iii) mice died within approximately 48 to 72 hours after administration of the 10 mg, whereas the group (ii) mice appeared normal. The cause of death of the group (iii) mice was undetermined; and, cannot necessarily be attributed to the administration of inventive compounds. Nonetheless, 10 mg was considered an upper limit with respect to toxicity.

Treatment of groups (i) and (ii) was repeated once a week, and tumor growth was monitored for each experimental and control group. After two weeks of treatment, no signs of toxicity were observed in the mice of group (ii) and, the dose administered to this group was incrementally increase ½ log scale each subsequent week. The following Table represents the dosages administered during the treatment schedule for mice of group (ii):

| Week | Dose (mg/mouse) |
| --- | --- |
| 1 | 2 |
| 2 | 2 |
| 3 | 4 |
| 4 | 5 |
| 5 | 5 |
| 6 | 5 |
| 7 | 5 |

Figure 27A:
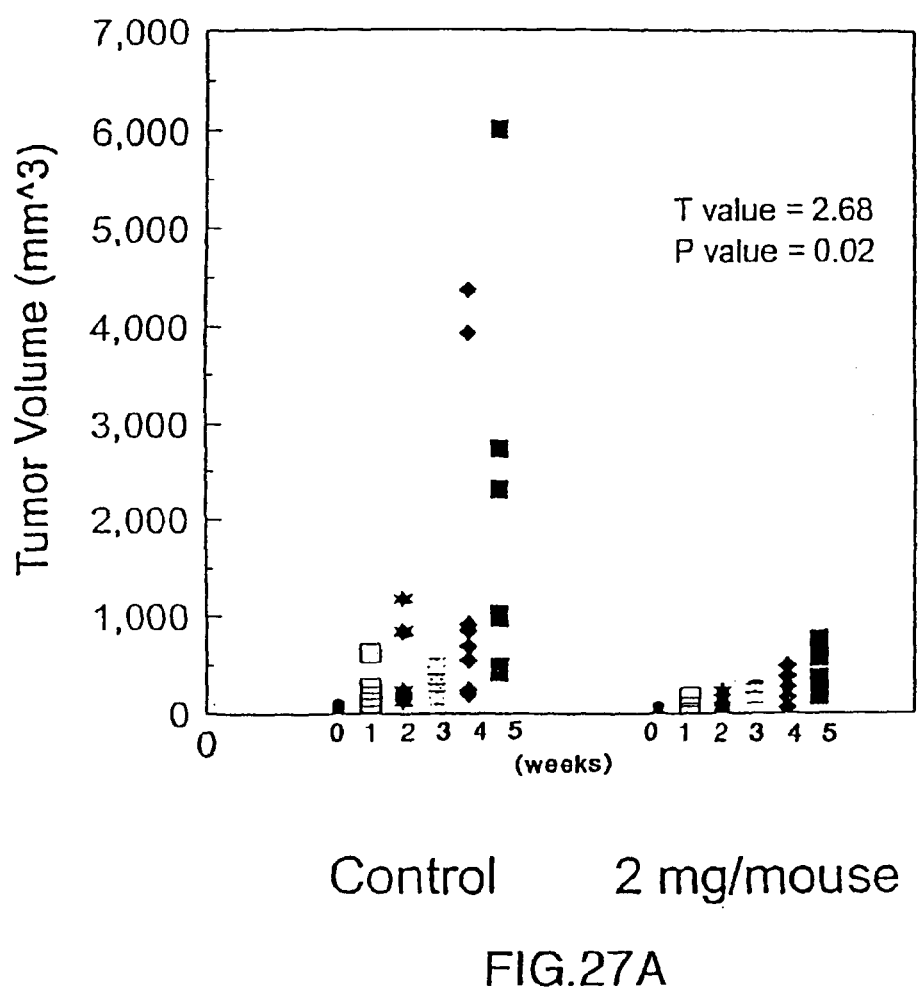
FIG. 27A shows the relative tumor volume during treatment of MDA MB 231 nude mouse model treated with pentamer.
Figure 27B:
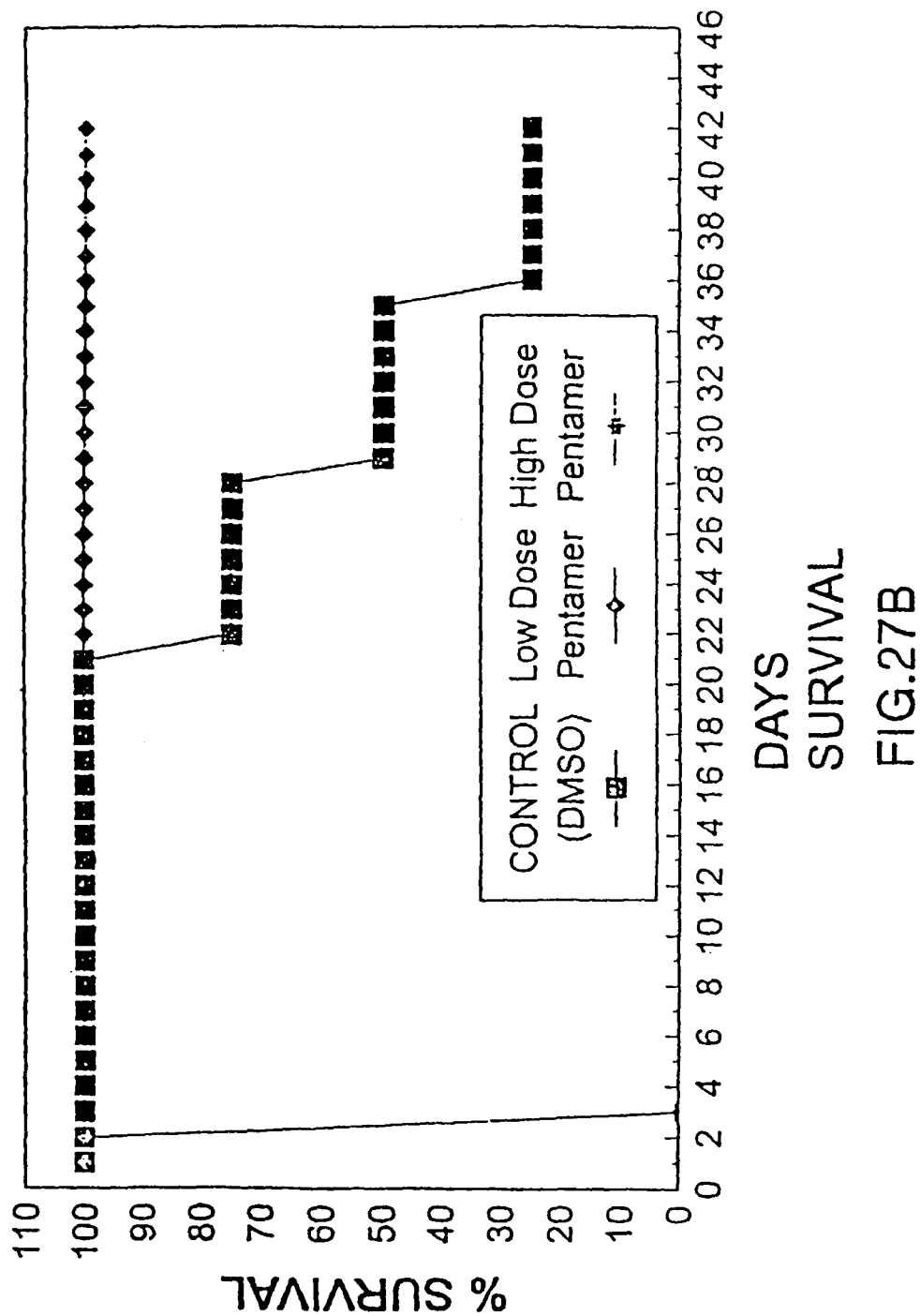
FIG. 27B shows the relative survival curve of pentamer treated MDA 231 nude mouse model.

The results of treatment are shown in FIGS. 27A and B and Table 10.

TABLE 10

IN VIVO ANTI-CANCER RESULTS

| DAY | % SURVIVAL GROUP (i) | % SURVIVAL GROUP (ii) | % SURVIVAL GROUP (iii) |
| --- | --- | --- | --- |
| 1 | 100 | 100 | 100 |
| 2 | 100 | 100 | 100 |
| 3 | 100 | 100 | 0 |
| 4 | 100 | 100 | |
| 5 | 100 | 100 | |
| 6 | 100 | 100 | |
| 7 | 100 | 100 | |
| 8 | 100 | 100 | |
| 9 | 100 | 100 | |
| 10 | 100 | 100 | |
| 11 | 100 | 100 | |
| 12 | 100 | 100 | |
| 13 | 100 | 100 | |
| 14 | 100 | 100 | |
| 15 | 100 | 100 | |
| 16 | 100 | 100 | |
| 17 | 100 | 100 | |
| 18 | 100 | 100 | |
| 19 | 100 | 100 | |
| 20 | 100 | 100 | |
| 21 | 100 | 100 | |
| 22 | 75 | 100 | |
| 23 | 75 | 100 | |
| 24 | 75 | 100 | |
| 25 | 75 | 100 | |
| 26 | 75 | 100 | |
| 27 | 75 | 100 | |
| 28 | 75 | 100 | |
| 29 | 50 | 100 | |
| 30 | 50 | 100 | |
| 31 | 50 | 100 | |
| 32 | 50 | 100 | |
| 33 | 50 | 100 | |
| 34 | 50 | 100 | |
| 35 | 50 | 100 | |
| 36 | 25 | 100 | |
| 37 | 25 | 100 | |
| 38 | 25 | 100 | |
| 39 | 25 | 100 | |
| 40 | 25 | 100 | |
| 41 | 25 | 100 | |
| 42 | 25 | 100 | |
| 43 | 25 | 80 | |
| 44 | 25 | 80 | |
| 45 | 25 | 80 | |
| 46 | 25 | 80 | |
| 47 | 25 | 80 | |
| 48 | 25 | 80 | |
| 49 | 25 | 80 | |
| 50 | 25 | 60 | |
| 51 | 25 | 60 | |
| 52 | 25 | 60 | |
| 53 | 25 | 60 | |
| 54 | 25 | 60 | |
| 55 | 25 | 60 | |
| 56 | 25 | 60 | |
| 57 | 0 | 40 | |
| 58 | | 40 | |
| 59 | | 40 | |
| 60 | | 40 | |
| 61 | | 40 | |
| 62 | | 40 | |
| 63 | | 40 | |
| 64 | | 40 | |

These results demonstrate that the inventive fractions and the inventive compounds indeed have utility in antineoplastic compositions, and are not toxic in low to medium dosages, with toxicity in higher dosages able to be determined without undue experimentation.

Example 22

Antimicrobial Activity of Cocoa Extracts

Method A:

A study was conducted to evaluate the antimicrobial activity of crude procyanidin extracts from cocoa beans against a variety of microorganisms important in food spoilage or pathogenesis. The cocoa extracts from Example 2, method A were used in the study. An agar medium appropriate for the growth of each test culture (99 mL) was seeded with 11 mL of each cell culture suspension in 0.45% saline (final population $10^2$-$10^4$ cfu/mL), and poured into petri dishes. Wells were cut into hardened agar with a #2 cork borer (5 mm diameter). The plates were refrigerated at 4° C. overnight, to allow for diffusion of the extract into the agar, and subsequently incubated at an appropriate growth temperature for the text organism. The results were as follows:

Sample Zone of Inhibition (mm)

| Extract Concentration (mg/mL) | B. sphericus | B. cereus | S. aureus | P. aeruginosa | B. subtilis |
|---|---|---|---|---|---|
| 0 | NI | NI | NI | NI | NI |
| 25 | NI | 12 | NI | 11 | NI |
| 250 | 12 | 20 | 19 | 19 | 11 |
| 500 | 14 | 21 | 21 | 21 | 13 |

NI = no inhibition

Antimicrobial activity of purified procyanidin extracts from cocoa beans was demonstrated in another study using the well diffusion assay described above (in Method A) with *Staphylococcus aureus* as the text culture. The results were as follows:

cocoa extracts: 10 mg/100 μL decaffeinated/detheobrominated acetone extract as in Example 13, method A
   10 mg/100 μL dimer (99% pure) as in Example 14, method D
   10 mg/100 μL tetramer (95% pure) as in Example 14, method D
   10 mg/100 μL hexamer (88% pure) as in Example 14, method D
   10 mg/100 μL octamer/nonamer (92% pure) as in Example 14, method D
   10 mg/100 μL nonamer & higher (87% pure) as in Example 14, method D Sample Zone of Inhibition (mm)

| | |
|---|---|
| 0.45% saline | 0 |
| Dimer | 33 |
| Tetramer | 27 |
| Hexamer | 24 |
| 0.45% saline | 0 |
| Octamer | 22 |
| Nonamer | 20 |
| Decaff./detheo. | 26 |

Method B:

Crude procyanidin extract as in Example 2, method 2 was added in varying concentrations to TSB (Trypticase Soy Broth) with phenol red (0.08 g/L), The TSB were inoculated with cultures of *Salmonella enteritidis* or *S. newport* ($10^5$ cfu/mL), and were incubated for 18 hours at 35° C. The results were as follows:

| | S. enteritidis | S. Newport |
|---|---|---|
| 0 mg/mL | + | + |
| 50 | + | + |
| 100 | + | + |
| 250 | + | − |
| 500 | − | − |
| 750 | − | − | where
+ = outgrowth, and
− = no growth, as evidenced by the change in broth culture from red to yellow with acid production.
Confirmation of inhibition was made by plating from TSB tubes onto XLD plates.

This Example demonstrates that the inventive compounds are useful in food preparation and preservation.

This Example further demonstrates that gram negative and gram positive bacterial growth can be inhibited by the inventive compounds. From this, the inventive compounds can be used to inhibit *Helicobacter pylori*. *Helicobacter pylori* has been implicated in causing gastric ulcers and stomach cancer. Accordingly, the inventive compounds can be used to treat or prevent these and other maladies of bacterial origin. Suitable routes of administration, dosages, and formulations can be determined without undue experimentation considering factors well known in the art such as the malady, and the age, weight, sex, general health of the subject.

Example 23

Halogen-Free Analytical Separation of Extract

Figure 28:
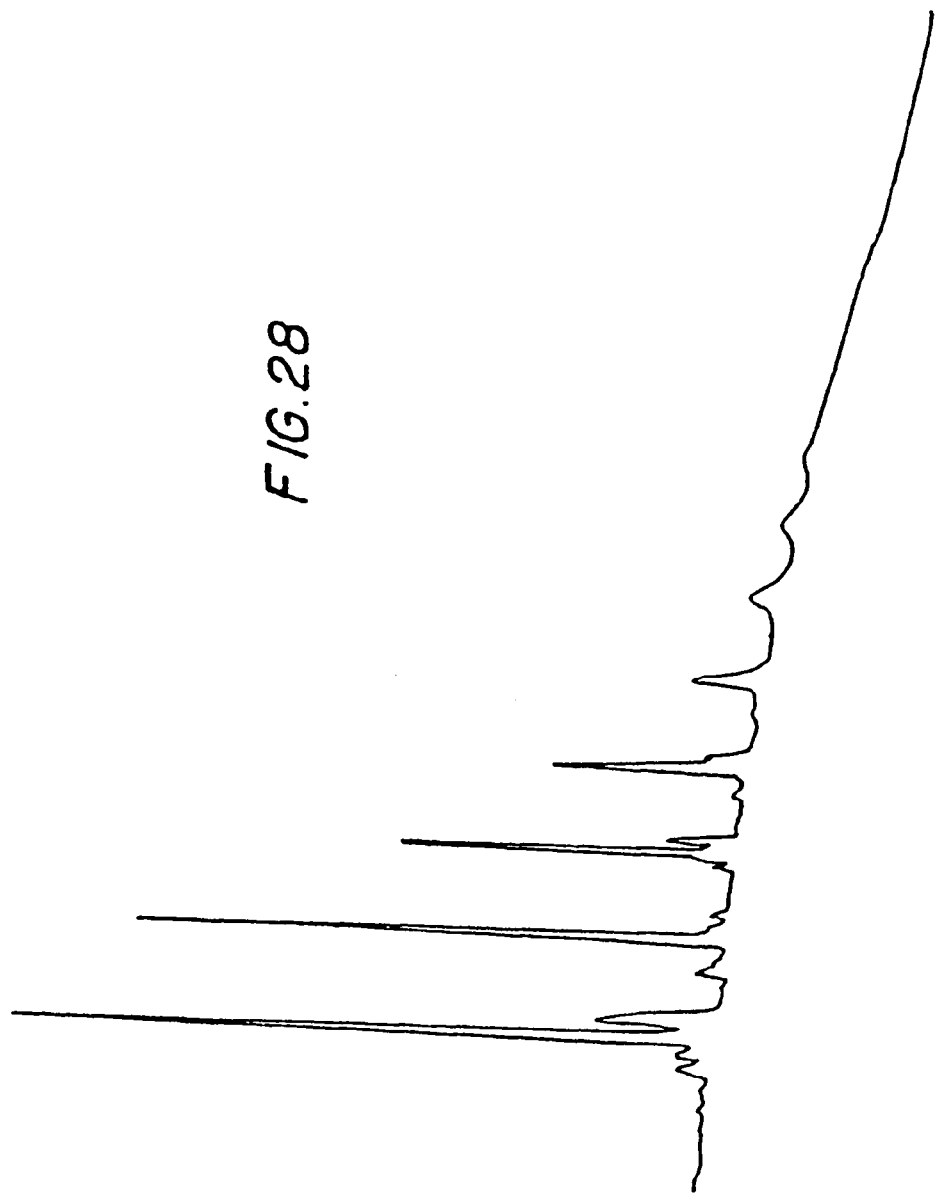
FIG. 28 shows the elution profile from halogen-free analytical separation of acetone extract of procyanidins from cocoa extract.

Procyanidins obtained from Example 2 were partially purified by Analytical Separation by Halogen-free Normal Phase Chromatography on 100 Å Supelcosil LC-Si 5 μm (250×4.6 mm), at a flow rate of 1.0 mL/min, and a column temperature of 37° C. Separations were aided by a linear gradient under the following conditions: (time, % A, % B); (0, 82, 14); (30, 67.6, 28.4); (60, 46, 50). Mobile phase composition was A=30/70% diethyl ether/Toluene; B=Methanol; and C=acetic acid/water (1:1). Components were detected by UV at 280 nm. A representative elution profile is shown in FIG. 28.

Example 24

Figure 29A:
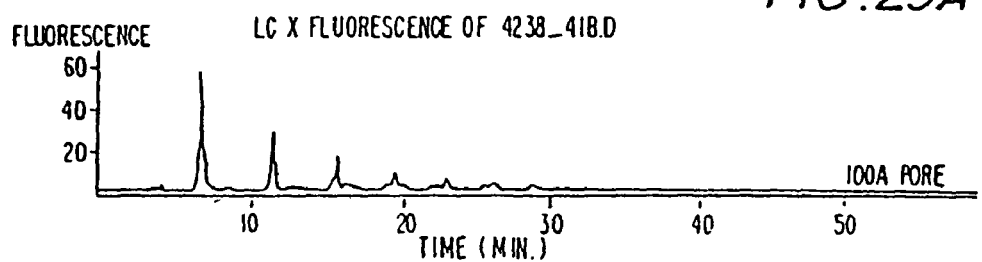
FIGS. 29A, 29B, and 29C show the effect if pore size of stationary phase for normal phase HPLC separation of procyanidins.
Figure 29B:
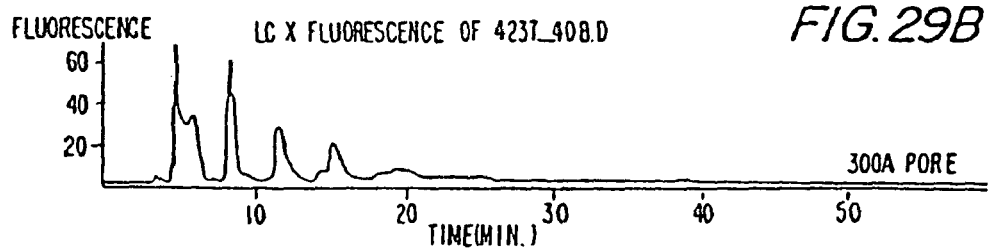
Figure 29C:
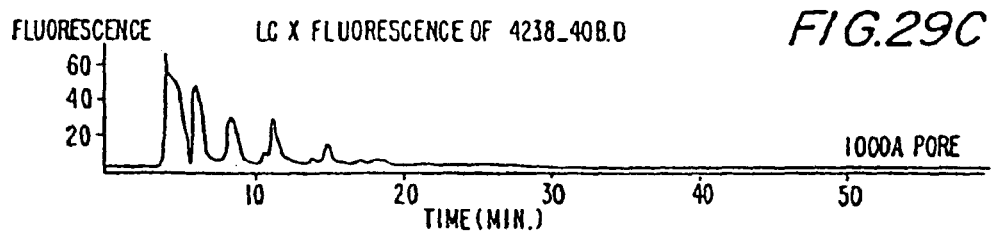

Effect of Pore Size of Stationary Phase for Normal Phase HPLC Separation of Procyanidins To improve the separation of procyanidins, the use of a larger pore size of the silica stationary phase was investigated. Separations were effected on Silica-300, 5 μm, 300 Å (250×2.0 mm), or, in the alternative, on Silica-1000, 5 μm, 1000 Å (250×2.0 mm). A linear gradient was employed as mobile phase composition was: A=Dichloromethane; B=Methanol; and C=acetic acid/water (1:1). Components were detected by fluorescence, wherein $\lambda_{ex}$=276 nm and $\lambda_{em}$=316 nm, by UV detector at 280 nm. The flow rate was 1.0 mL/min, and the oven temperature was 37° C. A representative chromatogram from three different columns (100 Å pore size, from Example 13, Method D) is shown in FIG. 29. This shows effective pore size for separation of procyanidins.

Example 25

Obtaining Desired Procyanidins Via Manipulating Fermentation

Microbial strains representative of the succession associated with cocoa fermentation were selected from the M&M/Mars cocoa culture collection. The following isolates were used:

Acetobacter aceti ATCC 15973
Lactobacillus sp. (BH 42)
Candida cruzii (BA 15)
Saccharomyces cerevisiae (BA 13)
Bacillus cereus (BE 35)
Bacillus sphaericus (ME 12)

Each strain was transferred from stock culture to fresh media. The yeasts and Acetobacter were incubated 72 hours at 26° C. and the bacilli and Lactobacillus were incubated 48 hours at 37° C. The slants were harvested with 5 mL phosphate buffer prior to use.

Cocoa beans were harvested from fresh pods and the pulp and testa removed. The beans were sterilized with hydrogen peroxide (35%) for 20 seconds, followed by treatment with catalase until cessation of bubbling. The beans were rinsed twice with sterile water and the process repeated. The beans were divided into glass jars and processed according to the regimens detailed in the following Table:

| Water | Ethanol/acid | Fermentation infusate | Model Fermentation |
|---|---|---|---|
| daily transfer to fresh water | daily transfer to solutions of alcohol and acid corresponding to levels determined at each stage of a model pulp fermentation | daily transfer to fermented pulp pasteurized on each successive day of fermentation | bench scale model fermentation in sterile pulp coinoculated with test strains |

The bench scale fermentation was performed in duplicate. All treatments were incubated as indicated below:
Day 1: 26° C.
Day 2: 26° C. to 50° C.
Day 3: 50° C.
Day 4: 45° C.
Day 5: 40° C.

Figure 30A:
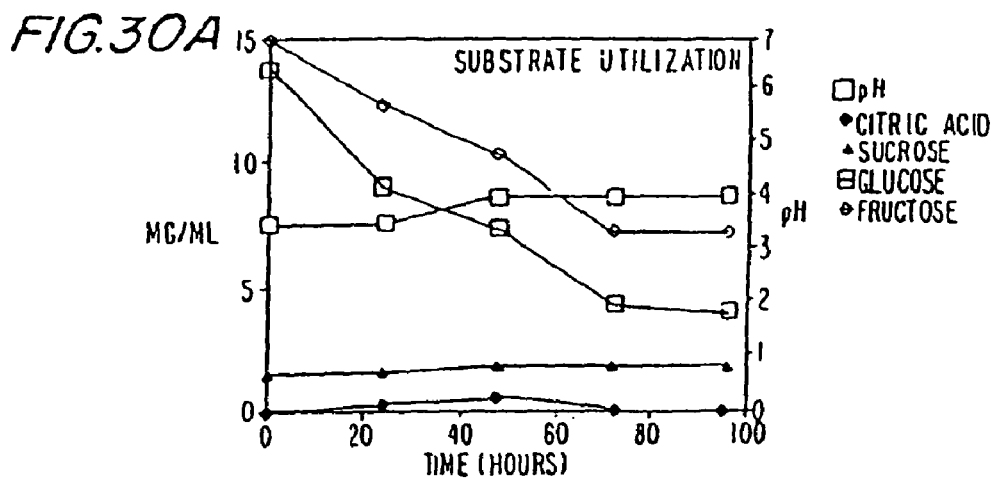
FIG. 30A shows the substrate utilization during fermentation of cocoa beans.
Figure 30B:
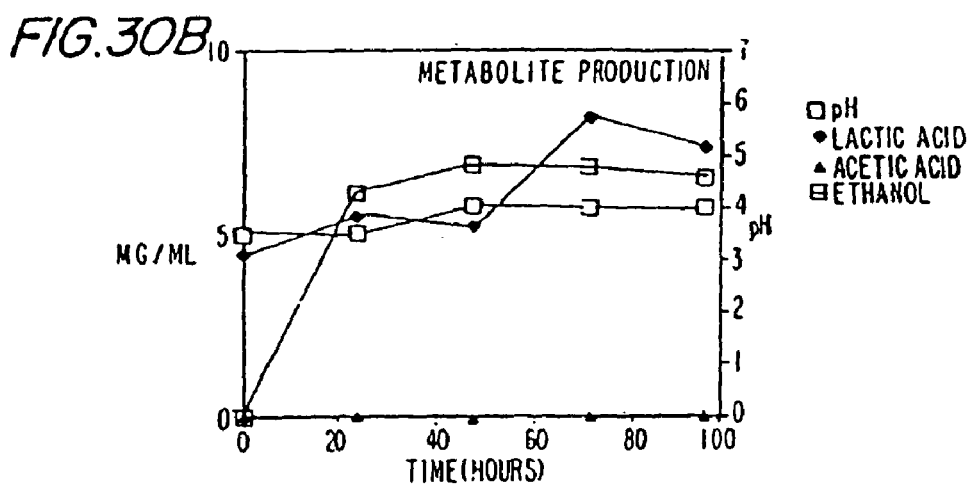
FIG. 30B shows the metabolite production during fermentation.
Figure 30C:
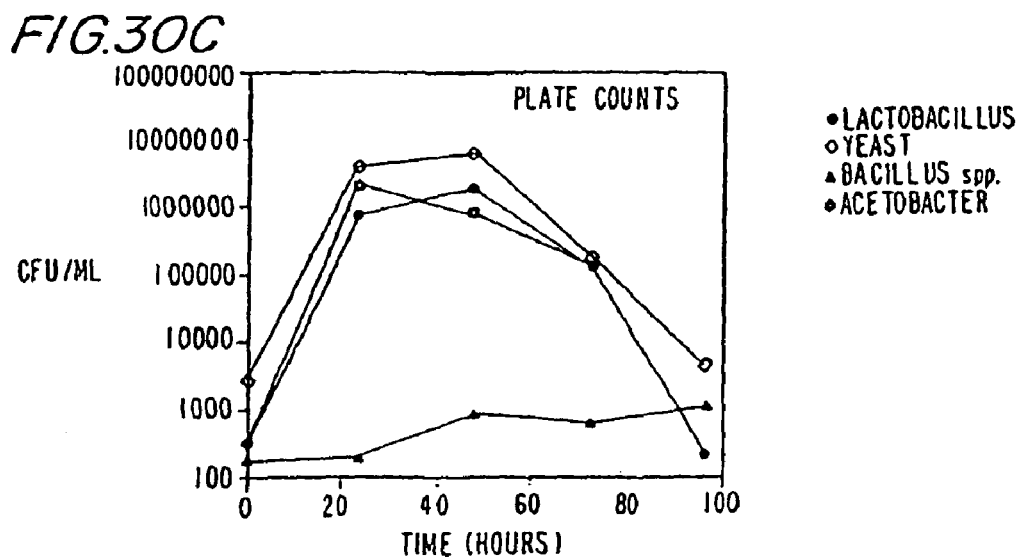
FIG. 30C shows the plate counts during fermentation of cocoa beans.
Figure 30D:
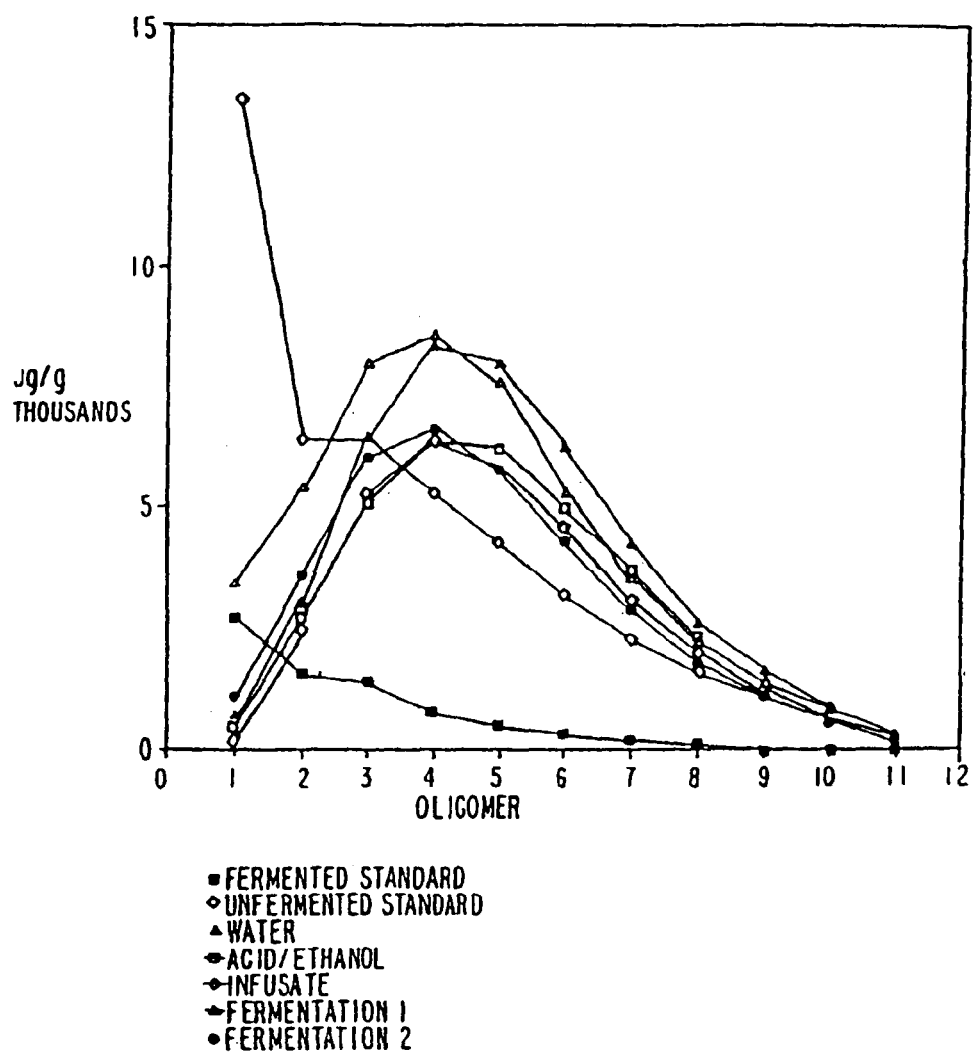
FIG. 30D shows the relative concentrations of each component in fermented solutions of cocoa beans.

The model fermentation was monitored over the duration of the study by plate counts to assess the microbial population and HPLC analysis of the fermentation medium for the production of microbial metabolites. After treatment, the beans were dried under a laminar flow hood to a water activity of 0.64 and were roasted at 66° C. for 15 min. Samples were prepared for procyanidin analysis. Three beans per treatment were ground and defatted with hexane, followed by extraction with an acetone:water:acetic acid (70:29.5:0.5%) solution. The acetone solution extract was filtered into vials and polyphenol levels were quantified by normal phase HPLC as in Example 13, method B. The remaining beans were ground and tasted. The cultural and analytical profiles of the model bench-top fermentation process is shown in FIGS. 30A-C. The procyanidin profiles of cocoa beans subjected to various fermentation treatments is shown in FIG. 30D.

This Example demonstrates that the invention need not be limited to any particular cocoa genotype; and, that by manipulating fermentation, the levels of procyanidins produced by a particular Theobroma or Herrania species or their inter or intra species specific crosses thereof can be modulated, e.g., enhanced.

The following Table shows procyanidin levels determined in specimens which are representative of the Theobroma genus and their inter and intra species specific crosses. Samples were prepared as in Examples 1 and 2 (methods 1 and 2), and analyzed as in Examples 13, method B. This data illustrates that the extracts containing the inventive compounds are found in Theobroma and Herrania species, and their intra and inter species specific crosses.

Theobroma and Herrania Species Procyanidin Levels
ppm (μg/g) in defatted powder
Oligomer

| SAMPLE | Monomer | Dimer | Trimer | Tetramer | Pentamer | Hexamer | Heptamer | Octamer | Nonamer | Decamer | Undecamer | Total |
|---|---|---|---|---|---|---|---|---|---|---|---|---|
| T. grandiflorum × T. obovatum 1[1] | 3822 | 3442 | 5384 | 4074 | 3146 | 2080 | 850 | 421 | 348 | 198 | tr+ | 23,765 |
| T. grandiflorum × T. obovatum 2[1] | 3003 | 4098 | 5411 | 3983 | 2931 | 1914 | 1090 | 577 | 356 | 198 | tr | 23,561 |
| T. grandiflorum × T. obovatum 3A[1] | 4990 | 4980 | 7556 | 5341 | 4008 | 2576 | 1075 | 598 | 301 | 144 | tr | 31,569 |
| T. grandiflorum × T. obovatum 3B[1] | 3880 | 4498 | 6488 | 4930 | 3706 | 2560 | 1208 | 593 | 323 | 174 | tr | 28,360 |
| T. grandiflorum × T. obovatum 4[1] | 2647 | 3591 | 5328 | 4240 | 3304 | 2380 | 1506 | 815 | 506 | 249 | tr | 24,566 |
| T. grandiflorum × T. obovatum 6[1] | 2754 | 3855 | 5299 | 3872 | 2994 | 1990 | 1158 | 629 | 359 | 196 | 88 | 23,194 |
| T. grandiflorum × T. obovatum SIN[1] | 3212 | 4134 | 7608 | 4736 | 3590 | 2274 | 936 | 446 | 278 | 126 | ND* | 23,750 |
| T. obovatum 1[1] | 3662 | 5683 | 9512 | 5358 | 3858 | 2454 | 1207 | 640 | 302 | 144 | ND | 32,820 |
| T. grandiflorum TEFFE[2] | 2608 | 2178 | 3090 | 2704 | 2241 | 1586 | 900 | 484 | 301 | 148 | tr | 16,240 |
| T. grandiflorum TEFFE × T. grandiflorum[2] | 4773 | 4096 | 5289 | 4748 | 3804 | 2444 | 998 | 737 | 335 | 156 | tr | 27,380 |

-continued

Theobroma and Herrania Species Procyanidin Levels
ppm (µg/g) in defatted powder

| SAMPLE | Monomer | Dimer | Trimer | Tetramer | Pentamer | Hexamer | Heptamer | Octamer | Nonamer | Decamer | Undecamer | Total |
|---|---|---|---|---|---|---|---|---|---|---|---|---|
| T. grandiflorum × T. subincanum[1] | 4752 | 3336 | 4916 | 3900 | 3064 | 2039 | 782 | 435 | 380 | 228 | ND | 23,832 |
| T. obovatum × T. subincanum[1] | 3379 | 3802 | 5836 | 3940 | 2868 | 1807 | 814 | 427 | 271 | 136 | tr | 23,280 |
| T. speciosum × T. sylvestris[1] | 902 | 346 | 1350 | 217 | 152 | 120 | 60 | tr | tr | ND | ND | 3,147 |
| T. microcarpum[2] | 5694 | 3250 | 2766 | 1490 | 822 | 356 | 141 | tr | ND | ND | ND | 14,519 |
| T. cacao, SIAL 659, t0 | 21,929 | 10,072 | 10,106 | 7788 | 5311 | 3242 | 1311 | 626 | 422 | 146 | tr | 60,753 |
| T. cacao, SIAL 659, t24 | 21,088 | 9762 | 9119 | 7094 | 4774 | 2906 | 1364 | 608 | 361 | 176 | tr | 57,252 |
| T. cacao, SIAL 659, t48 | 20,887 | 9892 | 9474 | 7337 | 4906 | 2929 | 1334 | 692 | 412 | 302 | tr | 58,165 |
| T. cacao, SIAL 659, t96 | 9552 | 5780 | 5062 | 3360 | 2140 | 1160 | 464 | 254 | 138 | tr | ND | 27,910 |
| T. cacao, SIAL 659, t120 | 8581 | 4665 | 4070 | 2527 | 1628 | 888 | 326 | 166 | 123 | tr | ND | 22,974 |
| Pod Rec. October 1996, Herrania mariae | 869 | 1295 | 545 | 347 | 175 | 97 | tr | *ND | ND | | | 3329 |
| Sample Rec. prior to October 1996, Herrania mariae | 130 | 354 | 151 | 131 | 116 | 51 | tr | ND | ND | | | 933 |

*ND = none detected
[1]sample designated CPATU
+tr = trace (<50 µg/g)
[2]sample designated ERJON

Example 26

Effect of Procyanidins on NO Method A

The purpose of this study is to establish the relationship between procyanidins (as in Example 14, method D) and NO, which is known to induce cerebral vascular dilation. The effects of monomers and higher oligomers, in concentrations ranging from 100 µg/mL to 0.1 µg/mL, on the production of nitrates (the catabolites of NO), from HUVEC (human umbilical vein endothelial cells) is evaluated. HUVEC (from Clonetics) is investigated in the presence or absence of each procyanidin for 24 to 48 hours. At the end of the experiments, the supernatants are collected and the nitrate content determined by calorimetric assay. In separate experiments, HUVEC is incubated with acetylcholine, which is known to induce NO production, in the presence or absence of procyanidins for 24 to 48 hours. At the end of the experiments, the supernatants are collected and nitrate content is determined by calorimetric assay. The role of NO is ascertained by the addition of nitroarginine or (1)-N-methyl arginine, which are specific blockers of NO synthase.

Method B. Vasorelaxation of Phenylephrine-Induced Contracted Rat Artery

Figure 31:
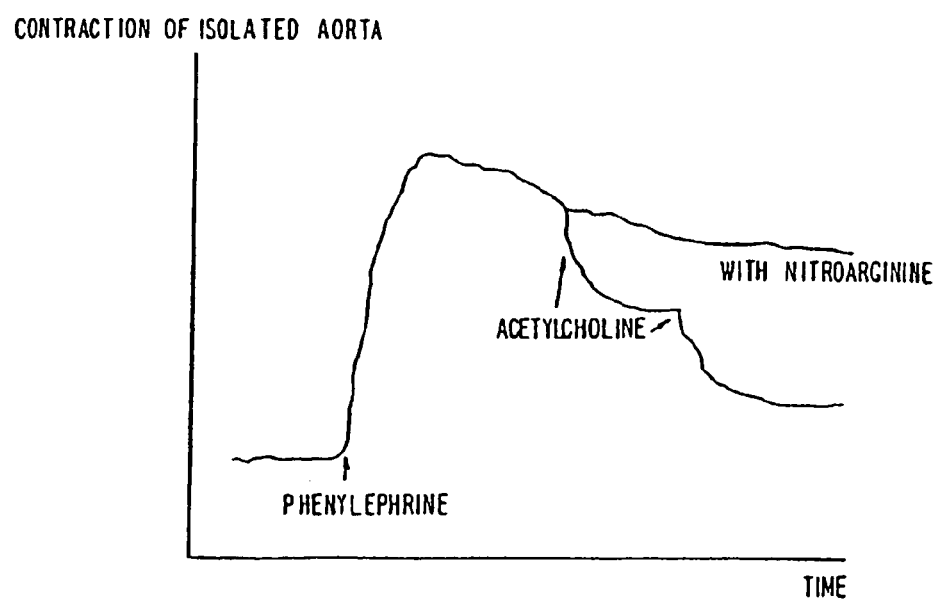
FIG. 31 shows the acetylcholine-induced relaxation of NO-related phenylephrine-precontracted rat aorta.

The effects of each of the procyanidins (100 µg/mL to 0.1 µg/mL on the rat artery is the target for study of vasorelaxation of phenylephrine-induced contracted rat artery. Isolated rat artery is incubated in the presence or absence of procyanidins (as in Example 14, method D) and alteration of the muscular tone is assessed by visual inspection. Both contraction or relaxation of the ray artery is determined. Then, using other organs, precontraction of the isolated rat artery is induced upon addition of epinephrine. Once the contraction is stabilized, procyanidins are added and contraction or relaxation of the rat artery is determined. The role of NO is ascertained by the addition of nitroarginine or (1)-N-methyl arginine. The acetylcholine-induced relaxation of NO, as it is effected by phenylephrine-precontracted rat aorta is shown in FIG. 31.

Method C. Induction of Hypotension in the Rat

This method is directed to the effect of each procyanidin (as in Example 14, method D) on blood pressure. Rats are instrumented in order to monitor systolic and diastolic blood pressure. Each of the procyanidins are injected intravenously (dosage range=100-0.1 µg/kg), and alteration of blood pressure is assessed. In addition, the effect of each procyanidin on the alteration of blood pressure evoked by epinephrine is determined. The role of NO is ascertained by the addition of nitroarginine or (1)-N-methyl arginine.

These studies, together with next Example, illustrate that the inventive compounds are useful in modulating vasodilation, and are further useful with respect to modulating blood pressure or addressing coronary conditions, and migraine headache conditions.

Example 27

Effects of Cocoa Polyphenols on Satiety

Using blood glucose levels as an indicator for the signal events which occur in vivo for the regulation of appetite and satiety, a series of simple experiments were conducted using a healthy male adult volunteer age 48 to determine whether cocoa polyphenols would modulate glucose levels. Cocoa polyphenols were partially purified from Brazilian cocoa beans according to the methods described by Clapperton et al. (1992). This material contained no caffeine or theobromine.

Fasting blood glucose levels were analyzed on a timed basis after ingestion of 10 fl. oz of Dexicola 75 (caffeine free) Glucose tolerance test beverage (Curtin Matheson 091-421) with and without 75 mg cocoa polyphenols. This level of polyphenols represented 0.1% of the total glucose of the test beverage and reflected the approximate amount that would be present in a standard 100 g chocolate bar. Blood glucose levels were determined by using the Accu-Chek III blood glucose monitoring system (Boehringer Mannheim Corporation). Blood glucose levels were measured before ingestion of test beverage, and after ingestion of the test beverage at the following timed intervals: 15, 30, 45, 60, 75, 90, 120 and 180 minutes. Before the start of each glucose tolerance test, high and low glucose level controls were determined. Each glucose tolerance test was performed in duplicate. A control test solution containing 75 mg cocoa polyphenols dissolved in 10 fl. oz. distilled water (no glucose) was also performed.

Table 11 below lists the dates and control values obtained for each glucose tolerance experiment performed in this study. FIG. 32 represents plots of the average values with standard deviations of blood glucose levels obtained throughout a three hour time course. It is readily apparent that there is a substantial increase in blood sugar levels was obtained after ingestion of a test mixture containing cocoa polyphenols. The difference between the two principal glucose tolerance profiles could not be resolved by the profile obtained after ingestion of a solution of cocoa polyphenols alone. The addition of cocoa polyphenols to the glucose test beverage raised the glucose tolerance profile significantly. This elevation in blood glucose levels is within the range considered to be mildly diabetic, even though the typical glucose tolerance profile was considered to be normal (Davidson, I. et al., Eds. Todd—Sandford Clinical Diagnosis by Laboratory Methods 14$^{th}$ edition; W.B. Saunders Co.; Philadelphia, Pa. 1969 Ch. 10, pp. 550-9). This suggests that the difference in additional glucose was released to the bloodstream, from the glycogen stores, as a result of the inventive compounds. Thus, the inventive compounds can be used to modulate blood glucose levels when in the presence of sugars.

TABLE 11

Glucose Tolerance Test Dates and Control Results

| WEEK | DESCRIPTION | HIGH CONTROL[a] | LOW CONTROL[b] |
|---|---|---|---|
| 0 | Glucose Tolerance | 265 mg/dL | 53 mg/dL |
| 1 | Glucose Tolerance with 0.1% polyphenols | 310 | 68 |
| 2 | Glucose Tolerance | 315 | 66 |
| 4 | Glucose Tolerance with 0.1% polyphenols | 325 | 65 |
| 5 | 0.1% polyphenols | 321 | 66 |

[a] = Expected range: 253-373 mg/dL
[b] = Expected range: 50-80 mg/dL

The subject also experienced a facial flush (erythema) and lightheadedness following ingestion of the inventive compounds, indicating modulation of vasodilation.

The data presented in Tables 12 and 13 illustrates the fact that extracts of the invention pertaining to cocoa raw materials and commercial chocolates, and inventive compounds contained therein can be used as a vehicle for pharmaceutical, veterinary and food science preparations and applications.

TABLE 12

Procyanidin Levels in Commercial Chocolates
µg/g

| Sample | Monomers | Dimers | Trimers | Tetramers | Pentamers | Hexamers | Heptamers and Higher | Total |
|---|---|---|---|---|---|---|---|---|
| Brand 1 | 366 | 166 | 113 | 59 | 56 | 23 | 18 | 801 |
| Brand 2 | 344 | 163 | 111 | 45 | 48 | ND* | ND | 711 |
| Brand 3 | 316 | 181 | 100 | 41 | 40 | 7 | ND | 685 |
| Brand 4 | 310 | 122 | 71 | 27 | 28 | 5 | ND | 563 |
| Brand 5 | 259 | 135 | 90 | 46 | 29 | ND | ND | 559 |
| Brand 6 | 308 | 139 | 91 | 57 | 47 | 14 | ND | 656 |
| Brand 7 | 196 | 98 | 81 | 58 | 54 | 19 | ND | 506 |
| Brand 8 | 716 | 472 | 302 | 170 | 117 | 18 | ND | 1,795 |
| Brand 9 | 1,185 | 951 | 633 | 298 | 173 | 25 | 21 | 3,286 |
| Brand 10 | 1,798 | 1,081 | 590 | 342 | 307 | 93 | ND | 4,211 |
| Brand 11 | 1,101 | 746 | 646 | 372 | 347 | 130 | 75 | 3,417 |
| Brand 12 | 787 | 335 | 160 | 20 | 10 | 8 | ND | 1,320 |

ND* = None detected.

TABLE 13

Procyanidin Levels in Cocoa Raw Materials
µg/g

| Sample | Monomers | Dimers | Trimers | Tetramers | Pentamers | Hexamers | Heptamers and Higher | Total |
|---|---|---|---|---|---|---|---|---|
| Unfermented | 13,440 | 6,425 | 6,401 | 5,292 | 4,236 | 3,203 | 5,913 | 44,910 |
| Fermented | 2,695 | 1,538 | 1,362 | 740 | 470 | 301 | 277 | 7,383 |
| Roasted | 2,656 | 1,597 | 921 | 337 | 164 | ND* | ND | 5,675 |
| Choc. Liquor | 2,805 | 1,446 | 881 | 442 | 184 | 108 | ND | 5,866 |
| Cocoa Hulls | 114 | 53 | 14 | ND | ND | ND | ND | 181 |
| Cocoa Powder 1% Fat | 506 | 287 | 112 | ND | ND | ND | ND | 915 |
| Cocoa Powder 11% Fat | 1,523 | 1,224 | 680 | 46 | ND | ND | ND | 3,473 |
| Red Dutch Cocoa Powder, pH 7.4, 11% fat | 1,222 | 483 | 103 | ND | ND | ND | ND | 1,808 |

TABLE 13-continued

Procyanidin Levels in Cocoa Raw Materials
μg/g

| Sample | Monomers | Dimers | Trimers | Tetramers | Pentamers | Hexamers | Heptamers and Higher | Total |
|---|---|---|---|---|---|---|---|---|
| Red Dutch Cocoa Powder, pH 8.2, 23% fat | 168 | 144 | 60 | ND | ND | ND | ND | 372 |

ND* = None detected.

Example 28

The Effect of Procyanidins on Cyclooxygenase 1 & 2

The effect of procyanidins on cyclooxygenase 1 & 2 (COX1/COX2) activities was assessed by incubating the enzymes, derived from ram seminal vesicle and sheep placenta, respectively, with arachidonic acid (5 μM) for 10 minutes at room temperature, in the presence of varying concentration of procyanidin solutions containing monomer to decamer and procyanidin mixture. Turnover was assessed by using PGE2 EIA kits from Interchim (France). Indomethacin was used as a reference compound. The results are presented in the following Table, wherein the $IC_{50}$ values are expressed in units of μM (except for S11, which represents a procyanidin mixture prepared from Example 13. Method A and where the samples S1 to S10 represent sequentially procyanidin oligomers (monomer through decamer) as in Example 14, Method D, and $IC_{50}$ is expressed in units of mg/mL).

| SAMPLE # | $IC_{50}$ COX-1 (*) | $IC_{50}$ COX-2 (*) | RATIO $IC_{50}$ COX2/COX1 |
|---|---|---|---|
| 1 | 0.074 | 0.197 | 2.66 |
| 2 | 0.115 | 0.444 | 3.86 |
| 3 | 0.258 | 0.763 | 2.96 |
| 4 | 0.154 | 3.73 | 24.22 |
| 5 | 0.787 | 3.16 | 4.02 |
| 6 | 1.14 | 1.99 | 1.75 |
| 7 | 1.89 | 4.06 | 2.15 |
| 8 | 2.25 | 7.2 | 3.20 |
| 9 | 2.58 | 2.08 | 0.81 |
| 10 | 3.65 | 3.16 | 0.87 |
| 11 | 0.0487 | 0.0741 | 1.52 |
| Indomethacin | 0.599 | 13.5 | 22.54 |

(*) expressed as uM with the exception of sample 11, which is mg/mL.

Figure 34A:
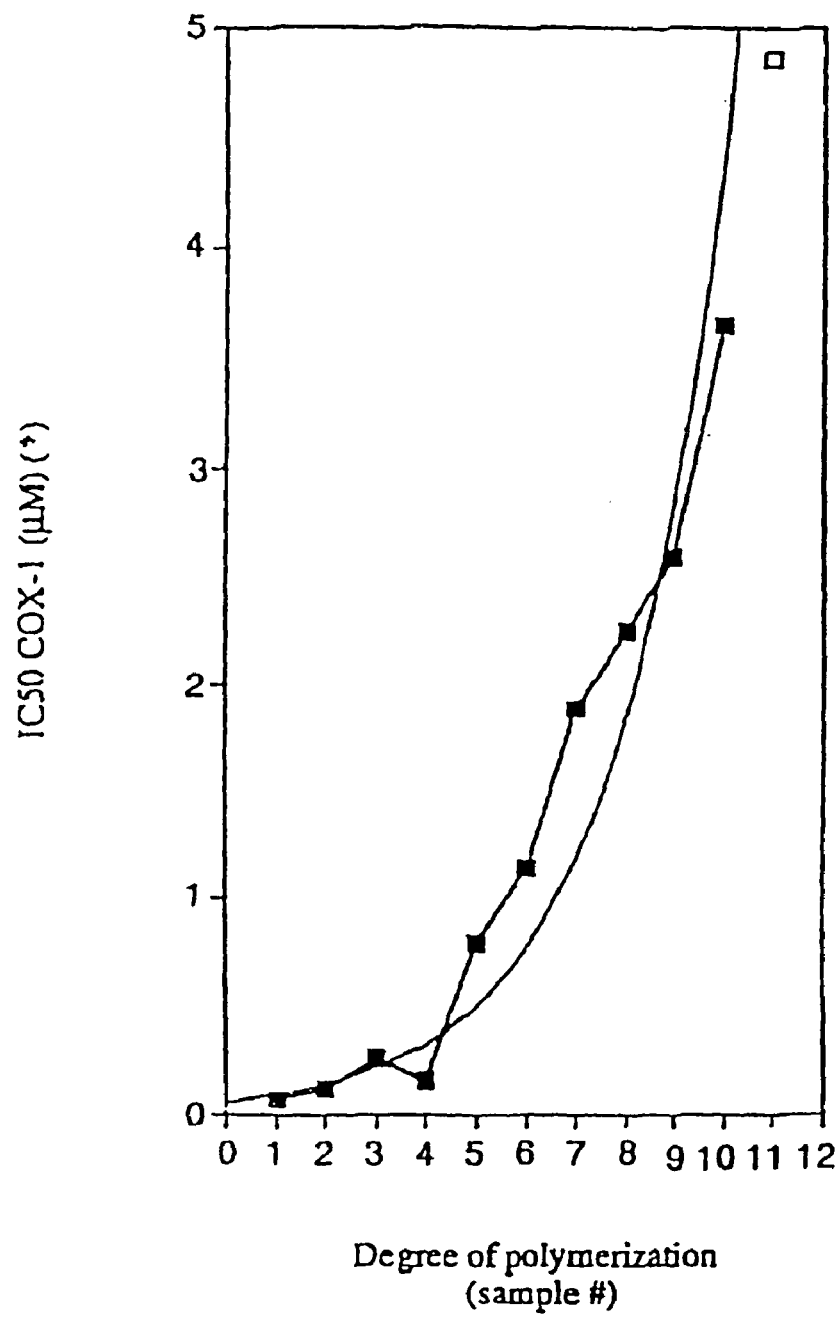
FIGS. 34A-B show the correlation between the degree of polymerization and $IC_{50}$ vs. COX-1/COX-2 (μM)
Figure 34B:
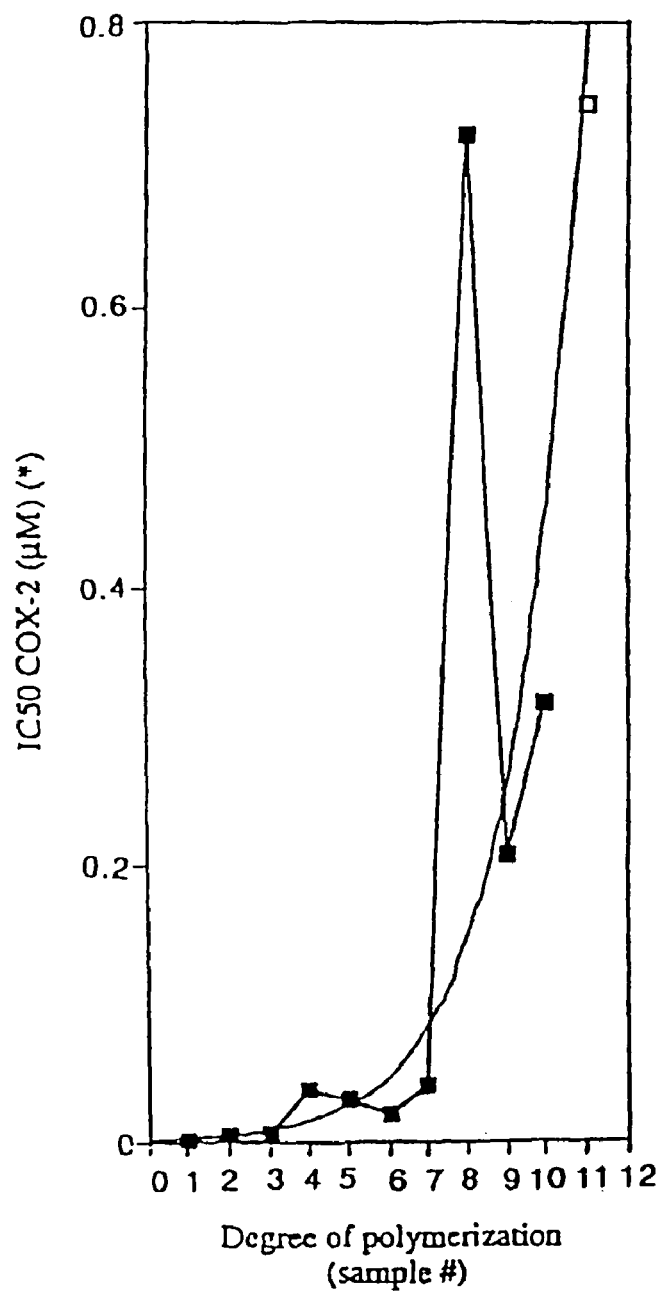
Figure 35:
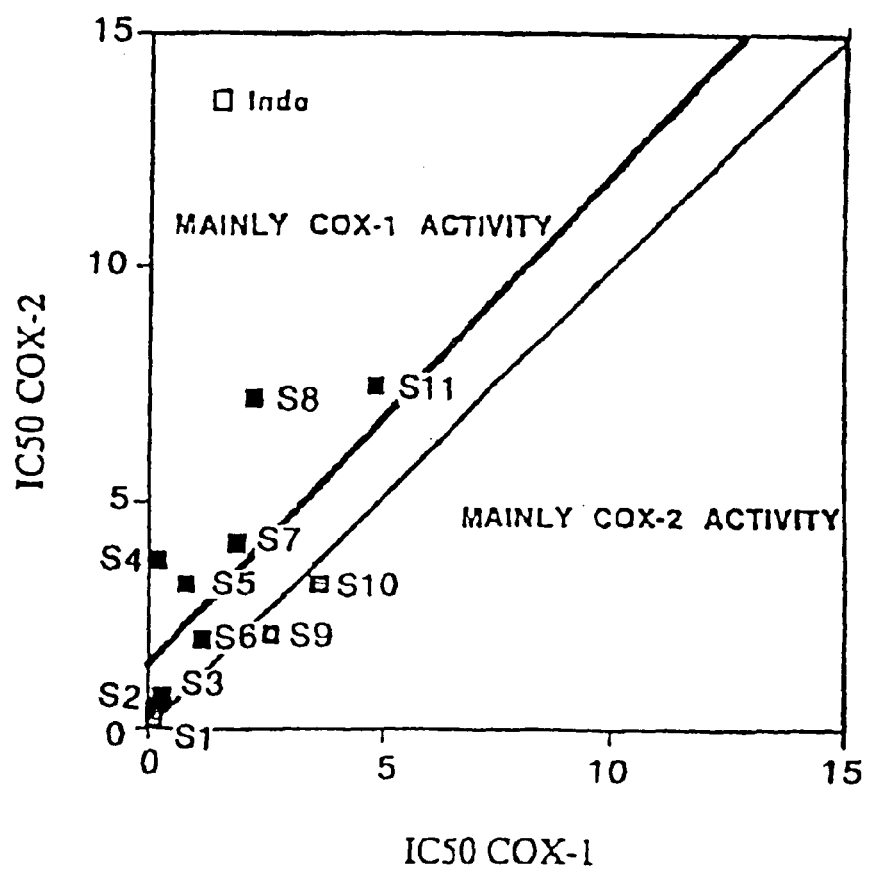
FIG. 35 shows the correlation between the effects of compounds on COX-1 and COX-2 activities expressed as μM.
Figure 36A:
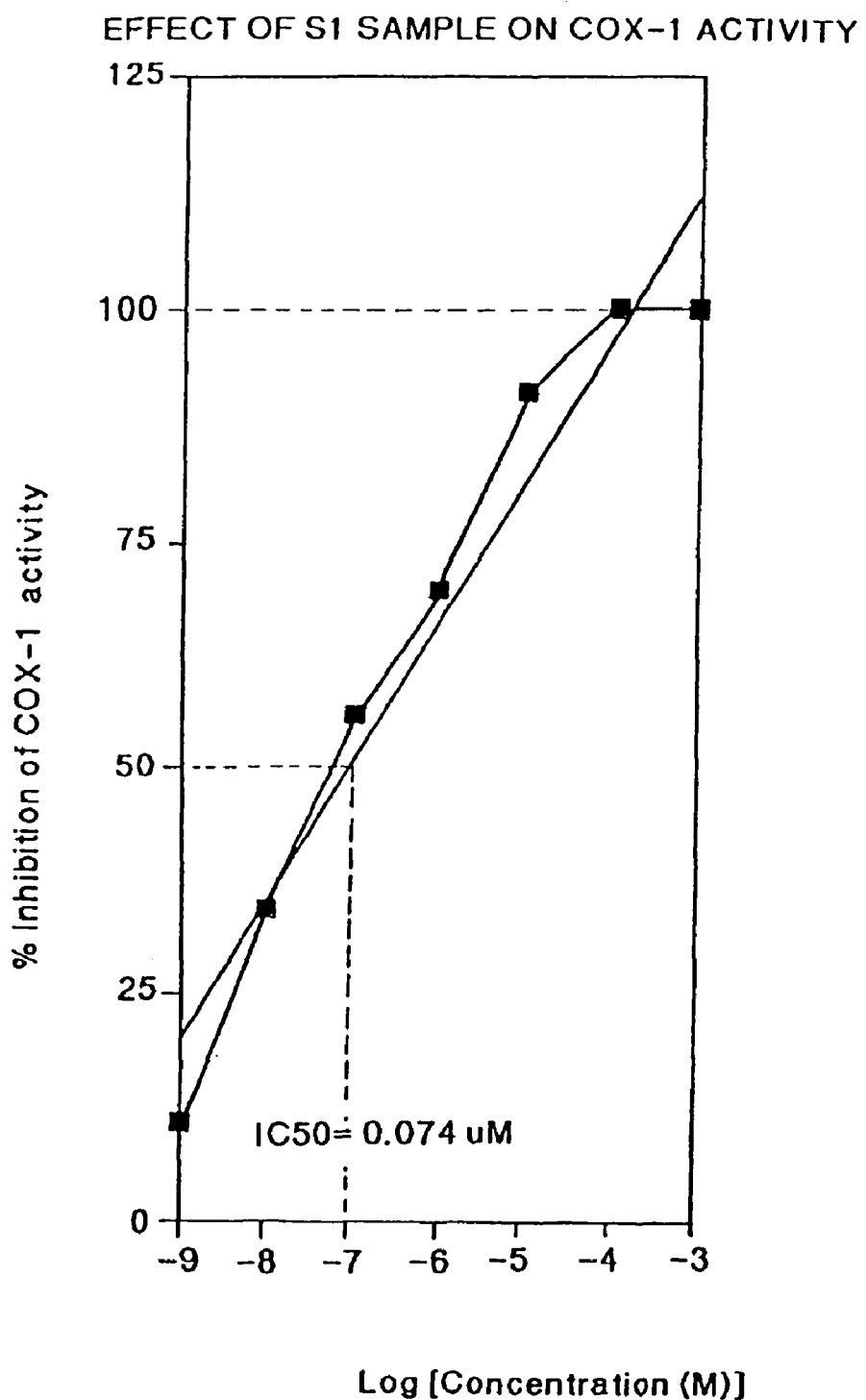
FIGS. 36A-V show the $IC_{50}$ values (μM) of samples containing procyanidins with COX-1/COX-2.
Figure 36B:
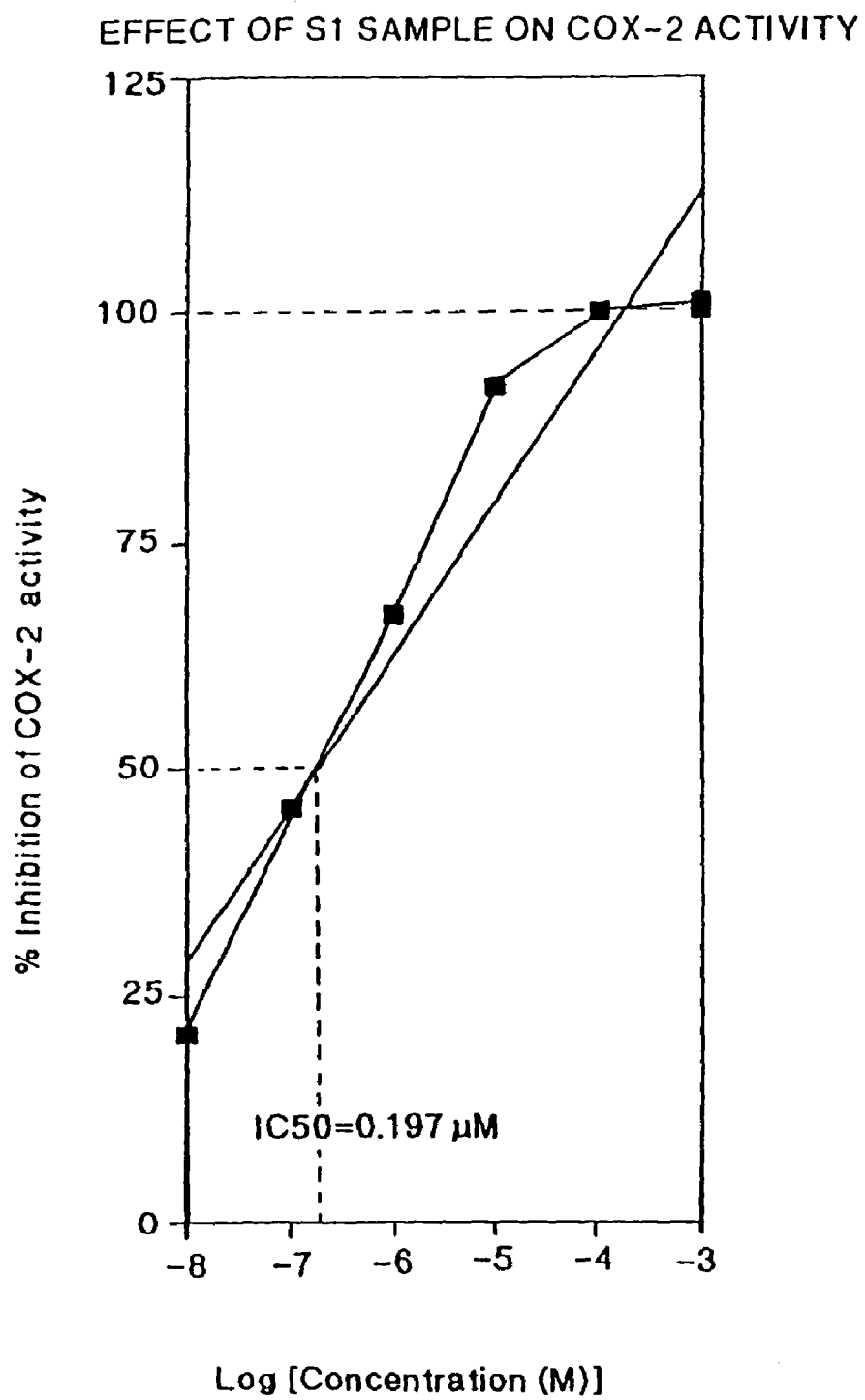
Figure 36C:
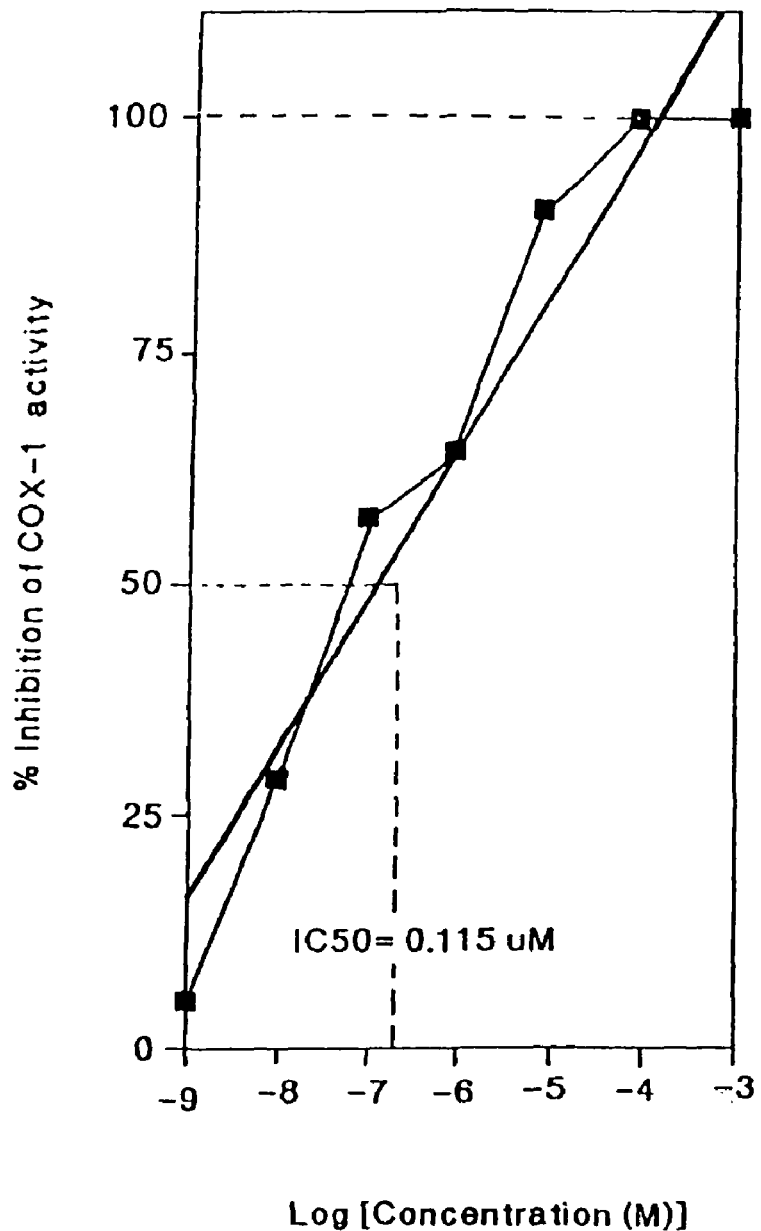
Figure 36D:
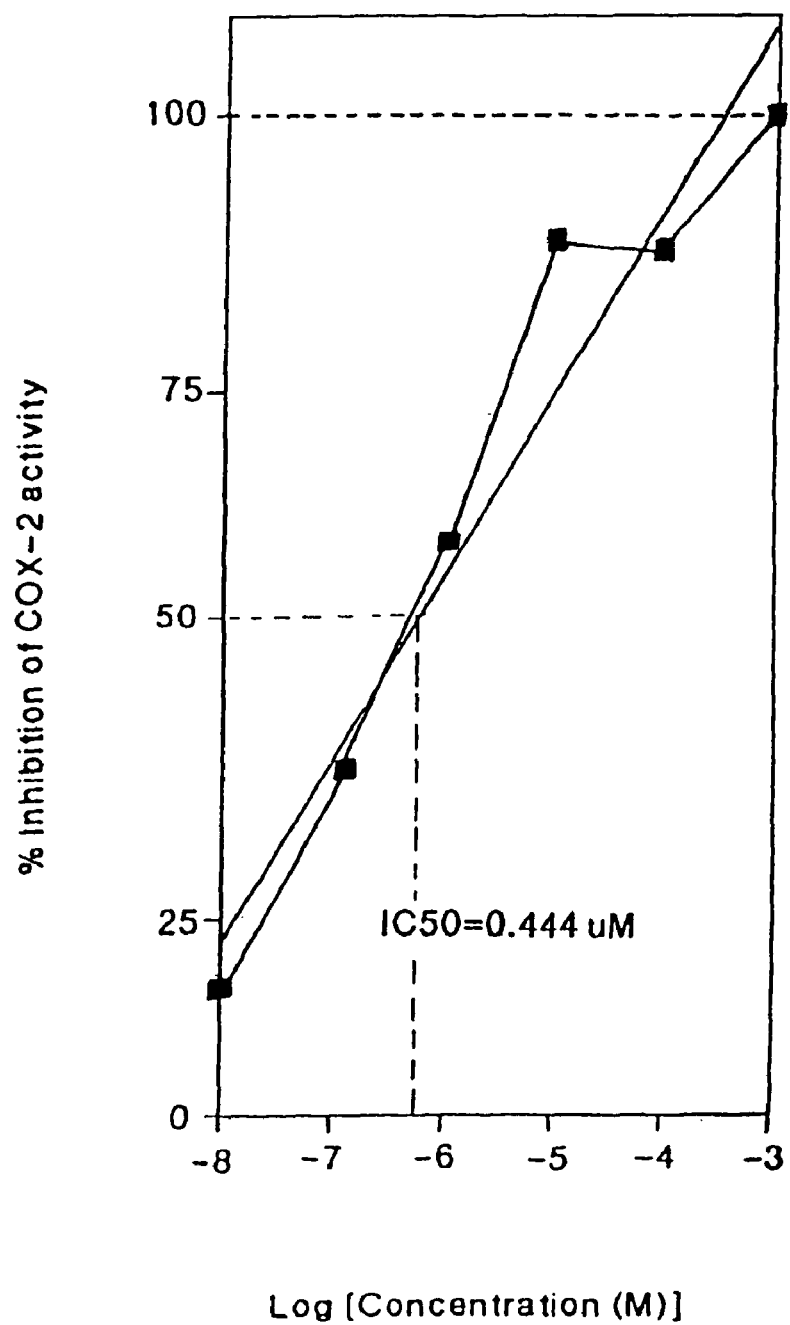
Figure 36E:
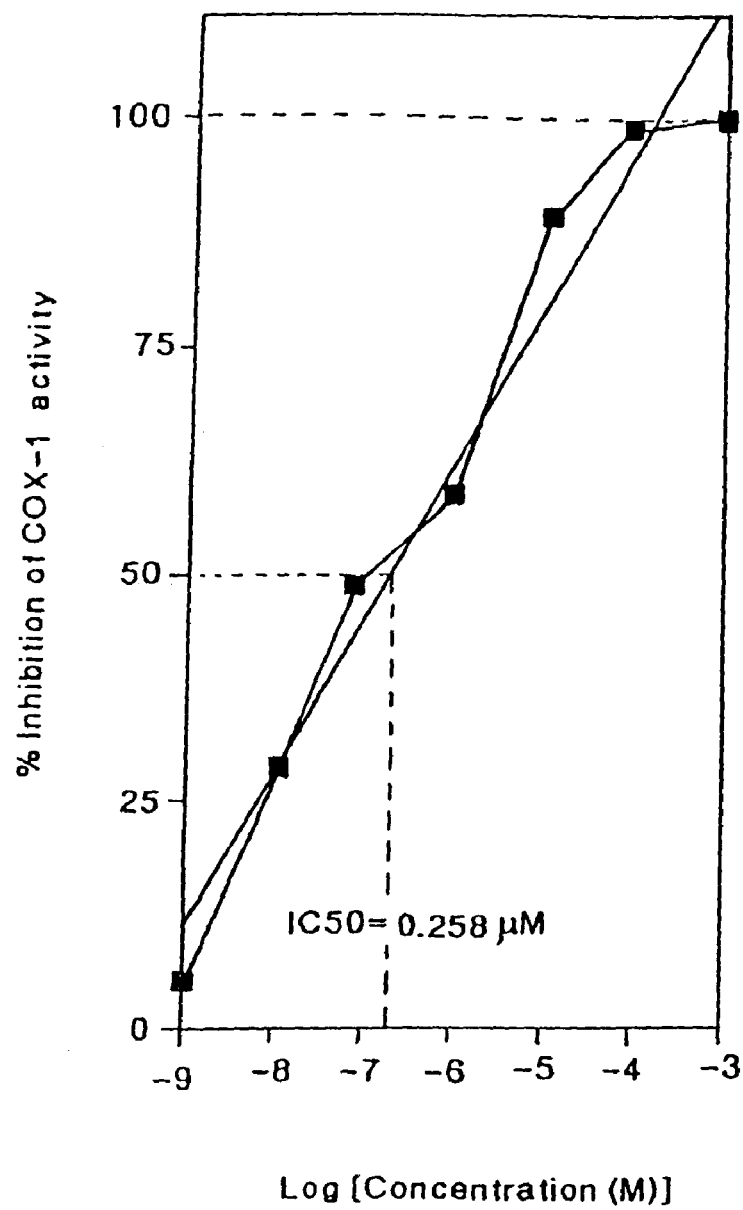
Figure 36F:
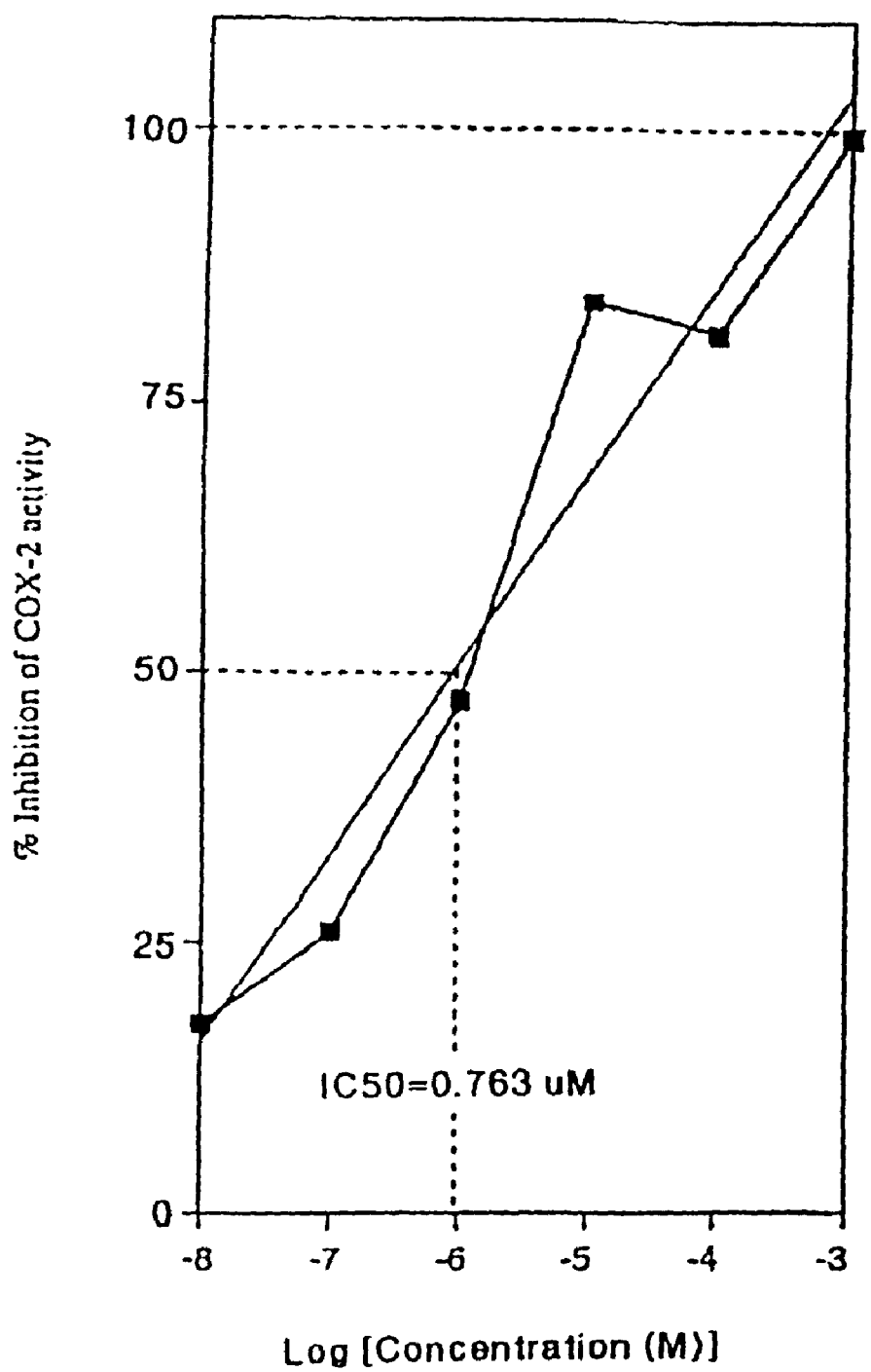
Figure 36G:
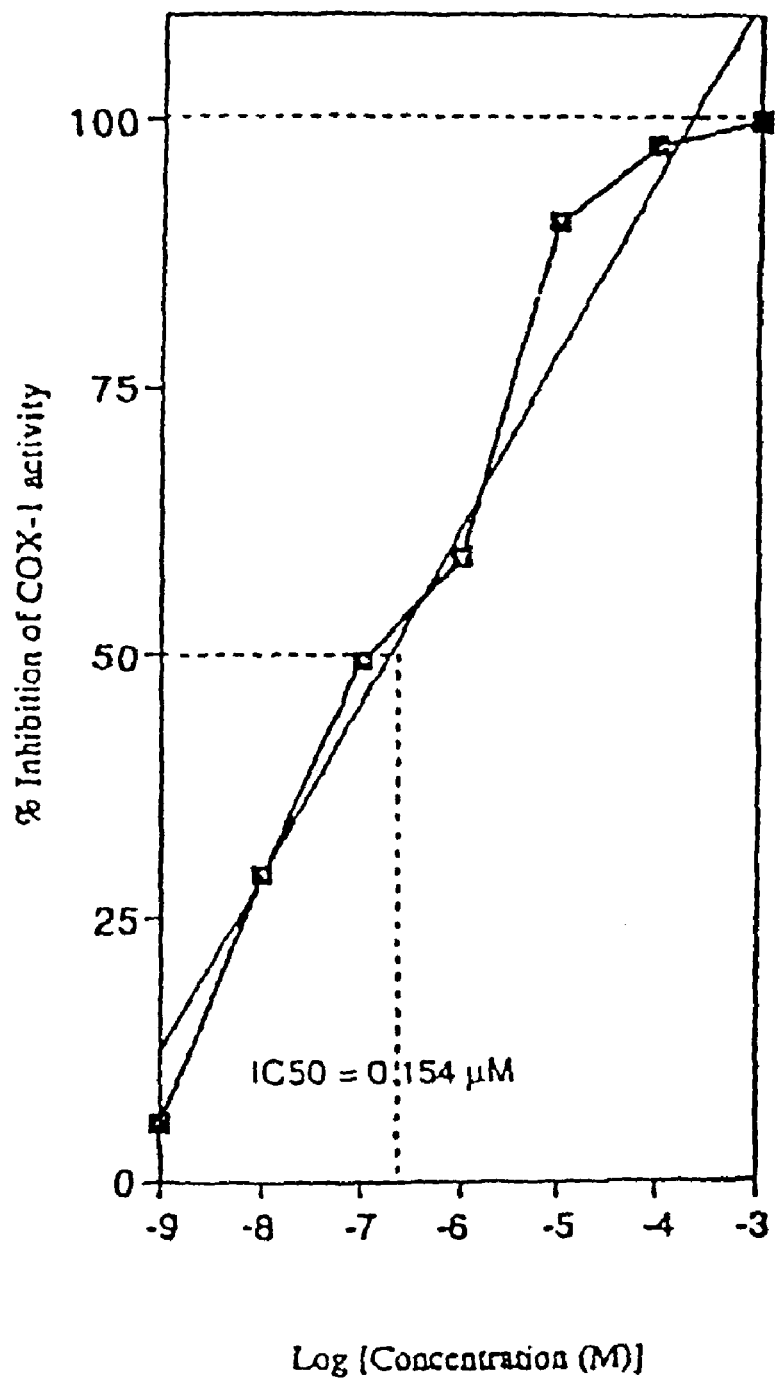
Figure 36H:
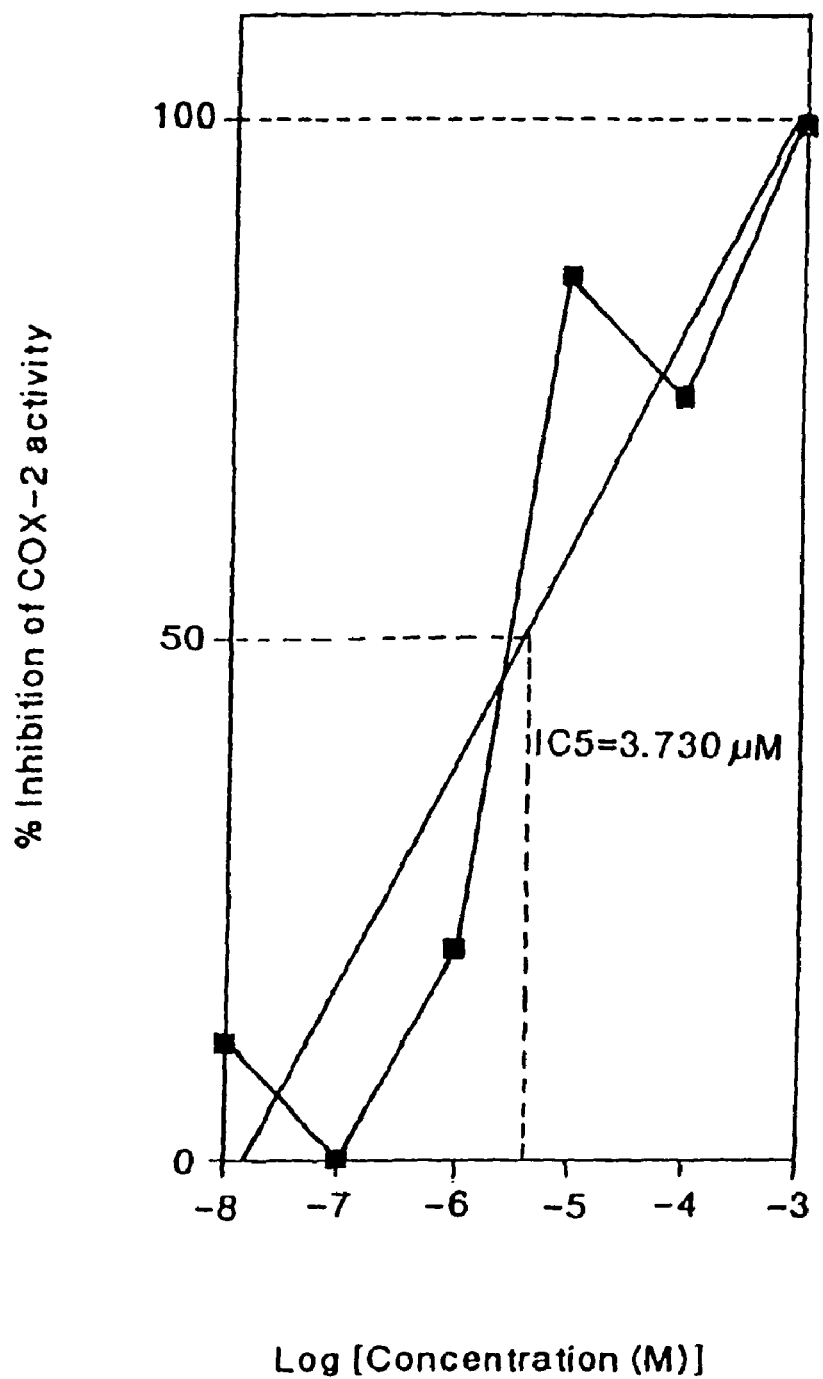
Figure 36I:
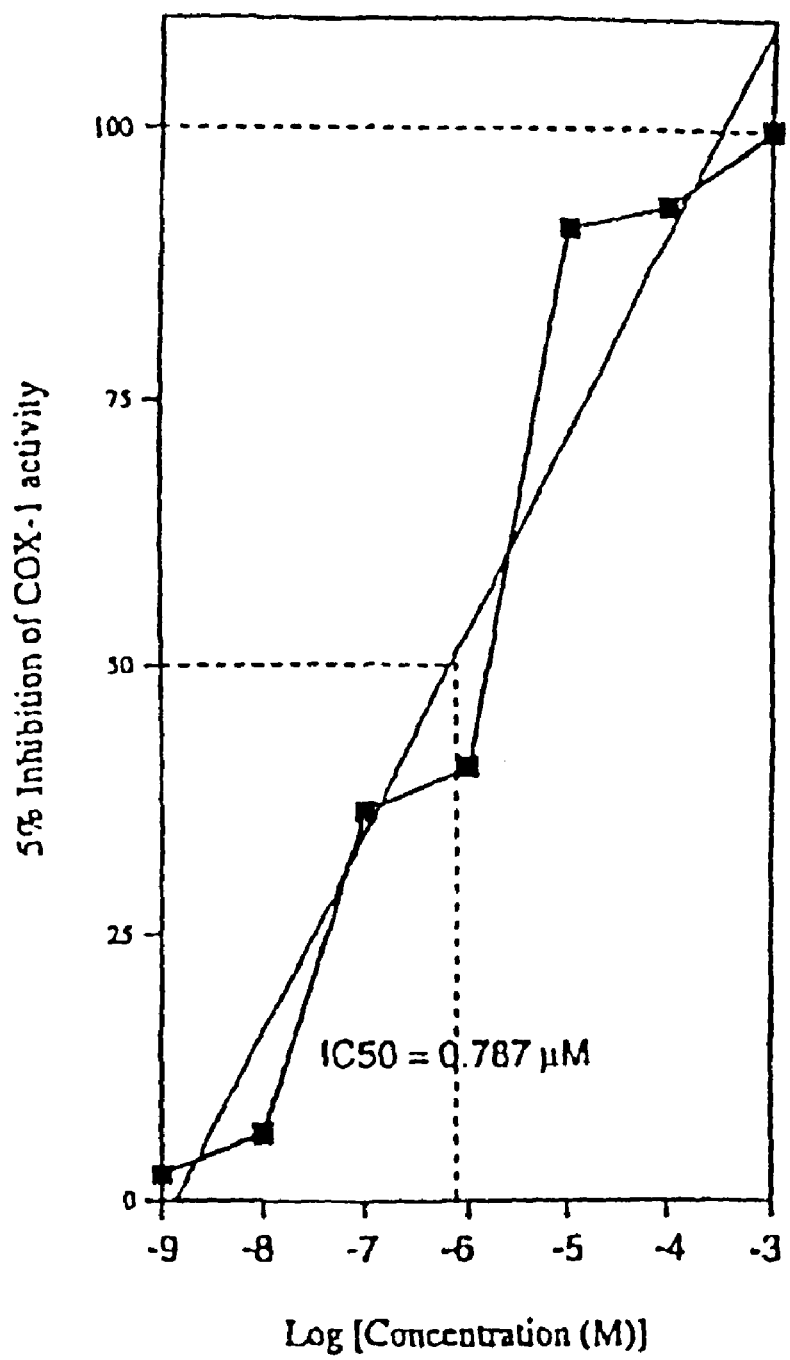
Figure 36J:
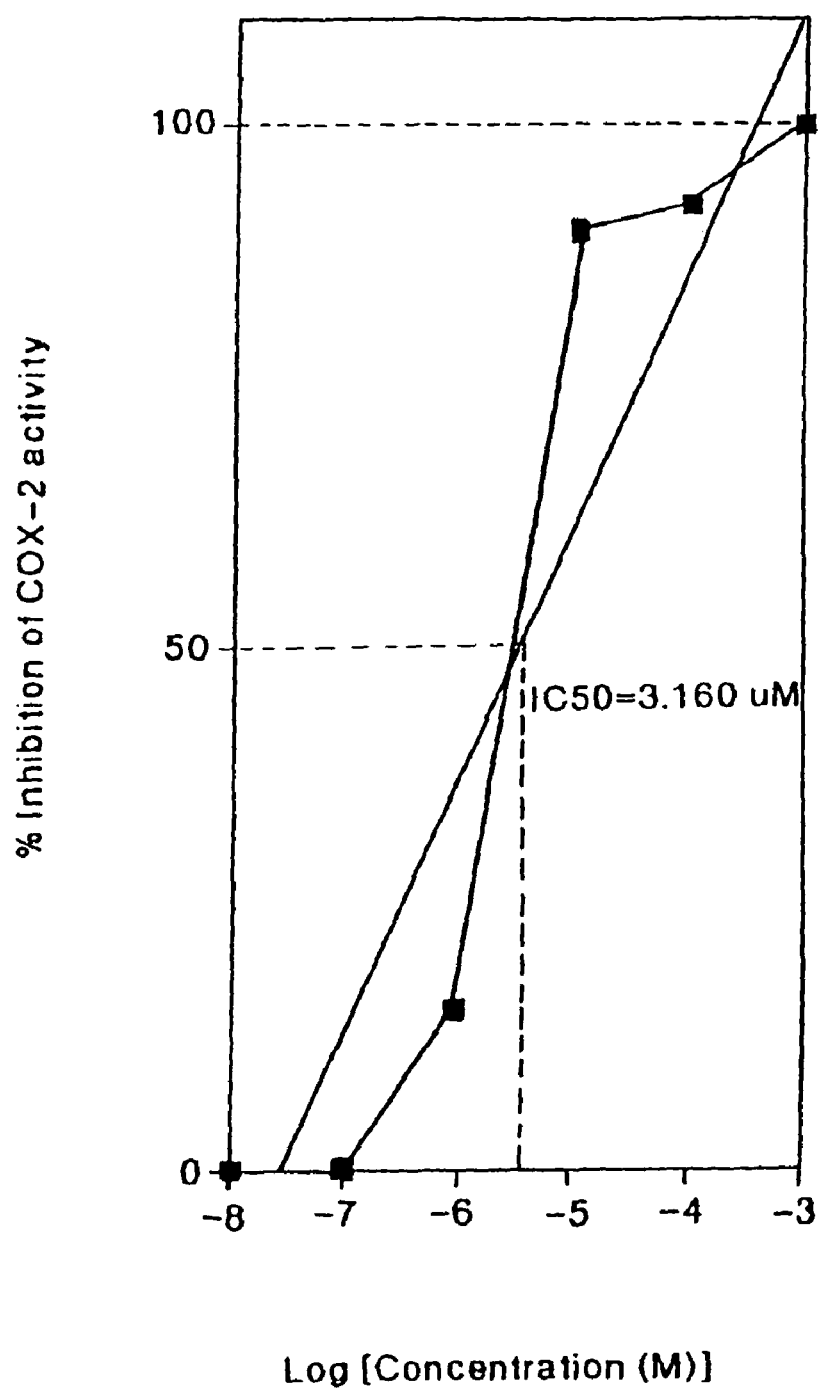
Figure 36K:
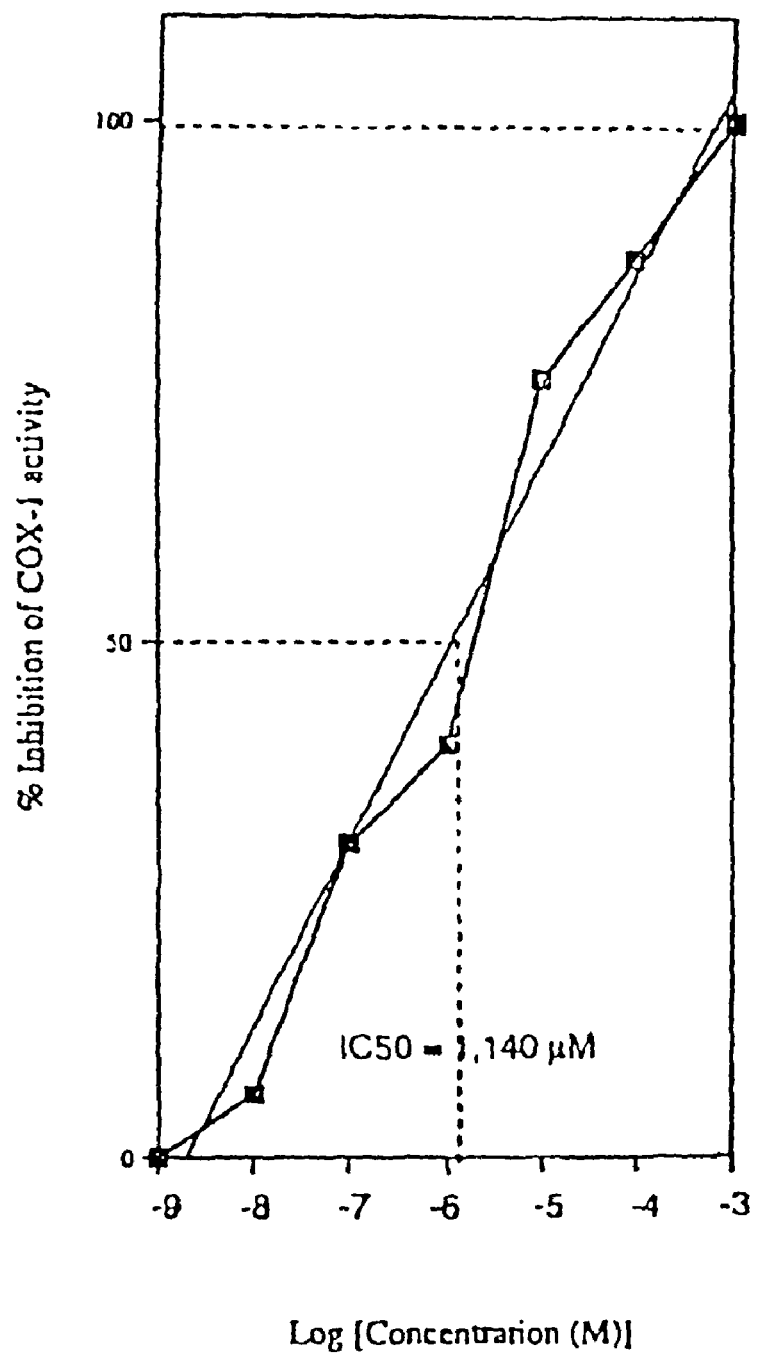
Figure 36L:
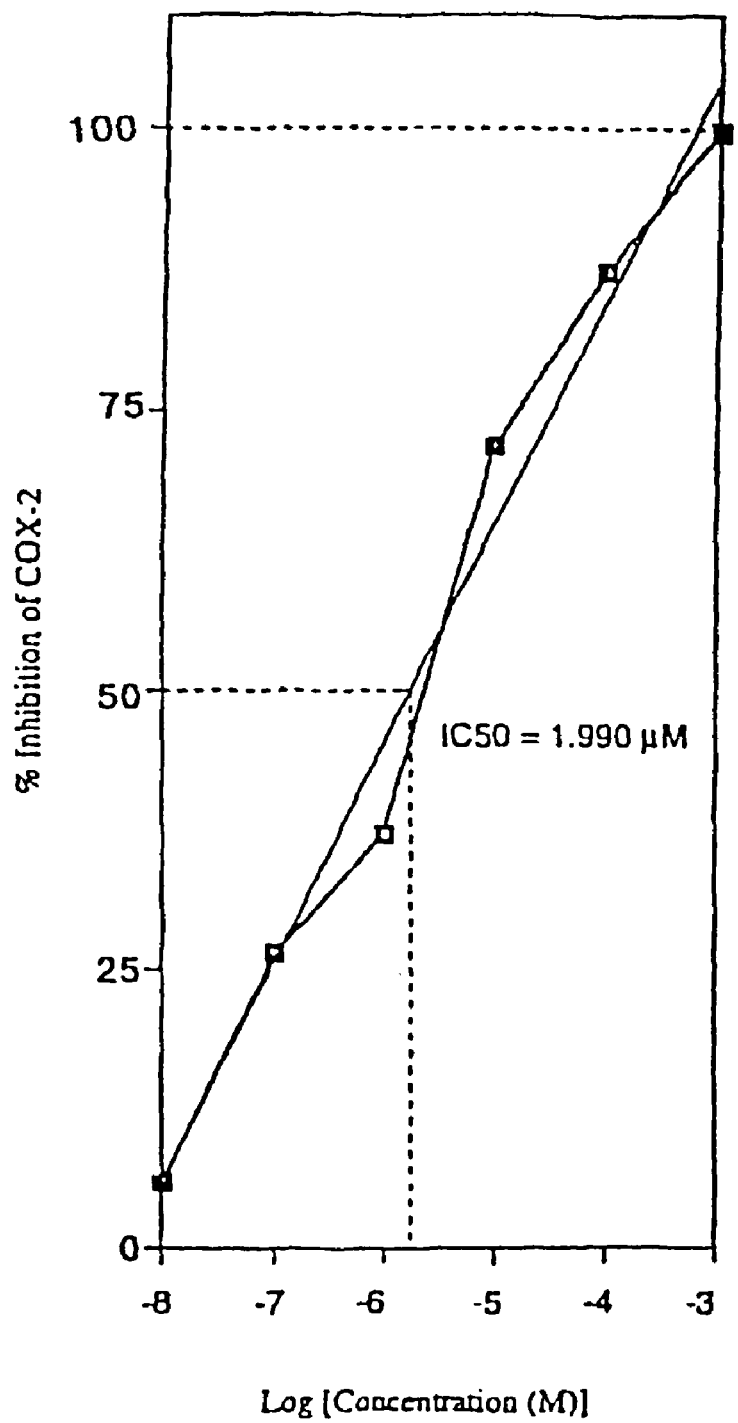
Figure 36M:
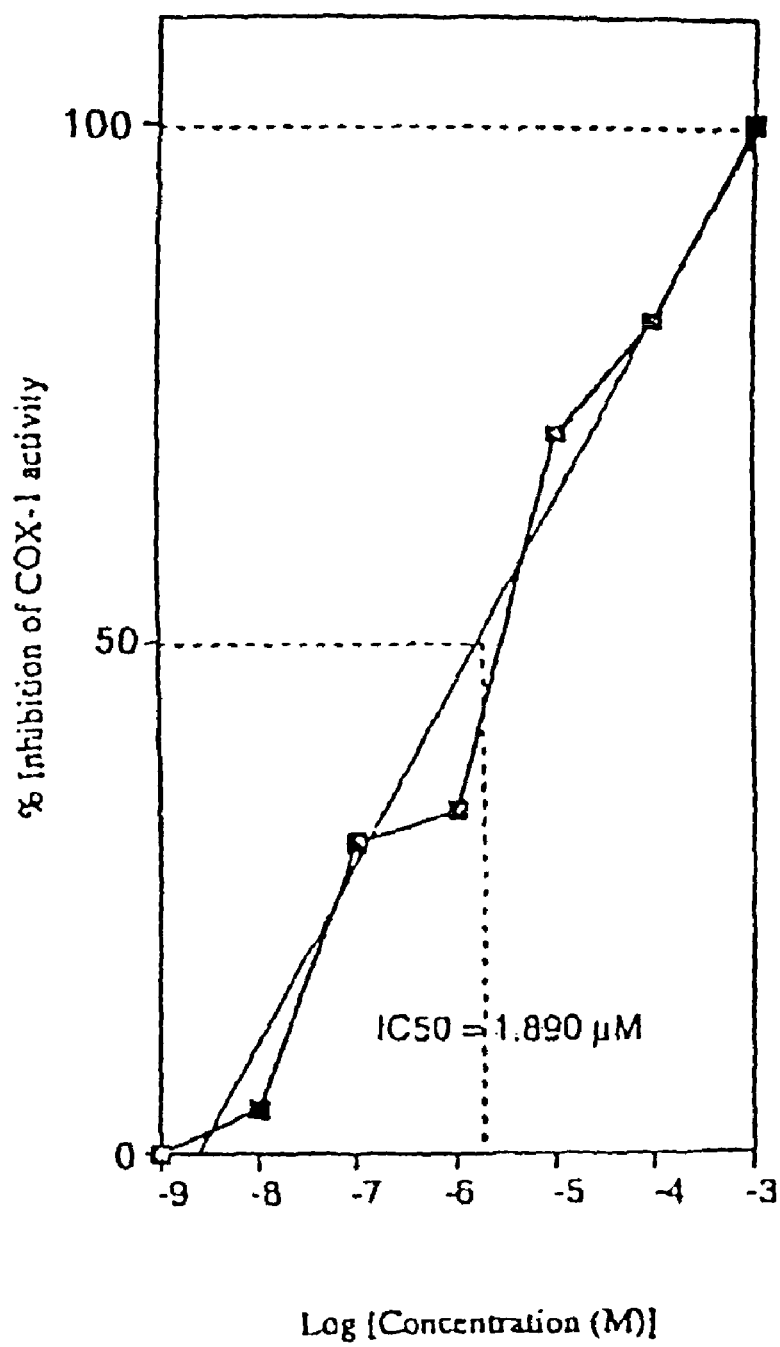
Figure 36N:
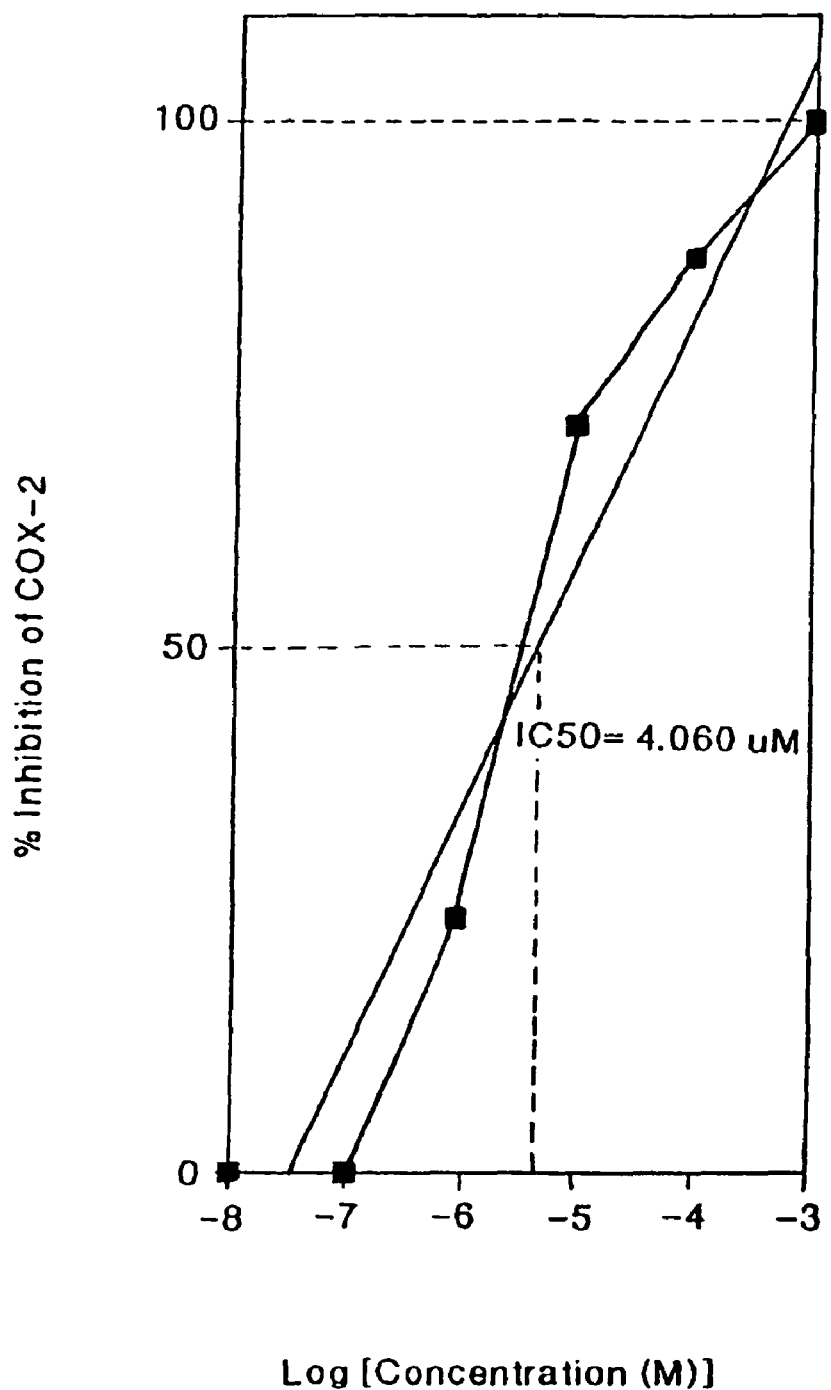
Figure 36O:
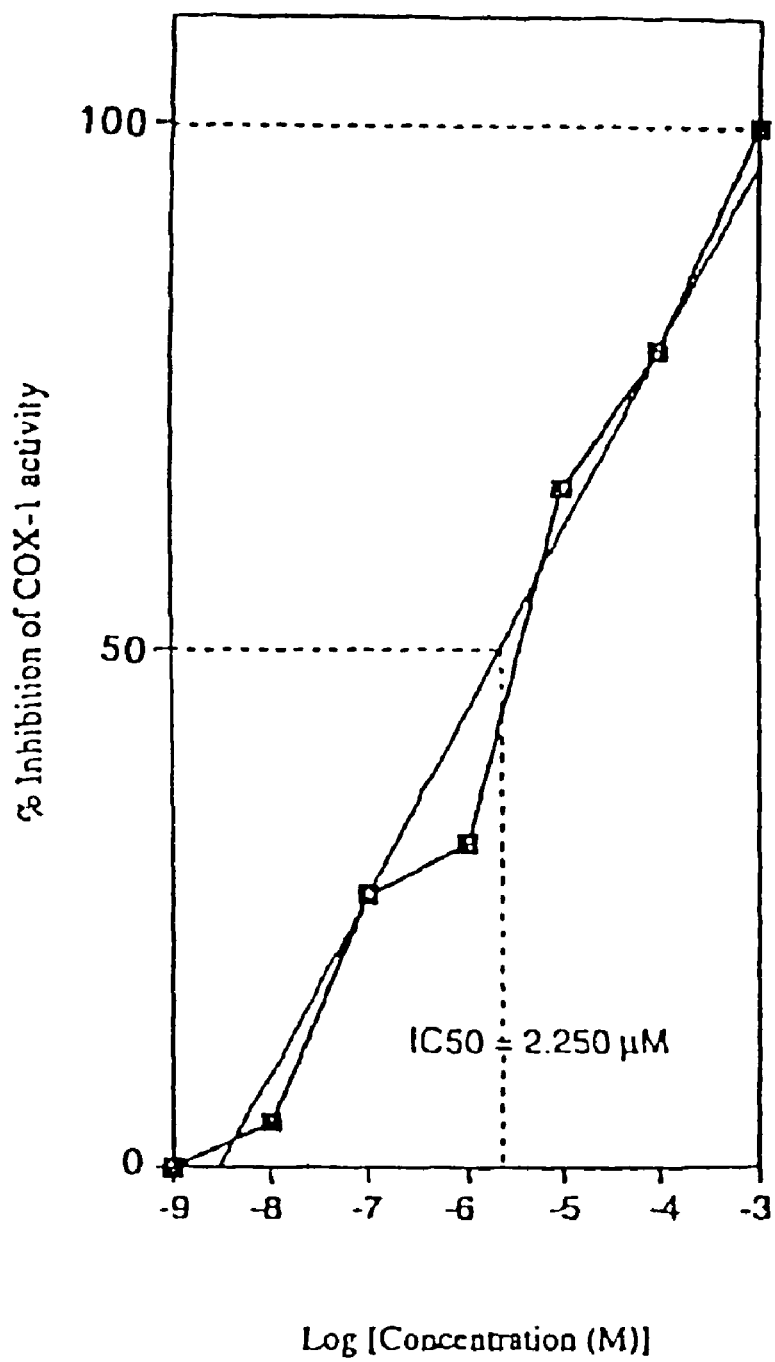
Figure 36P:
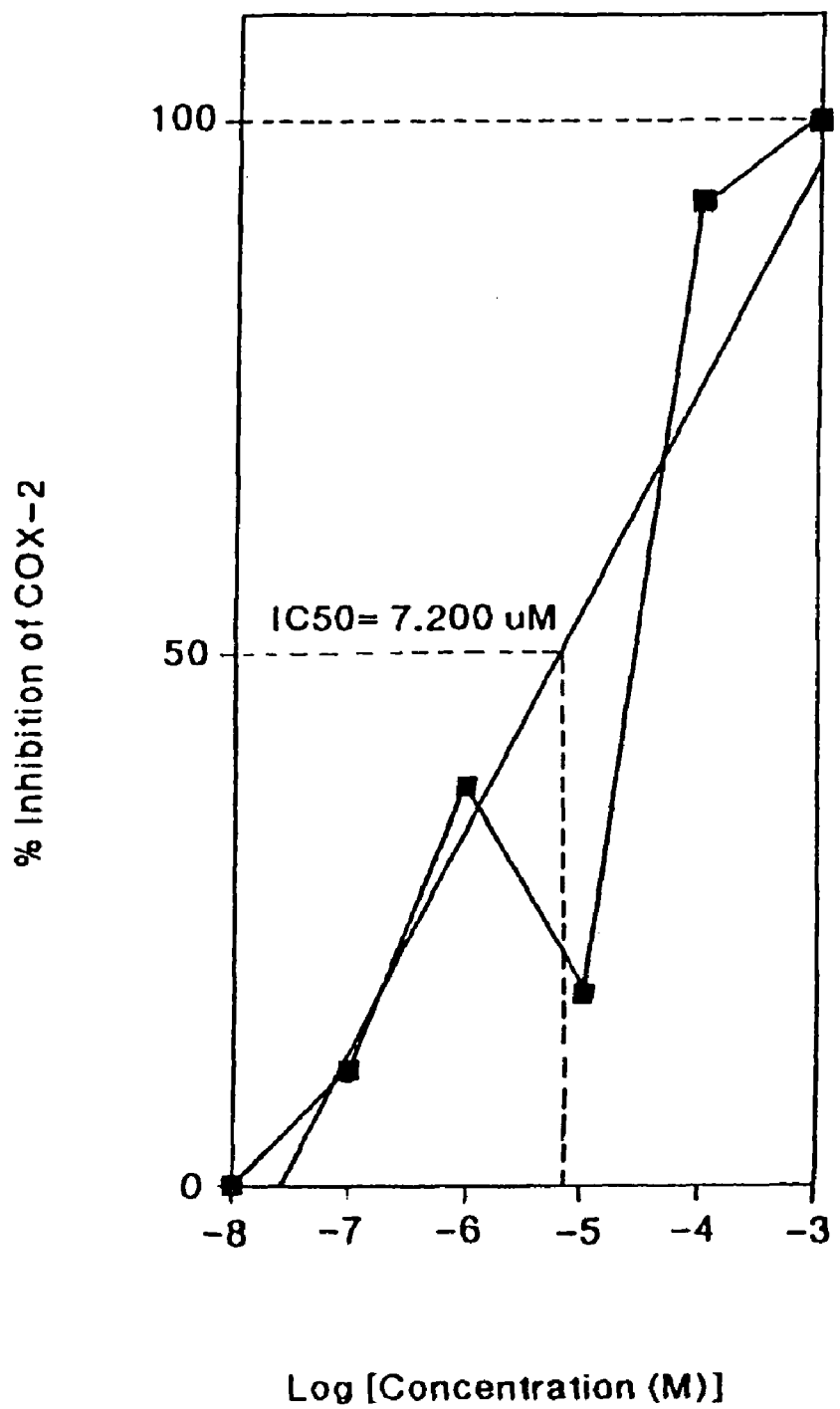
Figure 36Q:
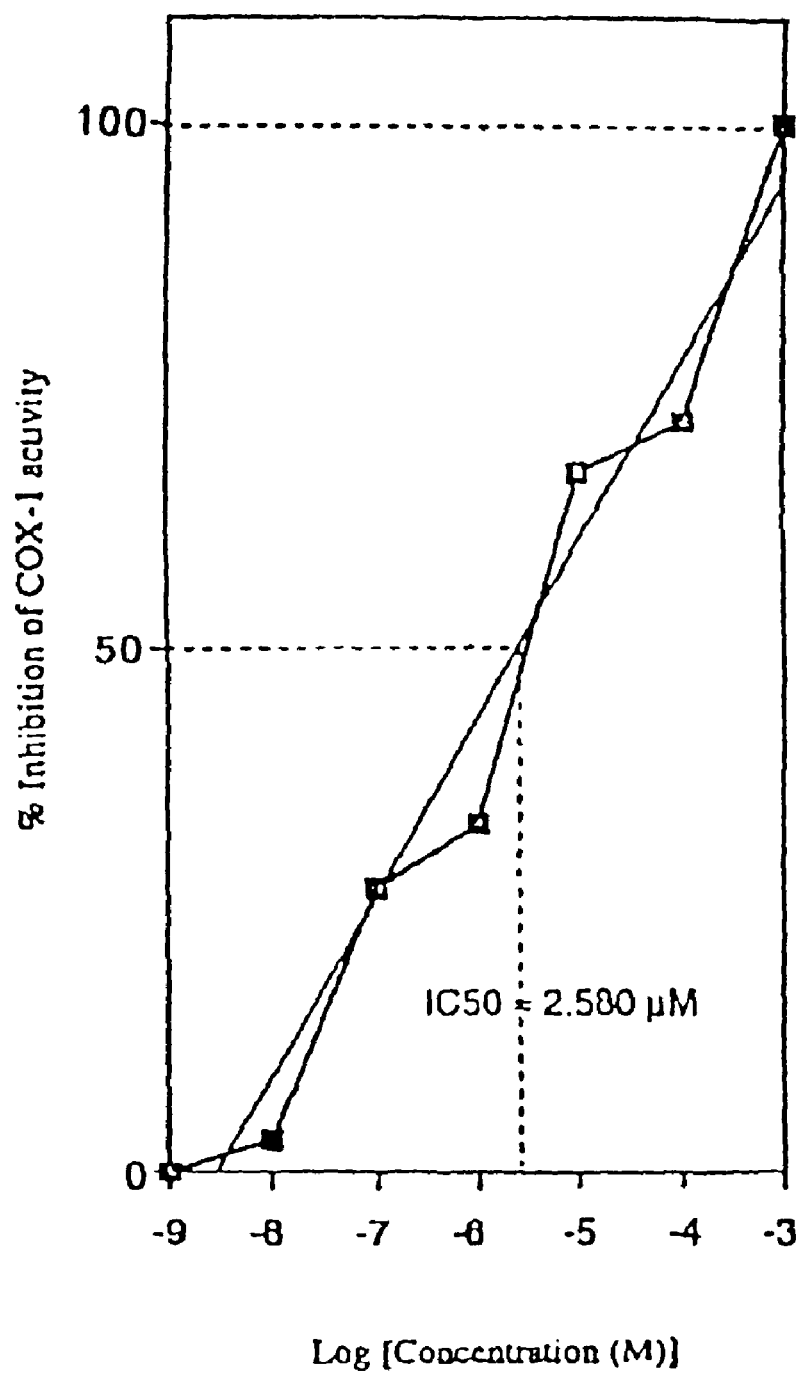
Figure 36R:
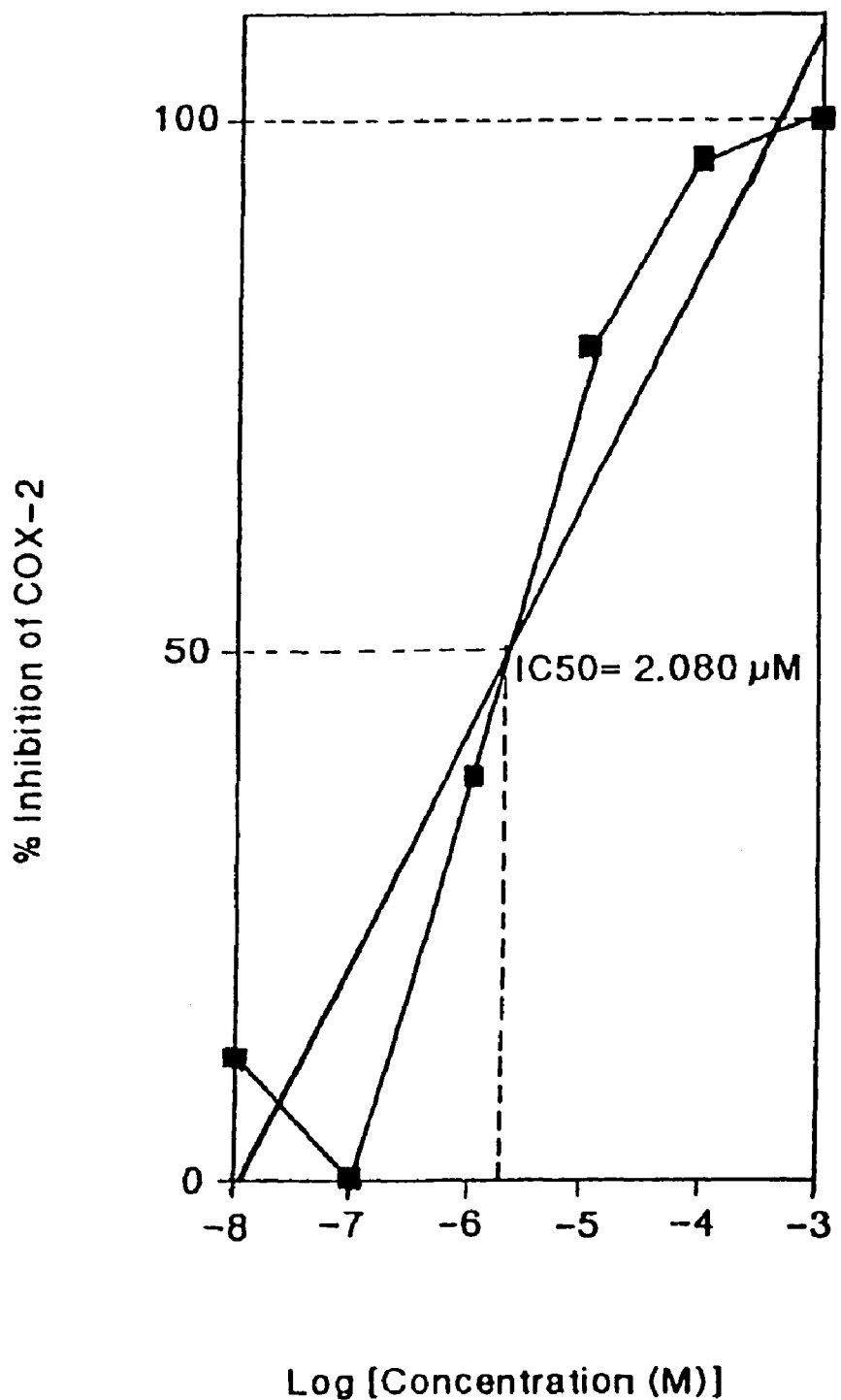
Figure 36S:
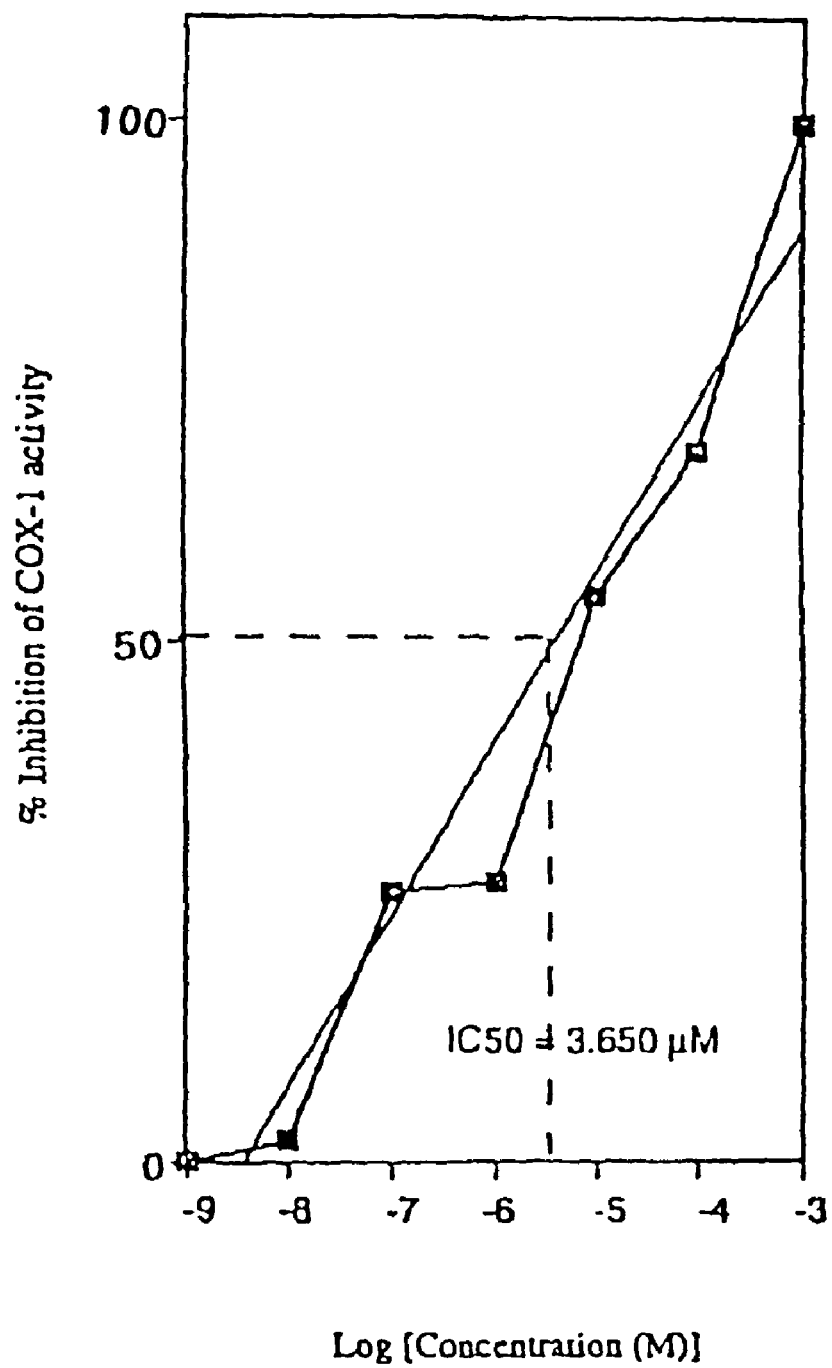
Figure 36T:
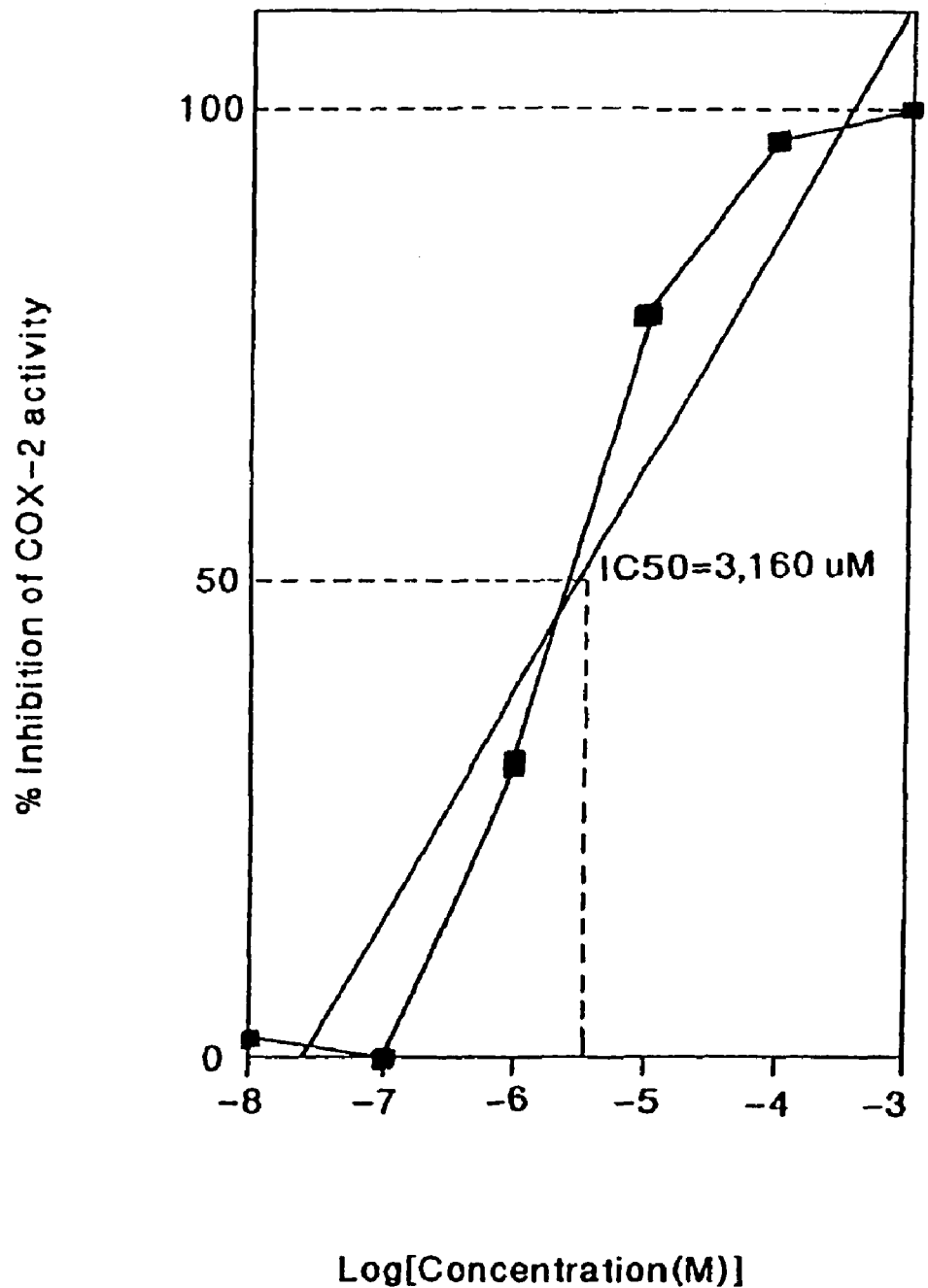
Figure 36U:
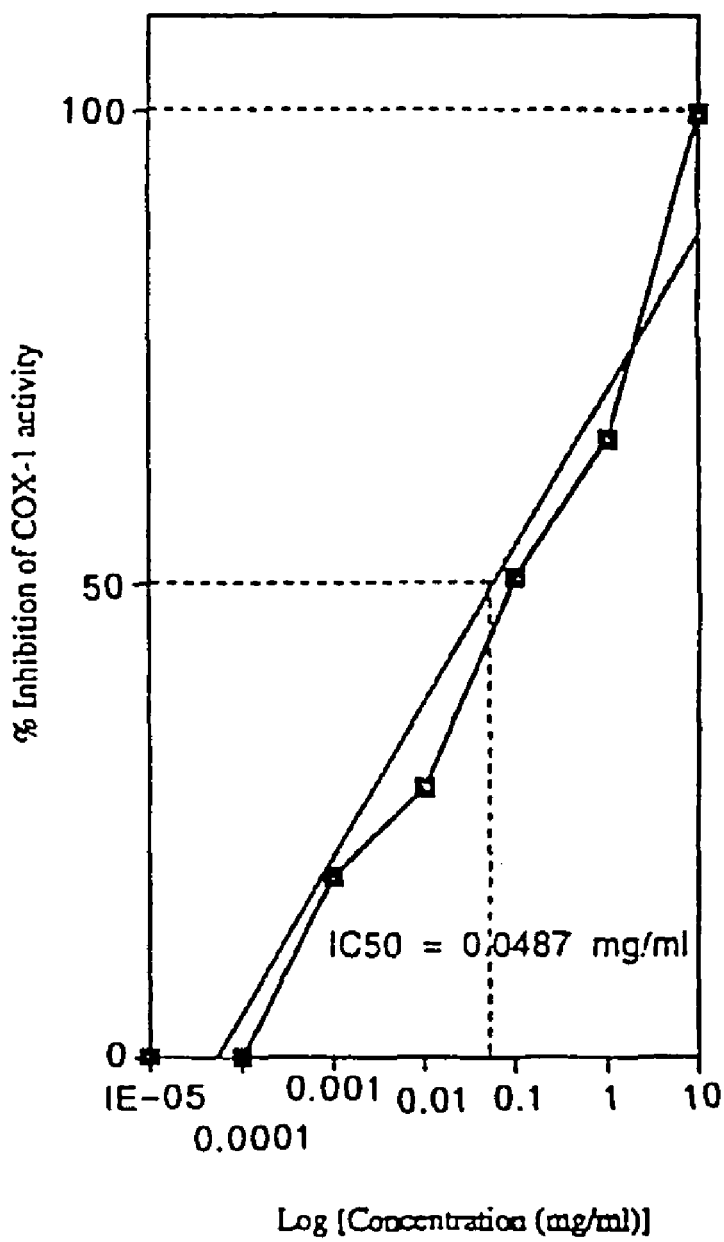
Figure 36V:
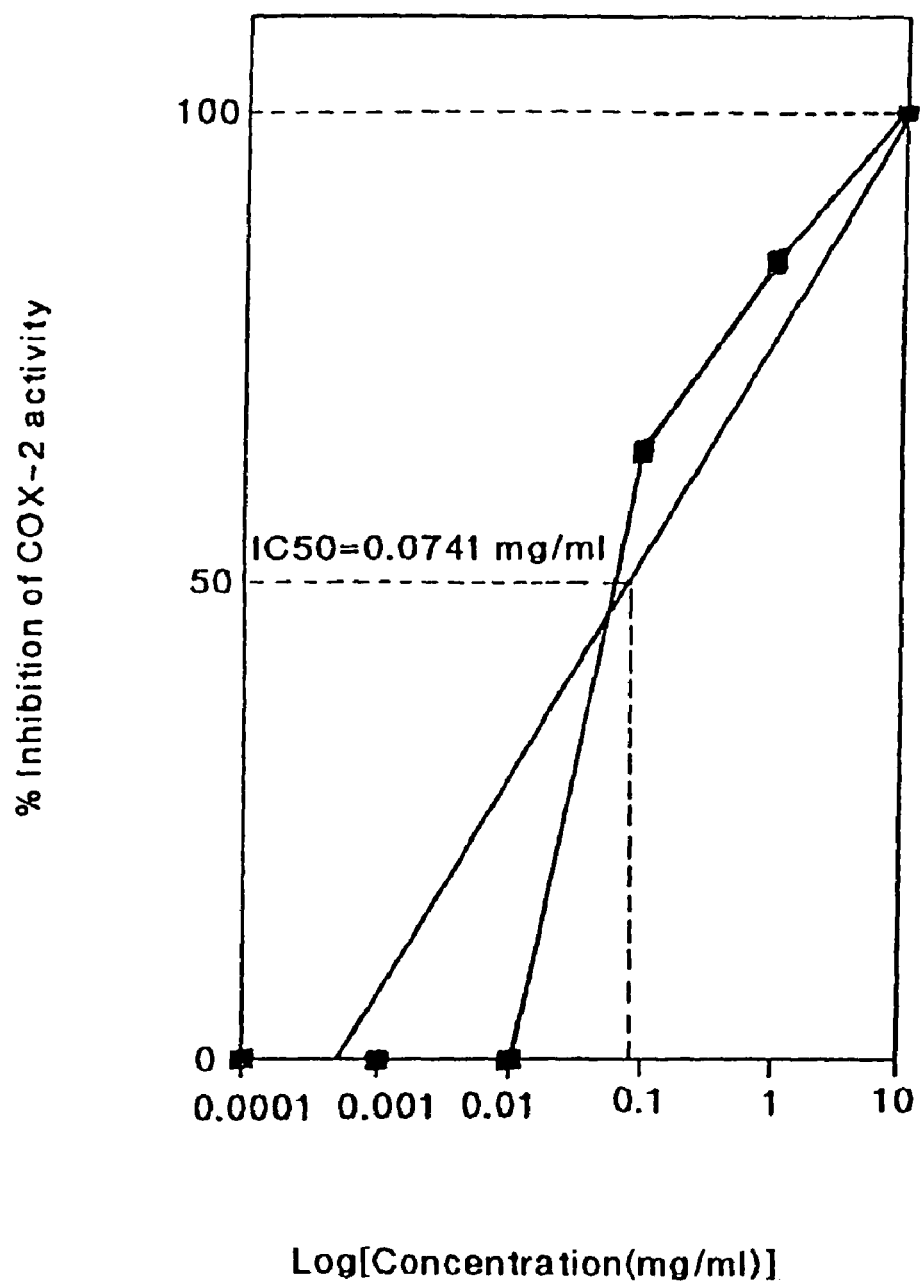

The results of the inhibition studies are presented in FIGS. 33 A and B, which shows the effects of Indomethacin on COX1 and COX2 activities. FIGS. 34 A and B shows the correlation between the degree of polymerization of the procyanidin and $IC_{50}$ with COX1 and COX2; FIG. 35 shows the correlation between $IC_{50}$ values on COX1 and COX2. And, FIGS. 36 A through Y show the $IC_{50}$ value of each sample (S1-S11) with COX1 and COX2.

These results indicate that the inventive compounds have analgesic, anti-coagulant, and anti-inflammatory utilities. Further, COX2 has been linked to colon cancer. Inhibition of COX2 activity by the inventive compounds illustrates a plausible mechanism by which the inventive compounds have antineoplastic activity against colon cancer.

COX1 and COX2 are also implicated in the synthesis of prostaglandins. Thus, the results in this Example also indicate that the inventive compounds can modulate renal functions, immune responses, fever, pain, mitogenesis, apoptosis, prostaglandin synthesis, ulceration (e.g., gastric), and reproduction. Note that modulation of renal function can affect blood pressure; again implicating the inventive compounds in modulating blood pressure, vasodilation, and coronary conditions (e.g., modulation of angiotensin, bradykinin).

Reference is made to Seibert et al., PNAS USA 91:12013-12017 (December, 1994), Mitchell et al., PNAS USA 90:11693-11697 (December 1994), Dewitt et al., Cell 83:345-348 (Nov. 3, 1995), Langenbach et al., Cell 83:483-92 (Nov. 3, 1995) and Sujii et al., Cell 83:493-501 (Nov. 3, 1995), Morham et al., Cell 83:473-82 (Nov. 3, 1995).

Reference is further made to Examples 9, 26, and 27. In Example 9, the anti-oxidant activity of inventive compounds is shown. In Example 26, the effect on NO is demonstrated. And, Example 27 provides evidence of a facial vasodilation. From the results in this Example, in combination with Examples 9, 26 and 27, the inventive compounds can modulate free radical mechanisms driving physiological effects. Similarly, lipoxygenase mediated free radical type reactions biochemically directed toward leukotriene synthesis can be modulated by the inventive compounds, thus affecting subsequent physiological effects (e.g., inflammation, immune response, coronary conditions, carcinogenic mechanisms, fever, pain, ulceration).

Thus, in addition to having analgesic properties, there may also be a synergistic effect by the inventive compounds when administered with other analgesics. Likewise, in addition to having antineoplastic properties, there may also be a synergistic effect by the inventive compounds when administered with other antineoplastic agents.

Example 29

Circular Dichroism/Study of Procyanidins

CD studies were undertaken in an effort to elucidate the structure of purified procyanidins as in Example 14, Method D. The spectra were collected at 25° C. using CD spectrum software AVIV 60DS V4.1f.

Samples were scanned from 300 nm to 185 nm, every 1.00 nm, at 1.50 nm bandwidth. Representative CD spectra are shown in FIGS. 43A through G, which show the CD spectra of dimer through octamer.

These results are indicative of the helical nature of the inventive compounds.

Example 30

Inhibitory Effects of Cocoa Procyanidins on *Helicobacter Pylori* and *Staphylococcus aureus*

A study was conducted to evaluate the antimicrobial activity of procyanidin oligomers against *Helicobacter pylori* and *Staphylococcus aureus*. Pentamer enriched material was prepared as described in Example 13, Method A and analyzed as described in Example 14, Method C, where 89% was pentamer, and 11% was higher oligomers (n is 6 to 12). Purified pentamer (96.3%) was prepared as described in Example 14, Method D.

*Helicobacter pylori* and *Staphylococcus aureus* were obtained from the American Type Culture Collection (ATCC). For *H. pylori*, the vial was rehydrated with 0.5 mL Trypticase Soy broth and the suspension transferred to a slant of fresh TSA containing 5% defibrinated sheep blood. The slant was incubated at 37° C. for 3 to 5 days under microaerophilic conditions in anaerobic jars (5 to 10% carbon dioxide; CampyPakPlus, BBL). When good growth was established in the pool of broth at the bottom of the slant, the broth was used to inoculate additional slants of TSA with sheep blood. Because viability decreased with continued subculturing, the broth harvested from the slants was pooled and stored at −80° C. Cultures for assay were used directly from the frozen vials. The *S. aureus* culture was maintained on TSA slants and transferred to fresh slants 24 h prior to use.

A cell suspension of each culture was prepared (*H. pylori*, $10^8$ to $10^9$ cfu/mL; *S. aureus* $10^6$ to $10^7$ cfu/mL) and 0.5 mL spread onto TSA plates with 5% sheep blood. Standard assay disks (Difco) were dipped into filter sterilized, serial dilutions of pentamer (23 mg/mL into sterile water). The test disks and the blank control disks (sterile water) were placed on the inoculated plates. Control disks containing 80 ug metronidazole (inhibitory to *H. pylori*) or 30 ug vancomycin (inhibitory to *S. aureus*) (BBL Sensidiscs) were also placed on the appropriate set of plates. The *H. pylori* inoculated plates were incubated under microaerophilic conditions. The *S. aureus* set was incubated aerobically. Zones of inhibition were measured following outgrowth.

TABLE 14

Bioassays with pentamer against *Helicobacter pylori* and *Staphylococcus aureus*

| Pentamer Enriched Fraction (mg/ml) | S. aureus Inhibition (mm) | H. pylori Inhibition (mm) |
|---|---|---|
| 0 | NI | NI |
| 15 | 0 | 10 |
| 31 | 10 | 10 |
| 62 | 11 | 11 |
| 125 | 13 | 13 |
| 250 | 15 | 13 |
| Vancomycin standard | 15 | — |
| Metronidazole standard | — | 11 |
| 96% pure pentamer | 15 | 11 |

NI = no inhibition

Example 31

No Dependent Hypotension in the Guinea Pig

The effect of five cocoa procyanidin fractions on guinea pig blood pressure were investigated. Briefly, guinea pigs (approximately 400 g body weight; male and female) were anesthetized upon injection of 40 mg/kg sodium pentobarbital. The carotid artery was cannulated for monitoring of the arterial blood pressure. Each of the five cocoa procyanidin fractions was injected intravenously (dose range 0.1 mg/kg-100 mg/kg) through the jugular vein. Alterations of blood pressure were recorded on a polygraph. In these experiments, the role of NO was ascertained by the administration of L-N-methylarginine (1 mg/kg) ten minutes prior to the administration of cocoa procyanidin fractions.

Cocoa procyanidin fractions were prepared and analyzed according to the procedures described in U.S. Pat. No. 5,554,645, hereby incorporated herein by reference.

Fraction A: Represents a preparative HPLC fraction comprised of monomers-tetramers. HPLC analysis revealed the following composition:

| Monomers | 47.2% |
|---|---|
| Dimers | 23.7 |
| Trimers | 18.7 |
| Tetramers | 10.3 |

Fraction B: Represents a preparative HPLC fraction comprised of pentamers-decamers. HPLC analysis revealed the following composition:

| Pentamers | 64.3% |
|---|---|
| Hexamers | 21.4 |
| Heptamers | 7.4 |
| Octamers | 1.9 |
| Nonamers | 0.9 |
| Decamers | 0.2 |

Fraction C: Represents an enriched cocoa procyanidin fraction used in the preparation of Fractions A and B (above). HPLC analysis revealed the following composition:

| Monomers | 34.3% |
|---|---|
| Dimers | 17.6 |
| Trimers | 16.2 |
| Tetramers | 12.6 |
| Pentamers | 8.5 |
| Hexamers | 5.2 |
| Heptamers | 3.1 |
| Octamers | 1.4 |
| Nonamers | 0.7 |
| Decamers | 0.3 |

Fraction D: Represents a procyanidin extract prepared from a milk chocolate. HPLC analysis revealed a composition similar to that listed in the Table 12 for Brand 8. Additionally, caffeine 10% and theobromine 6.3% were present.

Fraction E: Represents a procyanidin extract prepared from a dark chocolate prepared with alkalized liquor. HPLC analysis revealed a composition similar to that listed in the Table 12 for Brand 12. Additionally, caffeine 16.0% and theobromine 5.8% were present.

In three separate experiments, the effects of administering 10 mg/kg cocoa procyanidin fractions on arterial blood pressure of anesthetized guinea pigs was investigated. Upon intravenous injection, procyanidin fractions A and E evoked a decrease in blood pressure of about 20%. This decrease was only marginally different from that obtained from a solvent (DMSO) control (15±5%, n=5). In contrast, procyanidin fractions B, C and D (10 mg/kg) induced marked decreases in blood pressure, up to 50-60% for C. In these experiments the order of hypotensive effect was as follows: C>B>D>>A=E.

Figure 50A:
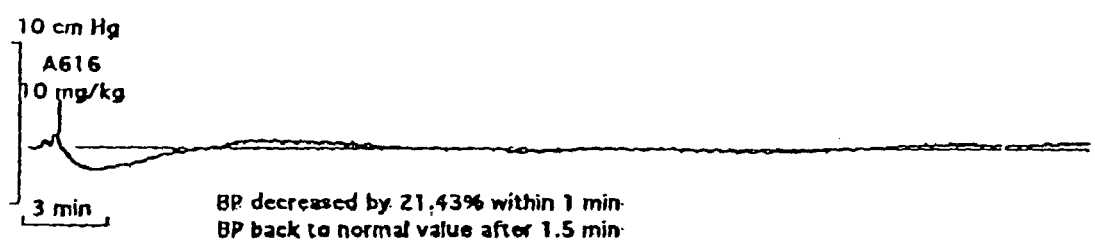
FIGS. 50A and B show the effects of cocoa procyanidin fraction A and C, respectively, on blood pressure; blood pressure levels decreased by 21.43% within 1 minute after administration of fraction A, and returned to normal after 15 minutes, while blood pressure decreased by 50.5% within 1 minute after administration of fraction C, and returned to normal after 5 minutes.
Figure 50B:
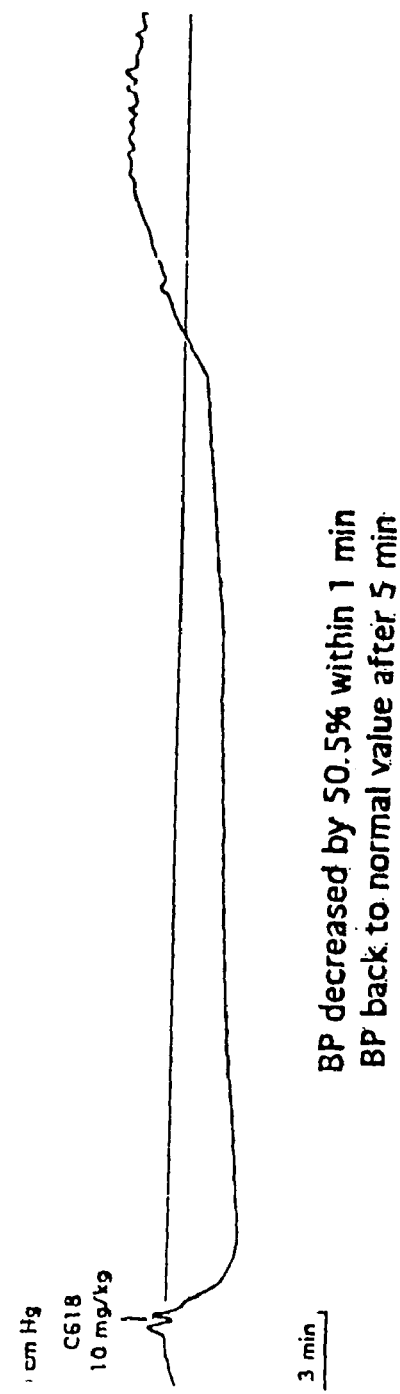
Figure 51:
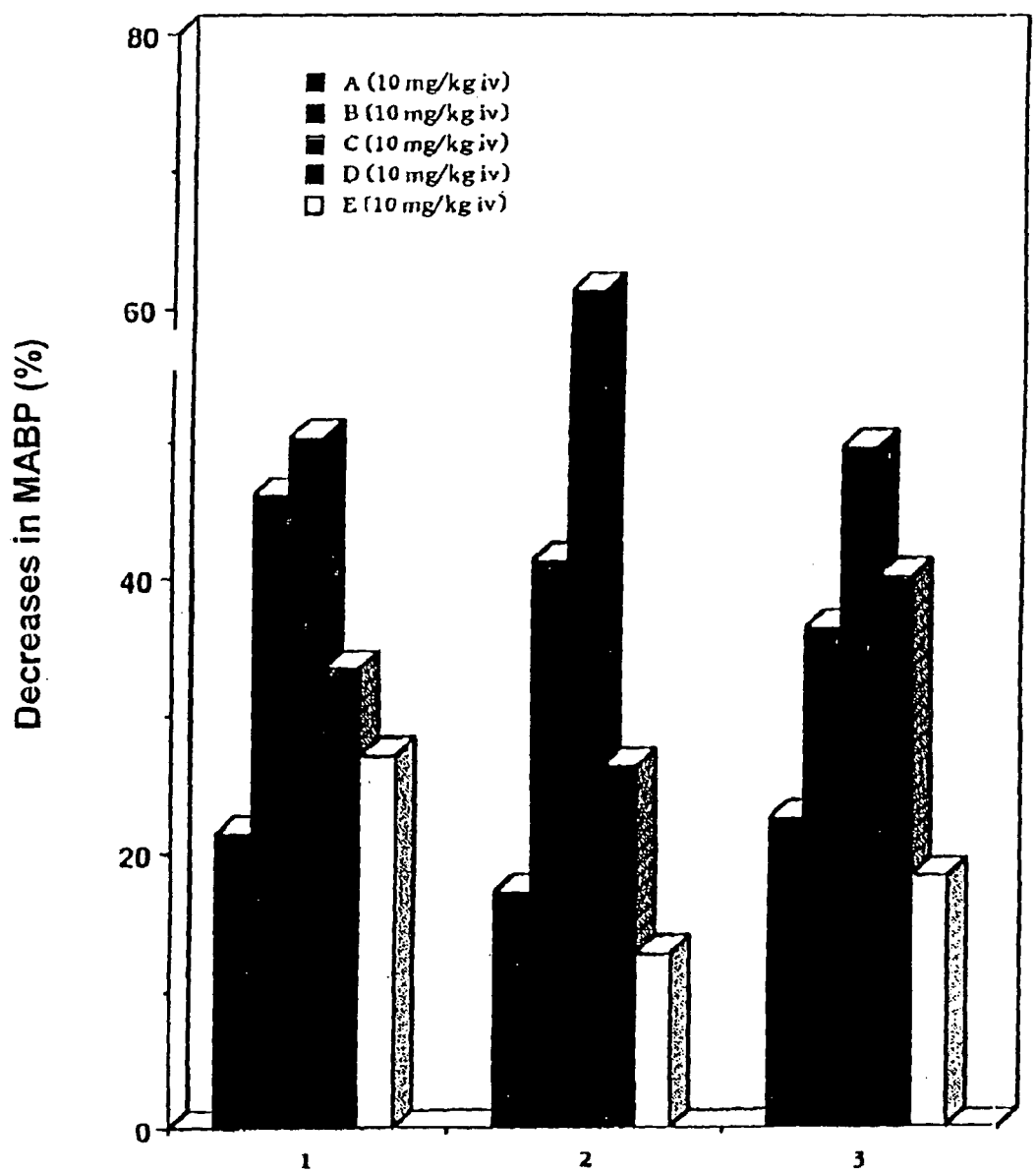
FIG. 51 shows the effect of cocoa procyanidin fractions on arterial blood pressure in anesthetized guinea pigs.

Typical recordings of blood pressure elicited after injection of procyanidin fractions appear in FIG. 50A for fraction A and FIG. 50B for fraction C. FIG. 51 illustrates the comparative effects on blood pressure by these fractions.

The possible contribution of NO in the hypotension in the guinea pig induced by administration of fraction C was analyzed using L-N-methyl arginine (LNMMA). This pharmacological agent inhibits the formation of NO by inhibiting NO synthase. L-NMMA was administered at the dose of 1 mg/kg, ten minutes prior to injection of the cocoa procyanidin fractions. Treatment of the animals with L-NMMA completely blocked the hypotension evoked by the procyanidin fraction C. Indeed, following treatment with this inhibitor, the alterations of blood pressure produced by fraction C were similar to those noted with solvent alone.

Example 32

Effect of Cocoa Procyanidin Fractions on NO Production in Human Umbilical Vein Endothelial Cells Human umbilical vein endothelial cells (HUVEC) were obtained from Clonetics and cultures were carried out according to the manufacturer's specifications. HUVEC cells were seeded at 5,000 cells/cm$^2$ in 12-well plates (Falcon). After the third passage under the same conditions, they were allowed to reach confluence. The supernatant was renewed with fresh medium containing defined concentrations of bradykinin (25, 50 and 100 nM) or cocoa procyanidin fractions A-E (100 µg/mL) as described in example 31. The culture was continued for 24 hr. and the cell free supernatants were collected and stored frozen prior to assessment of NO content as described below. In selected experiments, the NO synthase (NOS) antagonist, Nω-nitro-L-arginine methyl ester (L-NAME, 10 µM) was added to assess the involvement of NOS in the observed NO production.

HUVEC NO production was estimated by measuring nitrite concentration in the culture supernatant by the Griess reaction. Griess reagent was 1% sulfanilamide, 0.1% N-(1-naphthyl)-ethylenediamine dihydrochloride. Briefly, 50 µL aliquots were removed from the various supernatants in quadruplicate and incubated with 150 µL of the Griess reagent. The absorbency at 540 nm was determined in a multiscan (Labsystems Multiskans MCC/340) apparatus. Sodium nitrite was used at defined concentrations to establish standard curves. The absorbency of the medium without cells (blank) was subtracted from the value obtained with the cell containing supernatants.

Figure 52:
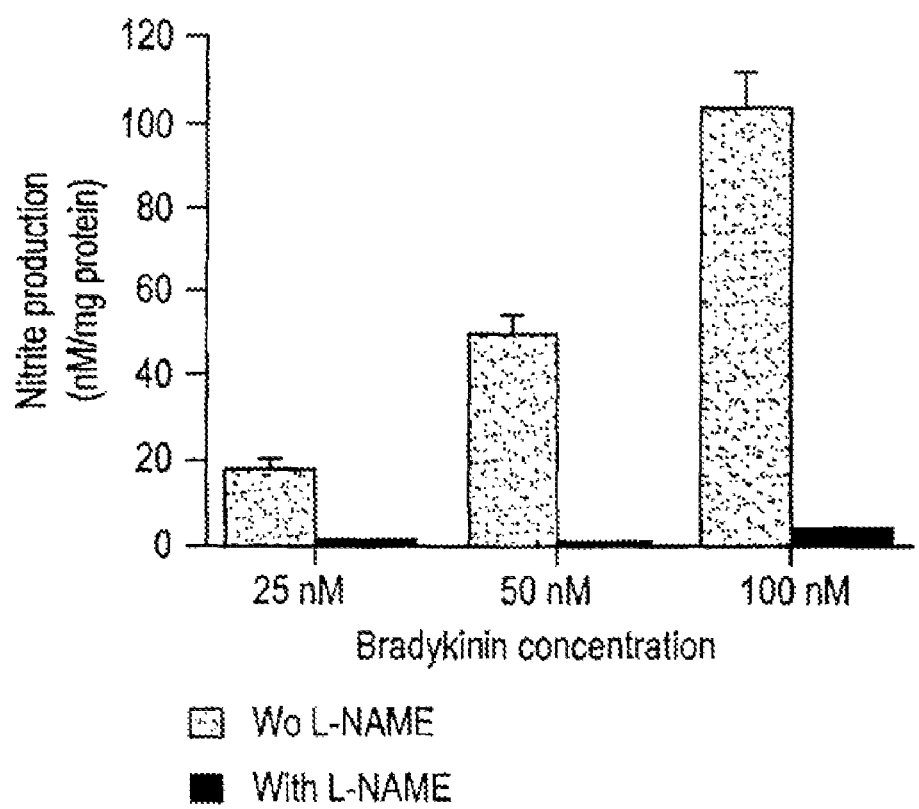
FIG. 52 shows the effect of bradykinin on NO production by HUVEC.

FIG. 52 illustrates the effect of bradykinin on NO production by HUVEC where a dose dependent release of NO was observed. The inhibitor L-NAME completely inhibited the bradykinin induced NO release.

Figure 53:
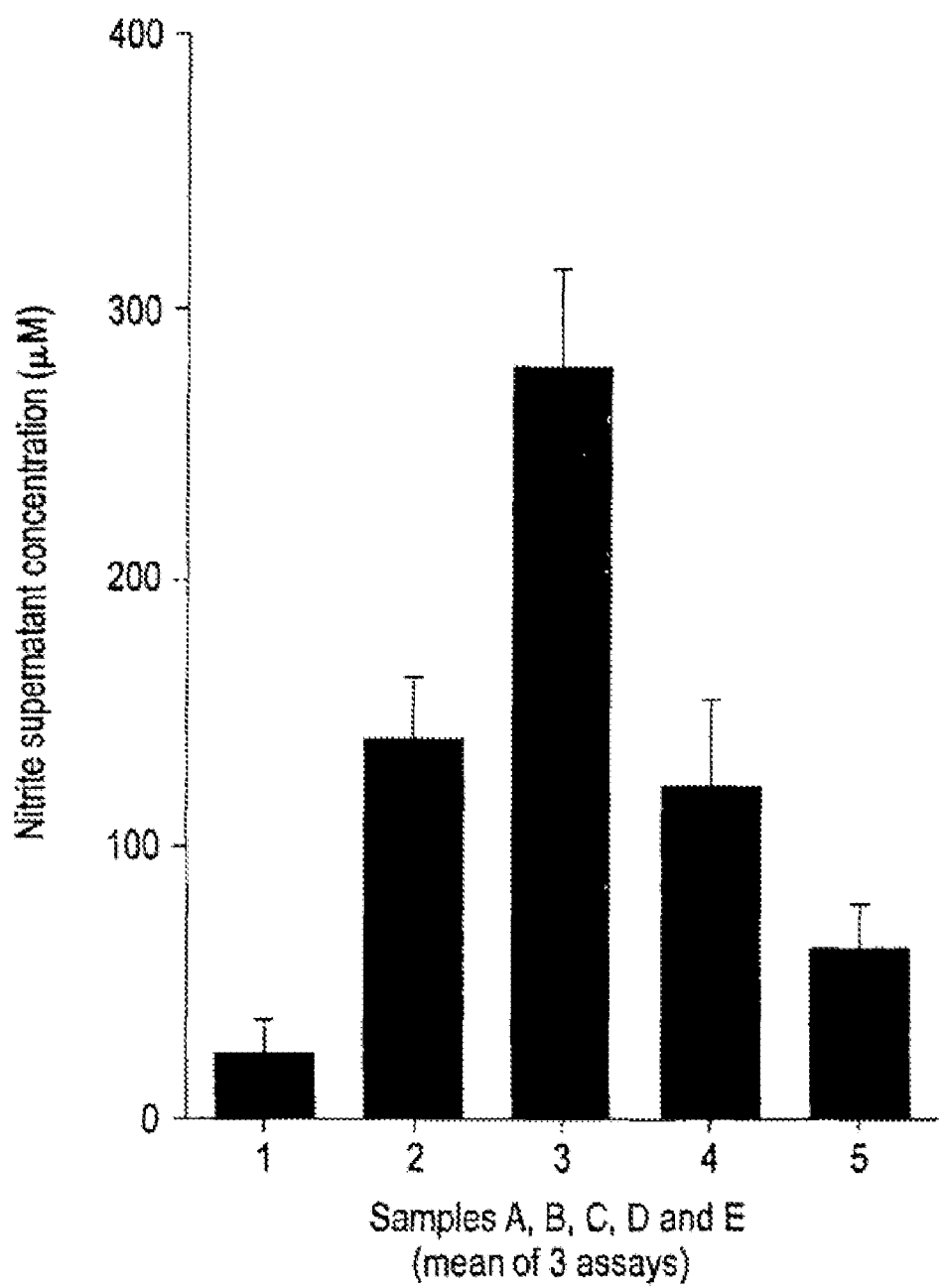
FIG. 53 shows the effect of cocoa procyanidin fractions on macrophage NO production by HUVEC.

FIG. 53 illustrates the effect of the cocoa procyanidin fractions on NO production by HUVEC cells. Fractions B, C and D induced a moderate but significant amount of NO production by HUVEC. By far, Fraction C was the most efficient fraction to induce NO formation as assessed by the production of nitrites, while Fraction E was nearly ineffective. The effect of Fraction C on NO production was dramatically reduced in the presence of L-NAME. Interestingly, Fractions B, C and D contained higher amounts of procyanidin oligomers than Fractions A and E. A distinguishing difference between Fractions D and E was that E was prepared from a dark chocolate which used alkalized cocoa liquor as part of the chocolate recipe. Alkalization leads to a base catalyzed polymerization of procyanidins which rapidly depletes the levels of these compounds. An analytical comparison of procyanidin levels found in these types of chocolate appear in the Table 12, where Brand 12 is a dark chocolate prepared with alkalized cocoa liquor and Brand 11 is a typical milk chocolate. Thus, extracts obtained from milk chocolates contain high proportions of procyanidin oligomers which are capable of inducing NO. The addition of the NO inhibitor L-NMMA to the Fraction C sample clearly led to the inhibition of NO. The results obtained from the procyanidin fractions were consistent to those observed with the bradykinin induced NO experiment (see FIG. 52).

As in the case of the HUVEC results, cocoa procyanidin fraction C elicited a major hypotensive effect in guinea pigs, whereas fractions A and E were the least effective. Again, the presence of high molecular weight procyanidin oligomers were implicated in the modulation of NO production.

Example 33

Effect of Cocoa Procyanidin Fractions on Macrophage NO Production

Fresh, human heparinized blood (70 mL) was added with an equal volume of phosphate buffer saline (PBS) at room temperature. A Ficoll-Hypaque solution was layered underneath the blood-PBS mixture using a 3 mL Ficoll-Hypaque to 10 mL blood-PBS dilution ratio. The tubes were centrifuged for 30 minutes at 2,000 rpm at 18-20° C. The upper layer containing plasma and platelets was discarded. The mononuclear cell layer was transferred to another centrifuge tube and the cells were washed 2× in Hanks balanced saline solution. The mononuclear cells were resuspended in complete RPMI 1640 supplemented with 10% fetal calf serum counted and the viability determined by the trypan blue exclusion method. The cell pellet was resuspended in complete RPMI 1640 supplemented with 20% fetal calf serum to a final concentration of 1×10$^6$ cells/mL. Aliquots of the cell suspension were plated into a 96 well culture plate and rinsed 3× with RPMI 1640 supplemented with 10% fetal calf serum and the nonadherent cells (lymphocytes) were discarded.

These cells were incubated for 48 hours in the presence or absence of five procyanidin fractions described in Example 31. At the end of the incubation period, the culture media were collected, centrifuged and cell free supernatants were stored frozen for nitrate assay determinations.

Macrophage NO production was determined by measuring nitrite concentrations by the Griess reaction. Greiss reagent was 1% sulfanilamide, 0.1% N-(1-naphthyl)-ethylenediamine dihydrochloride. Briefly, 50 µL aliquots were removed from the supernatants in quadruplicate and incubated with 150 µL of the Griess reagent. The absorbency at 540 nm was determined in a multiscan (Labsystems Multiskans MCC/340) apparatus. Sodium nitrite was used at defined concentrations to establish standard curves. The absorbency of the medium without cells (blank) was subtracted from the value obtained with the cell containing supernatants.

In a separate experiment, macrophages were primed for 12 hours in the presence of 5 U/mL gamma-interferon and then stimulated with 10 µg/mL LPS for the next 36 hours in the presence or absence of 100 µg/mL of the five procyanidin fractions.

Figure 54:
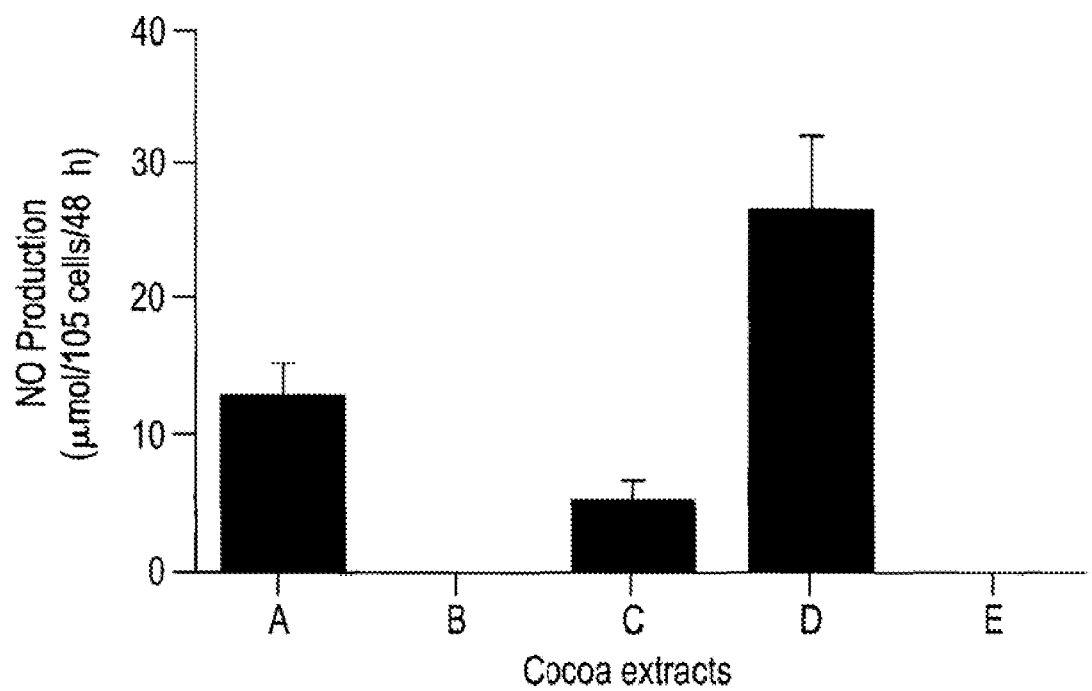
FIG. 54 shows the effect of cocoa extracts on LPS-induced nitrite production by γ-interferon-primed monocytes/macrophages. Cocoa extracts A, C, D enhanced the LPS-induced nitrite production by γ-interferon-primed monocytes/macrophages up to respectively 12.8, 5.2 and 26.8 μM nitrite. LPS stimulated monocytes/macrophages cultured in the absence of cocoa extract produced 4 μM nitrite.
Figure 55:
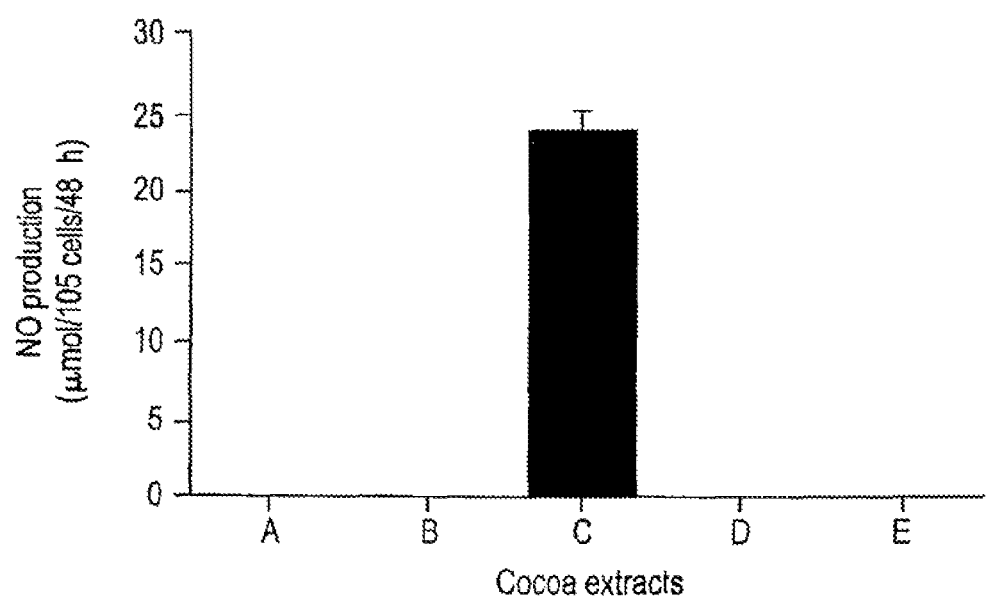
FIG. 55 shows the direct effect of cocoa extracts on nitrite production by monocytes/macrophages. Only extract C at 100 μg/ml induced production (24 μM) by monocytes/macrophages whereas the basal production by these cells was undetectable. The other extract did not evoke NO production, as assessed by the measure of nitrite in supernatants.

FIG. 54 indicates that only procyanidin fraction C, at 100 µg/mL, could induce NO production by monocytes/macrophages. Basal NO production by these cells was undetectable and no nitrite could be detected in any of the cocoa procyanidin fractions used at 100 µg/mL. FIG. 55 indicates that procyanidin fractions A and D enhanced LPS-induced NO production by γ-interferon primed monocytes/macrophages. Procyanidin fraction C was marginally effective, since LPS-stimulated monocytes/macrophages cultured in the absence of procyanidin fractions produced only 4µ mole/105 cells/48 hours. γ-Interferon alone was ineffective in inducing NO.

Collectively, these results demonstrate that mixtures of the inventive compounds used at specific concentrations are capable of inducing monocyte/macrophage NO production both independent and dependent of stimulation by LPS or cytokines.

From the foregoing, it is clear that the extract and cocoa polyphenols, particularly the inventive compounds, as well as the compositions, methods, and kits, of the invention have significant and numerous utilities.

The antineoplastic utility is clearly demonstrated by the in vivo and in vitro data herein and shows that inventive compounds can be used instead of or in conjunction with conventional antineoplastic agents.

The inventive compounds have antioxidant activity like that of BHT and BHA, as well as oxidative stability. Thus, the invention can be employed in place of or in conjunction with BHT or BHA in known utilities of BHA and BHT, such as an antioxidant, for instance, an antioxidant; food additive.

The invention can also be employed in place of or in conjunction with topoisomerase II-inhibitors in the presently known utilities therefor.

The inventive compounds can be used in food preservation or preparation, as well as in preventing or treating maladies of bacterial origin. Simply the inventive compounds can be used as an antimicrobial.

The inventive compounds can also be used as a cyclooxygenase and/or lipoxygenase, NO or NO-synthase, or blood or in vivo glucose modulator, and are thus useful for treatment or prevention or modulation of pain, fever, inflammation coronary conditions, ulceration, carcinogenic mechanisms, vasodilation, as well as an analgesic, anti-coagulant anti-inflammatory and an immune response modulator.

Further, the invention comprehends the use of the compounds or extracts as a vehicle for pharmaceutical preparations. Accordingly, there are many compositions and methods envisioned by the invention. For instance, antioxidant or preservative compositions, topoisomerase II-inhibiting compositions, methods for preserving food or any desired item such as from oxidation, and methods for inhibiting topoisomerase II. The compositions can comprise the inventive compounds. The methods can comprise contacting the food, item or topoisomerase II with the respective composition or with the inventive compounds. Other compositions, methods and embodiments of the invention are apparent from the foregoing.

In this regard, it is mentioned that the invention is from an edible source and, that the activity in vitro can demonstrate at least some activity in vivo; and from the in vitro and in vivo data herein, doses, routes of administration, and formulations can be obtained without undue experimentation.

Example 34

Micellar Electrokinetic Capillary Chromatography of Cocoa Procyanidins

Figure 56:
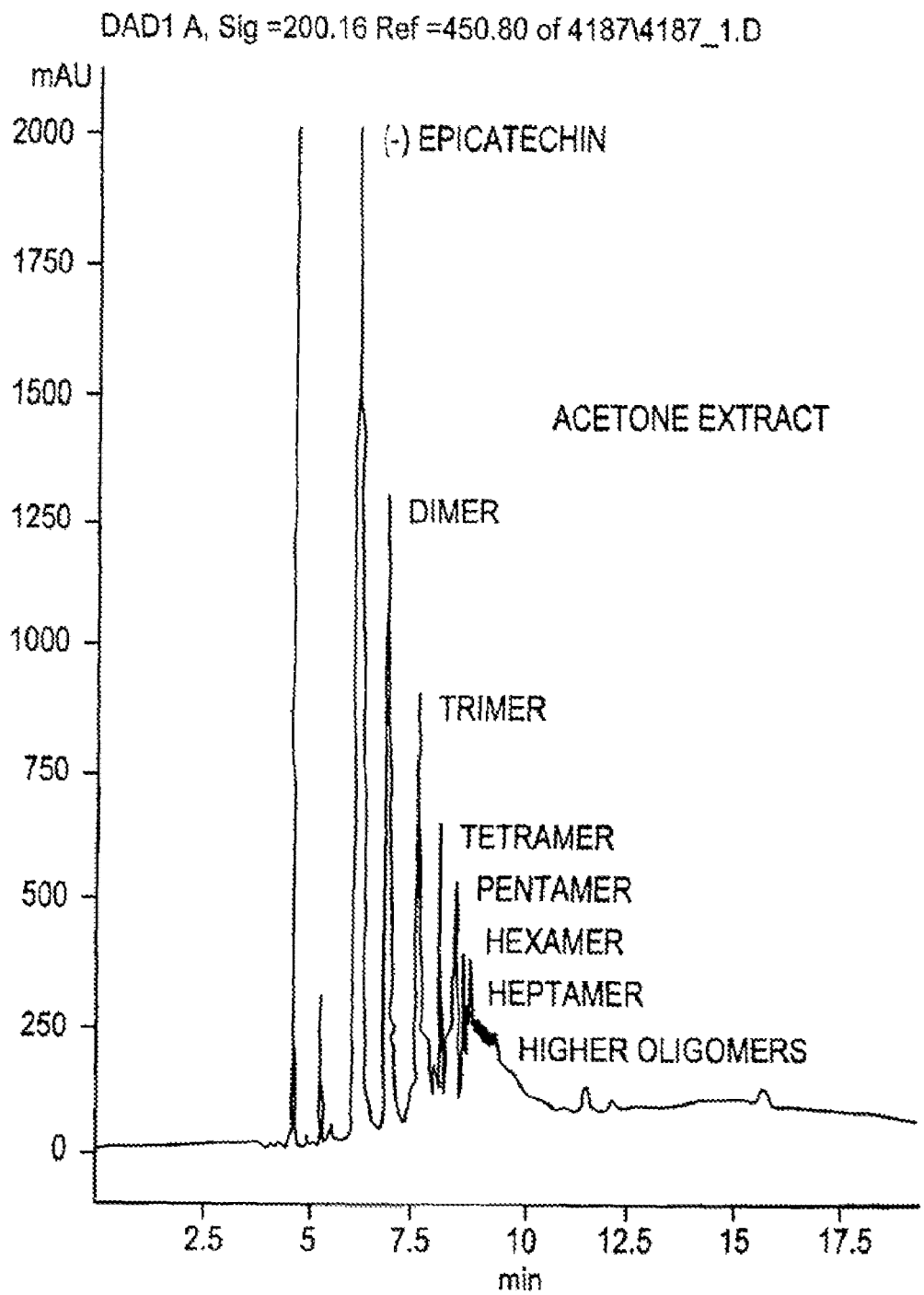
FIG. 56 shows a micellar electrokinetic capillary chromatographic separation of cocoa procyanidin oligomers.
Figure 57:
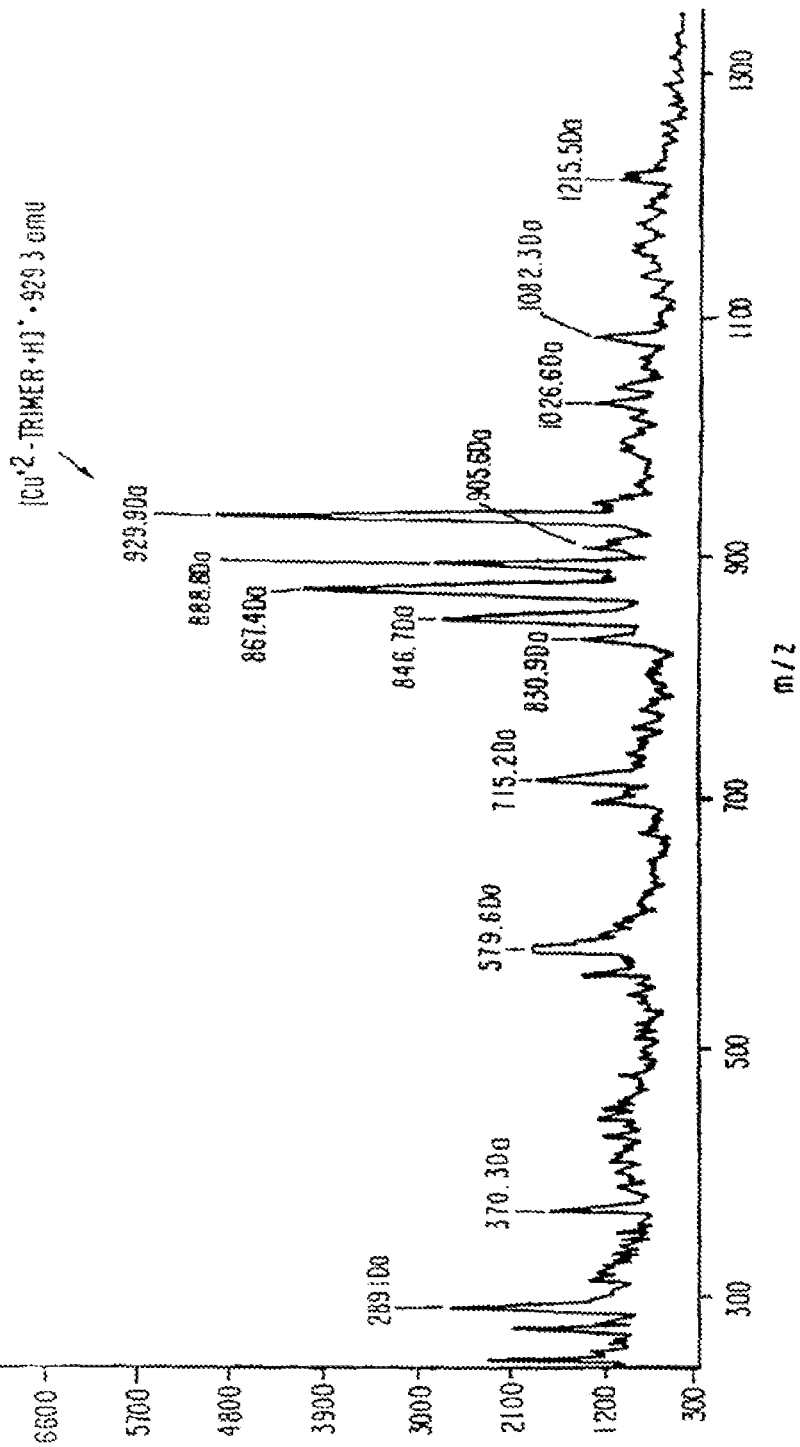
FIGS. 57 A-F show MALDI-TOF mass spectra for $Cu^{+2}$—, $Zn^{+2}$—, $Fe^{+2}$—, $Fe^{+3}$—, $Ca^{+2}$—, and $Mg^{+2}$- ions, respectively, complexed to a trimer.
Figure 57:
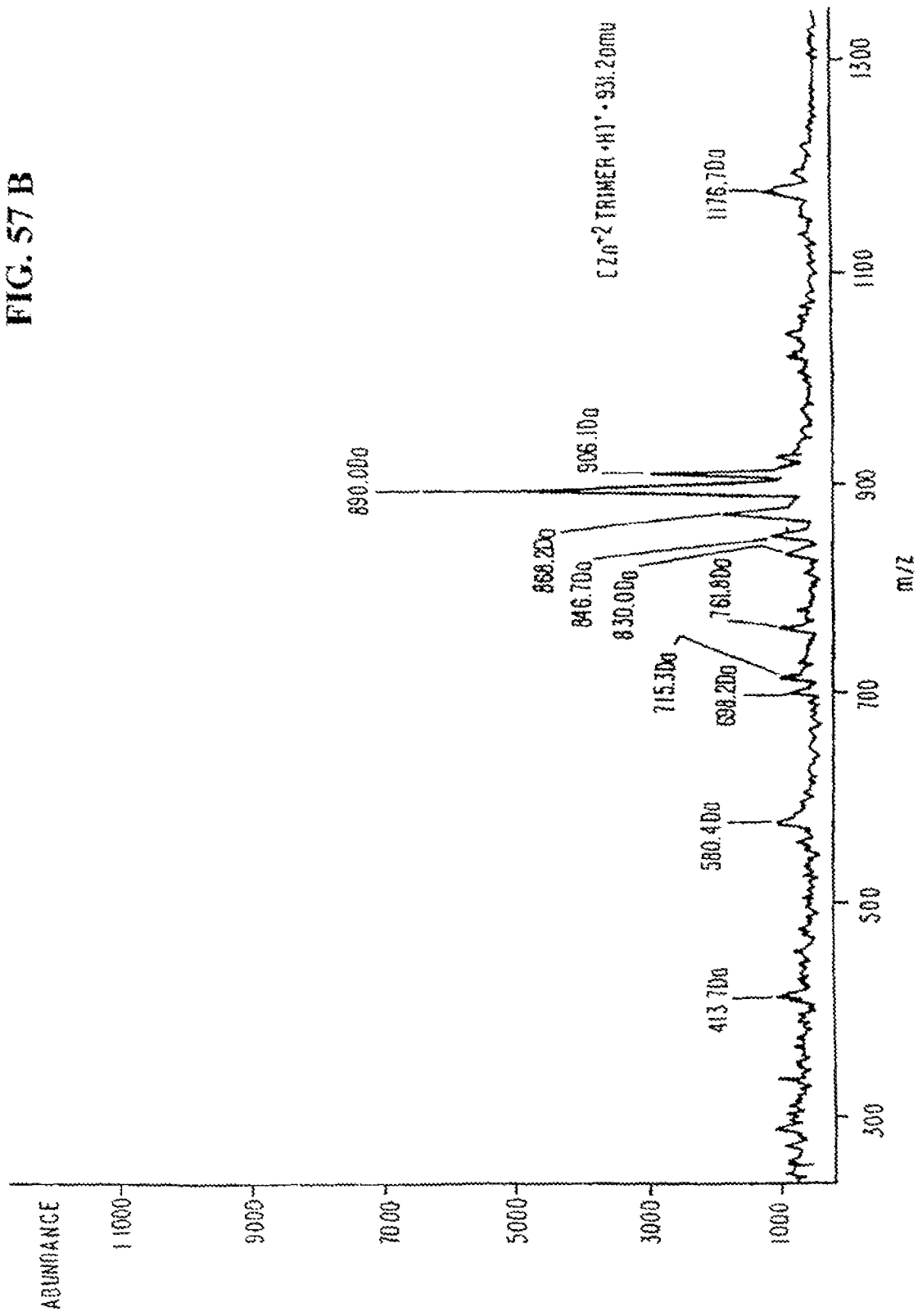
Figure 57:
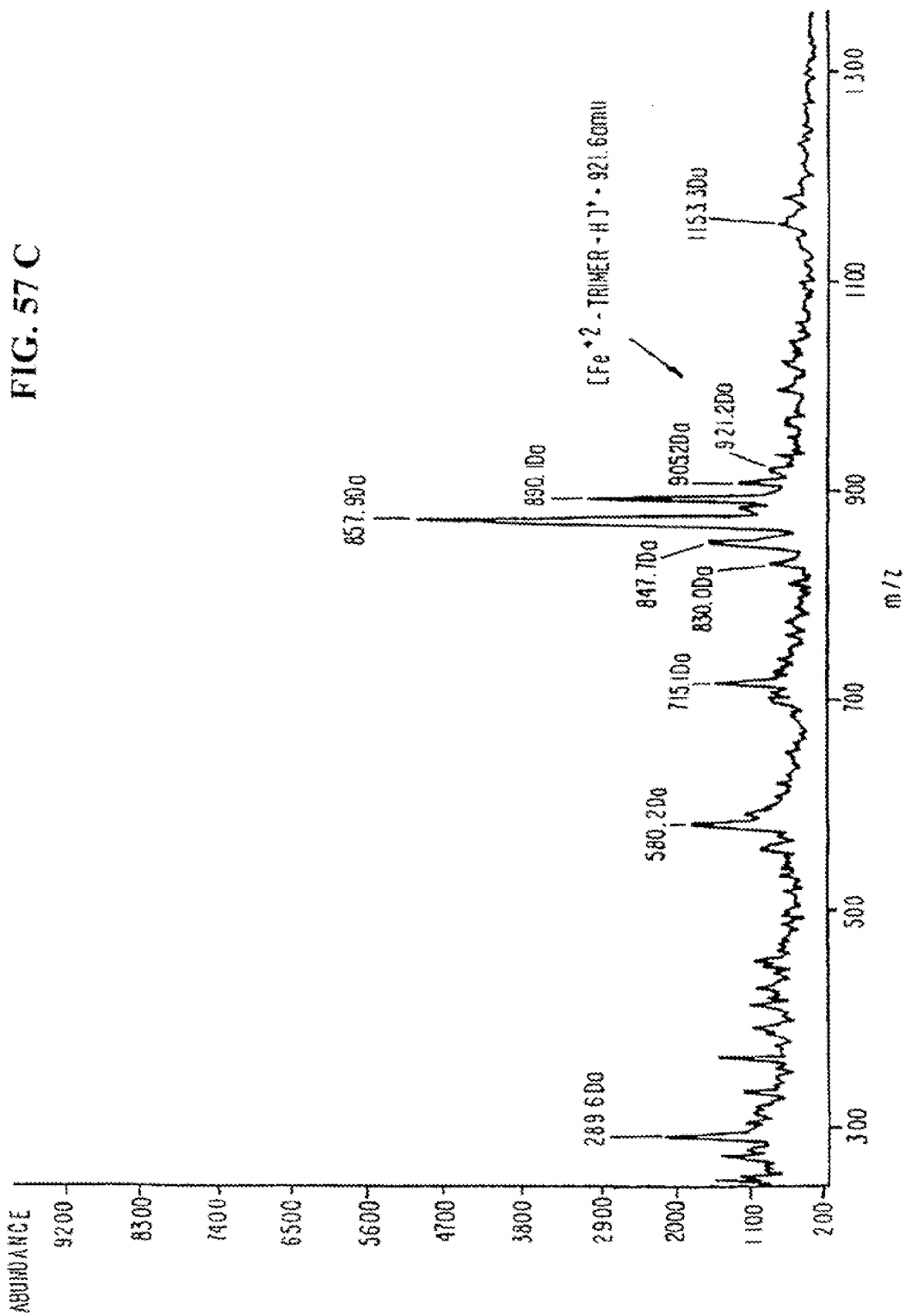
Figure 57:
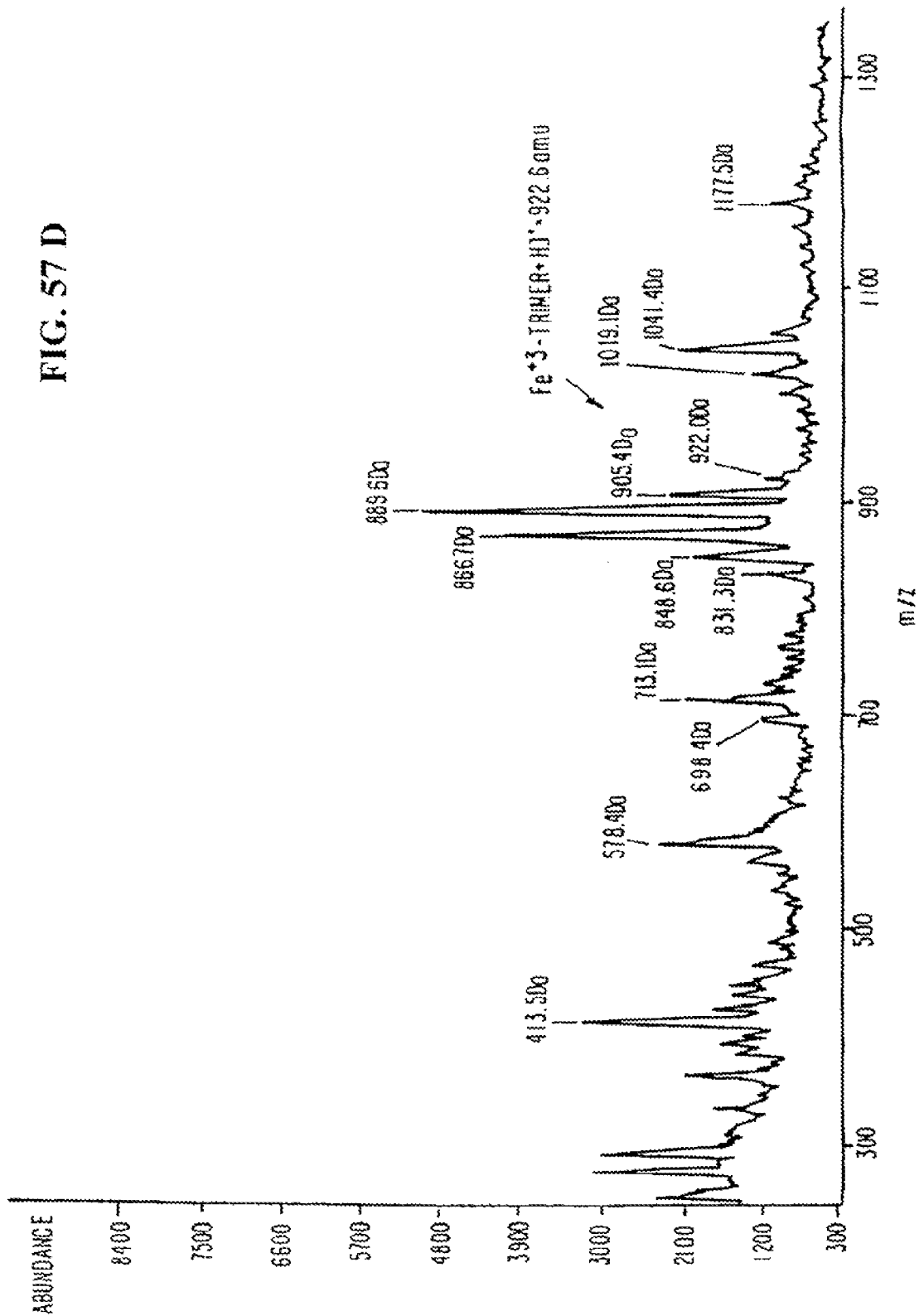
Figure 57:
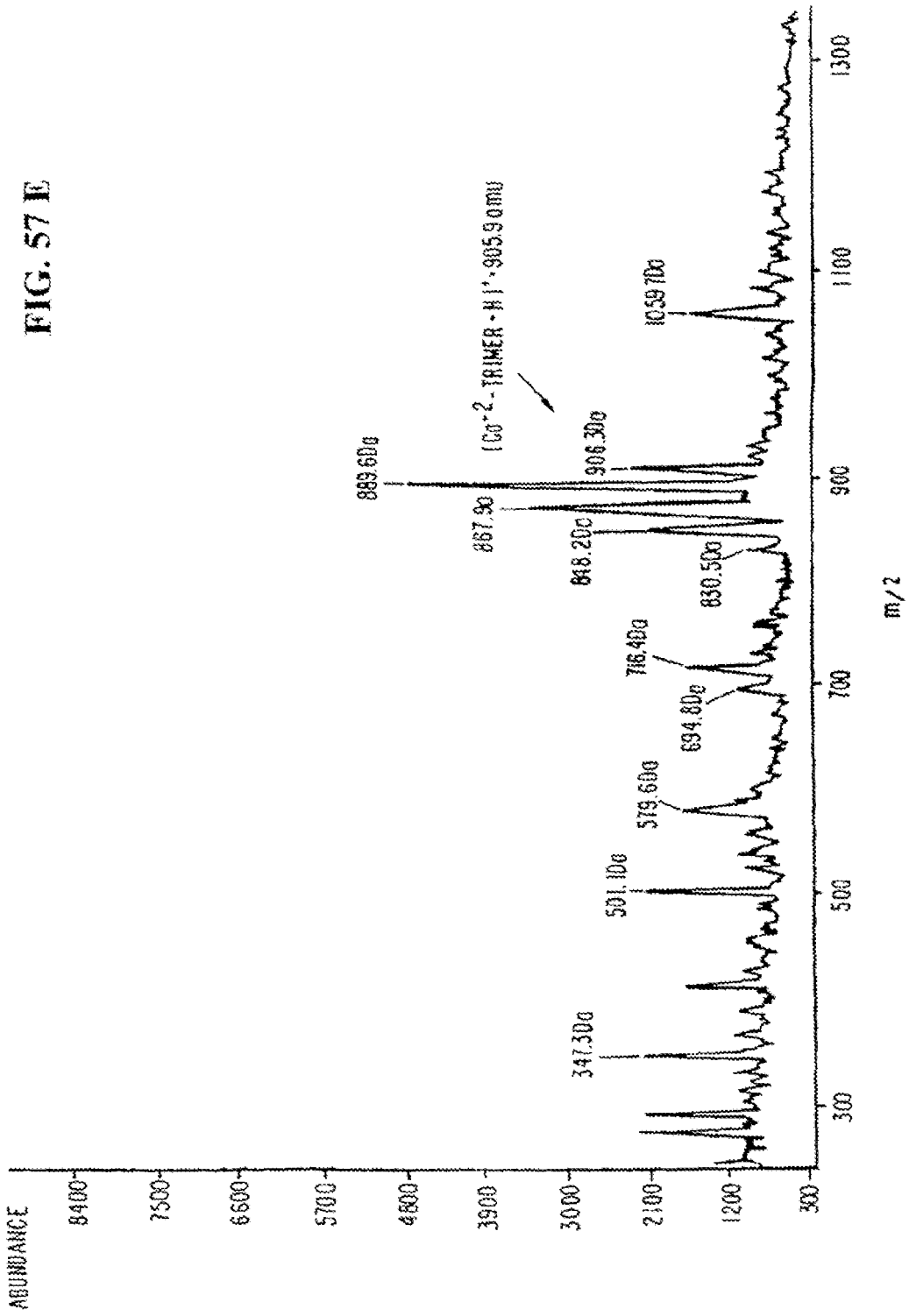
Figure 57:
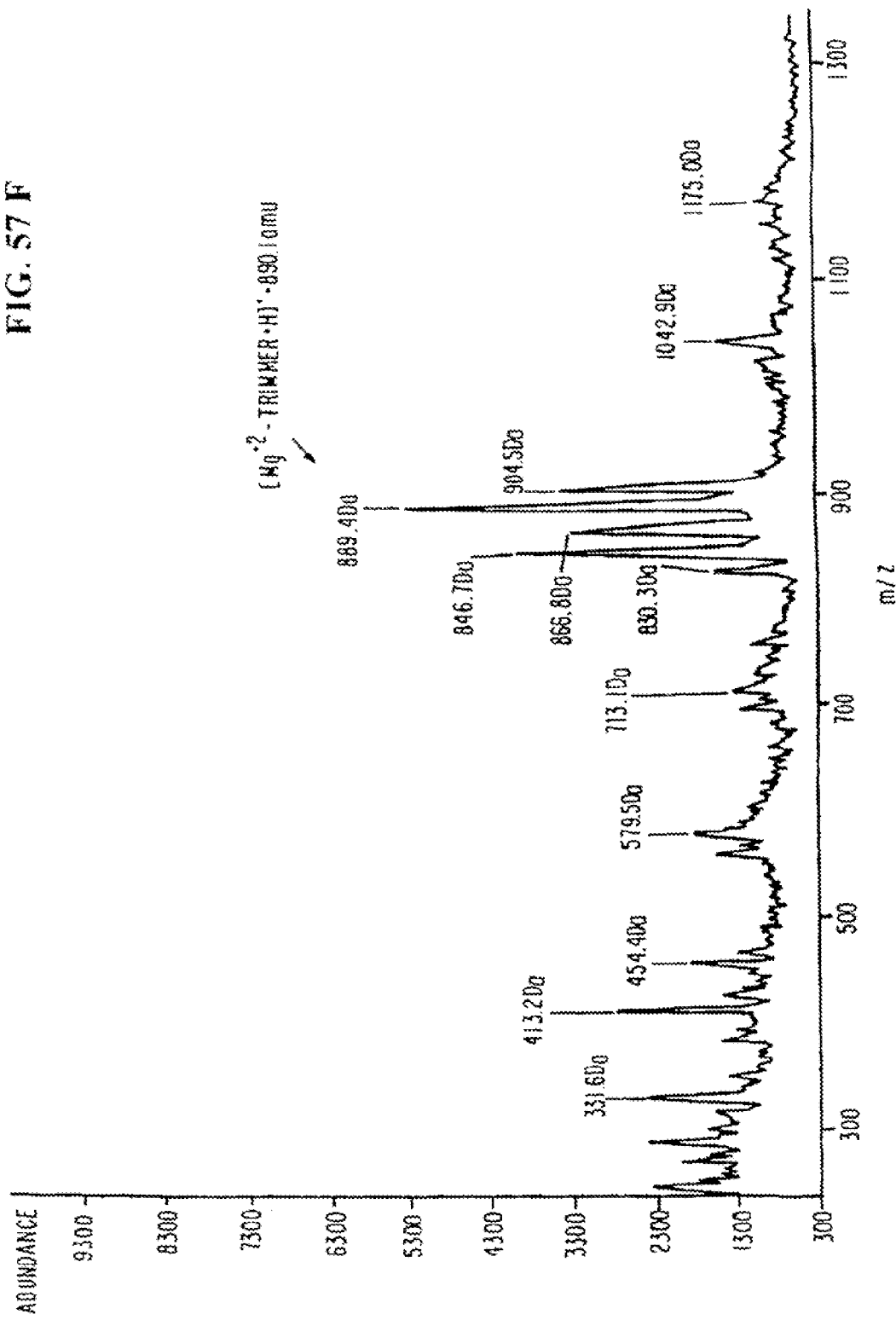

A rapid method was developed using micellar electrokinetic capillary chromatography (MECC) to separate procyanidin oligomers. The method is a modification of that reported by Delgado et al., 1994. The MECC method requires only 12 minutes to achieve the same separation as that obtained by a 70 minute normal phase HPLC analysis. FIG. 56 represents a MECC separation of cocoa procyanidins obtained by Example 2.

MECC Conditions:

The cocoa procyanidin extract was prepared by the method described in Example 2 and dissolved at a concentration of 1 mg/mL in MECC buffer consisting of 200 mM boric acid, 50 mM sodium dodecyl sulfate (electrophoresis pure) and NaOH to adjust to pH=8.5.

The sample was passed through a 0.45 um filter and electrophoresed using a Hewlett Packard HP-3D CZE System operated at the following conditions:
Inlet buffer: Run buffer as described above
Outlet buffer: Run buffer as described above
Capillary: 50 cm×75 um i.d. uncoated fused silica
Detection: 200 nm, with Diode Array Detector
Injection: 50 mBar for 3 seconds (150 mBar sec)
Voltage: 6 watts
Amperage: System limit (<300 uA)
Temperature: 25° C.
Capillary Condition: 5 min flush with run buffer before and after each run.

This method can be modified by profiling temperature, pressure, and voltage parameters, as well as including organic modifiers and chiral selective agents in the run buffer.

Example 35

MALDI-TOF/MS Analysis of Procyanidin Oligomers with Metal Salt Solutions

A series of MALDI-TOF/MS analyses were performed on trimers combined with various metal salt solutions to determine whether cation adducts of the oligomer could be detected. The significance of the experiment was to provide evidence that the procyanidin oligomers play a physiological role in vitro and in vivo by sesquestering or delivering metal cations important to physiological processes and disease.

The method used was as described in Example 15. Briefly, 2 uL of 10 mM solutions of zinc sulfate dihydrate, calcium chloride, magnesium sulfate, ferric chloride hexahydrate, ferrous sulfate heptahydrate, and cupric sulfate were individually combined with 4 uL of a trimer (10 mg/mL) purified to apparent homogeneity as described in Example 14, and 44 uL of DHB added.

The results (FIGS. 57A-F) showed [Metal–Trimer +H]+ ions for copper and iron (ferrous and ferric) whose m/z values matched ±1 amu standard deviation value for the theoretical calculated masses. The [Metal–Trimer +H]+masses for calcium and magnesium could not be unequivocally resolved from the [Metal–Trimer+H]+masses for sodium and potassium, whose m/z values were within the ±1 amu standard deviation values. No [Zn+2–Trimer +H]+ion could be detected. Since some of these cations are multi-valent, the possibility for multimetal-oligomer(s) ligand species and /or metal-multioligomer species were possible. However, scanning for these adducts at their predicted masses proved unsuccessful.

The results shown above for copper, iron, calcium, magnesium and zinc may be used as general teachings for subsequent analysis of the reaction between other metal ions and the inventive compounds, taking into account such factors as oxidation state and the relative position in the periodic table of the ion in question.

Example 36

MALDI-TOF/MS Analysis of High Molecular Weight Procyanidin Oligomers

An analytical examination was made on GPC eluants associated with high molecular weight procyanidin oligomers as prepared in Example 3, Method A. The objective was to determine whether procyanidin oligomers with n>12 were present. If present, these oligomers represent additional compounds of the invention. Adjustments to existing methods of isolation, separation and purification embodied in the invention can be made to obtain these oligomers for subsequent in vitro and in vivo evaluation for anti-cancer, anti-tumor or antineoplastic activity, antioxidant activity, inhibit DNA topoisomerase II enzyme, inhibit oxidative damage to DNA, and have antimicrobial, NO or NO-synthase, apoptosis, platelet aggregation, and blood or in vivo glucose-modulating activities, as well as efficacy as non-steroidal antiinflammatory agents.

Figure 58:
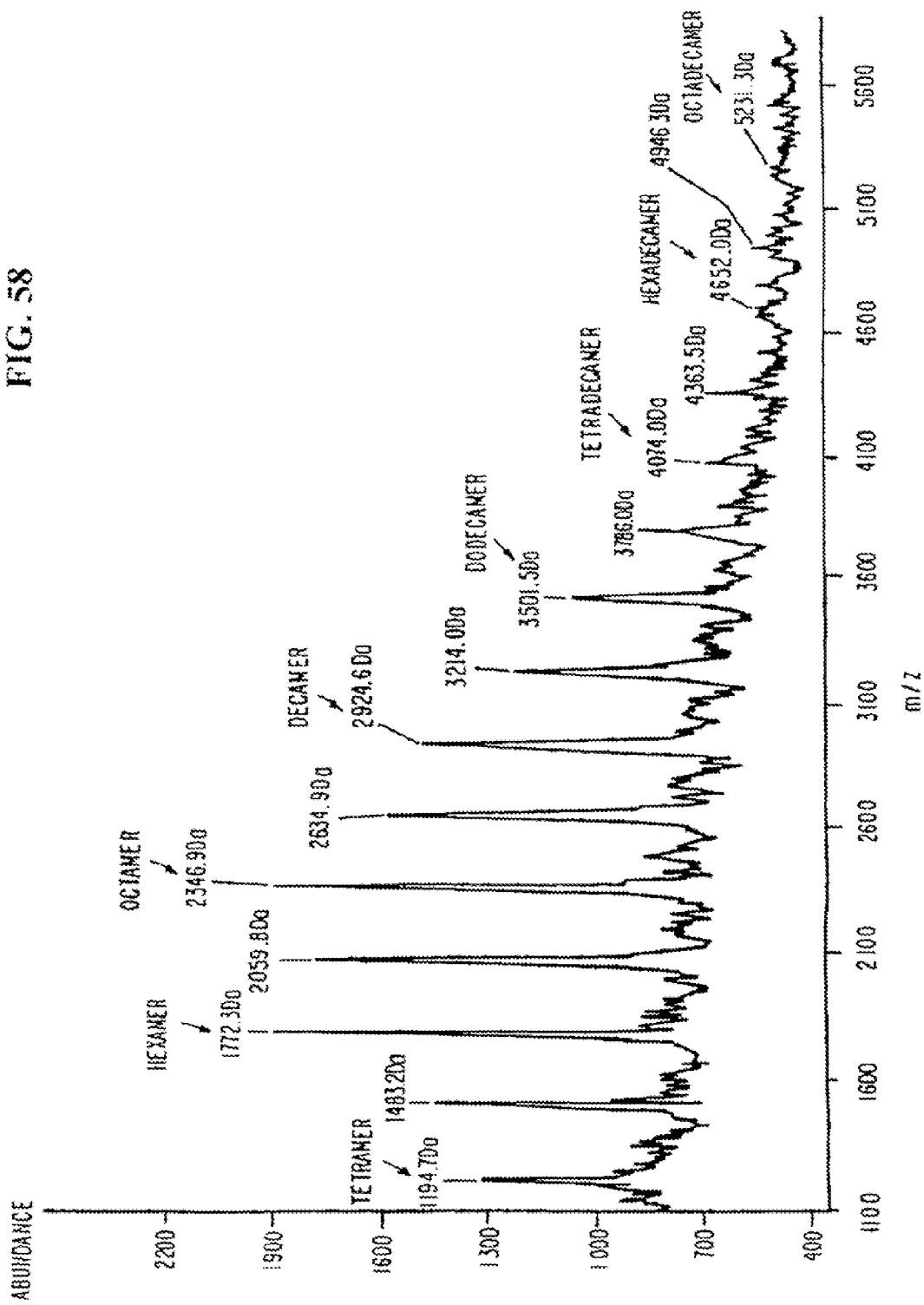
FIG. 58 shows a MALDI-TOF mass spectrum of cocoa procyanidin oligomers (tetramers to octadecamers)
Figure 59:
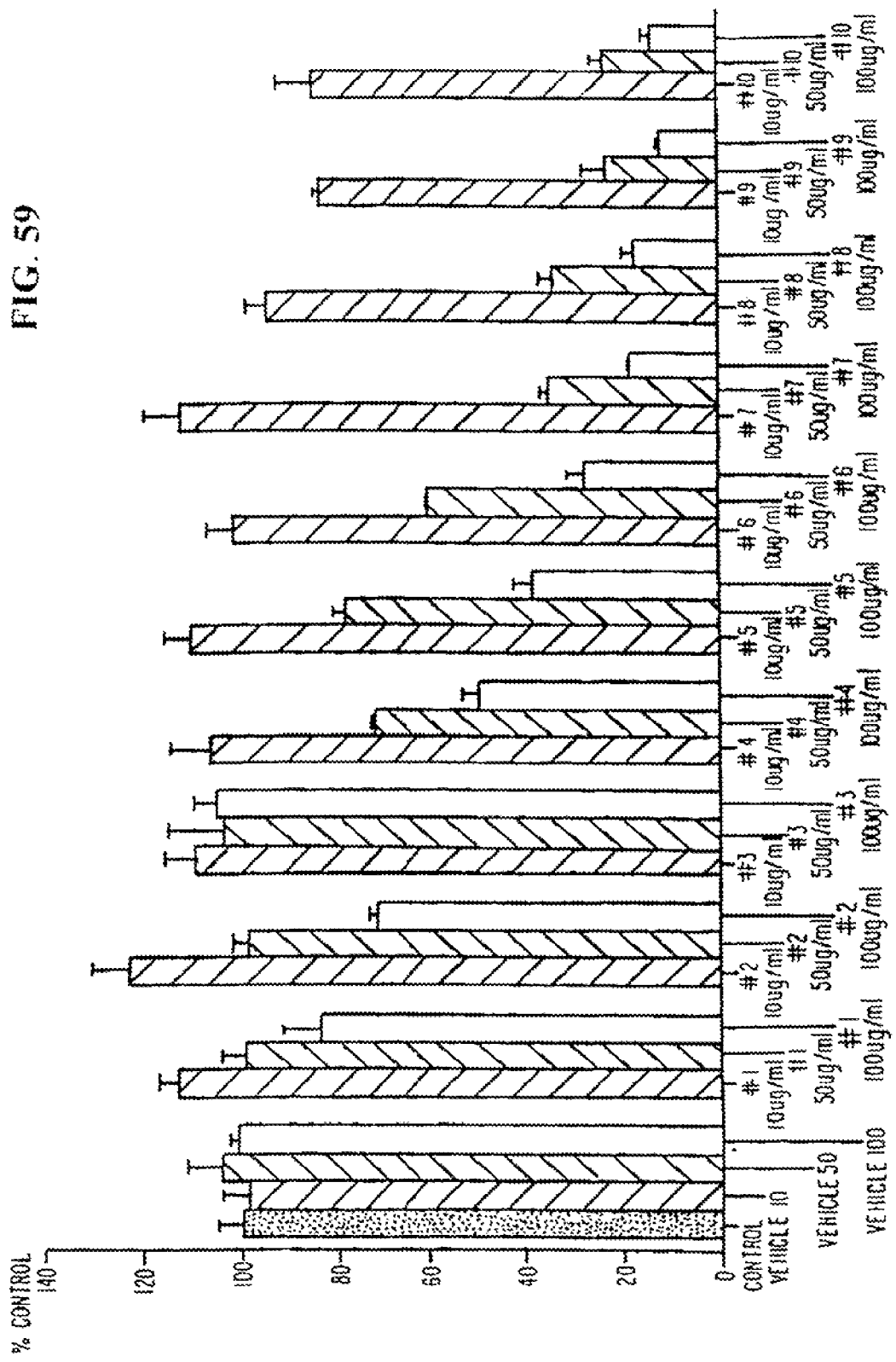
FIG. 59 shows the dose-response relationship of cocoa procyanidin oligomers and the feline FeA lymphoblastoid cell line producing leukemia virus.
Figure 60:
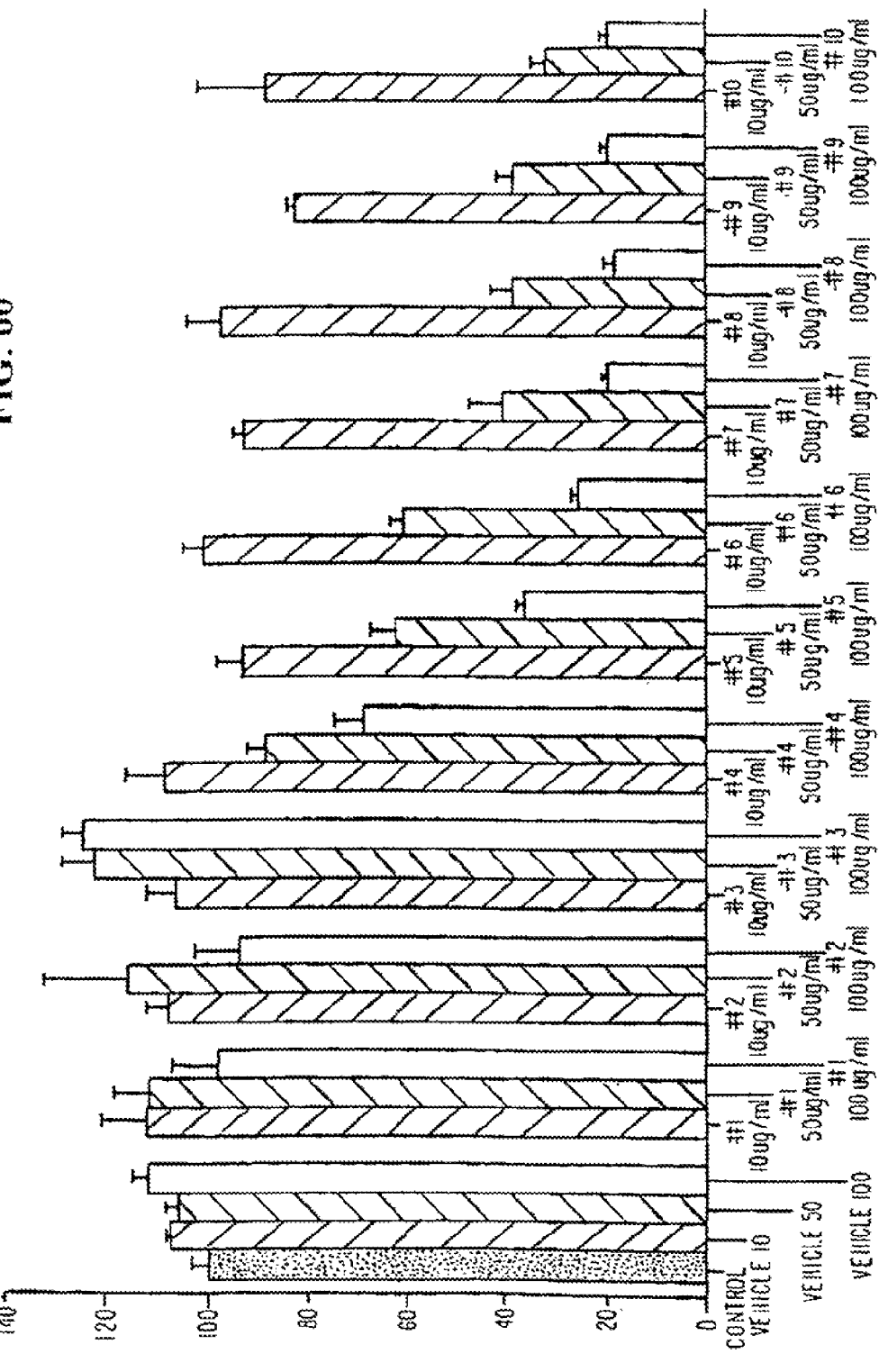
FIG. 60 shows the dose-response relationship of cocoa procyanidin oligomers and the feline CRFK normal kidney cell line.
Figure 61:
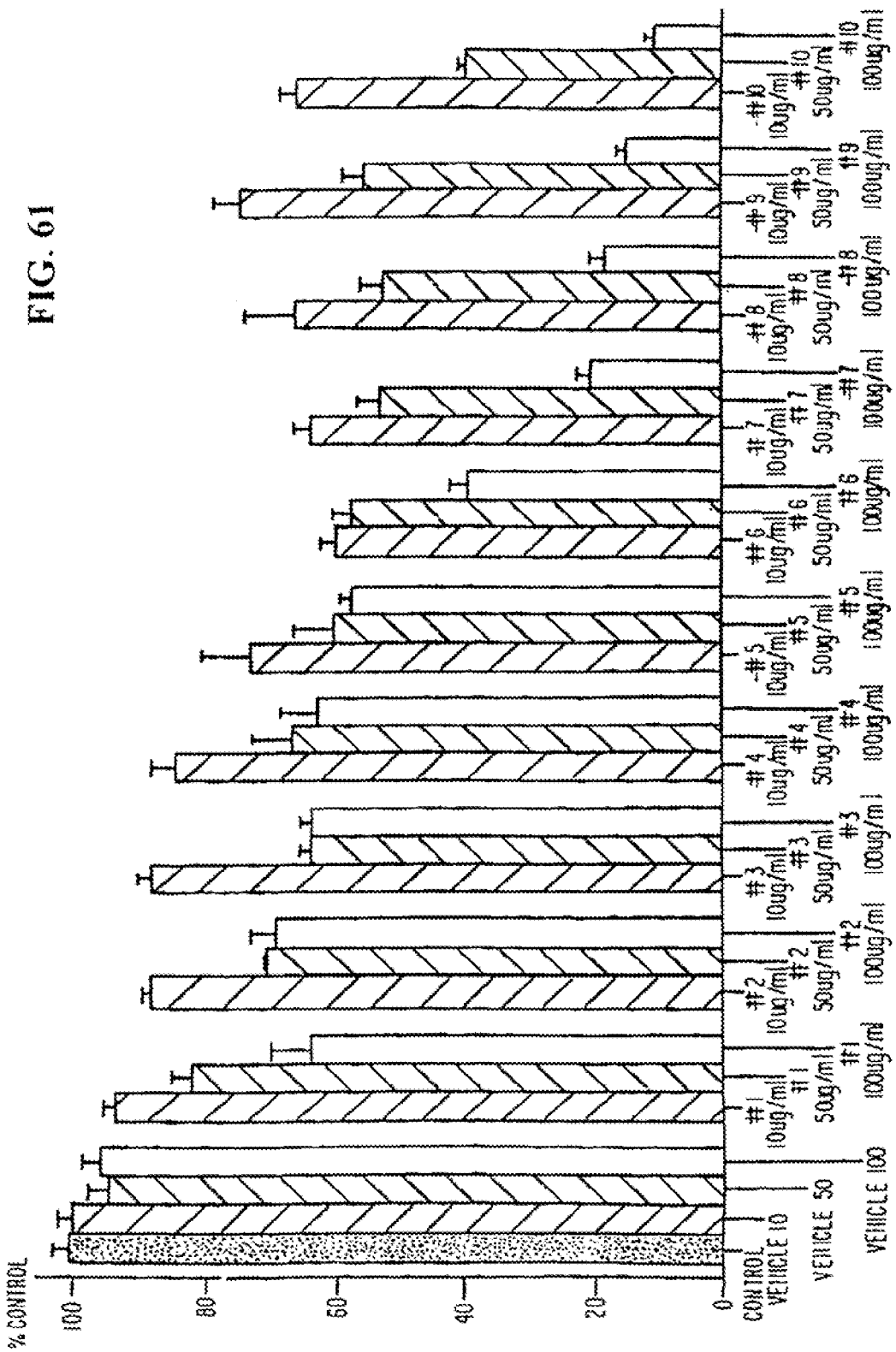
FIG. 61 shows the dose-response relationship of cocoa procyanidin oligomers and the canine MDCK normal kidney line.
Figure 62:
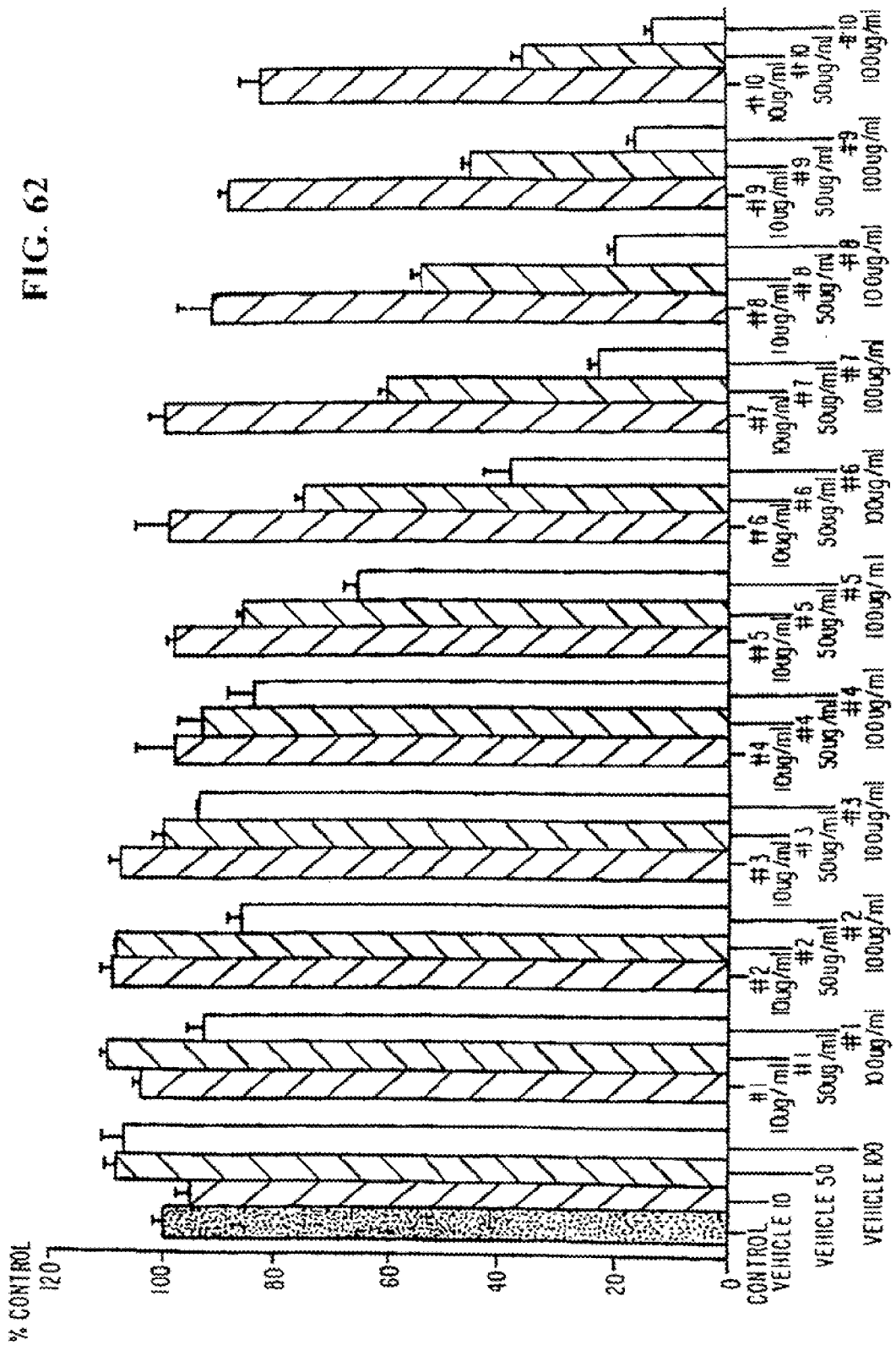
FIG. 62 shows the dose-response relationship between cocoa procyanidin oligomers and the canine GH normal kidney cell line.

FIG. 58 represents a MALDI-TOF mass spectrum of the GPC eluant sample described above. The [M +Na]+and/or [M +K]+and/or [M +2Na]+ions characterizing procyanidin oligomers representative of tetramers through octadecamers are clearly evident.

It was learned that an acid and heat treatment will cause the hydrolysis of procyanidin oligomers. Therefore, the invention comprehends the controlled hydrolysis of high molecular weight procyanidin oligomers (e.g. where n is 13 to 18) as a method to prepare lower molecular weight procyanidin oligomers (e.g. where n is 2 to 12).

Example 37

Dose Response Relationships of Procyanidin Oligomers and Canine and Feline Cell Lines The dose respone effects of procyanidin oligomers were evaluated against several canine and feline cell lines obtained from the Waltham Center for Pet Nutrition, Waltham on-the-Wolds, Melton Mowbray, Leicestershire, U.K. These cell lines were Canine normal kidney GH cell line;
Canine normal kidney MDCK cell line;
Feline normal kidney CRFK cell line; and
Feline lymphoblastoid FeA cell line producing leukemia virus which were cultured under the conditions described in Example 8, Method A.

Monomers and procyanidin oligomers, where n is 2 to 10 were purified as described in Example 14, Method D. The oligomers were also examined by analytical normal phase HPLC as described in Example 14, Method C, where the following results were obtained.

| Procyanidin | % Purity by HPLC |
| --- | --- |
| Monomers | 95.4 |
| Dimers | 98.0 |
| Trimers | 92.6 |
| Tetramers | 92.6 |
| Pentamers | 93.2 |
| Hexamers | 89.2 (Contains 4.4% pentamers) |
| Heptamers | 78.8 (Contains 18.0% hexamers) |
| Octamers | 76.3 (contains 16.4% heptamers) |
| Nonamers | 60.3 (Contains 27.6% octamers) |
| Decamers | 39.8 (Contains 22.2% nonamers, 16.5% octamers, and 13.6% heptamers) |

In those cases where the purity of the oligomer is <90%, methods embodied in the invention are used for their repurification.

Each cell line was dosed with monomers and each procyanidin oligomer at 10 ug/mL, 50 ug/mL and 100 ug/mL and the results shown in FIGS. 59-62. As shown in the Figures, high dose (100 ug/mL) administration of individual oligomers produced similar inhibitory effects on the feline FeA lymphoblastoid and feline normal kidney CRFK cell lines. In these cases, cytotoxicity appeared with the tetramer, and increasingly higher oligomers elicited increasingly higher cytotoxic effects. By contrast, high dose (100 ug/mL) administration of individual oligomers to canine GH and MDCK normal kidney cell lines required a higher oligomer to initiate the appearance of cytotoxicity. For the canine GH normal kidney cell line, cytotoxicity appeared with the pentamer. For the canine MDCK normal kidney cell line, cytotoxicity appeared with the hexamer. In both of these cases, the administration of higher oligomers produced increasing levels of cytotoxicity.

Example 38

Tablet Formulations

A tablet formulation was prepared using cocoa solids obtained by methods described in U.S. application Ser. No. 08/709,406 filed 6 Sep. 1996, hereby incorporated herein by reference. Briefly, this edible material is prepared by a process which enhances the natural occurrence of the compounds of the invention in contrast to their levels found in traditionally processed cocoa, such that the ratio of the initial amount of the compounds of the invention found in the unprocessed bean to that obtained after processing is less than or equal to 2. For simplicity, this cocoa solids material is designated herein as CP-cocoa solids. The inventive compound or compounds, e.g., in isolated and/or purified form may be used in tablets as described in this Example, instead of or in combination with CP-cocoa solids.

A tablet formula comprises the following (percentages expressed as weight percent):

| | |
| --- | --- |
| CP-cocoa solids | 24.0% |
| 4-Fold Natural vanilla extract (Bush Boake Allen) | 1.5% |
| Magnesium stearate (dry lubricant)(AerChem, Inc.) | 0.5% |
| Dipac tabletting sugar (Amstar Sugar Corp.) | 37.0% |
| Xylitol (American Xyrofin, Inc.) | 37.0% |
| | 100.0% |

The CP-cocoa solids and vanilla extract are blended together in a food processor for 2 minutes. The sugars and magnesium stearate are gently mixed together, followed by blending in the CP-cocoa solids/vanilla mix. This material is run through a Manesty Tablet Press (B3B) at maximum pressure and compaction to produce round tablets (15 mm×5 mm) weighing 1.5-1.8 gram. Another tablet of the above mentioned formula was prepared with a commercially available low fat natural cocoa powder (11% fat) instead of the CP-cocoa solids (11% fat). Both tablet formulas produced products having acceptable flavor characteristics and texture attributes.

An analysis of the two tablet formulas was performed using the procedures described in Example 4, Method 2. In this case, the analysis focused on the concentration of the pentamer and the total level of monomers and compounds of the invention where n is 2 to 12 which are reported below in Tab 15.

TABLE 15

| Tablet sample | pentamer (ug/g) | total (ug/g) | pentamer (ug/1.8 g serving) | total (ug/1.8 g serving) |
| --- | --- | --- | --- | --- |
| tablet with CP-cocoa solids | 239 | 8,277 | 430 | 14,989 |
| tablet with commercial low fat cocoa powder | ND | 868 | ND | 1563 |

ND = not detected

The data clearly showed a higher level of pentamer and total level of compounds of the invention in the CP-cocoa solids tablet than in the other tablet formula. Thus, tablet formulas prepared with CP-cocoa solids are an ideal delivery vehicle for the oral administration of compounds of the invention, for pharmaceutical, supplement and food applications.

The skilled artisan in this area can readily prepare other tablet formulas covering a wide range of flavors, colors, excipients, vitamins, minerals, OTC medicaments, sugar fillers, UV protectants (e.g., titanium dioxide, colorants, etc.), binders, hydrogels, and the like except for polyvinyl pyrrolidone which would irreversibly bind the compounds of the invention or combination of compounds. The amount of sugar fillers may be adjusted to manipulate the dosages of the compounds of the invention or combination of compounds.

Many apparent variations of the above are self-evident and possible without departing from the spirit and scope of the example.

Example 39

Capsule Formulations

A variation of Example 38 for the oral delivery of the compounds of the invention is made with push-fit capsules made of gelatin, as well as soft sealed capsules made of gelatin and a plasticizer such as glycerol. The push-fit capsules contain the compound of the invention or combination of compounds or CP-cocoa solids as described in Examples 38 and 40 in the form of a powder which can be optionally mixed with fillers such as lactose or sucrose to manipulate the dosages of the compounds of the invention. In soft capsules, the compound of the invention or combination of compounds or CP-cocoa solids are suspended in a suitable liquid such as fatty oils or cocoa butter or combinations therein. Since an inventive compound or compounds may be light-sensitive, e.g., sensitive to UV, a capsule can contain UV protectants such as titanium dioxide or suitable colors to protect against UV. The capsules can also contain fillers such as those mentioned in the previous Example.

Many apparent variations of the above are self-evident and possible to one skilled in the art without departing from the spirit and scope of the example.

Example 40

Standard of Identity (SOI) and Non-Standard of Identity (non-SOI) Dark and Milk Chocolate Formulations Formulations of the compounds of the invention or combination of compounds derived by methods embodied in the invention can be prepared into SOI and non-SOI dark and milk chocolates as a delivery vehicle for human and veterinary applications. Reference is made to copending U.S. application Ser. No. 08/709,406, filed Sep. 6, 1996, hereby incorporated herein by reference. U.S. Ser. No. 08/709,406 relates to a method of producing cocoa butter and/or cocoa solids having conserved levels of the compounds of the invention from cocoa beans using a unique combination of processing steps. Briefly, the edible cocoa solids obtained by this process conserves the natural occurrence of the compounds of the invention in contrast to their levels found in traditionally processed cocoa, such that the ratio of the initial amount of the compounds of the invention found in the unprocessed bean to that obtained after processing is less than or equal to 2. For simplicity, this cocoa solids material is designated herein as CP-cocoa solids. The CP-cocoa solids are used as a powder or liquor to prepare SOI and non-SOI chocolates, beverages, snacks, baked goods, and as an ingredient for culinary applications.

The term "SOI chocolate" as used herein shall mean any chocolate used in food in the United States that is subject to a Standard of Identity established by the U.S. Food and Drug Administration under the Federal Food, Drug and Cosmetic Act. The U.S. definitions and standards for various types of chocolate are well established. The term "non-SOI chocolate" as used herein shall mean any nonstandardized chocolates which have compositions which fall outside the specified ranges of the standardized chocolates.

Examples of nonstandardized chocolates result when the cocoa butter or milk fat are replaced partially or completely; or when the nutrative carbohydrate sweetener is replaced partially or completely; or flavors imitating milk, butter, cocoa powder, or chocolate are added or other additions or deletions in the formula are made outside the U.S. FDA Standards of Identity for chocolate or combinations thereof.

As a confection, chocolate can take the form of solid pieces of chocolate, such as bars or novelty shapes, and can also be incorporated as a component of other, more complex confections where chocolate is optionally combined with any Flavor & Extract Manufacturers Association (FEMA) material, natural juices, spices, herbs and extracts categorized as natural-flavoring substances; nature-identical substances; and artificial flavoring substances as defined by FEMA GRAS lists, FEMA and FDA lists, Council of Europe (CoE) lists, International Organization of the Flavor Industry (IOFI) adopted by the FAO/WHO Food Standard Programme, Codex Alimentarius, and Food Chemicals Codex and generally coats other foods such as caramel, nougat, fruit pieces, nuts, wafers or the like. These foods are characterized as microbiologically shelf-stable at 65-85° F. under normal atmospheric conditions. Other complex confections result from surrounding with chocolate soft inclusions such as cordial cherries or peanut butter. Other complex confections result from coating ice cream or other frozen or refrigerated desserts with chocolate. Generally, chocolate used to coat or surround foods must be more fluid than chocolates used for plain chocolate solid bars or novelty shapes.

Additionally, chocolate can also be a low fat chocolate comprising a fat and nonfat solids, having nutrative carbohydrate sweetener(s), and an edible emulsifier. As to low fat chocolate, reference is made to U.S. Pat. Nos. 4,810,516, 4,701,337, 5,464,649, 5,474,795, and WO 96/19923.

Dark chocolates derive their dark color from the amount of chocolate liquor, or alkalized liquor or cocoa solids or alkalized cocoa solids used in any given formulation. However, the use of alkalized cocoa solids or liquor would not be used in the dark chocolate formulations in the invention, since Example 27, Table 13 teaches the loss of the compounds of the invention due to the alkalization process.

Examples of formulations of SOI and non-SOI dark and milk chocolates are listed in Tables 16 and 17. In these formulations, the amount of the compounds of the invention present in CP-cocoa solids was compared to the compounds of the invention present in commercially available cocoa solids.

The following describes the processing steps used in preparing these chocolate formulations.

Process for Non-SOI Dark Chocolate
1. Keep all mixers and refiners covered throughout process to avoid light.
2. Batch all the ingredients excluding 40% of the free fat (cocoa butter and anhy. milk fat) maintaining temperature between 30-35° C.
3. Refine to 20 microns.
4. Dry conche for 1 hour at 35° C.
5. Add full lechithin and 10% cocoa butter at the beginning of the wet conche cycle; wet conche for 1 hour.
6. Add all remaining fat, standardize if necessary and mix for 1 hour at 3°5C.
7. Temper, mould and package chocolate.

Process for SOI Dark Chocolate
1. Batch all ingredients excluding milk fat at a temperature of 60° C.
2. Refine to 20 microns.
3. Dry conche for 3.5 hours at 60° C.
4. Add lecithin and milk fat and wet conche for 1 hour at 60° C.
5. Standardize if necessary and mix for 1 hour at 35° C.
Temper, mould and package chocolate.

Process for non-SOI Milk Chocolate
1. Keep all mixers and refiners covered throughout process to avoid light.
2. Batch sugar, whole milk powder, malted milk powder, and 66% of the cocoa butter, conche for 2 hours at 75° C.
3. Cool batch to 35° C. and add cocoa powder, ethyl vanillin, chocolate liquor and 21% of cocoa butter, mix 20 minutes at 35° C.
4. Refine to 20 microns.
5. Add remainder of cocoa butter, dry conche for 1.5 hour at 35° C.
6. Add anhy. milk fat and lecithin, wet conche for 1 hour at 35° C.
7. Standardize, temper, mould and package the chocolate.

Process for SOI Milk Chocolate
1. Batch all ingredients excluding 65% of cocoa butter and milk fat at a temperature of 60° C.
2. Refine to 20 microns.
3. Dry conche for 3.5 hours at 60° C.
4. Add lecithin, 10% of cocoa butter and anhy. milk fat; wet conche for 1 hour at 60° C.
5. Add remaining cocoa butter, standardize if necessary and mix for 1 hour at 35° C.
6. Temper, mould and package the chocolate.

The CP-cocoa solids and commercial chocolate liquors used in the formulations were analyzed for the pentamer and total level of monomers and compounds of the invention where n is 2 to 12 as described in Method 2, Example 4 prior to incorporation in the formulations. These values were then used to calculate the expected levels in each chocolate formula as shown in Tables 16 and 17. In the cases for the non-SOI dark chocolate and non-SOI milk chocolate, their products were similarly analyzed for the pentamer, and the total level of monomers and the compounds of the invention where n is 2 to 12. The results appear in Tables 16 and 17.

The results from these formulation examples indicated that SOI and non-SOI dark and milk chocolates formulated with CP-cocoa solids contained approximately 6.5 times more expected pentamer, and 3.5 times more expected total levels in the SOI and non-SOI dark chocolates; and approximately 4.5; 7.0 times more expected pentamer and 2.5; 3.5 times more expected total levels in the SOI and non-SOI milk chocolates, respectively.

Analyses of some of the chocolate products were not performed since the difference between the expected levels of the compounds of the invention present in finished chocolates prepared with CP-cocoa solids were dramatically higher than those formulas prepared with commercially available cocoa solids. However, the effects of processing was evaluated in the non-SOI dark and milk chocolate products. As shown in the tables, a 25-50% loss of the pentamer occurred, while slight differences in total levels were observed. Without wishing to be bound by any theory, it is believed that these losses are due to heat and/or low chain fatty acids from the milk ingredient (e.g. acetic acid, propionic acid and butyric acid) which can hydrolyze the oligomers (e.g. a trimer can hydrolyze to a monomer and dimer). Alternatively, time consuming processing steps can allow for oxidation or irreversible binding of the compounds of the invention to protein sources within the formula. Thus, the invention comprehends altering methods of chocolate formulation and processing to address these effects to prevent or minimize these losses.

The skilled artisan will recognize many variations in these examples to cover a wide range of formulas, ingredients, processing, and mixtures to rationally adjust the naturally occurring levels of the compounds of the invention for a variety of chocolate applications.

TABLE 16

Dark Chocolate Formulas Prepared with non-Alkalized Cocoa Ingredients

| Non-SOI Dark Chocolate Using CP-cocoa solids Formulation: | SOI Dark Chocolate Using CP-Cocoa Solids Formulation: | SOI Dark Chocolate Using Commercial Cocoa Solids Formulation: |
|---|---|---|
| 41.49% Sugar | 41.49% sugar | 41.49% sugar |
| 3% whole milk powder | 3% whole milk powder | 3% whole milk powder |
| 26% CP-cocoa solids | 52.65% CP-liquor | 52.65% com. liquor |
| 4.5% com. liquor | 2.35% anhy. milk fat | 2.35% anhy. milk fat |
| 21.75% cocoa butter | 0.01% vanillin | 0.01% vanillin |
| 2.75% anhy. milk fat | 0.5% lecithin | 0.5% lecithin |
| 0.01% vanillin | | |
| 0.5% lecithin | | |
| Total fat: 31% | Total fat: 31% | Total fat: 31% |
| Particle size: 20 microns | Particle size: 20 microns | Particle size: 20 microns |
| Expected Levels of pentamer and total oligomeric procyanidins (monomers and n = 2-12; units of ug/g) | | |
| Pentamer: 1205 | Pentamer: 1300 | Pentamer: 185 |
| Total: 13748 | Total: 14646 | Total: 3948 |
| Actual Levels of pentamer and total oligomeric procyandins (monomers and n = 2-12; units of ug/g) | | |
| Pentamer: 561 | Not performed | Not performed |
| Total: 14097 | | |

TABLE 17

Milk Chocolate Formulas Prepared with non-Alkalized Cocoa Ingredients

| Non-SOI MIlk Chocolate Using CP-cocoa solids Formulation: | SOI Milk Chocolate Using CP-Cocoa Solids Formulation: | SOI Milk Chocolate Using Commercial Cocoa Solids Formulation: |
|---|---|---|
| 46.9965% Sugar | 46.9965% sugar | 46.9965% sugar |
| 15.5% whole milk powder | 15.5% whole milk powder | 15.5% whole milk powder |
| 4.5% CP-cocoa solids | 13.9% CP-liquor | 13.9% com. liquor |
| 5.5% com. liquor | 1.6% anhy. milk fat | 1.60% anhy. milk fat |
| 21.4% cocoa butter | 0.0035% vanillin | 0.0035% vanillin |
| 1.6% anhy. milk fat | 0.5% lecithin | 0.5% lecithin |
| 0.035% vanillin | 17.5% cocoa butter | 17.5% cocoa butter |
| 0.5% lecithin | 4.0% malted milk powder | 4.0% malted milk powder |
| 4.0% malted milk powder | | |
| Total fat: 31.75% | Total fat: 31.75% | Total fat: 31.75% |
| Particle size: 20 microns | Particle size: 20 microns | Particle size: 20 microns |
| Expected Levels of pentamer and total oligomeric procyanidins (monomers and n = 2-12; units of ug/g) | | |
| Pentamer: 225 | Pentamer: 343 | Pentamer: 49 |
| Total: 2734 | Total: 3867 | Total: 1042 |
| Actual Levels of pentamer and total oligomeric procyandins (monomers and n = 2-12; units of ug/g) | | |
| Pentamer: 163 | Not performed | Not performed |
| Total: 2399 | | |

Example 41

Hydrolysis of Procyanidin Oligomers

Example 14, Method D describes the preparation normal phase HPLC procedure to purify the compounds of the invention. The oligomers are obtained as fractions dissolved in mobile phase. Solvent is then removed by standard vacuum distillation (20-29 in. Hg: 40° C.) on a Rotovap apparatus. It was observed that losses of a particular oligomer occurred with increases in smaller oligomers when the vacuum distillation residence time was prolonged or temperatures >40° C. were used.

Figure 63:
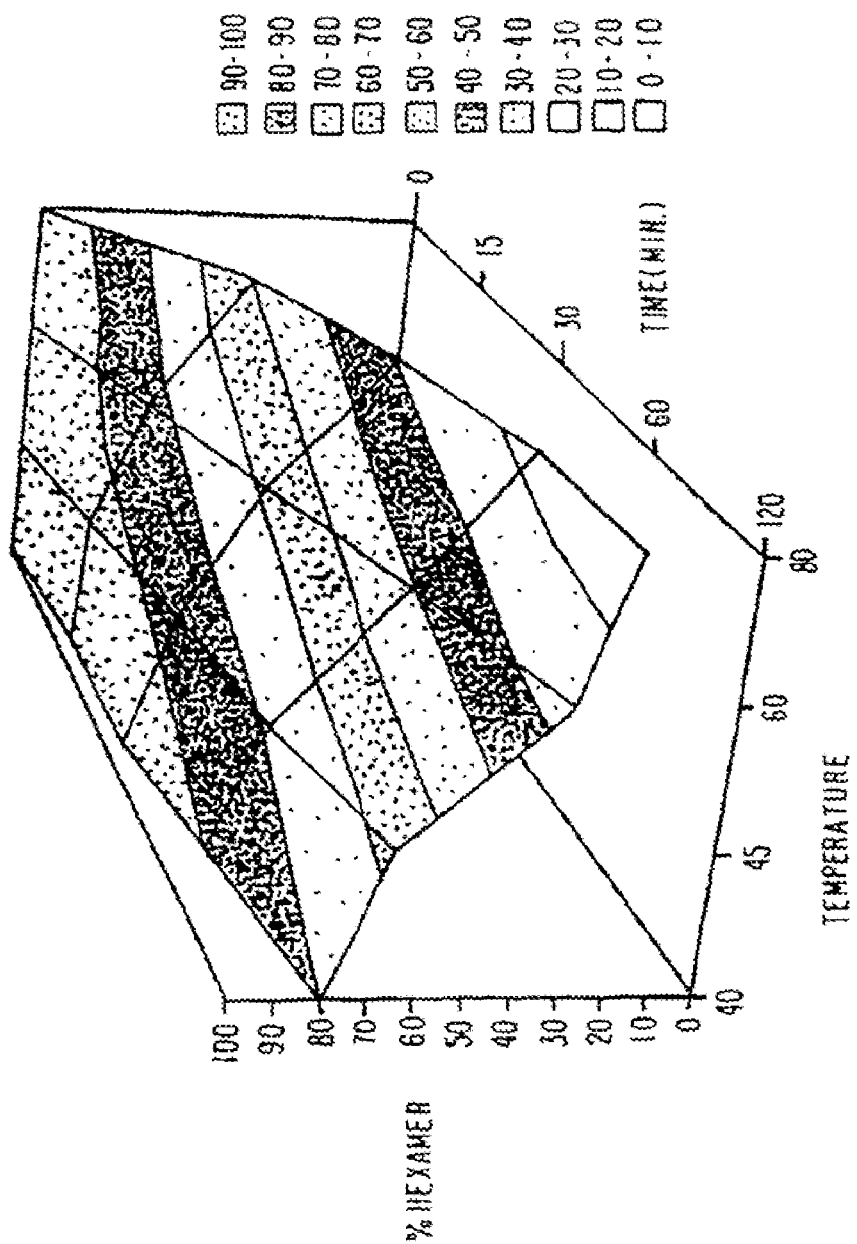
FIG. 63 shows time-temperature effects on hexamer hydrolysis.
Figure 64:
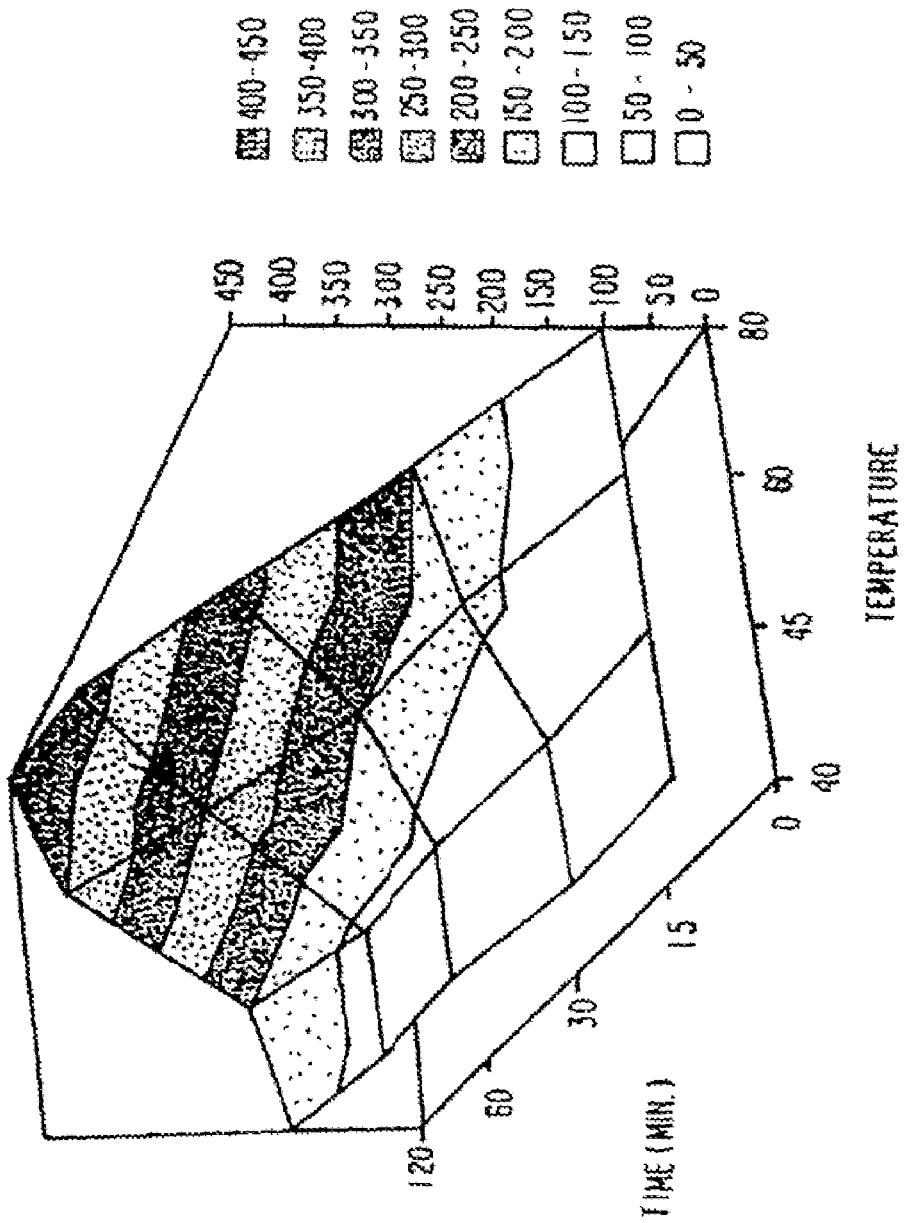
FIG. 64 shows time-temperature effects on trimer formation.

The losses of a particular oligomer with accompanying increases in smaller oligomers was attributed to a time-temperature acid hydrolysis from residual acetic acid present in the mobile phase solvent mixture. This observation was confirmed by the following experiment where 100 mg of hexamer was dissolved in 50 mL of the mobile phase containing methylene chloride, acetic acid, water, and methanol (see Example 14, Method D for solvent proportions) and subjected to a time-temperature dependent distillation. At specific times, an aliquot was removed for analytical normal phase HPLC analysis as described in Example 4, Method 2. The results are illustrated in FIGS. 63 and 64, where hexamer levels decreased in a time-temperature dependent fashion. FIG. 64 illustrates the appearance of one of the hydrolysis products (Trimer) in a time-temperature dependent fashion. Monomer and other oligomers (dimer to pentamer) also appeared in a time-temperature dependent fashion.

These results indicated that extreme care and caution must be taken during the handling of the inventive polymeric compounds.

The results provided above, together with that found in Examples 5, 15, 18, 19, 20 and 29, demonstrate that the method described above can be used to complement other methods embodied in the invention to identify any given oligomer of the invention.

For instance, the complete hydrolysis of any given oligomer which yields exclusively (+)-catechin or (−)-epicatechin eliminates many "mixed" monomer-based oligomer structure possibilities and reduces the stereochemical linkage possibilities characteristic for each monomer comprising any given oligomer.

Further, the complete hydrolysis of any given oligomer which yields both (+)-catechin and (−)-epicatechin in specific proportions provides the skilled artisan with information on the monomer composition of any given oligomer, and hence, the stereochemical linkage possibilities characteristic for each monomer comprising the oligomer.

The skilled artisan would recognize the fact that acid catalyzed epimerization of individual monomers can occur and suitable control experiments and nonvigorous hydrolysis conditions should be taken into account (e.g., the use of an organic acids, such as acetic acid, in lieu of concentrated HCl, $HNO_3$, etc).

Having thus described in detail the preferred embodiments of the present invention, it is to be understood that the invention defined by the appended claims is not to be limited by particular details set forth in the above descriptions as many apparent variations thereof are possible without departing from the spirit or scope of the present invention.

REFERENCES

1. Barrows, L. R., Borchers, A. H., and Paxton, M. B., Transfectant CHO Cells Expressing $O^6$-alkylguanine-DNA-alkyltransferase Display Increased Resistance to DNA Damage Other than $O^6$-guanine Alkylation, Carcinogenesis, 8:1853 (1987).
2. Boukharta, M., Jalbert, G. and Castonguay, A., Efficacy of Ellagitannins and Ellagic Acid as Cancer Chemopreventive Agents—Presented at the $XVI^{th}$ International Conference of the Groupe Polyphenols, Lisbon, Portugal, Jul. 13-16, 1992.
3. Burres, N. S., Sazesh, J., Gunawardana, G. P., and Clement, J. J., Antitumor Activity and Nucleic Acid Binding Properties of Dercitin, a New Acridine Alkaloid Isolated from a Marine Dercitus species Sponge, Cancer Research, 49, 5267-5274 (1989).
4. Caragay, A. B., Cancer Preventive Foods and Ingredients, Food Technology, 46:4, 65-79 (1992).
5. Chu, S. -C., Hsieh, Y. -S. and Lim, J. -Y., Inhibitory Effects of Flavonoids on Maloney Murine Leukemia Virus Reverse Transcriptase Activity, J. of Natural Products, 55:2, 179-183 (1992).
6. Clapperton, J., Hammerstone, J. F. Jr., Romanczyk, L. J. Jr., Chan, J., Yow, S., Lim, D. and Lockwood, R., Polyphenols and Cocoa Flavor—Presented at the $XVI^{th}$ International Conference of the Groupe Polyphenols, Lisbon, Portugal, Jul. 13-16, 1992.
7. Danks, M. K, Schmidt, C. A., Cirtain, M. C., Suttle, D. P., and Beck, W. T., Altered Catalytic Activity of and DNA Cleavage by DNA Topoisomerase II from Human Leukemic Cells Selected for Resistance to VM-26, Biochem., 27:8861 (1988).
8. Delcour, J. A., Ferreira, D. and Roux, D. G., Synthesis of Condensed Tannins, Part 9, The Condensation Sequence of Leucocyanidin with (+)-Catechin and with the Resultant Procyanidins, J. Chem. Soc. Perkin Trans. I, 1711-1717 (1983).

9. Deschner, E. E., Ruperto, J., Wong, G. and Newmark, H. L., Quercetin and Rutin as Inhibitors of Azoxymethanol—Induced Colonic Neoplasia, Carcinogenesis, 7, 1193-1196 (1991).
10. Designing Foods, Manipulating Foods to Promote Health, Inform, 4:4, 344-369 (1993).
11. Drake, F. H., Hofmann, G. A., Mong., S. -M., Bartus, J. O., Hertzberg, R. P., Johnson, R. K., Mattern, M. R., and Mirabelli, C. K., in vitro and Intercellular Inhibition of Topoisomerase II by the Antitumor Agent Membranone, Cancer Research, 49, 2578-2583 (1989).
12. Engels J. M. M., Genetic Resources of Cacao: A Catalogue of the CATIE Collection, Tech. Bull. 7, Turrialba, Costa Rica (1981).
13. Enriquez G. A. and Soria J. V., Cocoa Cultivars Register IICA, Turrialba, Cost Rica (1967).
14. Ferreira, D., Steynberg, J. P., Roux, D. G. and Brandt, E. V., Diversity of Structure and Function in Oligomeric Flavanoids, Tetrahedron, 48:10, 1743-1803 (1992).
15. Fesen, M. and Pommier, Y., Mammalian Topoisomerase II Activity is Modulated by the DNA Minor Groove Binder—Distainycin in Simian Virus 40 DNA, J. Biol. Chem., 264, 11354-11359 (1989).
16. Fry, D. W., Boritzki, T. J., Besserer, J. A., and Jackson, R. C., in vitro Strand Scission and Inhibition of Nucleic Acid Synthesis on L1210 Leukemia Cells by a New Class of DNA Complexes, the anthra [1,9-CD]pyrazol-6 (2H)-ones (anthrapyrazoles), Biochem. Pharmacol., 34, 3499-3508 (1985).
17. Hsiang, Y. -H., Jiang, J. B., and Liu, L. F., Topoisomerase II Mediated DNA Cleavage by Amonafide and Its Structural Analogs, Mol. Pharmacol., 36, 371-376 (1989).
18. Jalal, M. A. F. and Collin, H. A., Polyphenols of Mature Plant, Seedling and Tissue Cultures of *Theobroma Cacoa*, Phytochemistry, 6, 1377-1380 (1978).
19. Jeggo, P. A., Caldecott, K., Pidsley, S., and Banks, G. R., Sensitivity of Chinese Hamster Ovary Mutants Defective in DNA Double Strand Break Repair to Topoisomerase II Inhibitors, Cancer Res., 49:7057 (1989).
20. Kashiwada, Y., Nonaka, G. -I., Nishioka, I., Lee, K. J. -H., Bori, I., Fukushima, Y., Bastow, K. F., and Lee, K. -H., Tannin as Potent Inhibitors of DNA Topoisomerase II in vitro, J. Pharm. Sci., 82:5, 487-492 (1993).
21. Kato, R., Nakadate, T., Yamamoto, S. and Sugimura, T., Inhibition of 12-O-tetradecanoylphorbol-13-acetate Induced Tumor Promotion and Ornithine Decarboxylase Activity by Quercitin: Possible Involvement of lipoxygenase Inhibition, Carcinogenesis, 4, 1301-1305 (1983).
22. Kawada, S. -Z., Yamashita, Y., Fujii, N. and Nakano, H., Induction of Heat Stable Topoisomerase II-DNA Cleavable Complex by Nonintercalative Terpenoids, Terpentecin and Clerocidin, Cancer Research, 51, 2922-2929 (1991).
23. Kemp, L. M., Sedgwick, S. G. and Jeggo, P. A., X-ray Sensitive Mutants of Chinese Hamster Ovary Cells Defective in Double Strand Break Rejoining, Mutat. Res., 132: 189 (1984).
24. Kikkoman Corporation, Antimutagenic Agent Containing Proanthocyanidin Oligomer Preferably Having Flavan-3-ol-Diol Structure, JP 04190774-A, Jul. 7, 1992.
25. Lehrian, D. W.; Patterson, G. R. In Biotechnology; Reed, G., Ed.; Verlag Chemie: Weinheim, 1983, Vol. 5, Chapter 12.
26. Leonessa, F., Jacobson, M., Boyle, B., Lippman, J., McGarvey, M., and Clarke, R. Effect of Tamoxifen on the Multidrug-Resistant Phenotype in Human Breast Cancer Cells: Isobolograms, Drug Accumulation, and $M_r$ 170,000 Glycoprotein (gp 170) Binding Studies, Cancer Research, 54, 441-447 (1994).
27. Liu, L. F., DNA Toposimerase Poisons as Antitumor Drugs, Ann. Rev. Biochem., 58, 351-375 (1989).
28. McCord, J. D. and Kilara A. Control of Enzymatic Browning in Processed Mushrooms (*Agaricus bisporus*). J. Food Sci., 48:1479 (1983).
29. Miller, K. G., Liu, L. F. and Englund, P. A., Homogeneous Type II DNA Topoisomerase from Hela Cell Nuclei, J. Biol. Chem., 256:9334 (1981).
30. Mosmann, T., Rapid Colorimetric Assay for Cellular Growth and Survival: Application to Proliferation and Cytoxicity Assays, J. Immunol. Methods, 65, 55 (1983).
31. Muller, M. T., Helal, K., Soisson, S. and Spitzer, J. R., A Rapid and Quantitative Microtiter Assay for Eukaryotic Topoisomerase II, Nuc. Acid Res., 17:9499 (1989).
32. Nawata, H., Chong, M. T., Bronzert, D. and Lippman, M. E. Estradiol-Independent growth of a Subline of MCF-7 Human Breast Cancer Cells in Culture, J. Biol. Chem., 256:13, 6895-6902 (1981).
33. Okuda, T., Yoshida, T., and Hatano, T., Molecular Structures and Pharmacological Activities of Polyphenols—Oligomeric Hydrolyzable Tannins and Others—Presented at the $XVI^{th}$ International Conference of the Groupe Polyphenols, Lisbon, Portugal, Jul. 13-16, 1992.
34. Phenolic Compounds in Foods and Their Effects on Health II. Antioxidants & Cancer Prevention, Huang, M. -T., Ho, C. -T., and Lee, C. Y. editors, ACS Symposium Series 507, American Chemical Society, Washington, D.C. (1992).
35. Phenolic Compounds in Foods and Their Effects on Health I, Analysis, Occurrence & Chemistry, Ho, C. -T., Lee, C. Y., and Huang, M. -T editors, ACS Symposium Series 506, American Chemical Society, Washington, D.C. (1992).
36. Porter, L. J., Ma, Z. and Chan, B. G., Cocoa Procyanidins: Major Flavanoids and Identification of Some Minor Metabolites, Phytochemistry, 30, 1657-1663 (1991).
37. Revilla, E., Bourzeix, M. and Alonso, E., Analysis of Catechins and Procyanidins in Grape Seeds by HPLC with Photodiode Array Detection, Chromatographia, 31, 465-468 (1991).
38. Scudiero, D. A., Shoemaker, R. H., Paull, K. D., Monks, A., Tierney, S., Nofziger, T. H., Currens, M. J., Seniff, D., and Boyd, M. R. Evaluation of a Soluble Tetrazolium/Formazan Assay for Cell Growth and Drug Sensitivity in Culture Using Human and Other Tumor Cell Lines, Canur Research, 48, 4827-4833 (1988).
39. Self, R., Eagles, J., Galletti, G. C., Mueller-Harvey, I., Hartley, R. D., Lee, A. G. H., Magnolato, D., Richli, U., Gujur, R. and Haslam, E., Fast Atom Bombardment Mass Spectrometry of Polyphenols (syn. Vegetable Tannins), Biomed Environ. Mass Spec. 13, 449-468 (1986).
40. Tanabe, K., Ikegami, Y., Ishda, R. and Andoh, T., Inhibition of Topoisomerase II by Antitumor Agents bis(2,6-dioxopiperazine) Derivatives, Cancer Research, 51, 4903-4908 (1991).
41. Van Oosten, C. W., Poot, C. and A. C. Hensen, The Precision of the Swift Stability Test, Fette, Seifen, Anstrichmittel, 83:4, 133-135 (1981).
42. Wang, J. C., DNA Topoisomerases, Ann. Rev. Biochem., 54, 665-697 (1985).
43. Warters, R. L., Lyons, B. W., Li, T. M. and Chen, D. J., Topoisomerase II Activity in a DNA Double-Strand Break Repair Deficient Chinese Hamster Ovary Cell Line, Mutat. Res., 254:167 (1991).
44. Yamashita, Y., Kawada, S.-Z. and Nakano, H., Induction of Mammalian Topoismerase II Dependent DNA Cleavage by Nonintercalative Flavanoids, Genistein and Orbol., Biochem Pharm, 39:4, 737-744 (1990).
45. Yamashita, Y., Kawada, S. -Z., Fujii, N. and Nakano, H., Induction of Mammalian DNA Topoisomerase I and II Mediated DNA Cleavage by Saintopin, a New Antitumor Agent from Fungus, Biochem., 30, 5838-5845 (1991).
46. Feldman, P. L., Griffith, O. W., and Stuehr, D. J. The Surprising Life of Nitric Oxide, Chem. & Eng. News, Dec. 20, 1993, p. 26-38.
47. Jia, L., Bonaventura, C. and Stamler, J. S., S-Nitrosohaemoglobin: A Dynamic Activity of Blood Involved in Vascular Control, Nature, 380,221-226 (1996).
48. Radomski, M. W., Palmer, R. M. J. and Moncada, S. Comparative Pharmacology of Endothelium Derived Relaxing Factor, Nitric Oxide and Prostacyclin in Platelets, Brit J. Pharmacol, 92, 789-795 (1989).
49. Stamler, J. S., Mendelshon, M. E., Amarante, P., Smick, D., Andon, N., Davies, P. F., Cooke, J. P., and Loscalzo, N-Acetylcysteine Potentiates platelet Inhibitio By Edothelium—Derived Relaxing Factor, J. Circ. Research, 65, 789-795 (1989).
50. Bath, P. M. W., Hassall, D. G., Gladwin, A. M., Palmer, R. M. J. and Martin, J. F., Nitric Oxide and Prostacyclin. Divergence of Inhibitory Effects on Monocyte Chemotaxis and Adhesion to endothelium In Vitro. Arterioscl. Throm., 11, 254-260 (1991).
51. Garg, U. C. and Hassid, A. Nitric Oxide Generating Vasodilators and 8-Bromo-Cyclicguanosine Monophosphate Inhibit Mitogenesis and Proliferation of Cultured Rat Vascular Smoothe Muscle Cells, J. Clin. Invest., 83, 1774-1777 (1989).
52. Creager, M. A., Cooke, J. P., Mendelsohn, M. E., Gallagher, S. J., Coleman, S. M., Loscalzo, J. and Dzau, V. J. Impaired Vasodilation of Forearm Resistance Vessels in Hypercholesterolemic Humans, J. Clin. Invest., 86, 228-234 (1990).
53. Steinberg, D., Parthasarathy, S., Carew, T. E., Khoo, J. C. and Witztum, J. L. Beyond Cholesterol. Modifications of Low Density Lipoproteins that Increase its Atherogenicity. The New England J. of Med, 320, 915-924 (1989).
54. Tsuiji, M. and DuBois, R N. Alterations in Cellular Adhesion and Apoptosis in Epithelial Cells Overexpressing Prostaglandin Endoperoxide Synthase 2, Cell, 83, 493-501 (1995).
55. Marcus, A. J. Aspirin as Prophylaxis Colorectal Cancer, The New Eng. J. Med., 333:10, 656-658 (1995).
56. P. J. Pastricha, Bedi, A., O'Connor, K., Rashid, A., Akhatar, A. J., Zahurak, M. L., Piantadosi, S., Hamilton, S. R. and Giardiello, F. M. The Effects of Sulindac on Colorectal Proliferation and Apoptosis in Familial Adenomatous Polyopsis. Gastroenterology, 109, 994-998 (1995).
57. Lu, X., Xie, W., Reed, D., Bradshaw, W. and Simmons, D. Nonsteroidal Anti Inflammatory Drugs Cause Apoptosis and Induce Cyclooxygenase in Chicken Embryo Fibroblasts. P.N.A.S. U.S.A., 92, 7961-7965 (1995).
58. Gajewski, T. F. and Thompson, C. B. Apoptosis Meets Signal Transduction: Elimination of A BAD Influence. Cell, 87, 589-592 (1996).
59. Funk, C. D., Funk, L. B., Kennedy, M. E., Pong, A. S. and Fitzgerald, G. A. Human platelet/Erythroleukemiz Cell Prostaglandin G/H Synthase: cDNA Cloning, Expression and Gene Chromosomal Assignment, FASEB J., 5: 2304-2312 (1991).
60. Patrono, C. Aspirin as an Antiplatelet Drug. The New Eng. J. Med., 333: 18, 1287-1294 (1994).
61. Howell, T. H. and Williams, R. C. Nonsteroidal Antiinflammatory Drugs as Inhibitors of Periodonal Disease Progression. Crit. Rev. of Oral Biol & Med., 4: 2, 117-195 (1993).
62. Brisham, M. B. Oxidants and Free Radicals in Inflammatory Bowel Disease. Lancet, 344, 859-861 (1994).
63. Oates, J. A. The 1982 Nobel Prize in Physiology and Medicine, Science, 218, 765-768 (1996).
64. Hunter, T. and Pines, J. Cyclins and Cancer II: Cyclin D and CDK Inhibitors Come of Age, Cell, 79, 573-582 (1994).
65. King, R. W., Jackson, P. K. and Kirschner, M. W. Mitosis in Transition, Cell, 79, 563-571 (1994).
66. Sherr, C. J. GI Phase Progession: Cycling on Cue, Cell, 79, 551-555 (1994).
67. Nurse, P. Ordering S Phase and M Phase in the Cell Cycle, Cell, 79, 547-550 (1994).
68. DeCross, A. J., Marshall, B. J., McCallum, R. W., Hoffman, S. R., Barrett, L. J. and Guerrant, R. L. Metronidazole Susceptibility Testing for *Helicobacter pylori*: Comparison of Disk, Broth and Agar Dilution Methods and Their Clinical Relevance, J. Clin. Microbiol., 31, 1971-1974 (1993).
69. Anon., Flavor and Fragrance Materials—1981: Worldwide reference list of materials used in compounding flavors and fragrances, Chemical Sources Association, Allured Publishing Corp.
70. van Rensburg, H., van Heerden, P. S., Bezuidenhoudt, B. C. B. and Ferreira, D., The first enantioselective synthesis of trans- and cis-dihydroflavanols, Chem. Comm. 24, 2705-2706 (1996).
71. Lockhart, D. J., Dong, H., Byrne, M. C., Follette, M. T., Gallo, M. V., Chee, M. S., Mittmann, M., Wang, C., Kobayashi, M., Horton, H., Brown, E. L. Expression Monitoring by Hybridization to High-Density Oligonucleotide Assays, Nature Biotechnology, 14, 1675-1680 (1996).
72. Winyard, P. G. and Blake, D. R. Antioxidants, Redox-Regulated Transcription Factors, and Inflammation, Advances in Pharmacology, 38, 403-421 (1997).
73. Schwartz, M. A., Rose, B. F., Holton, R. A., Scott, S. W. and Vishnuvajjala, B. Intramolecular Oxidative Coupling of Diphenolic, Monophenolic and Nonphenolic Substrates, J. Am. Chem. Soc. 99: 8, 2571-2575 (1977).
74. Greene, T. W. "Protecting Groups in Organic Synthesis", Wiley, New York (1981).
75. Warren, S. "Designing Organic Syntheses. A Programmed Introduction to the Synthon Approach", Wiley, New York (1978).
76. Collman, J. P., Hegedus, L. S., Norton, J. R. and Finke, R. G. "Principles and Applications of Organotransition Metal Chemistry", University Science Books (1987).
77. Tsujii, M. and DuBois, R. N. Alterations in Cellular Adhesion and Apoptosis in Epithelial Cells Overexpressing Prostaglandin Endoperoxide Synthase 2, Cell, 83, 493-501 (1995).
78. Pashricha, P. J., Bedi, A., O'Connor, K., Rashid, A., Akhtar, D. J., Zahurak, M. L., Piantadosi, S., Hamilton, S. R. and Giardiello, F. M. The Effects of Sulindac on Colorectal Proliferation and Apoptosis in Familial Adenomatous Polyposis, Gastroenterology, 109, 994-998 (1995).
79. Verhagan, J. V., Haenen, G. R. M. M. and Bast, A. Nitric Oxide Radical Scavenging by Wines, J. Agric. Food Chem. 44, 3733-3734 (1996).
80. Aruoma, O. I. Assessment of Potential Prooxidant and Antioxidant Actions, J.A.O.C.S., 73: 12, 1617-1625.
81. Stoner, G. D. and Mukhtar, H. Polyphenols as Cancer Chemopreventive Agents, J. Cell. Biochem. 22, 169-180 (1995).
82. Gali, H. U., Perchellet, E. M., Klish, D. S., Johnson, J. M. and Perchellet, J-P. Antitumor-promoting activities of hydrolyzable tannins in mouse skin, Carcinogenesis, 13: 4, 715-718 (1992).
83. Tabib, K., Besancon, P. and Rouanet, J-M. Dietary Grape Seed Tannins Affect Lipoproteins, Lipoprotein Lipases and Tissue Lipids in Rats Fed Hypercholesterolemic Diets, J. Nutrition, 124:12, 2451-2457.

84. Paolino, V. J. and Kashket, S. Inhibition by Cocoa Extracts of Biosynthesis of Extracellular Polysaccharide by Human Oral Bacteria, Archs. Oral Biol. 30:4, 359-363 (1985).
85. Lockhart, D. J., Dong, H., Byrne, M. C., Follettie, M. T., Gallo, M. V., Chee, M. S., Mittmann, M., Wang, C., Kobayashi, M., Horton, H., and Brown, E. L., Expression monitoring by hybridization to high-density oligonucleotide arrays, Nature Biotech., 14, 1675-1680 (1996).
86. Kreiner, T. Rapid genetic sequence analysis using a DNA probe array system, Am Lab., March, 1996.
87. Lipshutz, R. J., Morris, D., Chee, M., Hubbell, E., Kozal, M. J., Shah, N., Shen, N., Yang, R. and Fodor, S. P. A. Using Oligonucleotide Probe Arrays to Access Genetic Diversity, Biotechniques, 19: 3, 442-447 (1995).
88. Borman, S. DNA Chips Come of Age, Chem. & Eng. News, 4243, Dec. 9, 1996
89. Tahara, H., Mihara, Y., Ishii, Y., Fujiwara, M., Endo, H., Maeda, S and Ide, T. Telomerase Activity in Cellular Immortalization, Cell Structure and Function, 20: 6, 1B-1615 (1995).
90. Heller, K., Kilian, A., Paityszek, M. A., and Kleinhofs, A. Telomerase activity in plant extracts, Mol. Gen. Genet. 252, 342-345 (1996).
91. Goffeau, A. Molecular fish on chips, Nature, 385, 202-203 (1997).
92. Friedrich, G. A. Moving beyond the genome projects, Nature Biotechnology, 14, 1234-1237 (1996).
93. Blanchard, R. K. and Cousins, R. J. Differential display of intestingal mRNAs regulated by dietary zinc., Proc. Natl. Acad. Sci. USA, 93, 6863-6868 (1996).
94. Pennisi, E. Opening the Way to Gene Activity, Science, 275: 155-157 (1997).
95. Medlin, J. The Amazing Shrinking Laboratory, Environmental Healt Perspectives, 103: 3, 244-246.
96. Luehrsen, K. R., Marr, L. L., van der Knaap, E. and Cumberledge, S. Analysis of Differential Display RT-PCR Products Using Fluorescent Primers and GENESCAN Software, Biotechniques, 22: 1, 168-174.
97. Geiss, F., Heinrich, M., Hunkler, D. and Rirnpler, H. Proanthocyanidins with (+)-Epicatechin Units from *Byronima Crassifolia* Bark, Phytochemistry, 39: 1, 635-643 (1995).
98. Iibuchi, S., Minoda, Y. and Yamada, K. Studies on Tannin Acyl Hydrolase of Microorganisms, Part II. A New Method Determining the Enzyme Activity Using the Change of Ultra Violet Absorption, Agr. Biol. Chem. 31: 5, 513-518 (1967).
99. Ferreira, D., Steynberg, J. P., Roux, D. G. and Brandt, E. V. Diversity of Structure and Function in Oligomeric Flavanoids, Tetrahedron, 48: 10, 1743-1803 (1992).

What is claimed is:

1. A method of treating hypertension comprising administering to a subject in need thereof a composition comprising an effective amount of epicatechin, and/or a pharmaceutically acceptable salt thereof wherein the subject is a human or a veterinary animal.
2. The method of claim 1, wherein the composition comprises an effective amount of epicatechin.
3. The method of claim 1, wherein the composition is a pharmaceutical composition.
4. The method of claim 2, wherein the composition is a pharmaceutical composition.
5. The method of claim 1, wherein the subject is a human.
6. The method of claim 5, wherein the composition comprises an effective amount of epicatechin.
7. The method of claim 1, wherein the composition is a food.
8. The method of claim 2, wherein the composition is a food.
9. The method of claim 8, wherein the food is a cocoa beverage.
10. The method of claim 9, wherein the cocoa beverage comprises non-alkalized cocoa solids.
11. The method of claim 8, wherein the food is a confectionery.
12. The method of claim 8, wherein the food is a chocolate.
13. The method of claim 12, wherein the chocolate comprises non-alkalized cocoa solids or liquor.
14. The method of claim 12, wherein the chocolate comprises CP-cocoa solids in powder or liquid form.
15. The method of claim 1, wherein the composition is a dietary supplement.
16. The method of claim 2, wherein the composition is a dietary supplement.
17. The method of claim 8, wherein the food is a pet food.
18. The method of claim 2, wherein the epicatechin is in the form of a cocoa extract or cocoa extract fraction.
19. A method of reducing blood pressure comprising administering to a subject suffering from high blood pressure a composition comprising epicatechin, and/or a pharmaceutically acceptable salt thereof in the amount effective to induce nitric oxide (NO)-dependent vasorelaxation, wherein the subject is a human or a veterinary animal.
20. The method of claim 19, wherein the composition comprises an effective amount of epicatechin.
21. The method of claim 19, wherein the subject is a human.
22. The method of claim 21, wherein the composition comprises an effective amount of epicatechin.
23. The method of claim 20, wherein the composition is a food.
24. The method of claim 21, wherein the composition is a food.
25. The method of claim 24, wherein the food is a cocoa beverage.
26. The method of claim 25 wherein the cocoa beverage comprises non-alkalized cocoa solids.
27. The method of claim 24, wherein the food is a confectionery.
28. The method of claim 24, wherein the food is a chocolate.
29. The method of claim 28, wherein the chocolate comprises non-alkalized cocoa solids or liquor.
30. The method of claim 28, wherein the chocolate comprises CP-cocoa solids in powder or liquid form.
31. The method of claim 19, wherein the composition is a dietary supplement.
32. The method of claim 20, wherein the composition is a dietary supplement.
33. The method of claim 20, wherein the epicatechin is in the form of a cocoa extract or cocoa extract fraction.

* * * * *